(12) United States Patent
Li

(10) Patent No.: US 7,888,466 B2
(45) Date of Patent: Feb. 15, 2011

(54) HUMAN G-PROTEIN CHEMOKINE RECEPTOR HSATU68

(75) Inventor: Yi Li, Sunnyvale, CA (US)

(73) Assignee: Human Genome Sciences, Inc., Rockville, MD (US)

( * ) Notice: Subject to any disclaimer, the term of this patent is extended or adjusted under 35 U.S.C. 154(b) by 1936 days.

(21) Appl. No.: 10/411,284

(22) Filed: Apr. 11, 2003

(65) Prior Publication Data

US 2003/0224426 A1 Dec. 4, 2003

Related U.S. Application Data

(63) Continuation-in-part of application No. 09/101,518, filed as application No. PCT/US96/00499 on Jan. 11, 1996, now abandoned.

(60) Provisional application No. 60/371,725, filed on Apr. 12, 2002.

(51) Int. Cl.
*C07K 14/00* (2006.01)
*C07H 21/04* (2006.01)
*C12N 15/00* (2006.01)
*C12P 21/00* (2006.01)

(52) U.S. Cl. .................. 530/350; 536/23.1; 435/69.5; 435/70.1

(58) Field of Classification Search .................. None
See application file for complete search history.

(56) References Cited

U.S. PATENT DOCUMENTS

| | | |
|---|---|---|
| 5,155,218 A | 10/1992 | Weinshank et al. |
| 5,374,506 A | 12/1994 | Murphy |
| 5,786,157 A | 7/1998 | Weinshank et al. |
| 5,882,855 A | 3/1999 | Weinshank et al. |
| 5,935,925 A | 8/1999 | Weinshank et al. |
| 6,140,064 A | 10/2000 | Loetscher et al. |
| 6,171,590 B1 | 1/2001 | Howard et al. |
| 6,184,358 B1 | 2/2001 | Loetscher et al. |

FOREIGN PATENT DOCUMENTS

| | | |
|---|---|---|
| EP | 1 098 664 | 8/2003 |
| WO | WO 91/17174 A1 | 11/1991 |
| WO | WO 92/00986 A1 | 1/1992 |
| WO | WO 92/18641 A1 | 10/1992 |
| WO | WO 93/06229 A1 | 4/1993 |
| WO | WO 98/11218 A1 | 3/1998 |
| WO | WO 98/32858 A2 | 7/1998 |
| WO | WO 99/50299 A1 | 10/1999 |
| WO | WO 00/18431 A1 | 4/2000 |
| WO | WO 00/22129 A1 | 4/2000 |
| WO | WO 2004/075863 | 9/2004 |
| WO | WO 2005/030793 A2 | 4/2005 |

OTHER PUBLICATIONS

Ji et al. Journal of Biol Chemistry 273: 17299-17302, 1998.*
Kouba et al. FEBS Lett 321: 173-178, 1993.*
Sambrook et al., Molecular Cloning. New York: Cold Spring Harbor Laboratory Press. 1989, 2nd ed., pp. 10.2-10.3 and 10.29-10.35.
Marchese et al., "Cloning of human genes encoding novel G protein-coupled receptors," Genomics 23(3):609-18, Oct. 1994.
Mills et al., "Orphan seven transmembrane domain receptors: reversing pharmacology," Trends in Biotechnol. 12:47-49, 1994.
Heiber et al., "Isolation of three novel human genes encoding G protein-coupled receptors," DNA Cell Biol. 14(1):25-35, Jan. 1995.
Loetscher et al., GenBank Accession No. P49682, "C-X-C chemokine receptor type 3 (CXC-R3) (CXCR-3) (CKR-L2)," Aug. 20, 2001.
Marchese et al., GenBank Accession No. U32674, "Human orphan receptor GPR9 (GPR9) gene, partial cds," Jun. 5, 1996.
Loetscher et al. "Chemokine receptor specific for IP10 and mig: structure, function, and expression in activated T-lymphocytes," J. Exp. Med. 184(3):963-969, 1996.
Loetscher et al., GenBank Accession No. X95876, "H.sapiens mRNA for G-protein coupled receptor," May 16, 1997.
Loetscher et al., GenBank Accession No. CAA65126, "G-protein coupled receptor [Homo sapiens ]," May 16, 1997.
Gutierrez et al., GenBank Accession No. Z79783, "H.sapiens G protein-coupled receptor CKR-L2," Jul. 26, 1997.
Gutierrez et al., GenBank Accession No. CAB02143, "G Protein-Coupled Receptor CKR-L2 [Homo sapiens]," Jul. 26, 1997.
Soto et al., "The CC chemokine 6Ckine binds the CXC chemokine receptor CXCR3," Proc. Natl. Acad. Sci. USA 95:8205-8210, Jul. 1998.
Geneseq Accession No. AAV26557, "Human IP-10/Mig receptor CXCR3 gene," Aug. 14, 1998.
Geneseq Accession No. AAW54371, "Human IP-10/Mig receptor CXCR3 protein," Aug. 14, 1998.
Tamaru et al., GenBank Accession No. BAA34045, "interferon-inducible protein 10 receptor [mus musculus]," Oct. 28, 1998.

(Continued)

*Primary Examiner*—Jeffrey Stucker
*Assistant Examiner*—Aditi Dutt
(74) *Attorney, Agent, or Firm*—Foley & Lardner LLP

(57) ABSTRACT

Human G-protein chemokine receptor polypeptides and DNA (RNA) encoding such polypeptides and a procedure for producing such polypeptides by recombinant techniques is disclosed. Also disclosed are methods for utilizing such polypeptides for identifying antagonists and agonists to such polypeptides and methods of using the agonists and antagonists therapeutically to treat conditions related to the underexpression and overexpression of the G-protein chemokine receptor polypeptides, respectively. Also disclosed are diagnostic methods for detecting a mutation in the G-protein chemokine receptor nucleic acid sequences and detecting a level of the soluble form of the receptors in a sample derived from a host.

10 Claims, 8 Drawing Sheets

OTHER PUBLICATIONS

Geneseq Accession No. AAW69999, "Rodent chemokine receptor HST01.1 amino acid sequence," Oct. 20, 1998.
Balashov et al., "CCR5+ and CXCR3+T cells are increased in multiple sclerosis and their ligands MIP-Iα and IP-10 are expressed in demyelinating brain lesions," Proc. Natl. Acad. Sci. USA 96:6873-6878, Jun. 1999.
Trentin et al., "The chemokine receptor CXCR3 is expressed on malignant B cells and mediates chemotaxis," J. Clin. Invest. 104(1):115-121, Jul. 1999.
Lu et al., "Structure and function of the murine chemokine receptor CXCR3," Eur. J. Immunol. 29(11):3804-12, Nov. 1999.
Koga et al., "T cell infiltration into class II MHC-disparate allografts and acute rejection is dependent on the IFN-γ -induced chemokine Mig," J. Immunol. 163:4878-4885, 1999.
Geneseq Accession No. AAZ32713, "Human chemokine receptor CXCR3b cDNA," Jan. 31, 2000.
Geneseq Accession No. AAY50129, "Human chemokine receptor CXCR3b," Jan. 31, 2000.
Wang et al., GenBank Accession No. AAF76982, "chemokine receptor CXCR3 [Rattus norvegicus]," Jun. 19, 2000.
Tamaru et al., GenBank Accession No. JE0349, "interferon-inducible protein 10 (IP-10) receptor—mouse," Jul. 21, 2000.
Jones et al., "Expression pattern of T-cell-associated chemokine receptors and their chemokines correlates with specific subtypes of T-cell non-Hodgkin lymphoma," Blood 96(2):685-690, Jul. 15, 2000.
Geneseq Accession No. AAY79372, "Human chemokine receptor CXCR3," Aug. 1, 2000.
Geneseq Accession No. AAA30593, "Human G protein-coupled receptor GPR9 cDNA," Aug. 21, 2000.
Geneseq Accession No. AAY90614, "Human G protein-coupled receptor GPR9," Aug. 21, 2000.
Geneseq Accession No. AAA30714, "DNA encoding human mutant G protein-coupled receptor GPR9 (M254K)," Aug. 21, 2000.
Geneseq Accession No. AAY90648, "Human mutant G protein-coupled receptor GPR9 (M254K)," Aug. 21, 2000.
Soto et al., GenBank Accession No. 088410, "C-X-C chemokine receptor type 3 (CXC-R3) (CXCR-3)," Aug. 20, 2001.
GenBank Accession No. NM_001504, "Homo sapiens G protein-coupled receptor 9 (GPR9)," Oct. 31, 2000.
GenBank Accession No. NP_001495, "G protein-coupled receptor 9; chemokine (C-X-C) receptor 3 [Homo sapiens]," Oct. 31, 2000.
GenBank Accession No. NP_034040, "chemokine (C-X-C) receptor 3 [mus musculus]," Nov. 1, 2000.
Hancock et al., "Requirement of the chemokine receptor CXCR3 for acute allograft rejection," J. Exp. Med. 192(10):1515-1519, Nov. 20, 2000.
Albanesi et al., "IL-4 enhances keratinocyte expression of CXCR3 agonistic chemokines," J. Immunol. 165:1395-1402, 2000.
Cascieri et al., "The chemokine/chemokine-receptor family: potential and progress for therapeutic intervention," Curr. Op. Chem. Bio. 4:420-427, 2000.
Simpson et al., "Expression of the interferon-γ -inducible chemokines IP-10 and Mig and their receptor, CXCR3, in multiple sclerosis lesions," Neuropath. & Applied Neurobiol. 26:133-142, 2000.
Wang et al., "Identification and molecular characterization of rat CXCR3: receptor expression and interferon-inducible protein-10 binding are increased in focal stroke," Mol. Pharmacol. 57:1190-1198, 2000.
Patel et al., "CXCR3 and CCR5 ligands in rheumatoid arthritis synovium," Clin. Immunol. 98(1):39-45, Jan. 2001.
Bonacchi et al., "Signal transduction by the chemokine receptor CXCR3," J. Biol. Chem. 276(13):9945-9954, Mar. 30, 2001.
Romagnani et al., "Cell cycle-dependent expression of CXC chemokine receptor 3 by endothelial cells mediates angiostatic activity," J. Clin. Invest. 107(1):53-63, 2001.
Sebastiani et al., "Chemokine receptor expression and function in CD4+ T lymphocytes with regulatory activity," J. Immunol. 166:996-1002, 2001.
R&D Systems Technical Data Sheet, "Monoclonal Anti-Human CXCR3 Antibody," Catalog No. MAB160, Dec. 2002.
BD Pharmingen Technical Data Sheet, "CD183 (CXCR3) Purified Mouse Anti-Human Monoclonal Antibody," Catalog No. 557183, Mar. 2002.
Qin et al., "The chemokine receptors CXCR3 and CCR5 mark subsets of T cells associated with certain inflammatory reactions," J. Clin. Invest. 101(4):746-753 (1998).
García-López et al., "CXCR3 chemokine receptor distribution in normal and inflamed tissues: expression on activated lymphocytes, endothelial cells, and dendritic cells," Lab. Invest. 81(3):409-418 (2001).
Jinquan et al., "CXCR3 expression and activation of eosinophils: role of IFN-☐-Inducible Protein 10 and Monokine Induced by IFN-☐," J. Immunol. 165:1548-1556 (2000).
Lasagni et al., "An alternatively spliced variant of CXCR3 mediates the inhibition of endothelial cell growth induced by IP-10, Mig, and I-TAC, and acts a functional receptor for Platelet Factor 4," J. Exp. Med. 197(11):1537-1549 (2003).
Genbank Accession No. AF469635, "Homo sapiens CXC chemokine receptor transcript variant B (GPR9) mRNA, complete cds, alternately spliced." (Jun. 2003).
Marchese et al., Genomics 29:335-344 (1995).
Suzuki et al., J. Biol. Chem. 269(28):18263-18266, (1994).
Arimilli, et al., "Chemokines in autoimmune diseases," *Immuno. Rev.*, 177:43-51 (2000).
Heise, et al., "Pharmacological Characterization of CXC Chemokine Receptor 3 (CXCR3) Ligands and a Small-Molecule Antagonist," *J. Pharmacol. Exp. Ther.* 313:1263-1271 (2005).

\* cited by examiner

FIG. 1A

```
  1 CCTGAAGGGAGAGCAGGGAGAGAGAGGACAGTGGCCAGAGAGGGCTCTGGGCACTGGAGG  60

61 GACGCTCTTCTTCCTGCCCAGGGGTCCCTGGGCCGATGGGATCACGCAGAAGAATGCGAG 120

121 AGAAGCAGCCTTTGAGAAGGGAAGTCACTATCCCAGAGCCCAGACTGAGCGGATGGAGTT 180
  1                                                        M E L  3

181 GAGGAAGTACGGCCCTGGAAGACTGGCGGGGACAGTTATAGGAGGAGCTGCTCAGAGTAA 240
  3   R K Y G P G R L A G T V I G G A A Q S K 23

241 ATCACAGACTAAATCAGACTCAATCACAAAAGAGTTCCTGCCAGGCCTTTACACAGCCCC 300
 23   S Q T K S D S I T K E F L P G L Y T A P 43

301 TTCCTCCCCGTTCCCGCCCTCACAGGTGAGTGACCACCAAGTGCTAAATGACGCCGAGGT 360
 43   S S P F P P S Q V S D H Q V L N D A E V 63

361 TGCCGCCCTCCTGGAGAACTTCAGCTCTTCCTATGACTATGGAGAAAACGAGAGTGACTC 420
 63   A A L L E N F S S S Y D Y G E N E S D S 83

421 GTGCTGTACCTCCCCGCCCTGCCCACAGGACTTCAGCCTGAACTTCGACCGGGCCTTCCT 480
 83   C C T S P P C P Q D F S L N F D R A F L 103

481 GCCAGCCCTCTACAGCCTCCTCTTTCTGCTGGGGCTGCTGGGCAACGGCGCGGTGGCAGC 540
103   P A L Y S L L F L L G L L G N G A V A A 123

541 CGTGCTGCTGAGCCGGCGGACAGCCCTGAGCAGCACCGACACCTTCCTGCTCCACCTAGC 600
123   V L L S R R T A L S S T D T F L L H L A 143

601 TGTAGCAGACACGCTGCTGGTGCTGACACTGCCGCTCTGGGCAGTGGACGCTGCCGTCCA 660
143   V A D T L L V L T L P L W A V D A A V Q 163

661 GTGGGTCTTTGGCTCTGGCCTCTGCAAAGTGGCAGGTGCCCTCTTCAACATCAACTTCTA 720
163   W V F G S G L C K V A G A L F N I N F Y 183

721 CGCAGGAGCCCTCCTGCTGGCCTGCATCAGCTTTGACCGCTACCTGAACATAGTTCATGC 780
183   A G A L L L A C I S F D R Y L N I V H A 203

781 CACCCAGCTCTACCGCCGGGGGCCCCCGGCCCGCGTGACCCTCACCTGCCTGGCTGTCTG 840
203   T Q L Y R R G P P A R V T L T C L A V W 223

841 GGGGCTCTGCCTGCTTTTCGCCCTCCCAGACTTCATCTTCCTGTCGGCCCACCACGACGA 900
223   G L C L L F A L P D F I F L S A H H D E 243
```

FIG. 1B

```
 901 GCGCCTCAACGCCACCCACTGCCAATACAACTTCCCACAGGTGGGCCGCACGGCTCTGCG  960
 243   R  L  N  A  T  H  C  Q  Y  N  F  P  Q  V  G  R  T  A  L  R 263

961 GGTGCTGCAGCTGGTGGCTGGCTTTCTGCTGCCCCTGCTGGTCATGGCCTACTGCTATGC 1020
 263   V  L  Q  L  V  A  G  F  L  L  P  L  L  V  M  A  Y  C  Y  A 283

1021 CCACATCCTGGCCGTGCTGCTGGTTTCCAGGGGCCAGCGGCGCCTGCGGGCCATGCGGCT 1080
 283   H  I  L  A  V  L  L  V  S  R  G  Q  R  R  L  R  A  M  R  L 303

1081 GGTGGTGGTGGTCGTGGTGGCCTTTGCCCTCTGCTGGACCCCCTATCACCTGGTGGTGCT 1140
 303   V  V  V  V  V  V  A  F  A  L  C  W  T  P  Y  H  L  V  V  L 323

1141 GGTGGACATCCTCATGGACCTGGGCGCTTTGGCCCGCAACTGTGGCCGAGAAAGCAGGGT 1200
 323   V  D  I  L  M  D  L  G  A  L  A  R  N  C  G  R  E  S  R  V 343

1201 AGACGTGGCCAAGTCGGTCACCTCAGGCCTGGGCTACATGCACTGCTGCCTCAACCCGCT 1260
 343   D  V  A  K  S  V  T  S  G  L  G  Y  M  H  C  C  L  N  P  L 363

1261 GCTCTATGCCTTTGTAGGGGTCAAGTTCCGGGAGCGGATGTGGATGCTGCTCTTGCGCCT 1320
 363   L  Y  A  F  V  G  V  K  F  R  E  R  M  W  M  L  L  L  R  L 383

1321 GGGCTGCCCCAACCAGAGAGGGCTCCAGAGGCAGCCATCGTCTTCCCGCCGGGATTCATC 1380
 383   G  C  P  N  Q  R  G  L  Q  R  Q  P  S  S  S  R  R  D  S  S 403

1381 CTGGTCTGAGACCTCAGAGGCCTCCTACTCGGGCTTGTGAGGCCGGAATCCGGGCTCCCC 1440
 403   W  S  E  T  S  E  A  S  Y  S  G  L  *                      415

1441 TTTCGCCCACAGTCTGACTTCCCCGCATTCCAGGCTCCTCCCTCCCTCTGCCGGCTCTGG 1500

1501 CTCTCCCCAATATCCTCGCTCCCGGGACTCACTGGCAGCCCCAGCACCACCAGGTCTCCC 1560

1561 GGGAAGCCACCCTCCCAGCTCTGAGGACTGCACCATTGCTGCTCCTTAGCTGCCAAGCCC 1620

1621 CATCCTGCCGCCCGAGGTGGCTGCCTGGAGCCCCACTGCCCTTCTCATTTGGAAACTAAA 1680

1681 ACTTCATCTTCCCCAAGTGCGGGGAGTACAAGGCATGGCGTAGAGGGTGCTGCCCCATGA 1740

1741 AGCCACAGCCCAGGCCTCCAGCTCAGCAGTGACTGTGGCCATGGTCCCCAAGACCTCTAT 1800

1801 ATTTGGTCTTTTATTTTTATGTCTAAAATCCTGCTTAAAACTTTTCAATAAACAAGATCG 1860

1861 TCAGGAAAAAAAAAAAA 1876
```

FIG. 2A

```
  1 CCAACCACAAGCACCAAAGCAGAGGGGCAGGCAGCACACCACCCAGCAGCCAGAGCACCA  60

61 GCCCAGCCATGGTCCTTGAGGTGAGTGACCACCAAGTGCTAAATGACGCCGAGGTTGCCG 120
  1           M  V  L  E  V  S  D  H  Q  V  L  N  D  A  E  V  A   18

121 CCCTCCTGGAGAACTTCAGCTCTTCCTATGACTATGGAGAAAACGAGAGTGACTCGTGCT 180
 18 A  L  L  E  N  F  S  S  S  Y  D  Y  G  E  N  E  S  D  S  C   38

181 GTACCTCCCCGCCCTGCCCACAGGACTTCAGCCTGAACTTCGACCGGGCCTTCCTGCCAG 240
 38 C  T  S  P  P  C  P  Q  D  F  S  L  N  F  D  R  A  F  L  P   58

241 CCCTCTACAGCCTCCTCTTTCTGCTGGGGCTGCTGGGCAACGGCGCGGTGGCAGCCGTGC 300
 58 A  L  Y  S  L  L  F  L  L  G  L  L  G  N  G  A  V  A  A  V   78

301 TGCTGAGCCGGCGGACAGCCCTGAGCAGCACCGACACCTTCCTGCTCCACCTAGCTGTAG 360
 78 L  L  S  R  R  T  A  L  S  S  T  D  T  F  L  L  H  L  A  V   98

361 CAGACACGCTGCTGGTGCTGACACTGCCGCTCTGGGCAGTGGACGCTGCCGTCCAGTGGG 420
 98 A  D  T  L  L  V  L  T  L  P  L  W  A  V  D  A  A  V  Q  W  118

421 TCTTTGGCTCTGGCCTCTGCAAAGTGGCAGGTGCCCTCTTCAACATCAACTTCTACGCAG 480
118 V  F  G  S  G  L  C  K  V  A  G  A  L  F  N  I  N  F  Y  A  138

481 GAGCCCTCCTGCTGGCCTGCATCAGCTTTGACCGCTACCTGAACATAGTTCATGCCACCC 540
138 G  A  L  L  L  A  C  I  S  F  D  R  Y  L  N  I  V  H  A  T  158

541 AGCTCTACCGCCGGGGGCCCCCGGCCCGCGTGACCCTCACCTGCCTGGCTGTCTGGGGGC 600
158 Q  L  Y  R  R  G  P  P  A  R  V  T  L  T  C  L  A  V  W  G  178

601 TCTGCCTGCTTTTCGCCCTCCCAGACTTCATCTTCCTGTCGGCCCACCACGACGAGCGCC 660
178 L  C  L  L  F  A  L  P  D  F  I  F  L  S  A  H  H  D  E  R  198

661 TCAACGCCACCCACTGCCAATACAACTTCCCACAGGTGGGCCGCACGGCTCTGCGGGTGC 720
198 L  N  A  T  H  C  Q  Y  N  F  P  Q  V  G  R  T  A  L  R  V  218

721 TGCAGCTGGTGGCTGGCTTTCTGCTGCCCCTGCTGGTCATGGCCTACTGCTATGCCCACA 780
218 L  Q  L  V  A  G  F  L  L  P  L  L  V  M  A  Y  C  Y  A  H  238
```

FIG. 2B

```
 781 TCCTGGCCGTGCTGCTGGTTTCCAGGGGCCAGCGGCGCCTGCGGGCCATGCGGCTGGTGG 840
 238 I   L   A   V   L   L   V   S   R   G   Q   R   R   L   R   A   M   R   L   V   258

841 TGGTGGTCGTGGTGGCCTTTGCCCTCTGCTGGACCCCCTATCACCTGGTGGTGCTGGTGG 900
 258 V   V   V   V   V   A   F   A   L   C   W   T   P   Y   H   L   V   V   L   V   278

901 ACATCCTCATGGACCTGGGCGCTTTGGCCCGCAACTGTGGCCGAGAAAGCAGGGTAGACG 960
 278 D   I   L   M   D   L   G   A   L   A   R   N   C   G   R   E   S   R   V   D   298

961 TGGCCAAGTCGGTCACCTCAGGCCTGGGCTACATGCACTGCTGCCTCAACCCGCTGCTCT 1020
 298 V   A   K   S   V   T   S   G   L   G   Y   M   H   C   C   L   N   P   L   L   318

1021 ATGCCTTTGTAGGGGTCAAGTTCCGGGAGCGGATGTGGATGCTGCTCTTGCGCCTGGGCT 1080
 318 Y   A   F   V   G   V   K   F   R   E   R   M   W   M   L   L   R   L   G   338

1081 GCCCCAACCAGAGAGGGCTCCAGAGGCAGCCATCGTCTTCCCGCCGGGATTCATCCTGGT 1140
 338 C   P   N   Q   R   G   L   Q   R   Q   P   S   S   S   R   R   D   S   S   W   358

1141 CTGAGACCTCAGAGGCCTCCTACTCGGGCTTGTGAGGCCGGAATCCGGGCTCCCCTTTCG 1200
 358 S   E   T   S   E   A   S   Y   S   G   L   *                               368

1201 CCCACAGTCTGACTTCCCCGCATTCCAGGCTCCTCCCTCCCTCTGCCGGCTCTGGCTCTC 1260

1261 CCCAATATCCTCGCTCCCGGGACTCACTGGCAGCCCCAGCACCACCAGGTCTCCCGGGAA 1320

1321 GCCACCCTCCCAGCTCTGAGGACTGCACCATTGCTGCTCCTTAGCTGCCAAGCCCCATCC 1380

1381 TGCCGCCCGAGGTGGCTGCCTGGAGCCCCACTGCCCTTCTCATTTGGAAACTAAAACTTC 1440

1441 ATCTTCCCCAAGTGCGGGGAGTACAAGGCATGGCGTAGAGGGTGCTGCCCCATGAAGCCA 1500

1501 CAGCCCAGGCCTCCAGCTCAGCAGTGACTGTGGCCATGGTCCCCAAGACCTCTATATTTG 1560

1561 CTCTTTTATTTTTATGTCTAAAATCCTGCTTAAAACTTTTCAATAAACAAGATCGTCAGG 1620

1621 ACCAAAAAAAAAAAAAAAAAAAAAAAAAAAAAAAAAAAAAAAAAAAAAA 1670
```

FIG. 3

```
 54 DHQVLNDAEVAALLENFSSSYDYGENESDSCCTSPPCPQDFSLNFDRAFL  103
    : :.::|   :. |.|:| |  ....   |......|.    ||::::  |:
  2 ESDSFEDFWKGEDLSNYSYSSTLPPFLLDAAPCEPE.....SLEINKYFV   46

104 PALYSLLFLLGLLGNGAVAAVLLSRRTALSSTDTFLLHLAVADTLLVLTL  153
    . : .|:|||:|||: |  |:| .|.: | ||.:||:||:|| |:.|||
 47 VIIYALVFLLSLLGNSLVMLVILYSRVGRSVTDVYLLNLALADLLFALTL   96

154 PLWAVDAAVQWVFGSGLCKVAGALFNINFYAGALLLACISFDRYLNIVHA  203
    |:||..  .|:||. ||||.: | ::|||.| ||||||.||||.||||
 97 PIWAASKVNGWIFGTFLCKVVSLLKEVNFYSGILLLACISVDRYLAIVHA  146

204 TQLYRRGPPARVTLTCLAVWGLCLLFALPDFIFLSAHHDERLNATHCQYN  253
    |. . .. |.:.||.:|||:||:||| ::|  .........:..::
147 TRTLTQ.KRYLVKFICLSIWGLSLLLALPVLLFRRTVYSSNVSPACYEDM  195

254 FPQVG..RTALRVLQLVAGFLLPLLVMAYCYAHILAVLLVSRGQRRLRAM  301
    ..: |  ||:|. ||::|||:| :||: .| .|: .: ..: |||
196 GNNTANWRMLLRILPQSFGFIVPLLIMLFCYGFTLRTLFKAHMGQKHRAM  245

302 RLVVVVVVAFALCWTPYHLVVLVDILMDLGALARNCGRESRVDVAKSVTS  351
    |::..||: | ||| ||:||:| |.||  ..:. .|:| .::| | ..|.
246 RVIFAVVLIFLLCWLPYNLVLLADTLMRTQVIQETCERRNHIDRALDATE  295

352 GLGYMHCCLNPLLYAFVGVKFRERMWMLLLRLGCPNQRGLQRQPSSSRRD  401
    ||.:|:||||||:|||.| |||. .:.:|   | .. :|.::...| :
296 ILGILHSCLNPLIYAFIGQKFRHGLLKILAIHGLISKDSLPKDSRPSFVG  345

402 SSWSETSEA  410
    ||.:.||..
346 SSSGHTSTT  254
```

FIG. 4

```
 25 SSYDYGENESDSCCTSPPCPQDFSLNFDRAFL          56
    |.|.|:..  ..   ...||..: ||::::  |:
 16 SNYSYSSTLPPFLLDAAPCEPE.SLEINKYFV          46

57 PALYSLLFLLGLLGNGAVAAVLLSRRTALSSTDTFLLHLAVADTLLVLTL  106
    . : .|:|||:||||: |  |:| .|.:  | ||.:||:||:||  |:.|||
 47 VIIYALVFLLSLLGNSLVMLVILYSRVGRSVTDVYLLNLALADLLFALTL   96

107 PLWAVDAAVQWVFGSGLCKVAGALFNINFYAGALLLACISFDRYLNIVHA  156
    |:||.. .  .|:||.  |||.:  |   ::|||.||  ||||||.||||.||||
 97 PIWAASKVNGWIFGTFLCKVVSLLKEVNFYSGILLLACISVDRYLAIVHA  146

157 TQLYRRGPPARVTLTCLAVWGLCLLFALPDFIFLSAHHDERLNATHCQYN  206
    |. . .  ..   |.:.||.:|||:||:|||  ::|   ..  ........::
147 TRTLTQ.KRYLVKFICLSIWGLSLLLALPVLLFRRTVYSSNVSPACYEDM  195

207 FPQVG..RTALRVLQLVAGFLLPLLVMAYCYAHILAVLLVSRGQRRLRAM  256
    ..:  |   ||:|.    ||::|||:|  :||: .| .|: .:  ..: |||
196 GNNTANWRMLLRILPQSFGFIVPLLIMLFCYGFTLRTLFKAHMGQKHRAM  245

257 RLVVVVVVAFALCWTPYHLVVLVDILMDLGALARNCGRESRVDVAKSVTS  306
    |::..||:  |  |||  ||:||:|  |.||  ...:  .|:|  ..::|  |  ..|
246 RVIFAVVLIFLLCWLPYNLVLLADTLMRTQVIQETCERRNHIDRALDATE  295

307 GLGYMHCCLNPLLYAFVGVKFRERMWMLLLRLGCPNQRGLQRQPSSSRRD  356
    ||.:|:|||||:|||:|  |||.  :::.:|   |    |   .. :|.::...|  :
296 ILGILHSCLNPLIYAFIGQKFRHGLLKILAIHGLISKDSLPKDSRPSFVG  345

357 SSWSETSEA     363
    ||..:.||..
346 SSSGHTSTT     354
```

HUMAN G-PROTEIN CHEMOKINE RECEPTOR HSATU68

CROSS REFERENCE TO RELATED APPLICATIONS

This application claims benefit under 35 U.S.C. §119(e) of U.S. Provisional Application No. 60/371, 725, filed Apr. 12, 2002, and is a continuation-in-part of U.S. Application Ser. No. 09/101,518, filed Dec. 21, 1998, now abandoned, which is the National Stage of International Application No. PCT/US96/00499, filed Jan. 11, 1996, all of which are hereby incorporated by reference in their entirety.

FIELD OF THE INVENTION

This invention relates to newly identified polynucleotides, polypeptides encoded by such polynucleotides, the use of such polynucleotides and polypeptides, as are vectors, host cells, and recombinant and synthetic methods for producing the same. More particularly, the polypeptides of the present invention are human 7-transmembrane receptors, which have been putatively identified as chemokine receptors, sometimes hereinafter referred to as "G-Protein Chemokine Receptor" or "HSATU68". The invention also relates to screening methods for identifying molecules that inhibit or activate the action of such polypeptides. The invention also relates to diagnostic and therapeutic methods using nucleic acid molecules and/or polypeptides of a G-protein chemokine receptor of the present invention.

BACKGROUND OF THE INVENTION

It is well established that many medically significant biological processes are mediated by proteins participating in signal transduction pathways that involve G-proteins and/or second messengers, e.g., cAMP (Lefkowitz, Nature, 351: 353-354 (1991)). Herein these proteins are referred to as proteins participating in pathways with G-proteins or PPG proteins. Some examples of these proteins include the GPC receptors, such as those for adrenergic agents and dopamine (Kobilka, B. K., et al., PNAS, 84:46-50 (1987); Kobilka, B. K., et al., Science, 238:650-656 (1987); Bunzow, J. R., et al., Nature, 336:783-787 (1988)), G-proteins themselves, effector proteins, e.g., phospholipase C, adenyl cyclase, and phosphodiesterase, and actuator proteins, e.g., protein kinase A and protein kinase C (Simon, M. I., et al., Science, 252:802-8 (1991)).

For example, in one form of signal transduction, the effect of hormone binding is activation of an enzyme, adenylate cyclase, inside the cell. Enzyme activation by hormones is dependent on the presence of the nucleotide GTP, and GTP also influences hormone binding. A G-protein connects the hormone receptors to adenylate cyclase. G-protein was shown to exchange GTP for bound GDP when activated by hormone receptors. The GTP-carrying form then binds to an activated adenylate cyclase. Hydrolysis of GTP to GDP, catalyzed by the G-protein itself, returns the G-protein to its basal, inactive form. Thus, the G-protein serves a dual role, as an intermediate that relays the signal from receptor to effector, and as a clock that controls the duration of the signal.

The membrane protein gene superfamily of G-protein coupled receptors has been characterized as having seven putative transmembrane domains. The domains are believed to represent transmembrane α-helices connected by extracellular or cytoplasmic loops. G-protein coupled receptors include a wide range of biologically active receptors, such as hormone, viral, growth factor and neuroreceptors.

G-protein coupled receptors have been characterized as including these seven conserved hydrophobic stretches of about 20 to 30 amino acids, connecting at least eight divergent hydrophilic loops. The G-protein family of coupled receptors includes dopamine receptors, which bind to neuroleptic drugs used for treating psychotic and neurological disorders. Other examples of members of this family include calcitonin, adrenergic, endothelin, cAMP, adenosine, muscarinic, acetylcholine, serotonin, histamine, thrombin, kinin, follicle stimulating hormone, opsins, endothelial differentiation gene-1 receptor and rhodopsins, odorant, cytomegalovirus receptors, etc.

G-protein coupled receptors can be intracellularly coupled by heterotrimeric G-proteins to various intracellular enzymes, ion channels and transporters (see, Johnson et al., Endoc. Rev., 10:317-331 (1989)). Different G-protein α-subunits preferentially stimulate particular effectors to modulate various biological functions in a cell. Phosphorylation of cytoplasmic residues of G-protein coupled receptors has been identified as an important mechanism for the regulation of G-protein coupling of some G-protein coupled receptors. G-protein coupled receptors are found in numerous sites within a mammalian host.

Chemokines, also referred to as intercrine cytokines, are a subfamily of structurally and functionally related cytokines. These molecules are 8-10 kd in size. In general, chemokines exhibit 20% to 75% homology at the amino acid level and are characterized by four conserved cysteine residues that form two disulfide bonds. Based on the arrangement of the first two cysteine residues, chemokines have been classified into two subfamilies, alpha and beta. In the alpha subfamily, the first two cysteines are separated by one amino acid and hence are referred to as the "C—X—C" subfamily. In the beta subfamily, the two cysteines are in an adjacent position and are, therefore, referred to as the "C—C" subfamily. Thus far, at least nine different members of this family have been identified in humans.

The intercrine cytokines exhibit a wide variety of functions. A hallmark feature is their ability to elicit chemotactic migration of distinct cell types, including monocytes, neutrophils, T lymphocytes, basophils and fibroblasts. Many chemokines have pro-inflammatory activity and are involved in multiple steps during an inflammatory reaction. These activities include stimulation of histamine release, lysosomal enzyme and leukotriene release, increased adherence of target immune cells to endothelial cells, enhanced binding of complement proteins, induced expression of granulocyte adhesion molecules and complement receptors, and respiratory burst. In addition to their involvement in inflammation, certain chemokines have been shown to exhibit other activities. For example, macrophage inflammatory protein 1 (MIP-1) is able to suppress hematopoietic stem cell proliferation, platelet factor-4 (PF-4) is a potent inhibitor of endothelial cell growth, Interleukin-8 (IL-8) promotes proliferation of keratinocytes, and GRO is an autocrine growth factor for melanoma cells.

In light of the diverse biological activities, it is not surprising that chemokines have been implicated in a number of physiological and disease conditions, including lymphocyte trafficking, wound healing, hematopoietic regulation and immunological disorders such as allergy, asthma and arthritis.

SUMMARY OF THE INVENTION

In accordance with one aspect of the present invention, there are provided novel mature receptor polypeptides as well as biologically active and diagnostically or therapeutically useful fragments, analogs and derivatives thereof. The receptor polypeptides of the present invention are of human origin. In a preferred aspect of the invention, the polypeptide of SEQ ID NO:4 is provided. In another aspect of the invention, the polypeptide of SEQ ID NO:2 is provided.

In accordance with another aspect of the present invention, there are provided isolated nucleic acid molecules encoding the receptor polypeptides of the present invention, including mRNAs, cDNAs, genomic DNA as well as antisense analogs thereof and biologically active and diagnostically or therapeutically useful fragments thereof. In a preferred aspect of the invention, nucleic acid molecules encoding the polypeptide of SEQ ID NO: 4 are provided. In another aspect of the invention, nucleic acid molecules encoding the polypeptide of SEQ ID NO:2 are provided.

In accordance with another aspect of the present invention there is provided an isolated nucleic acid molecule encoding a mature polypeptide expressed by the human cDNA contained in ATCC Deposit No. 97334.

In accordance with a further aspect of the present invention, there are provided processes for producing such receptor polypeptides by recombinant techniques comprising culturing recombinant prokaryotic and/or eukaryotic host cells, containing nucleic acid sequences encoding the receptor polypeptides of the present invention, under conditions promoting expression of said polypeptides and subsequent recovery of said polypeptides.

In accordance with yet a further aspect of the present invention, there are provided antibodies against such receptor polypeptides.

In accordance with another aspect of the present invention there are provided methods of screening for compounds that bind to and activate or inhibit activation of the receptor polypeptides of the present invention.

In accordance with still another embodiment of the present invention there are provided processes of administering compounds to a host which bind to and activate the receptor polypeptide of the present invention which are useful in stimulating haematopoiesis, wound healing, coagulation, angiogenesis, to treat tumors, chronic infections, leukemia, T-cell mediated auto-immune diseases, parasitic infections, psoriasis, and to stimulate growth factor activity.

In accordance with another aspect of the present invention there is provided a method of administering the receptor polypeptides of the present invention via gene therapy to treat conditions related to underexpression of the polypeptides or underexpression of a ligand for the receptor polypeptide.

In accordance with still another embodiment of the present invention there are provided processes of administering compounds to a host which bind to and inhibit activation of the receptor polypeptides of the present invention which are useful in the prevention and/or treatment of allergy, atherogenesis, anaphylaxis, malignancy, chronic and acute inflammation, histamine and IgE-mediated allergic reactions, prostaglandin-independent fever, bone marrow failure, silicosis, sarcoidosis, rheumatoid arthritis, shock and hypereosinophilic syndrome.

In accordance with yet another aspect of the present invention, there are provided nucleic acid probes comprising nucleic acid molecules of sufficient length to specifically hybridize to the polynucleotide sequences of the present invention.

In accordance with still another aspect of the present invention, there are provided diagnostic assays for detecting diseases related to mutations in the nucleic acid sequences encoding such polypeptides and for detecting an altered level of the soluble form of the receptor polypeptides.

In accordance with yet a further aspect of the present invention, there are provided processes for utilizing such receptor polypeptides, or polynucleotides encoding such polypeptides, for in vitro purposes related to scientific research, synthesis of DNA and manufacture of DNA vectors.

The present invention encompasses antibodies (including molecules comprising, or alternatively consisting of, antibody fragments or variants thereof) that specifically bind to a G-protein chemokine receptor polypeptide or polypeptide fragment or variant of a G-protein chemokine receptor. In particular, the invention encompasses antibodies (including molecules comprising, or alternatively consisting of, antibody fragments or variants thereof) that specifically bind to a polypeptide or polypeptide fragment or variant of human G-protein chemokine receptor. In a preferred aspect of the invention, such antibodies specifically bind to the polypeptide of SEQ ID NO:4. In an additional aspect of the invention, such antibodies specifically bind to the polypeptide of SEQ ID NO:4 expressed on the surface of a cell. In another aspect of the invention, antibodies of the present invention specifically bind to the polypeptide of SEQ ID NO:2.

The present invention relates to methods and compositions for preventing, treating or ameliorating a disease or disorder comprising administering to an animal, preferably a human, an effective amount of one or more antibodies or fragments or variants thereof, or related molecules, that specifically bind to a G-protein chemokine receptor or a fragment or variant thereof. In specific embodiments, the present invention relates to methods and compositions for preventing, treating or ameliorating a disease or disorder associated with the funtion of a G-protein chemokine receptor, the function of a ligand of a G-protein chemokine receptor, aberrant expression of a G-protein chemokine receptor, or abberant expression of a ligand of a G-protein chemokine receptor, comprising administering to an animal, preferably a human, an effective amount of one or more antibodies or fragments or variants thereof, or related molecules, that specifically bind to a G-protein chemokine receptor or a fragment or variant thereof. In highly preferred embodiments, the present invention relates to antibody-based methods and compositions for preventing, treating or ameliorating immune disorders. In highly preferred embodiments, the present invention encompasses methods and compositions for preventing, treating, or ameliorating lymphocyte-mediated immune disorders. In preferred embodiments, the antibodies of the invention may be used to prevent treat, or ameliorate a T-cell-mediated immune disorders. In preferred embodiments, the antibodies of the invention may be used to prevent treat, or ameliorate a B-cell-mediated immune disorders. In particular, the antibodies of the invention may be used to prevent treat, or ameliorate a lymphocyte-mediated autoimmune disorder (e.g. multiple sclerosis, Grave's disease, diabetes, or rheumatoid arthritis), inflammatory disorder (e.g., inflammatory bowel disease, asthma, allergic disorder, dermatitis, colitis, graft rejection), proliferative disorder (e.g. leukemia, T-cell lymphoma, B-cell lymphoma, prostate cancer, breast cancer, lung cancer, colon cancer, urinary cancer, non-Hodgkin's lymphoma, and renal cell carcinoma), and/or infectious disease (e.g., hepatitis infections, herpes simplex viral infections, and HIV infections).

The present invention also encompasses methods and compositions for detecting, diagnosing, or prognosing diseases or disorders comprising administering to an animal, preferably a human, an effective amount of one or more antibodies or fragments or variants thereof, or related molecules, that specifically bind to a G-protein chemokine receptor or a fragment or variant thereof. In specific embodiments, the present invention also encompasses methods and compositions for detecting, diagnosing, or prognosing diseases or disorders associated with the funtion of a G-protein chemokine receptor, the function of a ligand of a G-protein chemokine receptor, aberrant expression of a G-protein chemokine receptor, or abberant expression of a ligand of a G-protein chemokine receptor, comprising administering to an animal, preferably a human, an effective amount of one or more antibodies or fragments or variants thereof, or related molecules, that specifically bind to a G-protein chemokine receptor or a fragment or variant thereof. In highly preferred embodiments, the present invention relates to antibody-based methods and compositions for detecting, diagnosing, or prognosing a lymphocyte-mediated autoimmune disorder (e.g. multiple sclerosis, Grave's disease, diabetes, or rheumatoid arthritis), inflammatory disorder (e.g., inflammatory bowel disease, asthma, allergic disorder, dermatitis, colitis, graft rejection), proliferative disorder (e.g. leukemia, T-cell lymphoma, B-cell lymphoma, prostate cancer, breast cancer, lung cancer, colon cancer, urinary cancer, non-Hodgkin's lymphoma, and renal cell carcinoma), and/or infectious disease (e.g., hepatitis infections, herpes simplex viral infections, and HIV infections).

Another embodiment of the present invention includes the use of the antibodies of the invention as a diagnostic tool to monitor the expression of a G-protein chemokine receptor on cells.

The present invention also provides antibodies that bind one or more G-protein chemokine receptor polypeptides that are coupled to a detectable label, such as an enzyme, a fluorescent label, a luminescent label, or a bioluminescent label. The present invention also provides antibodies that bind one or more G-protein chemokine receptor polypeptides that are coupled to a therapeutic or cytotoxic agent. The present invention also provides antibodies that bind one or more G-protein chemokine receptor polypeptides that are coupled to a radioactive material.

The present invention also provides antibodies that bind one or more G-protein chemokine receptor polypeptides that act as either G-protein chemokine receptor agonists or G-protein chemokine receptor antagonists. In specific embodiments, the antibodies of the invention stimulate apoptosis of G-protein chemokine receptor expressing cells. In other specific embodiments, the antibodies of the invention inhibit ligand binding to a G-protein chemokine receptor. In other specific embodiments, the antibodies of the invention upregulate G-protein chemokine receptor expression.

The present invention also provides antibodies that downregulate G-protein chemokine receptor polypeptide expression. In still other specific embodiments, the anti-G-protein chemokine receptor polypeptide antibodies of the invention downregulate G-protein chemokine receptor polypeptide expression by promoting G-protein chemokine receptor polypeptide internalization.

The present invention further provides antibodies that inhibit or abolish the binding of the G-protein chemokine receptor ligand (e.g., IFN-gamma-induced monokine-2 (MIG; GenBank Acession Number X72755); IFN-inducible protein-10 (IP10; GenBank Acession Number X02530); interferon-inducible T cell-alpha chemoattractant (ITAC; GenBank Acession Number U59286)) to G-protein chemokine receptor expressing cells.

The present invention also provides for a nucleic acid molecule(s), generally isolated, encoding an antibody (including molecules, such as scFvs, VH domains, or VL domains, that comprise, or alternatively consist of, an antibody fragment or variant thereof) of the invention. The present invention also provides a host cell transformed with a nucleic acid molecule encoding an antibody (including molecules, such as scFvs, VH domains, or VL domains, that comprise, or alternatively consist of, an antibody fragment or variant thereof) of the invention and progeny thereof. The present invention also provides a method for the production of an antibody (including a molecule comprising, or alternatively consisting of, an antibody fragment or variant thereof) of the invention. The present invention further provides a method of expressing an antibody (including a molecule comprising, or alternatively consisting of, an antibody fragment or variant thereof) of the invention from a nucleic acid molecule. These and other aspects of the invention are described in further detail below.

These and other aspects of the present invention should be apparent to those skilled in the art from the teachings herein.

BRIEF DESCRIPTION OF THE DRAWINGS

The following drawings are illustrative of embodiments of the invention and are not meant to limit the scope of the invention as encompassed by the claims.

FIGS. 1A-B shows the cDNA sequence (SEQ ID NO: 1) and the corresponding deduced amino acid sequence (SEQ ID NO: 2) of a G-protein chemokine receptor of the present invention. The standard one-letter abbreviation for amino acids is used. Sequencing was performed using a 373 Automated DNA sequencer (Applied Biosystems, Inc.).

FIGS. 2A-B shows the cDNA sequence (SEQ ID NO: 3) and the corresponding deduced amino acid sequence of a G-protein chemokine receptor (SEQ ID NO: 4) of the present invention. The standard one-letter abbreviation for amino acids is used.

FIG. 3 illustrates an amino acid alignment of a G-protein chemokine receptor of the present invention (top) (SEQ ID NO:2) and the human interleukin-8 receptor beta (bottom) (SEQ ID NO:11).

FIG. 4 illustrates an amino acid alignment of a G-protein chemokine receptor of the present invention (top) (SEQ ID NO:4) and the human interleukin-8 receptor beta (bottom) (SEQ ID NO:11).

Figure 5:
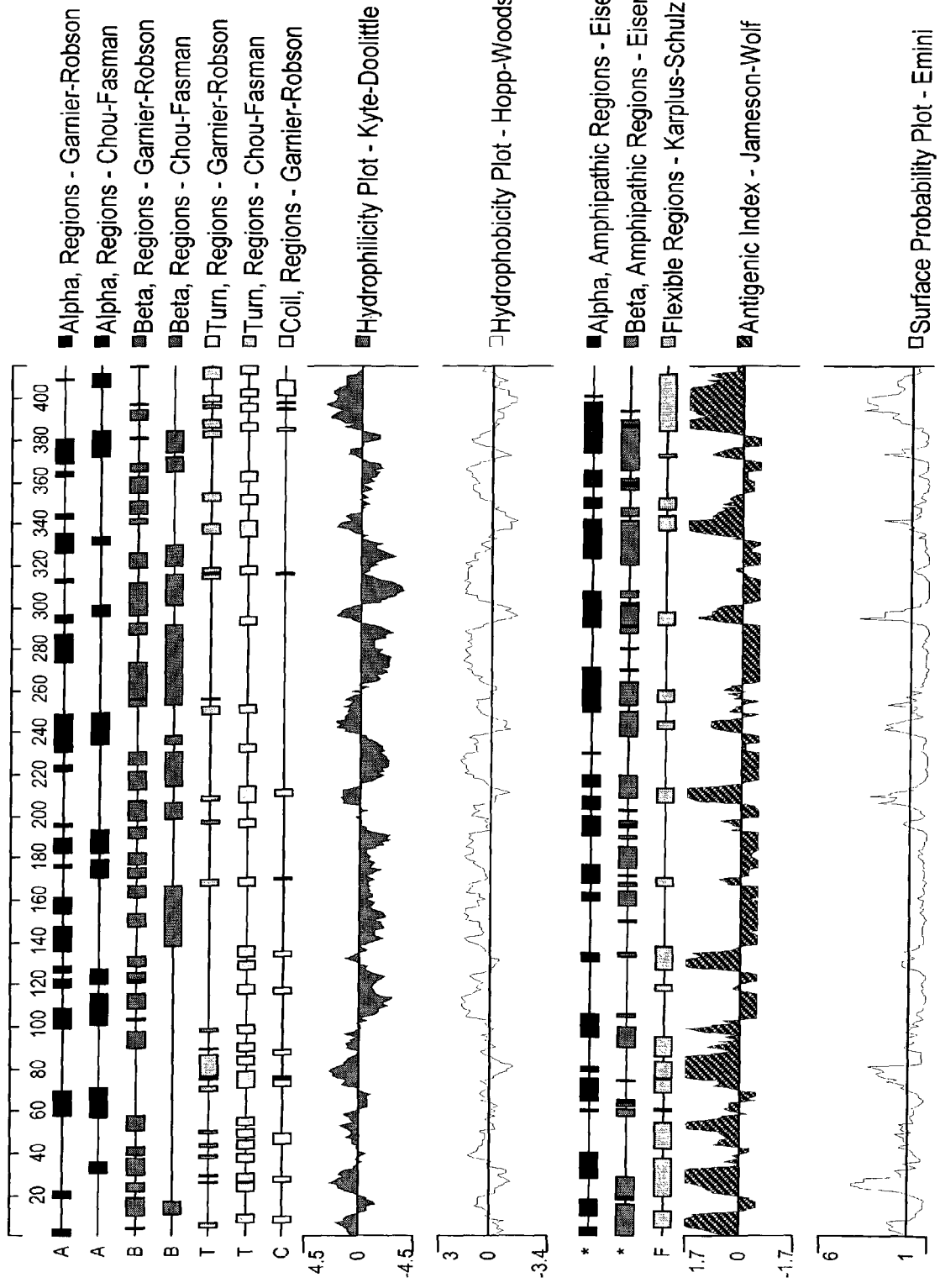
FIG. 5 shows an analysis of the amino acid sequence of a G-protein chemokine receptor of the present invention (SEQ ID NO:2). Alpha, beta, turn and coil regions; hydrophilicity; amphipathic regions; flexible regions; antigenic index and surface probability are shown. In the "Antigenic Index—Jameson-Wolf" graph, amino acid residues 4 to 8, 25 to 31, 51 to 54, 75 to 85, 127 to 131, 208 to 213, 336 to 341, 385 to 389, and 394 to 405 in FIG. 1 (SEQ ID NO:2) correspond to the shown highly antigenic regions of a G-protein chemokine receptor protein.

(SEQ ID NO:4) correspond to the shown highly antigenic regions of the G-protein chemokine receptor protein.

DETAILED DESCRIPTION

The present invention provides isolated nucleic acid molecules comprising a polynucleotide encoding a G-protein chemokine receptor polypeptide. In a preferred aspect of the invention, nucleic acid molecules encoding the polypeptide of SEQ ID NO:4 are provided. In another aspect of the invention, nucleic acid molecules encoding the polypeptide of SEQ ID NO:2 are provided.

Nucleic Acid Molecules

In accordance with a preferred aspect of the present invention, there is provided an isolated nucleic acid (polynucleotide) which encodes for the mature polypeptide having the deduced amino acid sequence of FIG. 2 (SEQ ID NO:4).

In accordance with an aspect of the present invention, there is provided an isolated nucleic acid (polynucleotide) which encodes for the mature polypeptide having the deduced amino acid sequence of FIG. 1 (SEQ ID NO:2).

In accordance with another aspect of the present invention there are provided isolated polynucleotides encoding a mature polypeptide expressed by the human cDNA contained in ATCC Deposit No. 97334, deposited with the American Type Culture Collection, 10801 University Boulevard, Manassas, Va. 20110-2209, USA, on Nov. 6, 1995. The deposited material is a cDNA insert, encoding a polypeptide of the present invention, cloned into a pBluescript SK(−) vector (Stratagene, La Jolla, Calif.), which will confer ampicillin resistance upon transformation.

The deposit(s) has been made under the terms of the Budapest Treaty on the International Recognition of the Deposit of Micro-organisms for purposes of Patent Procedure. The strain will be irrevocably and without restriction or condition released to the public upon the issuance of a patent. These deposits are provided merely as convenience to those of skill in the art and are not an admission that a deposit is required under 35 U.S.C. §112. The sequence of the polynucleotides contained in the deposited materials, as well as the amino acid sequence of the polypeptides encoded thereby, are incorporated herein by reference and are controlling in the event of any conflict with any description of sequences herein. A license may be required to make, use or sell the deposited materials, and no such license is hereby granted.

Polynucleotides of this invention were discovered in a human genomic library derived from human activated T cells. The polynucleotides of the invention are structurally related to the G protein-coupled receptor family. They include polynucleotides having open reading frames encoding a protein of 415 amino acid residues (SEQ ID NO:2), or preferably 368 amino acid residues (SEQ ID NO:4). The proteins exhibit homology at the amino acid level to a human interleukin-8 receptor beta (PCT application No. WO/9306229) as shown in FIG. 3 and FIG. 4.

A polynucleotide of the present invention may be in the form of RNA or in the form of DNA, which DNA includes cDNA, genomic DNA, and synthetic DNA. The DNA may be double-stranded or single-stranded, and if single stranded may be the coding strand or non-coding (anti-sense) strand. The coding sequence which encodes the mature polypeptide may be identical to the coding sequence shown in FIG. 1 (SEQ ID NO:1) which coding sequence, as a result of the redundancy or degeneracy of the genetic code, encodes the same mature polypeptide as the DNA of FIG. 1 (SEQ ID NO:1). In a preferred aspect of the invention, the coding sequence which encodes the mature polypeptide may also be identical to the coding sequence shown in FIG. 2 (SEQ ID NO: 3) which coding sequence, as a result of the redundancy or degeneracy of the genetic code, encodes the same mature polypeptide as the DNA of FIG. 2 (SEQ ID NO:3).

A polynucleotide which encodes for the mature polypeptide of FIG. 1 (SEQ ID NO: 2) or FIG. 2 (SEQ ID NO:4) may include: only the coding sequence for the mature polypeptide; the coding sequence for the mature polypeptide and additional coding sequence such as a transmembrane (TM) or intracellular domain; the coding sequence for the mature polypeptide (and optionally additional coding sequence) and non-coding sequence, such as introns or non-coding sequence 5' and/or 3' of the coding sequence for the mature polypeptide.

The present invention further relates to variants of the hereinabove described polynucleotides which encode for fragments, analogs and derivatives of the polypeptide having the deduced amino acid sequence of FIG. 1 (SEQ ID NO:2) or more preferably FIG. 2 (SEQ ID NO:4). The variant of the polynucleotide may be a naturally occurring allelic variant of the polynucleotide or a non-naturally occurring variant of the polynucleotide.

Thus, the present invention includes polynucleotides encoding the same mature polypeptide as shown in FIG. 1 (SEQ ID NO:2) or more preferably FIG. 2 (SEQ ID NO: 4) as well as variants of such polynucleotides which variants encode for a fragment, derivative or analog of the polypeptide of FIG. 1 (SEQ ID NO:2) or more preferably FIG. 2 (SEQ ID NO:4). Such nucleotide variants include deletion variants, substitution variants and addition or insertion variants.

As hereinabove indicated, the polynucleotide may have a coding sequence which is a naturally occurring allelic variant of the coding sequence shown in FIG. 1 (SEQ ID NO:1) or more preferably FIG. 2 (SEQ ID NO:3). As known in the art, an allelic variant is an alternate form of a polynucleotide sequence that may have a substitution, deletion or addition of one or more nucleotides, which does not substantially alter the function of the encoded polypeptide.

The polynucleotides may also encode for a soluble form of the G-protein chemokine receptor polypeptide, which is an extracellular portion of the polypeptide that has been cleaved from the TM and intracellular domains of the full-length polypeptide of the present invention.

The polynucleotides of the present invention may also have the coding sequence fused in frame to a marker sequence that allows for purification of the polypeptide of the present invention. The marker sequence may be a hexa-histidine tag supplied by a pQE vector (Qiagen) to provide for purification of the mature polypeptide fused to the marker in the case of a bacterial host, or, for example, the marker sequence may be a hemagglutinin (HA) tag when a mammalian host, e.g. COS-7 cells, is used. The HA tag corresponds to an epitope derived from the influenza hemagglutinin protein (Wilson, I., et al., Cell, 37:767 (1984)).

The term "gene" means the segment of DNA involved in producing a polypeptide chain; it includes regions preceding and following the coding region (leader and trailer) as well as intervening sequences (introns) between individual coding segments (exons).

Fragments of the full-length gene of the present invention may be used as a hybridization probe for a cDNA library to isolate the full-length cDNA and to isolate other cDNAs that have a high sequence similarity to the gene or similar biological activity. Probes of this type preferably have at least 15 bases, preferably 30 bases and most preferably, may contain, for example, 50 or more bases. The probe may also be used to identify a cDNA clone corresponding to a full-length transcript and a genomic clone or clones that contain the complete gene including regulatory and promotor regions, exons, and introns. An example of a screen comprises isolating the coding region of the gene by using the known DNA sequence to synthesize an oligonucleotide probe. Labeled oligonucleotides having a sequence complementary to that of the gene of the present invention are used to screen a library of human cDNA, genomic DNA or mRNA to determine which members of the library the probe hybridizes to.

The present invention further relates to polynucleotides that hybridize to the hereinabove-described sequences if there is at least 70%, preferably at least 90%, and more preferably at least 95% identity between the sequences. The present invention particularly relates to polynucleotides that hybridize under stringent conditions to the hereinabove-described polynucleotides. As herein used, the term "stringent conditions" means hybridization will occur only if there is at least 95% and preferably at least 97% identity between the sequences. The polynucleotides which hybridize to the hereinabove described polynucleotides in a preferred embodiment encode polypeptides which either retain substantially the same biological function or activity as the mature polypeptide encoded by the cDNA of FIG. 1 (SEQ ID NO:1), or more preferably, the same biological function or activity as the mature polypeptide encoded by the cDNA of FIG. 2 (SEQ ID NO:3).

Alternatively, the polynucleotide may have at least 15 bases, preferably 30 bases, and more preferably at least 50 bases which hybridize to a polynucleotide of the present invention and which has an identity thereto, as hereinabove described, and which may or may not retain activity. For example, such polynucleotides may be employed as probes for the polynucleotide of SEQ ID NO:1 or SEQ ID NO:3, for example, for recovery of the polynucleotide or as a diagnostic probe or as a PCR primer.

The determined nucleotide sequence of a G-protein chemokine receptor cDNA of (FIG. 1) SEQ ID NO:1 contains an open reading frame encoding a protein of about 415 amino acid residues. The amino acid sequence of a predicted mature G-protein Chemokine Receptor receptor is shown in SEQ ID NO:2 from amino acid residue about 1 to residue about 368.

The determined nucleotide sequence of another G-protein chemokine receptor cDNA of (FIG. 2) SEQ ID NO:3 contains an open reading frame encoding a protein of about 368 amino acid residues. The amino acid sequence of the predicted mature G-protein Chemokine Receptor receptor is shown in SEQ ID NO:4 from amino acid residue about 1 to residue about 368.

By "isolated" nucleic acid molecule(s) is intended a nucleic acid molecule, DNA or RNA, which has been removed from its native environment. For example, recombinant DNA molecules contained in a vector are considered isolated for the purposes of the present invention. Further examples of isolated DNA molecules include recombinant DNA molecules maintained in heterologous host cells or purified (partially or substantially) DNA molecules in solution. Isolated RNA molecules include in vivo or in vitro RNA transcripts of the DNA molecules of the present invention. Isolated nucleic acid molecules according to the present invention further include such molecules produced synthetically. However, a nucleic acid molecule contained in a clone that is a member of a mixed clone library (e.g., a genomic or cDNA library) and that has not been isolated from other clones of the library (e.g., in the form of a homogeneous solution containing the clone without other members of the library) or a chromosome isolated or removed from a cell or a cell lysate (e.g., a "chromosome spread", as in a karyotype), is not "isolated" for the purposes of this invention.

Isolated nucleic acid molecules of the present invention include DNA molecules comprising an open reading frame (ORF) shown in FIG. 1 (SEQ ID NO:1), and DNA molecules comprising the coding sequence for the complete (full-length) and/or mature G-protein Chemokine Receptor protein shown in FIG. 1 (SEQ ID NO:2); more preferably, DNA molecules comprising an open reading frame (ORF) shown in FIG. 2 (SEQ ID NO:3), and DNA molecules comprising the coding sequence for the complete (full-length) and/or mature G-protein Chemokine Receptor protein shown in FIG. 2 (SEQ ID NO:4); and DNA molecules which comprise a sequence substantially different from those described above, but which, due to the degeneracy of the genetic code, still encode the G-protein Chemokine Receptor protein. Of course, the genetic code is well known in the art. Thus, it would be routine for one skilled in the art to generate such degenerate variants.

The invention further provides an isolated nucleic acid molecule having the nucleotide sequence shown in FIG. 1 (SEQ ID NO:1), more preferably the nucleotide sequence shown in FIG. 2 (SEQ ID NO:3), or a nucleic acid molecule having a sequence complementary thereto. Such isolated molecules, particularly DNA molecules, are useful, for example, as probes for gene mapping by in situ hybridization with chromosomes, and for detecting expression of the G-protein Chemokine Receptor gene in human tissue, for instance, by Northern blot analysis.

The present invention is further directed to fragments of the isolated nucleic acid molecules described herein. By a fragment of an isolated DNA molecule having the nucleotide sequence of the nucleotide sequence shown in FIG. 1 (SEQ ID NO:1) or more preferably FIG. 2 (SEQ ID NO:3) is intended DNA fragments at least about 15 nt, and more preferably at least about 20 nt, at least about 24 nt, still more preferably at least about 30 nt, and even more preferably, at least about 40 nt, at least about 50 nt, at least about 100 nt, at least about 150 nt, at least about 200 nt, at least about 250 nt, at least about 300 nt in length which are useful, for example, as diagnostic probes and primers as discussed herein. Of course, larger fragments 350-1500 nt in length are also useful according to the present invention, as are fragments corresponding to most, if not all, of the nucleotide sequence as shown in FIG. 1 (SEQ ID NO:1), the nucleotide sequence shown in FIG. 2 (SEQ ID NO:3), or the complementary strand thereto. By a fragment at least 20 nt in length, for example, is intended fragments which include 20 or more contiguous bases from the nucleotide sequence of the nucleotide sequence as shown in FIG. 1 (SEQ ID NO:1) or FIG. 2 (SEQ ID NO:3). In this context "about" includes the particularly recited size, larger or smaller by several (5, 4, 3, 2, or 1) nucleotides, at either terminus or at both termini.

Preferably, the polynucleotide fragments of the invention encode polypeptides that demonstrate a G-protein Chemokine Receptor functional activity. By a polypeptide demonstrating a G-protein Chemokine Receptor "functional activity" is meant, a polypeptide capable of displaying one or more known functional activities associated with a full-length (complete) G-protein Chemokine Receptor protein. Such functional activities include, but are not limited to, biological activity (e.g., ability to mediate chemotaxis induced by G-protein Chemokin Receptor ligands (e.g. MIG (GenBank Acession Number X72755), IP-10 (GenBank Acession Number X02530), or ITAC (GenBank Acession Number U59286)), antigenicity (ability to bind or compete with a G-protein Chemokine Receptor polypeptide for binding to an anti-G-protein Chemokine Receptor antibody), immunogenicity (ability to generate antibody which binds to a G-protein Chemokine Receptor polypeptide), ability to form multimers with G-protein Chemokine Receptor polypeptides of the invention, and ability to bind to a receptor or ligand for a G-protein Chemokine Receptor polypeptide.

The functional activity of G-protein Chemokine Receptor polypeptides, and fragments, variants derivatives, and analogs thereof, can be assayed by various methods.

For example, in one embodiment where one is assaying for the ability to bind or compete with full-length G-protein Chemokine Receptor polypeptides for binding to anti-G-protein Chemokine Receptor antibody various immunoassays known in the art can be used, including but not limited to, competitive and non-competitive assay systems using techniques such as radioimmunoassays, ELISA (enzyme linked immunosorbent assay), "sandwich" immunoassays, immunoradiometric assays, gel diffusion precipitation reactions, immunodiffusion assays, in situ immunoassays (using colloidal gold, enzyme or radioisotope labels, for example), western blots, precipitation reactions, agglutination assays (e.g., gel agglutination assays, hemagglutination assays), complement fixation assays, immunofluorescence assays, protein A assays, and immunoelectrophoresis assays, etc. In one embodiment, antibody binding is detected by detecting a label on the primary antibody. In another embodiment, the primary antibody is detected by detecting binding of a secondary antibody or reagent to the primary antibody. In a further embodiment, the secondary antibody is labeled. Many means are known in the art for detecting binding in an immunoassay and are within the scope of the present invention.

In another embodiment, where a G-protein Chemokine Receptor ligand is identified (e.g., MIG, P-10 and ITAC), or the ability of a polypeptide fragment, variant or derivative of the invention to multimerize is being evaluated, binding can be assayed, e.g., by means well-known in the art, such as, for example, reducing and non-reducing gel chromatography, protein affinity chromatography, and affinity blotting. See generally, Phizicky, E., et al., *Microbiol Rev.* 59:94-123 (1995). In another embodiment, physiological correlates of G-protein Chemokine Receptor binding to its ligands (signal transduction) can be assayed (e.g. calcium flux assays).

In addition, assays described herein (and otherwise known in the art may routinely be applied to measure the ability of G-protein Chemokine Receptor polypeptides and fragments, variants derivatives and analogs thereof to elicit G-protein Chemokine Receptor related biological activity. For example, techniques described herein and otherwise known in the art may be applied or routinely modified to assay for the ability of the compositions of the invention to inhibit or stimulate Th1 cell migration (e.g., MIG-ITAC- or IP-10-mediated Th1 cell migration).

Other methods will be known to the skilled artisan and are within the scope of the invention.

Highly preferred nucleic acid fragments of the present invention include nucleic acid molecules encoding a member selected from the group: a polypeptide comprising or alternatively, consisting of, the G-protein Chemokine Receptor receptor extracellular domains; a polypeptide comprising, or alternatively consisting of, the G-protein Chemokine Receptor extracellular regions (amino acid residues from about 1 to about 59, about 114 to about 127, about 191 to about 223, and about 278 to about 307 in FIG. 2 (SEQ ID NO:4); a polypeptide comprising, or alternatively consisting of the G-protein Chemokine Receptor transmembrane domains (amino acid residues from about 60 to about 79, about 92 to about 113, about 128 to about 147, about 170 to about 190, about 224 to about 245, about 259 to about 277, and about 302 to about 322 in FIG. 2 (SEQ ID NO: 4)); and/or a polypeptide comprising, or alternatively consisting of, the G-protein Chemokine Receptor intracellular domain (amino acid residues from about 80 to about 91, about 148 to about 169, about 246 to about 258, and about 323 to about 368 in FIG. 2 (SEQ ID NO:4)). The location of these domains has been predicted by computer analysis, and one of ordinary skill would appreciate that the amino acid residues constituting these domains may vary slightly (e.g., by about 1 to 15 amino acid residues) depending on the criteria used to define each domain.

Preferred nucleic acid fragments of the invention encode full-length G-protein Chemokine Receptor polypeptides lacking the nucleotides encoding the amino terminal methionine in FIG. 1 (SEQ ID NO:1) or FIG. 2 (SEQ ID NO:3), as it is known that the methionine is cleaved naturally and such sequences may be useful in genetically engineering G-protein Chemokine Receptor expression vectors. Polypeptides encoded by such polynucleotides are also contemplated by the invention.

Preferred nucleic acid fragments of the present invention further include nucleic acid molecules encoding epitope-bearing portions of the G-protein Chemokine Receptor receptor proteins. In particular, such nucleic acid fragments of the present invention include nucleic acid molecules encoding: a polypeptide comprising amino acid residues from about 4 to about 8 in FIG. 1 (SEQ ID NO:2); a polypeptide comprising amino acid residues from about 25 to about 31 in FIG. 1 (SEQ ID NO:2); a polypeptide comprising amino acid residues from about 51 to about 54 in FIG. 1 (SEQ ID NO:2); a polypeptide comprising amino acid residues from about 75 to about 85 in FIG. 1 (SEQ ID NO: 2); a polypeptide comprising amino acid residues from about 127 to about 131 in FIG. 1 (SEQ ID NO:2); a polypeptide comprising amino acid residues from about 208 to about 213 in FIG. 1 (SEQ ID NO:2); a polypeptide comprising amino acid residues from about 336 to about 341 in FIG. 1 (SEQ ID NO:2); a polypeptide comprising amino acid residues from about 385 to about 389 in FIG. 1 (SEQ ID NO:2); and a polypeptide comprising amino acid residues from about 394 to about 405 in FIG. 1 (SEQ ID NO:2). More preferred nucleic acid fragments of the present invention include nucleic acid molecules encoding: a polypeptide comprising amino acid residues from about 28 to about 38 in FIG. 2 (SEQ ID NO:4); a polypeptide comprising amino acid residues from about 80 to about 84 in FIG. 2 (SEQ ID NO:4); a polypeptide comprising amino acid residues from about 161 to about 166 in FIG. 2 (SEQ ID NO:4); a polypeptide comprising amino acid residues from about 289 to about 294 in FIG. 2 (SEQ ID NO:4); a polypeptide comprising amino acid residues from about 338 to about 342 in FIG. 2 (SEQ ID NO:4); and a polypeptide comprising amino acid residues from about 347 to about 358 in FIG. 2 (SEQ ID NO:4). In this context, the above polypeptide fragments have been determined to be antigenic regions of the G-protein Chemokine Receptor proteins. Methods for determining other such epitope-bearing portions of the G-protein Chemokine Receptor proteins are described in detail below.

It is believed that the extracellular domains of G-protein Chemokine Receptor are important for interactions between G-protein Chemokine Receptor and its ligands (e.g., MIG, ITAC, IP-10). Accordingly, specific embodiments of the invention are directed to polynucleotides encoding these domains. In a specific embodiment the polynucleotides encoding G-protein Chemokine Receptor polypeptides of the invention comprise, or alternatively consist of one or more of the extracellular domains. Polypeptides encoded by these polynucleotides are also encompassed by the invention.

In additional embodiments, the polynucleotides of the invention encode functional attributes of G-protein Chemokine Receptor. Preferred embodiments of the invention in this regard include fragments that comprise alpha-helix and alpha-helix forming regions ("alpha-regions"), beta-sheet and beta-sheet forming regions ("beta-regions"), turn and turn-forming regions ("turn-regions"), coil and coil-forming regions ("coil-regions"), hydrophilic regions, hydrophobic regions, alpha amphipathic regions, beta amphipathic regions, flexible regions, surface-forming regions and high antigenic index regions of G-protein Chemokine Receptor.

Figure 6:
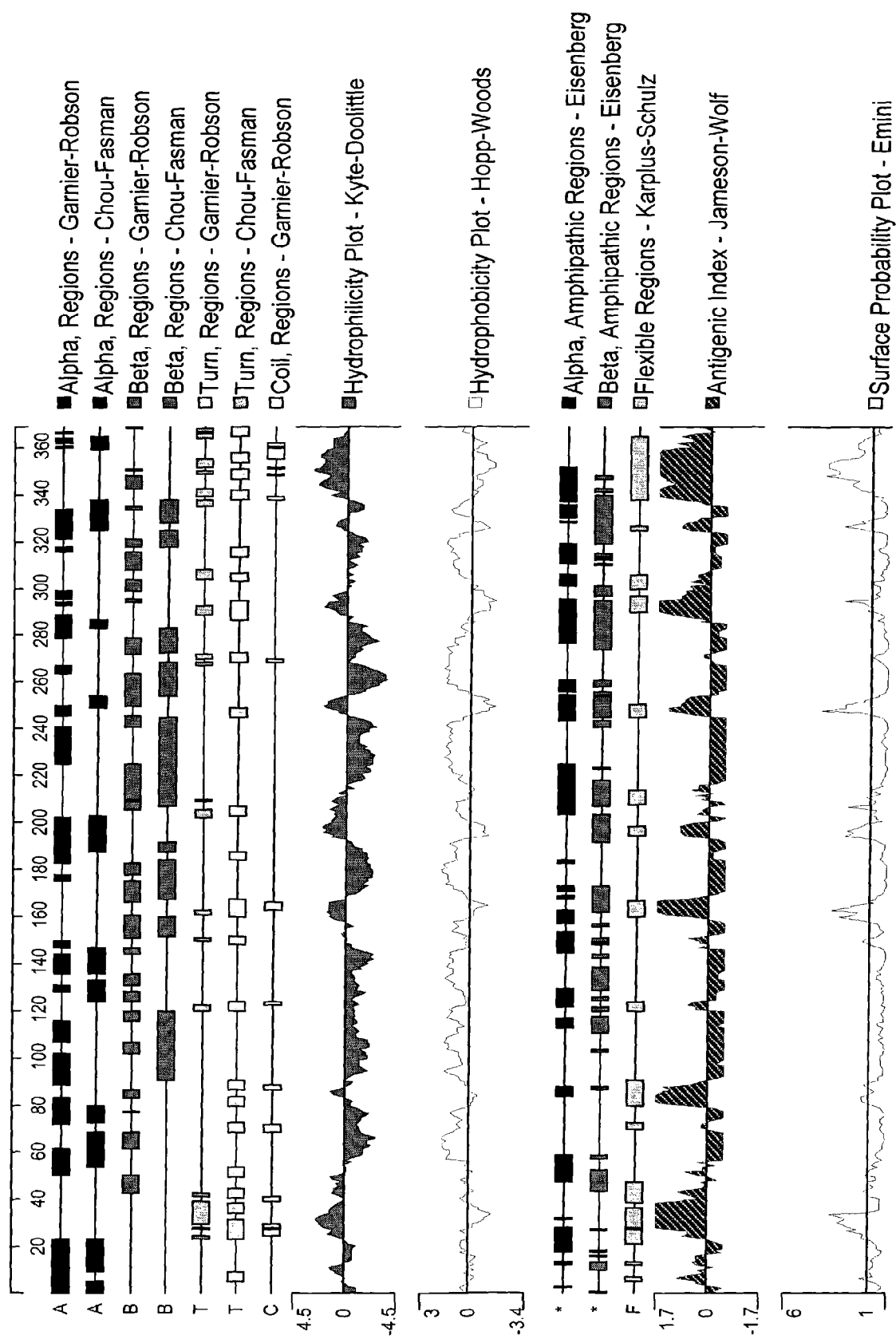
FIG. 6 shows an analysis of the amino acid sequence of a G-protein chemokine receptor of the present invention (SEQ ID NO:4). Alpha, beta, turn and coil regions; hydrophilicity; amphipathic regions; flexible regions; antigenic index and surface probability are shown. In the "Antigenic Index—Jameson-Wolf" graph, amino acid residues 28 to 38, 80 to 84, 161 to 166, 289 to 294, 338 to 342, and 347 to 358 in FIG. 2

The data representing the structural or functional attributes of G-protein Chemokine Receptors are set forth in FIG. 5, FIG. 6, Table I, and/or Table II, as described above, was generated using the various modules and algorithms of the DNA*STAR set on default parameters. In a preferred embodiment, the data presented in columns VIII, XI, XIII and XIV of Table I can be used to determine regions of G-protein Chemokine Receptor that exhibit a high degree of potential for antigenicity (column VIII of Table I represents hydrophilicity according to Kite-Doolittle; column IX of Table I represents hydrophobic according to Hop-Woods; column XIII of Table I represents antigenic index according to Jameson-Wolf; and column XIV of Table I represents surface probability according to Gemini). Regions of high antigenicity are determined from the data presented in columns VIII, XI, XIII and/or XIV by choosing values that represent regions of the polypeptide which are likely to be exposed on the surface of the polypeptide in an environment in which antigen recognition may occur in the process of initiation of an immune response.

Certain preferred regions in these regards are set out in FIG. 5 and FIG. 6, but may, as shown in Table I and Table II, be represented or identified by using tabular representations of the data presented in FIG. 5 or FIG. 6, respectively. The DNA*STAR computer algorithm used to generate FIG. 5 and FIG. 6 (set on the original default parameters) was used to present the data in FIG. 5 and FIG. 6 in a tabular format (See Table I and II, respectively). The tabular format of the data in FIG. 5 and FIG. 6 may be used to easily determine specific boundaries of a preferred region.

The above-mentioned preferred regions set out in FIG. 5, FIG. 6, Table I and in Table II, include, but are not limited to, regions of the aforementioned types identified by analysis of the amino acid sequences set out in FIG. 1 and FIG. 2. As set out in FIG. 5, FIG. 6, Table I, and in Table II, such preferred regions include Garner-Robson alpha-regions (Column I), beta-regions (Column III), turn-regions (Column V), and coil-regions (Column VII), Chou-Farman alpha-regions (Column II), beta-regions (Column IV), and turn-regions (Column VI), Kite-Doolittle hydrophilic regions (Column VIII), Hop-Woods hydrophobic regions (Column IX), Eisenberg alpha- (Column X) and beta- (Column XI) amphipathic regions, Karl's-Schulz flexible regions (Column XII), Jameson-Wolf regions of high antigenic index (Column XIII) and Gemini surface-forming regions (Column XIV).

TABLE I

| Res | Position | I | II | III | IV | V | VI | VII | VIII | IX | X | XI | XII | XIII | XIV |
|---|---|---|---|---|---|---|---|---|---|---|---|---|---|---|---|
| Met | 1 | A | . | . | . | . | . | . | 0.69 | −0.41 | * | * | . | 0.65 | 1.04 |
| Glu | 2 | A | . | . | . | . | . | . | 0.83 | −0.84 | * | * | . | 0.95 | 1.62 |
| Leu | 3 | A | . | . | . | . | . | . | 0.88 | −0.51 | * | * | . | 1.25 | 1.99 |
| Arg | 4 | . | . | B | . | . | . | . | 1.06 | −0.51 | * | * | . | 1.55 | 1.99 |
| Lys | 5 | . | . | . | . | T | . | . | 1.10 | −0.70 | . | * | F | 2.40 | 1.78 |
| Tyr | 6 | . | . | . | . | T | . | . | 1.81 | −0.27 | . | * | F | 2.40 | 2.13 |
| Gly | 7 | . | . | . | . | . | T | C | 1.00 | −0.96 | . | * | F | 3.00 | 2.13 |
| Pro | 8 | . | . | . | . | . | T | C | 1.22 | −0.27 | . | * | F | 2.25 | 0.88 |
| Gly | 9 | . | . | . | . | . | T | C | 0.77 | 0.23 | . | * | F | 1.35 | 0.57 |
| Arg | 10 | . | . | B | . | . | T | . | 0.41 | −0.10 | * | * | F | 1.45 | 0.57 |
| Leu | 11 | . | . | B | B | . | . | . | −0.20 | −0.04 | * | * | F | 0.75 | 0.53 |
| Ala | 12 | . | . | B | B | . | . | . | −0.74 | 0.17 | * | * | F | −0.15 | 0.40 |
| Gly | 13 | . | . | B | B | . | . | . | −0.88 | 0.43 | * | * | . | −0.60 | 0.14 |
| Thr | 14 | . | . | B | B | . | . | . | −0.88 | 0.86 | * | * | . | −0.60 | 0.17 |
| Val | 15 | . | . | B | B | . | . | . | −1.58 | 0.60 | * | * | . | −0.60 | 0.17 |
| Ile | 16 | . | . | B | B | . | . | . | −1.36 | 0.60 | * | . | . | −0.60 | 0.17 |
| Gly | 17 | . | . | B | . | . | . | . | −0.77 | 0.67 | * | . | . | −0.40 | 0.12 |
| Gly | 18 | . | . | B | . | . | . | . | −0.72 | 0.59 | . | * | . | −0.40 | 0.28 |
| Ala | 19 | A | . | . | . | . | . | . | −0.37 | 0.33 | . | . | . | −0.10 | 0.53 |
| Ala | 20 | A | . | . | . | . | . | . | 0.19 | −0.36 | . | * | F | 0.80 | 1.07 |
| Gln | 21 | A | . | . | . | . | . | . | 1.08 | −0.40 | . | * | F | 0.80 | 1.46 |
| Ser | 22 | . | . | B | . | . | T | . | 1.11 | −0.43 | . | * | F | 1.00 | 2.49 |
| Lys | 23 | . | . | B | . | . | T | . | 1.50 | −0.44 | . | * | F | 1.00 | 3.56 |
| Ser | 24 | . | . | B | . | . | T | . | 1.79 | −0.94 | . | * | F | 1.30 | 4.12 |
| Gln | 25 | . | . | B | . | . | T | . | 2.38 | −0.96 | . | * | F | 1.64 | 4.12 |
| Thr | 26 | . | . | . | . | T | . | . | 2.08 | −1.34 | . | * | F | 2.18 | 3.44 |
| Lys | 27 | . | . | . | . | . | T | C | 1.49 | −0.96 | . | * | F | 2.52 | 3.44 |
| Ser | 28 | . | . | . | . | . | T | C | 1.13 | −0.66 | * | * | F | 2.86 | 1.39 |
| Asp | 29 | . | . | . | . | T | T | . | 1.48 | −0.57 | . | . | F | 3.40 | 1.39 |
| Ser | 30 | . | . | B | . | . | T | . | 1.48 | −1.06 | * | . | F | 2.66 | 1.39 |
| Ile | 31 | . | A | B | . | . | . | . | 1.09 | −1.06 | * | . | F | 1.92 | 1.80 |
| Thr | 32 | . | A | B | . | . | . | . | 0.23 | −0.66 | * | . | F | 1.43 | 0.93 |
| Lys | 33 | . | A | B | . | . | . | . | 0.32 | 0.03 | * | . | F | 0.19 | 0.57 |
| Glu | 34 | . | A | B | . | . | . | . | −0.02 | 0.07 | * | . | F | 0.00 | 1.27 |
| Phe | 35 | . | A | B | . | . | . | . | −0.53 | −0.19 | * | . | F | 0.45 | 0.87 |
| Leu | 36 | . | . | B | . | . | T | . | 0.11 | 0.01 | * | . | F | 0.25 | 0.36 |
| Pro | 37 | . | . | B | . | . | T | . | 0.11 | 0.77 | * | . | F | −0.05 | 0.32 |
| Gly | 38 | . | . | . | . | T | T | . | −0.52 | 1.26 | * | . | . | 0.20 | 0.54 |
| Leu | 39 | . | . | B | . | . | T | . | −0.73 | 0.97 | * | . | . | −0.20 | 0.66 |
| Tyr | 40 | . | . | B | . | . | . | . | −0.33 | 0.71 | * | . | . | −0.40 | 0.66 |
| Thr | 41 | . | . | B | . | . | . | . | 0.18 | 0.67 | . | . | . | −0.40 | 0.89 |

TABLE I-continued

| Res | Position | I | II | III | IV | V | VI | VII | VIII | IX | X | XI | XII | XIII | XIV |
|---|---|---|---|---|---|---|---|---|---|---|---|---|---|---|---|
| Ala | 42 | . | . | B | . | . | . | T | . | 0.18 | 0.63 | . | . | F | 0.10 | 1.45 |
| Pro | 43 | . | . | . | . | . | T | T | . | −0.18 | 0.37 | . | . | F | 0.80 | 1.44 |
| Ser | 44 | . | . | . | . | . | T | T | . | 0.42 | 0.40 | . | . | F | 0.65 | 0.86 |
| Ser | 45 | . | . | . | . | . | . | T | C | 0.46 | 0.34 | . | . | F | 0.60 | 1.32 |
| Pro | 46 | . | . | . | . | . | . | . | C | 0.47 | 0.27 | . | . | F | 0.40 | 1.32 |
| Phe | 47 | . | . | . | . | . | . | . | C | 1.06 | 0.23 | . | . | F | 0.40 | 1.32 |
| Pro | 48 | . | . | . | . | . | . | T | C | 0.41 | 0.24 | . | . | F | 0.60 | 1.70 |
| Pro | 49 | . | . | . | . | . | T | T | . | 0.41 | 0.50 | . | . | F | 0.55 | 0.82 |
| Ser | 50 | . | . | . | . | . | T | T | . | 0.71 | 0.46 | . | . | F | 0.90 | 1.27 |
| Gln | 51 | . | . | B | . | . | . | T | . | 0.89 | −0.33 | . | . | F | 1.60 | 1.37 |
| Val | 52 | . | . | B | . | . | . | . | . | 1.59 | −0.26 | . | . | F | 1.60 | 1.20 |
| Ser | 53 | . | . | B | . | . | . | T | . | 0.94 | −0.29 | . | . | F | 2.00 | 1.55 |
| Asp | 54 | . | . | B | . | . | . | T | . | 0.34 | −0.03 | . | . | F | 1.65 | 0.67 |
| His | 55 | . | . | B | . | . | . | T | . | 0.64 | 0.26 | . | . | . | 0.70 | 0.74 |
| Gln | 56 | . | . | B | . | . | . | T | . | 0.64 | 0.01 | . | . | . | 0.50 | 0.89 |
| Val | 57 | . | A | B | . | . | . | . | . | 0.91 | −0.37 | . | . | . | 0.50 | 0.89 |
| Leu | 58 | A | A | . | . | . | . | . | . | 1.21 | 0.13 | . | * | . | −0.30 | 0.66 |
| Asn | 59 | . | . | . | . | . | . | . | . | 0.36 | −0.37 | . | * | . | 0.30 | 0.66 |
| Asp | 60 | A | A | . | . | . | . | . | . | −0.20 | −0.13 | * | * | F | 0.45 | 0.66 |
| Ala | 61 | A | A | . | . | . | . | . | . | −0.79 | −0.27 | . | . | . | 0.30 | 0.81 |
| Glu | 62 | A | A | . | . | . | . | . | . | −0.74 | −0.46 | . | . | . | 0.30 | 0.51 |
| Val | 63 | A | A | . | . | . | . | . | . | −0.74 | −0.17 | . | * | . | 0.30 | 0.25 |
| Ala | 64 | A | A | . | . | . | . | . | . | −0.74 | 0.51 | . | . | . | −0.60 | 0.20 |
| Ala | 65 | A | A | . | . | . | . | . | . | −0.74 | 0.01 | * | * | . | −0.30 | 0.20 |
| Leu | 66 | A | A | . | . | . | . | . | . | −0.86 | 0.41 | * | . | . | −0.60 | 0.44 |
| Leu | 67 | A | A | . | . | . | . | . | . | −1.16 | 0.56 | * | . | . | −0.60 | 0.38 |
| Glu | 68 | A | A | . | . | . | . | . | . | −0.60 | 0.44 | * | . | . | −0.60 | 0.50 |
| Asn | 69 | A | A | . | . | . | . | . | . | −0.31 | 0.33 | * | . | F | −0.15 | 0.82 |
| Phe | 70 | . | A | . | . | T | . | . | . | 0.03 | 0.03 | * | . | F | 0.40 | 1.33 |
| Ser | 71 | . | . | . | . | T | T | . | . | 0.84 | 0.10 | * | . | F | 0.80 | 1.20 |
| Ser | 72 | . | . | . | . | . | T | T | C | 1.41 | 0.10 | * | . | F | 0.60 | 1.25 |
| Ser | 73 | . | . | . | . | . | T | T | C | 1.07 | 0.46 | * | . | F | 0.64 | 2.26 |
| Tyr | 74 | . | . | . | . | . | T | T | C | 1.07 | 0.10 | * | * | F | 1.28 | 1.67 |
| Asp | 75 | . | . | . | . | . | T | T | . | 1.77 | −0.29 | * | . | . | 2.27 | 2.16 |
| Tyr | 76 | . | . | . | . | . | . | T | C | 2.07 | −0.27 | . | . | F | 2.56 | 2.59 |
| Gly | 77 | . | . | . | . | . | T | T | . | 2.07 | −0.66 | . | . | F | 3.40 | 2.86 |
| Glu | 78 | . | . | . | . | . | T | T | . | 2.37 | −1.03 | . | . | F | 3.06 | 2.30 |
| Asn | 79 | . | . | . | . | . | T | . | . | 2.31 | −1.03 | * | . | F | 2.83 | 2.45 |
| Glu | 80 | . | . | . | . | . | T | . | . | 1.64 | −1.40 | * | . | F | 2.80 | 3.32 |
| Ser | 81 | . | . | . | . | . | T | . | . | 1.22 | −1.26 | . | . | F | 2.77 | 1.03 |
| Asp | 82 | . | . | . | . | . | T | T | . | 1.26 | −0.69 | . | . | F | 2.79 | 0.34 |
| Ser | 83 | . | . | . | . | . | T | . | . | 0.96 | −0.60 | . | . | F | 3.10 | 0.29 |
| Cys | 84 | . | . | . | . | . | T | T | . | 0.74 | −0.21 | . | . | . | 2.34 | 0.29 |
| Cys | 85 | . | . | . | . | . | T | T | . | 0.53 | −0.17 | . | . | . | 2.03 | 0.26 |
| Thr | 86 | . | . | . | . | . | T | . | . | 0.17 | 0.26 | . | . | F | 1.07 | 0.30 |
| Ser | 87 | . | . | . | . | . | . | . | C | −0.04 | 0.44 | . | . | F | 0.26 | 0.30 |
| Pro | 88 | . | . | . | . | . | . | T | C | 0.26 | 0.30 | . | . | F | 0.45 | 0.88 |
| Pro | 89 | . | . | . | . | . | T | T | . | 0.92 | 0.13 | . | . | F | 0.80 | 1.05 |
| Cys | 90 | . | . | B | . | . | . | T | . | 0.89 | −0.36 | . | . | F | 1.00 | 1.31 |
| Pro | 91 | . | . | B | . | . | . | T | . | 0.90 | 0.04 | . | * | F | 0.25 | 0.74 |
| Gln | 92 | . | . | B | . | . | . | . | . | 0.39 | 0.00 | . | * | F | 0.65 | 0.64 |
| Asp | 93 | . | . | B | . | . | . | . | . | 0.60 | 0.26 | . | * | F | 0.05 | 0.98 |
| Phe | 94 | . | . | B | . | . | . | . | . | 0.11 | 0.09 | . | * | F | 0.42 | 1.02 |
| Ser | 95 | . | . | B | . | . | . | . | . | 0.78 | 0.44 | * | * | . | 0.04 | 0.51 |
| Leu | 96 | . | . | B | . | . | . | . | . | 1.10 | 0.04 | * | * | . | 0.56 | 0.51 |
| Asn | 97 | . | . | B | . | . | . | T | . | 0.51 | 0.04 | * | * | . | 1.13 | 1.15 |
| Phe | 98 | . | . | . | . | . | T | T | . | −0.19 | −0.24 | * | * | . | 2.20 | 0.87 |
| Asp | 99 | A | . | . | . | . | . | T | . | −0.30 | 0.16 | * | . | . | 0.98 | 0.91 |
| Arg | 100 | A | . | . | . | . | . | T | . | −0.21 | 0.16 | * | . | . | 0.76 | 0.47 |
| Ala | 101 | A | A | . | . | . | . | . | . | 0.01 | 0.19 | * | . | . | 0.14 | 0.84 |
| Phe | 102 | A | A | . | . | . | . | . | . | −0.80 | −0.10 | * | . | . | 0.52 | 0.51 |
| Leu | 103 | . | A | B | . | . | . | . | . | −0.34 | 0.59 | * | . | . | −0.60 | 0.21 |
| Pro | 104 | A | A | . | . | . | . | . | . | −0.64 | 1.34 | * | . | . | −0.60 | 0.33 |
| Ala | 105 | A | A | . | . | . | . | . | . | −1.57 | 1.23 | * | * | . | −0.60 | 0.51 |
| Leu | 106 | A | A | . | . | . | . | . | . | −1.79 | 1.13 | . | . | . | −0.60 | 0.51 |
| Tyr | 107 | A | A | . | . | . | . | . | . | −1.79 | 1.13 | . | . | . | −0.60 | 0.27 |
| Ser | 108 | A | A | . | . | . | . | . | . | −1.79 | 1.49 | . | . | . | −0.60 | 0.23 |
| Leu | 109 | . | A | B | . | . | . | . | . | −2.39 | 1.67 | . | . | . | −0.60 | 0.23 |
| Leu | 110 | . | A | B | . | . | . | . | . | −2.14 | 1.67 | . | . | . | −0.60 | 0.12 |
| Phe | 111 | . | A | B | . | . | . | . | . | −2.14 | 1.34 | . | . | . | −0.60 | 0.09 |
| Leu | 112 | . | A | B | . | . | . | . | . | −2.71 | 1.64 | . | . | . | −0.60 | 0.09 |
| Leu | 113 | . | A | B | . | . | . | . | . | −2.76 | 1.64 | . | . | . | −0.60 | 0.09 |
| Gly | 114 | . | A | B | . | . | . | . | . | −1.94 | 1.39 | . | . | . | −0.60 | 0.10 |
| Leu | 115 | . | A | B | . | . | . | . | . | −1.48 | 1.00 | . | . | . | −0.60 | 0.20 |
| Leu | 116 | . | . | . | . | . | T | . | C | −1.37 | 0.74 | . | . | . | 0.00 | 0.24 |
| Gly | 117 | . | . | . | . | . | T | . | C | −1.41 | 0.56 | . | . | F | 0.15 | 0.25 |
| Asn | 118 | . | . | . | . | . | T | . | C | −1.19 | 0.77 | . | . | F | 0.15 | 0.22 |

TABLE I-continued

| Res | Position | I | II | III | IV | V | VI | VII | VIII | IX | X | XI | XII | XIII | XIV |
|---|---|---|---|---|---|---|---|---|---|---|---|---|---|---|---|
| Gly | 119 | A | . | . | . | . | T | . | −1.43 | 0.59 | . | . | F | −0.05 | 0.27 |
| Ala | 120 | A | A | . | . | . | . | . | −1.48 | 0.40 | . | . | . | −0.30 | 0.28 |
| Val | 121 | . | A | B | . | . | . | . | −1.48 | 0.61 | . | . | . | −0.60 | 0.13 |
| Ala | 122 | A | A | . | . | . | . | . | −1.94 | 0.90 | . | . | . | −0.60 | 0.11 |
| Ala | 123 | . | A | B | . | . | . | . | −2.24 | 1.16 | . | . | . | −0.60 | 0.09 |
| Val | 124 | . | A | B | . | . | . | . | −1.79 | 1.04 | . | . | . | −0.60 | 0.16 |
| Leu | 125 | . | A | B | . | . | . | . | −1.09 | 0.40 | . | . | . | −0.30 | 0.31 |
| Leu | 126 | A | A | . | . | . | . | . | −0.54 | −0.10 | . | . | . | 0.56 | 0.59 |
| Ser | 127 | A | . | . | . | . | T | . | −0.54 | −0.11 | . | . | F | 1.52 | 1.16 |
| Arg | 128 | A | . | . | . | . | T | . | −0.77 | −0.26 | . | . | F | 1.78 | 1.42 |
| Arg | 129 | . | . | B | . | . | T | . | −0.21 | −0.26 | . | . | F | 2.04 | 1.42 |
| Thr | 130 | . | . | B | . | . | T | . | 0.30 | −0.56 | . | . | F | 2.60 | 1.42 |
| Ala | 131 | . | . | B | . | . | . | . | 0.80 | −0.56 | * | . | F | 1.99 | 0.97 |
| Leu | 132 | . | . | B | . | . | . | . | 1.10 | −0.07 | * | . | F | 1.43 | 0.71 |
| Ser | 133 | . | . | B | . | . | . | . | 0.68 | −0.07 | * | . | F | 1.17 | 0.83 |
| Ser | 134 | . | . | . | . | . | T | C | −0.13 | −0.07 | * | * | F | 1.46 | 1.18 |
| Thr | 135 | . | . | . | . | . | T | C | −0.63 | 0.21 | . | . | F | 0.60 | 1.24 |
| Asp | 136 | . | . | . | . | . | T | . | −0.86 | 0.21 | . | . | F | 0.25 | 0.76 |
| Thr | 137 | A | . | . | . | . | T | . | −0.08 | 0.51 | . | . | F | −0.05 | 0.47 |
| Phe | 138 | A | . | . | B | . | . | . | −0.59 | 0.63 | . | . | . | −0.60 | 0.44 |
| Leu | 139 | A | . | . | B | . | . | . | −0.88 | 0.83 | . | . | . | −0.60 | 0.22 |
| Leu | 140 | A | . | . | B | . | . | . | −1.42 | 1.33 | . | . | . | −0.60 | 0.15 |
| His | 141 | A | . | . | B | . | . | . | −2.01 | 1.49 | . | . | . | −0.60 | 0.13 |
| Leu | 142 | A | . | . | B | . | . | . | −1.70 | 1.20 | . | . | . | −0.60 | 0.16 |
| Ala | 143 | A | . | . | B | . | . | . | −1.31 | 0.51 | . | . | . | −0.60 | 0.33 |
| Val | 144 | A | . | . | B | . | . | . | −1.31 | 0.31 | . | . | . | −0.30 | 0.35 |
| Ala | 145 | A | . | . | B | . | . | . | −1.31 | 0.50 | . | . | . | −0.60 | 0.35 |
| Asp | 146 | A | . | . | B | . | . | . | −2.13 | 0.50 | . | . | . | −0.60 | 0.28 |
| Thr | 147 | A | . | . | B | . | . | . | −2.13 | 0.64 | . | . | . | −0.60 | 0.28 |
| Leu | 148 | . | . | B | B | . | . | . | −1.86 | 0.69 | . | . | . | −0.60 | 0.23 |
| Leu | 149 | . | . | B | B | . | . | . | −1.81 | 0.67 | . | . | . | −0.60 | 0.20 |
| Val | 150 | . | . | B | B | . | . | . | −1.43 | 1.36 | . | * | . | −0.60 | 0.11 |
| Leu | 151 | . | . | B | B | . | . | . | −2.24 | 1.30 | . | . | . | −0.60 | 0.21 |
| Thr | 152 | . | . | B | B | . | . | . | −2.22 | 1.30 | . | . | . | −0.60 | 0.21 |
| Leu | 153 | . | . | B | B | . | . | . | −2.00 | 1.53 | . | . | . | −0.60 | 0.30 |
| Pro | 154 | A | . | . | B | . | . | . | −2.04 | 1.39 | . | . | . | −0.60 | 0.37 |
| Leu | 155 | A | . | . | B | . | . | . | −1.19 | 1.34 | . | . | . | −0.60 | 0.19 |
| Trp | 156 | A | . | . | B | . | . | . | −0.97 | 0.86 | . | . | . | −0.60 | 0.38 |
| Ala | 157 | A | . | . | B | . | . | . | −1.24 | 0.67 | . | . | . | −0.60 | 0.25 |
| Val | 158 | A | . | . | B | . | . | . | −1.29 | 0.74 | . | * | . | −0.60 | 0.31 |
| Asp | 159 | A | . | . | B | . | . | . | −1.08 | 0.70 | . | * | . | −0.60 | 0.22 |
| Ala | 160 | A | . | . | B | . | . | . | −0.56 | 0.19 | * | * | . | −0.30 | 0.37 |
| Ala | 161 | A | . | . | B | . | . | . | −1.12 | 0.60 | * | * | . | −0.60 | 0.53 |
| Val | 162 | . | . | B | B | . | . | . | −1.23 | 0.60 | * | * | . | −0.60 | 0.23 |
| Gln | 163 | . | . | B | B | . | . | . | −0.72 | 1.39 | * | * | . | −0.60 | 0.20 |
| Trp | 164 | . | . | B | B | . | . | . | −1.02 | 1.31 | . | * | . | −0.60 | 0.20 |
| Val | 165 | . | . | B | B | . | . | . | −0.78 | 1.20 | . | . | . | −0.60 | 0.36 |
| Phe | 166 | . | . | B | B | . | . | . | −1.00 | 0.99 | . | . | . | −0.60 | 0.20 |
| Gly | 167 | . | . | . | . | T | T | . | −0.81 | 1.27 | . | * | F | 0.35 | 0.16 |
| Ser | 168 | . | . | . | . | T | T | . | −0.77 | 0.93 | . | * | F | 0.35 | 0.12 |
| Gly | 169 | . | . | . | . | T | T | . | −1.33 | 0.29 | * | . | F | 0.65 | 0.27 |
| Leu | 170 | . | . | . | . | T | T | C | −1.07 | 0.14 | . | . | F | 0.45 | 0.20 |
| Cys | 171 | . | A | B | . | . | . | . | −0.71 | 0.21 | * | . | . | −0.30 | 0.15 |
| Lys | 172 | . | A | B | . | . | . | . | −0.96 | 0.26 | * | * | . | −0.30 | 0.15 |
| Val | 173 | . | A | B | . | . | . | . | −1.47 | 0.33 | * | . | . | −0.30 | 0.18 |
| Ala | 174 | . | A | B | . | . | . | . | −1.82 | 0.33 | * | . | . | −0.30 | 0.28 |
| Gly | 175 | . | A | B | . | . | . | . | −1.01 | 0.54 | * | . | . | −0.60 | 0.12 |
| Ala | 176 | A | A | . | . | . | . | . | −1.23 | 0.94 | * | * | . | −0.60 | 0.27 |
| Leu | 177 | . | A | B | . | . | . | . | −1.28 | 0.99 | . | * | . | −0.60 | 0.18 |
| Phe | 178 | . | A | B | . | . | . | . | −1.12 | 0.89 | . | * | . | −0.60 | 0.30 |
| Asn | 179 | . | A | B | . | . | . | . | −0.78 | 1.24 | . | * | . | −0.60 | 0.26 |
| Ile | 180 | . | . | B | . | . | . | . | −1.02 | 1.50 | . | * | . | −0.40 | 0.49 |
| Asn | 181 | . | . | B | . | . | . | . | −0.78 | 1.31 | . | * | . | −0.40 | 0.57 |
| Phe | 182 | . | . | B | . | . | . | . | −0.56 | 0.96 | . | * | . | −0.40 | 0.35 |
| Tyr | 183 | A | A | . | . | . | . | . | −0.67 | 1.06 | . | * | . | −0.60 | 0.51 |
| Ala | 184 | A | A | . | . | . | . | . | −1.48 | 1.06 | . | * | . | −0.60 | 0.26 |
| Gly | 185 | A | A | . | . | . | . | . | −1.40 | 1.34 | . | * | . | −0.60 | 0.25 |
| Ala | 186 | A | A | . | . | . | . | . | −1.99 | 1.24 | . | . | . | −0.60 | 0.13 |
| Leu | 187 | A | A | . | . | . | . | . | −1.96 | 0.99 | . | . | . | −0.60 | 0.13 |
| Leu | 188 | A | A | . | . | . | . | . | −2.60 | 1.06 | . | . | . | −0.60 | 0.07 |
| Leu | 189 | A | A | . | . | . | . | . | −2.31 | 1.31 | . | . | . | −0.60 | 0.05 |
| Ala | 190 | . | A | B | . | . | . | . | −2.67 | 1.20 | . | * | . | −0.60 | 0.08 |
| Cys | 191 | . | A | B | . | . | . | . | −2.08 | 1.30 | * | . | . | −0.60 | 0.08 |
| Ile | 192 | . | A | B | . | . | . | . | −1.16 | 0.61 | * | . | . | −0.60 | 0.17 |
| Ser | 193 | . | A | B | . | . | . | . | −0.59 | −0.07 | * | . | . | 0.30 | 0.33 |
| Phe | 194 | . | . | B | . | . | . | . | −0.59 | 0.19 | * | . | . | −0.10 | 0.96 |
| Asp | 195 | A | . | . | . | . | T | . | 0.00 | 0.30 | * | * | . | 0.25 | 1.12 |

TABLE I-continued

| Res | Position | I | II | III | IV | V | VI | VII | VIII | IX | X | XI | XII | XIII | XIV |
|---|---|---|---|---|---|---|---|---|---|---|---|---|---|---|---|
| Arg | 196 | A | . | . | . | . | T | . | −0.22 | 0.01 | * | . | . | 0.25 | 1.35 |
| Tyr | 197 | . | . | . | . | T | T | . | −0.19 | 0.31 | * | * | . | 0.65 | 1.09 |
| Leu | 198 | . | . | B | . | . | T | . | 0.08 | 0.17 | * | . | . | 0.10 | 0.49 |
| Asn | 199 | . | . | B | B | . | . | . | 0.19 | 0.67 | * | . | . | −0.60 | 0.34 |
| Ile | 200 | . | . | B | B | . | . | . | −0.12 | 1.17 | * | . | . | −0.60 | 0.22 |
| Val | 201 | . | . | B | B | . | . | . | −0.23 | 0.90 | . | . | . | −0.60 | 0.38 |
| His | 202 | . | . | B | B | . | . | . | −0.80 | 0.61 | . | . | . | −0.60 | 0.41 |
| Ala | 203 | . | . | B | B | . | . | . | −0.23 | 0.90 | . | * | . | −0.60 | 0.48 |
| Thr | 204 | . | . | B | B | . | . | . | −0.12 | 0.97 | * | . | . | −0.45 | 1.02 |
| Gln | 205 | . | . | B | B | . | . | . | 0.88 | 0.33 | * | . | . | −0.15 | 1.46 |
| Leu | 206 | . | . | B | B | . | . | . | 1.39 | −0.17 | * | . | . | 0.45 | 2.84 |
| Tyr | 207 | . | . | B | . | . | . | T | . | 1.21 | −0.24 | * | . | F | 1.30 | 1.95 |
| Arg | 208 | . | . | . | . | . | T | T | . | 1.59 | −0.30 | * | . | F | 2.00 | 1.74 |
| Arg | 209 | . | . | . | . | . | T | T | . | 1.31 | −0.27 | * | * | F | 2.30 | 3.26 |
| Gly | 210 | . | . | . | . | . | T | C | 1.42 | −0.46 | . | * | F | 2.40 | 2.10 |
| Pro | 211 | . | . | . | . | . | T | C | 1.38 | −1.21 | . | * | F | 3.00 | 2.10 |
| Pro | 212 | . | . | . | . | . | T | C | 1.31 | −0.57 | . | * | F | 2.55 | 0.80 |
| Ala | 213 | . | . | B | . | . | T | . | 0.39 | −0.09 | . | * | F | 1.90 | 1.16 |
| Arg | 214 | . | . | B | . | . | T | . | −0.03 | 0.17 | . | * | . | 0.70 | 0.62 |
| Val | 215 | . | . | B | B | . | . | . | −0.36 | 0.23 | * | * | . | 0.00 | 0.58 |
| Thr | 216 | . | . | B | B | . | . | . | −0.96 | 0.37 | * | * | . | −0.30 | 0.31 |
| Leu | 217 | . | . | B | B | . | . | . | −1.33 | 0.56 | . | * | . | −0.60 | 0.13 |
| Thr | 218 | . | . | B | B | . | . | . | −1.60 | 1.06 | * | * | . | −0.60 | 0.18 |
| Cys | 219 | . | . | B | B | . | . | . | −2.00 | 1.06 | * | * | . | −0.60 | 0.09 |
| Leu | 220 | . | . | B | B | . | . | . | −1.49 | 1.49 | . | . | . | −0.60 | 0.12 |
| Ala | 221 | . | . | B | B | . | . | . | −1.99 | 1.23 | . | . | . | −0.60 | 0.08 |
| Val | 222 | A | . | . | B | . | . | . | −1.84 | 1.43 | . | . | . | −0.60 | 0.12 |
| Trp | 223 | A | . | . | B | . | . | . | −2.34 | 1.43 | . | . | . | −0.60 | 0.08 |
| Gly | 224 | A | . | . | B | . | . | . | −2.49 | 1.43 | . | . | . | −0.60 | 0.06 |
| Leu | 225 | . | . | B | B | . | . | . | −2.38 | 1.61 | . | . | . | −0.60 | 0.07 |
| Cys | 226 | . | . | B | B | . | . | . | −2.38 | 1.76 | . | . | . | −0.60 | 0.06 |
| Leu | 227 | . | . | B | B | . | . | . | −2.33 | 1.34 | . | . | . | −0.60 | 0.06 |
| Leu | 228 | . | . | B | B | . | . | . | −2.26 | 1.60 | . | . | . | −0.60 | 0.06 |
| Phe | 229 | . | . | B | B | . | . | . | −1.91 | 1.34 | . | . | . | −0.60 | 0.17 |
| Ala | 230 | . | . | B | B | . | . | . | −1.80 | 0.77 | * | . | . | −0.60 | 0.35 |
| Leu | 231 | A | . | . | . | . | T | . | −2.02 | 0.87 | . | . | . | −0.20 | 0.37 |
| Pro | 232 | A | . | . | . | . | T | . | −1.91 | 0.87 | . | . | . | −0.20 | 0.30 |
| Asp | 233 | A | . | . | . | . | T | . | −1.91 | 0.87 | . | . | . | −0.20 | 0.26 |
| Phe | 234 | A | . | . | . | . | T | . | −1.51 | 1.06 | . | . | . | −0.20 | 0.26 |
| Ile | 235 | A | A | . | B | . | . | . | −1.51 | 0.76 | . | . | . | −0.60 | 0.22 |
| Phe | 236 | A | A | . | B | . | . | . | −0.73 | 0.83 | . | . | . | −0.60 | 0.13 |
| Leu | 237 | A | A | . | B | . | . | . | −0.56 | 1.33 | . | . | . | −0.60 | 0.21 |
| Ser | 238 | A | A | . | B | . | . | . | −0.56 | 1.04 | . | . | . | −0.60 | 0.41 |
| Ala | 239 | A | A | . | . | . | . | . | 0.14 | 0.36 | . | * | . | −0.30 | 0.79 |
| His | 240 | A | A | . | . | . | . | . | 1.14 | −0.43 | . | * | . | 0.45 | 1.66 |
| His | 241 | A | A | . | . | . | . | . | 1.03 | −1.11 | . | * | . | 0.75 | 2.43 |
| Asp | 242 | A | A | . | . | . | . | . | 1.84 | −0.81 | . | * | F | 0.90 | 1.98 |
| Glu | 243 | A | A | . | . | . | . | . | 1.56 | −0.91 | . | * | F | 0.90 | 2.34 |
| Arg | 244 | A | A | . | . | . | . | . | 1.83 | −0.91 | . | * | F | 0.90 | 1.74 |
| Leu | 245 | A | A | . | . | . | . | . | 1.83 | −0.93 | . | * | F | 0.90 | 1.50 |
| Asn | 246 | A | A | . | . | . | . | . | 1.20 | −0.43 | . | * | . | 0.45 | 1.18 |
| Ala | 247 | A | A | . | . | . | . | . | 1.20 | 0.14 | . | * | . | −0.30 | 0.32 |
| Thr | 248 | A | A | . | . | . | . | . | 0.96 | 0.54 | . | * | . | −0.60 | 0.68 |
| His | 249 | . | A | . | . | T | . | . | 0.84 | 0.61 | . | * | . | −0.20 | 0.66 |
| Cys | 250 | . | . | . | . | T | T | . | 0.96 | 0.61 | . | * | . | 0.35 | 1.05 |
| Gln | 251 | . | . | . | . | T | T | . | 0.74 | 0.90 | * | . | . | 0.20 | 0.63 |
| Tyr | 252 | . | . | . | . | T | T | . | 1.33 | 0.84 | * | . | . | 0.20 | 0.72 |
| Asn | 253 | . | . | B | . | . | T | . | 0.79 | 0.74 | * | . | . | −0.05 | 2.32 |
| Phe | 254 | . | . | B | B | . | . | . | 0.48 | 0.81 | * | * | . | −0.60 | 0.99 |
| Pro | 255 | . | . | B | B | . | . | . | 1.26 | 0.84 | * | * | F | −0.45 | 0.63 |
| Gln | 256 | . | . | . | B | T | . | . | 0.94 | 0.09 | * | * | F | 0.25 | 0.76 |
| Val | 257 | . | . | B | B | . | . | . | 0.60 | 0.17 | * | * | F | 0.00 | 1.27 |
| Gly | 258 | . | . | B | B | . | . | . | −0.21 | −0.11 | * | * | F | 0.45 | 0.83 |
| Arg | 259 | . | . | B | B | . | . | . | 0.60 | 0.14 | * | * | F | −0.15 | 0.40 |
| Thr | 260 | . | . | B | B | . | . | . | −0.04 | −0.26 | * | * | F | 0.60 | 1.05 |
| Ala | 261 | . | . | B | B | . | . | . | −0.86 | −0.26 | * | * | . | 0.30 | 0.78 |
| Leu | 262 | . | . | B | B | . | . | . | 0.00 | 0.00 | * | * | . | 0.30 | 0.33 |
| Arg | 263 | . | . | B | B | . | . | . | −0.47 | 0.40 | * | * | . | −0.30 | 0.40 |
| Val | 264 | . | . | B | B | . | . | . | −1.43 | 0.60 | * | * | . | −0.60 | 0.32 |
| Leu | 265 | . | . | B | B | . | . | . | −1.71 | 0.74 | * | . | . | −0.60 | 0.29 |
| Gln | 266 | . | . | B | B | . | . | . | −1.47 | 0.56 | * | . | . | −0.60 | 0.15 |
| Leu | 267 | . | . | B | B | . | . | . | −1.36 | 0.99 | * | . | . | −0.60 | 0.20 |
| Val | 268 | . | . | B | B | . | . | . | −2.28 | 1.13 | * | . | . | −0.60 | 0.21 |
| Ala | 269 | . | . | B | B | . | . | . | −2.23 | 1.13 | * | . | . | −0.60 | 0.10 |
| Gly | 270 | . | . | B | B | . | . | . | −1.63 | 1.41 | * | * | . | −0.60 | 0.10 |
| Phe | 271 | . | . | B | B | . | . | . | −2.44 | 1.16 | * | . | . | −0.60 | 0.21 |
| Leu | 272 | . | . | B | B | . | . | . | −2.44 | 1.20 | * | . | . | −0.60 | 0.17 |

TABLE I-continued

| Res | Position | I | II | III | IV | V | VI | VII | VIII | IX | X | XI | XII | XIII | XIV |
|---|---|---|---|---|---|---|---|---|---|---|---|---|---|---|---|
| Leu | 273 | . | . | B | B | . | . | . | -2.44 | 1.39 | . | . | . | -0.60 | 0.14 |
| Pro | 274 | A | . | . | B | . | . | . | -2.46 | 1.60 | . | . | . | -0.60 | 0.12 |
| Leu | 275 | A | . | . | B | . | . | . | -2.70 | 1.43 | . | . | . | -0.60 | 0.15 |
| Leu | 276 | A | . | . | B | . | . | . | -2.24 | 1.24 | . | . | . | -0.60 | 0.18 |
| Val | 277 | A | . | . | B | . | . | . | -2.10 | 1.31 | . | . | . | -0.60 | 0.18 |
| Met | 278 | A | . | . | B | . | . | . | -1.53 | 1.46 | . | . | . | -0.60 | 0.12 |
| Ala | 279 | A | . | . | B | . | . | . | -1.91 | 1.53 | . | . | . | -0.60 | 0.22 |
| Tyr | 280 | A | . | . | B | . | . | . | -1.13 | 1.34 | . | * | . | -0.60 | 0.30 |
| Cys | 281 | A | . | . | B | . | . | . | -1.21 | 1.20 | . | . | . | -0.60 | 0.42 |
| Tyr | 282 | A | . | . | B | . | . | . | -1.17 | 1.27 | . | . | . | -0.60 | 0.29 |
| Ala | 283 | A | . | . | B | . | . | . | -1.16 | 1.46 | . | . | . | -0.60 | 0.15 |
| His | 284 | A | . | . | B | . | . | . | -1.42 | 1.20 | . | . | . | -0.60 | 0.29 |
| Ile | 285 | A | . | . | B | . | . | . | -1.99 | 1.27 | . | . | . | -0.60 | 0.14 |
| Leu | 286 | A | . | . | B | . | . | . | -2.13 | 1.20 | . | . | . | -0.60 | 0.11 |
| Ala | 287 | . | . | B | B | . | . | . | -2.74 | 1.39 | . | . | . | -0.60 | 0.07 |
| Val | 288 | . | . | B | B | . | . | . | -2.46 | 1.53 | . | * | . | -0.60 | 0.07 |
| Leu | 289 | . | . | B | B | . | . | . | -2.31 | 1.23 | . | * | . | -0.60 | 0.12 |
| Leu | 290 | . | . | B | B | . | . | . | -1.77 | 0.54 | . | * | . | -0.60 | 0.23 |
| Val | 291 | . | . | B | B | . | . | . | -0.96 | 0.47 | * | . | . | -0.60 | 0.30 |
| Ser | 292 | . | . | B | . | . | . | T | -0.26 | 0.23 | * | * | F | 0.25 | 0.63 |
| Arg | 293 | A | . | . | . | . | . | T | . | 0.71 | -0.46 | * | * | F | 1.00 | 1.50 |
| Gly | 294 | A | . | . | . | . | . | T | . | 0.71 | -1.14 | * | * | F | 1.30 | 3.96 |
| Gln | 295 | A | . | . | . | . | . | T | . | 1.63 | -1.10 | * | * | F | 1.30 | 2.43 |
| Arg | 296 | A | A | . | . | . | . | . | . | 1.90 | -1.49 | * | * | F | 0.90 | 2.43 |
| Arg | 297 | . | A | B | . | . | . | . | . | 1.60 | -0.99 | * | * | F | 0.90 | 2.49 |
| Leu | 298 | . | A | B | . | . | . | . | . | 1.60 | -0.80 | * | * | . | 0.75 | 1.42 |
| Arg | 299 | . | A | B | . | . | . | . | . | 1.13 | -1.20 | * | * | . | 0.75 | 1.42 |
| Ala | 300 | . | A | B | . | . | . | . | . | 0.28 | -0.51 | * | * | . | 0.60 | 0.60 |
| Met | 301 | . | . | B | B | . | . | . | . | -0.69 | 0.13 | * | . | . | -0.30 | 0.54 |
| Arg | 302 | . | . | B | B | . | . | . | . | -1.66 | 0.09 | . | * | . | -0.30 | 0.20 |
| Leu | 303 | . | . | B | B | . | . | . | . | -1.70 | 0.73 | . | . | . | -0.60 | 0.15 |
| Val | 304 | . | . | B | B | . | . | . | . | -2.67 | 0.87 | * | . | . | -0.60 | 0.11 |
| Val | 305 | . | . | B | B | . | . | . | . | -2.93 | 0.90 | * | * | . | -0.60 | 0.04 |
| Val | 306 | . | . | B | B | . | . | . | . | -2.92 | 1.54 | * | * | . | -0.60 | 0.04 |
| Val | 307 | . | . | B | B | . | . | . | . | -3.73 | 1.36 | * | * | . | -0.60 | 0.05 |
| Val | 308 | . | . | B | B | . | . | . | . | -3.51 | 1.50 | . | . | . | -0.60 | 0.06 |
| Val | 309 | . | . | B | B | . | . | . | . | -3.47 | 1.36 | . | . | . | -0.60 | 0.08 |
| Ala | 310 | . | . | B | B | . | . | . | . | -3.28 | 1.40 | . | . | . | -0.60 | 0.09 |
| Phe | 311 | . | . | B | B | . | . | . | . | -2.71 | 1.33 | . | . | . | -0.60 | 0.07 |
| Ala | 312 | A | . | . | B | . | . | . | . | -2.17 | 1.60 | . | . | . | -0.60 | 0.09 |
| Leu | 313 | A | . | . | B | . | . | . | . | -1.52 | 1.44 | . | . | . | -0.60 | 0.13 |
| Cys | 314 | . | . | . | B | T | . | . | . | -0.91 | 1.37 | . | . | . | -0.20 | 0.24 |
| Trp | 315 | . | . | . | B | T | . | . | . | -0.36 | 1.34 | . | . | . | -0.20 | 0.37 |
| Thr | 316 | . | . | . | . | . | T | C | . | -0.47 | 1.34 | . | . | . | 0.00 | 0.61 |
| Pro | 317 | . | . | . | . | . | T | T | . | -0.73 | 1.34 | . | . | . | 0.20 | 0.95 |
| Tyr | 318 | . | . | . | . | . | T | T | . | -0.78 | 1.41 | . | . | . | 0.20 | 0.67 |
| His | 319 | . | . | B | . | . | . | T | . | -0.92 | 1.14 | . | . | . | -0.20 | 0.34 |
| Leu | 320 | . | . | B | B | . | . | . | . | -1.49 | 1.34 | . | . | . | -0.60 | 0.18 |
| Val | 321 | . | . | B | B | . | . | . | . | -1.18 | 1.56 | . | * | . | -0.60 | 0.09 |
| Val | 322 | . | . | B | B | . | . | . | . | -1.86 | 0.80 | . | * | . | -0.60 | 0.11 |
| Leu | 323 | . | . | B | B | . | . | . | . | -2.42 | 0.99 | . | * | . | -0.60 | 0.09 |
| Val | 324 | . | . | B | B | . | . | . | . | -2.99 | 0.99 | * | * | . | -0.60 | 0.10 |
| Asp | 325 | . | . | B | B | . | . | . | . | -2.18 | 0.96 | * | * | . | -0.60 | 0.13 |
| Ile | 326 | A | . | . | B | . | . | . | . | -2.13 | 0.31 | * | * | . | -0.30 | 0.27 |
| Leu | 327 | A | . | . | B | . | . | . | . | -1.62 | 0.31 | * | * | . | -0.30 | 0.30 |
| Met | 328 | A | . | . | B | . | . | . | . | -1.40 | 0.10 | * | * | . | -0.30 | 0.18 |
| Asp | 329 | A | . | . | B | . | . | . | . | -1.36 | 0.60 | * | * | . | -0.60 | 0.26 |
| Leu | 330 | A | A | . | . | . | . | . | . | -1.94 | 0.60 | * | * | . | -0.60 | 0.26 |
| Gly | 331 | A | A | . | . | . | . | . | . | -0.94 | 0.41 | * | * | . | -0.60 | 0.26 |
| Ala | 332 | A | A | . | . | . | . | . | . | -0.13 | -0.20 | * | * | . | 0.30 | 0.31 |
| Leu | 333 | A | A | . | . | . | . | . | . | -0.20 | 0.20 | * | * | . | 0.04 | 0.60 |
| Ala | 334 | A | . | . | . | . | . | T | . | -0.54 | 0.09 | * | * | . | 0.78 | 0.33 |
| Arg | 335 | A | . | . | . | . | . | T | . | 0.38 | 0.09 | * | * | . | 1.12 | 0.32 |
| Asn | 336 | . | . | . | . | . | T | T | . | 0.72 | -0.41 | * | * | . | 2.46 | 0.76 |
| Cys | 337 | . | . | . | . | . | T | T | . | 1.01 | -1.10 | * | * | F | 3.40 | 1.30 |
| Gly | 338 | . | . | . | . | . | T | T | . | 1.93 | -1.21 | * | * | F | 2.91 | 0.89 |
| Arg | 339 | . | . | . | . | . | T | T | . | 1.67 | -1.21 | * | * | F | 2.72 | 1.08 |
| Glu | 340 | . | . | B | . | . | . | T | . | 1.56 | -0.97 | * | * | F | 1.98 | 1.50 |
| Ser | 341 | . | . | B | . | . | . | T | . | 0.70 | -1.54 | . | * | F | 1.64 | 2.53 |
| Arg | 342 | . | . | B | . | . | . | . | . | 0.78 | -1.33 | * | . | F | 0.95 | 0.96 |
| Val | 343 | A | . | . | . | . | . | . | . | 1.17 | -0.83 | . | . | F | 0.95 | 0.56 |
| Asp | 344 | A | . | . | . | . | . | . | . | 0.76 | -0.83 | . | * | . | 0.80 | 0.83 |
| Val | 345 | . | . | B | . | . | . | . | . | -0.10 | -0.83 | . | * | . | 0.80 | 0.57 |
| Ala | 346 | . | . | B | . | . | . | . | . | -0.11 | -0.19 | . | * | . | 0.50 | 0.57 |
| Lys | 347 | . | . | B | . | . | . | . | . | -0.52 | -0.34 | . | * | F | 0.65 | 0.49 |
| Ser | 348 | . | . | B | . | . | . | . | . | -0.01 | 0.04 | * | . | F | 0.05 | 0.89 |
| Val | 349 | . | . | B | . | . | . | . | . | -0.82 | -0.17 | * | . | F | 0.65 | 0.87 |

TABLE I-continued

| Res | Position | I | II | III | IV | V | VI | VII | VIII | IX | X | XI | XII | XIII | XIV |
|---|---|---|---|---|---|---|---|---|---|---|---|---|---|---|---|
| Thr | 350 | . | . | B | . | . | T | . | −0.31 | 0.01 | * | . | F | 0.25 | 0.36 |
| Ser | 351 | . | . | . | . | T | T | . | 0.03 | 0.44 | * | . | F | 0.35 | 0.27 |
| Gly | 352 | . | . | . | . | T | T | . | −0.61 | 0.81 | * | . | F | 0.35 | 0.56 |
| Leu | 353 | . | . | . | . | T | T | . | −0.34 | 0.79 | . | . | . | 0.20 | 0.38 |
| Gly | 354 | . | . | . | . | T | . | . | −0.16 | 0.80 | . | . | . | 0.00 | 0.39 |
| Tyr | 355 | . | . | B | . | . | . | . | −0.51 | 0.99 | . | . | . | −0.40 | 0.21 |
| Met | 356 | . | . | B | . | . | . | . | −1.02 | 1.13 | . | . | . | −0.40 | 0.14 |
| His | 357 | . | . | B | . | . | . | . | −0.68 | 1.13 | . | * | . | −0.40 | 0.11 |
| Cys | 358 | . | . | B | . | . | . | . | −0.08 | 1.10 | * | . | . | −0.40 | 0.12 |
| Cys | 359 | . | . | B | . | . | . | . | −0.54 | 0.77 | . | * | . | −0.40 | 0.18 |
| Leu | 360 | . | . | B | . | . | . | . | −1.11 | 0.84 | * | . | . | −0.40 | 0.11 |
| Asn | 361 | . | . | B | . | . | T | . | −0.76 | 1.03 | * | * | . | −0.20 | 0.17 |
| Pro | 362 | . | . | B | . | . | T | . | −1.31 | 1.21 | * | . | . | −0.20 | 0.50 |
| Leu | 363 | . | A | . | . | . | T | . | −1.34 | 1.14 | * | . | . | −0.20 | 0.61 |
| Leu | 364 | . | A | . | . | . | T | . | −1.53 | 1.24 | * | . | . | −0.20 | 0.33 |
| Tyr | 365 | . | . | B | B | . | . | . | −1.07 | 1.49 | * | . | . | −0.60 | 0.16 |
| Ala | 366 | . | . | B | B | . | . | . | −1.92 | 1.49 | . | * | . | −0.60 | 0.19 |
| Phe | 367 | . | . | B | B | . | . | . | −1.67 | 1.44 | . | * | . | −0.60 | 0.17 |
| Val | 368 | . | . | B | B | . | . | . | −1.56 | 0.76 | . | * | . | −0.60 | 0.22 |
| Gly | 369 | A | . | . | B | . | . | . | −0.63 | 0.79 | . | * | . | −0.60 | 0.19 |
| Val | 370 | A | . | . | B | . | . | . | −0.39 | 0.29 | . | * | . | −0.30 | 0.42 |
| Lys | 371 | A | . | . | B | . | . | . | 0.31 | −0.50 | . | * | . | 0.60 | 0.99 |
| Phe | 372 | A | A | . | . | . | . | . | 0.41 | −1.14 | . | * | F | 0.90 | 1.96 |
| Arg | 373 | A | A | . | . | . | . | . | 0.98 | −0.96 | . | * | F | 0.90 | 2.61 |
| Glu | 374 | A | A | . | . | . | . | . | 0.72 | −0.69 | . | * | . | 0.75 | 1.37 |
| Arg | 375 | A | A | . | B | . | . | . | 0.77 | −0.07 | * | * | . | 0.45 | 1.57 |
| Met | 376 | A | A | . | B | . | . | . | −0.09 | −0.17 | . | * | . | 0.30 | 0.66 |
| Trp | 377 | A | A | . | B | . | . | . | −0.20 | 0.51 | * | * | . | −0.60 | 0.31 |
| Met | 378 | A | A | . | B | . | . | . | −0.20 | 1.20 | * | * | . | −0.60 | 0.13 |
| Leu | 379 | A | A | . | B | . | . | . | −1.01 | 1.20 | * | * | . | −0.60 | 0.26 |
| Leu | 380 | A | A | . | B | . | . | . | −1.47 | 1.27 | * | * | . | −0.60 | 0.21 |
| Leu | 381 | . | A | B | B | . | . | . | −1.53 | 0.79 | * | * | . | −0.60 | 0.21 |
| Arg | 382 | . | A | . | B | T | . | . | −1.46 | 0.74 | * | * | . | 0.08 | 0.13 |
| Leu | 383 | . | A | . | B | T | . | . | −0.86 | 0.49 | . | * | . | 0.36 | 0.25 |
| Gly | 384 | . | A | . | B | T | . | . | −0.04 | 0.20 | * | * | . | 0.94 | 0.49 |
| Cys | 385 | . | . | . | . | . | T | C | 0.88 | −0.09 | * | * | F | 2.17 | 0.43 |
| Pro | 386 | . | . | . | . | . | T | T | 1.34 | −0.09 | * | * | F | 2.80 | 1.03 |
| Asn | 387 | . | . | . | . | . | T | T | 0.42 | −0.34 | * | . | F | 2.52 | 1.03 |
| Gln | 388 | . | . | . | . | . | T | T | 1.23 | −0.09 | * | * | F | 2.24 | 1.58 |
| Arg | 389 | . | . | . | . | . | T | . | 1.69 | −0.26 | * | * | F | 1.76 | 1.77 |
| Gly | 390 | . | . | B | . | . | . | . | 2.36 | −0.69 | * | . | F | 1.38 | 2.15 |
| Leu | 391 | . | . | B | . | . | . | . | 2.36 | −0.69 | * | . | F | 1.10 | 2.15 |
| Gln | 392 | . | . | B | . | . | . | . | 2.06 | −0.66 | * | . | F | 1.44 | 1.70 |
| Arg | 393 | . | . | B | . | . | . | . | 1.76 | −0.27 | * | . | F | 1.48 | 2.30 |
| Gln | 394 | . | . | B | . | . | T | . | 1.34 | −0.31 | * | * | F | 2.02 | 3.74 |
| Pro | 395 | . | . | . | . | . | T | C | 1.80 | −0.61 | * | . | F | 2.86 | 2.89 |
| Ser | 396 | . | . | . | . | T | T | . | 2.72 | −1.01 | * | . | F | 3.40 | 2.89 |
| Ser | 397 | . | . | B | . | . | T | . | 2.72 | −1.01 | * | . | F | 2.66 | 3.27 |
| Ser | 398 | . | . | . | . | . | . | C | 2.31 | −1.41 | * | . | F | 2.62 | 3.53 |
| Arg | 399 | . | . | . | . | T | . | . | 2.01 | −1.46 | . | . | F | 2.78 | 3.53 |
| Arg | 400 | . | . | . | . | T | . | . | 1.93 | −1.46 | . | . | F | 2.74 | 3.53 |
| Asp | 401 | . | . | . | . | T | . | . | 1.93 | −0.93 | * | . | F | 2.90 | 2.77 |
| Ser | 402 | . | . | . | . | . | T | C | 2.23 | −0.93 | . | . | F | 3.00 | 1.90 |
| Ser | 403 | . | . | . | . | . | T | C | 2.22 | −0.93 | . | . | F | 2.70 | 1.68 |
| Trp | 404 | . | . | . | . | . | T | C | 1.81 | −0.44 | . | . | F | 2.10 | 1.45 |
| Ser | 405 | . | . | . | . | . | . | C | 1.70 | −0.06 | . | . | F | 1.60 | 1.45 |
| Glu | 406 | . | A | . | . | . | . | C | 1.11 | −0.44 | . | . | F | 1.10 | 1.87 |
| Thr | 407 | . | A | . | . | . | . | C | 1.11 | −0.33 | . | . | F | 0.80 | 1.80 |
| Ser | 408 | . | A | . | . | . | . | C | 1.17 | −0.86 | . | . | F | 1.10 | 1.80 |
| Glu | 409 | A | A | . | . | . | . | . | 1.16 | −0.49 | . | . | . | 0.60 | 1.63 |
| Ala | 410 | . | A | . | . | T | . | . | 1.11 | −0.10 | . | . | F | 1.00 | 1.51 |
| Ser | 411 | . | A | . | . | T | . | . | 0.30 | −0.16 | . | . | F | 1.00 | 1.12 |
| Tyr | 412 | . | . | . | . | T | T | . | 0.22 | 0.14 | . | . | . | 0.50 | 0.53 |
| Ser | 413 | . | . | . | . | T | T | . | 0.13 | 0.57 | . | . | . | 0.20 | 0.67 |
| Gly | 414 | . | . | . | . | T | T | . | −0.26 | 0.50 | . | . | . | 0.20 | 0.64 |
| Leu | 415 | . | . | B | . | . | T | . | −0.06 | 0.54 | . | . | . | −0.20 | 0.52 |

TABLE II

| Res | Position | I | II | III | IV | V | VI | VII | VIII | IX | X | XI | XII | XIII | XIV |
|---|---|---|---|---|---|---|---|---|---|---|---|---|---|---|---|
| Met | 1 | A | A | . | . | . | . | . | −1.18 | 0.23 | . | * | . | −0.30 | 0.39 |
| Val | 2 | A | A | . | . | . | . | . | −1.09 | 0.44 | . | . | . | −0.60 | 0.23 |
| Leu | 3 | A | A | . | . | . | . | . | −0.70 | 0.40 | * | . | . | −0.30 | 0.24 |

TABLE II-continued

| Res | Position | I | II | III | IV | V | VI | VII | VIII | IX | X | XI | XII | XIII | XIV |
|---|---|---|---|---|---|---|---|---|---|---|---|---|---|---|---|
| Glu | 4 | A | A | . | . | . | . | . | −0.34 | −0.03 | . | . | . | 0.30 | 0.40 |
| Val | 5 | A | A | . | . | . | . | . | 0.04 | −0.14 | . | . | . | 0.30 | 0.74 |
| Ser | 6 | A | . | . | . | . | . | T | −0.21 | −0.39 | . | . | F | 1.00 | 1.55 |
| Asp | 7 | A | . | . | . | . | . | T | −0.17 | −0.43 | . | . | F | 0.85 | 0.67 |
| His | 8 | A | . | . | . | . | . | T | 0.64 | 0.26 | . | . | . | 0.10 | 0.74 |
| Gln | 9 | A | . | . | . | . | . | T | 0.64 | 0.01 | . | . | . | 0.10 | 0.89 |
| Val | 10 | A | A | . | . | . | . | . | 0.91 | −0.37 | . | . | . | 0.30 | 0.89 |
| Leu | 11 | A | A | . | . | . | . | . | 1.21 | 0.13 | . | * | . | −0.30 | 0.66 |
| Asn | 12 | A | A | . | . | . | . | . | 0.36 | −0.37 | . | * | . | 0.30 | 0.66 |
| Asp | 13 | A | A | . | . | . | . | . | −0.20 | −0.13 | * | * | F | 0.45 | 0.66 |
| Ala | 14 | A | A | . | . | . | . | . | −0.79 | −0.27 | . | . | . | 0.30 | 0.81 |
| Glu | 15 | A | A | . | . | . | . | . | −0.74 | −0.46 | . | . | . | 0.30 | 0.51 |
| Val | 16 | A | A | . | . | . | . | . | −0.74 | −0.17 | . | * | . | 0.30 | 0.25 |
| Ala | 17 | A | A | . | . | . | . | . | −0.74 | 0.51 | . | . | . | −0.60 | 0.20 |
| Ala | 18 | A | A | . | . | . | . | . | −0.74 | 0.01 | * | * | . | −0.30 | 0.20 |
| Leu | 19 | A | A | . | . | . | . | . | −0.86 | 0.41 | * | . | . | −0.60 | 0.44 |
| Leu | 20 | A | A | . | . | . | . | . | −1.16 | 0.56 | * | . | . | −0.60 | 0.38 |
| Glu | 21 | A | A | . | . | . | . | . | −0.60 | 0.44 | * | . | . | −0.60 | 0.50 |
| Asn | 22 | A | A | . | . | . | . | . | −0.31 | 0.33 | * | . | F | −0.15 | 0.82 |
| Phe | 23 | . | A | . | . | T | . | . | 0.03 | 0.03 | * | . | F | 0.40 | 1.33 |
| Ser | 24 | . | . | . | . | T | T | . | 0.84 | 0.10 | * | . | F | 0.80 | 1.20 |
| Ser | 25 | . | . | . | . | . | T | C | 1.41 | 0.10 | * | . | F | 0.60 | 1.25 |
| Ser | 26 | . | . | . | . | . | T | C | 1.07 | 0.46 | * | . | F | 0.64 | 2.26 |
| Tyr | 27 | . | . | . | . | . | T | C | 1.07 | 0.10 | * | * | F | 1.28 | 1.67 |
| Asp | 28 | . | . | . | . | T | T | . | 1.77 | −0.29 | * | . | . | 2.27 | 2.16 |
| Tyr | 29 | . | . | . | . | . | T | C | 2.07 | −0.27 | . | . | F | 2.56 | 2.59 |
| Gly | 30 | . | . | . | . | T | T | . | 2.07 | −0.66 | . | . | F | 3.40 | 2.86 |
| Glu | 31 | . | . | . | . | T | T | . | 2.37 | −1.03 | . | . | F | 3.06 | 2.30 |
| Asn | 32 | . | . | . | . | T | . | . | 2.31 | −1.03 | * | . | F | 2.83 | 2.45 |
| Glu | 33 | . | . | . | . | T | . | . | 1.64 | −1.40 | . | . | F | 2.80 | 3.32 |
| Ser | 34 | . | . | . | . | T | . | . | 1.22 | −1.26 | . | . | F | 2.77 | 1.03 |
| Asp | 35 | . | . | . | . | T | T | . | 1.26 | −0.69 | . | . | F | 2.79 | 0.34 |
| Ser | 36 | . | . | . | . | T | T | . | 0.96 | −0.60 | . | . | F | 3.10 | 0.29 |
| Cys | 37 | . | . | . | . | T | T | . | 0.74 | −0.21 | . | . | . | 2.34 | 0.29 |
| Cys | 38 | . | . | . | . | T | T | . | 0.53 | −0.17 | . | . | . | 2.03 | 0.26 |
| Thr | 39 | . | . | . | . | T | . | . | 0.17 | 0.26 | . | . | F | 1.07 | 0.30 |
| Ser | 40 | . | . | . | . | . | . | C | −0.04 | 0.44 | . | . | F | 0.26 | 0.30 |
| Pro | 41 | . | . | . | . | . | T | C | 0.26 | 0.30 | . | . | F | 0.45 | 0.88 |
| Pro | 42 | . | . | . | . | T | T | . | 0.92 | 0.13 | . | . | F | 0.80 | 1.05 |
| Cys | 43 | . | . | B | . | . | T | . | 0.89 | −0.36 | . | . | F | 1.00 | 1.31 |
| Pro | 44 | . | . | B | . | . | T | . | 0.90 | 0.04 | . | * | F | 0.25 | 0.74 |
| Gln | 45 | . | . | B | . | . | . | . | 0.39 | 0.00 | . | * | F | 0.05 | 0.64 |
| Asp | 46 | . | . | B | . | . | . | . | 0.60 | 0.26 | . | * | F | 0.05 | 0.98 |
| Phe | 47 | . | . | B | . | . | . | . | 0.11 | 0.09 | . | * | F | 0.42 | 1.02 |
| Ser | 48 | . | . | B | . | . | . | . | 0.78 | 0.44 | * | * | . | 0.04 | 0.51 |
| Leu | 49 | . | . | B | . | . | . | . | 1.10 | 0.04 | * | * | . | 0.56 | 0.51 |
| Asn | 50 | . | . | B | . | . | T | . | 0.51 | 0.04 | * | * | . | 1.13 | 1.15 |
| Phe | 51 | . | . | . | . | T | T | . | −0.19 | −0.24 | * | * | . | 2.20 | 0.87 |
| Asp | 52 | A | . | . | . | . | T | . | −0.30 | 0.16 | * | . | . | 0.98 | 0.91 |
| Arg | 53 | A | . | . | . | . | T | . | −0.21 | 0.16 | * | . | . | 0.76 | 0.47 |
| Ala | 54 | A | A | . | . | . | . | . | 0.01 | 0.19 | * | . | . | 0.14 | 0.84 |
| Phe | 55 | A | A | . | . | . | . | . | −0.80 | −0.10 | * | . | . | 0.52 | 0.51 |
| Leu | 56 | . | A | B | . | . | . | . | −0.34 | 0.59 | * | . | . | −0.60 | 0.21 |
| Pro | 57 | A | A | . | . | . | . | . | −0.64 | 1.34 | * | . | . | −0.60 | 0.33 |
| Ala | 58 | A | A | . | . | . | . | . | −1.57 | 1.23 | * | * | . | −0.60 | 0.51 |
| Leu | 59 | A | A | . | . | . | . | . | −1.79 | 1.13 | . | . | . | −0.60 | 0.51 |
| Tyr | 60 | A | A | . | . | . | . | . | −1.79 | 1.13 | . | . | . | −0.60 | 0.27 |
| Ser | 61 | A | A | . | . | . | . | . | −1.79 | 1.49 | . | . | . | −0.60 | 0.23 |
| Leu | 62 | . | A | B | . | . | . | . | −2.39 | 1.67 | . | . | . | −0.60 | 0.23 |
| Leu | 63 | . | A | B | . | . | . | . | −2.14 | 1.67 | . | . | . | −0.60 | 0.12 |
| Phe | 64 | . | A | B | . | . | . | . | −2.14 | 1.34 | . | . | . | −0.60 | 0.09 |
| Leu | 65 | . | A | B | . | . | . | . | −2.71 | 1.64 | . | . | . | −0.60 | 0.09 |
| Leu | 66 | . | A | B | . | . | . | . | −2.76 | 1.64 | . | . | . | −0.60 | 0.09 |
| Gly | 67 | . | A | B | . | . | . | . | −1.94 | 1.39 | . | . | . | −0.60 | 0.10 |
| Leu | 68 | . | A | B | . | . | . | . | −1.48 | 1.00 | . | . | . | −0.60 | 0.20 |
| Leu | 69 | . | . | . | . | . | T | C | −1.37 | 0.74 | . | . | . | 0.00 | 0.24 |
| Gly | 70 | . | . | . | . | . | T | C | −1.41 | 0.56 | . | . | F | 0.15 | 0.25 |
| Asn | 71 | . | . | . | . | . | T | C | −1.19 | 0.77 | . | . | F | 0.15 | 0.22 |
| Gly | 72 | A | . | . | . | . | T | . | −1.43 | 0.59 | . | . | F | −0.05 | 0.27 |
| Ala | 73 | A | A | . | . | . | . | . | −1.48 | 0.40 | . | . | . | −0.30 | 0.28 |
| Val | 74 | . | A | B | . | . | . | . | −1.48 | 0.61 | . | . | . | −0.60 | 0.13 |
| Ala | 75 | A | A | . | . | . | . | . | −1.94 | 0.90 | . | . | . | −0.60 | 0.11 |
| Ala | 76 | . | A | B | . | . | . | . | −2.24 | 1.16 | . | . | . | −0.60 | 0.09 |
| Val | 77 | . | A | B | . | . | . | . | −1.79 | 1.04 | . | . | . | −0.60 | 0.16 |
| Leu | 78 | . | A | B | . | . | . | . | −1.09 | 0.40 | . | . | . | −0.30 | 0.31 |
| Leu | 79 | A | A | . | . | . | . | . | −0.54 | −0.10 | . | . | . | 0.56 | 0.59 |
| Ser | 80 | A | . | . | . | . | T | . | −0.54 | −0.11 | . | . | F | 1.52 | 1.16 |

TABLE II-continued

| Res | Position | I | II | III | IV | V | VI | VII | VIII | IX | X | XI | XII | XIII | XIV |
|---|---|---|---|---|---|---|---|---|---|---|---|---|---|---|---|
| Arg | 81 | A | . | . | . | . | T | . | -0.77 | -0.26 | . | . | F | 1.78 | 1.42 |
| Arg | 82 | . | . | B | . | . | T | . | -0.21 | -0.26 | . | . | F | 2.04 | 1.42 |
| Thr | 83 | . | . | B | . | . | T | . | 0.30 | -0.56 | . | . | F | 2.60 | 1.42 |
| Ala | 84 | . | . | B | . | . | . | . | 0.80 | -0.56 | . | . | F | 1.99 | 0.97 |
| Leu | 85 | . | . | B | . | . | . | . | 1.10 | -0.07 | * | . | F | 1.43 | 0.71 |
| Ser | 86 | . | . | B | . | . | . | . | 0.68 | -0.07 | * | . | F | 1.17 | 0.71 |
| Ser | 87 | . | . | . | . | . | T | C | -0.13 | -0.07 | * | * | F | 1.46 | 0.83 |
| Thr | 88 | . | . | . | . | . | T | C | 0.63 | 0.21 | . | . | F | 0.60 | 1.18 |
| Asp | 89 | A | . | . | . | . | T | . | -0.86 | 0.21 | . | . | F | 0.25 | 1.24 |
| Thr | 90 | A | . | . | . | . | T | . | -0.08 | 0.51 | . | . | F | -0.05 | 0.76 |
| Phe | 91 | A | . | . | B | . | . | . | -0.59 | 0.63 | . | . | . | -0.60 | 0.47 |
| Leu | 92 | A | . | . | B | . | . | . | -0.88 | 0.83 | . | . | . | -0.60 | 0.44 |
| Leu | 93 | A | . | . | B | . | . | . | -1.42 | 1.33 | . | . | . | -0.60 | 0.22 |
| His | 94 | A | . | . | B | . | . | . | -2.01 | 1.49 | . | . | . | -0.60 | 0.15 |
| Leu | 95 | A | . | . | B | . | . | . | -1.70 | 1.20 | . | . | . | -0.60 | 0.13 |
| Ala | 96 | A | . | . | B | . | . | . | -1.31 | 0.51 | . | . | . | -0.60 | 0.16 |
| Val | 97 | A | . | . | B | . | . | . | -1.31 | 0.31 | . | . | . | -0.30 | 0.33 |
| Ala | 98 | A | . | . | B | . | . | . | -1.31 | 0.50 | . | . | . | -0.60 | 0.35 |
| Asp | 99 | A | . | . | B | . | . | . | -2.13 | 0.50 | . | . | . | -0.60 | 0.35 |
| Thr | 100 | A | . | . | B | . | . | . | -2.13 | 0.64 | . | . | . | -0.60 | 0.28 |
| Leu | 101 | . | . | B | B | . | . | . | -1.86 | 0.69 | . | . | . | -0.60 | 0.28 |
| Leu | 102 | . | . | B | B | . | . | . | -1.81 | 0.67 | . | . | . | -0.60 | 0.23 |
| Val | 103 | . | . | B | B | . | . | . | -1.43 | 1.36 | . | . | . | -0.60 | 0.20 |
| Leu | 104 | . | . | B | B | . | . | . | -2.24 | 1.30 | . | * | . | -0.60 | 0.11 |
| Thr | 105 | . | . | B | B | . | . | . | -2.22 | 1.30 | . | . | . | -0.60 | 0.21 |
| Leu | 106 | . | . | B | B | . | . | . | -2.00 | 1.53 | . | . | . | -0.60 | 0.21 |
| Pro | 107 | A | . | . | B | . | . | . | -2.04 | 1.39 | . | . | . | -0.60 | 0.30 |
| Leu | 108 | A | . | . | B | . | . | . | -1.19 | 1.34 | . | . | . | -0.60 | 0.37 |
| Trp | 109 | A | . | . | B | . | . | . | -0.97 | 0.86 | . | . | . | -0.60 | 0.19 |
| Ala | 110 | A | . | . | B | . | . | . | -1.24 | 0.67 | . | . | . | -0.60 | 0.38 |
| Val | 111 | A | . | . | B | . | . | . | -1.29 | 0.74 | . | * | . | -0.60 | 0.25 |
| Asp | 112 | A | . | . | B | . | . | . | -1.08 | 0.70 | . | * | . | -0.60 | 0.31 |
| Ala | 113 | A | . | . | B | . | . | . | -0.56 | 0.19 | * | * | . | -0.30 | 0.22 |
| Ala | 114 | A | . | . | B | . | . | . | -1.12 | 0.60 | * | * | . | -0.60 | 0.37 |
| Val | 115 | . | . | B | B | . | . | . | -1.23 | 0.60 | * | * | . | -0.60 | 0.53 |
| Gln | 116 | . | . | B | B | . | . | . | -0.72 | 1.39 | * | * | . | -0.60 | 0.23 |
| Trp | 117 | . | . | B | B | . | . | . | -1.02 | 1.31 | . | * | . | -0.60 | 0.20 |
| Val | 118 | . | . | B | B | . | . | . | -0.78 | 1.20 | . | . | . | -0.60 | 0.20 |
| Phe | 119 | . | . | B | B | . | . | . | -1.00 | 0.99 | . | . | . | -0.60 | 0.36 |
| Gly | 120 | . | . | . | . | . | . | . | -0.81 | 1.27 | . | * | F | 0.35 | 0.20 |
| Ser | 121 | . | . | . | . | T | T | . | -0.77 | 0.93 | . | * | F | 0.35 | 0.16 |
| Gly | 122 | . | . | . | . | T | T | . | -1.33 | 0.29 | * | . | F | 0.65 | 0.12 |
| Leu | 123 | . | . | . | . | T | T | C | -1.07 | 0.14 | * | . | F | 0.45 | 0.27 |
| Cys | 124 | . | A | . | . | . | T | . | -0.71 | 0.21 | * | . | . | -0.30 | 0.20 |
| Lys | 125 | . | A | B | . | . | . | . | -0.96 | 0.26 | * | * | . | -0.30 | 0.15 |
| Val | 126 | . | A | B | . | . | . | . | -1.47 | 0.33 | * | . | . | -0.30 | 0.15 |
| Ala | 127 | . | A | B | . | . | . | . | -1.82 | 0.33 | * | . | . | -0.30 | 0.18 |
| Gly | 128 | . | A | B | . | . | . | . | -1.01 | 0.54 | * | . | . | -0.60 | 0.28 |
| Ala | 129 | A | A | B | . | . | . | . | -1.23 | 0.94 | * | * | . | -0.60 | 0.12 |
| Leu | 130 | . | A | . | . | . | . | . | -1.28 | 0.99 | . | * | . | -0.60 | 0.27 |
| Phe | 131 | . | A | B | . | . | . | . | -1.12 | 0.89 | . | * | . | -0.60 | 0.18 |
| Asn | 132 | . | A | B | . | . | . | . | -0.78 | 1.24 | . | * | . | -0.60 | 0.30 |
| Ile | 133 | . | . | B | . | . | . | . | -1.02 | 1.50 | . | * | . | -0.40 | 0.26 |
| Asn | 134 | . | . | B | . | . | . | . | -0.78 | 1.31 | . | * | . | -0.40 | 0.49 |
| Phe | 135 | . | . | B | . | . | . | . | -0.56 | 0.96 | . | * | . | -0.40 | 0.57 |
| Tyr | 136 | . | A | B | . | . | . | . | -0.67 | 1.06 | . | * | . | -0.60 | 0.35 |
| Ala | 137 | A | A | . | . | . | . | . | -1.48 | 1.06 | . | * | . | -0.60 | 0.51 |
| Gly | 138 | A | A | . | . | . | . | . | -1.40 | 1.34 | . | * | . | -0.60 | 0.26 |
| Ala | 139 | A | A | . | . | . | . | . | -1.99 | 1.24 | . | . | . | -0.60 | 0.25 |
| Leu | 140 | A | A | . | . | . | . | . | -1.96 | 0.99 | . | . | . | -0.60 | 0.13 |
| Leu | 141 | A | A | . | . | . | . | . | -2.60 | 1.06 | . | . | . | -0.60 | 0.13 |
| Leu | 142 | A | A | . | . | . | . | . | -2.31 | 1.31 | . | . | . | -0.60 | 0.07 |
| Ala | 143 | . | A | B | . | . | . | . | -2.67 | 1.20 | . | * | . | -0.60 | 0.05 |
| Cys | 144 | . | A | B | . | . | . | . | -2.08 | 1.30 | . | . | . | -0.60 | 0.08 |
| Ile | 145 | . | A | B | . | . | . | . | -1.16 | 0.61 | * | . | . | -0.60 | 0.08 |
| Ser | 146 | . | A | B | . | . | . | . | -0.59 | -0.07 | * | . | . | 0.30 | 0.17 |
| Phe | 147 | . | . | B | . | . | . | . | -0.59 | 0.19 | * | . | . | -0.10 | 0.33 |
| Asp | 148 | A | . | . | . | . | . | . | 0.00 | -0.07 | * | * | . | 0.25 | 0.96 |
| Arg | 149 | . | . | . | . | . | T | . | -0.22 | 0.01 | * | . | . | 0.25 | 1.35 |
| Tyr | 150 | . | . | . | . | T | T | . | -0.19 | 0.31 | * | * | . | 0.65 | 1.09 |
| Leu | 151 | . | . | B | . | . | T | . | 0.08 | 0.17 | * | . | . | 0.10 | 0.49 |
| Asn | 152 | . | . | B | B | . | . | . | 0.19 | 0.67 | * | . | . | -0.60 | 0.34 |
| Ile | 153 | . | . | B | B | . | . | . | -0.12 | 1.17 | * | . | . | -0.60 | 0.22 |
| Val | 154 | . | . | B | B | . | . | . | -0.23 | 0.90 | . | . | . | -0.60 | 0.38 |
| His | 155 | . | . | B | B | . | . | . | -0.80 | 0.61 | . | . | . | -0.60 | 0.41 |
| Ala | 156 | . | . | B | B | . | . | . | -0.23 | 0.90 | . | * | . | -0.60 | 0.48 |
| Thr | 157 | . | . | B | B | . | . | . | -0.12 | 0.97 | * | . | . | -0.45 | 1.02 |

TABLE II-continued

| Res | Position | I | II | III | IV | V | VI | VII | VIII | IX | X | XI | XII | XIII | XIV |
|---|---|---|---|---|---|---|---|---|---|---|---|---|---|---|---|
| Gln | 158 | . | . | B | B | . | . | . | 0.88 | 0.33 | * | . | . | −0.15 | 1.46 |
| Leu | 159 | . | . | B | B | . | . | . | 1.39 | −0.17 | * | . | . | 0.45 | 2.84 |
| Tyr | 160 | . | . | B | . | . | T | . | 1.21 | −0.24 | * | . | F | 1.30 | 1.95 |
| Arg | 161 | . | . | . | . | . | T | T | . | 1.59 | −0.30 | * | . | F | 2.00 | 1.74 |
| Arg | 162 | . | . | . | . | . | T | T | . | 1.31 | −0.27 | * | * | F | 2.30 | 3.26 |
| Gly | 163 | . | . | . | . | . | T | C | 1.42 | −0.46 | . | * | F | 2.40 | 2.10 |
| Pro | 164 | . | . | . | . | . | T | C | 1.38 | −1.21 | . | * | F | 3.00 | 2.10 |
| Pro | 165 | . | . | . | . | . | T | C | 1.31 | −0.57 | . | * | F | 2.55 | 0.80 |
| Ala | 166 | . | . | . | . | . | T | . | 0.39 | −0.09 | . | * | F | 1.90 | 1.16 |
| Arg | 167 | . | . | B | . | . | T | . | −0.03 | 0.17 | . | * | . | 0.70 | 0.62 |
| Val | 168 | . | . | B | B | . | . | . | −0.36 | 0.23 | * | * | . | 0.00 | 0.58 |
| Thr | 169 | . | . | B | B | . | . | . | −0.96 | 0.37 | . | * | . | −0.30 | 0.31 |
| Leu | 170 | . | . | B | B | . | . | . | −1.33 | 0.56 | . | * | . | −0.60 | 0.13 |
| Thr | 171 | . | . | B | B | . | . | . | −1.60 | 1.06 | * | * | . | −0.60 | 0.18 |
| Cys | 172 | . | . | B | B | . | . | . | −2.00 | 1.06 | * | * | . | −0.60 | 0.09 |
| Leu | 173 | . | . | B | B | . | . | . | −1.49 | 1.49 | . | . | . | −0.60 | 0.12 |
| Ala | 174 | . | . | B | B | . | . | . | −1.99 | 1.23 | . | . | . | −0.60 | 0.08 |
| Val | 175 | A | . | . | B | . | . | . | −1.84 | 1.43 | . | . | . | −0.60 | 0.12 |
| Trp | 176 | A | . | . | B | . | . | . | −2.34 | 1.43 | . | . | . | −0.60 | 0.08 |
| Gly | 177 | A | . | . | B | . | . | . | −2.49 | 1.43 | . | . | . | −0.60 | 0.06 |
| Leu | 178 | . | . | B | B | . | . | . | −2.38 | 1.61 | . | . | . | −0.60 | 0.07 |
| Cys | 179 | . | . | B | B | . | . | . | −2.38 | 1.76 | . | . | . | −0.60 | 0.06 |
| Leu | 180 | . | . | B | B | . | . | . | −2.33 | 1.34 | . | . | . | −0.60 | 0.06 |
| Leu | 181 | . | . | B | B | . | . | . | −2.26 | 1.60 | . | . | . | −0.60 | 0.06 |
| Phe | 182 | . | . | B | B | . | . | . | −1.91 | 1.34 | . | . | . | −0.60 | 0.17 |
| Ala | 183 | . | . | B | B | . | . | . | −1.80 | 0.77 | * | . | . | −0.60 | 0.35 |
| Leu | 184 | A | . | . | . | . | T | . | −2.02 | 0.87 | . | . | . | −0.20 | 0.37 |
| Pro | 185 | A | . | . | . | . | T | . | −1.91 | 0.87 | . | . | . | −0.20 | 0.30 |
| Asp | 186 | A | . | . | . | . | T | . | −1.91 | 0.87 | . | . | . | −0.20 | 0.26 |
| Phe | 187 | A | . | . | . | . | T | . | −1.51 | 1.06 | . | . | . | −0.20 | 0.26 |
| Ile | 188 | A | . | . | B | . | . | . | −1.51 | 0.76 | . | . | . | −0.60 | 0.22 |
| Phe | 189 | A | A | . | B | . | . | . | −0.73 | 0.83 | . | . | . | −0.60 | 0.13 |
| Leu | 190 | A | A | . | B | . | . | . | −0.56 | 1.33 | . | . | . | −0.60 | 0.21 |
| Ser | 191 | A | A | . | B | . | . | . | −0.56 | 1.04 | . | . | . | −0.60 | 0.41 |
| Ala | 192 | A | A | . | . | . | . | . | 0.14 | 0.36 | . | * | . | −0.30 | 0.79 |
| His | 193 | A | A | . | . | . | . | . | 1.14 | −0.43 | . | * | . | 0.45 | 1.66 |
| His | 194 | A | A | . | . | . | . | . | 1.03 | −1.11 | . | * | F | 0.75 | 2.43 |
| Asp | 195 | A | A | . | . | . | . | . | 1.84 | −0.81 | . | * | F | 0.90 | 1.98 |
| Glu | 196 | A | A | . | . | . | . | . | 1.56 | −0.91 | . | * | F | 0.90 | 2.34 |
| Arg | 197 | A | A | . | . | . | . | . | 1.83 | −0.91 | . | * | F | 0.90 | 1.74 |
| Leu | 198 | A | A | . | . | . | . | . | 1.83 | −0.93 | . | * | . | 0.90 | 1.50 |
| Asn | 199 | A | A | . | . | . | . | . | 1.20 | −0.43 | . | * | . | 0.45 | 1.18 |
| Ala | 200 | A | A | . | . | . | . | . | 1.20 | 0.14 | . | * | . | −0.30 | 0.32 |
| Thr | 201 | A | A | . | . | . | . | . | 0.96 | 0.54 | . | * | . | −0.60 | 0.68 |
| His | 202 | . | A | . | . | T | . | . | 0.84 | 0.61 | . | * | . | −0.20 | 0.66 |
| Cys | 203 | . | . | . | . | T | T | . | 0.96 | 0.61 | . | * | . | 0.35 | 1.05 |
| Gln | 204 | . | . | . | . | T | T | . | 0.74 | 0.90 | * | . | . | 0.20 | 0.63 |
| Tyr | 205 | . | . | . | . | T | T | . | 1.33 | 0.84 | * | . | . | 0.20 | 0.72 |
| Asn | 206 | . | . | B | . | . | T | . | 0.79 | 0.74 | * | . | . | −0.05 | 2.32 |
| Phe | 207 | . | . | B | B | . | . | . | 0.48 | 0.81 | * | * | . | −0.60 | 0.99 |
| Pro | 208 | . | . | B | B | . | . | . | 1.26 | 0.84 | * | * | F | −0.45 | 0.63 |
| Gln | 209 | . | . | . | B | T | . | . | 0.94 | 0.09 | * | * | F | 0.25 | 0.76 |
| Val | 210 | . | . | B | B | . | . | . | 0.60 | 0.17 | * | * | F | 0.00 | 1.27 |
| Gly | 211 | . | . | B | B | . | . | . | −0.21 | −0.11 | * | * | F | 0.45 | 0.83 |
| Arg | 212 | . | . | B | B | . | . | . | 0.60 | 0.14 | * | * | F | −0.15 | 0.40 |
| Thr | 213 | . | . | B | B | . | . | . | −0.04 | −0.26 | * | * | F | 0.60 | 1.05 |
| Ala | 214 | . | . | B | B | . | . | . | −0.86 | −0.26 | * | * | . | 0.30 | 0.78 |
| Leu | 215 | . | . | B | B | . | . | . | 0.00 | 0.00 | * | * | . | 0.30 | 0.33 |
| Arg | 216 | . | . | B | B | . | . | . | −0.47 | 0.40 | * | * | . | −0.30 | 0.40 |
| Val | 217 | . | . | B | B | . | . | . | −1.43 | 0.60 | * | * | . | −0.60 | 0.32 |
| Leu | 218 | . | . | B | B | . | . | . | −1.71 | 0.74 | * | . | . | −0.60 | 0.29 |
| Gln | 219 | . | . | B | B | . | . | . | −1.47 | 0.56 | * | . | . | −0.60 | 0.15 |
| Leu | 220 | . | . | B | B | . | . | . | −1.36 | 0.99 | * | . | . | −0.60 | 0.20 |
| Val | 221 | . | . | B | B | . | . | . | −2.28 | 1.13 | * | . | . | −0.60 | 0.21 |
| Ala | 222 | . | . | B | B | . | . | . | −2.23 | 1.13 | * | . | . | −0.60 | 0.10 |
| Gly | 223 | . | . | B | B | . | . | . | −1.63 | 1.41 | * | * | . | −0.60 | 0.10 |
| Phe | 224 | . | . | B | B | . | . | . | −2.44 | 1.16 | * | . | . | −0.60 | 0.21 |
| Leu | 225 | . | . | B | B | . | . | . | −2.44 | 1.20 | . | . | . | −0.60 | 0.17 |
| Leu | 226 | . | . | B | B | . | . | . | −2.44 | 1.39 | . | . | . | −0.60 | 0.14 |
| Pro | 227 | A | . | . | B | . | . | . | −2.46 | 1.60 | . | . | . | −0.60 | 0.12 |
| Leu | 228 | A | . | . | B | . | . | . | −2.70 | 1.43 | . | . | . | −0.60 | 0.15 |
| Leu | 229 | A | . | . | B | . | . | . | −2.24 | 1.24 | . | . | . | −0.60 | 0.18 |
| Val | 230 | A | . | . | B | . | . | . | −2.10 | 1.31 | . | . | . | −0.60 | 0.18 |
| Met | 231 | A | . | . | B | . | . | . | −1.53 | 1.46 | . | . | . | −0.60 | 0.12 |
| Ala | 232 | A | . | . | B | . | . | . | −1.91 | 1.53 | . | . | . | −0.60 | 0.22 |
| Tyr | 233 | A | . | . | B | . | . | . | −1.13 | 1.34 | . | . | . | −0.60 | 0.30 |
| Cys | 234 | A | . | . | B | . | . | . | −1.21 | 1.20 | . | . | . | −0.60 | 0.42 |

TABLE II-continued

| Res | Position | I | II | III | IV | V | VI | VII | VIII | IX | X | XI | XII | XIII | XIV |
|---|---|---|---|---|---|---|---|---|---|---|---|---|---|---|---|
| Tyr | 235 | A | . | . | B | . | . | . | −1.17 | 1.27 | . | . | . | −0.60 | 0.29 |
| Ala | 236 | A | . | . | B | . | . | . | −1.16 | 1.46 | . | . | . | −0.60 | 0.15 |
| His | 237 | A | . | . | B | . | . | . | −1.42 | 1.20 | . | . | . | −0.60 | 0.29 |
| Ile | 238 | A | . | . | B | . | . | . | −1.99 | 1.27 | . | . | . | −0.60 | 0.14 |
| Leu | 239 | A | . | . | B | . | . | . | −2.13 | 1.20 | . | . | . | −0.60 | 0.11 |
| Ala | 240 | . | . | B | B | . | . | . | −2.74 | 1.39 | . | . | . | −0.60 | 0.07 |
| Val | 241 | . | . | B | B | . | . | . | −2.46 | 1.53 | . | * | . | −0.60 | 0.07 |
| Leu | 242 | . | . | B | B | . | . | . | −2.31 | 1.23 | . | * | . | −0.60 | 0.12 |
| Leu | 243 | . | . | B | B | . | . | . | −1.77 | 0.54 | . | * | . | −0.60 | 0.23 |
| Val | 244 | . | . | B | B | . | . | . | −0.96 | 0.47 | * | . | . | −0.60 | 0.30 |
| Ser | 245 | . | . | B | . | . | T | . | −0.26 | 0.23 | * | * | F | 0.25 | 0.63 |
| Arg | 246 | A | . | . | . | . | T | . | 0.71 | −0.46 | * | * | F | 1.00 | 1.50 |
| Gly | 247 | A | . | . | . | . | T | . | 0.71 | −1.14 | * | * | F | 1.30 | 3.96 |
| Gln | 248 | A | . | . | . | . | T | . | 1.63 | −1.10 | * | * | F | 1.30 | 2.43 |
| Arg | 249 | A | A | . | . | . | . | . | 1.90 | −1.49 | * | * | F | 0.90 | 2.43 |
| Arg | 250 | . | A | B | . | . | . | . | 1.60 | −0.99 | * | * | F | 0.90 | 2.49 |
| Leu | 251 | . | A | B | . | . | . | . | 1.60 | −0.80 | * | * | . | 0.75 | 1.42 |
| Arg | 252 | . | A | B | . | . | . | . | 1.13 | −1.20 | * | * | . | 0.75 | 1.42 |
| Ala | 253 | . | A | B | . | . | . | . | 0.28 | −0.51 | * | * | . | 0.60 | 0.60 |
| Met | 254 | . | . | B | B | . | . | . | −0.69 | 0.13 | * | . | . | −0.30 | 0.54 |
| Arg | 255 | . | . | B | B | . | . | . | −1.66 | 0.09 | . | * | . | −0.30 | 0.20 |
| Leu | 256 | . | . | B | B | . | . | . | −1.70 | 0.73 | * | . | . | −0.60 | 0.15 |
| Val | 257 | . | . | B | B | . | . | . | −2.67 | 0.87 | * | . | . | −0.60 | 0.11 |
| Val | 258 | . | . | B | B | . | . | . | −2.93 | 0.90 | * | * | . | −0.60 | 0.04 |
| Val | 259 | . | . | B | B | . | . | . | −2.92 | 1.54 | * | * | . | −0.60 | 0.04 |
| Val | 260 | . | . | B | B | . | . | . | −3.73 | 1.36 | * | * | . | −0.60 | 0.05 |
| Val | 261 | . | . | B | B | . | . | . | −3.51 | 1.50 | . | . | . | −0.60 | 0.06 |
| Val | 262 | . | . | B | B | . | . | . | −3.47 | 1.36 | . | . | . | −0.60 | 0.08 |
| Ala | 263 | . | . | B | B | . | . | . | −3.28 | 1.40 | . | . | . | −0.60 | 0.09 |
| Phe | 264 | . | . | B | B | . | . | . | −2.71 | 1.33 | . | . | . | −0.60 | 0.07 |
| Ala | 265 | A | . | . | B | . | . | . | −2.17 | 1.60 | . | . | . | −0.60 | 0.09 |
| Leu | 266 | A | . | . | B | . | . | . | −1.52 | 1.44 | . | . | . | −0.60 | 0.13 |
| Cys | 267 | . | . | . | B | T | . | . | −0.91 | 1.37 | . | . | . | −0.20 | 0.24 |
| Trp | 268 | . | . | . | B | T | . | . | −0.36 | 1.34 | . | . | . | −0.20 | 0.37 |
| Thr | 269 | . | . | . | . | . | T | C | −0.47 | 1.34 | . | . | . | 0.00 | 0.61 |
| Pro | 270 | . | . | . | . | T | T | . | −0.73 | 1.34 | . | . | . | 0.20 | 0.95 |
| Tyr | 271 | . | . | . | . | T | T | . | −0.78 | 1.41 | . | . | . | 0.20 | 0.67 |
| His | 272 | . | . | B | . | . | T | . | −0.92 | 1.14 | . | . | . | −0.20 | 0.34 |
| Leu | 273 | . | . | B | B | . | . | . | −1.49 | 1.34 | . | . | . | −0.60 | 0.18 |
| Val | 274 | . | . | B | B | . | . | . | −1.18 | 1.56 | . | * | . | −0.60 | 0.09 |
| Val | 275 | . | . | B | B | . | . | . | −1.86 | 0.80 | . | * | . | −0.60 | 0.11 |
| Leu | 276 | . | . | B | B | . | . | . | −2.42 | 0.99 | . | * | . | −0.60 | 0.09 |
| Val | 277 | . | . | B | B | . | . | . | −2.99 | 0.99 | . | * | . | −0.60 | 0.10 |
| Asp | 278 | . | . | B | B | . | . | . | −2.18 | 0.96 | * | * | . | −0.60 | 0.13 |
| Ile | 279 | A | . | . | B | . | . | . | −2.13 | 0.31 | * | * | . | −0.30 | 0.27 |
| Leu | 280 | A | . | . | B | . | . | . | −1.62 | 0.31 | * | * | . | −0.30 | 0.30 |
| Met | 281 | A | . | . | B | . | . | . | −1.40 | 0.10 | * | * | . | −0.30 | 0.18 |
| Asp | 282 | A | . | . | B | . | . | . | −1.36 | 0.60 | * | * | . | −0.60 | 0.26 |
| Leu | 283 | A | A | . | . | . | . | . | −1.94 | 0.60 | * | * | . | −0.60 | 0.26 |
| Gly | 284 | A | A | . | . | . | . | . | −0.94 | 0.41 | * | * | . | −0.60 | 0.26 |
| Ala | 285 | A | A | . | . | . | . | . | −0.13 | −0.20 | * | * | . | 0.30 | 0.31 |
| Leu | 286 | A | A | . | . | . | . | . | −0.20 | 0.20 | * | * | . | 0.04 | 0.60 |
| Ala | 287 | A | . | . | . | . | T | . | −0.54 | 0.09 | * | * | . | 0.78 | 0.33 |
| Arg | 288 | A | . | . | . | . | T | . | 0.38 | 0.09 | * | * | . | 1.12 | 0.32 |
| Asn | 289 | . | . | . | . | T | T | . | 0.72 | −0.41 | * | * | . | 2.46 | 0.76 |
| Cys | 290 | . | . | . | . | T | T | . | 1.01 | −1.10 | * | * | F | 3.40 | 1.30 |
| Gly | 291 | . | . | . | . | T | T | . | 1.93 | −1.21 | * | * | F | 2.91 | 0.89 |
| Arg | 292 | . | . | . | . | T | T | . | 1.67 | −1.21 | * | * | F | 2.72 | 1.08 |
| Glu | 293 | . | . | B | . | . | T | . | 1.56 | −0.97 | * | * | F | 1.98 | 1.50 |
| Ser | 294 | . | . | B | . | . | T | . | 0.70 | −1.54 | . | * | F | 1.64 | 2.53 |
| Arg | 295 | . | . | B | . | . | . | . | 0.78 | −1.33 | * | . | F | 0.95 | 0.96 |
| Val | 296 | A | . | . | . | . | . | . | 1.17 | −0.83 | . | . | F | 0.95 | 0.56 |
| Asp | 297 | A | . | . | . | . | . | . | 0.76 | −0.83 | . | * | . | 0.80 | 0.83 |
| Val | 298 | . | . | B | . | . | . | . | −0.10 | −0.83 | . | * | . | 0.80 | 0.57 |
| Ala | 299 | . | . | B | . | . | . | . | −0.11 | −0.19 | . | * | . | 0.50 | 0.57 |
| Lys | 300 | . | . | B | . | . | . | . | −0.52 | −0.34 | . | * | F | 0.65 | 0.49 |
| Ser | 301 | . | . | B | . | . | . | . | −0.01 | 0.04 | * | . | F | 0.05 | 0.89 |
| Val | 302 | . | . | B | . | . | . | . | −0.82 | −0.17 | * | . | F | 0.65 | 0.87 |
| Thr | 303 | . | . | B | . | . | T | . | −0.31 | 0.01 | * | . | F | 0.25 | 0.36 |
| Ser | 304 | . | . | . | . | T | T | . | 0.03 | 0.44 | * | . | F | 0.35 | 0.27 |
| Gly | 305 | . | . | . | . | T | T | . | −0.61 | 0.81 | * | . | F | 0.35 | 0.56 |
| Leu | 306 | . | . | . | . | T | T | . | −0.34 | 0.79 | . | . | . | 0.20 | 0.38 |
| Gly | 307 | . | . | . | . | T | . | . | −0.16 | 0.80 | . | . | . | 0.00 | 0.39 |
| Tyr | 308 | . | . | B | . | . | . | . | −0.51 | 0.99 | . | . | . | −0.40 | 0.21 |
| Met | 309 | . | . | B | . | . | . | . | −1.02 | 1.13 | . | . | . | −0.40 | 0.14 |
| His | 310 | . | . | B | . | . | . | . | −0.68 | 1.13 | . | * | . | −0.40 | 0.11 |
| Cys | 311 | . | . | B | . | . | . | . | −0.08 | 1.10 | * | . | . | −0.40 | 0.12 |

TABLE II-continued

| Res | Position | I | II | III | IV | V | VI | VII | VIII | IX | X | XI | XII | XIII | XIV |
|---|---|---|---|---|---|---|---|---|---|---|---|---|---|---|---|
| Cys | 312 | . | . | B | . | . | . | . | −0.54 | 0.77 | . | * | . | −0.40 | 0.18 |
| Leu | 313 | . | . | B | . | . | . | . | −1.11 | 0.84 | * | . | . | −0.40 | 0.11 |
| Asn | 314 | . | . | B | . | . | T | . | −0.76 | 1.03 | * | * | . | −0.20 | 0.17 |
| Pro | 315 | . | . | B | . | . | T | . | −1.31 | 1.21 | * | . | . | −0.20 | 0.50 |
| Leu | 316 | A | . | . | . | . | T | . | −1.34 | 1.14 | * | . | . | −0.20 | 0.61 |
| Leu | 317 | A | . | . | . | . | T | . | −1.53 | 1.24 | * | . | . | −0.20 | 0.33 |
| Tyr | 318 | . | . | B | B | . | . | . | −1.07 | 1.49 | * | . | . | −0.60 | 0.16 |
| Ala | 319 | . | . | B | B | . | . | . | −1.92 | 1.49 | . | * | . | −0.60 | 0.19 |
| Phe | 320 | . | . | B | B | . | . | . | −1.67 | 1.44 | . | * | . | −0.60 | 0.17 |
| Val | 321 | . | . | B | B | . | . | . | −1.56 | 0.76 | . | * | . | −0.60 | 0.22 |
| Gly | 322 | A | . | . | B | . | . | . | −0.63 | 0.79 | . | * | . | −0.60 | 0.19 |
| Val | 323 | A | . | . | B | . | . | . | −0.39 | 0.29 | . | * | . | −0.30 | 0.42 |
| Lys | 324 | A | . | . | B | . | . | . | 0.31 | −0.50 | . | * | . | 0.60 | 0.99 |
| Phe | 325 | A | A | . | . | . | . | . | 0.41 | −1.14 | . | * | F | 0.90 | 1.96 |
| Arg | 326 | A | A | . | . | . | . | . | 0.98 | −0.96 | . | * | F | 0.90 | 2.61 |
| Glu | 327 | A | A | . | . | . | . | . | 0.72 | −0.69 | . | * | . | 0.75 | 1.37 |
| Arg | 328 | A | A | . | B | . | . | . | 0.77 | −0.07 | * | * | . | 0.45 | 1.57 |
| Met | 329 | A | A | . | B | . | . | . | −0.09 | −0.17 | . | * | . | 0.30 | 0.66 |
| Trp | 330 | A | A | . | B | . | . | . | −0.20 | 0.51 | * | * | . | −0.60 | 0.31 |
| Met | 331 | A | A | . | B | . | . | . | −0.20 | 1.20 | * | * | . | −0.60 | 0.13 |
| Leu | 332 | A | A | . | B | . | . | . | −1.01 | 1.20 | * | * | . | −0.60 | 0.26 |
| Leu | 333 | A | A | . | B | . | . | . | −1.47 | 1.27 | * | * | . | −0.60 | 0.21 |
| Leu | 334 | . | A | B | B | . | . | . | −1.53 | 0.79 | * | * | . | −0.60 | 0.21 |
| Arg | 335 | . | A | . | B | T | . | . | −1.46 | 0.74 | * | * | . | 0.08 | 0.13 |
| Leu | 336 | . | A | . | B | T | . | . | −0.86 | 0.49 | . | * | . | 0.36 | 0.25 |
| Gly | 337 | . | A | . | B | T | . | . | −0.04 | 0.20 | * | * | . | 0.94 | 0.49 |
| Cys | 338 | . | . | . | . | . | T | C | 0.88 | −0.09 | * | * | F | 2.17 | 0.43 |
| Pro | 339 | . | . | . | . | T | T | . | 1.34 | −0.09 | * | * | F | 2.80 | 1.03 |
| Asn | 340 | . | . | . | . | T | T | . | 0.42 | −0.34 | * | . | F | 2.52 | 1.03 |
| Gln | 341 | . | . | . | . | T | T | . | 1.23 | −0.09 | * | * | F | 2.24 | 1.58 |
| Arg | 342 | . | . | . | . | . | T | . | 1.69 | −0.26 | * | * | F | 1.76 | 1.77 |
| Gly | 343 | . | . | B | . | . | . | . | 2.36 | −0.69 | * | . | F | 1.38 | 2.15 |
| Leu | 344 | . | . | B | . | . | . | . | 2.36 | −0.69 | * | . | F | 1.10 | 2.15 |
| Gln | 345 | . | . | B | . | . | . | . | 2.06 | −0.66 | * | . | F | 1.44 | 1.70 |
| Arg | 346 | . | . | B | . | . | . | . | 1.76 | −0.27 | * | . | F | 1.48 | 2.30 |
| Gln | 347 | . | . | B | . | . | T | . | 1.34 | −0.31 | * | * | F | 2.02 | 3.74 |
| Pro | 348 | . | . | . | . | . | T | C | 1.80 | −0.61 | * | . | F | 2.86 | 2.89 |
| Ser | 349 | . | . | . | . | T | T | . | 2.72 | −1.01 | * | . | F | 3.40 | 2.89 |
| Ser | 350 | . | . | B | . | . | T | . | 2.72 | −1.01 | * | . | F | 2.66 | 3.27 |
| Ser | 351 | . | . | . | . | . | . | C | 2.31 | −1.41 | * | . | F | 2.62 | 3.53 |
| Arg | 352 | . | . | . | . | T | . | . | 2.01 | −1.46 | . | . | F | 2.78 | 3.53 |
| Arg | 353 | . | . | . | . | T | . | . | 1.93 | −1.46 | . | . | F | 2.74 | 3.53 |
| Asp | 354 | . | . | . | . | T | T | . | 1.93 | −0.93 | . | . | F | 2.90 | 2.77 |
| Ser | 355 | . | . | . | . | . | T | C | 2.23 | −0.93 | . | . | F | 3.00 | 1.90 |
| Ser | 356 | . | . | . | . | . | T | C | 2.22 | −0.93 | . | . | F | 2.70 | 1.68 |
| Trp | 357 | . | . | . | . | . | T | C | 1.81 | −0.44 | . | . | F | 2.10 | 1.45 |
| Ser | 358 | . | . | . | . | . | . | C | 1.70 | −0.06 | . | . | F | 1.60 | 1.45 |
| Glu | 359 | . | A | . | . | . | . | C | 1.11 | −0.44 | . | . | F | 1.10 | 1.87 |
| Thr | 360 | . | A | . | . | . | . | C | 1.11 | −0.33 | . | . | F | 0.80 | 1.80 |
| Ser | 361 | . | A | . | . | . | . | C | 1.17 | −0.86 | . | . | F | 1.10 | 1.80 |
| Glu | 362 | A | A | . | . | . | . | . | 1.16 | −0.49 | . | . | F | 0.60 | 1.63 |
| Ala | 363 | . | A | . | . | T | . | . | 1.11 | −0.10 | . | . | F | 1.00 | 1.51 |
| Ser | 364 | . | A | . | . | T | . | . | 0.30 | −0.16 | . | . | F | 1.00 | 1.12 |
| Tyr | 365 | . | . | . | . | T | T | . | 0.22 | 0.14 | . | . | . | 0.50 | 0.53 |
| Ser | 366 | . | . | . | . | T | T | . | 0.13 | 0.57 | . | . | . | 0.20 | 0.67 |
| Gly | 367 | . | . | . | . | T | T | . | −0.26 | 0.50 | . | . | . | 0.20 | 0.64 |
| Leu | 368 | . | . | B | . | . | T | . | −0.06 | 0.54 | . | . | . | −0.20 | 0.52 |

In another preferred embodiment, the invention provides an isolated nucleic acid molecule comprising a polynucleotide which hybridizes under stringent hybridization conditions to a portion of the polynucleotide in a nucleic acid molecule of the invention described above, for instance, the sequence complementary to the coding and/or noncoding sequence depicted in FIGS. 2A and 2B (SEQ ID NO:3), the sequence of the cDNA clone contained in the deposit having ATCC Accession No. 97334, or fragments (such as, for example, the open reading frame or a fragment thereof) of these sequences, as described herein. By "stringent hybridization conditions" is intended overnight incubation at 42° C. in a solution comprising: 50% formamide, 5×SSC (750 mM NaCl, 75 mM trisodium citrate), 50 mM sodium phosphate (pH 7.6), 5×Denhardt's solution, 10% dextran sulfate, and 20 µg/ml denatured, sheared salmon sperm DNA, followed by washing the filters in 0.1×SSC at about 65° C.

By a polynucleotide which hybridizes to a "portion" of a polynucleotide is intended a polynucleotide (either DNA or RNA) hybridizing to at least about 15 nucleotides (nt), and more preferably at least about 20 nt, still more preferably at least about 30 nt, and even more preferably about 30-70 nt of the reference polynucleotide. These are useful, for example, as diagnostic probes and primers as discussed above and in more detail below. In this context "about" includes the particularly recited size, larger or smaller by several (5, 4, 3, 2, or 1) nucleotides, at either terminus or at both termini.

By a portion of a polynucleotide of "at least 20 nt in length," for example, is intended 20 or more contiguous nucleotides from the nucleotide sequence of the reference polynucleotide (e.g., the nucleotide sequence as shown in FIG. 1 (SEQ ID NO:1) or FIG. 2 (SEQ ID NO:3).

Of course, a polynucleotide which hybridizes only to a poly A sequence (such as the 3' terminal poly(A) tract of the G-protein Chemokine Receptor cDNA shown in FIG. 1 (SEQ ID NO:1) and FIG. 2 (SEQ ID NO:3), or to a complementary stretch of T (or U) resides, would not be included in a polynucleotide of the invention used to hybridize to a portion of a nucleic acid of the invention, since such a polynucleotide would hybridize to any nucleic acid molecule containing a poly (A) stretch or the complement thereof (e.g., practically any double-stranded cDNA clone generated using oligo dT as a primer).

In specific embodiments, the polynucleotides of the invention are less than 110000 kb, 50000 kb, 10000 kb, 1000 kb, 500 kb, 400 kb, 350 kb, 300 kb, 250 kb, 200 kb, 175 kb, 150 kb, 125 kb, 100 kb, 75 kb, 50 kb, 40 kb, 30 kb, 25 kb, 20 kb, 15 kb, 10 kb, 7.5 kb, or 5 kb in length.

In further embodiments, polynucleotides of the invention comprise at least 15, at least 30, at least 50, at least 100, or at least 250, at least 500, or at least 1000 contiguous nucleotides of G-protein Chemokine Receptor coding sequence, but consist of less than or equal to 107 kb, 75 kb, 50 kb, 30 kb, 25 kb, 20 kb, 15 kb, 10 kb, or 5 kb of genomic DNA that flanks the 5' or 3' coding nucleotide set forth in FIG. 1 (SEQ ID NO:1) or more preferably FIG. 2 (SEQ ID NO:3). In further embodiments, polynucleotides of the invention comprise at least 15, at least 30, at least 50, at least 100, or at least 250, at least 500, or at least 1000 contiguous nucleotides of G-protein Chemokine Receptor and/or coding sequence, but do not comprise all or a portion of any G-protein Chemokine Receptor intron. In another embodiment, the nucleic acid comprising G-protein Chemokine Receptor coding sequence does not contain coding sequences of a genomic flanking gene (i.e., 5' or 3' to the G-protein Chemokine Receptor gene in the genome). In other embodiments, the polynucleotides of the invention do not contain the coding sequence of more than 1000, 500, 250, 100, 50, 25, 20, 15, 10, 5, 4, 3, 2, or 1 genomic flanking gene(s).

As indicated, nucleic acid molecules of the present invention which encode a G-protein Chemokine Receptor polypeptide may include, but are not limited to, the coding sequence for the mature polypeptide, by itself; the coding sequence for the mature polypeptide and additional sequences, such as the coding sequence of the mature polypeptide, together with additional, non-coding sequences, including for example, but not limited to introns and non-coding 5' and 3' sequences, such as the transcribed, non-translated sequences that play a role in transcription, mRNA processing—including splicing and polyadenylation signals, for example—ribosome binding and stability of mRNA; additional coding sequence which codes for additional amino acids, such as those which provide additional functionalities. Thus, for instance, the polypeptide may be fused to a marker sequence, such as a peptide, which facilitates purification of the fused polypeptide. In certain preferred embodiments of this aspect of the invention, the marker sequence is a hexa-histidine peptide, such as the tag provided in a pQE vector (Qiagen, Inc.), among others, many of which are commercially available. As described in Gentz et al., *Proc. Natl. Acad. Sci. USA* 86: 821-824 (1989), for instance, hexa-histidine provides for convenient purification of the fusion protein. The "HA" tag is another peptide useful for purification which corresponds to an epitope derived from the influenza hemagglutinin protein, which has been described by Wilson et al., *Cell* 37:767-778 (1984). As discussed below, other such fusion proteins include the G-protein Chemokine Receptor receptor fused to Fc at the N- or C-terminus.

The present invention further relates to variants of the nucleic acid molecules of the present invention, which encode portions, analogs, or derivatives of the G-protein Chemokine Receptor receptor. Variants may occur naturally, such as a natural allelic variant. By an "allelic variant" is intended one of several alternate forms of a gene occupying a given locus on a chromosome of an organism. Genes II, Lewin, B., ed., John Wiley & Sons, New York (1985). Non-naturally occurring variants may be produced using art-known mutagenesis techniques.

Such variants include those produced by nucleotide substitutions, deletions or additions that may involve one or more nucleotides. The variants may be altered in coding or non-coding regions or both. Alterations in the coding regions may produce conservative or non-conservative amino acid substitutions, deletions, or additions. Especially preferred among these are silent substitutions, additions, and deletions, which do not alter the properties and activities of the G-protein Chemokine Receptor receptor or portions thereof. Also especially preferred in this regard are conservative substitutions.

Further embodiments of the invention include isolated nucleic acid molecules comprising, or alternatively consisting of, a polynucleotide having a nucleotide sequence identical to: (a) a nucleotide sequence encoding the polypeptide having the amino acid sequence shown in FIG. 1 (SEQ ID NO:2); (b) a nucleotide sequence encoding the polypeptide having the amino acid sequence in FIG. 1 (SEQ ID NO:2), but lacking the amino terminal methionine; (c) a nucleotide sequence encoding the polypeptide having the amino acid sequence at positions about 1 to about 415 in FIG. 1 (SEQ ID NO:2); (d) a nucleotide sequence encoding the G-protein Chemokine Receptor extracellular domain; (e) a nucleotide sequence encoding the G-protein Chemokine Receptor transmembrane domain; (f) a nucleotide sequence encoding the G-protein Chemokine Receptor receptor intracellular domain; (g) a nucleotide sequence encoding the G-protein Chemokine Receptor receptor extracellular and intracellular domains with all or part of the transmembrane domain deleted; and (h) a nucleotide sequence complementary to any of the nucleotide sequences in (a), (b), (c), (d), (e), (f), or (g) above. Polypeptides encoded by these polynucleotides are also encompassed by the invention.

Preferred embodiments of the invention include isolated nucleic acid molecules comprising, or alternatively consisting of, a polynucleotide having a nucleotide sequence identical to: (a) a nucleotide sequence encoding the polypeptide having the amino acid sequence shown in FIG. 2 (SEQ ID NO:4); (b) a nucleotide sequence encoding the polypeptide having the amino acid sequence in FIG. 2 (SEQ ID NO:4), but lacking the amino terminal methionine; (c) a nucleotide sequence encoding the polypeptide having the amino acid sequence at positions about 1 to about 368 in FIG. 2 (SEQ ID NO:4); (d) a nucleotide sequence encoding a G-protein Chemokine Receptor extracellular domain (e.g. amino acid residues from 1 to 59, 114 to 127, 191 to 223, and/or 278 to 307 in SEQ ID NO: 4); (e) a nucleotide sequence encoding a G-protein Chemokine Receptor transmembrane domain (e.g. amino acid residues from 60 to 79, 92 to 113, 128 to 147, 170 to 190, 224 to 245, 259 to 277, and/or 302 to 322 in SEQ ID NO:4); (f) a nucleotide sequence encoding a G-protein Chemokine Receptor receptor intracellular domain (e.g. amino acid residues from 80 to 91, 148 to 169, 246 to 258, and/or 323 to 368 in SEQ ID NO: 4); (g) a nucleotide sequence encoding the G-protein Chemokine Receptor receptor extracellular and intracellular domains with all or part of the transmembrane domain deleted; (h) the nucleotide sequence of the cDNA clone contained in the deposit having ATCC Accession No. 97768; and (i) a nucleotide sequence complementary to any of the nucleotide sequences in (a), (b), (c), (d), (e), (f), (g) or (h) above. Polypeptides encoded by these polynucleotides are also encompassed by the invention.

Further embodiments of the invention include isolated nucleic acid molecules comprising, or alternatively consisting of, a polynucleotide having a nucleotide sequence at least 90% identical, and more preferably at least 95%, 96%, 97%, 98%, or 99% identical to: (a) a nucleotide sequence encoding the polypeptide having the amino acid sequence shown in FIG. 1 (SEQ ID NO:2); (b) a nucleotide sequence encoding the polypeptide having the amino acid sequence in FIG. 1 (SEQ ID NO:2), but lacking the amino terninal methionine; (c) a nucleotide sequence encoding the polypeptide having the amino acid sequence at positions about 1 to about 415 in FIG. 1 (SEQ ID NO:2); (d) a nucleotide sequence encoding the G-protein Chemokine Receptor extracellular domain; (e) a nucleotide sequence encoding the G-protein Chemokine Receptor transmembrane domain; (f) a nucleotide sequence encoding the G-protein Chemokine Receptor receptor intracellular domain; (g) a nucleotide sequence encoding the G-protein Chemokine Receptor receptor extracellular and intracellular domains with all or part of the transmembrane domain deleted; and (h) a nucleotide sequence complementary to any of the nucleotide sequences in (a), (b), (c), (d), (e), (f), or (g) above. Polypeptides encoded by these polynucleotides are also encompassed by the invention.

Preferred embodiments of the invention include isolated nucleic acid molecules comprising, or alternatively consisting of, a polynucleotide having a nucleotide sequence at least 90% identical, and more preferably at least 95%, 96%, 97%, 98%, or 99% identical to: (a) a nucleotide sequence encoding the polypeptide having the amino acid sequence shown in FIG. 2 (SEQ ID NO:4); (b) a nucleotide sequence encoding the polypeptide having the amino acid sequence in FIG. 2 (SEQ ID NO:4), but lacking the amino terminal methionine; (c) a nucleotide sequence encoding the polypeptide having the amino acid sequence at positions about 1 to about 368 in FIG. 2 (SEQ ID NO:4); (d) a nucleotide sequence encoding a G-protein Chemokine Receptor extracellular domain (e.g. (e.g. amino acid residues from 1 to 59, 114 to 127, 191 to 223, and/or 278 to 307 in SEQ ID NO: 4); (e) a nucleotide sequence encoding a G-protein Chemokine Receptor transmembrane domain (e.g. amino acid residues from 60 to 79, 92 to 113, 128 to 147, 170 to 190, 224 to 245, 259 to 277, and/or 302 to 322 in SEQ ID NO:4); (f) a nucleotide sequence encoding a G-protein Chemokine Receptor receptor intracellular domain (e.g. amino acid residues from 80 to 91, 148 to 169, 246 to 258, and/or 323 to 368 in SEQ ID NO: 4); (g) a nucleotide sequence encoding the G-protein Chemokine Receptor receptor extracellular and intracellular domains with all or part of the transmembrane domain deleted; and (h) a nucleotide sequence complementary to any of the nucleotide sequences in (a), (b), (c), (d), (e), (f), or (g) above. Polypeptides encoded by these polynucleotides are also encompassed by the invention.

By a polynucleotide having a nucleotide sequence at least, for example, 95% "identical" to a reference nucleotide sequence encoding a G-protein Chemokine Receptor polypeptide is intended that the nucleotide sequence of the polynucleotide is identical to the reference sequence except that the polynucleotide sequence may include up to five mismatches per each 100 nucleotides of the reference nucleotide sequence encoding the G-protein Chemokine Receptor polypeptide. In other words, to obtain a polynucleotide having a nucleotide sequence at least 95% identical to a reference nucleotide sequence, up to 5% of the nucleotides in the reference sequence may be deleted or substituted with another nucleotide, or a number of nucleotides up to 5% of the total nucleotides in the reference sequence may be inserted into the reference sequence. These mismatches of the reference sequence may occur at the 5' or 3' terminal positions of the reference nucleotide sequence or anywhere between those terminal positions, interspersed either individually among nucleotides in the reference sequence or in one or more contiguous groups within the reference sequence. The reference (query) sequence may be the entire G-protein Chemokine Receptor encoding nucleotide sequence shown in FIG. 1 (SEQ ID NO:1), more preferably, the entire G-protein Chemokine Receptor encoding nucleotide sequence shown in FIG. 2 (SEQ ID NO:3), or any G-protein Chemokine Receptor polynucleotide fragment (e.g., a polynucleotide encoding the amino acid sequence of any of the G-protein Chemokine Receptor N- and/or C-terminal deletions described herein), variant, derivative or analog, as described herein.

As a practical matter, whether any particular nucleic acid molecule is at least 90%, 95%, 96%, 97%, 98% or 99% identical to, for instance, a nucleotide sequence of the present invention as shown in FIG. 1 (SEQ ID NO:1) and FIG. 2 (SEQ ID NO:3) can be determined conventionally using known computer programs such as the Bestfit program (Wisconsin Sequence Analysis Package, Version 8 for Unix, Genetics Computer Group, University Research Park, 575 Science Drive, Madison, Wis. 53711). Bestfit uses the local homology algorithm of Smith and Waterman, *Advances in Applied Mathematics* 2: 482-489 (1981), to find the best segment of homology between two sequences. When using Bestfit or any other sequence alignment program to determine whether a particular sequence is, for instance, 95% identical to a reference sequence according to the present invention, the parameters are set, of course, such that the percentage of identity is calculated over the full length of the reference nucleotide sequence and that gaps in homology of up to 5% of the total number of nucleotides in the reference sequence are allowed.

In a specific embodiment, the identity between a reference (query) sequence (a sequence of the present invention) and a subject sequence, also referred to as a global sequence alignment, is determined using the FASTDB computer program based on the algorithm of Brutlag et al. (Comp. App. Biosci. 6:237-245 (1990)). Preferred parameters used in a FASTDB alignment of DNA sequences to calculate percent identity are: Matrix=Unitary, k-tuple=4, Mismatch Penalty=1, Joining Penalty=30, Randomization Group Length=0, Cutoff Score=1, Gap Penalty=5, Gap Size Penalty 0.05, Window Size=500 or the length of the subject nucleotide sequence, whichever is shorter. According to this embodiment, if the subject sequence is shorter than the query sequence because of 5' or 3' deletions, not because of internal deletions, a manual correction is made to the results to take into consideration the fact that the FASTDB program does not account for 5' and 3' truncations of the subject sequence when calculating percent identity. For subject sequences truncated at the 5' or 3' ends, relative to the query sequence, the percent identity is corrected by calculating the number of bases of the query sequence that are 5' and 3' of the subject sequence, which are not matched/aligned, as a percent of the total bases of the query sequence. A determination of whether a nucleotide is matched/aligned is determined by results of the FASTDB sequence alignment. This percentage is then subtracted from the percent identity, calculated by the above FASTDB program using the specified parameters, to arrive at a final percent identity score. This corrected score is what is used for the purposes of this embodiment. Only bases outside the 5' and 3' bases of the subject sequence, as displayed by the FASTDB alignment, which are not matched/aligned with the query sequence, are calculated for the purposes of manually adjusting the percent identity score. For example, a 90 base subject sequence is aligned to a 100 base query sequence to determine percent identity. The deletions occur at the 5' end of the subject sequence and therefore, the FASTDB alignment does not show a matched/alignment of the first 10 bases at 5' end. The 10 unpaired bases represent 10% of the sequence (number of bases at the 5' and 3' ends not matched/total number of bases in the query sequence) so 10% is subtracted from the percent identity score calculated by the FASTDB program. If the remaining 90 bases were perfectly matched the final percent identity would be 90%. In another example, a 90 base subject sequence is compared with a 100 base query sequence. This time the deletions are internal deletions so that there are no bases on the 5' or 3' of the subject sequence that are not matched/aligned with the query. In this case the percent identity calculated by FASTDB is not manually corrected. Once again, only bases 5' and 3' of the subject sequence which are not matched/aligned with the query sequence are manually corrected for. No other manual corrections are made for the purposes of this embodiment.

The present application is directed to nucleic acid molecules comprising, or alternatively consisting of a nucleotide sequence at least 90%, 95%, 96%, 97%, 98%, or 99% identical to the nucleic acid sequence for example, shown in FIG. 1 (SEQ ID NO: 1) or more preferably FIG. 2 (SEQ ID NO:3), irrespective of whether they encode a polypeptide having G-protein Chemokine Receptor receptor activity. This is because even where a particular nucleic acid molecule does not encode a polypeptide having G-protein Chemokine Receptor functional activity, one of skill in the art would still know how to use the nucleic acid molecule, for instance, as a hybridization probe or a polymerase chain reaction (PCR) primer. Uses of the nucleic acid molecules of the present invention that do not encode a polypeptide having G-protein Chemokine Receptor receptor activity include, inter alia: (1) isolating the G-protein Chemokine Receptor gene or allelic variants thereof in a cDNA library; (2) in situ hybridization (e.g., "FISH") to metaphase chromosomal spreads to provide precise chromosomal location of the G-protein Chemokine Receptor receptor gene, as described in Verma et al., *Human Chromosomes: A Manual of Basic Techniques*, Pergamon Press, New York (1988); and (3) Northern Blot analysis for detecting G-protein Chemokine Receptor receptor mRNA expression in specific tissues.

Preferred, however, are nucleic acid molecules comprising, or alternatively consisting of, a nucleotide sequence at least 90%, 95%, 96%, 97%, 98% or 99% identical to for example, the nucleic acid sequence shown in FIG. 1 (SEQ ID NO:1) or more preferably FIG. 2 (SEQ ID NO:3), which do, in fact, encode a polypeptide having G-protein Chemokine Receptor functional activity. By "a polypeptide having G-protein Chemokine Receptor functional activity" is intended polypeptides exhibiting activity similar, but not necessarily identical, to an activity of the G-protein Chemokine Receptor receptor of the invention (either the full-length protein or, preferably, the mature protein), as measured in a particular biological assay.

Of course, due to the degeneracy of the genetic code, one of ordinary skill in the art will immediately recognize that a large number of the nucleic acid molecules having a sequence at least 90%, 95%, 96%, 97%, 98%, or 99% identical to, for example, the nucleic acid sequence shown in FIG. 2 (SEQ ID NO:3), will encode a polypeptide "having G-protein Chemokine Receptor functional activity." Similarly, a large number of the nucleic acid molecules having a sequence at least 90%, 95%, 96%, 97%, 98%, or 99% identical to, for example, a nucleic acid sequence shown in FIG. 1 (SEQ ID NO:1) will encode a polypeptide "having G-protein Chemokine Receptor functional activity." In fact, since degenerate variants of these nucleotide sequences all encode the same polypeptide, this will be clear to the skilled artisan even without performing a biological assay. It will be further recognized in the art that, for such nucleic-acid molecules that are not degenerate variants, a reasonable number will also encode a polypeptide having G-protein Chemokine Receptor functional activity. This is because the skilled artisan is fully aware of amino acid substitutions that are either less likely or not likely to significantly effect protein function (e.g., replacing one aliphatic amino acid with a second aliphatic amino acid).

For example, guidance concerning how to make phenotypically silent amino acid substitutions is provided in J. U. Bowie et al., "Deciphering the Message in Protein Sequences: Tolerance to Amino Acid Substitutions," *Science* 247:1306-1310 (1990), wherein the authors indicate that proteins are surprisingly tolerant of amino acid substitutions.

Polynucleotide Assays

This invention is also related to the use of G-protein Chemokine Receptor polynucleotides to detect complementary polynucleotides such as, for example, as a diagnostic reagent. Detection of a normal and mutated form of G-protein Chemokine Receptor associated with a dysfunction will provide a diagnostic tool that can add or define a diagnosis of a disease or susceptibility to a disease which results from under-expression over-expression or altered expression of G-protein Chemokine Receptor (or a soluble form thereof), such as, for example, tumors or autoimmune disease.

Individuals carrying mutations in the G-protein Chemokine Receptor gene may be detected at the DNA level by a variety of techniques. Nucleic acids for diagnosis may be obtained from a biological sample from a patient (e.g., a patient's cells, such as from blood, urine, saliva, tissue biopsy and autopsy material). The genomic DNA may be used directly for detection or may be amplified enzymatically by using PCR prior to analysis. (Saiki et al., *Nature* 324:163-166 (1986)). RNA or cDNA may also be used in the same ways. As an example, PCR primers complementary to the nucleic acid encoding G-protein Chemokine Receptor can be used to identify and analyze G-protein Chemokine Receptor expression and mutations. For example, deletions and insertions can be detected by a change in size of the amplified product in comparison to the normal genotype. Point mutations can be identified by hybridizing amplified DNA to radiolabeled G-protein Chemokine Receptor RNA or alternatively, radiolabeled G-protein Chemokine Receptor antisense DNA sequences. Perfectly matched sequences can routinely be distinguished from mismatched duplexes by techniques known in the art, such as, for example, RNase A digestion or by differences in melting temperatures.

Sequence differences between a reference gene and genes having mutations also may be revealed by direct DNA sequencing. In addition, cloned DNA segments may be employed as probes to detect specific DNA segments. The sensitivity of such methods can be greatly enhanced by appropriate use of PCR or another amplification method. For example, a sequencing primer is used with double-stranded PCR product or a single-stranded template molecule generated by a modified PCR. The sequence determination is performed by conventional procedures with radiolabeled nucleotide or by automatic sequencing procedures with fluorescent-tags.

Genetic testing based on DNA sequence differences may be achieved by detection of alteration in electrophoretic mobility of DNA fragments in gels, with or without denaturing agents. Small sequence deletions and insertions can be visualized by high resolution gel electrophoresis using techniques known in the art. DNA fragments of different sequences may be distinguished on denaturing formamide gradient gels in which the mobilities of different DNA fragments are retarded in the gel at different positions according to their specific melting or partial melting temperatures (see, e.g., Myers et al., *Science* 230:1242 (1985)).

Sequence changes at specific locations also may be revealed by nuclease protection assays, such as RNase and S1 protection or the chemical cleavage method (e.g., Cotton et al., *Proc. Natl. Acad. Sci. USA* 85: 4397-4401 (1985)).

Thus, the detection of a specific DNA sequence may be achieved by methods which include, but are not limited to, hybridization, RNase protection, chemical cleavage, direct DNA sequencing or the use of restriction enzymes, (e.g., restriction fragment length polymorphisms ("RFLP") and Southern blotting of genomic DNA.

In addition to more conventional gel-electrophoresis and DNA sequencing, mutations also can be detected by in situ analysis.

Vectors and Host Cells

The present invention also relates to vectors that include polynucleotides of the present invention, host cells which are genetically engineered with vectors of the invention and the production of polypeptides of the invention by recombinant techniques.

Host cells are genetically engineered (transduced or transformed or transfected) with the vectors of this invention that may be, for example, a cloning vector or an expression vector. The vector may be, for example, in the form of a plasmid, a viral particle, a phage, etc. The engineered host cells can be cultured in conventional nutrient media modified as appropriate for activating promoters, selecting transformants or amplifying the genes of the present invention. The culture conditions, such as temperature, pH and the like, are those previously used with the host cell selected for expression, and will be apparent to the ordinarily skilled artisan.

The polynucleotides of the present invention may be employed for producing polypeptides by recombinant techniques. Thus, for example, the polynucleotide may be included in any one of a variety of expression vectors for expressing a polypeptide. Such vectors include chromosomal, nonchromosomal and synthetic DNA sequences, e.g., derivatives of SV40; bacterial plasmids; phage DNA; baculovirus; yeast plasmids; vectors derived from combinations of plasmids and phage DNA, viral DNA such as vaccinia, adenovirus, fowl pox virus, and pseudorabies. However, any other vector may be used as long as it is replicable and viable in the host.

The appropriate DNA sequence may be inserted into the vector by a variety of procedures. In general, the DNA sequence is inserted into an appropriate restriction endonuclease site(s) by procedures known in the art. Such procedures and others are deemed to be within the scope of those skilled in the art.

The DNA sequence in the expression vector is operatively linked to an appropriate expression control sequence(s) (promoter) to direct mRNA synthesis. As representative examples of such promoters, there may be mentioned: LTR or SV40 promoter, the *E. coli*. lac or trp, the phage lambda $P_L$ promoter and other promoters known to control expression of genes in prokaryotic or eukaryotic cells or their viruses. The expression vector also contains a ribosome-binding site for translation initiation and a transcription terminator. The vector may also include appropriate sequences for amplifying expression.

In addition, the expression vectors preferably contain one or more selectable marker genes to provide a phenotypic trait for selection of transformed host cells such as dihydrofolate reductase or neomycin resistance for eukaryotic cell culture, or such as tetracycline or ampicillin resistance in *E. coli*.

The vector containing the appropriate DNA sequence as hereinabove described, as well as an appropriate promoter or control sequence, may be employed to transform an appropriate host to permit the host to express the protein.

As representative examples of appropriate hosts, there may be mentioned: bacterial cells, such as *E. coli*, Streptomyces, *Salmonella typhimurium*; fungal cells, such as yeast; insect cells such as Drosophila and Spodoptera Sf9; animal cells such as CHO, COS or Bowes melanoma; adenovirus; plant cells, etc. The selection of an appropriate host is deemed to be within the scope of those skilled in the art from the teachings herein.

More particularly, the present invention also includes recombinant constructs comprising one or more of the sequences as broadly described above. The constructs comprise a vector, such as a plasmid or viral vector, into which a sequence of the invention has been inserted, in a forward or reverse orientation. In a preferred aspect of this embodiment, the construct further comprises regulatory sequences, including, for example, a promoter, operably linked to the sequence. Large numbers of suitable vectors and promoters are known to those of skill in the art, and are commercially available. The following vectors are provided by way of example. Bacterial: pQE70, pQE60, pQE-9 (Qiagen), pbs, pD10, phagescript, psiX174, pbluescript SK, pbsks, pNH8A, pNH16a, pNH18A, pNH46A (Stratagene); ptrc99a, pKK223-3, pKK233-3, pDR540, pRIT5 (Pharmacia). Eukaryotic: pWL-NEO, pSV2CAT, pOG44, pXT1, pSG (Stratagene) pSVK3, pBPV, pMSG, pSVL (Pharmacia). However, any other plasmid or vector may be used as long as they are replicable and viable in the host.

Promoter regions can be selected from any desired gene using CAT (chloramphenicol transferase) vectors or other vectors with selectable markers. Two appropriate vectors are PKK232-8 and PCM7. Particular named bacterial promoters include lacI, lacZ, T3, T7, gpt, lambda $P_R$, $P_L$ and trp. Eukaryotic promoters include CMV immediate early, HSV thymidine kinase, early and late SV40, LTRs from retrovirus, and mouse metallothionein-I. Selection of the appropriate vector and promoter is well within the level of ordinary skill in the art.

In a further embodiment, the present invention relates to host cells containing the above-described constructs. The host cell can be a higher eukaryotic cell, such as a mammalian cell, or a lower eukaryotic cell, such as a yeast cell, or the host cell can be a prokaryotic cell, such as a bacterial cell. Introduction of the construct into the host cell can be effected by calcium phosphate transfection, DEAE-Dextran mediated transfection, or electroporation. (Davis, L., Dibner, M., Battey, I., Basic Methods in Molecular Biology, (1986)).

The constructs in host cells can be used in a conventional manner to produce the gene product encoded by the recombinant sequence. Alternatively, the polypeptides of the invention can be synthetically produced by conventional peptide synthesizers.

Mature proteins can be expressed in mammalian cells, yeast, bacteria, or other cells under the control of appropriate promoters. Cell-free translation systems can also be employed to produce such proteins using RNAs derived from the DNA constructs of the present invention. Appropriate cloning and expression vectors for use with prokaryotic and eukaryotic hosts are described by Sambrook, et al., Molecular Cloning: A Laboratory Manual, Second Edition, Cold Spring Harbor, N.Y., (1989), the disclosure of which is hereby incorporated by reference.

Transcription of the DNA encoding the polypeptides of the present invention by higher eukaryotes is increased by inserting an enhancer sequence into the vector. Enhancers are cis-acting elements of DNA, usually about from 10 to 300 bp that act on a promoter to increase its transcription. Examples including the SV40 enhancer on the late side of the replication origin bp 100 to 270, a cytomegalovirus early promoter enhancer, the polyoma enhancer on the late side of the replication origin, and adenovirus enhancers.

Generally, recombinant expression vectors will include origins of replication and selectable markers permitting transformation of the host cell, e.g., the ampicillin resistance gene of E. coli and S. cerevisiae TRP1 gene, and a promoter derived from a highly-expressed gene to direct transcription of a downstream structural sequence. Such promoters can be derived from operons encoding glycolytic enzymes such as 3-phosphoglycerate kinase (PGK), α-factor, acid phosphatase, or heat shock proteins, among others. The heterologous structural sequence is assembled in appropriate phase with translation initiation and termination sequences, and preferably, a leader sequence capable of directing secretion of translated protein into the periplasmic space or extracellular medium. Optionally, the heterologous sequence can encode a fusion protein including an N-terminal identification peptide imparting desired characteristics, e.g., stabilization or simplified purification of expressed recombinant product.

Useful expression vectors for bacterial use are constructed by inserting a structural DNA sequence encoding a desired protein together with suitable translation initiation and termination signals in operable reading phase with a functional promoter. The vector will comprise one or more phenotypic selectable markers and an origin of replication to ensure maintenance of the vector and to, if desirable, provide amplification within the host. Suitable prokaryotic hosts for transformation include E. coli, Bacillus subtilis, Salmonella typhimurium and various species within the genera Pseudomonas, Streptomyces, and Staphylococcus, although others may also be employed as a matter of choice.

As a representative but nonlimiting example, useful expression vectors for bacterial use can comprise a selectable marker and bacterial origin of replication derived from commercially available plasmids comprising genetic elements of the well known cloning vector pBR322 (ATCC 37017). Such commercial vectors include, for example, pKK223-3 (Pharmacia Fine Chemicals, Uppsala, Sweden) and GEM1 (Promega Biotec, Madison, Wis., USA). These pBR322 "backbone" sections are combined with an appropriate promoter and the structural sequence to be expressed.

Following transformation of a suitable host strain and growth of the host strain to an appropriate cell density, the selected promoter is induced by appropriate means (e.g., temperature shift or chemical induction) and cells are cultured for an additional period.

Cells are typically harvested by centrifugation, disrupted by physical or chemical means, and the resulting crude extract retained for further purification.

Microbial cells employed in expression of proteins can be disrupted by any convenient method, including freeze-thaw cycling, sonication, mechanical disruption, or use of cell lysing agents, such methods are well know to those skilled in the art.

Various mammalian cell culture systems can also be employed to express recombinant protein. Examples of mammalian expression systems include the COS-7 lines of monkey kidney fibroblasts, described by Gluzman, Cell, 23:175 (1981), and other cell lines capable of expressing a compatible vector, for example, the C127, 3T3, CHO, HeLa and BHK cell lines. Mammalian expression vectors will comprise an origin of replication, a suitable promoter and enhancer, and also any necessary ribosome binding sites, polyadenylation site, splice donor and acceptor sites, transcriptional termination sequences, and 5' flanking nontranscribed sequences. DNA sequences derived from the SV40 splice, and polyadenylation sites may be used to provide the required nontranscribed genetic elements.

The G-protein chemokine receptor polypeptides can be recovered and purified from recombinant cell cultures by methods including ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography. Protein refolding steps can be used, as necessary, in completing configuration of the mature protein. Finally, high performance liquid chromatography (HPLC) can be employed for final purification steps.

The polypeptides of the present invention may be a naturally purified product, or a product of chemical synthetic procedures, or produced by recombinant techniques from a prokaryotic or eukaryotic host (for example, by bacterial, yeast, higher plant, insect and mammalian cells in culture). Depending upon the host employed in a recombinant production procedure, the polypeptides of the present invention may be glycosylated or may be non-glycosylated. Polypeptides of the invention may also include an initial methionine amino acid residue.

The present invention also relates to vectors that include the isolated DNA molecules of the present invention, host cells which are genetically engineered with the recombinant vectors and/or nucleic acids of the invention and the production of G-protein Chemokine Receptor polypeptides or fragments thereof by recombinant techniques.

Host cells can be genetically engineered to incorporate nucleic acid molecules and express polypeptides of the present invention. The polynucleotides may be introduced alone or with other polynucleotides. Such other polynucleotides may be introduced independently, co-introduced or introduced joined to the polynucleotides of the invention.

In accordance with the present invention the vector may be, for example, a plasmid vector, a single or double-stranded phage vector, a single or double-stranded RNA or DNA viral vector. Such vectors may be introduced into cells as polynucleotides, preferably DNA, by well-known techniques for introducing DNA and RNA into cells. Viral vectors may be replication competent or replication defective. In the latter case viral propagation generally will occur only in complementing host cells.

Preferred among vectors, in certain respects, are those for expression of polynucleotides and polypeptides of the present invention. Generally, such vectors comprise cis-acting control regions effective for expression in a host operatively linked to the polynucleotide to be expressed. Appropriate trans-acting factors are supplied by the host, supplied by a complementing vector, or supplied by the vector itself upon introduction into the host.

The polynucleotides may be joined to a vector containing a selectable marker for propagation in a host. Generally, a plasmid vector is introduced in a precipitate, such as a calcium phosphate precipitate, or in a complex with a charged lipid. If the vector is a virus, it may be packaged in vitro using an appropriate packaging cell line and then transduced into host cells.

The DNA insert should be operatively linked to an appropriate promoter, such as the phage lambda PL promoter, the *E. coli* lac, trp and tac promoters, the SV40 early and late promoters and promoters of retroviral LTRs, to name a few. Other suitable promoters will be known to the skilled artisan. The expression constructs will further contain sites for transcription initiation, termination and, in the transcribed region, a nbosome-binding site for translation. The coding portion of the mature transcripts expressed by the constructs will preferably include a translation initiating at the beginning and a termination codon (UAA, UGA or UAG) appropriately positioned at the end of the polypeptide to be translated.

As indicated, the expression vectors will preferably include at least one selectable marker. Such markers include dihydrofolate reductase, neomycin resistance, or glutamine synthase for eukaryotic cell culture and tetracycline or ampicillin resistance genes for culturing in *E. coli* and other bacteria. Representative examples of appropriate hosts include, but are not limited to, bacterial cells, such as *E. coli*, Streptomyces and *Salmonella typhimurium* cells; fungal cells, such as yeast cells; insect cells such as Drosophila S2 and Spodoptera Sf9 cells; animal cells such as CHO, NSO, COS, 293, and Bowes melanoma cells; and plant cells. Appropriate culture mediums and conditions for the above-described host cells are known in the art.

Vectors which use glutamine synthase (GS) or DHFR as the selectable markers can be amplified in the presence of the drugs methionine sulphoximine or methotrexate, respectively. The availability of drugs that inhibit the function of the enzymes encoded by these selectable markers allows for selection of cell lines in which the vector sequences have been amplified after integration into the host cell's DNA. An advantage of glutamine synthase based vectors is the availabilty of cell lines (e.g., the murine myeloma cell line, NSO) that are glutamine synthase negative. Glutamine synthase expression systems can also function in glutamine synthase expressing cells (e.g. Chinese Hamster Ovary (CHO) cells) by providing additional inhibitor to prevent the functioning of the endogenous gene. Vectors that use glutamine synthase as the selectable marker include the pEE6 expression vector described in Stephens and Cockett, Nucl. Acids. Res 17:7110 (1989). A glutamine synthase expression system and components thereof are detailed in PCT publications: WO87/04462; WO86/05807; WO89/01036; WO89/10404; and WO91/06657, which are hereby incorporated in their entireties by reference herein. Additionally, glutamine synthase expression vectors that may be used according to the present invention are commercially available from suppliers including, for example, Lonza Biologics, Inc. (Portsmouth, N.H.). Expression and production of monoclonal antibodies using a GS expression system in murine myeloma cells is described in Bebbington et al., *Bio/technology* 10:169(1992) and in Biblia and Robinson *Biotechnol. Prog.* 11:1 (1995), which are herein incorporated by reference.

Among vectors preferred for use in bacteria include pQE70, pQE60 and pQE-9, available from Qiagen; pBS vectors, Phagescript vectors, Bluescript vectors, pNH8A, pNH16a, pNH18A, pNH46A, available from Stratagene; and ptrc99a, pKK223-3, pKK233-3, pDR540, pRIT5 available from Pharmacia. Among preferred eukaryotic vectors are pWLNEO, pSV2CAT, pOG44, pXT1 and pSG available from Stratagene; and pSVK3, pBPV, pMSG and pSVL available from Pharmacia. Other suitable vectors will be readily apparent to the skilled artisan.

The present invention also relates to host cells containing the above-described vector constructs described herein, and additionally encompasses host cells containing nucleotide sequences of the invention that are operably associated with one or more heterologous control regions (e.g., promoter and/or enhancer) using techniques known of in the art. The host cell can be a higher eukaryotic cell, such as a mammalian cell (e.g., a human derived cell), or a lower eukaryotic cell, such as a yeast cell, or the host cell can be a prokaryotic cell, such as a bacterial cell. The host strain may be chosen which modulates the expression of the inserted gene sequences, or modifies and processes the gene product in the specific fashion desired. Expression from certain promoters can be elevated in the presence of certain inducers; thus expression of the genetically engineered polypeptide may be controlled. Furthermore, different host cells have characteristics and specific mechanisms for the translational and post-translational processing and modification (e.g., phosphorylation, cleavage) of proteins. Appropriate cell lines can be chosen to ensure the desired modifications and processing of the foreign protein expressed.

Introduction of the construct into the host cell can be effected by calcium phosphate transfection, DEAE-dextran mediated transfection, cationic lipid-mediated transfection, electroporation, transduction, infection or other methods. Such methods are described in many standard laboratory manuals, such as Davis et al., *Basic Methods In Molecular Biology* (1986).

In addition to encompassing host cells containing the vector constructs discussed herein, the invention also encompasses primary, secondary, and immortalized host cells of vertebrate origin, particularly mammalian origin, that have been engineered to delete or replace endogenous genetic material (e.g., G-protein Chemokine Receptor coding sequence), and/or to include genetic material (e.g., heterologous polynucleotide sequences) that is operably associated with G-protein Chemokine Receptor polynucleotides of the invention, and which activates, alters, and/or amplifies endogenous G-protein Chemokine Receptor polynucleotides. For example, techniques known in the art may be used to operably associate heterologous control regions (e.g., promoter and/or enhancer) and endogenous G-protein Chemokine Receptor polynucleotide sequences via homologous recombination (see, e.g., U.S. Pat. No. 5,641,670, issued Jun. 24, 1997; International Publication Number WO 96/29411; International Publication Number WO 94/12650; Koller et al., *Proc. Natl. Acad. Sci. USA* 86:8932-8935 (1989); and Zijlstra et al., *Nature* 342:435-438 (1989), the disclosures of each of which are incorporated by reference in their entireties).

The G-protein Chemokine Receptor polypeptide may be expressed in a modified form, such as a fusion protein (comprising the polypeptide joined via a peptide bond to a heterologous protein sequence (of a different protein)), and may include not only secretion signals but also additional heterologous functional regions. Alternatively, such a fusion protein can be made by protein synthetic techniques, e.g., by use of a peptide synthesizer. Thus, a region of additional amino acids, particularly charged amino acids, may be added to the N-terminus of the polypeptide to improve stability and persistence in the host cell, during purification or during subsequent handling and storage. Also, peptide moieties may be added to the polypeptide to facilitate purification. Such regions may be removed prior to final preparation of the polypeptide. The addition of peptide moieties to polypeptides to engender secretion or excretion, to improve stability and to facilitate purification, among others, are familiar and routine techniques in the art.

In one embodiment, polynucleotides G-protein Chemokine Receptor polypeptides of the invention may be fused to signal sequences that will direct the localization of a protein of the invention to particular compartments of a prokaryotic or eukaryotic cell and/or direct the secretion of a protein of the invention from a prokaryotic or eukaryotic cell. For example, in E. coli, one may wish to direct the expression of the protein to the periplasmic space. Examples of signal sequences or proteins (or fragments thereof) to which the polypeptides of the invention may be fused in order to direct the expression of the polypeptide to the periplasmic space of bacteria include, but are not limited to, the pelB signal sequence, the maltose binding protein (MBP) signal sequence, MBP, the ompA signal sequence, the signal sequence of the periplasmic E. coli heat-labile enterotoxin B-subunit, and the signal sequence of alkaline phosphatase. Several vectors are commercially available for the construction of fusion proteins that will direct the localization of a protein, such as the pMAL series of vectors (particularly the pMAL-p series) available from New England Biolabs. In a specific embodiment, polynucleotides encoding Neutrokine-alpha and/or Neutrokine-alphaSV polypeptides of the invention may be fused to the pelB pectate lyase signal sequence to increase the efficiency of expression and purification of such polypeptides in Gram-negative bacteria. See, U.S. Pat. Nos. 5,576,195 and 5,846,818, the contents of which are herein incorporated by reference in their entireties.

Examples of signal peptides that may be fused to a polypeptide of the invention in order to direct its secretion in mammalian cells include, but are not limited to, the MPIF-1 signal sequence (amino acids 1-21 of GenBank Accession number AAB51134), the stanniocalcin signal sequence (MLQNSAVLLLLVISASA, SEQ ID NO:49), and a consensus signal sequence (MPTWAWWLFLVLLLALWAPARG, SEQ ID NO:50). A suitable signal sequence that may be used in conjunction with baculoviral expression systems is the gp67 signal sequence, (amino acids 1-19 of GenBank Accession Number AAA72759).

A preferred fusion protein comprises a heterologous region from immunoglobulin that is useful to solubilize proteins. For example, EP-A-O 464 533 (Canadian counterpart 2045869) discloses fusion proteins comprising various portions of constant region of immunoglobin molecules together with another human protein or part thereof. In many cases, the Fc part in a fusion protein is thoroughly advantageous for use in therapy and diagnosis and thus results, for example, in improved pharmacokinetic properties (EP-A 0232 262). On the other hand, for some uses, it would be desirable to be able to delete the Fc part after the fusion protein has been expressed, detected and purified in the advantageous manner described. This is the case when the Fc portion proves to be a hindrance to use in therapy and diagnosis, for example, when the fusion protein is to be used as an antigen for immunizations. In drug discovery, for example, human proteins, such as the hIL5-receptor, have been fused with Fc portions for the purpose of high-throughput screening assays to identify antagonists of hIL-5. See, D. Bennett et al., *Journal of Molecular Recognition* 8:52-58 (1995) and K. Johanson et al., *The Journal of Biological Chemistry* 270:16:9459-9471 (1995).

Polypeptides of the present invention include naturally purified products, products of chemical synthetic procedures, and products produced by recombinant techniques from a prokaryotic or eukaryotic host, including, for example, bacterial, yeast, higher plant, insect and mammalian cells. Depending upon the host employed in a recombinant production procedure, the polypeptides of the present invention may be glycosylated or non-glycosylated. In addition, polypeptides of the invention may also include an initial modified methionine residue, in some cases as a result of host-mediated processes.

In addition, proteins of the invention can be chemically synthesized using techniques known in the art (e.g., see Creighton, Proteins: Structures and Molecular Principles, W. H. Freeman & Co., N.Y. (1983), and Hunkapiller, et al., *Nature* 310:105-111 (1984)). For example, a polypeptide corresponding to a fragment of the G-protein Chemokine Receptor polypeptides of the invention can be synthesized by use of a peptide synthesizer. Furthermore, if desired, nonclassical amino acids or chemical amino acid analogs can be introduced as a substitution or addition into the G-protein Chemokine Receptor polypeptide sequence. Non-classical amino acids include, but are not limited to, to the D-isomers of the common amino acids, 2,4-diaminobutyric acid, a-amino isobutyric acid, 4-aminobutyric acid, Abu, 2-amino butyric acid, g-Abu, e-Ahx, 6-amino hexanoic acid, Aib, 2-amino isobutyric acid, 3-amino propionic acid, ornithine, norleucine, norvaline, hydroxyproline, sarcosine, citrulline, homocitrulline, cysteic acid, t-butylglycine, t-butylalanine, phenylglycine, cyclohexylalanine, b-alanine, fluoro-amino acids, designer amino acids such as b-methyl amino acids, Ca-methyl amino acids, Na-methyl amino acids, and amino acid analogs in general. Furthermore, the amino acid can be D (dextrorotary) or L (levorotary).

The invention additionally, encompasses G-protein Chemokine Receptor polypeptides which are differentially modified during or after translation, e.g., by glycosylation, acetylation, phosphorylation, amidation, derivatization by known protecting/blocking groups, proteolytic cleavage, linkage to an antibody molecule or other cellular ligand, etc. Any of numerous chemical modifications may be carried out by known techniques, including but not limited to, specific chemical cleavage by cyanogen bromide, trypsin, chymotrypsin, papain, VS protease, $NaBH_4$ acetylation, formylation, oxidation, reduction, metabolic synthesis in the presence of tunicamycin; etc.

Additional post-translational modifications encompassed by the invention include, for example, e.g., N-linked or O-linked carbohydrate chains, processing of N-terminal or C-terminal ends), attachment of chemical moieties to the amino acid backbone, chemical modifications of N-linked or O-linked carbohydrate chains, and addition or deletion of an N-terminal methionine residue as a result of procaryotic host cell expression. The polypeptides may also be modified with a detectable label, such as an enzymatic, fluorescent, isotopic or affinity label to allow for detection and isolation of the protein.

In specific embodiments, G-protein Chemokine Receptor polypetides of the invention are attached to macrocyclic chelators useful for conjugating radiometal ions, including but not limited to, $^{111}In$, $^{177}Lu$, $^{90}Y$, $^{166}Ho$, and $^{153}Sm$ to polypeptides. In a preferred embodiment, the radiometal ion associated with the macrocyclic chelators attached to G-protein Chemokine Receptor polypeptides of the invention is $^{111}$In. In another preferred embodiment, the radiometal ion associated with the macrocyclic chelator attached to G-protein Chemokine Receptor polypeptides of the invention is $^{90}$Y. In specific embodiments, the macrocyclic chelator is 1,4,7,10-tetraazacyclododecane-N, N',N'',N'''-tetraacetic acid (DOTA). In other specific embodiments, the DOTA is attached to G-protein Chemokine Receptor polypeptide of the invention via a linker molecule. Examples of linker molecules useful for conjugating DOTA to a polypeptide are commonly known in the art—see, for example, DeNardo et al., Clin Cancer Res. 4(10):2483-90, 1998; Peterson et al., Bioconjug. Chem. 10(4):553-7, 1999; and Zimmerman et al, Nucl. Med. Biol. 26(8):943-50, 1999 which are hereby incorporated by reference in their entirety. In addition, U.S. Pat. Nos. 5,652,361 and 5,756,065, which disclose chelating agents that may be conjugated to antibodies, and methods for making and using them, are hereby incorporated by reference in their entireties. Though U.S. Pat. Nos. 5,652,361 and 5,756,065 focus on conjugating chelating agents to antibodies, one skilled in the art could readily adapt the method disclosed therein in order to conjugate chelating agents to other polypeptides.

Also provided by the invention are chemically modified derivatives of G-protein Chemokine Receptor that may provide additional advantages such as increased solubility, stability and circulating time of the polypeptide, or decreased immunogenicity (see U.S. Pat. No. 4,179,337). The chemical moieties for derivitization may be selected from water soluble polymers such as polyethylene glycol, ethylene glycol/propylene glycol copolymers, carboxymethylcellulose, dextran, polyvinyl alcohol and the like. The polypeptides may be modified at random positions within the molecule, or at predetermined positions within the molecule and may include one, two, three or more attached chemical moieties.

The polymer may be of any molecular weight, and may be branched or unbranched. For polyethylene glycol, the preferred molecular weight is between about 1 kDa and about 100 kDa (the term "about" indicating that in preparations of polyethylene glycol, some molecules will weigh more, some less, than the stated molecular weight) for ease in handling and manufacturing. Other sizes may be used, depending on the desired therapeutic profile (e.g., the duration of sustained release desired, the effects, if any on biological activity, the ease in handling, the degree or lack of antigenicity and other known effects of the polyethylene glycol to a therapeutic protein or analog). For example, the polyethylene glycol may have an average molecular weight of about 200, 500, 1000, 1500, 2000, 2500, 3000, 3500, 4000, 4500, 5000, 5500, 6000, 6500, 7000, 7500, 8000, 8500, 9000, 9500, 10,000, 10,500, 11,000, 11,500, 12,000, 12,500, 13,000, 13,500, 14,000, 14,500, 15,000, 15,500, 16,000, 16,500, 17,000, 17,500, 18,000, 18,500, 19,000, 19,500, 20,000, 25,000, 30,000, 35,000, 40,000, 50,000, 55,000, 60,000, 65,000, 70,000, 75,000, 80,000, 85,000, 90,000, 95,000, or 100,000 kDa.

As noted above, the polyethylene glycol may have a branched structure. Branched polyethylene glycols are described, for example, in U.S. Pat. No. 5,643,575; Morpurgo et al., *Appl. Biochem. Biotechnol.* 56:59-72 (1996); Vorobjev et al., *Nucleosides Nucleotides* 18:2745-2750 (1999); and Caliceti et al., *Bioconjug. Chem.* 10:638-646 (1999), the disclosures of each of which are incorporated herein by reference.

The polyethylene glycol molecules (or other chemical moieties) should be attached to the protein with consideration of effects on functional or antigenic domains of the protein. There are a number of attachment methods available to those skilled in the art, e.g., EP 0 401 384, herein incorporated by reference (coupling PEG to G-CSF), see also Malik et al., *Exp. Hematol.* 20:1028-1035 (1992) (reporting pegylation of GM-CSF using tresyl chloride). For example, polyethylene glycol may be covalently bound through amino acid residues via a reactive group, such as, a free amino or carboxyl group. Reactive groups are those to which an activated polyethylene glycol molecule may be bound. The amino acid residues having a free amino group may include lysine residues and the N-terminal amino acid residues; those having a free carboxyl group may include aspartic acid residues glutamic acid residues and the C-terminal amino acid residue. Sulfhydryl groups may also be used as a reactive group for attaching the polyethylene glycol molecules. Preferred for therapeutic purposes is attachment at an amino group, such as attachment at the N-terminus or lysine group.

As suggested above, polyethylene glycol may be attached to proteins via linkage to any of a number of amino acid residues. For example, polyethylene glycol can be linked to a proteis via covalent bonds to lysine, histidine, aspartic acid, glutamic acid, or cysteine residues. One or more reaction chemistries may be employed to attach polyethylene glycol to specific amino acid residues (e.g., lysine, histidine, aspartic acid, glutamic acid, or cysteine) of the protein or to more than one type of amino acid residue (e.g., lysine, histidine, aspartic acid, glutamic acid, cysteine and combinations thereof) of the protein.

One may specifically desire proteins chemically modified at the N-terminus. Using polyethylene glycol as an illustration of the present composition, one may select from a variety of polyethylene glycol molecules (by molecular weight, branching, etc.), the proportion of polyethylene glycol molecules to protein (or peptide) molecules in the reaction mix, the type of pegylation reaction to be performed, and the method of obtaining the selected N-terminally pegylated protein. The method of obtaining the N-terminally pegylated preparation (i.e., separating this moiety from other monopegylated moieties if necessary) may be by purification of the N-terminally pegylated material from a population of pegylated protein molecules. Selective proteins chemically modified at the N-terminus modification may be accomplished by reductive alkylation, which exploits differential reactivity of different types of primary amino groups (lysine versus the N-terminal) available for derivatization in a particular protein. Under the appropriate reaction conditions, substantially selective derivatization of the protein at the N-terminus with a carbonyl group containing polymer is achieved.

As indicated above, pegylation of the proteins of the invention may be accomplished by any number of means. For example, polyethylene glycol may be attached to the protein either directly or by an intervening linker. Linkerless systems for attaching polyethylene glycol to proteins are described in Delgado et al., *Crit. Rev. Thera. Drug Carrier Sys.* 9:249-304 (1992); Francis et al., *Intern. J. of Hematol.* 68:1-18 (1998); U.S. Pat. No. 4,002,531; U.S. Pat. No. 5,349,052; WO 95/06058; and WO 98/32466, the disclosures of each of which are incorporated herein by reference.

One system for attaching polyethylene glycol directly to amino acid residues of proteins without an intervening linker employs tresylated MPEG, which is produced by the modification of monmethoxy polyethylene glycol (MPEG) using tresylchloride ($ClSO_2CH_2CF_3$). Upon reaction of protein with tresylated MPEG, polyethylene glycol is directly attached to amine groups of the protein. Thus, the invention includes protein-polyethylene glycol conjugates produced by reacting proteins of the invention with a polyethylene glycol molecule having a 2,2,2-trifluoreothane sulphonyl group.

Polyethylene glycol can also be attached to proteins using a number of different intervening linkers. For example, U.S. Pat. No. 5,612,460, the entire disclosure of which is incorporated herein by reference, discloses urethane linkers for connecting polyethylene glycol to proteins. Protein-polyethylene glycol conjugates wherein the polyethylene glycol is attached to the protein by a linker can also be produced by reaction of proteins with compounds such as MPEG-succinimidylsuccinate, MPEG activated with 1,1'-carbonyldiimidazole, MPEG-2,4,5-trichloropenylcarbonate, MPEG-p-nitrophenolcarbonate, and various MPEG-succinate derivatives. A number additional polyethylene glycol derivatives and reaction chemistries for attaching polyethylene glycol to proteins are described in WO 98/32466, the entire disclosure of which is incorporated herein by reference. Pegylated protein products produced using the reaction chemistries set out herein are included within the scope of the invention.

The number of polyethylene glycol moieties attached to each protein of the invention (i.e., the degree of substitution) may also vary. For example, the pegylated proteins of the invention may be linked, on average, to 1, 2, 3, 4, 5, 6, 7, 8, 9, 10, 12, 15, 17, 20, or more polyethylene glycol molecules. Similarly, the average degree of substitution within ranges such as 1-3, 2-4, 3-5, 4-6, 5-7, 6-8, 7-9, 8-10, 9-11, 10-12, 11-13, 12-14, 13-15, 14-16, 15-17, 16-18, 17-19, or 18-20 polyethylene glycol moieties per protein molecule. Methods for determining the degree of substitution are discussed, for example, in Delgado et al., *Crit. Rev. Thera. Drug Carrier Sys.* 9:249-304 (1992).

As mentioned the G-protein Chemokine Receptor proteins of the invention may be modified by either natural processes, such as posttranslational processing, or by chemical modification techniques that are well known in the art. It will be appreciated that the same type of modification may be present in the same or varying degrees at several sites in a given G-protein Chemokine Receptor polypeptide. G-protein Chemokine Receptor polypeptides may be branched, for example, as a result of ubiquitination, and they may be cyclic, with or without branching. Cyclic, branched, and branched cyclic G-protein Chemokine Receptor polypeptides may result from posttranslation natural processes or may be made by synthetic methods. Modifications include acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphotidylinositol, cross-linking, cyclization, disulfide bond formation, demethylation, formation of covalent cross-links, formation of cysteine, formation of pyroglutamate, formylation, gamma-carboxylation, glycosylation, GPI anchor formation, hydroxylation, iodination, methylation, myristoylation, oxidation, pegylation, proteolytic processing, phosphorylation, prenylation, racemization, selenoylation, sulfation, transfer-RNA mediated addition of amino acids to proteins such as arginylation, and ubiquitination. (See, for instance, PROTEINS—STRUCTURE AND MOLECULAR PROPERTIES, 2nd Ed., T. E. Creighton, W. H. Freeman and Company, New York (1993); POSTTRANSLATIONAL COVALENT MODIFICATION OF PROTEINS, B. C. Johnson, Ed., Academic Press, New York, pgs. 1-12 (1983); Seifter et al., *Meth Enzymol* 182:626-646 (1990); Rattan et al., *Ann NY Acad Sci* 663:48-62 (1992)).

The G-protein Chemokine Receptor polypeptides of the invention can be recovered and purified from chemical synthesis and recombinant cell cultures by standard methods which include, but are not limited to, ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography. Most preferably, high performance liquid chromatography ("HPLC") is employed for purification. Well-known techniques for refolding protein may be employed to regenerate active conformation when the polypeptide is denatured during isolation and/or purification.

G-protein Chemokine Receptor receptor polynucleotides and polypeptides may be used in accordance with the present invention for a variety of applications, particularly those that make use of the chemical and biological properties of G-protein Chemokine Receptor. Among these are applications in treatment of tumors, resistance to parasites, bacteria and viruses, to inhibit proliferation of B cells, to induce proliferation of T-cells, endothelial cells and certain hematopoietic cells, to treat restenosis, graft vs. host disease, to regulate anti-viral responses and to prevent certain autoimmune diseases after stimulation of G-protein Chemokine Receptor by an agonist. Additional applications relate to diagnosis and to treatment of disorders of cells, tissues and organisms. These aspects of the invention are discussed further below.

Transgenics and "Knock-Outs"

The G-protein Chemokine Receptor proteins of the invention can also be expressed in transgenic animals. Animals of any species, including, but not limited to, mice, rats, rabbits, hamsters, guinea pigs, pigs, micro-pigs, goats, sheep, cows and non-human primates, e.g., baboons, monkeys, and chimpanzees may be used to generate transgenic animals. In a specific embodiment, techniques described herein or otherwise known in the art are used to express polypeptides of the invention in humans, as part of a gene therapy protocol.

Any technique known in the art may be used to introduce the transgene (i.e., nucleic acids of the invention) into animals to produce the founder lines of transgenic animals. Such techniques include, but are not limited to, pronuclear microinjection (Paterson et al., *Appl. Microbiol. Biotechnol.* 40:691-698 (1994); Carver et al., *Biotechnology (NY)* 11:1263-1270 (1993); Wright et al., *Biotechnology (NY)* 9:830-834 (1991); and Hoppe et al., U.S. Pat. No. 4,873,191 (1989)); retrovirus mediated gene transfer into germ lines (Van der Putten et al., *Proc. Natl. Acad. Sci., USA* 82:6148-6152 (1985)), blastocysts or embryos; gene targeting in embryonic stem cells (Thompson et al., *Cell* 56:313-321 (1989)); electroporation of cells or embryos (Lo, *Mol Cell. Biol.* 3:1803-1814 (1983)); introduction of the polynucleotides of the invention using a gene gun (see, e.g., Ulmer et al., *Science* 259:1745 (1993); introducing nucleic acid constructs into embryonic pleuripotent stem cells and transferring the stem cells back into the blastocyst; and sperm-mediated gene transfer (Lavitrano et al., *Cell* 57:717-723 (1989); etc. For a review of such techniques, see Gordon, "Transgenic Animals," *Intl. Rev. Cytol.* 115:171-229 (1989), which is incorporated by reference herein in its entirety. Further, the contents of each of the documents recited in this paragraph are herein incorporated by reference in its entirety. Gordon, "Transgenic Animals," Intl. Rev. Cytol. 115:171-229 (1989), which is incorporated by reference herein in its entirety. See also, U.S. Pat. No. 5,464,764 (Capecchi, et al., Positive-Negative Selection Methods and Vectors); U.S. Pat. No. 5,631,153 (Capecchi, et al., Cells and Non-Human Organisms Containing Predetermined Genomic Modifications and Positive-Negative Selection Methods and Vectors for Making Same); U.S. Pat. No. 4,736,866 (Leder, et al., Transgenic Non-Human Animals); and U.S. Pat. No. 4,873,191 (Wagner, et al., Genetic Transformation of Zygotes); each of which is hereby incorporated by reference in its entirety.

Any technique known in the art may be used to produce transgenic clones containing polynucleotides of the invention, for example, nuclear transfer into enucleated oocytes of nuclei from cultured embryonic, fetal, or adult cells induced to quiescence (Campell et al., *Nature* 380:64-66 (1996); Wilmut et al., *Nature* 385:810-813 (1997)), each of which is herein incorporated by reference in its entirety).

The present invention provides for transgenic animals that carry the transgene in all their cells, as well as animals which carry the transgene in some, but not all their cells, i.e., mosaic animals or chimeric animals. The transgene may be integrated as a single transgene or as multiple copies such as in concatamers, e.g., head-to-head tandems or head-to-tail tandems. The transgene may also be selectively introduced into and activated in a particular cell type by following, for example, the teaching of Lasko et al. (*Proc. Natl. Acad. Sci. USA* 89:6232-6236 (1992)). The regulatory sequences required for such a cell-type specific activation will depend upon the particular cell type of interest, and will be apparent to those of skill in the art. When it is desired that the polynucleotide transgene be integrated into the chromosomal site of the endogenous gene, gene targeting is preferred. Briefly, when such a technique is to be utilized, vectors containing some nucleotide sequences homologous to the endogenous gene are designed for the purpose of integrating, via homologous recombination with chromosomal sequences, into and disrupting the function of the nucleotide sequence of the endogenous gene. The transgene may also be selectively introduced into a particular cell type, thus inactivating the endogenous gene in only that cell type, by following, for example, the teaching of Gu et. al. (*Science* 265:103-106 (1994)). The regulatory sequences required for such a cell-type specific inactivation will depend upon the particular cell type of interest, and will be apparent to those of skill in the art. The contents of each of the documents recited in this paragraph are herein incorporated by reference in its entirety.

Once transgenic animals have been generated, the expression of the recombinant gene may be assayed utilizing standard techniques. Initial screening may be accomplished by Southern blot analysis or PCR techniques to analyze animal tissues to verify that integration of the transgene has taken place. The level of mRNA expression of the transgene in the tissues of the transgenic animals may also be assessed using techniques which include, but are not limited to, Northern blot analysis of tissue samples obtained from the animal, in situ hybridization analysis, and reverse transcriptase-PCR (rt-PCR). Samples of transgenic gene-expressing tissue may also be evaluated immunocytochemically or immunohistochemically using antibodies specific for the transgene product.

Once the founder animals are produced, they may be bred, inbred, outbred, or crossbred to produce colonies of the particular animal. Examples of such breeding strategies include, but are not limited to: outbreeding of founder animals with more than one integration site in order to establish separate lines; inbreeding of separate lines in order to produce compound transgenics that express the transgene at higher levels because of the effects of additive expression of each transgene; crossing of heterozygous transgenic animals to produce animals homozygous for a given integration site in order to both augment expression and eliminate the need for screening of animals by DNA analysis; crossing of separate homozygous lines to produce compound heterozygous or homozygous lines; and breeding to place the transgene on a distinct background that is appropriate for an experimental model of interest.

Transgenic and "knock-out" animals of the invention have uses which include, but are not limited to, animal model systems useful in elaborating the biological function of G-protein Chemokine Receptor polypeptides, studying conditions and/or disorders associated with aberrant G-protein Chemokine Receptor expression, and in screening for compounds effective in ameliorating such conditions and/or disorders.

In further embodiments of the invention, cells that are genetically engineered to express the proteins of the invention, or alternatively, that are genetically engineered not to express the proteins of the invention (e.g., knockouts) are administered to a patient in vivo. Such cells may be obtained from the patient (i.e., animal, including human) or an MHC compatible donor and can include, but are not limited to fibroblasts, bone marrow cells, blood cells (e.g., lymphocytes), adipocytes, muscle cells, endothelial cells, etc. The cells are genetically engineered in vitro using recombinant DNA techniques to introduce the coding sequence of polypeptides of the invention into the cells, or alternatively, to disrupt the coding sequence and/or endogenous regulatory sequence associated with the polypeptides of the invention, e.g., by transduction (using viral vectors, and preferably vectors that integrate the transgene into the cell genome) or transfection procedures, including, but not limited to, the use of plasmids, cosmids, YACs, naked DNA, electroporation, liposomes, etc. The coding sequence of the polypeptides of the invention can be placed under the control of a strong constitutive or inducible promoter or promoter/enhancer to achieve expression, and preferably secretion, of the polypeptides of the invention. The engineered cells that express and preferably secrete the polypeptides of the invention can be introduced into the patient systemically, e.g., in the circulation, or intraperitoneally. Alternatively, the cells can be incorporated into a matrix and implanted in the body, e.g., genetically engineered fibroblasts can be implanted as part of a skin graft; genetically engineered endothelial cells can be implanted as part of a lymphatic or vascular graft. (See, for example, Anderson et al. U.S. Pat. No. 5,399,349; and Mulligan & Wilson, U.S. Pat. No. 5,460,959, each of which is incorporated by reference herein in its entirety).

When the cells to be administered are non-autologous or non-MHC compatible cells, they can be administered using well-known techniques that prevent the development of a host immune response against the introduced cells. For example, the cells may be introduced in an encapsulated form that, while allowing for an exchange of components with the immediate extracellular environment, does not allow the introduced cells to be recognized by the host immune system.

G-Protein Chemokine Receptor Receptor Polypeptides and Fragments

The present invention further relates to a G-protein chemokine receptor polypeptide which has the deduced amino acid sequence of FIG. 1 (SEQ ID NO:2) or more preferably FIG. 2 (SEQ ID NO:4), as well as fragments, analogs and derivatives of such polypeptide.

The terms "fragment," "derivative" and "analog" when referring to the polypeptides of the invention, means a polypeptide which either retains substantially the same biological function or activity as such polypeptide, i.e. functions as a G-protein chemokine receptor, or retains the ability to bind the ligand for the receptor, for example, a soluble form of the receptor. An analog includes a proprotein that can be activated by cleavage of the proprotein portion to produce an active mature polypeptide.

The polypeptide of the present invention may be a recombinant polypeptide, a natural polypeptide or a synthetic polypeptide, preferably a recombinant polypeptide.

The fragment, derivative, or analog of a polypeptide of FIG. 1 (SEQ ID NO: 2) or more preferably FIG. 2 (SEQ ID NO:4) may be (i) one in which one or more of the amino acid residues are substituted with a conserved or non-conserved amino acid residue (preferably a conserved amino acid residue) and such substituted amino acid residue may or may not be one encoded by the genetic code, or (ii) one in which one or more of the amino acid residues includes a substituent group, or (iii) one in which the mature polypeptide is fused with another compound, such as a compound to increase the half-life of the polypeptide (for example, polyethylene glycol), or (iv) one in which the additional amino acids are fused to the mature polypeptide for purification of the polypeptide or (v) one in which a fragment of the polypeptide is soluble, i.e. not membrane bound, yet still binds ligands to the membrane bound receptor. Such fragments, derivatives and analogs are deemed to be within the scope of those skilled in the art from the teachings herein.

The polypeptides and polynucleotides of the present invention are preferably provided in an isolated form, and preferably are purified to homogeneity.

Thus, the present invention is directed to polynucleotides having at least a 70% identity, preferably at least 90% and more preferably at least a 95% identity to a polynucleotide which encodes the polypeptide of SEQ ID NO:2 or more preferably SEQ ID NO: 4 and polynucleotides complementary thereto as well as portions thereof, which portions have at least 15 consecutive bases, preferably 30 consecutive bases and more preferably at least 50 consecutive bases and to polypeptides encoded by such polynucleotides.

As known in the art "similarity" between two polypeptides is determined by comparing the amino acid sequence and conserved amino acid substitutes thereto of the polypeptide to the sequence of a second polypeptide.

Fragments or portions of the polypeptides of the present invention may be employed for producing the corresponding full-length polypeptide by peptide synthesis, therefore, the fragments may be employed as intermediates for producing the full-length polypeptides. Fragments or portions of the polynucleotides of the present invention may be used to synthesize full-length polynucleotides of the present invention.

The term "gene" means the segment of DNA involved in producing a polypeptide chain; it includes regions preceding and following the coding region "leader and trailer" as well as intervening sequences (introns) between individual coding segments (exons).

The term "isolated" means that the material is removed from its original environment (e.g., the natural environment if it is naturally occurring). For example, a naturally-occurring polynucleotide or polypeptide present in a living animal is not isolated, but the same polynucleotide or polypeptide, separated from some or all of the coexisting materials in the natural system, is isolated. Such polynucleotides could be part of a vector and/or such polynucleotides or polypeptides could be part of a composition, and still be isolated in that such vector or composition is not part of its natural environment.

The G-protein Chemokine Receptor proteins (polypeptides) of the invention may be in monomers or multimers (i.e., dimers, trimers, tetramers, and higher multimers). Accordingly, the present invention relates to monomers and multimers of the G-protein Chemokine Receptor proteins (polypeptides) of the invention, their preparation, and compositions (preferably, pharmaceutical compositions) containing them.

In specific embodiments, the polypeptides of the invention are monomers, dimers, trimers or tetramers. In additional embodiments, the multimers of the invention are at least dimers, at least trimers, or at least tetramers.

Multimers encompassed by the invention may be homomers or heteromers. As used herein, the term homomer, refers to a multimer containing only G-protein Chemokine Receptor proteins of the invention (including G-protein Chemokine Receptor fragments, variants, and fusion proteins, as described herein). These homomers may contain G-protein Chemokine Receptor proteins having identical or different polypeptide sequences. In a specific embodiment, a homomer of the invention is a multimer containing only G-protein Chemokine Receptor proteins having an identical polypeptide sequence. In another specific embodiment, a homomer of the invention is a multimer containing G-protein Chemokine Receptor proteins having different polypeptide sequences (e.g., G-protein Chemokine Receptor proteins containing mutations). In specific embodiments, the multimer of the invention is a homodimer (e.g., containing G-protein Chemokine Receptor proteins having identical or different polypeptide sequences) or a homotrimer (e.g., containing G-protein Chemokine Receptor proteins having identical or different polypeptide sequences). In additional embodiments, the homomeric multimer of the invention is at least a homodimer, at least a homotrimer, or at least a homotetramer.

As used herein, the term heteromer refers to a multimer containing heterologous proteins (i.e., proteins containing only polypeptide sequences that do not correspond to a polypeptide sequences encoded by the G-protein Chemokine Receptor gene) in addition to the G-protein Chemokine Receptor proteins of the invention. In a specific embodiment, the multimer of the invention is a heterodimer, a heterotrimer, or a heterotetramer. In additional embodiments, the heteromeric multimer of the invention is at least a heterodimer, at least a heterotrimer, or at least a heterotetramer.

Multimers of the invention may be the result of hydrophobic, hydrophilic, ionic and/or covalent associations and/or may be indirectly linked, by for example, liposome formation. Thus, in one embodiment, multimers of the invention, such as, for example, homodimers or homotrimers, are formed when proteins of the invention contact one another in solution. In another embodiment, heteromultimers of the invention, such as, for example, heterotrimers or heterotetramers, are formed when proteins of the invention contact antibodies to the polypeptides of the invention (including antibodies to the heterologous polypeptide sequence in a fusion protein of the invention) in solution. In other embodiments, multimers of the invention are formed by covalent associations with and/or between the G-protein Chemokine Receptor proteins of the invention. Such covalent associations may involve one or more amino acid residues contained in the polypeptide sequence of the protein (e.g., the polypeptide sequence shown in FIG. 1 (SEQ ID NO:2) or FIG. 2 (SEQ ID NO:4)). In one instance, the covalent associations are cross-linking between cysteine residues located within the polypeptide sequences of the proteins which interact in the native (i.e., naturally occurring) polypeptide. In another instance, the covalent associations are the consequence of chemical or recombinant manipulation. Alternatively, such covalent associations may involve one or more amino acid residues contained in the heterologous polypeptide sequence in a G-protein Chemokine Receptor fusion protein. In one example, covalent associations are between the heterologous sequence contained in a fusion protein of the invention (see, e.g., U.S. Pat. No. 5,478,925). In a specific example, the covalent associations are between the heterologous sequence contained in a G-protein Chemokine Receptor-Fc fusion protein of the invention (as described herein). In another specific example, covalent associations of fusion proteins of the invention are between heterologous polypeptide sequences from another chemokine family ligand/receptor member that is capable of forming covalently associated multimers, such as for example, oseteoprotegerin (see, e.g., International Publication No. WO 98/49305, the contents of which are herein incorporated by reference in its entirety). In another embodiment, two or more G-protein Chemokine Receptor polypeptides of the invention are joined through synthetic linkers (e.g., peptide, carbohydrate or soluble polymer linkers). Examples include those peptide linkers described in U.S. Pat. No. 5,073,627 (hereby incorporated by reference). Proteins comprising multiple G-protein Chemokine Receptor polypeptides separated by peptide linkers may be produced using conventional recombinant DNA technology.

Another method for preparing multimer G-protein Chemokine Receptor polypeptides of the invention involves use of G-protein Chemokine Receptor polypeptides fused to a leucine zipper or isoleucine polypeptide sequence. Leucine zipper domains and isoleucine zipper domains are polypeptides that promote multimerization of the proteins in which they are found. Leucine zippers were originally identified in several DNA-binding proteins (Landschulz et al., *Science* 240:1759, (1988)), and have since been found in a variety of different proteins. Among the known leucine zippers are naturally occurring peptides and derivatives thereof that dimerize or trimerize. Examples of leucine zipper domains suitable for producing soluble multimeric G-protein Chemokine Receptor proteins are those described in PCT application WO 94/10308, hereby incorporated by reference. Recombinant fusion proteins comprising a soluble G-protein Chemokine Receptor polypeptide fused to a peptide that dimerizes or trimerizes in solution are expressed in suitable host cells, and the resulting soluble multimeric G-protein Chemokine Receptor is recovered from the culture supernatant using techniques known in the art.

In another example, proteins of the invention are associated by interactions between Flag® polypeptide sequence contained in Flag®-G-protein Chemokine Receptor fusion proteins of the invention. In a further embodiment, associated proteins of the invention are associated by interactions between heterologous polypeptide sequence contained in Flag®-G-protein Chemokine Receptor fusion proteins of the invention and anti-Flag® antibody.

The multimers of the invention may be generated using chemical techniques known in the art. For example, proteins desired to be contained in the multimers of the invention may be chemically cross-linked using linker molecules and linker molecule length optimization techniques known in the art (see, e.g., U.S. Pat. No. 5,478,925, which is herein incorporated by reference in its entirety). Additionally, multimers of the invention may be generated using techniques known in the art to form one or more inter-molecule cross-links between the cysteine residues located within the polypeptide sequence of the proteins desired to be contained in the multimer (see, e.g., U.S. Pat. No. 5,478,925, which is herein incorporated by reference in its entirety). Further, proteins of the invention may be routinely modified by the addition of cysteine or biotin to the C terminus or N-terminus of the polypeptide sequence of the protein and techniques known in the art may be applied to generate multimers containing one or more of these modified proteins (see, e.g., U.S. Pat. No. 5,478,925, which is herein incorporated by reference in its entirety). Additionally, techniques known in the art may be applied to generate liposomes containing the protein components desired to be contained in the multimer of the invention (see, e.g., U.S. Pat. No. 5,478,925, which is herein incorporated by reference in its entirety).

Alternatively, multimers of the invention may be generated using genetic engineering techniques known in the art. In one embodiment, proteins contained in multimers of the invention are produced recombinantly using fusion protein technology described herein or otherwise known in the art (see, e.g., U.S. Pat. No. 5,478,925, which is herein incorporated by reference in its entirety). In a specific embodiment, polynucleotides coding for a homodimer of the invention are generated by ligating a polynucleotide sequence encoding a polypeptide of the invention to a sequence encoding a linker polypeptide and then further to a synthetic polynucleotide encoding the translated product of the polypeptide in the reverse orientation from the original C-terminus to the N-terminus (lacking the leader sequence) (see, e.g., U.S. Pat. No. 5,478,925, which is herein incorporated by reference in its entirety). In another embodiment, recombinant techniques described herein or otherwise known in the art are applied to generate recombinant polypeptides of the invention which contain a transmembrane domain and which can be incorporated by membrane reconstitution techniques into liposomes (see, e.g., U.S. Pat. No. 5,478,925, which is herein incorporated by reference in its entirety).

The polypeptides of the present invention are preferably provided in an isolated form. By "isolated polypeptide" is intended a polypeptide removed from its native environment. Thus, a polypeptide produced and/or contained within a recombinant host cell is considered isolated for purposes of the present invention. Also intended as an "isolated polypeptide" are polypeptides that have been purified, partially or substantially, from a recombinant host cell. For example, a recombinantly produced version of the G-protein Chemokine Receptor polypeptide can be substantially purified by the one-step method described in Smith and Johnson, *Gene* 67:31-40 (1988).

Accordingly, in one embodiment, the invention provides an isolated G-protein Chemokine Receptor polypeptide having the amino acid sequence in FIG. 1 (SEQ ID NO: 2), more preferably the amino acid sequence in FIG. 2 (SEQ ID NO:4), or a polypeptide comprising a portion of the above polypeptides, such as for example, a mature G-protein Chemokine Receptor comprising amino acids 1 to 415 of FIG. 1 (SEQ ID NO: 2), more preferably a mature G-protein Chemokine Receptor comprising amino acids 1 to 368 of FIG. 2 (SEQ ID NO:4), a G-protein Chemokine Receptor extracellular domain, the G-protein Chemokine Receptor N-terminus, and/or a G-protein Chemokine Receptor intracellular domain.

In an additional embodiment, the invention provides an isolated G-protein Chemokine Receptor polypeptide having the amino acid sequence encoded by the polynucleotide sequence contained in ATCC Deposit No. 97334, or a polypeptide comprising a portion of such polypeptide, such as for example, the mature G-protein Chemokine Receptor encoded by the polynucleotide sequence contained in ATCC Deposit No. 97334, a G-protein Chemokine Receptor extracellular domain, the G-protein Chemokine Receptor N-terminus, and/or a G-protein Chemokine Receptor intracellular domain.

Polypeptide fragments of the present invention include polypeptides comprising or alternatively, consisting of: an amino acid sequence contained in FIG. 1 (SEQ ID NO: 2); and encoded by a nucleic acid containing a polynucleotide sequence which hybridizes (e.g., under stringent hybridization conditions) to the nucleotide sequence encoded by a nucleic acid containing a polynucleotide sequence which hybridizes to the complementary strand of the nucleotide sequence shown in FIG. 1 (SEQ ID NO:1). Polynucleotides encoding these polypeptides are also encompassed by the invention.

Prefered polypeptide fragments of the present invention include polypeptides comprising or alternatively, consisting of: an amino acid sequence contained in FIG. 2 (SEQ ID NO:4); and encoded by a nucleic acid containing a polynucleotide sequence which hybridizes (e.g., under stringent hybridization conditions) to the nucleotide sequence encoded by a nucleic acid containing a polynucleotide sequence which hybridizes to the complementary strand of the nucleotide sequence shown in FIG. 2 (SEQ ID NO:3). Polynucleotides encoding these polypeptides are also encompassed by the invention.

Protein fragments may be "free-standing," or comprised within a larger polypeptide of which the fragment forms a part or region, most preferably as a single continuous region. Representative examples of polypeptide fragments of the invention, include, for example, fragments that comprise or alternatively, consist of from about amino acid residues: residues 4 to 8, 25 to 31, 51 to 54, 75 to 85, 127 to 131, 208 to 213, 336 to 341, 385 to 389, and 394 to 405 of SEQ ID NO:2 (FIG. 1), or more preferably 28 to 38, 80 to 84, 161 to 166, 289 to 294, 338 to 342, and 347 to 358 of SEQ ID NO:4 (FIG. 2). Moreover, polypeptide fragments can be at least 10, 20, 30, 40, 50, 60, 70, 80, 90, 100, 110, 120, 130, 140, 150, 175, 200, 250, 300, 350, 400 or 500 amino acids in length. Polynucleotides encoding these polypeptides are also encompassed by the invention. In this context "about" includes the particularly recited ranges, larger or smaller by several (5, 4, 3, 2, or 1) amino acids, at either extreme or at both extremes. Polynucleotides encoding these polypeptides are also encompassed by the invention.

In additional embodiments, the polypeptide fragments of the invention comprise, or alternatively consist of, one or more G-protein Chemokine Receptor domains. Preferred polypeptide fragments of the present invention include a member selected from the group: (a) a polypeptide comprising or alternatively, consisting of, a G-protein Chemokine Receptor extracellular domain (e.g. amino acid residues from 1 to 59, 114 to 127, 191 to 223, and/or 278 to 307 in SEQ ID NO:4); (b) a polypeptide comprising or alternatively, consisting of, a G-protein Chemokine Receptor N-terminal region (predicted to constitute amino acid residues from about 1 to about 59 FIG. 2 (SEQ ID NO: 4); (c) a polypeptide comprising or alternatively, consisting of, a G-protein Chemokine Receptor transmembrane domain (e.g. amino acid residues from 60 to 79, 92 to 113, 128 to 147, 170 to 190, 224 to 245, 259 to 277, and/or 302 to 322 in SEQ ID NO: 4); (d) a polypeptide comprising or alternatively, consisting of, a -protein Chemokine Receptor intracellular domain (e.g. amino acid residues from 80 to 91, 148 to 169, 246 to 258, and/or 323 to 368 in SEQ ID NO:4); (e) a polypeptide comprising, or alternatively, consisting of, one, two, three, four or more, epitope bearing portions of the G-protein Chemokine Receptor protein; (f) a polypeptide encoded by the nucleotide sequence of the cDNA clone contained in the deposit having ATCC Accession No. 97768; or (g) any combination of polypeptides (a)-(f). Polynucleotides encoding these polypeptides are also encompassed by the invention.

As discussed above, it is believed that the extracellular domains of the G-protein Chemokine Receptor are important for interactions between G-protein Chemokine Receptor and its ligands. Accordingly, in preferred embodiments, polypeptide fragments of the invention comprise, or alternatively consist of amino acid residues in these domains. Polynucleotides encoding these polypeptides are also encompassed by the invention.

Among the especially preferred fragments of the invention are fragments characterized by structural or functional attributes of G-protein Chemokine Receptor. Such fragments include amino acid residues that comprise alpha-helix and alpha-helix forming regions ("alpha-regions"), beta-sheet and beta-sheet-forming regions ("beta-regions"), turn and turn-forming regions ("turn-regions"), coil and coil-forming regions ("coil-regions"), hydrophilic regions, hydrophobic regions, alpha amphipathic regions, beta amphipathic regions, surface forming regions, and high antigenic index regions (i.e., containing four or more contiguous amino acids having an antigenic index of greater than or equal to 1.5, as identified using the default parameters of the Jameson-Wolf program) of complete (i.e., full-length) G-protein Chemokine Receptor (FIG. 1 (SEQ ID NO:2) or FIG. 2 (SEQ ID NO:4)). Certain preferred regions are those set out in FIG. 5 and FIG. 6 and include, but are not limited to, regions of the aforementioned types identified by analysis of the amino acid sequence depicted in FIG. 1 (SEQ ID NO:2) and FIG. 2 (SEQ ID NO:4), such preferred regions include; Garner-Robson predicted alpha-regions, beta-regions, turn-regions, and coil-regions; Chou-Farman predicted alpha-regions, beta-regions, and turn-regions; Kite-Doolittle predicted hydrophilic; Hop-Woods predicted hydrophobic regions; Eisenberg alpha and beta amphipathic regions; Gemini surface-forming regions; and Jameson-Wolf high antigenic index regions, as predicted using the default parameters of these computer programs. Polynucleotides encoding these polypeptides are also encompassed by the invention.

As mentioned above, even if deletion of one or more amino acids from the N-terminus of a protein results in modification of loss of one or more biological functions of the protein, other functional activities (e.g., biological activities, ability bind G-protein Chemokine Receptor ligand (e.g., MIG, IP-10, and ITAC)) may still be retained. For example, the ability of shortened G-protein Chemokine Receptor muteins to induce and/or bind to antibodies which recognize the complete or mature forms of the polypeptides generally will be retained when less than the majority of the residues of the complete or mature polypeptide are removed from the N-terminus. Whether a particular polypeptide lacking N-terminal residues of a complete full-length polypeptide retains such immunologic activities can readily be determined by routine methods described herein and otherwise known in the art. It is not unlikely that a G-protein Chemokine Receptor mutein with a large number of deleted N-terminal amino acid residues may retain some biological or immunogenic activities. In fact, peptides composed of as few as six G-protein Chemokine Receptor amino acid residues may often evoke an immune response.

Accordingly, the present invention further provides polypeptides having one or more residues deleted from the amino terminus of the G-protein Chemokine Receptor amino acid sequence shown in FIG. 1, up to the alanine residue at position number 410 and polynucleotides encoding such polypeptides. In particular, the present invention provides polypeptides comprising the amino acid sequence of residues $n^1$-415 of FIG. 1, where $n^1$ is an integer from 2 to 410 corresponding to the position of the amino acid residue in FIG. 1 (SEQ ID NO:2).

More in particular, the invention provides polynucleotides encoding polypeptides comprising, or alternatively consisting of, the amino acid sequence of residues: L-3 to A-410; R-4 to A-410; K-5 to A-410; Y-6 to A-410; G-7 to A-410; P-8 to A-410; G-9 to A-410; R-10 to A-410; L-11 to A-410; A-12 to A-410; G-13 to A-410; T-14 to A-410; V-15 to A-410; I-16 to A-410; G-17 to A-410; G-18 to A-410; A-19 to A-410; A-20 to A-410; Q-21 to A-410; S-22 to A-410; K-23 to A-410; S-24 to A-410; Q-25 to A-410; T-26 to A-410; K-27 to A-410; S-28 to A-410; D-29 to A-410; S-30 to A-410; I-31 to A-410; T-32 to A-410; K-33 to A-410; E-34 to A-410; F-35 to A-410; L-36 to A-410; P-37 to A-410; G-38 to A-410; L-39 to A-410; Y-40 to A-410; T-41 to A-410; A-42 to A-410; P-43 to A-410; S-44 to A-410; S-45 to A-410; P-46 to A-410; F-47 to A-410; P-48 to A-410; P-49 to A-410; S-50 to A-410; Q-51 to A-410; V-52 to A-410; S-53 to A-410; D-54 to A-410; H-55 to A-410; Q-56 to A-410; V-57 to A-410; L-58 to A-410; N-59 to A-410; D-60 to A-410; A-61 to A-410; E-62 to A-410; V-63 to A-410; A-64 to A-410; A-65 to A-410; L-66 to A-410; L-67 to A-410; E-68 to A-410; N-69 to A-410; F-70 to A-410; S-71 to A-410; S-72 to A-410; S-73 to A-410; Y-74 to A-410; D-75 to A-410; Y-76 to A-410; G-77 to A-410; E-78 to A-410; N-79 to A-410; E-80 to A-410; S-81 to A-410; D-82 to A-410; S-83 to A-410; C-84 to A-410; C-85 to A-410; T-86 to A-410; S-87 to A-410; P-88 to A-410; P-89 to A-410; C-90 to A-410; P-91 to A-410; Q-92 to A-410; D-93 to A-410; F-94 to A-410; S-95 to A-410; L-96 to A-410; N-97 to A-410; F-98 to A-410; D-99 to A-410; R-100 to A-410; A-101 to A-410; F-102 to A-410; L-103 to A-410; P-104 to A-410; A-105 to A-410; L-106 to A-410; Y-107 to A-410; S-108 to A-410; L-109 to A-410; L-110 to A-410; F-111 to A-410; L-112 to A-410; L-113 to A-410; G-114 to A-410; L-115 to A-410; L-116 to A-410; G-117 to A-410; N-118 to A-410; G-119 to A-410; A-120 to A-410; V-121 to A-410; A-122 to A-410; A-123 to A-410; V-124 to A-410; L-125 to A-410; L-126 to A-410; S-127 to A-410; R-128 to A-410; R-129 to A-410; T-130 to A-410; A-131 to A-410; L-132 to A-410; S-133 to A-410; S-134 to A-410; T-135 to A-410; D-136 to A-410; T-137 to A-410; F-138 to A-410; L-139 to A-410; L-140 to A-410; H-141 to A-410; L-142 to A-410; A-143 to A-410; V-144 to A-410; A-145 to A-410; D-146 to A-410; T-147 to A-410; L-148 to A-410; L-149 to A-410; V-150 to A-410; L-151 to A-410; T-152 to A-410; L-153 to A-410; P-154 to A-410; L-155 to A-410; W-156 to A-410; A-157 to A-410; V-158 to A-410; D-159 to A-410; A-160 to A-410; A-161 to A-410; V-162 to A-410; Q-163 to A-410; W-164 to A-410; V-165 to A-410; F-166 to A-410; G-167 to A-410; S-168 to A-410; G-169 to A-410; L-170 to A-410; C-171 to A-410; K-172 to A-410; V-173 to A-410; A-174 to A-410; G-175 to A-410; A-176 to A-410; L-177 to A-410; F-178 to A-410; N-179 to A-410; I-180 to A-410; N-181 to A-410; F-182 to A-410; Y-183 to A-410; A-184 to A-410; G-185 to A-410; A-186 to A-410; L-187 to A-410; L-188 to A-410; L-189 to A-410; A-190 to A-410; C-191 to A-410; I-192 to A-410; S-193 to A-410; F-194 to A-410; D-195 to A-410; R-196 to A-410; Y-197 to A-410; L-198 to A-410; N-199 to A-410; I-200 to A-410; V-201 to A-410; H-202 to A-410; A-203 to A-410; T-204 to A-410; Q-205 to A-410; L-206 to A-410; Y-207 to A-410; R-208 to A-410; R-209 to A-410; G-210 to A-410; P-211 to A-410; P-212 to A-410; A-213 to A-410; R-214 to A-410; V-215 to A-410; T-216 to A-410; L-217 to A-410; T-218 to A-410; C-219 to A-410; L-220 to A-410; A-221 to A-410; V-222 to A-410; W-223 to A-410; G-224 to A-410; L-225 to A-410; C-226 to A-410; L-227 to A-410; L-228 to A-410; F-229 to A-410; A-230 to A-410; L-231 to A-410; P-232 to A-410; D-233 to A-410; F-234 to A-410; I-235 to A-410; F-236 to A-410; L-237 to A-410; S-238 to A-410; A-239 to A-410; H-240 to A-410; H-241 to A-410; D-242 to A-410; E-243 to A-410; R-244 to A-410; L-245 to A-410; N-246 to A-410; A-247 to A-410; T-248 to A-410; H-249 to A-410; C-250 to A-410; Q-251 to A-410; Y-252 to A-410; N-253 to A-410; F-254 to A-410; P-255 to A-410; Q-256 to A-410; V-257 to A-410; G-258 to A-410; R-259 to A-410; T-260 to A-410; A-261 to A-410; L-262 to A-410; R-263 to A-410; V-264 to A-410; L-265 to A-410; Q-266 to A-410; L-267 to A-410; V-268 to A-410; A-269 to A-410; G-270 to A-410; F-271 to A-410; L-272 to A-410; L-273 to A-410; P-274 to A-410; L-275 to A-410; L-276 to A-410; V-277 to A-410; M-278 to A-410; A-279 to A-410; Y-280 to A-410; C-281 to A-410; Y-282 to A-410; A-283 to A-410; H-284 to A-410; I-285 to A-410; L-286 to A-410; A-287 to A-410; V-288 to A-410; L-289 to A-410; L-290 to A-410; V-291 to A-410; S-292 to A-410; R-293 to A-410; G-294 to A-410; Q-295 to A-410; R-296 to A-410; R-297 to A-410; L-298 to A-410; R-299 to A-410; A-300 to A-410; M-301 to A-410; R-302 to A-410; L-303 to A-410; V-304 to A-410; V-305 to A-410; V-306 to A-410; V-307 to A-410; V-308 to A-410; V-309 to A-410; A-310 to A-410; F-311 to A-410; A-312 to A-410; L-313 to A-410; C-314 to A-410; W-315 to A-410; T-316 to A-410; P-317 to A-410; Y-318 to A-410; H-319 to A-410; L-320 to A-410; V-321 to A-410; V-322 to A-410; L-323 to A-410; V-324 to A-410; D-325 to A-410; I-326 to A-410; L-327 to A-410; M-328 to A-410; D-329 to A-410; L-330 to A-410; G-331 to A-410; A-332 to A-410; L-333 to A-410; A-334 to A-410; R-335 to A-410; N-336 to A-410; C-337 to A-410; G-338 to A-410; R-339 to A-410; E-340 to A-410; S-341 to A-410; R-342 to A-410; V-343 to A-410; D-344 to A-410; V-345 to A-410; A-346 to A-410; K-347 to A-410; S-348 to A-410; V-349 to A-410; T-350 to A-410; S-351 to A-410; G-352 to A-410; L-353 to A-410; G-354 to A-410; Y-355 to A-410; M-356 to A-410; H-357 to A-410; C-358 to A-410; C-359 to A-410; L-360 to A-410; N-361 to A-410; P-362 to A-410; L-363 to A-410; L-364 to A-410; Y-365 to A-410; A-366 to A-410; F-367 to A-410; V-368 to A-410; G-369 to A-410; V-370 to A-410; K-371 to A-410; F-372 to A-410; R-373 to A-410; E-374 to A-410; R-375 to A-410; M-376 to A-410; W-377 to A-410; M-378 to A-410; L-379 to A-410; L-380 to A-410; L-381 to A-410; R-382 to A-410; L-383 to A-410; G-384 to A-410; C-385 to A-410; P-386 to A-410; N-387 to A-410; Q-388 to A-410; R-389 to A-410; G-390 to A-410; L-391 to A-410; Q-392 to A-410; R-393 to A-410; Q-394 to A-410; P-395 to A-410; S-396 to A-410; S-397 to A-410; S-398 to A-410; R-399 to A-410; R-400 to A-410; D-401 to A-410; S-402 to A-410; S-403 to A-410; W-404 to A-410; S-405 to A-410; of SEQ ID NO:2. Polypeptides encoded by these polynucleotides are also encompassed by the invention. The present invention is also directed to nucleic acid molecules comprising, or alternatively, consisting of, a polynucleotide sequence at least 80%, 85%, 90%, 92%, 95%, 96%, 97%, 98% or 99% identical to the polynucleotide sequence encoding the G-protein chemokine receptor and/or G-protein chemokine receptor polypeptides described above. The present invention also encompasses the above polynucleotide sequences fused to a heterologous polynucleotide sequence. Polypeptides encoded by these nucleic acids and/or polynucleotide sequences are also encompassed by the invention, as are polypeptides comprising, or alternatively consisting of, an amino acid sequence at least 80%, 85%, 90%, 92%, 95%, 96%, 97%, 98% or 99% identical to the amino acid sequence described above, and polynucleotides that encode such polypeptides.

More preferably, the present invention provides polypeptides having one or more residues deleted from the amino terminus of the G-protein Chemokine Receptor amino acid sequence shown in FIG. 2, up to the alanine residue at position number 363 and polynucleotides encoding such polypeptides. In particular, the present invention provides polypeptides comprising the amino acid sequence of residues $n^1$-368 of FIG. 2, where n¹ is an integer from 2 to 363 corresponding to the position of the amino acid residue in FIG. 2 (SEQ ID NO:4).

N-terminal deletions of the Chemokine G-protein receptor polypeptide of the invention shown as SEQ ID NO:4 include polypeptides comprising the amino acid sequence of residues: L-3 to I-363; R-4 to I-363; K-5 to I-363; Y-6 to I-363; G-7 to I-363; P-8 to I-363; G-9 to I-363; R-10 to I-363; L-11 to I-363; A-12 to I-363; G-13 to I-363; T-14 to I-363; V-15 to I-363; I-16 to I-363; G-17 to I-363; G-18 to I-363; A-19 to I-363; A-20 to I-363; Q-21 to I-363; S-22 to I-363; K-23 to I-363; S-24 to I-363; Q-25 to I-363; T-26 to I-363; K-27 to I-363; S-28 to I-363; D-29 to I-363; S-30 to I-363; I-31 to I-363; T-32 to I-363; K-33 to I-363; E-34 to I-363; F-35 to I-363; L-36 to I-363; P-37 to I-363; G-38 to I-363; L-39 to I-363; Y-40 to I-363; T-41 to I-363; A-42 to I-363; P-43 to I-363; S-44 to I-363; S-45 to I-363; P-46 to I-363; F-47 to I-363; P-48 to I-363; P-49 to I-363; S-50 to I-363; Q-51 to I-363; V-52 to I-363; S-53 to I-363; D-54 to I-363; H-55 to I-363; Q-56 to I-363; V-57 to I-363; L-58 to I-363; N-59 to I-363; D-60 to I-363; A-61 to I-363; E-62 to I-363; V-63 to I-363; A-64 to I-363; A-65 to I-363; L-66 to I-363; L-67 to I-363; E-68 to I-363; N-69 to I-363; F-70 to I-363; S-71 to I-363; S-72 to I-363; S-73 to I-363; Y-74 to I-363; D-75 to I-363; Y-76 to I-363; G-77 to I-363; E-78 to I-363; N-79 to I-363; E-80 to I-363; S-81 to I-363; D-82 to I-363; S-83 to I-363; C-84 to I-363; C-85 to I-363; T-86 to I-363; S-87 to I-363; P-88 to I-363; P-89 to I-363; C-90 to I-363; P-91 to I-363; Q-92 to I-363; D-93 to I-363; F-94 to I-363; S-95 to I-363; L-96 to I-363; N-97 to I-363; F-98 to I-363; D-99 to I-363; R-100 to I-363; A-101 to I-363; F-102 to I-363; L-103 to I-363; P-104 to I-363; A-105 to I-363; L-106 to I-363; Y-107 to I-363; S-108 to I-363; L-109 to I-363; L-110 to I-363; F-111 to I-363; L-112 to I-363; L-113 to I-363; G-114 to I-363; L-115 to I-363; L-116 to I-363; G-117 to I-363; N-118 to I-363; G-119 to I-363; A-120 to I-363; V-121 to I-363; A-122 to I-363; A-123 to I-363; V-124 to I-363; L-125 to I-363; L-126 to I-363; S-127 to I-363; R-128 to I-363; R-129 to I-363; T-130 to I-363; A-131 to I-363; L-132 to I-363; S-133 to I-363; S-134 to I-363; T-135 to I-363; D-136 to I-363; T-137 to I-363; F-138 to I-363; L-139 to I-363; L-140 to I-363; H-141 to I-363; L-142 to I-363; A-143 to I-363; V-144 to I-363; A-145 to I-363; D-146 to I-363; T-147 to I-363; L-148 to I-363; L-149 to I-363; V-150 to I-363; L-151 to I-363; T-152 to I-363; L-153 to I-363; P-154 to I-363; L-155 to I-363; W-156 to I-363; A-157 to I-363; V-158 to I-363; D-159 to I-363; A-160 to I-363; A-161 to I-363; V-162 to I-363; Q-163 to I-363; W-164 to I-363; V-165 to I-363; F-166 to I-363; G-167 to I-363; S-168 to I-363; G-169 to I-363; L-170 to I-363; C-171 to I-363; K-172 to I-363; V-173 to I-363; A-174 to I-363; G-175 to I-363; A-176 to I-363; L-177 to I-363; F-178 to I-363; N-179 to I-363; I-180 to I-363; N-181 to I-363; F-182 to I-363; Y-183 to I-363; A-184 to I-363; G-185 to I-363; A-186 to I-363; L-187 to I-363; L-188 to I-363; L-189 to I-363; A-190 to I-363; C-191 to I-363; I-192 to I-363; S-193 to I-363; F-194 to I-363; D-195 to I-363; R-196 to I-363; Y-197 to I-363; L-198 to I-363; N-199 to I-363; I-200 to I-363; V-201 to I-363; H-202 to I-363; A-203 to I-363; T-204 to I-363; Q-205 to I-363; L-206 to I-363; Y-207 to I-363; R-208 to I-363; R-209 to I-363; G-210 to I-363; M-211 to I-363; V-212 to I-363; L-213 to I-363; E-214 to I-363; V-215 to I-363; S-216 to I-363; D-217 to I-363; H-218 to I-363; Q-219 to I-363; V-220 to I-363; L-221 to I-363; N-222 to I-363; D-223 to I-363; A-224 to I-363; E-225 to I-363; V-226 to I-363; A-227 to I-363; A-228 to I-363; L-229 to I-363; L-230 to I-363; E-231 to I-363; N-232 to I-363; F-233 to I-363; S-234 to I-363; S-235 to I-363; S-236 to I-363; Y-237 to I-363; D-238 to I-363; Y-239 to I-363; G-240 to I-363; E-241 to I-363; N-242 to I-363; E-243 to I-363; S-244 to I-363; D-245 to I-363; S-246 to I-363; C-247 to I-363; C-248 to I-363; T-249 to I-363; S-250 to I-363; P-251 to I-363; P-252 to I-363; C-253 to I-363; P-254 to I-363; Q-255 to I-363; D-256 to I-363; F-257 to I-363; S-258 to I-363; L-259 to I-363; N-260 to I-363; F-261 to I-363; D-262 to I-363; R-263 to I-363; A-264 to I-363; F-265 to I-363; L-266 to I-363; P-267 to I-363; A-268 to I-363; L-269 to I-363; Y-270 to I-363; S-271 to I-363; L-272 to I-363; L-273 to I-363; F-274 to I-363; L-275 to I-363; L-276 to I-363; G-277 to I-363; L-278 to I-363; L-279 to I-363; G-280 to I-363; N-281 to I-363; G-282 to I-363; A-283 to I-363; V-284 to I-363; A-285 to I-363; A-286 to I-363; V-287 to I-363; L-288 to I-363; L-289 to I-363; S-290 to I-363; R-291 to I-363; R-292 to I-363; T-293 to I-363; A-294 to I-363; L-295 to I-363; S-296 to I-363; S-297 to I-363; T-298 to I-363; D-299 to I-363; T-300 to I-363; F-301 to I-363; L-302 to I-363; L-303 to I-363; H-304 to I-363; L-305 to I-363; A-306 to I-363; V-307 to I-363; A-308 to I-363; D-309 to I-363; T-310 to I-363; L-311 to I-363; L-312 to I-363; V-313 to I-363; L-314 to I-363; T-315 to I-363; L-316 to I-363; P-317 to I-363; L-318 to I-363; W-319 to I-363; A-320 to I-363; V-321 to I-363; D-322 to I-363; A-323 to I-363; A-324 to I-363; V-325 to I-363; Q-326 to I-363; W-327 to I-363; V-328 to I-363; F-329 to I-363; G-330 to I-363; S-331 to I-363; G-332 to I-363; L-333 to I-363; C-334 to I-363; K-335 to I-363; V-336 to I-363; A-337 to I-363; G-338 to I-363; A-339 to I-363; L-340 to I-363; F-341 to I-363; N-342 to I-363; I-343 to I-363; N-344 to I-363; F-345 to I-363; Y-346 to I-363; A-347 to I-363; G-348 to I-363; A-349 to I-363; L-350 to I-363; L-352 to I-363; L-352 to I-363; A-353 to I-363; C-354 to I-363; I-355 to I-363; S-356 to I-363; F-357 to I-363; D-358 to I-363; of SEQ ID NO:4 shown in FIG. 2. Polypeptides encoded by these polynucleotides are also encompassed by the invention. The present invention is also directed to nucleic acid molecules comprising, or alternatively, consisting of, a polynucleotide sequence at least 80%, 85%, 90%, 92%, 95%, 96%, 97%, 98% or 99% identical to the polynucleotide sequence encoding the G-protein chemokine receptor and/or G-protein chemokine receptor polypeptides described above. The present invention also encompasses the above polynucleotide sequences fused to a heterologous polynucleotide sequence. Polypeptides encoded by these nucleic acids and/or polynucleotide sequences are also encompassed by the invention, as are polypeptides comprising, or alternatively consisting of, an amino acid sequence at least 80%, 85%, 90%, 92%, 95%, 96%, 97%, 98% or 99% identical to the amino acid sequence described above, and polynucleotides that encode such polypeptides.

Also as mentioned above, even if deletion of one or more amino acids from the C-terminus of a protein results in modification of loss of one or more biological functions of the protein, other functional activities (e.g., biological activities, ability to multimerize, ability to bind G-protein Chemokine Receptor ligand may still be retained). For example the ability of the shortened G-protein Chemokine Receptor mutein to induce and/or bind to antibodies which recognize the complete or mature forms of the polypeptide generally will be retained when less than the majority of the residues of the complete or mature polypeptide are removed from the C-terminus. Whether a particular polypeptide lacking C-terminal residues of a complete polypeptide retains such immunologic activities can readily be determined by routine methods described herein and otherwise known in the art. It is not unlikely that a G-protein Chemokine Receptor mutein with a large number of deleted C-terminal amino acid residues may retain some biological or immunogenic activities. In fact, peptides composed of as few as six G-protein Chemokine Receptor amino acid residues may often evoke an immune response.

Accordingly, the present invention further provides polypeptides having one or more residues deleted from the carboxy terminus of the amino acid sequence of the G-protein Chemokine Receptor polypeptide shown in FIG. 1, up to the tyrosine residue at position number 6, and polynucleotides encoding such polypeptides. In particular, the present invention provides polypeptides comprising the amino acid sequence of residues 1-$m^1$ of FIG. 1, where $m^1$ is an integer from 6 to 414 corresponding to the position of the amino acid residue in FIG. 1 (SEQ ID NO:2). More in particular, the invention provides polynucleotides encoding polypeptides comprising, or alternatively consisting of, the amino acid sequence of residues.

C-terminal deletions of the Chemokine G-protein receptor polypeptide of the invention shown as SEQ ID NO:2 include polypeptides comprising the amino acid sequence of residues: E-2 to E-409; E-2 to S-408; E-2 to T-407; E-2 to E-406; E-2 to S-405; E-2 to W-404; E-2 to S-403; E-2 to S-402; E-2 to D-401; E-2 to R-400; E-2 to R-399; E-2 to S-398; E-2 to S-397; E-2 to S-396; E-2 to P-395; E-2 to Q-394; E-2 to R-393; E-2 to Q-392; E-2 to L-391; E-2 to G-390; E-2 to R-389; E-2 to Q-388; E-2 to N-387; E-2 to P-386; E-2 to C-385; E-2 to G-384; E-2 to L-383; E-2 to R-382; E-2 to L-381; E-2 to L-380; E-2 to L-379; E-2 to M-378; E-2 to W-377; E-2 to M-376; E-2 to R-375; E-2 to E-374; E-2 to R-373; E-2 to F-372; E-2 to K-371; E-2 to V-370; E-2 to G-369; E-2 to V-368; E-2 to F-367; E-2 to A-366; E-2 to Y-365; E-2 to L-364; E-2 to L-363; E-2 to P-362; E-2 to N-361; E-2 to L-360; E-2 to C-359; E-2 to C-358; E-2 to H-357; E-2 to M-356; E-2 to Y-355; E-2 to G-354; E-2 to L-353; E-2 to G-352; E-2 to S-351; E-2 to T-350; E-2 to V-349; E-2 to S-348; E-2 to K-347; E-2 to A-346; E-2 to V-345; E-2 to D-344; E-2 to V-343; E-2 to R-342; E-2 to S-341; E-2 to E-340; E-2 to R-339; E-2 to G-338; E-2 to C-337; E-2 to N-336; E-2 to R-335; E-2 to A-334; E-2 to L-333; E-2 to A-332; E-2 to G-331; E-2 to L-330; E-2 to D-329; E-2 to M-328; E-2 to L-327; E-2 to I-326; E-2 to D-325; E-2 to V-324; E-2 to L-323; E-2 to V-322; E-2 to V-321; E-2 to L-320; E-2 to H-319; E-2 to Y-318; E-2 to L-323; E-2 to V-322; E-2 to V-321; E-2 to L-320; E-2 to H-319; E-2 to Y-312; E-2 to F-311; E-2 to A-310; E-2 to V-309; E-2 to V-308; E-2 to V-307; E-2 to V-306; E-2 to V-305; E-2 to V-304; E-2 to L-303; E-2 to R-302; E-2 to M-301; E-2 to A-300; E-2 to R-299; E-2 to L-298; E-2 to R-297; E-2 to R-296; E-2 to Q-295; E-2 to G-294; E-2 to R-293; E-2 to S-292; E-2 to V-291; E-2 to L-290; E-2 to L-289; E-2 to V-288; E-2 to A-287; E-2 to L-286; E-2 to I-285; E-2 to H-284; E-2 to A-283; E-2 to Y-282; E-2 to C-281; E-2 to Y-280; E-2 to A-279; E-2 to M-278; E-2 to V-277; E-2 to L-276; E-2 to L-275; E-2 to P-274; E-2 to L-273; E-2 to L-272; E-2 to F-271; E-2 to G-270; E-2 to A-269; E-2 to V-268; E-2 to L-267; E-2 to Q-266; E-2 to L-265; E-2 to V-264; E-2 to R-263; E-2 to L-262; E-2 to A-261; E-2 to T-260; E-2 to R-259; E-2 to G-258; E-2 to V-257; E-2 to Q-256; E-2 to P-255; E-2 to F-254; E-2 to N-253; E-2 to Y-252; E-2 to Q-251; to C-250; E-2 to H-249; E-2 to T-248; E-2 to A-247; E-2 to N-246; E-2 to L-245; E-2 to R-244; E-2 to E-243; E-2 to D-242; E-2 to H-241; E-2 to H -240; E-2 to A-239; E-2 to S-238; E-2 to L-237; E-2 to F-236; E-2 to I-235; E-2 to F-234; E-2 to D-233; E-2 to P-232; E-2 L-231; E-2 to A-230; E-2 to F-229; E-2 to L-228; E-2 to L-227; E-2 to C-226; E-2 to L-225; E-2 to G-224; E-2 to W-223; E-2 to V-222; E-2 to A-221; E-2 to L-220; E-2 to C-219; E-2 to T-218; E-2 to L-217; E-2 to T-216; E-2 to V-215; E-2 to R-214; E-2 to A-213; E-2 to P-212; E-2 to P-211; E-2 to G-210; E-2 to R-209; E-2 to R-208; E-2 to Y-207; E-2 to L-206; E-2 to Q-205; E-2 to T-204; E-2 to A-203; E-2 to H-202; E-2 to V-210; E-2 to I-200 E-2 to N-199; E-2 to L-198; E-2 to Y-197; E-2 to R-196; E-2 to D-195; E-2 to F-194; E-2 to S-193; E-2 to I-192; E-2 to C-191; E-2 to A-190; E-2 to L-189; E-2 to L-188; E-2 L-187; E-2 to A-186; E-2 to G-185; E-2 to A-184; E-2 to Y-183; E-2 to F-182; E-2 to N-181; E-2 to I-180; E-2 to N-179; E-2 to F-178; E-2 to L-177; E-2 to A-176; E-2 to G-175; E-2 to A-174; E-2 to V-173; E-2 to K-172; E-2 to C-171; E-2 to L-170; E-2 to G-169; E-2 to S-168; E-2 to G-167; E-2 to F-166; E-2 to V-165; E-2 to W-164; E-2 E-2 to Q-163; E-2 to V-162; E-2 to A-161; E-2 to A-160; E-2 to D-159; E-2 to V-158; E-2 to A-157; E-2 to W-156; E-2 to L-155; E-2 to P-154; E-2 to L-153; E-2 to T-152; E-2 to L-515; E-2 to V-150; E-2 to L-149; E-2 to L-148; E-2 to T-147; E-2 to D-146; E-2 to A-145; E-2 to V-144; E-2 to A-143; E-2 to L-142; E-2 to H-141; E-2 to L-140; E-2 to L-139; E-2 to F-138; E-2 T-137; E-2 to D-136; E-2 to T-135; E-2 to S-134; E-2 to S-133; E-2 to L-132; E-2 to A-131; E-2 to T-130; E-2 to R-129; E-2 to R-128; E-2 to S-127; E-2 to L-126; E-2 to L-125; E-2 to V-124; E-2 to A-123; E-2 to A-122; E-2 to V-121; E-2 to A-120; E-2 to G-199; E-2 to N-118; E-2 to G-117; E-2 to L-116; E-2 to L-115; E-2 to G-114; E-2 to L-113; E-2 to L-112; E-2 to F-111; E-2 to L-110; E-2 to L-109; E-2 to S-108; E-2 to Y-107; E-2 to L-106; E-2 to A-105; E-2 to P-104; E-2 to L-103; E-2 to F-102; E-2 to A-101; E-2 to R-100; E-2 to D-99; E-2 to F-98; E-2 to N-97; E-2 to L-96; E-2 to S-95; E-2 to F-94; E-2 to D-93; E-2 to Q-92; E-2 to P-91; E-2 to C-90; E-2 to P-89; E-2 to P-88; E-2 to S-87; E-2 to T-86; E-2 to C-85; E-2 to C-84; E-2 to S-83; E-2 to D-82; E-2 to S-81; E-2 to E-80; E-2 to N-79; E-2 to E-78; E-2 to G-77; E-2 to Y-76; E-2 to D-75; E-2 to Y-74; E-2 to S-73; E-2 to S-72; E-2 to S-71; E-2 to F-70; E-2 to N-69; E-2 to E-68; E-2 to L-67; E-2 to L-66; E-2 to A-65; E-2 to A-64; E-2 to V-63; E-2 to E-62; E-2 to A-61; E-2 to D-60; E-2 to N-59; E-2 to L-58; E-2 to V-57; E-2 to Q-56; E-2 to H-55; E-2 to D-54; E-2 to S-53; E-2 to V-52; E-2 to Q-51; E-2 to S-50; E-2 to P-49; E-2 to P-48; E-2 to F-47; E-2 to P-46; E-2 to S-45; E-2 to S-44; E-2 to P-43; E-2 to A-42; E-2 to T-41; E-2 to Y-40; E-2 to L-39; E-2 to G-38; E-2 to P-37; E-2 to L-36; E-2 to F-35; E-2 to E-34; E-2 to K-33; E-2 to T-32; E-2 to I-31; E-2 to S-30; E-2 to D-29; E-2 to S-28; E-2 to K-27; E-2 to T-26; E-2 to Q-25; E-2 to S-24; E-2 to K-23; E-2 to S-22; E-2 to Q-21; E-2 to A-20; E-2 to A-19; E-2 to G-18; E-2 to G-17; E-2 to I-16; E-2 to V-15; E-2 to T-14; E-2 to G-13; E-2 to A-12; E-2 to L-11; E-2 to R-10; E-2 to G-9; E-2 to P-8 of the G-protein Chemokine Receptor sequence shown in FIG. 1. Polypeptides encoded by these polynucleotides are also encompassed by the invention. The present invention is also directed to nucleic acid molecules comprising, or alternatively, consisting of, a polynucleotide sequence at least 80%, 85%, 90%, 92%, 95%, 96%, 97%, 98% or 99% identical to the polynucleotide sequence encoding the G-protein chemokine receptor and/or G-protein chemokine receptor polypeptides described above. The present invention also encompasses the above polynucleotide sequences fused to a heterologous polynucleotide sequence. Polypeptides encoded by these nucleic acids and/or polynucleotide sequences are also encompassed by the invention, as are polypeptides comprising, or alternatively consisting of, an amino acid sequence at least 80%, 85%, 90%, 92%, 95%, 96%, 97%, 98% or 99% identical to the amino acid sequence described above, and polynucleotides that encode such polypeptides.

More preferably, the present invention provides polypeptides having one or more residues deleted from the carboxy terminus of the amino acid sequence of the G-protein Chemokine Receptor polypeptide shown in FIG. 2, up to the serine residue at position number 6, and polynucleotides encoding such polypeptides. In particular, the present invention provides polypeptides comprising the amino acid sequence of residues 1-m$^1$ of FIG. 2, where m$^1$ is an integer from 6 to 367 corresponding to the position of the amino acid residue in FIG. 2 (SEQ ID NO:4). More in particular, the invention provides polynucleotides encoding polypeptides comprising, or alternatively consisting of, the amino acid sequence of residues.

Likewise, C-terminal deletions of the Chemokine G-protein receptor polypeptide of the invention shown as SEQ ID NO:4 include polypeptides comprising the amino acid sequence of residues: E-2 to N-362; E-2 to L-361; E-2 to Y-360; E-2 to R-359; E-2 to D-358; E-2 to F-357; E-2 to S-356; E-2 to I-355; E-2 to C-354; E-2 to A-353; E-2 to L-352; E-2 to L-351; E-2 to L-350; E-2 to A-349; E-2 to G-348; E-2 to E-2 to A-347; E-2 Y-346; E-2 to F-345; E-2 to N-344; E-2 to I-343; E-2 to N-342; E-2 to F-341; E-2 to L-340; E-2 to A-339; E-2 to G-338; E-2 to A-337; E-2 to V-336; E-2 to K-335; to E-2 to C-334; E-2 to L-333; E-2 to G-332; E-2 to S-331; E-2 to G-330; E-2 to F-329; E-2 to V-328; E-2 to W-327; E-2 to Q-326; E-2 to V-325; E-2 to A-324; E-2 to A-323; E-2 to D-322; E-2 to V-321; E-2 to A-320; E-2 to W-319; E-2 to L-318; E-2 to P-317; E-2 E-2 to L-316; E-2 to T-315; E-2 to L-314; E-2 to V-313; E-2 to L-312; E-2 to L-311; E-2 to T-310; E-2 to D-309; E-2 to A-308; E-2 to V-307; E-2 to A-306; E-2 to L-305; E-2 to H-304; E-2 to L-303; E-2 to L-302; E-2 to F-301; E-2 to T-300; E-2 to D-299; E-2 to T-298; E-2 to S-297; E-2 to S-296; E-2 to L-295; E-2 to A-294; E-2 to T-293; E-2 to R-292; E-2 to R-291; E-2 to S-290; E-2 to L-289; E-2 to L-288; E-2 to V-287; E-2 to A-286; E-2 to A-285; E-2 to V-284; E-2 to A-283; E-2 to G-282; E-2 to N-281; E-2 to G-280; E-2 to L-279; E-2 to L-278; E-2 to G-277; E-2 to L-276; E-2 to L-275; E-2 to F-274; E-2 to L-273; E-2 to L-272; E-2 to S-271; E-2 to Y-270; E-2 to L-269; E-2 to A-268; E-2 to P-267; E-2 to L-266; E-2 to F-265; E-2 to A-264; E-2 to R-263; E-2 to D-262; E-2 to F-261; E-2 to N-260; E-2 to L-259; E-2 to S-258; E-2 to F-257; E-2 to D-256; E-2 to Q-255; E-2 to P-254; E-2 to C-253; E-2 to P-252; E-2 to P-251; E-2 to S-250; E-2 to T-249; E-2 to C-248; E-2 to C-247; E-2 to S-246; E-2 to D-245; E-2 to S-244; E-2 to E-243; E-2 to N-242; E-2 to E-241; E-2 to G-240; E-2 to Y-239; E-2 to D-238; E-2 to Y-237; E-2 to S-236; E-2 to S-235; E-2 to S-234; E-2 to F-233; E-2 to N-232; E-2 to E-231; E-2 to L-230; E-2 to L-229; E-2 to A-228; E-2 to A-227; E-2 to V-226; E-2 to E-225; E-2 to A-224; E-2 to D-223; E-2 to N-222; E-2 to L-221; E-2 to V-220; E-2 to Q-219; E-2 to H-218; E-2 to D-217; E-2 to S-216; E-2 to V-215; E-2 to E-214; E-2 to L-213; E-2 to V-212; E-2 to M-211; E-2 to G-210; E-2 to R-209; E-2 to R-208; E-2 to Y-207; E-2 to L-206; E-2 to Q-205; E-2 to T-402; E-2 to A-203; E-2 to H-202; E-2 to V-201; E-2 to I-200; E-2 to N-199; E-2 to L-198; E-2 to Y-197; E-2 to R-196; E-2 to D-195; E-2 to F-194; E-2 to S-193; E-2 to I-192; E-2 to C-191; E-2 to A-190; E-2 to L-189; E-2 to L-188; E-2 to L-187; E-2 to A-186; E-2 to G-185; E-2 to A-184; E-2 to Y-183; E-2 to F-182; E-2 to N-181; E-2 to I-180; E-2 to N-179; E-2 to F-178; E-2 to L-177; E-2 to A-176; E-2 to G-175; E-2 to A-174; E-2 to V-173; E-2 to K-172; E-2 to C-171; E-2 to L-170; E-2 to G-169; E-2 to S-168; E-2 to G-167; E-2 to F-166; E-2 to V-165; E-2 to W-164; E-2 to Q-163; E-2 to V-162; E-2 to A-161; E-2 to A-160; E-2 to D-159; E-2 to V-158; E-2 to A-157; E-2 to W-156; E-2 to L-155; E-2 to P-154; E-2 to L-153; E-2 to T-152; E-2 to L-151; E-2 to V-150; E-2 to L-149; E-2 to L-148; E-2 to T-147; E-2 to D-146; E-2 to A-145; E-2 to V-144; E-2 to A-143; E-2 to L-142; E-2 to H-141; E-2 to L-140; E-2 to L-139; E-2 to F-138; E-2 to T-137; E-2 to D-136; E-2 to T-135; E-2 to S-134; E-2 to S-133; E-2 to L-132; E-2 to A-131; E-2 to T-130; E-2 to R-129; E-2 to R-128; E-2 to S-127; E-2 to L-126; E-2 to L-125; E-2 to V-124; E-2 to A-123; E-2 to A-122; E-2 to V-121; E-2 to A-120; E-2 to G-119; E-2 to N-118; E-2 to G-117; E-2 to L-116; E-2 to L-115; E-2 to G-114; E-2 to L-113; E-2 to L-112; E-2 to F-111; E-2 to L-110; E-2 to L-109; E-2 to S-108; E-2 to Y-107; E-2 to L-106; E-2 to A-105; E-2 to P-104; E-2 to L-103; E-2 to F-102; E-2 to A-101; E-2 to R-100; E-2 to D-99; E-2 to F-98; E-2 to N-97; E-2 to L-96; E-2 to S-95; E-2 to F-94; E-2 to D-93; E-2 to Q-92; E-2 P-91; E-2 to C-90; E-2 to P-89; E-2 to P-88; E-2 to S-87; E-2 to T-86; E-2 to C-85; E-2 to C-84; E-2 to S-83; E-2 to D-82; E-2 to S-81; E-2 to E-80; E-2 to N-79; E-2 to E-78; E-2 to G-77; E-2 to Y-76; E-2 to D-75; E-2 to Y-74; E-2 to S-73; E-2 to S-72; E-2 to S-71; E-2 to F-70; E-2 to N-69; E-2 to E-68; E-2 to L-67; E-2 to L-66; E-2 to A-65; E-2 to A-64; E-2 to V-63; E-2 to E-62; E-2 to A-61; E-2 to D-60; E-2 to N-59; E-2 to L-58; E-2 to V-57; E-2 to Q-56; E-2 to H-55; E-2 to D-54; E-2 to S-53; E-2 to V-52; E-2 to Q-51; E-2 to S-50; E-2 to P-49; E-2 to P-48; E-2 to F-47; E-2 to P-46; E-2 to S-45; E-2 to S-44; E-2 to P-43; E-2 to A-42; E-2 to T-41; E-2 to Y-40; E-2 to L-39; E-2 to G-38; E-2 to P-37; E-2 to L-36; E-2 to F-35; E-2 to E-34; E-2 to K-33; E-2 to T-32; E-2 to I-31; E-2 to S-30; E-2 to D-29; E-2 to S-28; E-2 to K-27; E-2 to T-26; E-2 to Q-25; E-2 to S-24; E-2 to K-23; E-2 to S-22; E-2 to Q-21; E-2 to A-20; E-2 to A-19; E-2 to G-18; E-2 to G-17; E-2 to I-16; E-2 to V-15; E-2 to T-14; E-2 to G-13; E-2 to A-12; E-2 to L-11; E-2 to R-10; E-2 to G-9; E-2 to P-8; of SEQ ID NO: 4 shown in FIG. 2. Polypeptides encoded by these polynucleotides are also encompassed by the invention. The present invention is also directed to nucleic acid molecules comprising, or alternatively, consisting of, a polynucleotide sequence at least 80%, 85%, 90%, 92%, 95%, 96%, 97%, 98% or 99% identical to the polynucleotide sequence encoding the G-protein chemokine receptor and/or G-protein chemokine receptor polypeptides described above. The present invention also encompasses the above polynucleotide sequences fused to a heterologous polynucleotide sequence. Polypeptides encoded by these nucleic acids and/or polynucleotide sequences are also encompassed by the invention, as are polypeptides comprising, or alternatively consisting of, an amino acid sequence at least 80%, 85%, 90%, 92%, 95%, 96%, 97%, 98% or 99% identical to the amino acid sequence described above, and polynucleotides that encode such polypeptides.

The invention also provides polypeptides having one or more amino acids deleted from both the amino and the carboxyl termini, which may be described generally as having residues n$^1$-m$^1$ and/or n$^2$-m$^1$ of FIG. 1 (SEQ ID NO:2) or more preferably of FIG. 2 (SEQ ID NO:4), where n$^1$, n$^2$, and m$^1$ are integers as described above. Thus, any of the above listed N- or C-terminal deletions can be combined to produce a N- and C-terminal deleted G-protein Chemokine Receptor polypeptide.

The present invention encompasses G-protein Chemokine Receptor polypeptides comprising, or alternatively consisting of, an epitope of the polypeptide having an amino acid sequence of FIG. 1 (SEQ ID NO:2), more preferably an epitope of the polypeptide having an amino acid sequence of FIG. 2 (SEQ ID NO:4), an epitope of the polypeptide sequence encoded by a polynucleotide that hybridizes to the complement of the sequence of SEQ ID NO:1 under stringent hybridization conditions or lower stringency hybridization conditions as defined supra, or more preferably an epitope of the polypeptide sequence encoded by a polynucleotide that hybridizes to the complement of the sequence of SEQ ID NO:3 under stringent hybridization conditions or lower stringency hybridization conditions as defined supra. The present invention further encompasses polynucleotide sequences encoding an epitope of a G-protein Chemokine Receptor polypeptide sequence of the invention (such as, for example, the sequence disclosed in SEQ ID NO:2 or SEQ ID NO:4), polynucleotide sequences of the complementary strand of a polynucleotide sequence encoding an epitope of the invention, and polynucleotide sequences which hybridize to the complementary strand under stringent hybridization conditions or lower stringency hybridization conditions defined supra.

The term "epitopes," as used herein, refers to portions of a polypeptide having antigenic or immunogenic activity in an animal, preferably a mammal, and most preferably in a human. In a preferred embodiment, the present invention encompasses a polypeptide comprising an epitope, as well as the polynucleotide encoding this polypeptide. An "immunogenic epitope," as used herein, is defined as a portion of a protein that elicits an antibody response in an animal, as determined by any method known in the art, for example, by the methods for generating antibodies described infra. (See, for example, Geysen et al., Proc. Natl. Acad. Sci. USA 81:3998-4002 (1983)). The term "antigenic epitope," as used herein, is defined as a portion of a protein to which an antibody can specifically bind its antigen as determined by any method well known in the art, for example, by the immunoassays described herein. Immunospecific binding excludes non-specific binding but does not necessarily exclude cross-reactivity with other antigens. Antigenic epitopes need not necessarily be immunogenic.

Fragments which function as epitopes may be produced by any conventional means. (See, e.g., Houghten, Proc. Natl. Acad. Sci. USA 82:5131-5135 (1985), further described in U.S. Pat. No. 4,631,211).

In the present invention, antigenic epitopes preferably contain a sequence of at least 4, at least 5, at least 6, at least 7, more preferably at least 8, at least 9, at least 10, at least 11, at least 12, at least 13, at least 14, at least 15, at least 20, at least 25, at least 30, at least 40, at least 50, and, most preferably, between about 15 to about 30 amino acids. Preferred polypeptides comprising immunogenic or antigenic epitopes are at least 10, 15, 20, 25, 30, 35, 40, 45, 50, 55, 60, 65, 70, 75, 80, 85, 90, 95, or 100 amino acid residues in length.

Non-limiting examples of antigenic polypeptides or peptides that can be used to generate G-protein Chemokine Receptor-specific antibodies include: a polypeptide comprising, or alternatively consisting of, amino acid residues from about 4 to about 8 in FIG. 1 (SEQ ID NO:2); a polypeptide comprising amino acid residues from about 25 to about 31 in FIG. 1 (SEQ ID NO:2); a polypeptide comprising amino acid residues from about 51 to about 54 in FIG. 1 (SEQ ID NO:2); a polypeptide comprising amino acid residues from about 75 to about 85 in FIG. 1 (SEQ ID NO:2); a polypeptide comprising amino acid residues from about 127 to about 131 in FIG. 1 (SEQ ID NO:2); a polypeptide comprising amino acid residues from about 208 to about 213 in FIG. 1 (SEQ ID NO:2); a polypeptide comprising amino acid residues from about 336 to about 341 in FIG. 1 (SEQ ID NO:2); a polypeptide comprising amino acid residues from about 385 to about 389 in FIG. 1 (SEQ ID NO:2); and a polypeptide comprising amino acid residues from about 394 to about 405 in FIG. 1 (SEQ ID NO:2). Prefered non-limiting examples of antigenic polypeptides or peptides that can be used to generate G-protein Chemokine Receptor-specific antibodies include: a polypeptide comprising amino acid residues from about 28 to about 38 in FIG. 2 (SEQ ID NO:4); a polypeptide comprising amino acid residues from about 80 to about 84 in FIG. 2 (SEQ ID NO:4); a polypeptide comprising amino acid residues from about 161 to about 166 in FIG. 2 (SEQ ID NO:4); a polypeptide comprising amino acid residues from about 289 to about 294 in FIG. 2 (SEQ ID NO:4); a polypeptide comprising amino acid residues from about 338 to about 342 in FIG. 2 (SEQ ID NO:4); and a polypeptide comprising amino acid residues from about 347 to about 358 in FIG. 2 (SEQ ID NO:4). In this context, "about" means the particularly recited ranges and ranges larger or smaller by several, a few, 5, 4, 3, 2 or 1 amino acid residues at either or both the amino- and carboxy-termini. These polypeptide fragments have been determined to bear antigenic epitopes of the G-protein Chemokine Receptor polypeptide by the analysis of the Jameson-Wolf antigenic index, as shown in FIG. 5, FIG. 6, Table II, and Table I, above. Additional non-exclusive preferred antigenic epitopes include the antigenic epitopes disclosed herein, as well as portions thereof. Antigenic epitopes are useful, for example, to raise antibodies, including monoclonal antibodies that specifically bind the epitope. Preferred antigenic epitopes include the antigenic epitopes disclosed herein, as well as any combination of two, three, four, five or more of these antigenic epitopes. Antigenic epitopes can be used as the target molecules in immunoassays. (See, for instance, Wilson et al., Cell 37:767-778 (1984); Sutcliffe et al., Science 219:660-666 (1983)).

Similarly, immunogenic epitopes can be used, for example, to induce antibodies according to methods well known in the art. (See, for instance, Sutcliffe et al., supra; Wilson et al., supra; Chow et al., Proc. Natl. Acad. Sci. USA 82:910-914; and Bittle et al., J. Gen. Virol. 66:2347-2354 (1985). Preferred immunogenic epitopes include the immunogenic epitopes disclosed herein, as well as any combination of two, three, four, five or more of these immunogenic epitopes. The polypeptides comprising one or more immunogenic epitopes may be presented for eliciting an antibody response together with a carrier protein, such as an albumin, to an animal system (such as rabbit or mouse), or, if the polypeptide is of sufficient length (at least about 25 amino acids), the polypeptide may be presented without a carrier. However, immunogenic epitopes comprising as few as 8 to 10 amino acids have been shown to be sufficient to raise antibodies capable of binding to, at the very least, linear epitopes in a denatured polypeptide (e.g., in Western blotting).

Epitope-bearing polypeptides of the present invention may be used to induce antibodies according to methods well known in the art including, but not limited to, in vivo immunization, in vitro immunization, and phage display methods. See, e.g., Sutcliffe et al., supra; Wilson et al., supra, and Bittle et al., J. Gen. Virol., 66:2347-2354 (1985). If in vivo immunization is used, animals may be immunized with free peptide; however, anti-peptide antibody titer may be boosted by coupling the peptide to a macromolecular carrier, such as keyhole limpet -hemacyanin (KLH) or tetanus toxoid. For instance, peptides containing cysteine residues may be coupled to a carrier using a linker such as maleimidobenzoyl-N-hydroxysuccinimide ester (MBS), while the peptides may be coupled to carriers using a more general linking agent such as glutaraldehyde. Animals such as rabbits, rats and mice are immunized with either free or carrier-coupled peptides, for instance, by intraperitoneal and/or intradermal injection of emulsions containing about 100 µg of peptide or carrier protein and Freund's adjuvant or any other adjuvant known for stimulating an immune response. Several booster injections may be needed, for instance, at intervals of about two weeks, to provide a useful titer of anti-peptide antibody that can be detected, for example, by ELISA assay using free peptide adsorbed to a solid surface. The titer of anti-peptide antibodies in serum from an immunized animal may be increased by selection of anti-peptide antibodies, for instance, by adsorption to the peptide on a solid support and elution of the selected antibodies according to methods well known in the art.

As one of skill in the art will appreciate, and as discussed above, the polypeptides of the present invention comprising an immunogenic or antigenic epitope can be fused to other polypeptide sequences. For example, the polypeptides of the present invention may be fused with the constant domain of immunoglobulins (IgA, IgE, IgG, IgM), or portions thereof (CH1, CH2, CH3, or any combination thereof and portions thereof), or albumin (including but not limited to recombinant human albumin or fragments or variants thereof (see, e.g., U.S. Pat. No. 5,876,969, issued Mar. 2, 1999, EP Patent 0 413 622, and U.S. Pat. No. 5,766,883, issued Jun. 16, 1998, herein incorporated by reference in their entirety)) resulting in chimeric polypeptides. Such fusion proteins may facilitate purification and may increase half-life in vivo. This has been shown for chimeric proteins consisting of the first two domains of the human CD4-polypeptide and various domains of the constant regions of the heavy or light chains of mammalian immunoglobulins. See, e.g., EP 394,827; Traunecker et al., Nature, 331:84-86 (1988). Enhanced delivery of an antigen across the epithelial barrier to the immune system has been demonstrated for antigens (e.g., insulin) conjugated to an FcRn binding partner such as IgG or Fc fragments (see, e.g., PCT Publications WO 96/22024 and WO 99/04813). IgG Fusion proteins that have a disulfide-linked dimeric structure due to the IgG portion desulfide bonds have also been found to be more efficient in binding and neutralizing other molecules than monomeric polypeptides or fragments thereof alone. See, e.g., Fountoulakis et al., J. Biochem., 270:3958-3964 (1995). Nucleic acids encoding the above epitopes can also be recombined with a gene of interest as an epitope tag (e.g., the hemagglutinin ("HA") tag or flag tag) to aid in detection and purification of the expressed polypeptide. For example, a system described by Janknecht et al. allows for the ready purification of non-denatured fusion proteins expressed in human cell lines (Janknecht et al., 1991, Proc. Natl. Acad. Sci. USA 88:8972-897). In this system, the gene of interest is subcloned into a vaccinia recombination plasmid such that the open reading frame of the gene is translationally fused to an amino-terminal tag consisting of six histidine residues. The tag serves as a matrix-binding domain for the fusion protein. Extracts from cells infected with the recombinant vaccinia virus are loaded onto Ni2+ nitriloacetic acid-agarose column and histidine-tagged proteins can be selectively eluted with imidazole-containing buffers.

Additional fusion proteins of the invention may be generated through the techniques of gene-shuffling, motif-shuffling, exon-shuffling, and/or codon-shuffling (collectively referred to as "DNA shuffling"). DNA shuffling may be employed to modulate the activities of polypeptides of the invention, such methods can be used to generate polypeptides with altered activity, as well as agonists and antagonists of the polypeptides. See, generally, U.S. Pat. Nos. 5,605,793; 5,811, 238; 5,830,721; 5,834,252; and 5,837,458, and Patten et al., Curr. Opinion Biotechnol. 8:724-33 (1997); Harayama, Trends Biotechnol. 16(2):76-82 (1998); Hansson, et al., J. Mol. Biol. 287:265-76 (1999); and Lorenzo and Blasco, Biotechniques 24(2):308-13 (1998) (each of these patents and publications are hereby incorporated by reference in its entirety). In one embodiment, alteration of G-protein Chemokine Receptor polynucleotides corresponding to FIG. 1 (SEQ ID NO:1) or FIG. 2 (SEQ ID NO:3) and the polypeptides encoded by these polynucleotides may be achieved by DNA shuffling. DNA shuffling involves the assembly of two or more DNA segments by homologous or site-specific recombination to generate variation in the polynucleotide sequence. In another embodiment, polynucleotides of the invention, or the encoded polypeptides, may be altered by being subjected to random mutagenesis by error-prone PCR, random nucleotide insertion or other methods prior to recombination. In another embodiment, one or more components, motifs, sections, parts, domains, fragments, etc., of a polynucleotide encoding a polypeptide of the invention may be recombined with one or more components, motifs, sections, parts, domains, fragments, etc. of one or more heterologous molecules.

It will be recognized in the art that some amino acid sequences of G-protein Chemokine Receptor can be varied without significant effect on the structure or function of the protein. If such differences in sequence are contemplated, it should be remembered that there will be critical areas on the protein which determine activity. Thus, the invention further includes variations of the G-protein Chemokine Receptor receptor, which show substantial G-protein Chemokine Receptor receptor activity or which include regions of G-protein Chemokine Receptor proteins, such as the protein portions discussed herein. Such mutants include deletions, insertions, inversions, repeats, and type substitutions. As indicated above, guidance concerning which amino acid changes are likely to be phenotypically silent can be found in J. U. Bowie et al., Science 247:1306-1310 (1990).

Thus, the fragment, derivative, or analog of the polypeptide of FIG. 1 (SEQ ID NO: 2) or more preferably FIG. 2 (SEQ ID NO:4), may be (i) one in which at least one or more of the amino acid residues are substituted with a conserved or non-conserved amino acid residue (preferably a conserved amino acid residue(s), and more preferably at least one but less than ten conserved amino acid residues) and such substituted amino acid residue may or may not be one encoded by the genetic code, or (ii) one in which one or more of the amino acid residues includes a substituent group, or (iii) one in which the mature polypeptide is fused with another compound, such as a compound to increase the half-life of the polypeptide (for example, polyethylene glycol), or (iv) one in which the additional amino acids are fused to the mature polypeptide, such as an IgG Fc fusion. region peptide or leader or secretory sequence or a sequence which is employed for purification of the mature polypeptide or a proprotein sequence. Such fragments, derivatives and analogs are deemed to be within the scope of those skilled in the art from the teachings herein.

Of particular interest are substitutions of charged amino acids with another charged amino acid and with neutral or negatively charged-amino acids. The latter results in proteins with reduced positive charge to improve the characteristics of the G-protein Chemokine Receptor receptor protein. The prevention of aggregation is highly desirable. Aggregation of proteins not only results in a loss of activity but can also be problematic when preparing pharmaceutical formulations, because they can be immunogenic. (Pinckard et al., *Clin Exp.*

*Immunol.* 2:331-340 (1967); Robbins et al., *Diabetes* 36:838-845 (1987); Cleland et al. *Crit. Rev. Therapeutic Drug Carrier Systems* 10:307-377 (1993)).

The replacement of amino acids can also change the selectivity of binding to cell surface receptors. Ostade et al., *Nature* 361:266-268 (1993), describes certain mutations resulting in selective binding of TNF-α to only one of the two known types of TNF receptors. Thus, the G-protein Chemokine Receptor polypeptides receptor of the present invention may include one or more amino acid substitutions, deletions, or additions, either from natural mutations or human manipulation.

As indicated, changes are preferably of a minor nature, such as conservative amino acid substitutions that do not significantly affect the folding or activity of the protein (see Table III).

TABLE III

| Conservative Amino Acid Substitutions | |
|---|---|
| Aromatic | Phenylalanine |
|  | Tryptophan |
|  | Tyrosine |
| Hydrophobic | Leucine |
|  | Isoleucine |
|  | Valine |
| Polar | Glutamine |
|  | Asparagine |
| Basic | Arginine |
|  | Lysine |
|  | Histidine |
| Acidic | Aspartic Acid |
|  | Glutamic Acid |
| Small | Alanine |
|  | Serine |
|  | Threonine |
|  | Methionine |
|  | Glycine |

In specific embodiments, the number of substitutions, additions or deletions in the amino acid sequence of FIG. 1 or FIG. 2 and/or any of the polypeptide fragments described herein (e.g., the extracellular domain or intracellular domain) is 75, 70, 60, 50, 40, 35, 30, 25, 20, 15, 10, 9, 8, 7, 6, 5, 4, 3, 2, 1 or 30-20, 20-15, 20-10, 15-10, 10-1, 5-10, 1-5, 1-3 or 1-2.

In another embodiment, site directed changes at the amino acid level of G-protein Chemokine Receptor can be made by replacing a particular amino acid with a conservative substitution. Preferred conservative substitution mutations of the G-protein Chemokine Receptor amino acid sequence provided in SEQ ID NO:4 include: For example preferred complementary mutations include: M1 replaced with A, G, I, L, S, T, or V; V2 replaced with A, G, I, L, S, T, or M; L3 replaced with A, G, I, S, T, M, or V; E4 replaced with D; V5 replaced with A, G, I, L, S, T, or M; S6 replaced with A, G, I, L, T, M, or V; D7 replaced with E; H8 replaced with K, or R; Q9 replaced with N; V10 replaced with A, G, I, L, S, T, or M; L11 replaced with A, G, I, S, T, M, or V; N12 replaced with Q; D13 replaced with E; A14 replaced with G, I, L, S, T, M, or V; E15 replaced with D; V16 replaced with A, G, I, L, S, T, or M; A17 replaced with G, I, L, S, T, M, or V; A18 replaced with G, I, L, S, T, M, or V; L19 replaced with A, G, I, S, T, M, or V; L20 replaced with A, G, I, S, T, M, or V; E21 replaced with D; N22 replaced with Q; F23 replaced with W, or Y; S24 replaced with A, G, I, L, T, M, or V; S25 replaced with A, G, I, L, T, M, or V; S26 replaced with A, G, I, L, T, M, or V; Y27 replaced with F, or W; D28 replaced with E; Y29 replaced with F, or W; G30 replaced with A, I, L, S, T, M, or V; E31 replaced with D; N32 replaced with Q; E33 replaced with D; S34 replaced with A, G, I, L, T, M, or V; D35 replaced with E; S36 replaced with A, G, I, L, T, M, or V; T39 replaced with A, G, I, L, S, M, or V; S40 replaced with A, G, I, L, T, M, or V; Q45 replaced with N; D46 replaced with E; F47 replaced with W, or Y; S48 replaced with A, G, I, L, T, M, or V; L49 replaced with A, G, I, S, T, M, or V; N50 replaced with Q; F51 replaced with W, or Y; D52 replaced with E; R53 replaced with H, or K; A54 replaced with G, I, L, S, T, M, or V; F55 replaced with W, or Y; L56 replaced with A, G, I, S, T, M, or V; A58 replaced with G, I, L, S, T, M, or V; L59 replaced with A, G, I, S, T, M, or V; Y60 replaced with F, or W; S61 replaced with A, G, I, L, T, M, or V; L62 replaced with A, G, I, S, T, M, or V; L63 replaced with A, G, I, S, T, M, or V; F64 replaced with W, or Y; L65 replaced with A, G, I, S, T, M, or V; L66 replaced with A, G, I, S, T, M, or V; G67 replaced with A, I, L, S, T, M, or V; L68 replaced with A, G, I, S, T, M, or V; L69 replaced with A, G, I, S, T, M, or V; G70 replaced with A, I, L, S, T, M, or V; N71 replaced with Q; G72 replaced with A, I, L, S, T, M, or V; A73 replaced with G, I, L, S, T, M, or V; V74 replaced with A, G, I, L, S, T, or M; A75 replaced with G, I, L, S, T, M, or V; A76 replaced with G, I, L, S, T, M, or V; V77 replaced with A, G, I, L, S, T, or M; L78 replaced with A, G, I, S, T, M, or V; L79 replaced with A, G, I, S, T, M, or V; S80 replaced with A, G, I, L, T, M, or V; R81 replaced with H, or K; R82 replaced with H, or K; T83 replaced with A, G, I, L, S, M, or V; A84 replaced with G, I, L, S, T, M, or V; L85 replaced with A, G, I, S, T, M, or V; S86 replaced with A, G, I, L, T, M, or V; S87 replaced with A, G, I, L, T, M, or V; T88 replaced with A, G, I, L, S, M, or V; D89 replaced with E; T90 replaced with A, G, I, L, S, M, or V; F91 replaced with W, or Y; L92 replaced with A, G, I, S, T, M, or V; L93 replaced with A, G, I, S, T, M, or V; H94 replaced with K, or R; L95 replaced with A, G, I, S, T, M, or V; A96 replaced with G, I, L, S, T, M, or V; V97 replaced with A, G, I, L, S, T, or M; A98 replaced with G, I, L, S, T, M, or V; D99 replaced with E; T100 replaced with A, G, I, L, S, M, or V; L101 replaced with A, G, I, S, T, M, or V; L102 replaced with A, G, I, S, T, M, or V; V103 replaced with A, G, I, L, S, T, or M; L104 replaced with A, G, I, S, T, M, or V; T105 replaced with A, G, I, L, S, M, or V; L106 replaced with A, G, I, S, T, M, or V; L108 replaced with A, G, I, S, T, M, or V; W109 replaced with F, or Y; A110 replaced with G, I, L, S, T, M, or V; V111 replaced with A, G, I, L, S, T, or M; D112 replaced with E; A113 replaced with G, I, L, S, T, M, or V; A114 replaced with G, I, L, S, T, M, or V; V115 replaced with A, G, I, L, S, T, or M; Q116 replaced with N; W117 replaced with F, or Y; V118 replaced with A, G, I, L, S, T, or M; F119 replaced with W, or Y; G120 replaced with A, I, L, S, T, M, or V; S121 replaced with A, G, I, L, T, M, or V; G122 replaced with A, I, L, S, T, M, or V; L123 replaced with A, G, I, S, T, M, or V; K125 replaced with H, or R; V126 replaced with A, G, I, L, S, T, or M; A127 replaced with G, I, L, S, T, M, or V; G128 replaced with A, I, L, S, T, M, or V; A129 replaced with G, I, L, S, T, M, or V; L130 replaced with A, G, I, S, T, M, or V; F131 replaced with W, or Y; N132 replaced with Q; I133 replaced with A, G, L, S, T, M, or V; N134 replaced with Q; F135 replaced with W, or Y; Y136 replaced with F, or W; A137 replaced with G, I, L, S, T, M, or V; G138 replaced with A, I, L, S, T, M, or V; A139 replaced with G, I, L, S, T, M, or V; L140 replaced with A, G, I, S, T, M, or V; L141 replaced with A, G, I, S, T, M, or V; L142 replaced with A, G, I, S, T, M, or V; A143 replaced with G, I, L, S, T, M, or V; I145 replaced with A, G, L, S, T, M, or V; S146 replaced with A, G, I, L, T, M, or V; F147 replaced with W, or Y; D148 replaced with E; R149 replaced with H, or K; Y150 replaced with F, or W; L151 replaced with A, G, I, S, T, M, or V; N152 replaced with Q; I153 replaced with A, G, L, S, T, M, or V; V154 replaced with A, G, I, L, S, T, or M; H155 replaced with K, or R; A156 replaced with G, I, L, S, T, M, or V; T157 replaced with A, G, I, L, S, M, or V; Q158 replaced with N; L159 replaced with A, G, I, S, T, M, or V; Y160 replaced with F, or W; R161 replaced with H, or K; R162 replaced with H, or K; G163 replaced with A, I, L, S, T, M, or V; A166 replaced with G, I, L, S, T, M, or V; R167 replaced with H, or K; V168 replaced with A, G, I, L, S, T, or M; T169 replaced with A, G, I, L, S, M, or V; L170 replaced with A, G, I, S, T, M, or V; T171 replaced with A, G, I, L, S, M, or V; L173 replaced with A, G, I, S, T, M, or V; A174 replaced with G, I, L, S, T, M, or V; V175 replaced with A, G, I, L, S, T, or M; W176 replaced with F, or Y; G177 replaced with A, I, L, S, T, M, or V; L178 replaced with A, G, I, S, T, M, or V; L180 replaced with A, G, I, S, T, M, or V; L181 replaced with A, G, I, S, T, M, or V; F182 replaced with W, or Y; A183 replaced with G, I, L, S, T, M, or V; L184 replaced with A, G, I, S, T, M, or V; D186 replaced with E; F187 replaced with W, or Y; I188 replaced with A, G, L, S, T, M, or V; F189 replaced with W, or Y; L190 replaced with A, G, I, S, T, M, or V; S191 replaced with A, G, I, L, T, M, or V; A192 replaced with G, I, L, S, T, M, or V; H193 replaced with K, or R; H194 replaced with K, or R; D195 replaced with E; E196 replaced with D; R197 replaced with H, or K; L198 replaced with A, G, I, S, T, M, or V; N199 replaced with Q; A200 replaced with G, I, L, S, T, M, or V; T201 replaced with A, G, I, L, S, M, or V; H202 replaced with K, or R; Q204 replaced with N; Y205 replaced with F, or W; N206 replaced with Q; F207 replaced with W, or Y; Q209 replaced with N; V210 replaced with A, G, I, L, S, T, or M; G211 replaced with A, I, L, S, T, M, or V; R212 replaced with H, or K; T213 replaced with A, G, I, L, S, M, or V; A214 replaced with G, I, L, S, T, M, or V; L215 replaced with A, G, I, S, T, M, or V; R216 replaced with H, or K; V217 replaced with A, G, I, L, S, T, or M; L218 replaced with A, G, I, S, T, M, or V; Q219 replaced with N; L220 replaced with A, G, I, S, T, M, or V; V221 replaced with A, G, I, L, S, T, or M; A222 replaced with G, I, L, S, T, M, or V; G223 replaced with A, I, L, S, T, M, or V; F224 replaced with W, or Y; L225 replaced with A, G, I, S, T, M, or V; L226 replaced with A, G, I, S, T, M, or V; L228 replaced with A, G, I, S, T, M, or V; L229 replaced with A, G, I, S, T, M, or V; V230 replaced with A, G, I, L, S, T, or M; M231 replaced with A, G, I, L, S, T, or V; A232 replaced with G, I, L, S, T, M, or V; Y233 replaced with F, or W; Y235 replaced with F, or W; A236 replaced with G, I, L, S, T, M, or V; H237 replaced with K, or R; I238 replaced with A, G, L, S, T, M, or V; L239 replaced with A, G, I, S, T, M, or V; A240 replaced with G, I, L, S, T, M, or V; V241 replaced with A, G, I, L, S, T, or M; L242 replaced with A, G, I, S, T, M, or V; L243 replaced with A, G, I, S, T, M, or V; V244 replaced with A, G, I, L, S, T, or M; S245 replaced with A, G, I, L, T, M, or V; R246 replaced with H, or K; G247 replaced with A, I, L, S, T, M, or V; Q248 replaced with N; R249 replaced with H, or K; R250 replaced with H, or K; L251 replaced with A, G, I, S, T, M, or V; R252 replaced with H, or K; A253 replaced with G, I, L, S, T, M, or V; M254 replaced with A, G, I, L, S, T, or V; R255 replaced with H, or K; L256 replaced with A, G, I, S, T, M, or V; V257 replaced with A, G, I, L, S, T, or M; V258 replaced with A, G, I, L, S, T, or M; V259 replaced with A, G, I, L, S, T, or M; V260 replaced with A, G, I, L, S, T, or M; V261 replaced with A, G, I, L, S, T, or M; V262 replaced with A, G, I, L, S, T, or M; A263 replaced with G, I, L, S, T, M, or V; F264 replaced with W, or Y; A265 replaced with G, I, L, S, T, M, or V; L266 replaced with A, G, I, S, T, M, or V; W268 replaced with F, or Y; T269 replaced with A, G, I, L, S, M, or V; Y271 replaced with F, or W; H272 replaced with K, or R; L273 replaced with A, G, I, S, T, M, or V; V274 replaced with A, G, I, L, S, T, or M; V275 replaced with A, G, I, L, S, T, or M; L276 replaced with A, G, I, S, T, M, or V; V277 replaced with A, G, I, L, S, T, or M; D278 replaced with E; I279 replaced with A, G, L, S, T, M, or V; L280 replaced with A, G, I, S, T, M, or V; M281 replaced with A, G, I, L, S, T, or V; D282 replaced with E; L283 replaced with A, G, I, S, T, M, or V; G284 replaced with A, I, L, S, T, M, or V; A285 replaced with G, I, L, S, T, M, or V; L286 replaced with A, G, I, S, T, M, or V; A287 replaced with G, I, L, S, T, M, or V; R288 replaced with H, or K; N289 replaced with Q; G291 replaced with A, I, L, S, T, M, or V; R292 replaced with H, or K; E293 replaced with D; S294 replaced with A, G, I, L, T, M, or V; R295 replaced with H, or K; V296 replaced with A, G, I, L, S, T, or M; D297 replaced with E; V298 replaced with A, G, I, L, S, T, or M; A299 replaced with G, I, L, S, T, M, or V; K300 replaced with H, or R; S301 replaced with A, G, I, L, T, M, or V; V302 replaced with A, G, I, L, S, T, or M; T303 replaced with A, G, I, L, S, M, or V; S304 replaced with A, G, I, L, T, M, or V; G305 replaced with A, I, L, S, T, M, or V; L306 replaced with A, G, I, S, T, M, or V; G307 replaced with A, I, L, S, T, M, or V; Y308 replaced with F, or W; M309 replaced with A, G, I, L, S, T, or V; H310 replaced with K, or R; L313 replaced with A, G, I, S, T, M, or V; N314 replaced with Q; L316 replaced with A, G, I, S, T, M, or V; L317 replaced with A, G, I, S, T, M, or V; Y318 replaced with F, or W; A319 replaced with G, I, L, S, T, M, or V; F320 replaced with W, or Y; V321 replaced with A, G, I, L, S, T, or M; G322 replaced with A, I, L, S, T, M, or V; V323 replaced with A, G, I, L, S, T, or M; K324 replaced with H, or R; F325 replaced with W, or Y; R326 replaced with H, or K; E327 replaced with D; R328 replaced with H, or K; M329 replaced with A, G, I, L, S, T, or V; W330 replaced with F, or Y; M331 replaced with A, G, I, L, S, T, or V; L332 replaced with A, G, I, S, T, M, or V; L333 replaced with A, G, I, S, T, M, or V; L334 replaced with A, G, I, S, T, M, or V; R335 replaced with H, or K; L336 replaced with A, G, I, S, T, M, or V; G337 replaced with A, I, L, S, T, M, or V; N340 replaced with Q; Q341 replaced with N; R342 replaced with H, or K; G343 replaced with A, I, L, S, T, M, or V; L344 replaced with A, G, I, S, T, M, or V; Q345 replaced with N; R346 replaced with H, or K; Q347 replaced with N; S349 replaced with A, G, I, L, T, M, or V; S350 replaced with A, G, I, L, T, M, or V; S351 replaced with A, G, I, L, T, M, or V; R352 replaced with H, or K; R353 replaced with H, or K; D354 replaced with E; S355 replaced with A, G, I, L, T, M, or V; S356 replaced with A, G, I, L, T, M, or V; W357 replaced with F, or Y; S358 replaced with A, G, I, L, T, M, or V; E359 replaced with D; T360 replaced with A, G, I, L, S, M, or V; S361 replaced with A, G, I, L, T, M, or V; E362 replaced with D; A363 replaced with G, I, L, S, T, M, or V; S364 replaced with A, G, I, L, T, M, or V; Y365 replaced with F, or W; S366 replaced with A, G, I, L, T, M, or V; G367 replaced with A, I, L, S, T, M, or V; L368 replaced with A, G, I, S, T, M, or V. Polynucleotides encoding these polypeptides are also encompassed by the invention. The resulting G-protein Chemokine Receptor of the invention may be routinely screened for G-protein Chemokine Receptor functional activity and/or physical properties (such as, for example, enhanced or reduced stability and/or solubility). Preferably, the resulting proteins of the invention have an increased and/or a decreased G-protein Chemokine Receptor functional activity. More preferably, the resulting G-protein Chemokine Receptor proteins of the invention have more than one increased and/or decreased G-protein Chemokine Receptor functional activity and/or physical property.

In another embodiment, site directed changes at the amino acid level of G-protein Chemokine Receptor can be made by replacing a particular amino acid with a conservative substitution. Preferred conservative substitution mutations of the G-protein Chemokine Receptor amino acid sequence provided in SEQ ID NO:2 include: M1 replaced with A, G, I, L, S, T, or V; E2 replaced with D; L3 replaced with A, G, I, S, T, M, or V; R4 replaced with H, or K; K5 replaced with H, or R; Y6 replaced with F, or W; G7 replaced with A, I, L, S, T, M, or V; G9 replaced with A, I, L, S, T, M, or V; R10 replaced with H, or K; L11 replaced with A, G, I, S, T, M, or V; A12 replaced with G, I, L, S, T, M, or V; G13 replaced with A, I, L, S, T, M, or V; T14 replaced with A, G, I, L, S, M, or V; V15 replaced with A, G, I, L, S, T, or M; I16 replaced with A, G, L, S, T, M, or V; G17 replaced with A, I, L, S, T, M, or V; G18 replaced with A, I, L, S, T, M, or V; A19 replaced with G, I, L, S, T, M, or V; A20 replaced with G, I, L, S, T, M, or V; Q21 replaced with N; S22 replaced with A, G, I, L, T, M, or V; K23 replaced with H, or R; S24 replaced with A, G, I, L, T, M, or V; Q25 replaced with N; T26 replaced with A, G, I, L, S, M, or V; K27 replaced with H, or R; S28 replaced with A, G, I, L, T, M, or V; D29 replaced with E; S30 replaced with A, G, I, L, T, M, or V; I31 replaced with A, G, L, S, T, M, or V; T32 replaced with A, G, I, L, S, M, or V; K33 replaced with H, or V; E34 replaced with D; F35 replaced with W, or Y; L36 replaced with A, G, I, S, T, M, or V; G38 replaced with A, I, L, S, T, M, or V; L39 replaced with A, G, I, S, T, M, or V; Y40 replaced with F, or W; T41 replaced with A, G, I, L, S, M, or V; A42 replaced with G, I, L, S, T, M, or V; S44 replaced with A, G, I, L, T, M, or V; S45 replaced with A, G, I, L, T, M, or V; F47 replaced with W, or Y; S50 replaced with A, G, I, L, T, M, or V; Q51 replaced with N; V52 replaced with A, G, I, L, S, T, or M; S53 replaced with A, G, I, L, T, M, or V; D54 replaced with E; H55 replaced with K, or R; Q56 replaced with N; V57 replaced with A, G, I, S, T, or M; L58 replaced with A, G, I, S, T, M, or V; N59 replaced with Q; D60 replaced with E; A61 replaced with G, I, L, S, T, M, or V; E62 replaced with D; V63 replaced with A, G, I, L, S, T, or M; A64 replaced with G, I, L, S, T, M, or V; A65 replaced with G, I, L, S, T, M, or V; L66 replaced with A, G, I, S, T, M, or V; L67 replaced with A, G, I, S, T, M, or V; E68 replaced with D; N69 replaced with Q; F70 replaced with W, or Y; S71 replaced with A, G, I, L, T, M, or V; S72 replaced with A, G, I, L, T, M, or V; S73 replaced with A, G, I, L, T, M, or V; Y74 replaced with F, or W; D75 replaced with E; Y76 replaced with F, or W; G77 replaced with A, I, L, S, T, M, or V; E78 replaced with D; N79 replaced with Q; E80 replaced with D; S81 replaced with A, G, I, L, T, M, or V; D82 replaced with E; S83 replaced with A, G, I, L, T, M, or V; T86 replaced with A, G, I, L, S, M, or V; S87 replaced with A, G, I, L, T, M, or V; Q92 replaced with N; D93 replaced with E; F94 replaced with W, or Y; S95 replaced with A, G, I, L, T, M, or V; L96 replaced with A, G, I, S, T, M, or V; N97 replaced with Q; F98 replaced with W, or Y; D99 replaced with E; R100 replaced with H, or K; A101 replaced with G, I, L, S, T, M, or V; F102 replaced with W, or Y; L103 replaced with A, G, I, S, T, M, or V; A105 replaced with G, I, L, S, T, M, or V; L106 replaced with A, G, I, S, T, M, or V; Y107 replaced with F, or W; S108 replaced with A, G, I, L, T, M, or V; L109 replaced with A, G, I, S, T, M, or V; L110 replaced with A, G, I, S, T, M, or V; F111 replaced with W, or Y; L112 replaced with A, G, I, S, T, M, or V; L113 replaced with A, G, I, S, T, M, or V; G114 replaced with A, I, L, S, T, M, or V; L115 replaced with A, G, I, S, T, M, or V; L116 replaced with A, G, I, S, T, M, or V; G117 replaced with A, I, L, S, T, M, or V; N118 replaced with Q; G119 replaced with A, I, L, S, T, M, or V; A120 replaced with G, I, L, S, T, M, or V; V121 replaced with A, G, I, L, S, T, or M; A122 replaced with G, I, L, S, T, M, or V; A123 replaced with G, I, L, S, T, M, or V; V124 replaced with A, G, I, L, S, T, or M; L125 replaced with A, G, I, S, T, M, or V; L126 replaced with A, G, I, S, T, M, or V; S127 replaced with A, G, I, L, T, M, or V; R128 replaced with H, or K; R129 replaced with H, or K; T130 replaced with A, G, I, L, S, M, or V; A131 replaced with G, I, L, S, T, M, or V; L132 replaced with A, G, I, S, T, M, or V; S133 replaced with A, G, I, L, T, M, or V; S134 replaced with A, G, I, L, T, M, or V; T135 replaced with A, G, I, L, S, M, or V; D136 replaced with E; T137 replaced with A, G, I, L, S, M, or V; F138 replaced with W, or Y; L139 replaced with A, G, I, S, T, M, or V; L140 replaced with A, G, I, S, T, M, or V; H141 replaced with K, or R; L142 replaced with A, G, I, S, T, M, or V; A143 replaced with G, I, L, S, T, M, or V; V144 replaced with A, G, I, L, S, T, or M; A145 replaced with G, I, L, S, T, M, or V; D146 replaced with E; T147 replaced with A, G, I, L, S, M, or V; L148 replaced with A, G, I, S, T, M, or V; L149 replaced with A, G, I, S, T, M, or V; V150 replaced with A, G, I, L, S, T, or M; L151 replaced with A, G, I, S, T, M, or V; T152 replaced with A, G, I, L, S, M, or V; L153 replaced with A, G, I, S, T, M, or V; L155 replaced with A, G, I, S, T, M, or V; W156 replaced with F, or Y; A157 replaced with G, I, L, S, T, M, or V; V158 replaced with A, G, I, L, S, T, or M; D159 replaced with E; A160 replaced with G, I, L, S, T, M, or V; A161 replaced with G, I, L, S, T, M, or V; V162 replaced with A, G, I, L, S, T, or M; Q163 replaced with N; W164 replaced with F, or Y; V165 replaced with A, G, I, L, S, T, or M; F166 replaced with W, or Y; G167 replaced with A, I, L, S, T, M, or V; S168 replaced with A, G, I, L, T, M, or V; G169 replaced with A, I, L, S, T, M, or V; L170 replaced with A, G, I, S, T, M, or V; K172 replaced with H, or R; V173 replaced with A, G, I, L, S, T, or M; A174 replaced with G, I, L, S, T, M, or V; G175 replaced with A, I, L, S, T, M, or V; A176 replaced with G, I, L, S, T, M, or V; L177 replaced with A, G, I, S, T, M, or V; F178 replaced with W, or Y; N179 replaced with Q; I180 replaced with A, G, L, S, T, M, or V; N181 replaced with Q; F182 replaced with W, or Y; Y183 replaced with F, or W; A184 replaced with G, I, L, S, T, M, or V; G185 replaced with A, I, L, S, T, M, or V; A186 replaced with G, I, L, S, T, M, or V; L187 replaced with A, G, I, S, T, M, or V; L188 replaced with A, G, I, S, T, M, or V; L189 replaced with A, G, I, S, T, M, or V; A190 replaced with G, I, L, S, T, M, or V; I192 replaced with A, G, L, S, T, M, or V; S193 replaced with A, G, I, L, T, M, or V; F194 replaced with W, or Y; D195 replaced with E; R196 replaced with H, or K; Y197 replaced with F, or W; L198 replaced with A, G, I, S, T, M, or V; N199 replaced with Q; I200 replaced with A, G, L, S, T, M, or V; V201 replaced with A, G, I, L, S, T, or M; H202 replaced with K, or R; A203 replaced with G, I, L, S, T, M, or V; T204 replaced with A, G, I, L, S, M, or V; Q205 replaced with N; L206 replaced with A, G, I, S, T, M, or V; Y207 replaced with F, or W; R208 replaced with H, or K; R209 replaced with H, or K; G210 replaced with A, I, L, S, T, M, or V; A213 replaced with G, I, L, S, T, M, or V; R214 replaced with H, or K; V215 replaced with A, G, I, L, S, T, or M; T216 replaced with A, G, I, L, S, M, or V; L217 replaced with A, G, I, S, T, M, or V; T218 replaced with A, G, I, L, S, M, or V; L220 replaced with A, G, I, S, T, M, or V; A221 replaced with G, I, L, S, T, M, or V; V222 replaced with A, G, I, L, S, T, or M; W223 replaced with F, or Y; G224 replaced with A, I, L, S, T, M, or V; L225 replaced with A, G, I, S, T, M, or V; L227 replaced with A, G, I, S, T, M, or V; L228 replaced with A, G, I, S, T, M, or V; F229 replaced with W, or Y; A230 replaced with G, I, L, S, T, M, or V; L231 replaced with A, G, I, S, T, M, or V; D233 replaced with E; F234 replaced with W, or Y; I235 replaced with A, G, L, S, T, M, or V; F236 replaced with W, or Y; L237 replaced with A, G, I, S, T, M, or V; S238 replaced with A, G, I, L, T, M, or V; A239 replaced with G, I, L, S, T, M, or V; H240 replaced with K, or R; H241 replaced with K, or R; D242 replaced with E; E243 replaced with D; R244 replaced with H, or K; L245 replaced with A, G, I, S, T, M, or V; N246 replaced with Q; A247 replaced with G, I, L, S, T, M, or V; T248 replaced with A, G, I, L, S, M, or V; H249 replaced with K, or R; Q251 replaced with N; Y252 replaced with F, or W; N253 replaced with Q; F254 replaced with W, or Y; Q256 replaced with N; V257 replaced with A, G, I, L, S, T, or M; G258 replaced with A, I, L, S, T, M, or V; R259 replaced with H, or K; T260 replaced with A, G, I, L, S, M, or V; A261 replaced with G, I, L, S, T, M, or V; L262 replaced with A, G, I, S, T, M, or V; V264 replaced with A, G, I, L, S, T, or M; L265 replaced with A, G, I, S, T, M, or V; Q266 replaced with N; L267 replaced with A, G, I, S, T, M, or V; V268 replaced with A, G, I, L, S, T, or M; A269 replaced with G, I, L, S, T, M, or V; G270 replaced with A, I, L, S, T, M, or V; F271 replaced with W, or Y; L272 replaced with A, G, I, S, T, M, or V; L273 replaced with A, G, I, S, T, M, or V; L275 replaced with A, G, I, S, T, M, or V; L276 replaced with A, G, I, S, T, M, or V; V277 replaced with A, G, I, L, S, T, or M; M278 replaced with A, G, I, L, S, T, or V; A279 replaced with G, I, L, S, T, M, or V; Y280 replaced with F, or W; Y282 replaced with F, or W; A283 replaced with G, I, L, S, T, M, or V; H284 replaced with K, or R; I285 replaced with A, G, L, S, T, M, or V; L286 replaced with A, G, I, S, T, M, or V; A287 replaced with G, I, L, S, T, M, or V; V288 replaced with A, G, I, L, S, T, or M; L289 replaced with A, G, I, S, T, M, or V; L290 replaced with A, G, I, S, T, M, or V; V291 replaced with A, G, I, L, S, T, or M; S292 replaced with A, G, I, L, T, M, or V; R293 replaced with H, or K; G294 replaced with A, I, L, S, T, M, or V; Q295 replaced with N; R296 replaced with H, or K; R297 replaced with H, or K; L298 replaced with A, G, I, S, T, M, or V; R299 replaced with H, or K; A300 replaced with G, I, L, S, T, M, or V; M301 replaced with A, G, I, L, S, T, or V; R302 replaced with H, or K; L303 replaced with A, G, I, S, T, M, or V; V304 replaced with A, G, I, L, S, T, or M; V305 replaced with A, G, I, L, S, T, or M; V306 replaced with A, G, I, L, S, T, or M; V307 replaced with A, G, I, L, S, T, or M; V308 replaced with A, G, I, L, S, T, or M; V309 replaced with A, G, I, L, S, T, or M; A310 replaced with G, I, L, S, T, M, or V; F311 replaced with W, or Y; A312 replaced with G, I, L, S, T, M, or V; L313 replaced with A, G, I, S, T, M, or V; W315 replaced with F, or Y; T316 replaced with A, G, I, L, S, M, or V; Y318 replaced with F, or W; H319 replaced with K, or R; L320 replaced with A, G, I, S, T, M, or V; V321 replaced with A, G, I, L, S, T, or M; V322 replaced with A, G, I, L, S, T, or M; L323 replaced with A, G, I, S, T, M, or V; V324 replaced with A, G, I, L, S, T, or M; D325 replaced with E; I326 replaced with A, G, L, S, T, M, or V; L327 replaced with A, G, I, S, T, M, or V; M328 replaced with A, G, I, L, S, T, or V; D329 replaced with E; L330 replaced with A, G, I, S, T, M, or V; G331 replaced with A, I, L, S, T, M, or V; A332 replaced with G, I, L, S, T, M, or V; L333 replaced with A, G, I, S, T, M, or V; L334 replaced with G, I, L, S, T, M, or V; R335 replaced with H, or K; N336 replaced with Q; G338 replaced with A, I, L, S, T, M, or V; R339 replaced with H, or K; E340 replaced with D; S341 replaced with A, G, I, L, T, M, or V; R342 replaced with H, or K; V343 replaced with A, G, I, L, S, T, or M; D344 replaced with E; V345 replaced with A, G, I, L, S, T, or M; A346 replaced with G, I, L, S, T, M, or V; K347 replaced with H, or R; S348 replaced with A, G, I, L, T, M, or V; V349 replaced with A, G, I, L, S, T, or M; T350 replaced with A, G, I, L, S, M, or V; S351 replaced with A, G, I, L, T, M, or V; G352 replaced with A, I, L, S, T, M, or V; L353 replaced with A, G, I, S, T, M, or V; G354 replaced with A, I, L, S, T, M, or V; Y355 replaced with F, or W; M356 replaced with A, G, I, L, S, T, or V; H357 replaced with K, or R; L360 replaced with A, G, I, S, T, M, or V; N361 replaced with Q; L363 replaced with A, G, I, S, T, M, or V; L364 replaced with A, G, I, S, T, M, or V; Y365 replaced with F, or W; A366 replaced with G, I, L, S, T, M, or V; F367 replaced with W, or Y; V368 replaced with A, G, I, L, S, T, or M; G369 replaced with A, I, L, S, T, M, or V; V370 replaced with A, G, I, L, S, T, or M; K371 replaced with H, or R; F372 replaced with W, or Y; R373 replaced with H, or K; E374 replaced with D; R375 replaced with H, or K; M376 replaced with A, G, I, L, S, T, or V; W377 replaced with F, or Y; M378 replaced with A, G, I, L, S, T, or V; L379 replaced with A, G, I, S, T, M, or V; L380 replaced with A, G, I, S, T, M, or V; L381 replaced with A, G, I, S, T, M, or V; R382 replaced with H, or K; L383 replaced with A, G, I, S, T, M, or V; G384 replaced with A, I, L, S, T, M, or V; N387 replaced with Q; Q388 replaced with N; R389 replaced with H, or K; G390 replaced with A, I, L, S, T, M, or V; L391 replaced with A, G, I, S, T, M, or V; Q392 replaced with N; R393 replaced with H, or K; Q394 replaced with N; S396 replaced with A, G, I, L, T, M, or V; S397 replaced with A, G, I, L, T, M, or V; S398 replaced with A, G, I, L, T, M, or V; R399 replaced with H, or K; R400 replaced with H, or K; D401 replaced with E; S402 replaced with A, G, I, L, T, M, or V; S403 replaced with A, G, I, L, T, M, or V; W404 replaced with F, or Y; S405 replaced with A, G, I, L, T, M, or V; E406 replaced with D; T407 replaced with A, G, I, L, S, M, or V; S408 replaced with A, G, I, L, T, M, or V; E409 replaced with D; A410 replaced with G, I, L, S, T, M, or V; S411 replaced with A, G, I, L, T, M, or V; Y412 replaced with F, or W; S413 replaced with A, G, I, L, T, M, or V; G414 replaced with A, I, L, S, T, M, or V; L415 replaced with A, G, I, S, T, M, or V. Polynucleotides encoding these polypeptides are also encompassed by the invention. The resulting G-protein Chemokine Receptor of the invention may be routinely screened for G-protein Chemokine Receptor functional activity and/or physical properties (such as, for example, enhanced or reduced stability and/or solubility). Preferably, the resulting proteins of the invention have an increased and/or a decreased G-protein Chemokine Receptor functional activity. More preferably, the resulting G-protein Chemokine Receptor proteins of the invention have more than one increased and/or decreased G-protein Chemokine Receptor functional activity and/or physical property.

Amino acids in the G-protein Chemokine Receptor proteins of the present invention that are essential for function can be identified by methods known in the art, such as site-directed mutagenesis or alanine-scanning mutagenesis (Cunningham and Wells, *Science* 244:1081-1085 (1989)). The latter procedure introduces single alanine mutations at every residue in the molecule. The resulting mutant molecules are then tested for biological activity such as receptor binding or in vitro proliferative activity. Sites that are critical for ligand-receptor binding can also be determined by structural analysis such as crystallization, nuclear magnetic resonance or photoaffinity labeling (Smith et al., *J. Mol. Biol.* 224:899-904 (1992) and de Vos et al. *Science* 255:306-312 (1992)).

Of special interest are substitutions of charged amino acids with other charged or neutral amino acids that may produce proteins with highly desirable improved characteristics, such as less aggregation. Aggregation may not only reduce activity but also be problematic when preparing pharmaceutical formulations, because aggregates can be immunogenic (Pinckard et al., *Clin. Exp. Immunol.* 2:331-340 (1967); Robbins et al., Diabetes 36: 838-845 (1987); Cleland et al., *Crit. Rev. Therapeutic Drug Carrier Systems* 10:307-377 (1993).

In another embodiment, the invention provides for polypeptides having amino acid sequences containing non-conservative substitutions of the amino acid sequence provided in SEQ ID NO:4. For example, non-conservative substitutions of the G-protein Chemokine Receptor protein sequence provided in SEQ ID NO:4 include: M1 replaced with D, E, H, K, R, N, Q, F, W, Y, P, or C; V2 replaced with D, E, H, K, R, N, Q, F, W, Y, P, or C; L3 replaced with D, E, H, K, R, N, Q, F, W, Y, P, or C; E4 replaced with H, K, R, A, G, I, L, S, T, M, V, N, Q, F, W, Y, P, or C; V5 replaced with D, E, H, K, R, N, Q, F, W, Y, P, or C; S6 replaced with D, E, H, K, R, N, Q, F, W, Y, P, or C; D7 replaced with H, K, R, A, G, I, L, S, T, M, V, N, Q, F, W, Y, P, or C; H8 replaced with D, E, A, G, I, L, S, T, M, V, N, Q, F, W, Y, P, or C; Q9 replaced with D, E, H, K, R, A, G, I, L, S, T, M, V, F, W, Y, P, or C; V10 replaced with D, E, H, K, R, N, Q, F, W, Y, P, or C; L11 replaced with D, E, H, K, R, N, Q, F, W, Y, P, or C; N12 replaced with D, E, H, K, R, A, G, I, L, S, T, M, V, F, W, Y, P, or C; D13 replaced with H, K, R, A, G, I, L, S, T, M, V, N, Q, F, W, Y, P, or C; A14 replaced with D, E, H, K, R, N, Q, F, W, Y, P, or C; E15 replaced with H, K, R, A, G, I, L, S, T, M, V, N, Q, F, W, Y, P, or C; V16 replaced with D, E, H, K, R, N, Q, F, W, Y, P, or C; A17 replaced with D, E, H, K, R, N, Q, F, W, Y, P, or C; A18 replaced with D, E, H, K, R, N, Q, F, W, Y, P, or C; L19 replaced with D, E, H, K, R, N, Q, F, W, Y, P, or C; L20 replaced with D, E, H, K, R, N, Q, F, W, Y, P, or C; E21 replaced with H, K, R, A, G, I, L, S, T, M, V, N, Q, F, W, Y, P, or C; N22 replaced with D, E, H, K, R, A, G, I, L, S, T, M, V, F, W, Y, P, or C; F23 replaced with D, E, H, K, R, N, Q, A, G, I, L, S, T, M, V, P, or C; S24 replaced with D, E, H, K, R, N, Q, F, W, Y, P, or C; S25 replaced with D, E, H, K, R, N, Q, F, W, Y, P, or C; S26 replaced with D, E, H, K, R, N, Q, F, W, Y, P, or C; Y27 replaced with D, E, H, K, R, N, Q, A, G, I, L, S, T, M, V, P, or C; D28 replaced with H, K, R, A, G, I, L, S, T, M, V, N, Q, F, W, Y, P, or C; Y29 replaced with D, E, H, K, R, N, Q, A, G, I, L, S, T, M, V, P, or C; G30 replaced with D, E, H, K, R, N, Q, F, W, Y, P, or C; E31 replaced with H, K, R, A, G, I, L, S, T, M, V, N, Q, F, W, Y, P, or C; N32 replaced with D, E, H, K, R, A, G, I, L, S, T, M, V, F, W, Y, P, or C; E33 replaced with H, K, R, A, G, I, L, S, T, M, V, N, Q, F, W, Y, P, or C; S34 replaced with D, E, H, K, R, N, Q, F, W, Y, P, or C; D35 replaced with H, K, R, A, G, I, L, S, T, M, V, N, Q, F, W, Y, P, or C; S36 replaced with D, E, H, K, R, N, Q, F, W, Y, P, or C; C37 replaced with D, E, H, K, R, A, G, I, L, S, T, M, V, N, Q, F, W, Y, or P; C38 replaced with D, E, H, K, R, A, G, I, L, S, T, M, V, N, Q, F, W, Y, or P; T39 replaced with D, E, H, K, R, N, Q, F, W, Y, P, or C; S40 replaced with D, E, H, K, R, N, Q, F, W, Y, P, or C; P41 replaced with D, E, H, K, R, A, G, I, L, S, T, M, V, N, Q, F, W, Y, or C; P42 replaced with D, E, H, K, R, A, G, I, L, S, T, M, V, N, Q, F, W, Y, or C; C43 replaced with D, E, H, K, R, A, G, I, L, S, T, M, V, N, Q, F, W, Y, or P; P44 replaced with D, E, H, K, R, A, G, I, L, S, T, M, V, N, Q, F, W, Y, or C; Q45 replaced with D, E, H, K, R, A, G, I, L, S, T, M, V, F, W, Y, P, or C; D46 replaced with H, K, R, A, G, I, L, S, T, M, V, N, Q, F, W, Y, P, or C; F47 replaced with D, E, H, K, R, N, Q, A, G, I, L, S, T, M, V, P, or C; S48 replaced with D, E, H, K, R, N, Q, F, W, Y, P, or C; L49 replaced with D, E, H, K, R, N, Q, F, W, Y, P, or C; N50 replaced with D, E, H, K, R, A, G, I, L, S, T, M, V, F, W, Y, P, or C; F51 replaced with D, E, H, K, R, N, Q, A, G, I, L, S, T, M, V, P, or C; D52 replaced with H, K, R, A, G, I, L, S, T, M, V, N, Q, F, W, Y, P, or C; R53 replaced with D, E, A, G, I, L, S, T, M, V, N, Q, F, W, Y, P, or C; A54 replaced with D, E, H, K, R, N, Q, F, W, Y, P, or C; F55 replaced with D, E, H, K, R, N, Q, A, G, I, L, S, T, M, V, P, or C; L56 replaced with D, E, H, K, R, N, Q, F, W, Y, P, or C; P57 replaced with D, E, H, K, R, A, G, I, L, S, T, M, V, N, Q, F, W, Y, or C; A58 replaced with D, E, H, K, R, N, Q, F, W, Y, P, or C; L59 replaced with D, E, H, K, R, N, Q, F, W, Y, P, or C; Y60 replaced with D, E, H, K, R, N, Q, A, G, I, L, S, T, M, V, P, or C; S61 replaced with D, E, H, K, R, N, Q, F, W, Y, P, or C; L62 replaced with D, E, H, K, R, N, Q, F, W, Y, P, or C; L63 replaced with D, E, H, K, R, N, Q, F, W, Y, P, or C; F64 replaced with D, E, H, K, R, N, Q, A, G, I, L, S, T, M, V, P, or C; L65 replaced with D, E, H, K, R, N, Q, F, W, Y, P, or C; L66 replaced with D, E, H, K, R, N, Q, F, W, Y, P, or C; G67 replaced with D, E, H, K, R, N, Q, F, W, Y, P, or C; L68 replaced with D, E, H, K, R, N, Q, F, W, Y, P, or C; L69 replaced with D, E, H, K, R, N, Q, F, W, Y, P, or C; G70 replaced with D, E, H, K, R, N, Q, F, W, Y, P, or C; N71 replaced with D, E, H, K, R, A, G, I, L, S, T, M, V, F, W, Y, P, or C; G72 replaced with D, E, H, K, R, N, Q, F, W, Y, P, or C; A73 replaced with D, E, H, K, R, N, Q, F, W, Y, P, or C; V74 replaced with D, E, H, K, R, N, Q, F, W, Y, P, or C; A75 replaced with D, E, H, K, R, N, Q, F, W, Y, P, or C; A76 replaced with D, E, H, K, R, N, Q, F, W, Y, P, or C; V77 replaced with D, E, H, K, R, N, Q, F, W, Y, P, or C; L78 replaced with D, E, H, K, R, N, Q, F, W, Y, P, or C; L79 replaced with D, E, H, K, R, N, Q, F, W, Y, P, or C; S80 replaced with D, E, H, K, R, N, Q, F, W, Y, P, or C; R81 replaced with D, E, A, G, I, L, S, T, M, V, N, Q, F, W, Y, P, or C; R82 replaced with D, E, A, G, I, L, S, T, M, V, N, Q, F, W, Y, P, or C; T83 replaced with D, E, H, K, R, N, Q, F, W, Y, P, or C; A84 replaced with D, E, H, K, R, N, Q, F, W, Y, P, or C; L85 replaced with D, E, H, K, R, N, Q, F, W, Y, P, or C; S86 replaced with D, E, H, K, R, N, Q, F, W, Y, P, or C; S87 replaced with D, E, H, K, R, N, Q, F, W, Y, P, or C; T88 replaced with D, E, H, K, R, N, Q, F, W, Y, P, or C; D89 replaced with H, K, R, A, G, I, L, S, T, M, V, N, Q, F, W, Y, P, or C; T90 replaced with D, E, H, K, R, N, Q, F, W, Y, P, or C; F91 replaced with D, E, H, K, R, N, Q, A, G, I, L, S, T, M, V, P, or C; L92 replaced with D, E, H, K, R, N, Q, F, W, Y, P, or C; L93 replaced with D, E, H, K, R, N, Q, F, W, Y, P, or C; H94 replaced with D, E, A, G, I, L, S, T, M, V, N, Q, F, W, Y, P, or C; L95 replaced with D, E, H, K, R, N, Q, F, W, Y, P, or C; A96 replaced with D, E, H, K, R, N, Q, F, W, Y, P, or C; V97 replaced with D, E, H, K, R, N, Q, F, W, Y, P, or C; A98 replaced with D, E, H, K, R, N, Q, F, W, Y, P, or C; D99 replaced with H, K, R, A, G, I, L, S, T, M, V, N, Q, F, W, Y, P, or C; T100 replaced with D, E, H, K, R, N, Q, F, W, Y, P, or C; L101 replaced with D, E, H, K, R, N, Q, F, W, Y, P, or C; L102 replaced with D, E, H, K, R, N, Q, F, W, Y, P, or C; V103 replaced with D, E, H, K, R, N, Q, F, W, Y, P, or C; L104 replaced with D, E, H, K, R, N, Q, F, W, Y, P, or C; T105 replaced with D, E, H, K, R, N, Q, F, W, Y, P, or C; L106 replaced with D, E, H, K, R, N, Q, F, W, Y, P, or C; P107 replaced with D, E, H, K, R, A, G, I,L, S, T, M, V, N, Q, F, W, Y, or C; L108 replaced with D, E, H, K, R, N, Q, F, W, Y, P, or C; W109 replaced with D, E, H, K, R, N, Q, A, G, I, L, S, T, M, V, P, or C; A110 replaced with D, E, H, K, R, N, Q, F, W, Y, P, or C; V111 replaced with D, E, H, K, R, N, Q, F, W, Y, P, or C; D112 replaced with H, K, R, A, G, I, L, S, T, M, V, N, Q, F, W, Y, P, or C; A113 replaced with D, E, H, K, R, N, Q, F, W, Y, P, or C; A114 replaced with D, E, H, K, R, N, Q, F, W, Y, P, or C; V115 replaced with D, E, H, K, R, N, Q, F, W, Y, P, or C; Q116 replaced with D, E, H, K, R, A, G, I, L, S, T, M, V, F, W, Y, P, or C; W117 replaced with D, E, H, K, R, N, Q, A, G, I, L, S, T, M, V, P, or C; V118 replaced with D, E, H, K, R, N, Q, F, W, Y, P, or C; F119 replaced with D, E, H, K, R, N, Q, A, G, I, L, S, T, M, V, P, or C; G120 replaced with D, E, H, K, R, N, Q, F, W, Y, P, or C; S121 replaced with D, E, H, K, R, N, Q, F, W, Y, P, or C; G122 replaced with D, E, H, K, R, N, Q, F, W, Y, P, or C; L123 replaced with D, E, H, K, R, N, Q, F, W, Y, P, or C; C124 replaced with D, E, H, K, R, A, G, I, L, S, T, M, V, N, Q, F, W, Y, or P; K125 replaced with D, E, A, G, I, L, S, T, M, V, N, Q, F, W, Y, P, or C; V126 replaced with D, E, H, K, R, N, Q, F, W, Y, P, or C; A127 replaced with D, E, H, K, R, N, Q, F, W, Y, P, or C; G128 replaced with D, E, H, K, R, N, Q, F, W, Y, P, or C; A129 replaced with D, E, H, K, R, N, Q, F, W, Y, P, or C; L130 replaced with D, E, H, K, R, N, Q, F, W, Y, P, or C; F131 replaced with D, E, H, K, R, N, Q, A, G, I, L, S, T, M, V, P, or C; N132 replaced with D, E, H, K, R, A, G, I, L, S, T, M, V, F, W, Y, P, or C; I133 replaced with D, E, H, K, R, N, Q, F, W, Y, P, or C; N134 replaced with D, E, H, K, R, A, G, I, L, S, T, M, V, F, W, Y, P, or C; F135 replaced with D, E, H, K, R, N, Q, A, G, I, L, S, T, M, V, P, or C; Y136 replaced with D, E, H, K, R, N, Q, A, G, I, L, S, T, M, V, P, or C; A137 replaced with D, E, H, K, R, N, Q, F, W, Y, P, or C; G138 replaced with D, E, H, K, R, N, Q, F, W, Y, P, or C; A139 replaced with D, E, H, K, R, N, Q, F, W, Y, P, or C; L140 replaced with D, E, H, K, R, N, Q, F, W, Y, P, or C; L141 replaced with D, E, H, K, R, N, Q, F, W, Y, P, or C; L142 replaced with D, E, H, K, R, N, Q, F, W, Y, P, or C; A143 replaced with D, E, H, K, R, N, Q, F, W, Y, P, or C; C144 replaced with D, E, H, K, R, A, G, I, L, S, T, M, V, N, Q, F, W, Y, or P; I145 replaced with D, E, H, K, R, N, Q, F, W, Y, P, or C; S146 replaced with D, E, H, K, R, N, Q, F, W, Y, P, or C; F147 replaced with D, E, H, K, R, N, Q, A, G, I, L, S, T, M, V, P, or C; D148 replaced with H, K, R, A, G, I, L, S, T, M, V, N, Q, F, W, Y, P, or C; R149 replaced with D, E, A, G, I, L, S, T, M, V, N, Q, F, W, Y, P, or C; Y150 replaced with D, E, H, K, R, N, Q, A, G, I, L, S, T, M, V, P, or C; L151 replaced with D, E, H, K, R, N, Q, F, W, Y, P, or C; N152 replaced with D, E, H, K, R, A, G, I, L, S, T, M, V, F, W, Y, P, or C; I153 replaced with D, E, H, K, R, N, Q, F, W, Y, P, or C; V154 replaced with D, E, H, K, R, N, Q, F, W, Y, P, or C; H155 replaced with D, E, A, G, I, L, S, T, M, V, N, Q, F, W, Y, P, or C; A156 replaced with D, E, H, K, R, N, Q, F, W, Y, P, or C; T157 replaced with D, E, H, K, R, N, Q, F, W, Y, P, or C; Q158 replaced with D, E, H, K, R, A, G, I, L, S, T, M, V, F, W, Y, P, or C; L159 replaced with D, E, H, K, R, N, Q, F, W, Y, P, or C; Y160 replaced with D, E, H, K, R, N, Q, A, G, I, L, S, T, M, V, P, or C; R161 replaced with D, E, A, G, I, L, S, T, M, V, N, Q, F, W, Y, P, or C; R162 replaced with D, E, A, G, I, L, S, T, M, V, N, Q, F, W, Y, P, or C; G163 replaced with D, E, H, K, R, N, Q, F, W, Y, P, or C; P164 replaced with D, E, H, K, R, A, G, I, L, S, T, M, V, N, Q, F, W, Y, or C; P165 replaced with D, E, H, K, R, A, G, I, L, S, T, M, V, N, Q, F, W, Y, or C; A166 replaced with D, E, H, K, R, N, Q, F, W, Y, P, or C; R167 replaced with D, E, A, G, I, L, S, T, M, V, N, Q, F, W, Y, P, or C; V168 replaced with D, E, H, K, R, N, Q, F, W, Y, P, or C; T169 replaced with D, E, H, K, R, N, Q, F, W, Y, P, or C; L170 replaced with D, E, H, K, R, N, Q, F, W, Y, P, or C; T171 replaced with D, E, H, K, R, N, Q, F, W, Y, P, or C; C172 replaced with D, E, H, K, R, A, G, I, L, S, T, M, V, N, Q, F, W, Y, or P; L173 replaced with D, E, H, K, R, N, Q, F, W, Y, P, or C; A174 replaced with D, E, H K, R, N, Q, F, W, Y, P, or C; V175 replaced with D, E, H, K, R, N, Q, F, W, Y, P, or C; W176 replaced with D, E, H, K, R, N, Q, A, G, I, L, S, T, M, V, P, or C; G177 replaced with D, E, H, K, R, N, Q, F, W, Y, P, or C; L178 replaced with D, E, H, K, R, N, Q, F, W, Y, P, or C; C179 replaced with D, E, H, K, R, A, G, I, L, S, T, M, V, N, Q, F, W, Y, or P; L180 replaced with D, E, H, K, R, N, Q, F, W, Y, P, or C; L181 replaced with D, E, H, K, R, N, Q, F, W, Y, P, or C; F182 replaced with D, E, H, K, R, N, Q, A, G, I, L, S, T, M, V, P, or C; A183 replaced with D, E, H, K, R, N, Q, F, W, Y, P, or C; L184 replaced with D, E, H, K, R, N, Q, F, W, Y, P, or C; P185 replaced with D, E, H, K, R, A, G, I, L, S, T, M, V, N, Q, F, W, Y,or C; D186 replaced with H, K, R, A, G, I, L, S, T, M, V, N, Q, F, W, Y, P, or C; F187 replaced with D, E, H, K, R, N, Q, A, G, I, L, S, T, M, V, P, or C; I188 replaced with D, E, H, K, R, N, Q, F, W, Y, P, or C; F189 replaced with D, E, H, K, R, N, Q, A, G, I, L, S, T, M, V, P, or C; L190 replaced with D, E, H, K, R, N, Q, F, W, Y, P, or C; S191 replaced with D, E, H, K, RN, Q, F, W, Y, P, or C; A192 replaced with D, E, H, K, R, N, Q, F, W, Y, P, or C; H193 replaced with D, E, A, G, I, L, S, T, M, V, N, Q, F, W, Y, P, or C; H194 replaced with D, E, A, G, I, L, S, T, M, V, N, Q, F, W, Y, P, or C; D195 replaced with H, K, R, A, G, I, L, S, T, M, V, N, Q, F, W, Y, P, or C; E196 replaced with H, K, R, A, G, I, L, S, T, M, V, N, Q, F, W, Y, P, or C; R197 replaced with D, E, A, G, I, L, S, T, M, V, N, Q, F, W, Y, P, or C; L198 replaced with D, E, H, K, R, N, Q, F, W, Y, P, or C; N199 replaced with D, E, H, K, R, A, G, I, L, S, T, M, V, F, W, Y, P, or C; A200 replaced with D, E, H, K, R, N, Q, F, W, Y, P, or C; T201 replaced with D, E, H, K, R, N, Q, F, W, Y, P, or C; H202 replaced with D, E, A, G, I, L, S, T, M, V, N, Q, F, W, Y, P, or C; C203 replaced with D, E, H, K, R, A, G, I, L, S, T, M, V, N, Q, F, W, Y, or P; Q204 replaced with D, E, H, K, R, A, G, I, L, S, T, M, V, F, W, Y, P, or C; Y205 replaced with D, E, H, K, R, N, Q, A, G, I, L, S, T, M, V, P, or C; N206 replaced with D, E, H, K, R, A, G, I, L, S, T, M, V, F, W, Y, P, or C; F207 replaced with D, E, H, K, R, N, Q, A, G, I, L, S, T, M, V, P, or C; P208 replaced with D, E, H, K, R, A, G, I, L, S, T, M, V, N, Q, F, W, Y, or C; Q209 replaced with D, E, H, K, R, A, G, I, L, S, T, M, V, F, W, Y, P, or C; V210 replaced with D, E, H, K, R, N, Q, F, W, Y, P, or C; G211 replaced with D, E, H, K, R, N, Q, F, W, Y, P, or C; R212 replaced with D, E, A, G, I, L, S, T, M, V, N, Q, F, W, Y, P, or C; T213 replaced with D, E, H, K, R, N, Q, F, W, Y, P, or C; A214 replaced with D, E, H, K, R, N, Q, F, W, Y, P, or C; L215 replaced with D, E, H, K, R, N, Q, F, W, Y, P, or C; R216 replaced with D, E, A, G, I, L, S, T, M, V, N, Q, F, W, Y, P, or C; V217 replaced with D, E, H, K, R, N, Q, F, W, Y, P, or C; L218 replaced with D, E, H, K, R, N, Q, F, W, Y, P, or C; Q219 replaced with D, E, H, K, R, A, G, I, L, S, T, M, V, F, W, Y, P, or C; L220 replaced with D, E, H, K, R, N, Q, F, W, Y, P, or C; V221 replaced with D, E, H, K, R, N, Q, F, W, Y, P, or C; A222 replaced with D, E, H, K, R, N, Q, F, W, Y, P, or C; G223 replaced with D, E, H, K, R, N, Q, F, W, Y, P, or C; F224 replaced with D, E, H, K, R, N, Q, A, G, I, L, S, T, M, V, P, or C; L225 replaced with D, E, H, K, R, N, Q, F, W, Y, P, or C; L226 replaced with D, E, H, K, R, N, Q, F, W, Y, P, or C; P227 replaced with D, E, H, K, R, A, G, I, L, S, T, M, V, N, Q, F, W, Y, or C; L228 replaced with D, E, H, K, R, N, Q, F, W, Y, P, or C; L229 replaced with D, E, H, K, R, N, Q, F, W, Y, P, or C; V230 replaced with D, E, H, K, R, N, Q, F, W, Y, P, or C; M231 replaced with D, E, H, K, R, N, Q, F, W, Y, P, or C; A232 replaced with D, E, H, K, R, N, Q, F, W, Y, P, or C; Y233 replaced with D, E, H, K, R, N, Q, A, G, I, L, S, T, M, V, P, or C; C234 replaced with D, E, H, K, R, A, G, I, L, S, T, M, V, N, Q, F, W, Y, or P; Y235 replaced with D, E, H, K, R, N, Q, A, G, I, L, S, T, M, V, P, or C; A236 replaced with D, E, H, K, R, N, Q, F, W, Y, P, or C; H237 replaced with D, E, A, G, I, L, S, T, M, V, N, Q, F, W, Y, P, or C; I238 replaced with D, E, H, K, R, N, Q, F, W, Y, P, or C; L239 replaced with D, E, H, K, R, N, Q, F, W, Y, P, or C; A240 replaced with D, E, H, K, R, N, Q, F, W, Y, P, or C; V241 replaced with D, E, H, K, R, N, Q, F, W, Y, P, or C; L242 replaced with D, E, H, K, R, N, Q, F, W, Y, P, or C; L243 replaced with D, E, H, K, R, N, Q, F, W, Y, P, or C; V244 replaced with D, E, H, K, R, N, Q; F, W, Y, P, or C; S245 replaced with D, E, H, K, R, N, Q, F, W, Y, P, or C; R246 replaced with D, E, A, G, I, L, S, T, M, V, N, Q, F, W, Y, P, or C; G247 replaced with D, E, H, K, R, N, Q, F, W, Y, P, or C; Q248 replaced with D, E, H, K, R, A, G, I, L, S, T, M, V, F, W, Y, P, or C; R249 replaced with D, E, A, G, I, L, S, T, M, V, N, Q, F, W, Y, P, or C; R250 replaced with D, E, A, G, I, L, S, T, M, V, N, Q, F, W, Y, P, or C; L251 replaced with D, E, H, K, R, N, Q, F, W, Y, P, or C; R252 replaced with D, E, A, G, I, L, S, T, M, V, N, Q, F, W, Y, P, or C; A253 replaced with D, E, H, K, R, N, Q, F, W, Y, P, or C; M254 replaced with D, E, H, K, R, N, Q, F, W, Y, P, or C; R255 replaced with D, E, A, G, I, L, S, T, M, V, N, Q, F, W, Y, P, or C; L256 replaced with D, E, H, K, R, N, Q, F, W, Y, P, or C; V257 replaced with D, E, H, K, R, N, Q, F, W, Y, P, or C; V258 replaced with D, E, H, K, R, N, Q, F, W, Y, P, or C; V259 replaced with D, E, H, K, R, N, Q, F, W, Y, P, or C; V260 replaced with D, E, H, K, R, N, Q, F, W, Y, P, or C; V261 replaced with D, E, H, K, R, N, Q, F, W, Y, P, or C; V262 replaced with D, E, H, K, R, N, Q, F, W, Y, P, or C; A263 replaced with D, E, H, K, R, N, Q, F, W, Y, P, or C; F264 replaced with D, E, H, K, R, N, Q, A, G, I, L, S, T, M, V, P, or C; A265 replaced with D, E, H, K, R, N, Q, F, W, Y, P, or C; L266 replaced with D, E, H, K, R, N, Q, F, W, Y, P, or C; C267 replaced with D, E, H, K, R, A, G, I, L, S, T, M, V, N, Q, F, W, Y, or P; W268 replaced with D, E, H, K, R, N, Q, A, G, I, L, S, T, M, V, P, or C; T269 replaced with D, E, H, K, R, N, Q, F, W, Y, P, or C; P270 replaced with D, E, H, K, R, A, G, I, L, S, T, M, V, N, Q, F, W, Y, or C; Y271 replaced with D, E, H, K, R, N, Q, A, G, I, L, S, T, M, V, P, or C; H272 replaced with D, E, A, G, I, L, S, T, M, V, N, Q, F, W, Y, P, or C; L273 replaced with D, E, H, K, R, N, Q, F, W, Y, P, or C; V274 replaced with D, E, H, K, R, N, Q, F, W, Y, P, or C; V275 replaced with D, E, H, K, R, N, Q, F, W, Y, P, or C; L276 replaced with D, E, H, K, R, N, Q, F, W, Y, P, or C; V277 replaced with D, E, H, K, R, N, Q, F, W, Y, P, or C; D278 replaced with H, K, R, A, G, I, L, S, T, M, V, N, Q, F, W, Y, P, or C; I279 replaced with D, E, H, K, R, N, Q, F, W, Y, P, or C; L280 replaced with D, E, H, K, R, N, Q, F, W, Y, P, or C; M281 replaced with D, E, H, K, R, N, Q, F, W, Y, P, or C; D282 replaced with H, K, R, A, G, I, L, S, T, M, V, N, Q, F, W, Y, P, or C; L283 replaced with D, E, H, K, R, N, Q, F, W, Y, P, or C; G284 replaced with D, E, H, K, R, N, Q, F, W, Y, P, or C; A285 replaced with D, E, H, K, R, N, Q, F, W, Y, P, or C; L286 replaced with D, E, H, K, R, N, Q, F, W, Y, P, or C; A287 replaced with D, E, H, K, R, N, Q, F, W, Y, P, or C; R288 replaced with D, E, A, G, I, L, S, T, M, V, N, Q, F, W, Y, P, or C; N289 replaced with D, E, H, K, R, A, G, I, L, S, T, M, V, F, W, Y, P, or C; C290 replaced with D, E, H, K, R, A, G, I, L, S, T, M, V, N, Q, F, W, Y, or P; G291 replaced with D, E, H, K, R, N, Q, F, W, Y, P, or C; R292 replaced with D, E, A, G, I, L, S, T, M, V, N, Q, F, W, Y, P, or C; E293 replaced with H, K, R, A, G, I, L, S, T, M, V, N, Q, F, W, Y, P, or C; S294 replaced with D, E, H, K, R, N, Q, F, W, Y, P, or C; R295 replaced with D, E, A, G, I, L, S, T, M, V, N, Q, F, W, Y, P, or C; V296 replaced with D, E, H, K, R, N, Q, F, W, Y, P, or C; D297 replaced with H, K, R, A, G, I, L, S, T, M, V, N, Q, F, W, Y, P, or C; V298 replaced with D, E, H, K, R, N, Q, F, W, Y, P, or C; A299 replaced with D, E, H, K, R, N, Q, F, W, Y, P, or C; K300 replaced with D, E, A, G, I, L, S, T, M, V, N, Q, F, W, Y, P, or C; S301 replaced with D, E, H, K, R, N, Q, F, W, Y, P, or C; V302 replaced with D, E, H, K, R, N, Q, F, W, Y, P, or C; T303 replaced with D, E, H, K, R, N, Q, F, W, Y, P, or C; S304 replaced with D, E, H, K, R, N, Q, F, W, Y, P, or C; G305 replaced with D, E, H, K, R, N, Q, F, W, Y, P, or C; L306 replaced with D, E, H, K, R, N, Q, F, W, Y, P, or C; G307 replaced with D, E, H, K, R, N, Q, F, W, Y, P, or C; Y308 replaced with D, E, H, K, R, N, Q, A, G, I, L, S, T, M, V, P, or C; M309 replaced with D, E, H, K, R, N, Q, F, W, Y, P, or C; H310 replaced with D, E, A, G, I, L, S, T, M, V, N, Q, F, W, Y, P, or C; C311 replaced with D, E, H, K, R, A, G, I, L, S, T, M, V, N, Q, F, W, Y, or P; C312 replaced with D, E, H, K, R, A, G, I, L, S, T, M, V, N, Q, F, W, Y, or P; L313 replaced with D, E, H, K, R, N, Q, F, W, Y, P, or C; N314 replaced with D, E, H, K, R, A, G, I, L, S, T, M, V, F, W, Y, P, or C; P315 replaced with D, E, H, K, R, A, G, I, L, S, T, M, V, N, Q, F, W, Y, or C; L316 replaced with D, E, H, K, R, N, Q, F, W, Y, P, or C; L317 replaced with D, E, H, K, R, N, Q, F, W, Y, P, or C; Y318 replaced with D, E, H, K, R, N, Q, A, G, I, L, S, T, M, V, P, or C; A319 replaced with D, E, H, K, R, N, Q, F, W, Y, P, or C; F320 replaced with D, E, H, K, R, N, Q, A, G, I, L, S, T, M, V, P, or C; V321 replaced with D, E, H, K, R, N, Q, F, W, Y, P, or C; G322 replaced with D, E, H, K, R, N, Q, F, W, Y, P, or C; V323 replaced with D, E, H, K, R, N, Q, F, W, Y, P, or C; K324 replaced with D, E, A, G, I, L, S, T, M, V, N, Q, F, W, Y, P, or C; F325 replaced with D, E, H, K, R, N, Q, A, G, I, L, S, T, M, V, P, or C; R326 replaced with D, E, A, G, I, L, S, T, M, V, N, Q, F, W, Y, P, or C; E327 replaced with H, K, R, A, G, I, L, S, T, M, V, N, Q, F, W, Y, P, or C; R328 replaced with D, E, A, G, I, L, S, T, M, V, N, Q, F, W, Y, P, or C; M329 replaced with D, E, H, K, R, N, Q, F, W, Y, P, or C; W330 replaced with D, E, H, K, R, N, Q, A, G, I, L, S, T, M, V, P, or C; M331 replaced with D, E, H, K, R, N, Q, F, W, Y, P, or C; L332 replaced with D, E, H, K, R, N, Q, F, W, Y, P, or C; L333 replaced with D, E, H, K, R, N, Q, F, W, Y, P, or C; L334 replaced with D, E, H, K, R, N, Q, F, W, Y, P, or C; R335 replaced with D, E, A, G, I, L, S, T, M, V, N, Q, F, W, Y, P, or C; L336 replaced with D, E, H, K, R, N, Q, F, W, Y, P, or C; G337 replaced with D, E, H, K, R, N, Q, F, W, Y, P, or C; C338 replaced with D, E, H, K, R, A, G, I, L, S, T, M, V, N, Q, F, W, Y, or P; P339 replaced with D, E, H, K, R, A, G, I, L, S, T, M, V, N, Q, F, W, Y, or C; N340 replaced with D, E, H, K, R, A, G, I, L, S, T, M, V, F, W, Y, P, or C; Q341 replaced with D, E, H, K, R, A, G, I, L, S, T, M, V, F, W, Y, P, or C; R342 replaced with D, E, A, G, I, L, S, T, M, V, N, Q, F, W, Y, P, or C; G343 replaced with D, E, H, K, R, N, Q, F, W, Y, P, or C; L344 replaced with D, E, H, K, R, N, Q, F, W, Y, P, or C; Q345 replaced with D, E, H, K, R, A, G, I, L, S, T, M V, F, W, Y, P, or C; R346 replaced with D, E, A, G, I, L, S, T, M, V, N, Q, F, W, Y, P, or C; Q347 replaced with D, E, H, K, R, A, G, I, L, S, T, M, V, F, W, Y, P, or C; P348 replaced with D, E, H, K, R, A, G, I, L, S, T, M, V, N, Q, F, W, Y, or C; S349 replaced with D, E, H, K, R, N, Q, F, W, Y, P, or C; S350 replaced with D, E, H, K, R, N, Q, F, W, Y, P, or C; S351 replaced with D, E, H, K, R, N, Q, F, W, Y, P, or C; R352 replaced with D, E, A, G, I, L, S, T, M, V, N, Q, F, W, Y, P, or C; R353 replaced with D, E, A, G, I, L, S, T, M, V, N, Q, F, W, Y, P, or C; D354 replaced with H, K, R, A, G, I, L, S, T, M, V, N, Q, F, W, Y, P, or C; S355 replaced with D, E, H, K, R, N, Q, F, W, Y, P, or C; S356 replaced with D, E, H, K, R, N, Q, F, W, Y, P, or C; W357 replaced with D, E, H, K, R, N, Q, A, G, I, L, S, T, M, V, P, or C; S358 replaced with D, E, H, K, R, N, Q, F, W, Y, P, or C; E359 replaced with H, K, R, A, G, I, L, S, T, M, V, N, Q, F, W, Y, P, or C; T360 replaced with D, E, H, K, R, N, Q, F, W, Y, P, or C; S361 replaced with D, E, H, K, R, N, Q, F, W, Y, P, or C; E362 replaced with H, K, R, A, G, I, L, S, T, M, V, N, Q, F, W, Y, P, or C; A363 replaced with D, E, H, K, R, N, Q, F, W, Y, P, or C; S364 replaced with D, E, H, K, R, N, Q, F, W, Y, P, or C; Y365 replaced with D, E, H, K, R, N, Q, A, G, I, L, S, T, M, V, P, or C; S366 replaced with D, E, H, K, R, N, Q, F, W, Y, P, or C; G367 replaced with D, E, H, K, R, N, Q, F, W, Y, P, or C; L368 replaced with D, E, H, K, R, N, Q, F, W, Y, P, or C. Polynucleotides encoding these polypeptides are also encompassed by the invention. The resulting G-protein Chemokine Receptor proteins of the invention may be routinely screened for G-protein Chemokine Receptor functional activities and/or physical properties (such as, for example, enhanced or reduced stability and/or solubility) described throughout the specification and known in the art. Preferably, the resulting proteins of the invention have an increased and/or a decreased G-protein Chemokine Receptor functional activity. More preferably, the resulting G-protein Chemokine Receptor proteins of the invention have more than one increased and/or decreased G-protein Chemokine Receptor functional activity and/or physical property.

In another embodiment, the invention provides for polypeptides having amino acid sequences containing non-conservative substitutions of the amino acid sequence provided in SEQ ID NO:2. For example, non-conservative substitutions of the G-protein Chemokine Receptor protein sequence provided in SEQ ID NO:2 include: M1 replaced with D, E, H, K, R, N, Q, F, W, Y, P, or C; E2 replaced with H, K, R, A, G, I, L, S, T, M, V, N, Q, F, W, Y, P, or C; L3 replaced with D, E, H, K, R, N, Q, F, W, Y, P, or C; R4 replaced with D, E, A, G, I, L, S, T, M, V, N, Q, F, W, Y, P, or C; K5 replaced with D, E, A, G, I, L, S, T, M, V, N, Q, F, W, Y, P, or C; Y6 replaced with D, E, H, K, R, N, Q, A, G, I, L, S, T, M, V, P, or C; G7 replaced with D, E, H, K, R, N, Q, F, W, Y, P, or C; P8 replaced with D, E, H, K, R, A, G, I, L, S, T, M, V, N, Q, F, W, Y, or C; G9 replaced with D, E, H, K, R, N, Q, F, W, Y, P, or C; R10 replaced with D, E, A, G, I, L, S, T, M, V, N, Q, F, W, Y, P, or C; L11 replaced with D, E, H, K, R, N, Q, F, W, Y, P, or C; A12 replaced with D, E, H, K, R, N, Q, F, W, Y, P, or C; G13 replaced with D, E, H, K, R, N, Q, F, W, Y, P, or C; T14 replaced with D, E, H, K, R, N, Q, F, W, Y, P, or C; V15 replaced with D, E, H, K, R, N, Q, F, W, Y, P, or C; I16 replaced with D, E, H, K, R, N, Q, F, W, Y, P, or C; G17 replaced with D, E, H, K, R, N, Q, F, W, Y, P, or C; G18 replaced with D, E, H, K, R, N, Q, F, W, Y, P, or C; A19 replaced with D, E, H, K, R, N, Q, F, W, Y, P, or C; A20 replaced with D, E, H, K, R, N, Q, F, W, Y, P, or C; Q21 replaced with D, E, H, K, R, A, G, I, L, S, T, M, V, F, W, Y, P, or C; S22 replaced with D, E, H, K, R, N, Q, F, W, Y, P, or C; K23 replaced with D, E, A, G, I, L, S, T, M, V, N, Q, F, W, Y, P, or C; S24 replaced with D, E, H, K, R, N, Q, F, W, Y, P, or C; Q25 replaced with D, E, H, K, R, A, G, I, L, S, T, M, V, F, W, Y, P, or C; T26 replaced with D, E, H, K, R, N, Q, F, W, Y, P, or C; K27 replaced with D, E, A, G, I, L, S, T, M, V, N, Q, F, W, Y, P, or C; S28 replaced with D, E, H, K, R, N, Q, F, W, Y, P, or C; D29 replaced with H, K, R, A, G, I, L, S, T, M, V, N, Q, F, W, Y, P, or C; S30 replaced with D, E, H, K, R, N, Q, F, W, Y, P, or C; I31 replaced with D, E, H, K, R, N, Q, F, W, Y, P, or C; T32 replaced with D, E, H, K, R, N, Q, F, W, Y, P, or C; K33 replaced with D, E, A, G, I, L, S, T, M, V, N, Q, F, W, Y, P, or C; E34 replaced with H, K, R, A, G, I, L, S, T, M, V, N, Q, F, W, Y, P, or C; F35 replaced with D, E, H, K, R, N, Q, A, G, I, L, S, T, M, V, P, or C; L36 replaced with D, E, H, K, R, N, Q, F, W, Y, P, or C; P37 replaced with D, E, H, K, R, A, G, I, L, S, T, M, V, N, Q, F, W, Y, or C; G38 replaced with D, E, H, K, R, N, Q, F, W, Y, P, or C; L39 replaced with D, E, H, K, R, N, Q, F, W, Y, P, or C; Y40 replaced with D, E, H, K, R, N, Q, A, G, I, L, S, T, M, V, P, or C; T41 replaced with D, E, H, K, R, N, Q, F, W, Y, P, or C; A42 replaced with D, E, H, K, R, N, Q, F, W, Y, P, or C; P43 replaced with D, E, H, K, R, A, G, I, L, S, T, M, V, N, Q, F, W, Y, or C; S44 replaced with D, E, H, K, R, N, Q, F, W, Y, P, or C; S45 replaced with D, E, H, K, R, N, Q, F, W, Y, P, or C; P46 replaced with D, E, H, K, R, A, G, I, L, S, T, M, V, N, Q, F, W, Y, or C; F47 replaced with D, E, H, K, R, N, Q, A, G, I, L, S, T, M, V, P, or C; P48 replaced with D, E, H, K, R, A, G, I, L, S, T, M, V, N, Q, F, W, Y, or C; P49 replaced with D, E, H, K, R, A, G, I, L, S, T, M, V, N, Q, F, W, Y, or C; S50 replaced with D, E, H, K, R, N, Q, F, W, Y, P, or C; Q51 replaced with D, E, H, K, R, A, G, I, L, S, T, M, V, F, W, Y, P, or C; V52 replaced with D, E, H, K, R, N, Q, F, W, Y, P, or C; S53 replaced with D, E, H, K, R, N, Q, F, W, Y, P, or C; D54 replaced with H, K, R, A, G, I, L, S, T, M, V, N, Q, F, W, Y, P, or C; H55 replaced with D, E, A, G, I, L, S, T, M, V, N, Q, F, W, Y, P, or C; Q56 replaced with D, E, H, K, R, A, G, I, L, S, T, M, V, F, W, Y, P, or C; V57 replaced with D, E, H, K, R, N, Q, F, W, Y, P, or C; L58 replaced with D, E, H, K, R, N, Q, F, W, Y, P, or C; N59 replaced with D, E, H, K, R, A, G, I, L, S, T, M, V, F, W, Y, P, or C; D60 replaced with H, K, R, A, G, I, L, S, T, M, V, N, Q, F, W, Y, P, or C; A61 replaced with D, E, H, K, R, N, Q, F, W, Y, P, or C; E62 replaced with H, K, R, A, G, I, L, S, T, M, V, N, Q, F, W, Y, P, or C; V63 replaced with D, E, H, K, R, N, Q, F, W, Y, P, or C; A64 replaced with D, E, H, K, R, N, Q, F, W, Y, P, or C; A65 replaced with D, E, H, K, R, N, Q, F, W, Y, P, or C; L66 replaced with D, E, H, K, R, N, Q, F, W, Y, P, or C; L67 replaced with D, E, H, K, R, N, Q, F, W, Y, P, or C; E68 replaced with H, K, R, A, G, I, L, S, T, M, V, N, Q, F, W, Y, P, or C; N69 replaced with D, E, H, K, R, A, G, I, L, S, T, M, V, F, W, Y, P, or C; F70 replaced with D, E, H, K, R, N, Q, A, G, I, L, S, T, M, V, P, or C; S71 replaced with D, E, H, K, R, N, Q, F, W, Y, P, or C; S72 replaced with D, E, H, K, R, N, Q, F, W, Y, P, or C; S73 replaced with D, E, H, K, R, N, Q, F, W, Y, P, or C; Y74 replaced with D, E, H, K, R, N, Q, A, G, I, L, S, T, M, V, P, or C; D75 replaced with H, K, R, A, G, I, L, S, T, M, V, N, Q, F, W, Y, P, or C; Y76 replaced with D, E, H, K, R, N, Q, A, G, I, L, S, T, M, V, P, or C; G77 replaced with D, E, H, K, R, N, Q, F, W, Y, P, or C; E78 replaced with H, K, R, A, G, I, L, S, T, M, V, N, Q, F, W, Y, P, or C; N79 replaced with D, E, H, K, R, A, G, I, L, S, T, M, V, F, W, Y, P, or C; E80 replaced with H, K, R, A, G, I, L, S, T, M, V, N, Q, F, W, Y, P, or C; S81 replaced with D, E, H, K, R, N, Q, F, W, Y, P, or C; D82 replaced with H, K, R, A, G, I, L, S, T, M, V, N, Q, F, W, Y, P, or C; S83 replaced with D, E, H, K, R, N, Q, F, W, Y, P, or C; C84 replaced with D, E, H, K, R, A, G, I, L, S, T, M, V, N, Q, F, W, Y, or P; C85 replaced with D, E, H, K, R, A, G, I, L, S, T, M, V, N, Q, F, W, Y, or P; T86 replaced with D, E, H, K, R, N, Q, F, W, Y, P, or C; S87 replaced with D, E, H, K, R, N, Q, F, W, Y, P, or C; P88 replaced with D, E, H, K, R, A, G, I, L, S, T, M, V, N, Q, F, W, Y, or C; P89 replaced with D, E, H, K, R, A, G, I, L, S, T, M, V, N, Q, F, W, Y, or C; C90 replaced with D, E, H, K, R, A, G, I, L, S, T, M, V, N, Q, F, W, Y, or P; P91 replaced with D, E, H, K, R, A, G, I, L, S, T, M, V, N, Q, F, W, Y, or C; Q92 replaced with D, E, H, K, R, A, G, I, L, S, T, M, V, F, W, Y, P, or C; D93 replaced with H, K, R, A, G, I, L, S, T, M, V, N, Q, F, W, Y, P, or C; F94 replaced with D, E, H, K, R, N, Q, A, G, I, L, S, T, M, V, P, or C; S95 replaced with D, E, H, K, R, N, Q, F, W, Y, P, or C; L96 replaced with D, E, H, K, R, N, Q, F, W, Y, P, or C; N97 replaced with D, E, H, K, R, A, G, I, L, S, T, M, V, F, W, Y, P, or C; F98 replaced with D, E, H, K, R, N, Q, A, G, I, L, S, T, M, V, P, or.C; D99 replaced with H, K, R, A, G, I, L, S, T, M, V, N, Q, F, W, Y, P, or C; R100 replaced with D, E, A, G, I, L, S, T, M, V, N, Q, F, W, Y, P, or C; A101 replaced with D, E, H, K, R, N, Q, F, W, Y, P, or C; F102 replaced with D, E, H, K, R, N, Q, A, G, I, L, S, T, M, V, P, or C; L103 replaced with D, E, H, K, R, N, Q, F, W, Y, P, or C; P104 replaced with D, E, H, K, R, A, G, I, L, S, T, M, V, N, Q, F, W, Y, or C; A105 replaced with D, E, H, K, R, N, Q, F, W, Y, P, or C; L106 replaced with D, E, H, K, R, N, Q, F, W, Y, P, or C; Y107 replaced with D, E, H, K, R, N, Q, A, G, L, S, T, M, V, P, or C; S108 replaced with D, E, H, K, R, N, Q, F, W, Y, P, or C; L109 replaced with D, E, H, K, R, N, Q, F, W, Y, P, or C; L110 replaced with D, E, H, K, R, N, Q, F, W, Y, P, or C; F111 replaced with D, E, H, K, R, N, Q, A, G, I, L, S, T, M, V, P, or C; L112 replaced with D, E, H, K, R, N, Q, F, W, Y, P, or C; L113 replacedwith D, E, H, K, R, N, Q, F, W, Y, P, or C; G114 replaced with D, E, H, K, R, N, Q, F, W, Y, P, or C; L115 replaced with D, E, H, K, R, N, Q, F, W, Y, P, or C; L116 replaced with D, E, H, K, R, N, Q, F, W, Y, P, or C; G117 replaced with D, E, H, K, R, N, Q, F, W, Y, P, or C; N118 replaced with D, E, H, K, R, A, G, I, L, S, T, M, V, F, W, Y, P, or C; G119 replaced with D, E, H, K, R, N, Q, F, W, Y, P, or C; A120 replaced with D, E, H, K, R, N, Q, F, W, Y, P, or C; V121 replaced with D, E, H, K, R, N, Q, F, W, Y, P, or C; A122 replaced with D, E, H, K, R, N, Q, F, W, Y, P, or C; A123 replaced with D, E, H, K, R, N, Q, F, W, Y, P, or C; V124 replaced with D, E, H, K, R, N, Q, F, W, Y, P, or C; L125 replaced with D, E, H, K, R, N, Q, F, W, Y, P, or C; L126 replaced with D, E, H, K, R, N, Q, F, W, Y, P, or C; S127 replaced with D, E, H, K, R, N, Q, F, W, Y, P, or C; R128 replaced with D, E, A, G, I, L, S, T, M, V, N, Q, F, W, Y, P, or C; R129 replaced with D, E, A, G, I, L, S, T, M, V, N, Q, F, W, Y, P, or C; T130 replaced with D, E, H, K, R, N, Q, F, W, Y, P, or C; A131 replaced with D, E, H, K, R, N, Q, F, W, Y, P, or C; L132 replaced with D, E, H, K, R, N, Q, F, W, Y, P, or C; S133 replaced with D, E, H, K, R, N, Q, F, W, Y, P, or C; S134 replaced with D, E, H, K, R, N, Q, F, W, Y, P, or C; T135 replaced with D, E, H, K, R, N, Q, F, W, Y, P, or C; D136 replaced with H, K, R, A, G, I, L, S, T, M, V, N, Q, F, W, Y, P, or C; T137 replaced with D, E, H, K, R, N, Q, F, W, Y, P, or C; F138 replaced with D, E, H, K, R, N, Q, A, G, I, L, S, T, M, V, P, or C; L139 replaced with D, E, H, K, R, N, Q, F, W, Y, P, or C; L140 replaced with D, E, H, K, R, N, Q, F, W, Y, P, or C;

H141 replaced with D, E, A, G, I, L, S, T, M, V, N, Q, F, W, Y, P, or C; L142 replaced with D, E, H, K, R, N, Q, F, W, Y, P, or C; A143 replaced with D, E, H, K, R, N, Q, F, W, Y, P, or C; V144 replaced with D, E, H, K, R, N, Q, F, W, Y, P, or C; A145 replaced with D, E, H, K, R, N, Q, F, W, Y, P, or C; D146 replaced with H, K, R, A, G, I, L, S, T, M, V, N, Q, F, W, Y, P, or C; T147 replaced with D, E, H, K, R, N, Q, F, W, Y, P, or C; L148 replaced with D, E, H, K, R, N, Q, F, W, Y, P, or C; L149 replaced with D, E, H, K, R, N, Q, F, W, Y, P, or C; V150 replaced with D, E, H, K, R, N, Q, F, W, Y, P, or C; L151 replaced with D, E, H, K, R, N, Q, F, W, Y, P, or C; T152 replaced with D, E, H, K, R, N, Q, F, W, Y, P, or C; L153 replaced with D, E, H, K, R, N, Q, F, W, Y, P, or C; P154 replaced with D, E, H, K, R, A, G, I, L, S, T, M, V, N, Q, F, W, Y, or C; L155 replaced with D, E, H, K, R, N, Q, F, W, Y, P, or C; W156 replaced with D, E, H, K, R, N, Q, A, G, I, L, S, T, M, V, P, or C; A157 replaced with D, E, H, K, R, N, Q, F, W, Y, P, or C; V158 replaced with D, E, H, K, R, N, Q, F, W, Y, P, or C; D159 replaced with H, K, R, A, G, I, L, S, T, M, V, N, Q, F, W, Y, P, or C; A160 replaced with D, E, H, K, R, N, Q, F, W, Y, P, or C; A161 replaced with D, E, H, K, R, N, Q, F, W, Y, P, or C; V162 replaced with D, E, H, K, R, N, Q, F, W, Y, P, or C; Q163 replaced with D, E, H, K, R, A, G, I, L, S, T, M, V, F, W, Y, P, or C; W164 replaced with D, E, H, K, R, N, Q, A, G, I, L, S, T, M, V, P, or C; V165 replaced with D, E, H, K, R, N, Q, F, W, Y, P, or C; F166 replaced with D, E, H, K, R, N, Q, A, G, I, L, S, T, M, V, P, or C; G167 replaced with D, E, H, K, R, N, Q, F, W, Y, P, or C; S168 replaced with D, E, H, K, R, N, Q, F, W, Y, P, or C; G169 replaced with D, E, H, K, R, N, Q, F, W, Y, P, or C; L170 replaced with D, E, H, K, R, N, Q, F, W, Y, P, or C; C171 replaced with D, E, H, K, R, A, G, I, L, S, T, M, V, N, Q, F, W, Y, or P; K172 replaced with D, E, A, G, I, L, S, T, M, V, N, Q, F, W, Y, P, or C; V173 replaced with D, E, H, K, R, N, Q, F, W, Y, P, or C; A174 replaced with D, E, H, K, R, N, Q, F, W, Y, P, or C; G175 replaced with D, E, H, K, R, N, Q, F, W, Y, P, or C; A176 replaced with D, E, H, K, R, N, Q, F, W, Y, P, or C; L177 replaced with D, E, H, K, R, N, Q, F, W, Y, P, or C; F178 replaced with D, E, H, K, R, N, Q, A, G, I, L, S, T, M, V, P, or C; N179 replaced with D, E, H, K, R, A, G, I, L, S, T, M, V, F, W, Y, P, or C; I180 replaced with D, E, H, K, R, N, Q, F, W, Y, P, or C; N181 replaced with D, E, H, K, R, A, G, I, L, S, T, M, V, F, W, Y, P, or C; F182 replaced with D, E, H, K, R, N, Q, A, G, I, L, S, T, M, V, P, or C; Y183 replaced with D, E, H, K, R, N, Q, A, G, I, L, S, T, M, V, P, or C; A184 replaced with D, E, H, K, R, N, Q, F, W, Y, P, or C; G185 replaced with D, E, H, K, R, N, Q, F, W, Y, P, or C; A186 replaced with D, E, H, K, R, N, Q, F, W, Y, P, or C; L187 replaced with D, E, H, K, R, N, Q, F, W, Y, P, or C; L188 replaced with D, E, H, K, R, N, Q, F, W, Y, P, or C; L189 replaced with D, E, H, K, R, N, Q, F, W, Y, P, or C; A190 replaced with D, E, H, K, R, N, Q, F, W, Y, P, or C; C191 replaced with D, E, H, K, R, A, G, I, L, S, T, M, V, N, Q, F, W, Y, or P; I192 replaced with D, E, H, K, R, N, Q, F, W, Y, P, or C; S193 replaced with D, E, H, K, R, N, Q, F, W, Y, P, or C; F194 replaced with D, E, H, K, R, N, Q, A, G, I, L, S, T, M, V, P, or C; D195 replaced with H, K, R, A, G, I, L, S, T, M, V, N, Q, F, W, Y, P, or C; R196 replaced with D, E, A, G, I, L, S, T, M, V, N, Q, F, W, Y, P, or C; Y197 replaced with D, E, H, K, R, N, Q, A, G, I, L, S, T, M, V, P, or C; L198 replaced with D, E, H, K, R, N, Q, F, W, Y, P, or C; N199 replaced with D, E, H, K, R, A, G, I, L, S, T, M, V, F, W, Y, P, or C; I200 replaced with D, E, H, K, R, N, Q, F, W, Y, P, or C; V201 replaced with D, E, H, K, R, N, Q, F, W, Y, P, or C; H202 replaced with D, E, A, G, I, L, S, T, M, V, N, Q, F, W, Y, P, or C; A203 replaced with D, E, H, K, R, N, Q, F, W, Y, P, or C; T204 replaced with D, E, H, K, R, N, Q, F, W, Y, P, or C; Q205 replaced with D, E, H, K, R, A, G, I, L, S, T, M, V, F, W, Y, P, or C; L206 replaced with D, E, H, K, R, N, Q, F, W, Y, P, or C; Y207 replaced with D, E, H, K, R, N, Q, A, G, I, L, S, T, M, V, P, or C; R208 replaced with D, E, A, G, I, L, S, T, M, V, N, Q, F, W, Y, P, or C; R209 replaced with D, E, A, G, I, L, S, T, M, V, N, Q, F, W, Y, P, or C; G210 replaced with D, E, H, K, R, N, Q, F, W, Y, P, or C; P211 replaced with D, E, H, K, R, A, G, I, L, S, T, M, V, N, Q, F, W, Y, or C; P212 replaced with D, E, H, K, R, A, G, I, L, S, T, M, V, N, Q, F, W, Y, or C; A213 replaced with D, E, H, K, R, N, Q, F, W, Y, P, or C; R214 replaced with D, E, A, G, I, L, S, T, M, V, N, Q, F, W, Y, P, or C; V215 replaced with D, E, H, K, R, N, Q, F, W, Y, P, or C; T216 replaced with D, E, H, K, R, N, Q, F, W, Y, P, or C; L217 replaced with D, E, H, K, R, N, Q, F, W, Y, P, or C; T218 replaced with D, E, H, K, R, N, Q, F, W, Y, P, or C; C219 replaced with D, E, H, K, R, A, G, I, L, S, T, M, V, N, Q, F, W, Y, or P; L220 replaced with D, E, H, K, R, N, Q, F, W, Y, P, or C; A221 replaced with D, E, H, K, R, N, Q, F, W, Y, P, or C; V222 replaced with D, E, H, K, R, N, Q, F, W, Y, P, or C; W223 replaced with D, E, H, K, R, N, Q, A, G, I, L, S, T, M, V, P, or C; G224 replaced with D, E, H, K, R, N, Q, F, W, Y, P, or C; L225 replaced with D, E, H, K, R, N, Q, F, W, Y, P, or C; C226 replaced with D, E, H, K, R, A, G, I, L, S, T, M, V, N, Q, F, W, Y, or P; L227 replaced with D, E, H, K, R, N, Q, F, W, Y, P, or C; L228 replaced with D, E, H, K, R, N, Q, F, W, Y, P, or C; F229 replaced with D, E, H, K, R, N, Q, A, G, I, L, S, T, M, V, P, or C; A230 replaced with D, E, H, K, R, N, Q, F, W, Y, P, or C; L231 replaced with D, E, H, K, R, N, Q, F, W, Y, P, or C; P232 replaced with D, E, H, K, R, A, G, I, L, S, T, M, V, N, Q, F, W, Y, or C; D233 replaced with H, K, R, A, G, I, L, S, T, M, V, N, Q, F, W, Y, P, or C; F234 replaced with D, E, H, K, R, N, Q, A, G, I, L, S, T, M, V, P, or C; I235 replaced with D, E, H, K, R, N, Q, F, W, Y, P, or C; F236 replaced with D, E, H, K, R, N, Q, A, G, I, L, S, T, M, V, P, or C; L237 replaced with D, E, H, K, R, N, Q, F, W, Y, P, or C; S238 replaced with D, E, H, K, R, N, Q, F, W, Y, P, or C; A239 replaced with D, E, H, K, R, N, Q, F, W, Y, P, or C; H240 replaced with D, E, A, G, I, L, S, T, M, V, N, Q, F, W, Y, P, or C; H241 replaced with D, E, A, G, I, L, S, T, M, V, N, Q, F, W, Y, P, or C; D242 replaced with H, K, R, A, G, I, L, S, T, M, V, N, Q, F, W, Y, P, or C; E243 replaced with H, K, R, A, G, I, L, S, T, M, V, N, Q, F, W, Y, P, or C; R244 replaced with D, E, A, G, I, L, S, T, M, V, N, Q, F, W, Y, P, or C; L245 replaced with D, E, H, K, R, N, Q, F, W, Y, P, or C; N246 replaced with D, E, H, K, R, A, G, I, L, S, T, M, V, F, W, Y, P, or C; A247 replaced with D, E, H, K, R, N, Q, F, W, Y, P, or C; T248 replaced with D, E, H, K, R, N, Q, F, W, Y, P, or C; H249 replaced with D, E, A, G, I, L, S, T, M, V, N, Q, F, W, Y, P, or C; C250 replaced with D, E, H, K, R, A, G, I, L, S, T, M, V, N, Q, F, W, Y, or P; Q251 replaced with D, E, H, K, R, A, G, I, L, S, T, M, V, F, W, Y, P, or C; Y252 replaced with D, E, H, K, R, N, Q, A, G, I, L, S, T, M, V, P, or C; N253 replaced with D, E, H, K, R, A, G, I, L, S, T, M, V, F, W, Y, P, or C; F254 replaced with D, E, H, K, R, N, Q, A, G, I, L, S, T, M, V, P, or C; P255 replaced with D, E, H, K, R, A, G, I, L, S, T, M, V, N, Q, F, W, Y, or C; Q256 replaced with D, E, H, K, R, A, G, I, L, S, T, M, V, F, W, Y, P, or C; V257 replaced with D, E, H, K, R, N, Q, F, W, Y, P, or C; G258 replaced with D, E, H, K, R, N, Q, F, W, Y, P, or C; R259 replaced with D, E, A, G, I, L, S, T, M, V, N, Q, F, W, Y, P, or C; T260 replaced with D, E, H, K, R, N, Q, F, W, Y, P, or C; A261 replaced with D, E, H, K, R, N, Q, F, W, Y, P, or C; L262 replaced with D, E, H, K, R, N, Q, F, W, Y, P, or C; R263 replaced with D, E, A, G, I, L, S, T, M, V, N, Q, F, W, Y, P, or C; V264 replaced with D, E, H, K, R, N, Q, F, W, Y, P, or C; L265 replaced with D, E, H, K, R, N, Q, F, W, Y, P, or C; Q266 replaced with D, E, H, K, R, A, G, I, L, S, T, M, V, F, W, Y, P, or C; L267 replaced with D, E, H, K, R, N, Q, F, W, Y, P, or C; V268 replaced with D, E, H, K, R, N, Q, F, W, Y, P, or C; A269 replaced with D, E, H, K, R, N, Q, F, W, Y, P, or C; G270 replaced with D, E, H, K, R, N, Q, F, W, Y, P, or C; F271 replaced with D, E, H, K, R, N, Q, A, G, I, L, S, T, M, V, P, or C; L272 replaced with D, E, H, K, R, N, Q, F, W, Y, P, or C; L273 replaced with D, E, H, K, R, N, Q, F, W, Y, P, or C; P274 replaced with D, E, H, K, R, A, G, I, L, S, T, M, V, N, Q, F, W, Y, or C; L275 replaced with D, E, H, K, R, N, Q, F, W, Y, P, or C; L276 replaced with D, E, H, K, R, N, Q, F, W, Y, P, or C; V277 replaced with D, E, H, K, R, N, Q, F, W, Y, P, or C; M278 replaced with D, E, H, K, R, N, Q, F, W, Y, P, or C; A279 replaced with D, E, H, K, R, N, Q, F, W, Y, P, or C; Y280 replaced with D, E, H, K, R, N, Q, A, G, I, L, S, T, M, V, P, or C; C281 replaced with D, E, H, K, R, A, G, I, L, S, T, M, V, N, Q, F, W, Y, or P; Y282 replaced with D, E, H, K, R, N, Q, A, G, I, L, S, T, M, V, P, or C; A283 replaced with D, E, H, K, R, N, Q, F, W, Y, P, or C; H284 replaced with D, E, A, G, I, L, S, T, M, V, N, Q, F, W, Y, P, or C; I285 replaced with D, E, H, K, R, N, Q, F, W, Y, P, or C; L286 replaced with D, E, H, K, R, N, Q, F, W, Y, P, or C; A287 replaced with D, E, H, K, R, N, Q, F, W, Y, P, or C; V288 replaced with D, E, H, K, R, N, Q, F, W, Y, P, or C; L289 replaced with D, E, H, K, R, N, Q, F, W, Y, P, or C; L290 replaced with D, E, H, K, R, N, Q, F, W, Y, P, or C; V291 replaced with D, E, H, K, R, N, Q, F, W, Y, P, or C; S292 replaced with D, E, H, K, R, N, Q, F, W, Y, P, or C; R293 replaced with D, E, A, G, I, L, S, T, M, V, N, Q, F, W, Y, P, or C; G294 replaced with D, E, H, K, R, N, Q, F, W, Y, P, or C; Q295 replaced with D, E, H, K, R, A, G, I, L, S, T, M, V, F, W, Y, P, or C; R296 replaced with D, E, A, G, I, L, S, T, M, V, N, Q, F, W, Y, P, or C; R297 replaced with D, E, A, G, I, L, S, T, M, V, N, Q, F, W, Y, P, or C; L298 replaced with D, E, H, K, R, N, Q, F, W, Y, P, or C; R299 replaced with D, E, A, G, I, L, S, T, M, V, N, Q, F, W, Y, P, or C; A300 replaced with D, E, H, K, R, N, Q, F, W, Y, P, or C; M301 replaced with D, E, H, K, R, N, Q, F, W, Y, P, or C; R302 replaced with D, E, A, G, I, L, S, T, M, V, N, Q, F, W, Y, P, or C; L303 replaced with D, E, H, K, R, N, Q, F, W, Y, P, or C; V304 replaced with D, E, H, K, R, N, Q, F, W, Y, P, or C; V305 replaced with D, E, H, K, R, N, Q, F, W, Y, P, or C; V306 replaced with D, E, H, K, R, N, Q, F, W, Y, P, or C; V307 replaced with D, E, H, K, R, N, Q, F, W, Y, P, or C; V308 replaced with D, E, H, K, R, N, Q, F, W, Y, P, or C; V309 replaced with D, E, H, K, R, N, Q, F, W, Y, P, or C; A310 replaced with D, E, H, K, R, N, Q, F, W, Y, P, or C; F311 replaced with D, E, H, K, R, N, Q, A, G, I, L, S, T, M, V, P, or C; A312 replaced with D, E, H, K, R, N, Q, F, W, Y, P, or C; L313 replaced with D, E, H, K, R, N, Q, F, W, Y, P, or C; C314 replaced with D, E, H, K, R, A, G, I, L, S, T, M, V, N, Q, F, W, Y, or P; W315 replaced with D, E, H, K, R, N, Q, A, G, I, L, S, T, M, V, P, or C; T316 replaced with D, E, H, K, R, N, Q, F, W, Y, P, or C; P317 replaced with D, E, H, K, R, A, G, I, L, S, T, M, V, N, Q, F, W, Y, or C; Y318 replaced with D, E, H, K, R, N, Q, A, G, I, L, S, T, M, V, P, or C; H319 replaced with D, E, A, G, I, L, S, T, M, V, N, Q, F, W, Y, P, or C; L320 replaced with D, E, H, K, R, N, Q, F, W, Y, P, or C; V321 replaced with D, E, H, K, R, N, Q, F, W, Y, P, or C; V322 replaced with D, E, H, K, R, N, Q, F, W, Y, P, or C; L323 replaced with D, E, H, K, R, N, Q, F, W, Y, P, or C; V324 replaced with D, E, H, K, R, N, Q, F, W, Y, P, or C; D325 replaced with H, K, R, A, G, I, L, S, T, M, V, N, Q, F, W, Y, P, or C; 1326 replaced with D, E, H, K, R, N, Q, F, W, Y, P, or C; L327 replaced with D, E, H, K, R, N, Q, F, W, Y, P, or C; M328 replaced with D, E, H, K, R, N, Q, F, W, Y, P, or C; D329 replaced with H, K, R, A, G, I, L, S, T, M, V, N, Q, F, W, Y, P, or C; L330 replaced with D, E, H, K, R, N, Q, F, W, Y, P, or C; G331 replaced with D, E, H, K, R, N, Q, F, W, Y, P, or C; A332 replaced with D, E, H, K, R, N, Q, F, W, Y, P, or C; L333 replaced with D, E, H, K, R, N, Q, F, W, Y, P, or C; A334 replaced with D, E, H, K, R, N, Q, F, W, Y, P, or C; R335 replaced with D, E, A, G, I, L, S, T, M, V, N, Q, F, W, Y, P, or C; N336 replaced with D, E, H, K, R, A, G, I, L, S, T, M, V, F, W, Y, P, or C; C337 replaced with D, E, H, K, R, A, G, I, L, S, T, M, V, N, Q, F, W, Y, or P; G338 replaced with D, E, H, K, R, N, Q, F, W, Y, P, or C; R339 replaced with D, E, A, G, I, L, S, T, M, V, N, Q, F, W, Y, P, or C; E340 replaced with H, K, R, A, G, I, L, S, T, M, V, N, Q, F, W, Y, P, or C; S341 replaced with D, E, H, K, R, N, Q, F, W, Y, P, or C; R342 replaced with D, E, A, G, I, L, S, T, M, V, N, Q, F, W, Y, P, or C; V343 replaced with D, E, H, K, R, N, Q, F, W, Y, P, or C; D344 replaced with H, K, R, A, G, I, L, S, T, M, V, N, Q, F, W, Y, P, or C; V345 replaced with D, E, H, K, R, N, Q, F, W, Y, P, or C; A346 replaced with D, E, H, K, R, N, Q, F, W, Y, P, or C; K347 replaced with D, E, A, G, I, L, S, T, M, V, N, Q, F, W, Y, P, or C; S348 replaced with D, E, H, K, R, N, Q, F, W, Y, P, or C; V349 replaced with D, E, H, K, R, N, Q, F, W, Y, P, or C; T350 replaced with D, E, H, K, R, N, Q, F, W, Y, P, or C; S351 replaced with D, E, H, K, R, N, Q, F, W, Y, P, or C; G352 replaced with D, E, H, K, R, N, Q, F, W, Y, P, or C; L353 replaced with D, E, H, K, R, N, Q, F, W, Y, P, or C; G354 replaced with D, E, H, K, R, N, Q, F, W, Y, P, or C; Y355 replaced with D, E, H, K, R, N, Q, A, G, I, L, S, T, M, V, P, or C; M356 replaced with D, E, H, K, R, N, Q, F, W, Y, P, or C; H357 replaced with D, E, A, G, I, L, S, T, M, V, N, Q, F, W, Y, P, or C; C358 replaced with D, E, H, K, R, A, G, I, L, S, T, M, V, N, Q, F, W, Y, or P; C359 replaced with D, E, H, K, R, A, G, I, L, S, T, M, V, N, Q, F, W, Y, or P; L360 replaced with D, E, H, K, R, N, Q, F, W, Y, P, or C; N361 replaced with D, E, H, K, R, A, G, I, L, S, T, M, V, F, W, Y, P, or C; P362 replaced with D, E, H, K, R, A, G, I, L, S, T, M, V, N, Q, F, W, Y, or C; L363 replaced with D, E, H, K, R, N, Q, F, W, Y, P, or C; L364 replaced with D, E, H, K, R, N, Q, F, W, Y, P, or C; Y365 replaced with D, E, H, K, R, N, Q, A, G, I, L, S, T, M, V, P, or C; A366 replaced with D, E, H, K, R, N, Q, F, W, Y, P, or C; F367 replaced with D, E, H, K, R, N, Q, A, G, I, L, S, T, M, V, P, or C; V368 replaced with D, E, H, K, R, N, Q, F, W, Y, P, or C; G369 replaced with D, E, H, K, R, N, Q, F, W, Y, P, or C; V370 replaced with D, E, H, K, R, N, Q, F, W, Y, P, or C; K371 replaced with D, E, A, G, I, L, S, T, M, V, N, Q, F, W, Y, P, or C; F372 replaced with D, E, H, K, R, N, Q, A, G, I, L, S, T, M, V, P, or C; R373 replaced with D, E, A, G, I, L, S, T, M, V, N, Q, F, W, Y, P, or C; E374 replaced with H, K, R, A, G, I, L, S, T, M, V, N, Q, F, W, Y, P, or C; R375 replaced with D, E, A, G, I, L, S, T, M, V, N, Q, F, W, Y, P, or C; M376 replaced with D, E, H, K, R, N, Q, F, W, Y, P, or C; W377 replaced with D, E, H, K, R, N, Q, A, G, I, L, S, T, M, V, P, or C; M378 replaced with D, E, H, K, R, N, Q, F, W, Y, P, or C; L379 replaced with D, E, H, K, R, N, Q, F, W, Y, P, or C; L380 replaced with D, E, H, K, R, N, Q, F, W, Y, P, or C; L381 replaced with D, E, H, K, R, N, Q, F, W, Y, P, or C; R382 replaced with D, E, A, G, I, L, S, T, M, V, N, Q, F, W, Y, P, or C; L383 replaced with D, E, H, K, R, N, Q, F, W, Y, P, or C; G384 replaced with D, E, H, K, R, N, Q, F, W, Y, P, or C; C385 replaced with D, E, H, K, R, A, G, I, L, S, T, M, V, N, Q, F, W, Y, or P; P386 replaced with D, E, H, K, R, A, G, I, L, S, T, M, V, N, Q, F, W, Y, or C; N387 replaced with D, E, H, K, R, A, G, I, L, S, T, M, V, F, W, Y, P, or C; Q388 replaced with D, E, H, K, R, A, G, I, L, S, T, M, V, F, W, Y, P, or C; R389 replaced with D, E, A, G, I, L, S, T, M, V, N, Q, F, W, Y, P, or C; G390 replaced with D, E, H, K, R, N, Q, F, W, Y, P, or C; L391 replaced with D, E, H, K, R, N, Q, F, W, Y, P, or C; Q392 replaced with D, E, H, K, R, A, G, I, L, S, T, M, V, F, W, Y, P, or C; R393 replaced with D, E, A, G, I, L, S, T, M, V, N, Q, F, W, Y, P, or C; Q394 replaced with D, E, H, K, R, A, G, I, L, S, T, M, V, F, W, Y, P, or C; P395 replaced with D, E H, K, R, A, G, I, L, S, T, M, V, N, Q, F, W, Y, or C; S396 replaced with D, E, H, K, R, N, Q, F, W, Y, P, or C; S397 replaced with D, E, H, K, R, N, Q, F, W, Y, P, or C; S398 replaced with D, E, H, K, R, N, Q, F, W, Y, P, or C; R399 replaced with D, E, A, G, I, L, S, T, M, V, N, Q, F, W, Y, P, or C; R400 replaced with D, E, A, G, I, L, S, T, M, V, N, Q, F, W, Y, P, or C; D401 replaced with H, K, R, A, G, I, L, S, T, M, V, N, Q, F, W, Y, P, or C; S402 replaced with D, E, H, K, R, N, Q, F, W, Y, P, or C; S403 replaced with D, E, H, K, R, N, Q, F, W, Y, P, or C; W404 replaced with D, E, H, K, R, N, Q, A, G, I, L, S, T, M, V, P, or C; S405 replaced with D, E, H, K, R, N, Q, F, W, Y, P, or C; E406 replaced with H, K, R, A, G, I, L, S, T, M, V, N, Q, F, W, Y, P, or C; T407 replaced with D, E, H, K, R, N, Q, F, W, Y, P, or C; S408 replaced with D, E, H, K, R, N, Q, F, W, Y, P, or C; E409 replaced with H, K, R, A, G, I, L, S, T, M, V, N, Q, F, W, Y, P, or C; A410 replaced with D, E, H, K, R, N, Q, F, W, Y, P, or C; S411 replaced with D, E, H, K, R, N, Q, F, W, Y, P, or C; Y412 replaced with D, E, H, K, R, N, Q, A, G, I, L, S, T, M, V, P, or C; S413 replaced with D, E, H, K, R, N, Q, F, W, Y, P, or C; G414 replaced with D, E, H, K, R, N, Q, F, W, Y, P, or C; L415 replaced with D, E, H, K, R, N, Q, F, W, Y, P, or C. Polynucleotides encoding these polypeptides are also encompassed by the invention. The resulting G-protein Chemokine Receptor proteins of the invention may be routinely screened for G-protein Chemokine Receptor functional activities and/or physical properties (such as, for example, enhanced or reduced stability and/or solubility) described throughout the specification and known in the art. Preferably, the resulting proteins of the invention have an increased and/or a decreased G-protein Chemokine Receptor functional activity. More preferably, the resulting G-protein Chemokine Receptor proteins of the invention have more than one increased and/or decreased G-protein Chemokine Receptor functional activity and/or physical property.

To improve or alter the characteristics of G-protein Chemokine Receptor polypeptides, protein engineering may be employed. Recombinant DNA technology known to those skilled in the art can be used to create novel mutant proteins or "muteins including single or multiple amino acid substitutions, deletions, additions or fusion proteins. Such modified polypeptides can show, e.g., enhanced activity or increased stability. In addition, they may be purified in higher yields and show better solubility than the corresponding natural polypeptide, at least under certain purification and storage conditions.

Non-naturally occurring variants may be produced using art-known mutagenesis techniques, which include, but are not limited to oligonucleotide mediated mutagenesis, alanine scanning, PCR mutagenesis, site directed mutagenesis (see e.g., Carter et al., *Nucl. Acids Res.* 13:4331 (1986); and Zoller et al., *Nucl. Acids Res.* 10:6487 (1982)), cassette mutagenesis (see e.g., Wells et al., *Gene* 34:315 (1985)), restriction selection mutagenesis (see e.g., Wells et al., *Philos. Trans. R. Soc. London SerA* 317:415 (1986)).

Thus, the invention also encompasses G-protein Chemokine Receptor derivatives and analogs that have one or more amino acid residues deleted, added, or substituted to generate G-protein Chemokine Receptor polypeptides that are better suited for expression, scale up, etc., in the host cells chosen. For example, cysteine residues can be deleted or substituted with another amino acid residue in order to eliminate disulfide bridges; N-linked glycosylation sites can be altered or eliminated to achieve, for example, expression of a homogeneous product that is more easily recovered and purified from yeast hosts which are known to hyperglycosylate N-linked sites. To this end, a variety of amino acid substitutions at one or both of the first or third amino acid positions on any one or more of the glycosylation recognitions sequences in the G-protein Chemokine Receptor polypeptides of the invention, and/or an amino acid deletion at the second position of any one or more such recognition sequences will prevent glycosylation of the G-protein Chemokine Receptor at the modified tripeptide sequence (see, e.g., Miyajimo et al., *EMBO J* 5(6):1193-1197). Additionally, one or more of the amino acid residues of the polypeptides of the invention (e.g., arginine and lysine residues) may be deleted or substituted with another residue to eliminate undesired processing by proteases such as, for example, furins or kexins.

The polypeptides of the present invention include a polypeptide comprising, or alternatively, consisting of a polypeptide comprising, or alternatively, consisting of amino acids from about 1 to about 415 in FIG. 1 (SEQ ID NO:2); more preferably a polypeptide comprising, or alternatively, consisting of amino acids from about 1 to about 368 in FIG. 2 (SEQ ID NO:4); more preferably a polypeptide comprising, or alternatively, consisting of the G-protein Chemokine Receptor extracellular domain (e.g. amino acid residues from 1 to 59, 114 to 127, 191 to 223, and/or 278 to 307 in SEQ ID NO: 4); a polypeptide comprising, or alternatively, consisting of the G-protein Chemokine Receptor amino terminus; a polypeptide comprising, or alternatively, consisting of the G-protein Chemokine Receptor transmembrane domain (e.g. amino acid residues from 60 to 79, 92 to 113, 128 to 147, 170 to 190, 224 to 245, 259 to 277, and/or 302 to 322 in SEQ ID NO: 4); a polypeptide comprising, or alternatively, consisting of a intracellular domain of G-protein Chemokine Receptor (e.g. amino acid residues from 80 to 91, 148 to 169, 246 to 258, and/or 323 to 368 in SEQ ID NO:4); a polypeptide encoded by the nucleotide sequence of the cDNA clone contained in the deposit having ATCC Accession No. 97768; and a polypeptide comprising, or alternatively, consisting of the G-protein Chemokine Receptor extracellular domain and one of the G-protein Chemokine Receptor intracellular domains with all or part of the transmembrane domain deleted; as well as polypeptides which are at least 80% identical, more preferably at least 90% or 95% identical, still more preferably at least 96%, 97%, 98%, 99% or 100% identical to the polypeptides described above (e.g., the polypeptide of FIG. 2 (SEQ ID NO:4)), and also include portions of such polypeptides with at least 30 amino acids and more preferably at least 50 or at least 100 amino acids. Polynucleotides encoding these polypeptides are also encompassed by the invention.

By a polypeptide having an amino acid sequence at least, for example, 95% "identical" to a reference amino acid sequence of a G-protein Chemokine Receptor polypeptide is intended that the amino acid sequence of the polypeptide is identical to the reference sequence except that the polypeptide sequence may include up to five amino acid alterations per each 100 amino acids of the reference amino acid of the G-protein Chemokine Receptor receptor. In other words, to obtain a polypeptide having an amino acid sequence at least 95% identical to a reference amino acid sequence, up to 5% of the amino acid residues in the reference sequence may be deleted or substituted with another amino acid, or a number of amino acids up to 5% of the total amino acid residues in the reference sequence may be inserted into the reference sequence. These alterations of the reference sequence may occur at the amino or carboxy terminal positions of the reference amino acid sequence or anywhere between those terminal positions, interspersed either individually among residues in the reference sequence or in one or more contiguous groups within the reference sequence.

As a practical matter, whether any particular polypeptide is at least 90%, 95%, 96%, 97%, 98%, or 99% identical to, for instance, the amino acid sequence shown in FIG. 1 (SEQ ID NO:2) or FIG. 2 (SEQ ID NO:4), can be determined conventionally using known computer programs such the Bestfit program (Wisconsin Sequence Analysis Package, Version 8 for Unix, Genetics Computer Group, University Research Park, 575 Science Drive, Madison, Wis. 53711). When using Bestfit or any other sequence alignment program to determine whether a particular sequence is, for instance, 95% identical to a reference sequence according to the present invention, the parameters are set, of course, such that the percentage of identity is calculated over the full length of the reference amino acid sequence and that gaps in homology of up to 5% of the total number of amino acid residues in the reference sequence are allowed.

In a specific embodiment, the identity between a reference (query) sequence (a sequence of the present invention) and a subject sequence, also referred to as a global sequence alignment, is determined using the FASTDB computer program based on the algorithm of Brutlag et al. (*Comp. App. Biosci.* 6:237-245 (1990)). Preferred parameters used in a FASTDB amino acid alignment are: Matrix=PAM 0, k-tuple=2, Mismatch Penalty=1, Joining Penalty=20, Randomization Group Length=0, Cutoff Score=1, Window Size=sequence length, Gap Penalty=5, Gap Size Penalty=0.05, Window Size=500 or the length of the subject amino acid sequence, whichever is shorter. According to this embodiment, if the subject sequence is shorter than the query sequence due to N- or C-terminal deletions, not because of internal deletions, a manual correction is made to the results to take into consideration the fact that the FASTDB program does not account for N- and C-terminal truncations of the subject sequence when calculating global percent identity. For subject sequences truncated at the N- and C-termini, relative to the query sequence, the percent identity is corrected by calculating the number of residues of the query sequence that are N- and C-terminal of the subject sequence, which are not matched/aligned with a corresponding subject residue, as a percent of the total bases of the query sequence. A determination of whether a residue is matched/aligned is determined by results of the FASTDB sequence alignment. This percentage is then subtracted from the percent identity, calculated by the above FASTDB program using the specified parameters, to arrive at a final percent identity score. This final percent identity score is what is used for the purposes of this embodiment. Only residues to the N- and C-termini of the subject sequence, which are not matched/aligned with the query sequence, are considered for the purposes of manually adjusting the percent identity score. That is, only query residue positions outside the farthest N- and C-terminal residues of the subject sequence. For example, a 90 amino acid residue subject sequence is aligned with a 100 residue query sequence to determine percent identity. The deletion occurs at the N-terminus of the subject sequence and therefore, the FASTDB alignment does not show a matching/alignment of the first 10 residues at the N-terminus. The 10 unpaired residues represent 10% of the sequence (number of residues at the N- and C-termini not matched/total number of residues in the query sequence) so 10% is subtracted from the percent identity score calculated by the FASTDB program. If the remaining 90 residues were perfectly matched the final percent identity would be 90%. In another example, a 90 residue subject sequence is compared with a 100 residue query sequence. This time the deletions are internal deletions so there are no residues at the N- or C-termini of the subject sequence that are not matched/aligned with the query. In this case the percent identity calculated by FASTDB is not manually corrected. Once again, only residue positions outside the N- and C-terminal ends of the subject sequence, as displayed in the FASTDB alignment, which are not matched/aligned with the query sequence are manually corrected for. No other manual corrections are made for the purposes of this embodiment.

The present application is also directed to proteins cotaining polypeptides at least 90%, 95%, 96%, 97%, 98% or 99% identical to the G-protein Chemokine Receptor polypeptide sequence set forth as $n^1$-$m^1$, and/or $n^2$-$m^2$ herein. In preferred embodiments, the application is directed to proteins containing polypeptides at least 90%, 95%, 96%, 97%, 98% or 99% identical to polypeptides having the amino acid sequence of the specific G-protein Chemokine Receptor N- and C-terminal deletions recited herein. Polynucleotides encoding these polypeptides are also encompassed by the invention.

In certain preferred embodiments, G-protein Chemokine Receptor proteins of the invention comprise fusion proteins as described above wherein the G-protein Chemokine Receptor polypeptides are those described as $n^1$-$m^1$, and/or $n^2$-$m^2$ herein. In preferred embodiments, the application is directed to nucleic acid molecules at least 90%, 95%, 96%, 97%, 98% or 99% identical to the nucleic acid sequences encoding polypeptides having the amino acid sequence of the specific N- and C-terminal deletions recited herein. Polynucleotides encoding these polypeptides are also encompassed by the invention.

Epitopes and Antibodies

The polypeptides, their fragments or other derivatives, or analogs thereof, or cells expressing them can be used as an immunogen to produce antibodies thereto. These antibodies can be, for example, polyclonal or monoclonal antibodies. The present invention also includes chimeric, single chain, and humanized antibodies, as well as Fab fragments, or the product of a Fab expression library. Various procedures known in the art may be used for the production of such antibodies and fragments.

Antibodies generated against the polypeptides corresponding to a sequence of the present invention can be obtained by direct injection of the polypeptides into an animal or by administering the polypeptides to an animal, preferably a nonhuman. The antibody so obtained will then bind the polypeptides itself. In this manner, even a sequence encoding only a fragment of the polypeptides can be used to generate antibodies binding the whole native polypeptides. Such antibodies can then be used to isolate the polypeptide from tissue expressing that polypeptide.

For preparation of monoclonal antibodies, any technique that provides antibodies produced by continuous cell line cultures can be used. Examples include the hybridoma technique (Kohler and Milstein, 1975, Nature, 256:495-497), the trioma technique, the human B-cell hybridoma technique (Kozbor et al., 1983, Immunology Today 4:72), and the EBV-hybridoma technique to produce human monoclonal antibodies (Cole, et al., 1985, in Monoclonal Antibodies and Cancer Therapy, Alan R. Liss, Inc., pp. 77-96).

Techniques described for the production of single chain antibodies (U.S. Pat. No. 4,946,778) can be adapted to produce single chain antibodies to immunogenic polypeptide products of this invention. Also, transgenic mice may be used to express humanized antibodies to immunogenic polypeptide products of this invention.

The above-described antibodies may be employed to isolate the polypeptide of the present invention by attachment of the antibody to a solid support and performing affinity chromatography by passing the polypeptide desired to be purified over the column and recovering the purified polypeptide.

The present invention encompasses polypeptides comprising, or alternatively consisting of, an epitope of the polypeptide having an amino acid sequence of SEQ ID NO:2 or more preferably SEQ ID NO:4, or an epitope of the polypeptide sequence encoded by a polynucleotide sequence contained in ATCC Deposit No. 97334, or encoded by a polynucleotide that hybridizes to the complement of the sequence of SEQ ID NO:1 or more preferably SEQ ID NO:3, or contained in ATCC Deposit No. 97334, under stringent hybridization conditions or lower stringency hybridization conditions as defined supra. The present invention further encompasses polynucleotide sequences encoding an epitope of a polypeptide sequence of the invention (such as, for example, the sequence disclosed in SEQ ID NO:1 or more preferably SEQ ID NO:3), polynucleotide sequences of the complementary strand of a polynucleotide sequence encoding an epitope of the invention, and polynucleotide sequences which hybridize to the complementary strand under stringent hybridization conditions or lower stringency hybridization conditions defined supra.

The term "epitopes," as used herein, refers to portions of a polypeptide having antigenic or immunogenic activity in an animal, preferably a mammal, and most preferably in a human. In a preferred embodiment, the present invention encompasses a polypeptide comprising an epitope, as well as the polynucleotide encoding this polypeptide. An "immunogenic epitope," as used herein, is defined as a portion of a protein that elicits an antibody response in an animal, as determined by any method known in the art, for example, by the methods for generating antibodies described infra. (See, for example, Geysen et al, , Proc. Natl. Acad. Sci. USA 81:3998-4002 (1983)). The term "antigenic epitope," as used herein, is defined as a portion of a protein to which an antibody can specifically bind its antigen as determined by any method well known in the art, for example, by the immunoassays described herein. Specific binding excludes non-specific binding but does not necessarily exclude cross-reactivity with other antigens. Antigenic epitopes need not necessarily be immunogenic. Regions having a high antigenicity index are shown in Table I, Table II, FIG. 5, and FIG. 6. Either the full-length protein or a peptide fragment can be used to immunize an animal.

Antibodies are preferably prepared against these regions or from discrete fragments in these regions. However, antibodies can be prepared against any region of the peptide as described herein. A preferred fragment produces an antibody that diminishes or completely prevents ligand binding. Antibodies can be developed against the entire receptor or portions of the receptor, for example, any of the extracellular loops (e.g. amino acid residues from 1 to 59, 114 to 127, 191 to 223, and/or 278 to 307 in SEQ ID NO:4), or any portions of these regions. Antibodies may also be developed against specific functional sites, such as the site of ligand binding, the site of G-protein coupling, or sites that are glycosylated, phosphorylated, myristoylated, or amidated.

Fragments which function as epitopes may be produced by any conventional means. (See, e.g., Houghten, Proc. Natl. Acad. Sci. USA 82:5131-5135 (1985), further described in U.S. Pat. No. 4,631,211).

In the present invention, antigenic epitopes preferably contain a sequence of at least 4, at least 5, at least 6, at least 7, more preferably at least 8, at least 9, at least 10, at least 11, at least 12, at least 13, at least 14, at least 15, at least 20, at least 25, at least 30, at least 40, at least 50, and, most preferably, between about 15 to about 30 amino acids. Preferred polypeptides comprising immunogenic or antigenic epitopes are at least 10, 15, 20, 25, 30, 35, 40, 45, 50, 55, 60, 65, 70, 75, 80, 85, 90, 95, or 100 amino acid residues in length. Additional non-exclusive preferred antigenic epitopes include the antigenic epitopes disclosed herein, as well as portions thereof. Antigenic epitopes are useful, for example, to raise antibodies, including monoclonal antibodies, which specifically bind the epitope. Preferred antigenic epitopes include the antigenic epitopes disclosed herein, as well as any combination of two, three, four, five or more of these antigenic epitopes. Antigenic epitopes can be used as the target molecules in immunoassays. (See, for instance, Wilson et al., Cell 37:767-778 (1984); Sutcliffe et al., Science 219:660-666 (1983)).

Similarly, immunogenic epitopes can be used, for example, to induce antibodies according to methods well known in the art. (See, for instance, Sutcliffe et al., supra; Wilson et al., supra; Chow et al., Proc. Natl. Acad. Sci. USA 82:910-914; and Bittle et al., J. Gen. Virol. 66:2347-2354 (1985). Preferred immunogenic epitopes include the immunogenic epitopes disclosed herein, as well as any combination of two, three, four, five or more of these immunogenic epitopes. The polypeptides comprising one or more immunogenic epitopes may be presented for eliciting an antibody response together with a carrier protein, such as an albumin, to an animal system (such as rabbit or mouse), or, if the polypeptide is of sufficient length (at least about 25 amino acids), the polypeptide may be presented without a carrier. However, immunogenic epitopes comprising as few as 8 to 10 amino acids have been shown to be sufficient to raise antibodies capable of binding to, at the very least, linear epitopes in a denatured polypeptide (e.g., in Western blotting).

Epitope-bearing polypeptides of the present invention may be used to induce antibodies according to methods well known in the art including, but not limited to, in vivo immunization, in vitro immunization, and phage display methods. See, e.g., Sutcliffe et al., supra; Wilson et al., supra, and Bittle et al., J. Gen. Virol., 66:2347-2354 (1985). If in vivo immunization is used, animals may be immunized with free peptide; however, anti-peptide antibody titer may be boosted by coupling the peptide to a macromolecular carrier, such as keyhole limpet hemacyanin (KLH) or tetanus toxoid. For instance, peptides containing cysteine residues may be coupled to a carrier using a linker such as maleimidobenzoyl-N-hydroxysuccinimide ester (MBS), while other peptides may be coupled to carriers using a more general linking agent such as glutaraldehyde.

Epitope bearing peptides of the invention may also be synthesized as multiple antigen peptides (MAPs), first described by J. P. Tam in *Proc. Natl. Acad. Sci. USA.* 85:5409, which is incorporated by reference herein in its entirety. MAPs consist of multiple copies of a specific peptide attached to a non-immunogenic lysine core. Map peptides usually contain four or eight copies of the peptide often referred to as MAP-4 or MAP-8 peptides. By way of non-limiting example, MAPs may be synthesized onto a lysine core matrix attached to a polyethylene glycol-polystyrene (PEG-PS) support. The peptide of interest is synthesized onto the lysine residues using 9-fluorenylmethoxycarbonyl (Fmoc) chemistry. For example, Applied Biosystems (Foster City, Calif.) offers MAP resins, such as, for example, the Fmoc Resin 4 Branch and the Fmoc Resin 8 Branch that can be used to synthesize MAPs. Cleavage of MAPs from the resin is performed with standard trifloroacetic acid (TFA)-based cocktails known in the art. Purification of MAPs, except for desalting, is not necessary. MAP peptides may be used as an immunizing vaccine that elicits antibodies that recognize both the MAP and the native protein from which the peptide was derived.

Epitope bearing polypeptides of the invention may be modified, for example, by the addition of amino acids at the amino- and/or carboxy-termini of the peptide. Such modifications may be performed, for example, to alter the conformation of the epitope bearing polypeptide such that the epitope will have a conformation more closely related to the structure of the epitope in the native protein. An example of a modified epitope-bearing polypeptide of the invention is a polypeptide in which one or more cysteine residues have been added to the polypeptide to allow for the formation of a disulfide bond between two cysteines, resulting in a stable loop structure of the epitope bearing polypeptide under non-reducing conditions. Disulfide bonds may form between a cysteine residue added to the polypeptide and a cysteine residue of the naturally occurring epitope, or may form between two cysteines that have both been added to the naturally occurring epitope bearing polypeptide. Additionally, it is possible to modify one or more amino acid residues of the naturally occurring epitope bearing polypeptide by substituting them with cysteines to promote the formation of disulfide bonded loop. structures. Cyclic thioether molecules of synthetic peptides may be routinely generated using techniques known in the art and are described in PCT publication WO 97/46251, incorporated in its entirety by reference herein. Other modifications of epitope-bearing polypeptides contemplated by this invention include biotinylation.

Animals such as rabbits, rats and mice are immunized with either free or carrier-coupled polypeptides, peptides, or MAP peptides, for instance, by intraperitoneal and/or intradermal injection of emulsions containing about 100 µg of peptide or carrier protein and Freund's adjuvant or any other adjuvant known for stimulating an immune response. Several booster injections may be needed, for instance, at intervals of about two weeks, to provide a useful titer of anti-peptide antibody that can be detected, for example, by ELISA assay using free peptide adsorbed to a solid surface. The titer of anti-peptide antibodies in serum from an immunized animal may be increased by selection of anti-peptide antibodies, for instance, by adsorption to the peptide on a solid support and elution of the selected antibodies according to methods well known in the art.

As one of skill in the art will appreciate, and as discussed above, the polypeptides of the present invention comprising an immunogenic or antigenic epitope can be fused to other polypeptide sequences. For example, the polypeptides of the present invention may be fused with the constant domain of immunoglobulins (IgA, IgE, IgG, IgM), or portions thereof (CH1, CH2, CH3, or any combination thereof and portions thereof) or albumin (including but not limited to recombinant human albumin or fragments or variants thereof (see, e.g., U.S. Pat. No. 5,876,969, issued Mar. 2, 1999, EP Patent 0 413 622, and U.S. Pat. No. 5,766,883, issued Jun. 16, 1998, herein incorporated by reference in their entirety)), resulting in chimeric polypeptides. Such fusion proteins may facilitate purification and may increase half-life in vivo. This has been shown for chimeric proteins consisting of the first two domains of the human CD4-polypeptide and various domains of the constant regions of the heavy or light chains of mammalian immunoglobulins. See, e.g., EP 394,827; Traunecker et al., Nature, 331:84-86 (1988). Enhanced delivery of an antigen across the epithelial barrier to the immune system has been demonstrated for antigens (e.g., insulin) conjugated to an FcRn binding partner such as IgG or Fc fragments (see, e.g., PCT Publications WO 96/22024 and WO 99/04813). IgG Fusion proteins that have a disulfide-linked dimeric structure due to the IgG portion disulfide bonds have also been found to be more efficient in binding and neutralizing other molecules than monomeric polypeptides or fragments thereof alone. See, e.g., Fountoulakis et al., J. Biochem., 270:3958-3964 (1995). Nucleic acids encoding the above epitopes can also be recombined with a gene of interest as an epitope tag (e.g., the hemagglutinin ("HA") tag or flag tag) to aid in detection and purification of the expressed polypeptide. For example, a system described by Janknecht et al. allows for the ready purification of non-denatured fusion proteins expressed in human cell lines (Janknecht et al., 1991, Proc. Natl. Acad. Sci. USA 88:8972-897). In this system, the gene of interest is subcloned into a vaccinia recombination plasmid such that the open reading frame of the gene is translationally fused to an amino-terminal tag consisting of six histidine residues. The tag serves as a matrix-binding domain for the fusion protein. Extracts from cells infected with the recombinant vaccinia virus are loaded onto Ni2+ nitriloacetic acid-agarose column and histidine-tagged proteins can be selectively eluted with imidazole-containing buffers.

Additional fusion proteins of the invention may be generated through the techniques of gene-shuffling, motif-shuffling, exon-shuffling, and/or codon-shuffling (collectively referred to as "DNA shuffling"). DNA shuffling may be employed to modulate the activities of polypeptides of the invention, such methods can be used to generate polypeptides with altered activity, as well as agonists and antagonists of the polypeptides. See, generally, U.S. Pat. Nos. 5,605,793; 5,811, 238; 5,830,721; 5,834,252; and 5,837,458, and Patten et al., Curr. Opinion Biotechnol. 8:724-33 (1997); Harayama, Trends Biotechnol. 16(2):76-82 (1998); Hansson, et al., J. Mol. Biol. 287:265-76 (1999); and Lorenzo and Blasco, Biotechniques 24(2):308-13 (1998) (each of these patents and publications are hereby incorporated by reference in its entirety). In one embodiment, alteration of polynucleotides corresponding to SEQ ID NO:1 or SEQ ID NO:3 and the polypeptides encoded by these polynucleotides may be achieved by DNA shuffling. DNA shuffling involves the assembly of two or more DNA segments by homologous or site-specific recombination to generate variation in the polynucleotide sequence. In another embodiment, polynucleotides of the invention, or the encoded polypeptides, may be altered by being subjected to random mutagenesis by error-prone PCR, random nucleotide insertion or other methods prior to recombination. In another embodiment, one or more components, motifs, sections, parts, domains, fragments, etc., of a polynucleotide encoding a polypeptide of the invention may be recombined with one or more components, motifs, sections, parts, domains, fragments, etc. of one or more heterologous molecules.

Antibodies

Further polypeptides of the invention relate to antibodies and T-cell antigen receptors (TCR) which specifically bind a polypeptide, polypeptide fragment, or variant of SEQ ID NO:2, more preferably SEQ ID NO:4, and/or an epitope of the present invention (as determined by immunoassays well known in the art for assaying specific antibody-antigen binding).

The basic antibody structural unit is known to comprise a tetramer. Each tetramer is composed of two identical pairs of polypeptide chains, each pair having one "light" (about 25 kDa) and one "heavy" chain (about 50-70 kDa). The amino-terminal portion of each chain includes a variable region of about 100 to 110 or more amino acids primarily responsible for antigen recognition. The carboxy-terminal portion of each chain defines a constant region primarily responsible for effector function. Human light chains are classified as kappa and lambda light chains. Heavy chains are classified as mu, delta, gamma, alpha, or epsilon, and define the antibody's isotype as IgM, IgD, lgG, IgA, and IgE, respectively. See generally, *Fundamental Immunology* Ch. 7 (Paul, W., ed., 2nd ed. Raven Press, N.Y. (1989)) (incorporated by reference in its entirety for all purposes). The variable regions of each light/heavy chain pair form the antibody-binding site.

Thus, an intact IgG antibody has two binding sites. Except in bifunctional or bispecific antibodies, the two binding sites are the same.

The chains all exhibit the same general structure of relatively conserved framework regions (FR) joined by three hyper variable regions, also called complementarity determining regions or CDRs. The CDRs from the heavy and the light chains of each pair are aligned by the framework regions, enabling binding to a specific epitope. From N-terminal to C-terminal, both light and heavy chains comprise the domains FR1, CDR1, FR2, CDR2, FR3, CDR3 and FR4. The assignment of amino acids to each domain is in accordance with the definitions of Kabat *Sequences of Proteins of Immunological Interest* (National Institutes of Health, Bethesda, Md. (1987 and 1991)), or Chothia & Lesk *J Mol. Biol.* 196: 901-917 (1987); Chothia et al. *Nature* 342:878-883 (1989).

A bispecific or bifunctional antibody is an artificial hybrid antibody having two different heavy/light chain pairs and two different binding sites. Bispecific antibodies can be produced by a variety of methods including fusion of hybridomas or linking of Fab' fragments. See, e.g., Songsivilai & Lachmann *Clin. Exp. Immunol.* 79: 315-321 (1990), Kostelny et al. *J Immunol.* 148:1547 1553 (1992). In addition, bispecific antibodies may be formed as "diabodies" (Holliger et al. "Diabodies': small bivalent and bispecific antibody fragments" PNAS USA 90:6444-6448 (1993)) or "Janusins" (Traunecker et al. "Bispecific single chain molecules (Janusins) target cytotoxic lymphocytes on HIV infected cells" *EMBO J* 10:3655-3659 (1991) and Traunecker et al. "Janusin: new molecular design for bispecific reagents" *Int J Cancer Suppl* 7:51-52 (1992)).

Antibodies of the invention include, but are not limited to, polyclonal, monoclonal, multispecific, human, humanized or chimeric antibodies, single chain antibodies, Fab fragments, F(ab') fragments, fragments produced by a Fab expression library, anti-idiotypic (anti-Id) antibodies (including, e.g., anti-Id antibodies to antibodies of the invention), intracellularly-made antibodies (i.e., intrabodies), and epitope-binding fragments of any of the above. The term "antibody," as used herein, refers to immunoglobulin molecules and immunologically active portions of immunoglobulin molecules, i.e., molecules that contain an antigen-binding site that specifically binds an antigen. The immunoglobulin molecules of the invention can be of any type (e.g., IgG, IgE, IgM, IgD, IgA and IgY), class (e.g., IgG1, IgG2, IgG3, IgG4, IgA1 and IgA2) or subclass of immunoglobulin molecule. In a preferred embodiment, the immunoglobulin is an IgG1 isotype. In another preferred embodiment, the immunoglobulin is an IgG2 isotype. In another preferred embodiment, the immunoglobulin is an IgG4 isotype. Immunoglobulins may have both a heavy and light chain. An array of IgG, IgE, IgM, IgD, IgA, and IgY heavy chains may be paired with a light chain of the kappa or lambda forms.

Most preferably the antibodies are human antigen-binding antibody fragments of the present invention and include, but are not limited to, Fab, Fab' and F(ab')2, Fd, single-chain Fvs (scFv), single-chain antibodies, disulfide-linked Fvs (sdFv) and fragments comprising either a VL or VH domain. Antigen-binding antibody fragments, including single-chain antibodies, may comprise the variable region(s) alone or in combination with the entirety or a portion of the following: hinge region, CH1, CH2, and CH3 domains. Also included in the invention are antigen-binding fragments also comprising any combination of variable region(s) with a hinge region, CH1, CH2, and CH3 domains. The antibodies of the invention may be from any animal origin including birds and mammals. Preferably, the antibodies are human, murine (e.g., mouse and rat), donkey, ship rabbit, goat, guinea pig, camel, horse, or chicken. As used herein, "human" antibodies include antibodies having the amino acid sequence of a human immunoglobulin and include antibodies isolated from human immunoglobulin libraries or from animals transgenic for one or more human immunoglobulin and that do not express endogenous immunoglobulins, as described infra and, for example in, U.S. Pat. No. 5,939,598 by Kucherlapati et al.

The antibodies of the present invention may be monospecific, bispecific, trispecific or of greater multispecificity. Multispecific antibodies may be specific for different epitopes of a polypeptide of the present invention or may be specific for both a polypeptide of the present invention as well as for a heterologous epitope; such as a heterologous polypeptide or solid support material. See, e.g., PCT publications WO 93/17715; WO 92/08802; WO 91/00360; WO 92/05793; Tutt, et al., J. Immunol. 147:60-69 (1991); U.S. Pat. Nos. 4,474,893; 4,714,681; 4,925,648; 5,573,920; 5,601,819; Kostelny et al., J. Immunol. 148:1547-1553 (1992).

Antibodies of the present invention may be described or specified in terms of the epitope(s) or portion(s) of a polypeptide of the present invention that they recognize or specifically bind. The epitope(s) or polypeptide portion(s) may be specified as described herein, e.g., by N-terminal and C-terminal positions, by size in contiguous amino acid residues, or listed in the Tables and Figures. Preferred epitopes of the invention include: Lys4-Gly8, Gln25-Ile31, Gln51-Asp54, Asp75-Cys85, Ser127-Ala131, Arg208-Ala213, Asn336-Ser341, Cys385-Arg389, Gln394-Ser405 of SEQ ID NO:2, as well as polynucleotides that encode these epitopes. More preferred epitopes of the invention include: Asp28-Cys38, Ser80-Ala84, Arg161-Ala166, Asn289-Ser294, Cys338-Arg342, Gln347-Ser358 of SEQ ID NO:4, as well as polynucleotides that encode these epitopes. Even more preferred epitopes of the invention include peptides corresponding the extracellular loops of the G-protein Chemokine receptor of the invention or fragments and variants thereof, e.g. amino acid residues from 1 to 59, 114 to 127, 191 to 223, and/or 278 to 307 in SEQ ID NO:4). Antibodies that specifically bind any epitope or polypeptide of the present invention may also be excluded. Therefore, the present invention includes antibodies that specifically bind polypeptides of the present invention, and allows for the exclusion of the same.

Antibodies of the present invention may also be described or specified in terms of their cross-reactivity. Antibodies that do not bind any other analog, ortholog, or homolog of a polypeptide of the present invention are included. Antibodies that bind polypeptides with at least 95%, at least 90%, at least 85%, at least 80%, at least 75%, at least 70%, at least 65%, at least 60%, at least 55%, and at least 50% identity (as calculated using methods known in the art and described herein) to a polypeptide of the present invention are also included in the present invention. In specific embodiments, antibodies of the present invention cross-react with murine, monkey, rat and/or rabbit homologs of human proteins and the corresponding epitopes thereof. Antibodies that do not bind polypeptides with less than 95%, less than 90%, less than 85%, less than 80%, less than 75%, less than 70%, less than 65%, less than 60%, less than 55%, and less than 50% identity (as calculated using methods known in the art and described herein) to a polypeptide of the present invention are also included in the present invention. In a specific embodiment, the above-described cross-reactivity is with respect to any single specific antigenic or immunogenic polypeptide, or combination(s) of 2, 3, 4, 5, or more of the specific antigenic and/or immunogenic polypeptides disclosed herein. Further included in the present invention are antibodies that bind polypeptides encoded by polynucleotides that hybridize to a polynucleotide of the present invention under stringent hybridization conditions (as described herein).

The antibodies of the invention (including molecules comprising, or alternatively consisting of, antibody fragments or variants thereof) may bind specifically to that specifically bind to a polypeptide or polypeptide fragment or variant of a human G-protein chemokine receptor (SEQ ID NO:2 or more preferably SEQ ID NO:4) and/or monkey G-protein chemokine receptor. Preferably, preferably the antibodies of the invention bind specifically to a human G-protein chemokine receptor. Preferably, the antibodies of the invention bind specifically to a human and monkey G-protein chemokine receptor. Also preferably, the antibodies of the invention bind specifically to a human G-protein chemokine receptor and a murine G-protein chemokine receptor. More preferably, antibodies of the invention, bind specifically and with higher affinity to a human G-protein chemokine receptor than to a murine G-protein chemokine receptor.

In preferred embodiments, the antibodies of the present invention (including molecules comprising, or alternatively consisting of, antibody fragments or variants thereof), specifically bind to a G-protein chemokine receptor and do not cross-react with any other antigens. In preferred embodiments, the antibodies of the invention specifically bind to G-protein chemokine receptor and do not cross-react with other chemokine receptors such as, for example, US28, CCR1, CCR2, CCR3, CCR4, CCR5, CCR6, CCR7, CCR8, CCR9, CXCR1, CXCR2, CXCR4, and/or CXCR5.

In other preferred embodiments, the antibodies of the invention specifically bind to a G-protein chemokine receptor and cross-react with other chemokine receptors such as, for example, US28, CCR1, CCR2, CCR3, CCR4, CCR5, CCR6, CCR7, CCR8, CCR9, CXCR1, CXCR2, CXCR4, and/or CXCR5. In more preferred embodiments, the antibodies of the invention specifically bind to a G-protein chemokine receptor and do cross-react with the Interleukin 8 receptor, CXCR1, and/or CXCR2.

In a preferred embodiment, antibodies of the invention preferentially bind a G-protein chemokine receptor (SEQ ID NO:2 or more preferably SEQ ID NO:4), or fragments and variants thereof relative to their ability to bind other antigens, (such as, for example, other chemokine receptors or Interleukin 8 receptor).

By way of non-limiting example, an antibody may be considered to bind a first antigen preferentially if it binds said first antigen with a dissociation constant ($K_D$) that is less than the antibody's $K_D$ for the second antigen. In another non-limiting embodiment, an antibody may be considered to bind a first antigen preferentially if it binds said first antigen with an affinity that is at least one order of magnitude less than the antibody's $K_D$ for the second antigen. In another non-limiting embodiment, an antibody may be considered to bind a first antigen preferentially if it binds said first antigen with an affinity that is at least two orders of magnitude less than the antibody's $K_D$ for the second antigen.

In another non-limiting embodiment, an antibody may be considered to bind a first antigen preferentially if it binds said first antigen with an off rate ($k_{off}$) that is less than the antibody's $k_{off}$ for the second antigen. In another non-limiting embodiment, an antibody may be considered to bind a first antigen preferentially if it binds said first antigen with an affinity that is at least one order of magnitude less than the antibody's $k_{off}$ for the second antigen. In another non-limiting embodiment, an antibody may be considered to bind a first antigen preferentially if it binds said first antigen with an affinity that is at least two orders of magnitude less than the antibody's $k_{off}$ for the second antigen.

Antibodies of the present invention may also be described or specified in terms of their binding affinity to a polypeptide of the invention. Preferred binding affinities include those with a dissociation constant or Kd less than $5 \times 10^{-2}$ M, $10^{-2}$ M, $5 \times 10^{-3}$ M, $10^{-3}$ M, $5 \times 10^{-4}$ M, $10^{-4}$ M. More preferred binding affinities include those with a dissociation constant or Kd less than $5 \times 10^{-5}$ M, $10^{-5}$ M, $5 \times 10^{-6}$ M, $10^{-6}$ M, $5 \times 10^{-7}$ M, $10^{-7}$ M, $5 \times 10^{-8}$ M or $10^{-8}$ M. Even more preferred binding affinities include those with a dissociation constant or Kd less than $5 \times 10^{-9}$ M, $10^{-9}$ M, $5 \times 10^{-10}$ M, $10^{-10}$ M, $5 \times 10^{-11}$ M, $10^{-11}$ M, $5 \times 10^{-12}$ M, $10^{-12}$ M, $5 \times 10^{-13}$ M, $10^{-13}$ M, $5 \times 10^{-14}$ M, $10^{-14}$ M, $5 \times 10^{-15}$ M, or $10^{-15}$ M.

In specific embodiments, antibodies of the invention bind G-protein chemokine receptor polypeptides or fragments or variants thereof with an off rate ($k_{off}$) of less than or equal to $5 \times 10^{-2}$ sec$^{-1}$, $10^{-2}$ sec$^{-1}$, $5 \times 10^{-3}$ sec$^{-1}$ or $10^{-3}$ sec$^{-1}$. More preferably, antibodies of the invention bind G-protein chemokine receptor polypeptides or fragments or variants thereof with an off rate ($k_{off}$) less than or equal to $5 \times 10^{-4}$ sec$^{-1}$, $10^{-4}$ sec$^{-1}$, $5 \times 10^{-5}$ sec$^{-1}$, or $10^{-5}$ sec$^{-1}$ $5 \times 10^{-6}$ sec$^{-1}$, $10^{-6}$ sec$^{-1}$, $5 \times 10^{-7}$ sec$^{-1}$ or $10^{-7}$ sec$^{-1}$.

In other embodiments, antibodies of the invention bind G-protein chemokine receptor polypeptides or fragments or variants thereof with an on rate ($k_{on}$) of greater than or equal to $10^3$ M$^{-1}$ sec$^{-1}$, $5 \times 10^3$ M$^{-1}$ sec$^{-1}$, $10^4$ M$^{-1}$ sec$^{-1}$ or $5 \times 10^4$ M$^{-1}$ sec$^{-1}$. More preferably, antibodies of the invention bind G-protein chemokine receptor polypeptides or fragments or variants thereof with an on rate ($k_{on}$) greater than or equal to $10^5$ M$^{-1}$ sec$^{-1}$, $5 \times 10^5$ M$^{-1}$ sec$^{-1}$, $10^6$ M$^{-1}$ sec$^{-1}$, or $5 \times 10^6$ M$^{-1}$ sec$^{-1}$ or $10^7$ M$^{-1}$ sec$^{-1}$.

The invention also provides antibodies that competitively inhibit binding of an antibody to an epitope of the invention as determined by any method known in the art for determining competitive binding, for example, the immunoassays described herein. In preferred embodiments, the antibody competitively inhibits binding to the epitope by at least 95%, at least 90%, at least 85%, at least 80%, at least 75%, at least 70%, at least 60%, or at least 50%.

Antibodies of the present invention may act as agonists or antagonists of the polypeptides of the present invention. For example, the present invention includes antibodies that disrupt the receptor/ligand interactions with the polypeptides of the invention either partially or fully. Preferably, antibodies of the present invention bind an antigenic epitope disclosed herein, or a portion thereof. The invention features both receptor-specific antibodies and ligand-specific antibodies. The invention also features receptor-specific antibodies that do not prevent ligand binding but prevent receptor activation. Receptor activation (i.e., signaling) may be determined by techniques described herein or otherwise known in the art. For example, receptor activation can be determined by detecting the phosphorylation (e.g., tyrosine or serine/threonine) of the receptor or its substrate by immunoprecipitation followed by western blot analysis (for example, as described supra). In specific embodiments, antibodies are provided that inhibit ligand activity or receptor activity by at least 95%, at least 90%, at least 85%, at least 80%, at least 75%, at least 70%, at least 60%, or at least 50% of the activity in absence of the antibody.

The invention also features receptor-specific antibodies which both prevent ligand binding and receptor activation as well as antibodies that recognize the receptor-ligand complex, and, preferably, do not specifically recognize the unbound receptor or the unbound ligand. Likewise, included in the invention are neutralizing antibodies that bind the ligand and prevent binding of the ligand to the receptor, as well as antibodies that bind the ligand, thereby preventing receptor activation, but do not prevent the ligand from binding the receptor. Further included in the invention are antibodies that activate the receptor. These antibodies may act as receptor agonists, i.e., potentiate or activate either all or a subset of the biological activities of the ligand-mediated receptor activation, for example, by inducing dimerization of the receptor. The antibodies may be specified as agonists, antagonists or inverse agonists for biological activities comprising the specific biological activities of the peptides of the invention disclosed herein. The above antibody agonists can be made using methods known in the art. See, e.g., PCT publication WO 96/40281; U.S. Pat. No. 5,811,097; Deng et al., Blood 92(6):1981-1988 (1998); Chen et al., Cancer Res. 58(16): 3668-3678 (1998); Harrop et al., J. Immunol. 161(4):1786-1794 (1998); Zhu et al., Cancer Res. 58(15):3209-3214 (1998); Yoon et al., J. Immunol. 160(7):3170-3179 (1998); Prat et al., J. Cell. Sci. 111(Pt2):237-247 (1998); Pitard et al., J. Immunol. Methods 205(2):177-190 (1997); Liautard et al., Cytokine 9(4):233-241 (1997); Carlson et al., J. Biol. Chem. 272(17):11295-11301 (1997); Taryman et al., Neuron 14(4): 755-762 (1995); Muller et al., Structure 6(9):1153-1167 (1998); Bartunek et al., Cytokine 8(1):14-20 (1996) (which are all incorporated by reference herein in their entireties).

The invention also encompasses antibodies (including molecules comprising, or alternatively consisting of, antibody fragments or variants thereof) that have one or more of the same biological characteristics as one or more of the antibodies described herein. By "biological characteristics" is meant, the in vitro or in vivo activities or properties of the antibodies, such as, for example, the ability to bind to a G-protein chemokine receptor (e.g., G-protein chemokine receptor expressed on a cell surface, membrane-embedded G-protein chemokine receptor, and/or a fragment or variant of a G-protein chemokine receptor); the ability to substantially inhibit or abolish the binding of the G-protein chemokine receptor to a G-protein chemokine receptor ligand (e.g. MIG, IP-10, or ITAC); the ability to downregulate G-protein chemokine receptor expression on the surface of cells; the ability to inhibit or abolish G-protein chemokine receptor mediated biological activity (e.g., the ability to inhibit or abolish recruitment of Th1 cells, NK cells, or eosinophils (or other G-protein chemokine receptor expressing cells) in response to proinflammatory signals, or the ability to induce an intracellular calcium flux in G-protein chemokine receptor expressing cells). Optionally, the antibodies of the invention will bind to the same epitope as at least one of the antibodies specifically referred to herein. Such epitope binding can be routinely determined using assays known in the art.

The present invention also provides for antibodies (including molecules comprising, or alternatively consisting of, antibody fragments or variants thereof), that neutralize G-protein chemokine receptor, said antibodies comprising, or alternatively consisting of, a portion (e.g., VH CDR1, VH CDR2, VH CDR3, VL CDR1, VL CDR2, and/or VL CDR3) of a VH or VL domain of an antibody of the invention. An antibody that "neutralizes G-protein chemokine receptor or a fragment or variant thereof" is, for example, an antibody that diminishes or abolishes the ability of G-protein chemokine receptor or a fragment or variant thereof to bind to its ligand (e.g., ITAC, MIG, and IP-10); that inhibits or abolishs recruitment of Th1 cells, NK cells, eosinophils, or other G-protein chemokine receptor expressing cells in response to proinflammatory signals; and/or that abolishes or inhibits the G-protein chemokine receptor signaling cascade (e.g., calcium flux initiated by an activated G-protein chemokine receptor). In one embodiment, an antibody that neutralizes G-protein chemokine receptor, comprises, or alternatively consists of, a polypeptide having the amino acid sequence of a VH domain of an antibody of the invention, or a fragment or variant thereof and a VL domain of an antibody of the invention, or a fragment or variant thereof. In another embodiment, an antibody that neutralizes G-protein chemokine receptor, comprises, or alternatively consists of, a polypeptide having the amino acid sequence of a VH domain and a VL domain from a single antibody (or scFv or Fab fragment) of the invention, or fragments or variants thereof. In one embodiment, an antibody that neutralizes G-protein chemokine receptor, comprises, or alternatively consists of, a polypeptide having the amino acid sequence of a VH domain of an antibody of the invention, or a fragment or variant thereof. In another embodiment, an antibody that neutralizes G-protein chemokine receptor, comprises, or alternatively consists of, a polypeptide having the amino acid sequence of a VL domain of an antibody of the invention, or a fragment or variant thereof. In another embodiment, an antibody that neutralizes G-protein chemokine receptor or a fragment or variant thereof, comprises, or alternatively consists of, a polypeptide having the amino acid sequence of a VH CDR domain of an antibody of the invention, or a fragment or variant thereof. In a preferred embodiment, an antibody that neutralizes G-protein chemokine receptor or a fragment or variant thereof, comprises, or alternatively consists of, a polypeptide having the amino acid sequence of a VH CDR3 of an antibody of the invention, or a fragment or variant thereof. In another embodiment, an antibody that neutralizes G-protein chemokine receptor or a fragment or variant thereof, comprises, or alternatively consists of, a polypeptide having the amino acid sequence of a VL CDR of an antibody of the invention, or a fragment or variant thereof. In another preferred embodiment, an antibody that neutralizes G-protein chemokine receptor or a fragment or variant thereof, comprises, or alternatively consists of, a polypeptide having the amino acid sequence of a VL CDR3 of an antibody of the invention, or a fragment or variant thereof. Nucleic acid molecules encoding these antibodies are also encompassed by the invention.

The present invention also provides for antibodies (including molecules comprising, or alternatively consisting of, antibody fragments or variants thereof), that inhibits or abolishes recruitment of Th1 cells, NK cells, eosinophils, or other G-protein chemokine receptor expressing cells in response to proinflammatory signals, as determined by any method known in the art. Said antibodies may comprise, or alternatively consist of, a portion (e.g., VH CDR1, VH CDR2, VH CDR3, VL CDR1, VL CDR2, or VL CDR3) of a VH or VL domain having an amino acid sequence of an antibody of the invention or a fragment or variant thereof. In one embodiment, an antibody that inhibits or abolishes recruitment of Th1 cells, NK cells, eosinophils, or other G-protein chemokine receptor expressing cells in response to proinflammatory signals, comprises, or alternatively consists of, a polypeptide having the amino acid sequence of a VH domain of an antibody of the invention, or a fragment or variant thereof and a VL domain of an antibody of the invention, or a fragment or variant thereof. In another embodiment, an antibody that inhibits or abolishes recruitment of Th1 cells, NK cells, eosinophils, or other G-protein chemokine receptor expressing cells in response to proinflammatory signals, comprises, or alternatively consists of, a polypeptide having the amino acid sequence of a VH domain and a VL domain from a single antibody (or scFv or Fab fragment) of the invention, or fragments or variants thereof. In one embodiment, an antibody that inhibits or abolishes recruitment of Th1 cells, NK cells, eosinophils, or other G-protein chemokine receptor expressing cells in response to proinflammatory signals, comprises, or alternatively consists of, a polypeptide having the amino acid sequence of a VH domain of an antibody of the invention, or a fragment or variant thereof. In another embodiment, an antibody that inhibits or abolishes recruitment of Th1 cells, NK cells, eosinophils, or other G-protein chemokine receptor expressing cells in response to proinflammatory signals comprises, or alternatively consists of, a polypeptide having the amino acid sequence of a VL domain of an antibody of the invention, or a fragment or variant thereof. In a preferred embodiment, an antibody that inhibits or abolishes recruitment of Th1 cells, NK cells, eosinophils, or other G-protein chemokine receptor expressing cells in response to proinflammatory signals, comprises, or alternatively consists of, a polypeptide having the amino acid sequence of a VH CDR3 of an antibody of the invention, or a fragment or variant thereof. In another preferred embodiment, an antibody that inhibits or abolishes recruitment of Th1 cells, NK cells, eosinophils, or other G-protein chemokine receptor expressing cells in response to proinflammatory signals, comprises, or alternatively consists of, a polypeptide having the amino acid sequence of a VL CDR3 of an antibody of the invention, or a fragment or variant thereof. Nucleic acid molecules encoding these antibodies are also encompassed by the invention.

The present invention also provides for antibodies (including molecules comprising, or alternatively consisting of, antibody fragments or variants thereof), that downregulates the cell-surface expression of G-protein chemokine receptor, as determined by any method known in the art such as, for example, FACS analysis. By way of a non-limiting hypothesis, such down regulation may be the result of antibody-induced internalization of G-protein chemokine receptor. Said antibodies may comprise, or alternatively consist of, a portion (e.g., VH CDR1, VH CDR2, VH CDR3, VL CDR1, VL CDR2, or VL CDR3) of a VH or VL domain having an amino acid sequence of an antibody of the invention or a fragment or variant thereof. In one embodiment, an antibody that downregulates the cell-surface expression of G-protein chemokine receptor, comprises, or alternatively consists of, a polypeptide having the amino acid sequence of a VH domain of an antibody of the invention, or a fragment or variant thereof and a VL domain of an antibody of the invention, or a fragment or variant thereof. In another embodiment, an antibody that downregulates the cell-surface expression of G-protein chemokine receptor, comprises, or alternatively consists of, a polypeptide having the amino acid sequence of a VH domain and a VL domain from a single antibody (or scFv or Fab fragment) of the invention, or fragments or variants thereof In one embodiment, an antibody that downregulates the cell-surface expression of G-protein chemokine receptor, comprises, or alternatively consists of, a polypeptide having the amino acid sequence of a VH domain of an antibody of the invention, or a fragment or variant thereof. In another embodiment, an antibody that downregulates the cell-surface expression of G-protein chemokine receptor, comprises, or alternatively consists of, a polypeptide having the amino acid sequence of a VL domain of an antibody of the invention, or a fragment or variant thereof. In a preferred embodiment, an antibody that downregulate the cell-surface expression of G-protein chemokine receptor, comprises, or alternatively consists of, a polypeptide having the amino acid sequence of a VH CDR3 of an antibody of the invention, or a fragment or variant thereof In another preferred embodiment, an antibody that downregulates the cell-surface expression of G-protein chemokine receptor, comprises, or alternatively consists of, a polypeptide having the amino acid sequence of a VL CDR3 of an antibody of the invention, or a fragment or variant thereof. Nucleic acid molecules encoding these antibodies are also encompassed by the invention.

The present invention also provides for antibodies (including molecules comprising, or alternatively consisting of, antibody fragments or variants thereof), that enhance the activity of G-protein chemokine receptor, said antibodies comprising, or alternatively consisting of, a portion (e.g., VH CDR1, VH CDR2, VH CDR3, VL CDR1, VL CDR2, or VL CDR3) of a VH or VL domain of an antibody of the invention, or a fragment or variant thereof By way of non-limiting example, an antibody that "enhances the activity of G-protein chemokine receptor or a fragment or variant thereof" is an antibody increases the ability of G-protein chemokine receptor to bind to stimulate chemotaxis of Th1 cells (or other G-protein chemokine receptor expressing cells), and/or to stimulate the G-protein chemokine receptor signaling cascade (e.g., to initiate an intracellular calcium flux). In one embodiment, an antibody that that enhances the activity of G-protein chemokine receptor, comprises, or alternatively consists of, a polypeptide having the amino acid sequence of a VH domain of an antibody of the invention, or a fragment or variant thereof and a VL domain of an antibody of the invention, or a fragment or variant thereof. In another embodiment, an antibody that enhances the activity of G-protein chemokine receptor, comprises, or alternatively consists of, a polypeptide having the amino acid sequence of a VH domain and a VL domain from a single antibody (or scFv or Fab fragment) of the invention, or fragments or variants thereof. In one embodiment, an antibody that enhances the activity of G-protein chemokine receptor or a fragment or variant thereof, comprises, or alternatively consists of, a polypeptide having the amino acid sequence of a VH domain of an antibody of the invention, or a fragment or variant thereof. In another embodiment, an antibody that enhances the activity of G-protein chemokine receptor or a fragment or variant thereof, comprises, or alternatively consists of, a polypeptide having the amino acid sequence of a VL domain of an antibody of the invention, or a fragment or variant thereof. In another embodiment, an antibody that enhances the activity of G-protein chemokine receptor or a fragment or variant thereof, comprises, or alternatively consists of, a polypeptide having the amino acid sequence of a VH CDR domain referred to in of an antibody of the invention or a fragment or variant thereof. In a preferred embodiment, an antibody that enhances the activity of G-protein chemokine receptor or a fragment or variant thereof, comprises, or alternatively consists of, a polypeptide having the amino acid sequence of a VH CDR3 of an antibody of the invention, or a fragment or variant thereof. In another embodiment, an antibody that enhances G-protein chemokine receptor or a fragment or variant thereof, comprises, or alternatively consists of, a polypeptide having the amino acid sequence of a VL CDR domain of an antibody of the invention, or a fragment or variant thereof. In another preferred embodiment, an antibody that enhances the activity of G-protein chemokine receptor or a fragment or variant thereof, comprises, or alternatively consists of, a polypeptide having the amino acid sequence of a VL CDR3 of an antibody of the invention, or a fragment or variant thereof. Nucleic acid molecules encoding these antibodies are also encompassed by the invention.

The present invention also provides for fusion proteins comprising, or alternatively consisting of, an antibody (including molecules comprising, or alternatively consisting of, antibody fragments or variants thereof), that specifically binds to G-protein chemokine receptor, and a heterologous polypeptide. Preferably, the heterologous polypeptide to which the antibody is fused to is useful for function or is useful to target the G-protein chemokine receptor expressing cells, including but not limited to, Mip-1-beta; a CD4 binding polypeptide such as an anti-CD4 antibody; a CXCR4 binding polypeptides such as stromal derived factor 1-alpha (SDF1-alpha); and/or a CCR3 binding protein, such as Mip1-alpha). In an alternative preferred embodiment, the heterologous polypeptide to which the antibody is fused to is useful for T cell, macrophage, and/or monocyte cell function or is useful to target the antibody to a T cell, macrophage, or monocyte, including but not limited to, Mip-1-beta; a CD4 binding polypeptide such as an anti-CD4 antibody; a CXCR4 binding polypeptides such as stromal derived factor 1-alpha (SDF1-alpha); and/or a CCR3 binding protein, such as Mip 1-alpha). In one embodiment, a fusion protein of the invention comprises, or alternatively consists of, a polypeptide having the amino acid sequence of any one or more of the VH domains of an antibody of the invention or the amino acid sequence of any one or more of the VL domains of an antibody of the invention or fragments or variants thereof, and a heterologous polypeptide sequence. In another embodiment, a fusion protein of the present invention comprises, or alternatively consists of, a polypeptide having the amino acid sequence of any one, two, three, or more of the VH CDRs of an antibody of the invention, or the amino acid sequence of any one, two, three, or more of the VL CDRs of an antibody of the invention, or fragments or variants thereof, and a heterologous polypeptide sequence. In a preferred embodiment, the fusion protein comprises, or alternatively consists of, a polypeptide having the amino acid sequence of, a VH CDR3 of an antibody of the invention, or fragment or variant thereof, and a heterologous polypeptide sequence, which fusion protein specifically binds to G-protein chemokine receptor. In another embodiment, a fusion protein comprises, or alternatively consists of a polypeptide having the amino acid sequence of at least one VH domain of an antibody of the invention and the amino acid sequence of at least one VL domain of an antibody of the invention or fragments or variants thereof, and a heterologous polypeptide sequence. Preferably, the VH and VL domains of the fusion protein correspond to a single antibody (or scFv or Fab fragment) of the invention. In yet another embodiment, a fusion protein of the invention comprises, or alternatively consists of a polypeptide having the amino acid sequence of any one, two, three or more of the VH CDRs of an antibody of the invention and the amino acid sequence of any one, two, three or more of the VL CDRs of an antibody of the invention, or fragments or variants thereof, and a heterologous polypeptide sequence. Preferably, two, three, four, five, six, or more of the VHCDR(s) or VLCDR(s) correspond to single antibody (or scFv or Fab fragment) of the invention. Nucleic acid molecules encoding these fusion proteins are also encompassed by the invention.

Antibodies of the present invention may be used, for example, but not limited to, to purify, detect, and target the polypeptides of the present invention, including both in vitro and in vivo diagnostic and therapeutic methods. For example, the antibodies have use in immunoassays for qualitatively and quantitatively measuring levels of the polypeptides of the present invention in biological samples. See, e.g., Harlow et al., Antibodies: A Laboratory Manual, (Cold Spring Harbor Laboratory Press, 2nd ed. 1988) (incorporated by reference herein in its entirety).

By way of another non-limiting example, antibodies of the invention may be administered to individuals as a form of passive immunization. Alternatively, antibodies of the present invention may be used for epitope mapping to identify the epitope(s) bound by the antibody. Epitopes identified in this way may, in turn, for example, be used as vaccine candidates, i.e., to immunize an individual to elicit antibodies against the naturally occurring forms of G-protein chemokine receptor.

As discussed in more detail below, the antibodies of the present invention may be used either alone or in combination with other compositions. The antibodies may further be recombinantly fused to a heterologous polypeptide at the N- or C-terminus or chemically conjugated (including covalently and non-covalently conjugations) to polypeptides or other compositions. For example, antibodies of the present invention may be recombinantly fused or conjugated to molecules useful as labels in detection assays and effector molecules such as heterologous polypeptides, drugs, radionuclides, or toxins. See, e.g., PCT publications WO 92/08495; WO 91/14438; WO 89/12624; U.S. Pat. No. 5,314,995; and EP 396,387.

The antibodies of the invention include derivatives that are modified, i.e, by the covalent attachment of any type of molecule to the antibody. For example, but not by way of limitation, the antibody derivatives include antibodies that have been modified, e.g., by glycosylation, acetylation, pegylation, phosphylation, amidation, derivatization by known protecting/blocking groups, proteolytic cleavage, linkage to a cellular ligand or other protein, etc. Any of numerous chemical modifications may be carried out by known techniques, including, but not limited to specific chemical cleavage, acetylation, formylation, metabolic synthesis of tunicamycin, etc. Additionally, the derivative may contain one or more non-classical amino acids.

The antibodies of the present invention may be generated by any suitable method known in the art. Polyclonal antibodies to an antigen-of-interest can be produced by various procedures well known in the art. For example, a polypeptide of the invention can be administered to various host animals including, but not limited to, rabbits, mice, rats, etc. to induce the production of sera containing polyclonal antibodies specific for the antigen. Various adjuvants may be used to increase the immunological response, depending on the host species, and include but are not limited to, Freund's (complete and incomplete), mineral gels such as aluminum hydroxide, surface active substances such as lysolecithin, pluronic polyols, polyanions, peptides, oil emulsions, keyhole limpet hemocyanins, dinitrophenol, and potentially useful human adjuvants such as BCG (bacille Calmette-Guerin) and corynebacterium parvum. Such adjuvants are also well known in the art.

Monoclonal antibodies can be prepared using a wide variety of techniques known in the art including the use of hybridoma, recombinant, and phage display technologies, or a combination thereof. For example, monoclonal antibodies can be produced using hybridoma techniques including those known in the art and taught, for example, in Harlow et al., Antibodies: A Laboratory Manual, (Cold Spring Harbor Laboratory Press, 2nd ed. 1988); Hammerling, et al., in: Monoclonal Antibodies and T-Cell Hybridomas 563-681 (Elsevier, N.Y., 1981) (said references incorporated by reference in their entireties). The term "monoclonal antibody" as used herein is not limited to antibodies produced through hybridoma technology. The term "monoclonal antibody" refers to an antibody that is derived from a single clone, including any eukaryotic, prokaryotic, or phage clone, and not the method by which it is produced.

Methods for producing and screening for specific antibodies using hybridoma technology are routine and well known in the art and are discussed in detail in the Examples (e.g., Example 6). In a non-limiting example, mice can be immunized with a polypeptide of the invention or a cell expressing such peptide. Once an immune response is detected, e.g., antibodies specific for the antigen are detected in the mouse serum, the mouse spleen is harvested and splenocytes isolated. The splenocytes are then fused by well known techniques to any suitable myeloma cells, for example cells from cell line SP20 available from the ATCC. Hybridomas are selected and cloned by limited dilution. The hybridoma clones are then assayed by methods known in the art for cells that secrete antibodies capable of binding a polypeptide of the invention. Ascites fluid, which generally contains high levels of antibodies, can be generated by immunizing mice with positive hybridoma clones.

Accordingly, the present invention provides methods of generating monoclonal antibodies as well as antibodies produced by the method comprising culturing a hybridoma cell secreting an antibody of the invention wherein, preferably, the hybridoma is generated by fusing splenocytes isolated from a mouse immunized with an antigen of the invention with myeloma cells and then screening the hybridomas resulting from the fusion for hybridoma clones that secrete an antibody able to bind a polypeptide of the invention.

Another well-known method for producing both polyclonal and monoclonal human B cell lines is transformation using Epstein Barr Virus (EBV). Protocols for generating EBV-transformed B cell lines are commonly known in the art, such as, for example, the protocol outlined in Chapter 7.22 of Current Protocols in Immunology, Coligan et al., Eds., 1994, John Wiley & Sons, NY, which is hereby incorporated in its entirety by reference herein. The source of B cells for transformation is commonly human peripheral blood, but B cells for transformation may also be derived from other sources including, but not limited to, lymph nodes, tonsil, spleen, tumor tissue, and infected tissues. Tissues are generally made into single cell suspensions prior to EBV transformation. Additionally, steps may be taken to either physically remove or inactivate T cells (e.g., by treatment with cyclosporin A) in B cell-containing samples, because T cells from individuals seropositive for anti-EBV antibodies can suppress B cell immortalization by EBV. In general, the sample containing human B cells is innoculated with EBV, and cultured for 3-4 weeks. A typical source of EBV is the culture supernatant of the B95-8 cell line (ATCC #VR-1492). Physical signs of EBV transformation can generally be seen towards the end of the 3-4 week culture period. By phase-contrast microscopy, transformed cells may appear large, clear, hairy and tend to aggregate in tight clusters of cells. Initially, EBV lines are generally polyclonal. However, over prolonged periods of cell cultures, EBV lines may become monoclonal or polyclonal as a result of the selective outgrowth of particular B cell clones. Alternatively, polyclonal EBV transformed lines may be subcloned (e.g., by limiting dilution culture) or fused with a suitable fusion partner and plated at limiting dilution to obtain monoclonal B cell lines. Suitable fusion partners for EBV transformed cell lines include mouse myeloma cell lines (e.g., SP2/0, X63-Ag8.653), heteromyeloma cell lines (human×mouse; e.g, SPAM-8, SBC-H20, and CB-F7), and human cell lines (e.g., GM 1500, SKO-007, RPMI 8226, and KR-4). Thus, the present invention also provides a method of generating polyclonal or monoclonal human antibodies against polypeptides of the invention or fragments thereof, comprising EBV-transformation of human B cells.

Antibody fragments which recognize specific epitopes may be generated by known techniques. For example, Fab and F(ab')2 fragments of the invention may be produced by proteolytic cleavage of immunoglobulin molecules, using enzymes such as papain (to produce Fab fragments) or pepsin (to produce F(ab')2 fragments). F(ab')2 fragments contain the variable region, the light chain constant region and the CH1 domain of the heavy chain.

For example, the antibodies of the present invention can also be generated using various phage display methods known in the art. In phage display methods, functional antibody domains are displayed on the surface of phage particles which carry the polynucleotide sequences encoding them. In a particular embodiment, such phage can be utilized to display antigen binding domains expressed from a repertoire or combinatorial antibody library (e.g., human or murine). Phage expressing an antigen binding domain that binds the antigen of interest can be selected or identified with antigen, e.g., using labeled antigen or antigen bound or captured to a solid surface or bead. Phage used in these methods are typically filamentous phage including fd and M13 binding domains expressed from phage with Fab, Fv or disulfide stabilized Fv antibody domains recombinantly fused to either the phage gene III or gene VIII protein. Examples of phage display methods that can be used to make the antibodies of the present invention include those disclosed in Brinkman et al., J. Immunol. Methods 182:41-50 (1995); Ames et al., J. Immunol. Methods 184:177-186 (1995); Kettleborough et al., Eur. J. Immunol. 24:952-958 (1994); Persic et al., Gene 187 9-18 (1997); Burton et al., Advances in Immunology 57:191-280 (1994); PCT application No. PCT/GB91/01134; PCT publications WO 90/02809; WO 91/10737; WO 92/01047; WO 92/18619; WO 93/11236; WO 95/15982; WO 95/20401; and U.S. Pat. Nos. 5,698,426; 5,223,409; 5,403,484; 5,580,717; 5,427,908; 5,750,753; 5,821,047; 5,571,698; 5,427,908; 5,516,637; 5,780,225; 5,658,727; 5,733,743 and 5,969,108; each of which is incorporated herein by reference in its entirety.

As described in the above references, after phage selection, the antibody coding regions from the phage can be isolated and used to generate whole antibodies, including human antibodies, or any other desired antigen binding fragment, and expressed in any desired host, including mammalian cells, insect cells, plant cells, yeast, and bacteria, e.g., as described in detail below. For example, techniques to recombinantly produce Fab, Fab' and F(ab')2 fragments can also be employed using methods known in the art such as those disclosed in PCT publication WO 92/22324; Mullinax et al., BioTechniques 12(6):864-869 (1992); and Sawai et al., AJRI 34:26-34 (1995); and Better et al., Science 240:1041-1043 (1988) (said references incorporated by reference in their entireties).

Examples of techniques which can be used to produce single-chain Fvs and antibodies include those described in U.S. Pat. Nos. 4,946,778 and 5,258,498; Huston et al., Methods in Enzymology 203:46-88 (1991); Shu et al., PNAS 90:7995-7999 (1993); and Skerra et al., Science 240:1038-1040 (1988). For some uses, including in vivo use of antibodies in humans and in vitro detection assays, it may be preferable to use chimeric, humanized, or human antibodies. A chimeric antibody is a molecule in which different portions of the antibody are derived from different animal species, such as antibodies having a variable region derived from a murine monoclonal antibody and a human immunoglobulin constant region. Methods for producing chimeric antibodies are known in the art. See e.g., Morrison, Science 229:1202 (1985); Oi et al., BioTechniques 4:214 (1986); Gillies et al., (1989) J. Immunol. Methods 125:191-202; U.S. Pat. Nos. 5,807,715; 4,816,567; and 4,816,397, which are incorporated herein by reference in their entirety. Humanized antibodies are antibody molecules from non-human species antibody that binds the desired antigen having one or more complementarity determining regions (CDRs) from the non-human species and a framework regions from a human immunoglobulin molecule. Often, framework residues in the human framework regions will be substituted with the corresponding residue from the CDR donor antibody to alter, preferably improve, antigen binding. These framework substitutions are identified by methods well known in the art, e.g., by modeling of the interactions of the CDR and framework residues to identify framework residues important for antigen binding and sequence comparison to identify unusual framework residues at particular positions. (See, e.g., Queen et al., U.S. Pat. No. 5,585,089; Riechmann et al., Nature 332:323 (1988), which are incorporated herein by reference in their entireties.) Antibodies can be humanized using a variety of techniques known in the art including, for example, CDR-grafting (EP 239,400; PCT publication WO 91/09967; U.S. Pat. Nos. 5,225,539; 5,530,101; and 5,585,089), veneering or resurfacing (EP 592,106; EP 519,596; Padlan, Molecular Immunology 28(4/5):489-498 (1991); Studnicka et al., Protein Engineering 7(6):805-814 (1994); Roguska. et al., PNAS 91:969-973 (1994)), and chain shuffling (U.S. Pat. No. 5,565,332).

Completely human antibodies are particularly desirable for therapeutic treatment of human patients. Human antibodies can be made by a variety of methods known in the art including phage display methods described above using antibody libraries derived from human immunoglobulin sequences. See also, U.S. Pat. Nos. 4,444,887 and 4,716,111; and PCT publications WO 98/46645, WO 98/50433, WO 98/24893, WO 98/16654, WO 96/34096, WO 96/33735, and WO 91/10741; each of which is incorporated herein by reference in its entirety.

Human antibodies can also be produced using transgenic mice which are incapable of expressing functional endogenous immunoglobulins, but which can express human immunoglobulin genes. For example, the human heavy and light chain immunoglobulin gene complexes may be introduced randomly or by homologous recombination into mouse embryonic stem cells. Alternatively, the human variable region, constant region, and diversity region may be introduced into mouse embryonic stem cells in addition to the human heavy and light chain genes. The mouse heavy and light chain immunoglobulin genes may be rendered nonfunctional separately or simultaneously with the introduction of human immunoglobulin loci by homologous recombination. In particular, homozygous deletion of the JH region prevents endogenous antibody production. The modified embryonic stem cells are expanded and microinjected into blastocysts to produce chimeric mice. The chimeric mice are then bred to produce homozygous offspring which express human antibodies. The transgenic mice are immunized in the normal fashion with a selected antigen, e.g., all or a portion of a polypeptide of the invention. Monoclonal antibodies directed against the antigen can be obtained from the immunized, transgenic mice using conventional hybridoma technology. The human immunoglobulin transgenes harbored by the transgenic mice rearrange during B cell differentiation, and subsequently undergo class switching and somatic mutation. Thus, using such a technique, it is possible to produce therapeutically useful IgG, IgA, IgM and IgE antibodies. For an overview of this technology for producing human antibodies, see Lonberg and Huszar, Int. Rev. Immunol. 13:65-93 (1995). For a detailed discussion of this technology for producing human antibodies and human monoclonal antibodies and protocols for producing such antibodies, see, e.g., PCT publications WO 98/24893; WO 92/01047; WO 96/34096; WO 96/33735; European Patent No. 0 598 877; U.S. Pat. Nos. 5,413,923; 5,625,126; 5,633,425; 5,569,825; 5,661,016; 5,545,806; 5,814,318; 5,885,793; 5,916,771; 5,939,598; 6,075,181; and 6,114,598, which are incorporated by reference herein in their entirety. In addition, companies such as Abgenix, Inc. (Fremont, Calif.) and Genpharm (San Jose, Calif.) can be engaged to provide human antibodies directed against a selected antigen using technology similar to that described above.

Completely human antibodies which recognize a selected epitope can be generated using a technique referred to as "guided selection." In this approach a selected non-human monoclonal antibody, e.g., a mouse antibody, is used to guide the selection of a completely human antibody recognizing the same epitope. (Jespers et al., Bio/technology 12:899-903 (1988)).

Further, antibodies to the polypeptides of the invention can, in turn, be utilized to generate anti-idiotype antibodies that "mimic" polypeptides of the invention using techniques well known to those skilled in the art. (See, e.g., Greenspan & Bona, FASEB J. 7(5):437-444; (1989) and Nissinoff, J. Immunol. 147(8):2429-2438 (1991)). For example, antibodies which bind to and competitively inhibit polypeptide multimerization and/or binding of a polypeptide of the invention to a ligand can be used to generate anti-idiotypes that "mimic" the polypeptide multimerization and/or binding domain and, as a consequence, bind to and neutralize polypeptide and/or its ligand. Such neutralizing anti-idiotypes or Fab fragments of such anti-idiotypes can be used in therapeutic regimens to neutralize polypeptide ligand. For example, such anti-idiotypic antibodies can be used to bind a polypeptide of the invention and/or to bind its ligands/receptors, and thereby activate or block its biological activity.

Intrabodies are antibodies, often scFvs, which expressed from a recombinant nucleic aicd molecule and engineered to be retained intracellularly (e.g., retained in the cytoplasm, endoplasmic reticulum, or periplasm). Intrabodies may be used, for example, to ablate the function of a protein to which the intrabody binds. The expression of intrabodies may also be regulated through the use of inducible promoters in the nucleic acid expression vector comprising the intrabody. Intrabodies of the invention can be produced using methods known in the art, such as those disclosed and reviewed in Chen et al., *Hum. Gene Ther.* 5:595-601 (1994); Marasco, W. A., *Gene Ther.* 4:11-15 (1997); Rondon and Marasco, *Annu. Rev. Microbiol.* 51:257-283 (1997); Proba et al., *J. Mol. Biol.* 275:245-253 (1998); Cohen et al., *Oncogene* 17:2445-2456 (1998); Ohage and Steipe, *J. Mol. Biol.* 291:1119-1128 (1999); Ohage et al., *J. Mol. Biol.* 291:1129-1134 (1999); Wirtz and Steipe, *Protein Sci.* 8:2245-2250 (1999); Zhu et al., *J. Immunol. Methods* 231:207-222 (1999); and references cited therein. In particular, a CCR5 intrabody has been produced by Steinberger et al., *Proc. Natl. Acad. Sci. USA* 97:805-810 (2000).

XenoMotise Technology

Antibodies in accordance with the invention are preferably prepared the utilization of a transgenic mouse that has a substantial portion of the human antibody producing genome inserted but that is rendered deficient in the production of endogenous, murine, antibodies (e.g., XenoMouse strains available from Abgenix Inc., Fremont, Calif.). Such mice, then, are capable of producing human immunoglobulin molecules and antibodies and are deficient in the production of murine immunoglobulin molecules and antibodies. Technologies utilized for achieving the same are disclosed in the patents, applications, and references disclosed herein.

The ability to clone and reconstruct megabase-sized human loci in YACs and to introduce them into the mouse germline provides a powerful approach to elucidating the functional components of very large or crudely mapped loci as well as generating useful models of human disease. Furthermore, the utilization of such technology for substitution of mouse loci with their human equivalents could provide unique insights into the expression and regulation of human gene products during development, their communication with other systems, and their involvement in disease induction and progression.

An important practical application of such a strategy is the "humanization" of the mouse humoral immune system. Introduction of human immunoglobulin (Ig) loci into mice in which the endogenous Ig genes have been inactivated offers the opportunity to study the mechanisms underlying programmed expression and assembly of antibodies as well as their role in B cell development. Furthermore, such a strategy could provide an ideal source for production of fully human monoclonal antibodies (Mabs) an important milestone towards fulfilling the promise of antibody therapy in human disease.

Fully human antibodies are expected to minimize the immunogenic and allergic responses intrinsic to mouse or mouse-derivatized Monoclonal antibodies and thus to increase the efficacy and safety of the administered antibodies. The use of fully human antibodies can be expected to provide a substantial advantage in the treatment of chronic and recurring human diseases, such as cancer, which require repeated antibody administrations.

One approach towards this goal was to engineer mouse strains deficient in mouse antibody production with large fragments of the human Ig loci in anticipation that such mice would produce a large repertoire of human antibodies in the absence of mouse antibodies. Large human Ig fragments would preserve the large variable gene diversity as well as the proper regulation of antibody production and expression. By exploiting the mouse machinery for antibody diversification and selection and the lack of immunological tolerance to human proteins, the reproduced human antibody repertoire in these mouse strains should yield high affinity antibodies against any antigen of interest, including human antigens. Using the hybridoma technology, antigen-specific human Monoclonal antibodies with the desired specificity could be readily produced and selected.

This general strategy was demonstrated in connection with the generation of the first XenoMouse™ strains as published in 1994. See Green et al. *Nature Genetics* 7:13-21 (1994). The XenoMouse™ strains were engineered with yeast artificial chromosomes (YACS) containing 245 kb and 10 190 kb-sized germline configuration fragments of the human heavy chain locus and kappa light chain locus, respectively, which contained core variable and constant region sequences. Id. The human Ig containing YACs proved to be compatible with the mouse system for both rearrangement and expression of antibodies and were capable of substituting for the inactivated mouse Ig genes. This was demonstrated by their ability to induce B-cell development, to produce an adult-like human repertoire of fully human antibodies, and to generate antigen-specific human monoclonal antibodies. These results also suggested that introduction of larger portions of the human Ig loci containing greater numbers of V genes, additional regulatory elements, and human Ig constant regions might recapitulate substantially the full repertoire that is characteristic of the human humoral response to infection and immunization. The work of Green et al. was recently extended to the introduction of greater than approximately 80% of the human antibody repertoire through introduction of megabase sized, germline configuration YAC fragments of the human heavy chain loci and kappa light chain loci, respectively, to produce XenoMouse™ mice. See Mendez et al. *Nature Genetics* 15:146-156 (1997), Green and Jakobovits *J Exp. Med.* 188: 483-495 (1998), Green, *Journal of Immunological Methods* 231:11-23 (1999) and U.S. patent application Ser. No. 08/759,620, filed Dec. 3, 1996, the disclosures of which are hereby incorporated by reference.

Such approach is further discussed and delineated in U.S. patent application Ser. Nos. 07/466,008, filed Jan. 12, 1990, 07/710,515, filed Nov. 8, 1990, 07/919,297, filed Jul. 24, 1992, 07/922,649, filed Jul. 30, 1992, filed 08/031,801, filed Mar. 15,1993, 08/112,848, filed Aug. 27, 1993, 08/234,145, filed Apr. 28, 1994, 08/376,279, filed Jan. 20, 1995, 08/430, 938, Apr. 27, 1995, 0-8/464,584, filed Jun. 5, 1995, 08/464, 582, filed Jun. 5, 1995, 08/471,191, filed Jun. 5, 1995, 08/462, 837, filed Jun. 5, 1995, 08/486,853, filed Jun. 5, 1995, 08/486, 857, filed Jun. 5, 1995, 08/486,859, filed Jun. 5, 1995, 08/462, 513, filed Jun. 5, 1995, 08/724,752, filed Oct. 2, 1996, and 08/759,620, filed Dec. 3, 1996. See also Mendez et al. *Nature Genetics* 15:146-156 (1997) and Green and Jakobovits *J Exp. Med.* 188:483 495 (1998). See also European Patent No., EP 0 471 151 B1, grant published Jun. 12, 1996, International Patent Application No., WO 94/02602, published Feb. 3, 1994, International Patent Application No., WO 96/34096, published Oct. 31, 1996, and WO 98/24893, published Jun. 11, 1998. The disclosures of each of the above-cited patents, applications, and references are hereby incorporated by reference in their entirety.

Human anti-mouse antibody (HAMA) responses have led the industry to prepare chimeric or otherwise humanized antibodies. While chimeric antibodies have a human constant region and a murine variable region, it is expected that certain human anti-chimeric antibody (HACA) responses will be observed, particularly in chronic or multi-dose utilizations of the antibody. Thus, it would be desirable to provide fully human antibodies against G-protein chemokine receptor polypeptides in order to vitiate concerns and/or effects of HAMA or HACA responses.

In one embodiment of the present invention, antibodies that specifically bind to a G-protein chemokine receptor or a fragment or variant thereof, comprise a polypeptide having the amino acid sequence of any one of the heavy chains expressed by at least one of the antibodies of the invention and/or any one of the light chains expressed by at least one of the antibodies of the invention. In another embodiment of the present invention, antibodies that specifically bind to a G-protein chemokine receptor or a fragment or variant thereof, comprise a polypeptide having the amino acid sequence of any one of the VH domains of a heavy chain expressed by at least one of the antibodies of the invention and/or any one of the VL domains of a light chain expressed by at least one of the antibodies of the invention. In preferred embodiments, antibodies of the present invention comprise the amino acid sequence of a VH domain and VL domain expressed by the same cell line selected from the group consisting of the antibodies of the invention. In alternative embodiments, antibodies of the present invention comprise the amino acid sequence of a VH domain and a VL domain from different antibodies of the invention. Molecules comprising, or alternatively consisting of, antibody fragments or variants of the VH and/or VL domains expressed by at least one of the antibodies of the invention that specifically bind to a G-protein chemokine receptor are also encompassed by the invention, as are nucleic acid molecules encoding these VH and VL domains, molecules, fragments and/or variants.

The present invention also provides antibodies that specifically bind to a polypeptide, or polypeptide fragment or variant of a G-protein chemokine receptor, wherein said antibodies comprise, or alternatively consist of, a polypeptide having an amino acid sequence of any one, two, three, or more of the VH CDRs contained in a heavy chain expressed by one or more antibodies of the invention. In particular, the invention provides antibodies that specifically bind a G-protein chemokine receptor, comprising, or alternatively consisting of, a polypeptide having the amino acid sequence of a VH CDR1 contained in a heavy chain expressed by one or more antibodies of the invention. In another embodiment, antibodies that specifically bind a G-protein chemokine receptor, comprise, or alternatively consist of, a polypeptide having the amino acid sequence of a VH CDR2 contained in a heavy chain expressed by one or more antibodies of the invention. In a preferred embodiment, antibodies that specifically bind a G-protein chemokine receptor, comprise, or alternatively consist of a polypeptide having the amino acid sequence of a VH CDR3 contained in a heavy chain expressed by one or more antibodies of the invention. Molecules comprising, or alternatively consisting of, these antibodies, or antibody fragments or variants thereof, that specifically bind to G-protein chemokine receptor or a G-protein chemokine receptor fragment or variant thereof are also encompassed by the invention, as are nucleic acid molecules encoding these antibodies, molecules, fragments and/or variants.

The present invention also provides antibodies that specifically bind to a polypeptide, or polypeptide fragment or variant of a G-protein chemokine receptor, wherein said antibodies comprise, or alternatively consist of, a polypeptide having an amino acid sequence of any one, two, three, or more of the VL CDRs contained in a light chain expressed by one or more antibodies of the invention. In particular, the invention provides antibodies that specifically bind a G-protein chemokine receptor, comprising, or alternatively consisting of, a polypeptide having the amino acid sequence of a VL CDR1 contained in a light chain expressed by one or more antibodies of the invention. In another embodiment, antibodies that specifically bind a G-protein chemokine receptor, comprise, or alternatively consist of, a polypeptide having the amino acid sequence of a VL CDR2 contained in a light chain expressed by one or more antibodies of the invention. In a preferred embodiment, antibodies that specifically bind a G-protein chemokine receptor, comprise, or alternatively consist of a polypeptide having the amino acid sequence of a VL CDR3 contained in a light chain expressed by one or more antibodies of the invention. Molecules comprising, or alternatively consisting of, these antibodies, or antibody fragments or variants thereof, that specifically bind to G-protein chemokine receptor or a G-protein chemokine receptor fragment or variant thereof are also encompassed by the invention, as are nucleic acid molecules encoding these antibodies, molecules, fragments and/or variants.

The present invention also provides antibodies (including molecules comprising, or alternatively consisting of, antibody fragments or variants) that specifically bind to a G-protein chemokine receptor polypeptide or polypeptide fragment or variant of a G-protein chemokine receptor, wherein said antibodies comprise, or alternatively consist of, one, two, three, or more VH CDRs and one, two, three or more VL CDRs, as contained in a heavy chain or light chain expressed by one or more antibodies of the invention. In particular, the invention provides for antibodies that specifically bind to a polypeptide or polypeptide fragment or variant of a G-protein chemokine receptor, wherein said antibodies comprise, or alternatively consist of, a VH CDR1 and a VL CDR1, a VH CDR1 and a VL CDR2, a VH CDR1 and a VL CDR3, a VH CDR2 and a VL CDR1, VH CDR2 and VL CDR2, a VH CDR2 and a VL CDR3, a VH CDR3 and a VH CDR1, a VH CDR3 and a VL CDR2, a VH CDR3 and a VL CDR3, or any combination thereof, of the VH CDRs and VL CDRs contained in a heavy chain or light chain expressed by one or more antibodies of the invention. Molecules comprising, or alternatively consisting of, fragments or variants of these antibodies that specifically bind to G-protein chemokine receptor are also encompassed by the invention, as are nucleic acid molecules encoding these antibodies, molecules, fragments or variants.

Nucleic Acid Molecules Encoding Anti-G-protein Chemokine Receptor Antibodies

The present invention also provides for nucleic acid molecules, generally isolated, encoding an antibody of the invention (including molecules comprising, or alternatively consisting of, antibody fragments or variants thereof). In a specific embodiment, a nucleic acid molecule of the invention encodes an antibody (including molecules comprising, or alternatively consisting of, antibody fragments or variants thereof), comprising, or alternatively consisting of, a VH domain having an amino acid sequence of any one of the VH domains of a heavy chain expressed by at least one of the antibodies of the invention and a VL domain having an amino acid sequence of a light chain expressed by at least one of the antibodies of the invention. In another embodiment, a nucleic acid molecule of the invention encodes an antibody (including molecules comprising, or alternatively consisting of, antibody fragments or variants thereof, comprising, or alternatively consisting of, a VH domain having an amino acid sequence of any one of the VH domains of a heavy chain expressed by at least one of the antibodies of the invention or a VL domain having an amino acid sequence of a light chain expressed by at least one of the antibodies of the invention.

The present invention also provides antibodies that comprise, or alternatively consist of, variants (including derivatives) of the antibody molecules (e.g., the VH domains and/or VL domains) described herein, which antibodies specifically bind to a G-protein chemokine receptor or fragment or variant thereof. Standard techniques known to those of skill in the art can be used to introduce mutations in the nucleotide sequence encoding a molecule of the invention, including, for example, site-directed mutagenesis and PCR-mediated mutagenesis which result in amino acid substitutions. Preferably, the variants (including derivatives) encode less than 50 amino acid substitutions, less than 40 amino acid substitutions, less than 30 amino acid substitutions, less than 25 amino acid substitutions, less than 20 amino acid substitutions, less than 15 amino acid substitutions, less than 10 amino acid substitutions, less than 5 amino acid substitutions, less than 4 amino acid substitutions, less than 3 amino acid substitutions, or less than 2 amino acid substitutions relative to the reference VH domain, VHCDR1, VHCDR2, VHCDR3, VL domain, VLCDR1, VLCDR2, or VLCDR3. A "conservative amino acid substitution" is one in which the amino acid residue is replaced with an amino acid residue having a side chain with a similar charge. Families of amino acid residues having side chains with similar charges have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Alternatively, mutations can be introduced randomly along all or part of the coding sequence, such as by saturation mutagenesis, and the resultant mutants can be screened for biological activity to identify mutants that retain activity (e.g., the ability to bind a G-protein chemokine receptor).

For example, it is possible to introduce mutations only in framework regions or only in CDR regions of an antibody molecule. Introduced mutations may be silent or neutral missense mutations, i.e., have no, or little, effect on an antibody's ability to bind antigen. These types of mutations may be useful to optimize codon usage, or improve a hybriodma's antibody production. Alternatively, non-neutral missense mutations may alter an antibody's ability to bind antigen. The location of most silent and neutral missense mutations is likely to be in the framework regions, while the location of most non-neutral missense mutations is likely to be in CDR, though this is not an absolute requirement. One of skill in the art would be able to design and test mutant molecules with desired properties such as no alteration in antigen binding activity or alteration in binding activity (e.g., improvements in antigen binding activity or change in antibody specificity). Following mutagenesis, the encoded protein may routinely be expressed and the functional and/or biological activity of the encoded protein, (e.g., ability to specifically, bind a G-protein chemokine receptor) can be determined using techniques described herein or by routinely modifying techniques known in the art.

In a specific embodiment, an antibody of the invention (including a molecule comprising, or alternatively consisting of, an antibody fragment or variant thereof), that specifically binds G-protein chemokine receptor polypeptides or fragments or variants thereof, comprises, or alternatively consists of, an amino acid sequence encoded by a nucleotide sequence that hybridizes to a nucleotide sequence that is complementary to that encoding one of the VH or VL domains expressed by one or more the antibodies of the invention under stringent conditions, e.g., hybridization to filter-bound DNA in 6× sodium chloride/sodium citrate (SSC) at about 45° C. followed by one or more washes in 0.2×SSC/0.1% SDS at about 50-65° C., under highly stringent conditions, e.g., hybridization to filter-bound nucleic acid in 6×SSC at about 45° C. followed by one or more washes in 0.1×SSC/0.2% SDS at about 68° C., or under other stringent hybridization conditions which are known to those of skill in the art (see, for example, Ausubel, F. M. et al., eds., 1989, *Current Protocols in Molecular Biology*, Vol. I, Green Publishing Associates, Inc. and John Wiley & Sons, Inc., New York at pages 6.3.1-6.3.6 and 2.10.3). Nucleic acid molecules encoding these antibodies are also encompassed by the invention.

It is well known within the art that polypeptides, or fragments or variants thereof, with similar amino acid sequences often have similar structure and many of the same biological activities. Thus, in one embodiment an antibody (including a molecule comprising, or alternatively consisting of, an antibody fragment or variant thereof), that specifically binds to a G-protein chemokine receptor polypeptide or fragments or variants of a G-protein chemokine receptor polypeptide, comprises, or alternatively consists of, a VH domain having an amino acid sequence that is at least 35%, at least 40%, at least 45%, at least 50%, at least 55%, at least 60%, at least 65%, at least 70%, at least 75%, at least 80%, at least 85%, at least 90%, at least 95%, or at least 99% identical, to the amino acid sequence of a VH domain of a heavy chain expressed by at least one of the antibodies of the invention.

In another embodiment, an antibody (including a molecule comprising, or alternatively consisting of, an antibody fragment or variant thereof), that specifically binds to a G-protein chemokine receptor polypeptide or fragments or variants of a G-protein chemokine receptor polypeptide, comprises, or alternatively consists of, a VL domain having an amino acid sequence that is at least 35%, at least 40%, at least 45%, at least 50%, at least 55%, at least 60%, at least 65%, at least 70%, at least 75%, at least 80%, at least 85%, at least 90%, at least 95%, or at least 99% identical, to the amino acid sequence of a VL domain of a light chain expressed by at least one of the antibodies of the invention.

Polynucleotides Encoding Antibodies

Antibodies of the invention (including antibody fragments or variants) can be produced by any method known in the art. For example, it will be appreciated that antibodies in accordance with the present invention can be expressed in cell lines other than hybridoma cell lines. Sequences encoding the cDNAs or genomic clones for the particular antibodies can be used for transformation of a suitable mammalian or nonmammalian host cells or to generate phage display libraries, for example. Additionally, polypeptide antibodies of the invention may be chemically synthesized or produced through the use of recombinant expression systems.

One way to produce the antibodies of the invention would be to clone the VH and/or VL domains expressed by any one or more of the antibodies of the invention. In order to isolate the VH and VL domains from a suitable protein source (e.g., scfv expression construct or hybridoma cell lines), PCR primers including VH or VL nucleotide sequences (See Example 13), may be used to amplify the expressed VH and VL sequences. The PCR products may then be cloned using vectors, for example, which have a PCR product cloning site consisting of a 5' and 3' single T nucleotide overhang, that is complementary to the overhanging single adenine nucleotide added onto the 5' and 3' end of PCR products by many DNA polymerases used for PCR reactions. The VH and VL domains can then be sequenced using conventional methods known in the art.

The cloned VH and VL genes may be placed into one or more suitable expression vectors. By way of non-limiting example, PCR primers including VH or VL nucleotide sequences, a restriction site, and a flanking sequence to protect the restriction site may be used to amplify the VH or VL sequences. Utilizing cloning techniques known to those of skill in the art, the PCR amplified VH domains may be cloned into vectors expressing the appropriate immunoglobulin constant region, e.g., the human IgG1 or IgG4 constant region for VH domains, and the human kappa or lambda constant regions for kappa and lambda VL domains, respectively. Preferably, the vectors for expressing the VH or VL domains comprise a promoter suitable to direct expression of the heavy and light chains in the chosen expression system, a secretion signal, a cloning site for the immunoglobulin variable domain, immunoglobulin constant domains, and a selection marker such as neomycin. The VH and VL domains may also be cloned into a single vector expressing the necessary constant regions. The heavy chain conversion vectors and light chain conversion vectors are then co-transfected into cell lines to generate stable or transient cell lines that express full-length antibodies, e.g., IgG, using techniques known to those of skill in the art (See, for example, Guo et al., J. Clin. Endocrinol. Metab. 82:925-31 (1997), and Ames et al., J. Immunol. Methods 184:177-86 (1995) which are herein incorporated in their entireties by reference).

The invention further provides polynucleotides comprising a nucleotide sequence encoding an antibody of the invention and fragments thereof. The invention also encompasses polynucleotides that hybridize under stringent or lower stringency hybridization conditions, e.g., as defined supra, to polynucleotides that encode an antibody, preferably, that specifically binds to a polypeptide of the invention, preferably, an antibody that binds to a polypeptide having the amino acid sequence of SEQ ID NO:2 or more preferably SEQ ID NO:4.

The polynucleotides may be obtained, and the nucleotide sequence of the polynucleotides determined, by any method known in the art. For example, if the nucleotide sequence of the antibody is known, a polynucleotide encoding the antibody may be assembled from chemically synthesized oligonucleotides (e.g., as described in Kutmeier et al., BioTechniques 17:242 (1994)), which, briefly, involves the synthesis of overlapping oligonucleotides containing portions of the sequence encoding the antibody, annealing and ligating of those oligonucleotides, and then amplification of the ligated oligonucleotides by PCR.

Alternatively, a polynucleotide encoding an antibody may be generated from nucleic acid from a suitable source. If a clone containing a nucleic acid encoding a particular antibody is not available, but the sequence of the antibody molecule is known, a nucleic acid encoding the immunoglobulin may be chemically synthesized or obtained from a suitable source (e.g., an antibody cDNA library, or a cDNA library generated from, or nucleic acid, preferably poly A+ RNA, isolated from, any tissue or cells expressing the antibody, such as hybridoma cells selected to express an antibody of the invention) by PCR amplification using synthetic primers hybridizable to the 3' and 5' ends of the sequence or by cloning using an oligonucleotide probe specific for the particular gene sequence to identify, e.g., a cDNA clone from a cDNA library that encodes the antibody. Amplified nucleic acids generated by PCR may then be cloned into replicable cloning vectors using any method well known in the art.

Once the nucleotide sequence and corresponding amino acid sequence of the antibody is determined, the nucleotide sequence of the antibody may be manipulated using methods well known in the art for the manipulation of nucleotide sequences, e.g., recombinant DNA techniques, site directed mutagenesis, PCR, etc. (see, for example, the techniques described in Sambrook et al., 1990, Molecular Cloning, A Laboratory Manual, 2d Ed., Cold Spring Harbor Laboratory, Cold Spring Harbor, N.Y. and Ausubel et al., eds., 1998, Current Protocols in Molecular Biology, John Wiley & Sons, NY, which are both incorporated by reference herein in their entireties), to generate antibodies having a different amino acid sequence, for example to create amino acid substitutions, deletions, and/or insertions.

In a specific embodiment, the amino acid sequence of the heavy and/or light chain variable domains may be inspected to identify the sequences of the complementarity determining regions (CDRs) by methods that are well known in the art, e.g., by comparison to known amino acid sequences of other heavy and light chain variable regions to determine the regions of sequence hypervariability. Using routine recombinant DNA techniques, one or more of the CDRs may be inserted within framework regions, e.g., into human framework regions to humanize a non-human antibody, as described supra. The framework regions may be naturally occurring or consensus framework regions, and preferably human framework regions (see, e.g., Chothia et al., J. Mol. Biol. 278: 457-479 (1998) for a listing of human framework regions). Preferably, the polynucleotide generated by the combination of the framework regions and CDRs encodes an antibody that specifically binds a polypeptide of the invention. Preferably, as discussed supra, one or more amino acid substitutions may be made within the framework regions, and, preferably, the amino acid substitutions improve binding of the antibody to its antigen. Additionally, such methods may be used to make amino acid substitutions or deletions of one or more variable region cysteine residues participating in an intrachain disulfide bond to generate antibody molecules lacking one or more intrachain disulfide bonds. Other alterations to the polynucleotide are encompassed by the present invention and within the skill of the art.

For some uses, such as for in vitro affinity maturation of an antibody of the invention, it may be useful to express the VH and VL domains of the heavy and light chains of one or more antibodies of the invention as single chain antibodies or Fab fragments in a phage display library. For example, the cDNAs encoding the VH and VL domains of one or more antibodies of the invention may be expressed in all possible combinations using a phage display library, allowing for the selection of VH/VL combinations that bind a G-protein chemokine receptor polypeptide with preferred binding characteristics such as improved affinity or improved off rates. Additionally, VH and VL segments—the CDR regions of the VH and VL domains of one or more antibodies of the invention, in particular, may be mutated in vitro. Expression of VH and VL domains with "mutant" CDRs in a phage display library allows for the selection of VH/VL combinations that bind a G-protein chemokine receptor receptor polypeptides with preferred binding characteristics such as improved affinity or improved off rates.

In phage display methods, functional antibody domains are displayed on the surface of phage particles which carry the polynucleotide sequences encoding them. In particular, DNA sequences encoding VH and VL domains are amplified from animal cDNA libraries (e.g., human or murine cDNA libraries of lymphoid tissues) or synthetic cDNA libraries. The DNA encoding the VH and VL domains are joined together by an scFv linker by PCR and cloned into a phagemid vector (e.g., p CANTAB 6 or pComb 3 HSS). The vector is electroporated in E. coli and the E. coli is infected with helper phage. Phage used in these methods are typically filamentous phage including fd and M13 and the VH and VL domains are usually recombinantly fused to either the phage gene III or gene VIII. Phage expressing an antigen binding domain that binds to an antigen of interest (i.e., a G-protein chemokine receptor polypeptide or a fragment thereof) can be selected or identified with antigen, e.g., using labeled antigen or antigen bound or captured to a solid surface or bead. Examples of phage display methods that can be used to make the antibodies of the present invention include, but are not limited to, those disclosed in Brinkman et al., J. Immunol. Methods 182:41-50 (1995); Ames et al., J. Immunol. Methods 184: 177-186 (1995); Kettleborough et al., Eur. J. Immunol. 24:952-958 (1994); Persic et al., Gene 187 9-18 (1997); Burton et al., Advances in Immunology 57:191-280(1994); PCT application No. PCT/GB91/O1 134; PCT publications WO 90/02809; WO 91/10737; WO 92/01047; WO 92/18719; WO 93/1 1236; WO 95/15982; WO 95/20401; WO97/13844; and U.S. Pat. Nos. 5,698,426; 5,223,409; 5,403,484; 5,580,717; 5,427,908; 5,750,753; 5,821,047; 5,571,698; 5,427,908; 5,516,717; 5,780,225; 5,658,727; 5,735,743 and 5,969,108; each of which is incorporated herein by reference in its entirety.

In addition, techniques developed for the production of "chimeric antibodies" (Morrison et al., Proc. Natl. Acad. Sci. 81:851-855 (1984); Neuberger et al., Nature 312:604-608 (1984); Takeda et al., Nature 314:452-454 (1985)) by splicing genes from a mouse antibody molecule of appropriate antigen specificity together with genes from a human antibody molecule of appropriate biological activity can be used. As described supra, a chimeric antibody is a molecule in which different portions are derived from different animal species, such as those having a variable region derived from a murine mAb and a human immunoglobulin constant region, e.g., humanized antibodies.

Alternatively, techniques described for the production of single chain antibodies (U.S. Pat. No. 4,946,778; Bird, Science 242:423-42 (1988); Huston et al., Proc. Natl. Acad. Sci. USA 85:5879-5883 (1988); and Ward et al., Nature 334:544-54 (1989)) can be adapted to produce single chain antibodies. Single chain antibodies are formed by linking the heavy and light chain fragments of the Fv region via an amino acid bridge, resulting in a single chain polypeptide. Techniques for the assembly of functional Fv fragments in *E. coli* may also be used (Skerra et al., Science 242:1038-1041 (1988)).

Methods of Producing Antibodies

The antibodies of the invention can be produced by any method known in the art for the synthesis of antibodies, in particular, by chemical synthesis, by intracellular immunization (i.e., intrabody technology), or preferably, by recombinant expression techniques. Methods of producing antibodies include, but are not limited to, hybridoma technology, EBV transformation, and other methods discussed herein as well as through the use recombinant DNA technology, as discussed below.

Recombinant expression of an antibody of the invention, or fragment, derivative, variant or analog thereof, (e.g., a heavy or light chain of an antibody of the invention or a single chain antibody of the invention), requires construction of an expression vector containing a polynucleotide that encodes the antibody. Once a polynucleotide encoding an antibody molecule or a heavy or light chain of an antibody, or portion thereof (preferably containing the heavy or light chain variable domain), of the invention has been obtained, the vector for the production of the antibody molecule may be produced by recombinant DNA technology using techniques well known in the art. Thus, methods for preparing a protein by expressing a polynucleotide containing an antibody encoding nucleotide sequence are described herein. Methods which are well known to those skilled in the art can be used to construct expression vectors containing antibody coding sequences and appropriate transcriptional and translational control signals. These methods include, for example, in vitro recombinant DNA techniques, synthetic techniques, and in vivo genetic recombination. The invention, thus, provides replicable vectors comprising a nucleotide sequence encoding an antibody molecule of the invention, or a heavy or light chain thereof, or a heavy or light chain variable domain, operably linked to a promoter. Such vectors may include the nucleotide sequence encoding the constant region of the antibody molecule (see, e.g., PCT Publication WO 86/05807; PCT Publication WO 89/01036; and U.S. Pat. No. 5,122,464) and the variable domain of the antibody may be cloned into such a vector for expression of the entire heavy or light chain.

The expression vector is transferred to a host cell by conventional techniques and the transfected cells are then cultured by conventional techniques to produce an antibody of the invention. Thus, the invention includes host cells containing a polynucleotide encoding an antibody of the invention, or a heavy or light chain thereof, or a single chain antibody of the invention, operably linked to a heterologous promoter. In preferred embodiments for the expression of double-chained antibodies, vectors encoding both the heavy and light chains may be co-expressed in the host cell for expression of the entire immunoglobulin molecule, as detailed below.

A variety of host-expression vector systems may be utilized to express the antibody molecules of the invention. Such host-expression systems represent vehicles by which the coding sequences of interest may be produced and subsequently purified, but also represent cells which may, when transformed or transfected with the appropriate nucleotide coding sequences, express an antibody molecule of the invention in situ. These include but are not limited to microorganisms such as bacteria (e.g., *E. coli, B. subtilis*) transformed with recombinant bacteriophage DNA, plasmid DNA or cosmid DNA expression vectors containing antibody coding sequences; yeast (e.g., Saccharomyces, Pichia) transformed with recombinant yeast expression vectors containing antibody coding sequences; insect cell systems infected with recombinant virus expression vectors (e.g., baculovirus) containing antibody coding sequences; plant cell systems infected with recombinant virus expression vectors (e.g., cauliflower mosaic virus, CaMV; tobacco mosaic virus, TMV) or transformed with recombinant plasmid expression vectors (e.g., Ti plasmid) containing antibody coding sequences; or mammalian cell systems (e.g., COS, CHO, BHK, 293, 3T3, NSO cells) harboring recombinant expression constructs containing promoters derived from the genome of mammalian cells (e.g., metallothionein promoter) or from mammalian viruses (e.g., the adenovirus late promoter; the vaccinia virus 7.5K promoter). Preferably, bacterial cells such as *Escherichia coli*, and more preferably, eukaryotic cells, especially for the expression of whole recombinant antibody molecule, are used for the expression of a recombinant antibody molecule. For example, mammalian cells such as Chinese hamster ovary cells (CHO), in conjunction with a vector such as the major intermediate early gene promoter element from human cytomegalovirus is an effective expression system for antibodies (Foecking et al., Gene 45:101 (1986); Cockett et al., Bio/Technology 8:2 (1990)).

In bacterial systems, a number of expression vectors may be advantageously selected depending upon the use intended for the antibody molecule being expressed. For example, when a large quantity of such a protein is to be produced, for the generation of pharmaceutical compositions of an antibody molecule, vectors which direct the expression of high levels of fusion protein products that are readily purified may be desirable. Such vectors include, but are not limited, to the *E. coli* expression vector pUR278 (Ruther et al., EMBO J. 2:1791 (1983)), in which the antibody coding sequence may be ligated individually into the vector in frame with the lac Z coding region so that a fusion protein is produced; pIN vectors (Inouye & Inouye, Nucleic Acids Res. 13:3101-3109 (1985); Van Heeke & Schuster, J. Biol. Chem. 24:5503-5509 (1989)); and the like. pGEX vectors may also be used to express foreign polypeptides as fusion proteins with glutathione S-transferase (GST). In general, such fusion proteins are soluble and can easily be purified from lysed cells by adsorption and binding to matrix glutathione-agarose beads followed by elution in the presence of free glutathione. The pGEX vectors are designed to include thrombin or factor Xa protease cleavage sites so that the cloned target gene product can be released from the GST moiety.

In an insect system, *Autographa californica* nuclear polyhedrosis virus (AcNPV) is used as a vector to express foreign genes. The virus grows in *Spodoptera frugiperda* cells. The antibody coding sequence may be cloned individually into non-essential regions (for example the polyhedrin gene) of the virus and placed under control of an AcNPV promoter (for example the polyhedrin promoter).

In mammalian host cells, a number of viral-based expression systems may be utilized. In cases where an adenovirus is used as an expression vector, the antibody coding sequence of interest may be ligated to an adenovirus transcription/translation control complex, e.g., the late promoter and tripartite leader sequence. This chimeric gene may then be inserted in the adenovirus genome by in vitro or in vivo recombination. Insertion in a non-essential region of the viral genome (e.g., region E1 or E3) will result in a recombinant virus that is viable and capable of expressing the antibody molecule in infected hosts. (e.g., see Logan & Shenk, Proc. Natl. Acad. Sci. USA 81:355-359 (1984)). Specific initiation signals may also be required for efficient translation of inserted antibody coding sequences. These signals include the ATG initiation codon and adjacent sequences. Furthermore, the initiation codon must be in phase with the reading frame of the desired coding sequence to ensure translation of the entire insert. These exogenous translational control signals and initiation codons can be of a variety of origins, both natural and synthetic. The efficiency of expression may be enhanced by the inclusion of appropriate transcription enhancer elements, transcription terminators, etc. (see Bittner et al., Methods in Enzymol. 153:51-544 (1987)).

In addition, a host cell strain may be chosen which modulates the expression of the inserted sequences, or modifies and processes the gene product in the specific fashion desired. Such modifications (e.g., glycosylation) and processing (e.g., cleavage) of protein products may be important for the function of the protein. Different host cells have characteristic and specific mechanisms for the post-translational processing and modification of proteins and gene products. Appropriate cell lines or host systems can be chosen to ensure the correct modification and processing of the foreign protein expressed. To this end, eukaryotic host cells which possess the cellular machinery for proper processing of the primary transcript, glycosylation, and phosphorylation of the gene product may be used. Such mammalian host cells include but are not limited to CHO, VERY, BHK, Hela, COS, MDCK, 293, 3T3, W138, and in particular, breast cancer cell lines such as, for example, BT483, Hs578T, HTB2, BT20 and T47D, and normal mammary gland cell line such as, for example, CRL7030 and Hs578Bst.

For long-term, high-yield production of recombinant proteins, stable expression is preferred. For example, cell lines which stably express the antibody molecule may be engineered. Rather than using expression vectors which contain viral origins of replication, host cells can be transformed with DNA controlled by appropriate expression control elements (e.g., promoter, enhancer, sequences, transcription terminators, polyadenylation sites, etc.), and a selectable marker. Following the introduction of the foreign DNA, engineered cells may be allowed to grow for 1-2 days in an enriched media, and then are switched to a selective media. The selectable marker in the recombinant plasmid confers resistance to the selection and allows cells to stably integrate the plasmid into their chromosomes and grow to form foci which in turn can be cloned and expanded into cell lines. This method may advantageously be used to engineer cell lines which express the antibody molecule. Such engineered cell lines may be particularly useful in screening and evaluation of compounds that interact directly or indirectly with the antibody molecule.

A number of selection systems may be used, including but not limited to the herpes simplex virus thymidine kinase (Wigler et al., Cell 11:223 (1977)), hypoxanthine-guanine phosphoribosyltransferase (Szybalska & Szybalski, Proc. Natl. Acad. Sci. USA 48:202 (1992)), and adenine phosphoribosyltransferase (Lowy et al., Cell 22:817 (1980)) genes can be employed in tk-, hgprt- or aprt-cells, respectively. Also, antimetabolite resistance can be used as the basis of selection for the following genes: dhfr, which confers resistance to methotrexate (Wigler et al., Natl. Acad. Sci. USA 77:357 (1980); O'Hare et al., Proc. Natl. Acad. Sci. USA 78:1527 (1981)); gpt, which confers resistance to mycophenolic acid (Mulligan & Berg, Proc. Natl. Acad. Sci. USA 78:2072 (1981)); neo, which confers resistance to the aminoglycoside G-418 Clinical Pharmacy 12:488-505; Wu and Wu, Biotherapy 3:87-95 (1991); Tolstoshev, Ann. Rev. Pharmacol. Toxicol. 32:573-596 (1993); Mulligan, Science 260:926-932 (1993); and Morgan and Anderson, Ann. Rev. Biochem. 62:191-217 (1993); May, 1993, TIB TECH 11(5):155-215); and hygro, which confers resistance to hygromycin (Santerre et al., Gene 30:147 (1984)). Methods commonly known in the art of recombinant DNA technology may be routinely applied to select the desired recombinant clone, and such methods are described, for example, in Ausubel et al. (eds.), Current Protocols in Molecular Biology, John Wiley & Sons, NY (1993); Kriegler, Gene Transfer and Expression, A Laboratory Manual, Stockton Press, NY (1990); and in Chapters 12 and 13, Dracopoli et al. (eds), Current Protocols in Human Genetics, John Wiley & Sons, NY (1994); Colberre-Garapin et al., J. Mol. Biol. 150:1 (1981), which are incorporated by reference herein in their entireties.

The expression levels of an antibody molecule can be increased by vector amplification (for a review, see Bebbington and Hentschel, The use of vectors based on gene amplification for the expression of cloned genes in mammalian cells in DNA cloning, Vol.3. (Academic Press, New York, 1987)). When a marker in the vector system expressing antibody is amplifiable, increase in the level of inhibitor present in culture of host cell will increase the number of copies of the marker gene. Since the amplified region is associated with the antibody gene, production of the antibody will also increase (Crouse et al., Mol. Cell. Biol. 3:257 (1983)).

Vectors which use glutamine synthase (GS) or DAFR as the selectable markers can be amplified in the presence of the drugs methionine sulphoximine or methotrexate, respectively. An advantage of glutamine synthase based vectors are the availability of cell lines (e.g., the murine myeloma cell line, NSO) which are glutamine synthase negative. Glutamine synthase expression systems can also function in glutamine synthase expressing cells (e.g. Chinese Hamster Ovary (CHO) cells) by providing additional inhibitor to prevent the functioning of the endogenous gene. Vectors that use glutamine synthase as the selectable marker include, but are not limited to, the pEE6 expression vector described in Stephens and Cockett, *Nucl. Acids. Res* 17:7110 (1989). A glutamine synthase expression system and components thereof are detailed in PCT-publications: WO87/04462; WO86/05807; WO89/01036; WO89/10404; and WO91/06657 which are incorporated in their entireties by reference herein. Additionally, glutamine synthase expression vectors that may be used according to the present invention are commercially available from suppliers, including, for example Lonza Biologics, Inc. (Portsmouth, N.H.). Expression and production of monoclonal antibodies using a GS expression system in murine myeloma cells is described in Bebbington et al., *Bio/technology* 10:169(1992) and in Biblia and Robinson *Biotechnol. Prog.* 11:1 (1995) which are incorporated in their entireties by reference herein.

The host cell may be co-transfected with two expression vectors of the invention, the first vector encoding a heavy chain derived polypeptide and the second vector encoding a light chain derived polypeptide. The two vectors may contain identical selectable markers which enable equal expression of heavy and light chain polypeptides. Alternatively, a single vector may be used which encodes, and is capable of expressing, both heavy and light chain polypeptides. In such situations, the light chain should be placed before the heavy chain to avoid an excess of toxic free heavy chain (Proudfoot, Nature 322:52 (1986); Kohler, Proc. Natl. Acad. Sci. USA 77:2197 (1980)). The coding sequences for the heavy and light chains may comprise cDNA or genomic DNA.

Once an antibody molecule of the invention has been produced by an animal, chemically synthesized, or recombinantly expressed, it may be purified by any method known in the art for purification of an immunoglobulin molecule, for example, by chromatography (e.g., ion exchange, affinity, particularly by affinity for the specific antigen after Protein A, and sizing column chromatography), centrifugation, differential solubility, or by any other standard technique for the purification of proteins. In addition, the antibodies of the present invention or fragments thereof can be fused to heterologous polypeptide sequences described herein or otherwise known in the art, to facilitate purification.

Antibody Conjugates

The present invention encompasses antibodies recombinantly fused or chemically conjugated (including both covalently and non-covalently conjugations) to a polypeptide (or portion thereof, preferably at least 10, 20, 30, 40, 50, 60, 70, 80, 90 or 100 amino acids of the polypeptide) of the present invention to generate fusion proteins. The fusion does not necessarily need to be direct, but may occur through linker sequences. The antibodies may be specific for antigens other than polypeptides (or portion thereof, preferably at least 10, 20, 30, 40, 50, 60, 70, 80, 90 or 100 amino acids of the polypeptide) of the present invention. For example, antibodies may be used to target the polypeptides of the present invention to particular cell types, either in vitro or in vivo, by fusing or conjugating the polypeptides of the present invention to antibodies specific for particular cell surface receptors. Polypeptides and/or antibodies of the present invention (including fragments or variants thereof) may be fused to either the N- or C-terminal end of the heterologous protein (e.g., immunoglobulin Fc polypeptide or human serum albumin polypeptide). Antibodies of the invention may also be fused to albumin (including but not limited to recombinant human serum albumin (see, e.g., U.S. Pat. No. 5,876,969, issued Mar. 2, 1999, EP Patent 0 413 622, and U.S. Pat. No. 5,766,883, issued Jun. 16, 1998, herein incorporated by reference in their entirety)), resulting in chimeric polypeptides. In a preferred embodiment, polypeptides and/or antibodies of the present invention (including fragments or variants thereof) are fused with the mature form of human serum albumin (i.e., amino acids 1-585 of human serum albumin as shown in FIGS. 1 and 2 of EP Patent 0 322 094) which is herein incorporated by reference in its entirety. In another preferred embodiment, polypeptides and/or antibodies of the present invention (including fragments or variants thereof) are fused with polypeptide fragments comprising, or alternatively consisting of, amino acid residues 1-z of human serum albumin, where z is an integer from 369 to 419, as described in U.S. Pat. No. 5,766,883 herein incorporated by reference in its entirety. Polynucleotides encoding fusion proteins of the invention are also encompassed by the invention. Such fusion proteins may, for example, facilitate purification and may increase half-life in vivo. Antibodies fused or conjugated to the polypeptides of the present invention may also be used in in vitro immunoassays and purification methods using methods known in the art. See e.g., Harbor et al., supra, and PCT publication WO 93/21232; EP 439,095; Naramura et al., Immunol. Lett. 39:91-99 (1994); U.S. Pat. No. 5,474,981; Gillies et at., PNAS 89:1428-1432 (1992); Fell et al., J. Immunol. 146: 2446-2452(1991), which are incorporated by reference in their entireties.

The present invention further includes compositions comprising the polypeptides of the present invention fused or conjugated to antibody domains other than the variable regions. For example, the polypeptides of the present invention may be fused or conjugated to an antibody Fc region, or portion thereof. The antibody portion fused to a polypeptide of the present invention may comprise the constant region, hinge region, CH1 domain, CH2 domain, and CH3 domain or any combination of whole domains or portions thereof. The polypeptides may also be fused or conjugated to the above antibody portions to form multimers. For example, Fc portions fused to the polypeptides of the present invention can form dimers through disulfide bonding between the Fc portions. Higher multimeric forms can be made by fusing the polypeptides to portions of IgA and IgM. Methods for fusing or conjugating the polypeptides of the present invention to antibody portions are known in the art. See, e.g., U.S. Pat. Nos. 5,336,603; 5,622,929; 5,359,046; 5,349,053; 5,447,851; 5,112,946; EP 307,434; EP 367,166; PCT publications WO 96/04388; WO 91/06570; Ashkenazi et al., Proc. Natl. Acad. Sci. USA 88:10535-10539 (1991); Zheng et al., J. Immunol. 154:5590-5600 (1995); and Vil et al., Proc. Natl. Acad. Sci. USA 89:11337-11341(1992) (said references incorporated by reference in their entireties).

As discussed, supra, the polypeptides corresponding to a polypeptide, polypeptide fragment, or a variant of SEQ ID NO:2 or SEQ ID NO:4 may be fused or conjugated to the above antibody portions to increase the in vivo half life of the polypeptides or for use in immunoassays using methods known in the art. Further, the polypeptides corresponding to SEQ ID NO:2 or more preferably SEQ ID NO:4 may be fused or conjugated to the above antibody portions to facilitate purification. One reported example describes chimeric proteins consisting of the first two domains of the human CD4-polypeptide and various domains of the constant regions of the heavy or light chains of mammalian immunoglobulins. (EP 394,827; Traunecker et al., Nature 331:84-86 (1988). The polypeptides of the present invention fused or conjugated to an antibody having disulfide-linked dimeric structures (due to the IgG) may also be more efficient in binding and neutralizing other molecules, than the monomeric secreted protein or protein fragment alone. (Fountoulakis et al., J. Biochem. 270: 3958-3964 (1995)). In many cases, the Fc part in a fusion protein is beneficial in therapy and diagnosis, and thus can result in, for example, improved pharmacokinetic properties. (EP A 232,262). Alternatively, deleting the Fc part after the fusion protein has been expressed, detected, and purified, would be desired. For example, the Fc portion may hinder therapy and diagnosis if the fusion protein is used as an antigen for immunizations. In drug discovery, for example, human proteins, such as hIL-5, have been fused with Fc portions for the purpose of high-throughput screening assays to identify antagonists of hIL-5. (See, Bennett et al., J. Molecular Recognition 8:52-58 (1995); Johanson et al., J. Biol. Chem. 270:9459-9471 (1995).

Moreover, the antibodies or fragments thereof of the present invention can be fused to marker sequences, such as a peptide to facilitate purification. In preferred embodiments, the marker amino acid sequence is a hexa-histidine peptide, such as the tag provided in a pQE vector (QFAGEN, Inc., 9259 Eton Avenue, Chatsworth, Calif., 91311), among others, many of which are commercially available. As described in Gentz et al., Proc. Natl. Acad. Sci USA 86:821-824 (1989), for instance, hexa-histidine provides for convenient purification of the fusion protein. Other peptide tags useful for purification include, but are not limited to, the "HA" tag, which corresponds to an epitope derived from the influenza hemagglutinin protein (Wilson et al., Cell 37:767 (1984)) and the "flag" tag.

The present invention further encompasses antibodies or fragments thereof conjugated to a diagnostic or therapeutic agent. The antibodies can be used diagnostically to, for example, monitor the development or progression of a tumor as part of a clinical testing procedure to, e.g., determine the efficacy of a given treatment regimen. Detection can be facilitated by coupling the antibody to a detectable substance. Examples of detectable substances include various enzymes, prosthetic groups, fluorescent materials, luminescent materials, bioluminescent materials, radioactive materials, positron emitting metals using various positron emission tomographies, and nonradioactive paramagnetic metal ions. The detectable substance may be coupled or conjugated either directly to the antibody (or fragment thereof) or indirectly, through an intermediate (such as, for example, a linker known in the art) using techniques known in the art. See, for example, U.S. Pat. No. 4,741,900 for metal ions which can be conjugated to antibodies for use as diagnostics according to the present invention. Examples of suitable enzymes include horseradish peroxidase, alkaline phosphatase, beta-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine; dichlorotriazinylamine fluorescein, dansyl chloride or phycoerythrin; an example of a luminescent material includes luminol; examples of bioluminescent materials include luciferase, luciferin, and aequorin; and examples of suitable radioactive material include iodine ($^{121}$I, $^{123}$I, $^{125}$I, $^{131}$I), carbon ($^{14}$C), sulfur ($^{35}$S), tritium ($^{3}$H), indium ($^{111}$In, $^{112}$In, $^{113m}$In, $^{115m}$In), technetium ($^{99}$Tc, $^{99m}$Tc), thallium ($^{201}$Ti), gallium ($^{68}$Ga, $^{67}$Ga), palladium ($^{103}$Pd), molybdenum ($^{99}$Mo), xenon ($^{133}$Xe), fluorine ($^{18}$F), $^{153}$Sm, $^{177}$Lu, $^{159}$Gd, $^{149}$Pm, $^{140}$La, $^{175}$Yb, $^{166}$Ho, $^{90}$Y, $^{47}$Sc, $^{186}$Re, $^{188}$Re, $^{142}$Pr, $^{105}$Rh, and $^{97}$Ru;

In specific embodiments, G-protein chemokine receptor polypeptides of the invention are attached to macrocyclic chelators useful for conjugating radiometal ions, including but not limited to, $^{111}$In, $^{177}$Lu, $^{90}$Y, $^{166}$Ho, and $^{153}$Sm, to polypeptides. In a preferred embodiment, the radiometal ion associated with the macrocyclic chelators attached to G-protein chemokine receptor polypeptides of the invention is $^{111}$In. In another preferred embodiment, the radiometal ion associated with the macrocyclic chelator attached to G-protein chemokine receptor polypeptides of the invention is $^{90}$Y. In specific embodiments, the macrocyclic chelator is 1,4,7, 10-tetraazacyclododecane-N,N',N",N"'-tetraacetic acid (DOTA). In other specific embodiments, the DOTA is attached to G-protein chemokine receptor polypeptide of the invention via a linker molecule. Examples of linker molecules useful for conjugating DOTA to a polypeptide are commonly known in the art—see, for example, DeNardo et al., Clin Cancer Res. 4(10):2483-90, 1998; Peterson et al., Bioconjug. Chem. 10(4):553-7, 1999; and Zimmerman et al, Nucl. Med. Biol. 26(8):943-50, 1999 which are hereby incorporated by reference in their entirety. In addition, U.S. Pat. Nos. 5,652, 361 and 5,756,065, which disclose chelating agents that may be conjugated to antibodies, and methods for making and using them, are hereby incorporated by reference in their entireties. Though U.S. Pat. Nos. 5,652,361 and 5,756,065 focus on conjugating chelating agents to antibodies, one skilled in the art could readily adapt the methods disclosed therein in order to conjugate chelating agents to other polypeptides.

A cytotoxin or cytotoxic agent includes any agent that is detrimental to cells. Examples include paclitaxol, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, and puromycin and analogs or homologs thereof. Therapeutic agents include, but are not limited to, antimetabolites (e.g., methotrexate, 6-mercaptopurine, 6-thioguanine, cytarabine, 5-fluorouracil decarbazine), alkylating agents (e.g., mechlorethamine, thioepa chlorambucil, melphalan, carmustine (BSNU) and lomustine (CCNU), cyclothosphamide, busulfan, dibromomannitol, streptozotocin, mitomycin C, and cis-dichlorodiamine platinum (II) (DDP) cisplatin), anthracyclines (e.g., daunorubicin (formerly daunomycin) and doxorubicin), antibiotics (e.g., dactinomycin (formerly actinomycin), bleomycin, mithramycin, and anthramycin (AMC)), and anti-mitotic agents (e.g., vincristine and vinblastine).

The antibody conjugates of the invention can be used for modifying a given biological response, the therapeutic agent or drug moiety is not to be construed as limited to classical chemical therapeutic agents. For example, the drug moiety may be a protein or polypeptide possessing a desired biological activity. Such proteins may include, for example, a toxin such as abrin, ricin A, pseudomonas exotoxin, or diphtheria toxin; a protein such as tumor necrosis factor, a-interferon, β-interferon, nerve growth factor, platelet derived growth factor, tissue plasminogen activator, an apoptotic agent, e.g., TNF-alpha, TNF-beta, AIM I (See, International Publication No. WO 97/33899), AIM II (See, International Publication No. WO 97/34911), Fas Ligand (Takahashi et al., *Int. Immunol.*, 6:1567-1574 (1994)), VEGI (See, International Publication No. WO 99/23105), a thrombotic agent or an anti-angiogenic agent, e.g., angiostatin or endostatin; or, biological response modifiers such as, for example, lymphokines, interleukin-1 ("IL-1"), interleukin-2 ("IL-2"), interleukin-6 ("IL-6"), granulocyte macrophage colony-stimulating factor ("GM-CSF"), granulocyte colony stimulating factor ("G-CSF"), or other growth factors.

Antibodies may also be attached to solid supports, which are particularly useful for immunoassays or purification of the target antigen. Such solid supports include, but are not limited to, glass, cellulose, polyacrylamide, nylon, polystyrene, polyvinyl chloride or polypropylene.

Techniques for conjugating such therapeutic moiety to antibodies are well known, see, e.g., Arnon et al., "Monoclonal Antibodies For Immunotargeting Of Drugs In Cancer Therapy", in Monoclonal Antibodies And Cancer Therapy, Reisfeld et al. (eds.), pp. 243-56 (Alan R. Liss, Inc. 1985); Hellstrom et al., "Antibodies For Drug Delivery", in Controlled Drug Delivery (2nd Ed.), Robinson et al. (eds.), pp. 623-53 (Marcel Dekker, Inc. 1987); Thorpe, "Antibody Carriers Of Cytotoxic Agents In Cancer Therapy: A Review", in Monoclonal Antibodies '84: Biological And Clinical Applications, Pinchera et al. (eds.), pp. 475-506 (1985); "Analysis, Results, And Future Prospective Of The Therapeutic Use Of Radiolabeled Antibody In Cancer Therapy", in Monoclonal Antibodies For Cancer Detection And Therapy, Baldwin et al. (eds.), pp. 303-16 (Academic Press 1985), and Thorpe et al., "The Preparation And Cytotoxic Properties Of Antibody-Toxin Conjugates", immunol. Rev. 62:119-58 (1982).

Alternatively, an antibody can be conjugated to a second antibody to form an antibody heteroconjugate as described by Segal in U.S. Pat. No. 4,676,980, which is incorporated herein by reference in its entirety.

An antibody, with or without a therapeutic moiety conjugated to it, administered alone or in combination with cytotoxic factor(s) and/or cytokine(s) can be used as a therapeutic.

Immunophenotyping

The antibodies of the invention may be utilized for immunophenotyping of cell lines and biological samples. The translation product of the gene of the present invention may be useful as a cell specific marker, or more specifically as a cellular marker that is differentially expressed at various stages of differentiation and/or maturation of particular cell types. Monoclonal antibodies directed against a specific epitope, or combination of epitopes, will allow for the screening of cellular populations expressing the marker. Various techniques can be utilized using monoclonal antibodies to screen for cellular populations expressing the marker(s), and include magnetic separation using antibody-coated magnetic beads, "panning" with antibody attached to a solid matrix (i.e., plate), and flow cytometry (See, e.g., U.S. Pat. No. 5,985,660; and Morrison et al., Cell, 96:737-49 (1999)).

These techniques allow for the screening of particular populations of cells, such as might be found with hematological malignancies (i.e. minimal residual disease (MRD) in acute leukemic patients) and "non-self" cells in transplantations to prevent Graft-versus-Host Disease (GVHD). Alternatively, these techniques allow for the screening of hematopoietic stem and progenitor cells capable of undergoing proliferation and/or differentiation, as might be found in human umbilical cord blood.

Assays For Antibody Binding

The antibodies of the invention may be assayed for specific binding by any method known in the art. The immunoassays which can be used include but are not limited to competitive and non-competitive assay systems using techniques such as BIAcore analysis, FACS (Fluorescence activated cell sorter) analysis, immunofluorescence, immunocytochemistry, western blots, radioimmunoassays, ELISA (enzyme linked immunosorbent assay), "sandwich" immunoassays, immunoprecipitation assays, precipitin reactions, gel diffusion precipitin reactions, immunodiffusion assays, agglutination assays, complement-fixation assays, immunoradiometric assays, fluorescent immunoassays, protein A immunoassays, to name but a few. Such assays are routine and well known in the art (see, e.g., Ausubel et al, eds, 1994, Current Protocols in Molecular Biology, Vol. 1, John Wiley & Sons, Inc., New York, which is incorporated by reference herein in its entirety). Exemplary immunoassays are described briefly below (but are not intended by way of limitation).

Immunoprecipitation protocols generally comprise lysing a population of cells in a lysis buffer such as RIPA buffer (1% NP-40 or Triton X-100, 1% sodium deoxycholate, 0.1% SDS, 0.15 M NaCl, 0.01 M sodium phosphate at pH 7.2, 1% Trasylol) supplemented with protein phosphatase and/or protease inhibitors (e.g., EDTA, PMSF, aprotinin, sodium vanadate), adding the antibody of interest to the cell lysate, incubating for a period of time (e.g., 1-4 hours) at 4° C., adding protein A and/or protein G sepharose beads to the cell lysate, incubating for about an hour or more at 4° C., washing the beads in lysis buffer and resuspending the beads in SDS/sample buffer. The ability of the antibody of interest to immunoprecipitate a particular antigen can be assessed by, e.g., western blot analysis. One of skill in the art would be knowledgeable as to the parameters that can be modified to increase the binding of the antibody to an antigen and decrease the background (e.g., pre-clearing the cell lysate with sepharose beads). For further discussion regarding immunoprecipitation protocols see, e.g., Ausubel et al, eds, 1994, Current Protocols in Molecular Biology, Vol. 1, John Wiley & Sons, Inc., New York at 10.16.1.

Western blot analysis generally comprises preparing protein samples, electrophoresis of the protein samples in a polyacrylamide gel (e.g., 8%-20% SDS-PAGE depending on the molecular weight of the antigen), transferring the protein sample from the polyacrylamide gel to a membrane such as nitrocellulose, PVDF or nylon, blocking the membrane in blocking solution (e.g., PBS with 3% BSA or non-fat milk), washing the membrane in washing buffer (e.g., PBS-Tween 20), blocking the membrane with primary antibody (the antibody of interest) diluted in blocking buffer, washing the membrane in washing buffer, blocking the membrane with a secondary antibody (which recognizes the primary antibody, e.g., an anti-human antibody) conjugated to an enzymatic substrate (e.g., horseradish peroxidase or alkaline phosphatase) or radioactive molecule (e.g., 32P or 125I) diluted in blocking buffer, washing the membrane in wash buffer, and detecting the presence of the antigen. One of skill in the art would be knowledgeable as to the parameters that can be modified to increase the signal detected and to reduce the background noise. For further discussion regarding western blot protocols see, e.g., Ausubel et al, eds, 1994, Current Protocols in Molecular Biology, Vol. 1, John Wiley & Sons, Inc., New York at 10.8.1.

ELISAs comprise preparing antigen, coating the well of a 96 well microtiter plate with the antigen, adding the antibody of interest conjugated to a detectable compound such as an enzymatic substrate (e.g., horseradish peroxidase or alkaline phosphatase) to the well and incubating for a period of time, and detecting the presence of the antigen. In ELISAs the antibody of interest does not have to be conjugated to a detectable compound; instead, a second antibody (which recognizes the antibody of interest) conjugated to a detectable compound may be added to the well. Further, instead of coating the well with the antigen, the antibody may be coated to the well. In this case, a second antibody conjugated to a detectable compound may be added following the addition of the antigen of interest to the coated well. One of skill in the art would be knowledgeable as to the parameters that can be modified to increase the signal detected as well as other variations of ELISAs known in the art. For further discussion regarding ELISAs see, e.g., Ausubel et al, eds, 1994, Current Protocols in Molecular Biology, Vol. 1, John Wiley & Sons, Inc., New York at 11.2.1.

The binding affinity of an antibody to an antigen and the off-rate of an antibody-antigen interaction can be determined by competitive binding assays. One example of a competitive binding assay is a radioimmunoassay comprising the incubation of labeled antigen (e.g., $^{3}$H or $^{125}$I), or fragment or variant thereof, with the antibody of interest in the presence of increasing amounts of unlabeled antigen, and the detection of the antibody bound to the labeled antigen. The affinity of the antibody of interest for a particular antigen and the binding off-rates can be determined from the data by scatchard plot analysis. Competition with a second antibody can also be determined using radioimmunoassays. In this case, the antigen is incubated with antibody of interest conjugated to a labeled compound (e.g., compound labeled with $^{3}$H or $^{125}$I) in the presence of increasing amounts of an unlabeled second antibody. This kind of competitive assay between two antibodies, may also be used to determine if two antibodies bind the same or different epitopes.

In a preferred embodiment, BIAcore kinetic analysis is used to determine the binding on and off rates of antibodies (including antibody fragments or variants thereof) to a G-protein chemokine receptor, or fragments of G-protein chemokine receptor BIAcore kinetic analysis comprises analyzing the binding and dissociation of antibodies from chips with, for instance, immobilized G-protein chemokine receptor on their surface.

Therapeutic Uses

The present invention is further directed to antibody-based therapies which involve administering antibodies of the invention to an animal, preferably a mammal, and most preferably a human, patient for treating one or more of the disclosed diseases, disorders, or conditions. Therapeutic compounds of the invention include, but are not limited to, antibodies of the invention (including fragments, analogs and derivatives thereof as described herein) and nucleic acids encoding antibodies of the invention (including fragments, analogs and derivatives thereof and anti-idiotypic antibodies as described herein). The antibodies of the invention can be used to treat, inhibit or prevent diseases, disorders or conditions associated with aberrant expression and/or activity of a polypeptide of the invention, including, but not limited to, any one or more of the diseases, disorders, or conditions described herein. The treatment and/or prevention of diseases, disorders, or conditions associated with aberrant expression and/or activity of a polypeptide of the invention includes, but is not limited to, alleviating symptoms associated with those diseases, disorders or conditions. Antibodies of the invention may be provided in pharmaceutically acceptable compositions as known in the art or as described herein.

A summary of the ways in which the antibodies of the present invention may be used therapeutically includes binding polynucleotides or polypeptides of the present invention locally or systemically in the body or by direct cytotoxicity of the antibody, e.g. as mediated by complement (CDC) or by effector cells (ADCC). Some of these approaches are described in more detail below. Armed with the teachings provided herein, one of ordinary skill in the art will know how to use the antibodies of the present invention for diagnostic, monitoring or therapeutic purposes without undue experimentation.

The antibodies of this invention may be advantageously utilized in combination with other monoclonal or chimeric antibodies, or with lymphokines or hematopoietic growth factors (such as, e.g., IL-2, IL-3 and IL-7), for example, which serve to increase the number or activity of effector cells that interact with the antibodies.

The antibodies of the invention may be administered alone or in combination with other types of treatments (e.g., radiation therapy, chemotherapy, hormonal therapy, immunotherapy, anti-tumor agents, and anti-retroviral agents. In a highly preferred embodiment, antibodies of the invention may be administered alone or in combination with anti-inflammatory agents. Generally, administration of products of a species origin or species reactivity (in the case of antibodies) that is the same species as that of the patient is preferred. Thus, in a preferred embodiment, human antibodies, fragments derivatives, analogs, or nucleic acids, are administered to a human patient for therapy or prophylaxis.

It is preferred to use high affinity and/or potent in vivo inhibiting and/or neutralizing antibodies against polypeptides or polynucleotides of the present invention, fragments or regions thereof, for both immunoassays directed to and therapy of disorders related to polynucleotides or polypeptides, including fragments thereof, of the present invention. Such antibodies, fragments, or regions, will preferably have an affinity for polynucleotides or polypeptides of the invention, including fragments thereof. Preferred binding affinities include those with a dissociation constant or Kd less than $5\times10^{-2}$ M, $10^{-2}$ M, $5\times10^{-3}$ M, $10^{-3}$ M, $5\times10^{-4}$ M, $10^{-4}$ M. More preferred binding affinities include those with a dissociation constant or Kd less than $5\times10^{-5}$ M, $10^{-5}$ M, $5\times10^{-6}$ M, $10^{-6}$ M, $5\times10^{-7}$ M, $10^{7}$ M, $5\times10^{-8}$ M or $10^{-8}$ M. Even more preferred binding affinities include those with a dissociation constant or Kd less than $5\times10^{-9}$ M, $10^{-9}$ M, $5\times10^{-10}$ M, $10^{-10}$ M, $5\times10^{-11}$ M, $10^{-11}$ M, $5\times10^{-12}$ M, $10^{-12}$ M, $5\times10^{-13}$ M, $10^{-13}$ M, $5\times10^{-14}$ M, $10^{-14}$ M, $5\times10^{-15}$ M, or $10^{-15}$ M.

Gene Therapy

In a specific embodiment, nucleic acids comprising sequences encoding antibodies or functional derivatives thereof, are administered to treat, inhibit or prevent a disease or disorder associated with aberrant expression and/or activity of a polypeptide of the invention, by way of gene therapy. Gene therapy refers to therapy performed by the administration to a subject of an expressed or expressible nucleic acid. In this embodiment of the invention, the nucleic acids produce their encoded protein that mediates a therapeutic effect.

Any of the methods for gene therapy available in the art can be used according to the present invention. Exemplary methods are described below.

For general reviews of the methods of gene therapy, see Goldspiel et al., Clinical Pharmacy 12:488-505 (1993); Wu and Wu, Biotherapy 3:87-95 (1991); Tolstoshev, Ann. Rev. Pharmacol. Toxicol. 32:573-596 (1993); Mulligan, Science 260:926-932 (1993); and Morgan and Anderson, Ann. Rev. Biochem. 62:191-217 (1993); May, TIBTECH 11(5):155-215 (1993). Methods commonly known in the art of recombinant DNA technology which can be used are described in Ausubel et al. (eds.), Current Protocols in Molecular Biology, John Wiley & Sons, NY (1993); and Kriegler, Gene Transfer and Expression, A Laboratory Manual, Stockton Press, NY (1990).

In a preferred aspect, the compound comprises nucleic acid sequences encoding an antibody, said nucleic acid sequences being part of expression vectors that express the antibody or fragments or chimeric proteins or heavy or light chains thereof in a suitable host. In particular, such nucleic acid sequences have promoters operably linked to the antibody coding region, said promoter being inducible or constitutive, and, optionally, tissue-specific. In another particular embodiment, nucleic acid molecules are used in which the antibody coding sequences and any other desired sequences are flanked by regions that promote homologous recombination at a desired site in the genome, thus providing for intrachromosomal expression of the antibody encoding nucleic acids (Koller and Smithies, Proc. Natl. Acad. Sci. USA 86:8932-8935 (1989); Zijlstra et al., Nature 342:435-438 (1989). In specific embodiments, the expressed antibody molecule is a single chain antibody; alternatively, the nucleic acid sequences include sequences encoding both the heavy and light chains, or fragments thereof, of the antibody.

Delivery of the nucleic acids into a patient may be either direct, in which case the patient is directly exposed to the nucleic acid or nucleic acid-carrying vectors, or indirect, in which case, cells are first transformed with the nucleic acids in vitro, then transplanted into the patient. These two approaches are known, respectively, as in vivo or ex vivo gene therapy.

In a specific embodiment, the nucleic acid sequences are directly administered in vivo, where it is expressed to produce the encoded product. This can be accomplished by any of numerous methods known in the art, e.g., by constructing them as part of an appropriate nucleic acid expression vector and administering it so that they become intracellular, e.g., by infection using defective or attenuated retrovirals or other viral vectors (see U.S. Pat. No. 4,980,286), or by direct injection of naked DNA, or by use of microparticle bombardment (e.g., a gene gun; Biolistic, Dupont), or coating with lipids or cell-surface receptors or transfecting agents, encapsulation in liposomes, microparticles, or microcapsules, or by administering them in linkage to a peptide which is known to enter the nucleus, by administering it in linkage to a ligand subject to receptor-mediated endocytosis (see, e.g., Wu and Wu, J. Biol. Chem. 262:4429-4432 (1987)) (which can be used to target cell types specifically expressing the receptors), etc. In another embodiment, nucleic acid-ligand complexes can be formed in which the ligand comprises a fusogenic viral peptide to disrupt endosomes, allowing the nucleic acid to avoid lysosomal degradation. In yet another embodiment, the nucleic acid can be targeted in vivo for cell specific uptake and expression, by targeting a specific receptor (see, e.g., PCT Publications WO 92/06180; WO 92/22635; WO92/20316; WO93/14188, WO 93/20221). Alternatively, the nucleic acid can be introduced intracellularly and incorporated within host cell DNA for expression, by homologous recombination (Koller and Smithies, Proc. Natl. Acad. Sci. USA 86:8932-8935 (1989); Zijlstra et al., Nature 342:435-438 (1989)).

In a specific embodiment, viral vectors that contain nucleic acid sequences encoding an antibody of the invention are used. For example, a retroviral vector can be used (see Miller et al., Meth. Enzymol. 217:581-599 (1993)). These retroviral vectors contain the components necessary for the correct packaging of the viral genome and integration into the host cell DNA. The nucleic acid sequences encoding the antibody to be used in gene therapy are cloned into one or more vectors, which facilitates delivery of the gene into a patient. More detail about retroviral vectors can be found in Boesen et al., Biotherapy 6:291-302 (1994), which describes the use of a retroviral vector to deliver the mdr1 gene to hematopoietic stem cells in order to make the stem cells more resistant to chemotherapy. Other references illustrating the use of retroviral vectors in gene therapy are: Clowes et al., J. Clin. Invest. 93:644-651 (1994); Kiem et al., Blood 83:1467-1473 (1994); Salmons and Gunzberg, Human Gene Therapy 4:129-141 (1993); and Grossman and Wilson, Curr. Opin. in Genetics and Devel. 3:110-114 (1993).

Adenoviruses are other viral vectors that can be used in gene therapy. Adenoviruses are especially attractive vehicles for delivering genes to respiratory epithelia. Adenoviruses naturally infect respiratory epithelia where they cause a mild disease. Other targets for adenovirus-based delivery systems are liver, the central nervous system, endothelial cells, and muscle. Adenoviruses have the advantage of being capable of infecting non-dividing cells. Kozarsky and Wilson, Current Opinion in Genetics and Development 3:499-503 (1993) present a review of adenovirus-based gene therapy. Bout et al., Human Gene Therapy 5:3-10 (1994) demonstrated the use of adenovirus vectors to transfer genes to the respiratory epithelia of rhesus monkeys. Other instances of the use of adenoviruses in gene therapy can be found in Rosenfeld et al., Science 252:431-434 (1991); Rosenfeld et al., Cell 68:143-155 (1992); Mastrangeli et al., J. Clin. Invest. 91:225-234 (1993); PCT Publication W094/12649; and Wang, et al., Gene Therapy 2:775-783 (1995). In a preferred embodiment, adenovirus vectors are used.

Adeno-associated virus (AAV) has also been proposed for use in gene therapy (Walsh et al., Proc. Soc. Exp. Biol. Med. 204:289-300 (1993); U.S. Pat. No 5,436,146).

Another approach to gene therapy involves transferring a gene to cells in tissue culture by such methods as electroporation, lipofection, calcium phosphate mediated transfection, or viral infection. Usually, the method of transfer includes the transfer of a selectable marker to the cells. The cells are then placed under selection to isolate those cells that have taken up and are expressing the transferred gene. Those cells are then delivered to a patient.

In this embodiment, the nucleic acid is introduced into a cell prior to administration in vivo of the resulting recombinant cell. Such introduction can be carried out by any method known in the art, including but not limited to transfection, electroporation, microinjection, infection with a viral or bacteriophage vector containing the nucleic acid sequences, cell fusion, chromosome-mediated gene transfer, microcell-mediated gene transfer, spheroplast fusion, etc. Numerous techniques are known in the art for the introduction, of foreign genes into cells (see, e.g., Loeffler and Behr, Meth. Enzymol. 217:599-618 (1993); Cohen et al., Meth. Enzymol. 217:618-644 (1993); Cline, Pharmac. Ther. 29:69-92m (1985) and may be used in accordance with the present invention, provided that the necessary developmental and physiological functions of the recipient cells are not disrupted. The technique should provide for the stable transfer of the nucleic acid to the cell, so that the nucleic acid is expressible by the cell and preferably heritable and expressible by its cell progeny.

The resulting recombinant cells can be delivered to a patient by various methods known in the art. Recombinant blood cells (e.g., hematopoietic stem or progenitor cells) are preferably administered intravenously. The amount of cells envisioned for use depends on the desired effect, patient state, etc., and can be determined by one skilled in the art.

Cells into which a nucleic acid can be introduced for purposes of gene therapy encompass any desired, available cell type, and include but are not limited to epithelial cells, endothelial cells, keratinocytes, fibroblasts, muscle cells, hepatocytes; blood cells such as Tlymphocytes, Blymphocytes, monocytes, macrophages, neutrophils, eosinophils, megakaryocytes, granulocytes; various stem or progenitor cells, in particular hematopoietic stem or progenitor cells, e.g., as obtained from bone marrow, umbilical cord blood, peripheral blood, fetal liver, etc.

In a preferred embodiment, the cell used for gene therapy is autologous to the patient.

In an embodiment in which recombinant cells are used in gene therapy, nucleic acid sequences encoding an antibody are introduced into the cells such that they are expressible by the cells or their progeny, and the recombinant cells are then administered in vivo for therapeutic effect. In a specific embodiment, stem or progenitor cells are used. Any stem and/or progenitor cells which can be isolated and maintained in vitro can potentially be used in accordance with this embodiment of the present invention (see e.g. PCT Publication WO 94/08598; Stemple and Anderson, Cell 71:973-985 (1992); Rheinwald, Meth. Cell Bio. 21A:229 (1980); and Pittelkow and Scott, Mayo Clinic Proc. 61:771 (1986)).

In a specific embodiment, the nucleic acid to be introduced for purposes of gene therapy comprises an inducible promoter operably linked to the coding region, such that expression of the nucleic acid is controllable by controlling the presence or absence of the appropriate inducer of transcription. Demonstration of Therapeutic or Prophylactic Activity The compounds or pharmaceutical compositions of the invention are preferably tested in vitro, and then in vivo for the desired therapeutic or prophylactic activity, prior to use in humans. For example, in vitro assays to demonstrate the therapeutic or prophylactic utility of a compound or pharmaceutical composition include, the effect of a compound on a cell line or a patient tissue sample. The effect of the compound or composition on the cell line and/or tissue sample can be determined utilizing techniques known to those of skill in the art including, but not limited to, rosette formation assays and cell lysis assays. In accordance with the invention, in vitro assays which can be used to determine whether administration of a specific compound is indicated, include in vitro cell culture assays in which a patient tissue sample is grown in culture, and exposed to or otherwise administered a compound, and the effect of such compound upon the tissue sample is observed.

Therapeutic/Prophylactic Administration and Composition

The invention provides methods of treatment, inhibition and prophylaxis by administration to a subject of an effective amount of a compound or pharmaceutical composition of the invention, preferably an antibody of the invention. In a preferred aspect, the compound is substantially purified (e.g., substantially free from substances that limit its effect or produce undesired side-effects). The subject is preferably an animal, including but not limited to animals such as cows, pigs, horses, chickens, cats, dogs, etc., and is preferably a mammal, and most preferably human.

Formulations and methods of administration that can be employed when the compound comprises a nucleic acid or an immunoglobulin are described above; additional appropriate formulations and routes of administration can be selected from among those described herein below.

Various delivery systems are known and can be used to administer a compound of the invention, e.g., encapsulation in liposomes, microparticles, microcapsules, recombinant cells capable of expressing the compound, receptor-mediated endocytosis (see, e.g., Wu and Wu, J. Biol. Chem. 262:4429-4432 (1987)), construction of a nucleic acid as part of a retroviral or other vector, etc. Methods of introduction include but are not limited to intradermal, intramuscular, intraperitoneal, intravenous, subcutaneous, intranasal, epidural, and oral routes. The compounds or compositions may be administered by any convenient route, for example by infusion or bolus injection, by absorption through epithelial or mucocutaneous linings (e.g., oral mucosa, rectal and intestinal mucosa, etc.) and may be administered together with other biologically active agents. Administration can be systemic or local. In addition, it may be desirable to introduce the pharmaceutical compounds or compositions of the invention into the central nervous system by any suitable route, including intraventricular and intrathecal injection; intraventricular injection may be facilitated by an intraventricular catheter, for example, attached to a reservoir, such as an Ommaya reservoir. Pulmonary administration can also be employed, e.g., by use of an inhaler or nebulizer, and formulation with an aerosolizing agent.

In a specific embodiment, it may be desirable to administer the pharmaceutical compounds or compositions of the invention locally to the area in need of treatment; this may be achieved by, for example, and not by way of limitation, local infusion during surgery, topical application, e.g., in conjunction with a wound dressing after surgery, by injection, by means of a catheter, by means of a suppository, or by means of an implant, said implant being of a porous, non-porous, or gelatinous material, including membranes, such as sialastic membranes, or fibers. Preferably, when administering a protein, including an antibody, of the invention, care must be taken to use materials to which the protein does not absorb.

In another embodiment, the compound or composition can be delivered in a vesicle, in particular a liposome (see Langer, Science 249:1527-1533 (1990); Treat et al., in Liposomes in the Therapy of Infectious Disease and Cancer, Lopez-Berestein and Fidler (eds.), Liss, New York, pp. 353-365 (1989); Lopez-Berestein, ibid., pp. 317-327; see generally ibid.)

In yet another embodiment, the compound or composition can be delivered in a controlled release system. In one embodiment, a pump may be used (see Langer, supra; Sefton, CRC Crit. Ref. Biomed. Eng. 14:201 (1987); Buchwald et al., Surgery 88:507 (1980); Saudek et al., N. Engl. J. Med. 321:574 (1989)). In another embodiment, polymeric materials can be used (see Medical Applications of Controlled Release, Langer and Wise (eds.), CRC Pres., Boca Raton, Fla. (1974); Controlled Drug Bioavailability, Drug Product Design and Performance, Smolen and Ball (eds.), Wiley, New York (1984); Ranger and Peppas, I., Macromol. Sci. Rev. Macromol. Chem. 23:61 (1983); see also Levy et al., Science 228:190 (1985); During et al., Ann. Neurol. 25:351 (1989); Howard et al., J.Neurosurg. 71:105 (1989)). In yet another embodiment, a controlled release system can be placed in proximity of the therapeutic target, i.e., the brain, thus requiring only a fraction of the systemic dose (see, e.g., Goodson, in Medical Applications of Controlled Release, supra, vol. 2, pp. 115-138 (1984)).

Other controlled release systems are discussed in the review by Langer (Science 249:1527-1533 (1990)).

In a specific embodiment where the compound of the invention is a nucleic acid encoding a protein, the nucleic acid can be administered in vivo to promote expression of its encoded protein, by constructing it as part of an appropriate nucleic acid expression vector and administering it so that it becomes intracellular, e.g., by use of a retroviral vector (see U.S. Pat. No. 4,980,286), or by direct-injection, or by use of microparticle bombardment (e.g., a gene gun; Biolistic, Dupont), or coating with lipids or cell-surface receptors or transfecting agents, or by administering it in linkage to a homeobox-like peptide which is known to enter the nucleus (see e.g., Joliot et al., Proc. Natl. Acad. Sci. USA 88:1864-1868 (1991)), etc. Alternatively, a nucleic acid can be introduced intracellularly and incorporated within host cell DNA for expression, by homologous recombination.

The present invention also provides pharmaceutical compositions. Such compositions comprise a therapeutically effective amount of a compound, and a pharmaceutically acceptable carrier. In a specific embodiment, the term "pharmaceutically acceptable" means approved by a regulatory agency of the Federal or a state government or listed in the U.S. Pharmacopeia or other generally recognized pharmacopeia for use in animals, and more particularly in humans. The term "carrier" refers to a diluent, adjuvant, excipient, or, vehicle with which the therapeutic is administered. Such pharmaceutical carriers can be sterile liquids, such as water and oils, including those of petroleum, animal, vegetable or synthetic origin, such as peanut oil, soybean oil, mineral oil, sesame oil and the like. Water is a preferred carrier when the pharmaceutical composition is administered intravenously. Saline solutions and aqueous dextrose and glycerol solutions can also be employed as liquid carriers, particularly for injectable solutions. Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The composition, if desired, can also contain minor amounts of wetting or emulsifying agents, or pH buffering agents. These compositions can take the form of solutions, suspensions, emulsion, tablets, pills, capsules, powders, sustained-release formulations and the like. The composition can be formulated as a suppository, with traditional binders and carriers such as triglycerides. Oral formulation can include standard carriers such as pharmaceutical grades of mannitol, lactose, starch, magnesium stearate, sodium saccharine, cellulose, magnesium carbonate, etc. Examples of suitable pharmaceutical carriers are described in "Remington's Pharmaceutical Sciences" by E. W. Martin. Such compositions will contain a therapeutically effective amount of the compound, preferably in purified form, together with a suitable amount of carrier so as to provide the form for proper administration to the patient. The formulation should suit the mode of administration.

In a preferred embodiment, the composition is formulated in accordance with routine procedures as a pharmaceutical composition adapted for intravenous administration to human beings. Typically, compositions for intravenous administration are solutions in sterile isotonic aqueous buffer. Where necessary, the composition may also include a solubilizing agent and a local anesthetic such as lignocaine to ease pain at the site of the injection. Generally, the ingredients are supplied either separately or mixed together in unit dosage form, for example, as a dry lyophilized powder or water free concentrate in a hermetically sealed container such as an ampoule or sachette indicating the quantity of active agent. Where the composition is to be administered by infusion, it can be dispensed with an infusion bottle containing sterile pharmaceutical grade water or saline. Where the composition is administered by injection, an ampoule of sterile water for injection or saline can be provided so that the ingredients may be mixed prior to administration.

The compounds of the invention can be formulated as neutral or salt forms. Pharmaceutically acceptable salts include those formed with anions such as those derived from hydrochloric, phosphoric, acetic, oxalic, tartaric acids, etc., and those formed with cations such as those derived from sodium, potassium, ammonium, calcium, ferric hydroxides, isopropylamine, triethylamine, 2-ethylamino ethanol, histidine, procaine, etc.

The amount of the compound of the invention which will be effective in the treatment, inhibition and prevention of a disease or disorder associated with aberrant expression and/or activity of a polypeptide of the invention can be determined by standard clinical techniques. In addition, in vitro assays may optionally be employed to help identify optimal dosage ranges. The precise dose to be employed in the formulation will also depend on the route of administration, and the seriousness of the disease or disorder, and should be decided according to the judgment of the practitioner and each patient's circumstances. Effective doses may be extrapolated from dose-response curves derived from in vitro or animal model test systems.

For antibodies, the dosage administered to a patient is typically 0.1 mg/kg to 100 mg/kg of the patient's body weight. Preferably, the dosage administered to a patient is between 0.1 mg/kg and 20 mg/kg of the patient's body weight, more preferably 1 mg/kg to 10 mg/kg of the patient's body weight. Generally, human antibodies have a longer half-life within the human body than antibodies from other species due to the immune response to the foreign polypeptides. Thus, lower dosages of human antibodies and less frequent administration is often possible. Further, the dosage and frequency of administration of antibodies of the invention may be reduced by enhancing uptake and tissue penetration (e.g., into the brain) of the antibodies by modifications such as, for example, lipidation.

The invention also provides a pharmaceutical pack or kit comprising one or more containers filled with one or more of the ingredients of the pharmaceutical compositions of the invention. Optionally associated with such container(s) can be a notice in the form prescribed by a governmental agency regulating the manufacture, use or sale of pharmaceuticals or biological products, which notice reflects approval by the agency of manufacture, use or sale for human administration.

Diagnosis and Imaging

Labeled antibodies, and derivatives and analogs thereof, which specifically bind to a polypeptide of interest can be used for diagnostic purposes to detect, diagnose, or monitor diseases, disorders, and/or conditions associated with the expression and/or activity of a polypeptide of the invention. The invention provides for the detection of aberrant expression of a polypeptide of interest, comprising (a) assaying the expression of the polypeptide of interest in cells or body fluid of an individual using one or more antibodies specific to the polypeptide interest and (b) comparing the level of gene expression with a standard gene expression level, whereby an increase or decrease in the assayed polypeptide gene expression level compared to the standard expression level is indicative of aberrant expression.

The invention provides a diagnostic assay for diagnosing a disorder, comprising (a) assaying the expression of the polypeptide of interest in cells or body fluid of an individual using one or more antibodies specific to the polypeptide interest and (b) comparing the level of gene expression with a standard gene expression level, whereby an increase or decrease in the assayed polypeptide gene expression level compared to the standard expression level is indicative of a particular disorder. With respect to cancer, the presence of a relatively high amount of transcript in biopsied tissue from an individual may indicate a predisposition for the development of the disease, or may provide a means for detecting the disease prior to the appearance of actual clinical symptoms. A more definitive diagnosis of this type may allow health professionals to employ preventative measures or aggressive treatment earlier thereby preventing the development or further progression of the cancer.

Antibodies of the invention can be used to assay protein levels in a biological sample using classical immunohistological methods known to those of skill in the art (e.g., see Jalkanen, et al., J. Cell. Biol. 101:976-985 (1985); Jalkanen, et al., J. Cell. Biol. 105:3087-3096 (1987)). Other antibody-based methods useful for detecting protein gene expression include immunoassays, such as the enzyme linked immunosorbent assay (ELISA) and the radioimmunoassay (RIA). Suitable antibody assay labels are known in the art and include enzyme labels, such as, glucose oxidase; radioisotopes, such as iodine (125I, 121I), carbon (14C), sulfur (35S), tritium (3H), indium (112In), and technetium (99Tc); luminescent labels, such as luminol; and fluorescent labels, such as fluorescein and rhodamine, and biotin.

One aspect of the invention is the detection and diagnosis of a disease or disorder associated with aberrant expression of a polypeptide of interest in an animal, preferably a mammal and most preferably a human. In one embodiment, diagnosis comprises; a) administering (for example, parenterally, subcutaneously, or intraperitoneally) to a subject an effective amount of a labeled molecule which specifically binds to the polypeptide of interest; b) waiting for a time interval following the administering for permitting the labeled molecule to preferentially concentrate at sites in the subject where the polypeptide is expressed (and for unbound labeled molecule to be cleared to background level); c) determining background level; and d) detecting the labeled molecule in the subject, such that detection of labeled molecule above the background level indicates that the subject has a particular disease or disorder associated with aberrant expression of the polypeptide of interest. Background level can be determined by various methods including, comparing the amount of labeled molecule detected to a standard value previously determined for a particular system.

It will be understood in the art that the size of the subject and the imaging system used will determine the quantity of imaging moiety needed to produce diagnostic images. In the case of a radioisotope moiety, for a human subject, the quantity of radioactivity injected will normally range from about 5 to 20 millicuries of 99mTc. The labeled antibody or antibody fragment will then preferentially accumulate at the location of cells which contain the specific protein. In vivo tumor imaging is described in S. W. Burchiel et al., "Immunopharmacokinetics of Radiolabeled Antibodies and Their Fragments." (Chapter 13 in Tumor Imaging: The Radiochemical Detection of Cancer, S. W. Burchiel and B. A. Rhodes, eds., Masson Publishing Inc. (1982).

Depending on several variables, including the type of label used and the mode of administration, the time interval following the administration for permitting the labeled molecule to preferentially concentrate at sites in the subject and for unbound labeled molecule to be cleared to background level is 6 to 48 hours or 6 to 24 hours or 6 to 12 hours. In another embodiment the time interval following administration is 5 to 20 days or 5 to 10 days.

In an embodiment, monitoring of the disease or disorder is carried out by repeating the method for diagnosing the disease or disease, for example, one month after initial diagnosis, six months after initial diagnosis, one year after initial diagnosis, etc.

Presence of the labeled molecule can be detected in the patient using methods known in the art for in vivo scanning. These methods depend upon the type of label used. Skilled artisans will be able to determine the appropriate method for detecting a particular label. Methods and devices that may be used in the diagnostic methods of the invention include, but are not limited to, computed tomography (CT), whole body scan such as position emission tomography (PET), magnetic resonance imaging (MRI), and sonography.

In a specific embodiment, the molecule is labeled with a radioisotope and is detected in the patient using a radiation responsive surgical instrument (Thurston et al., U.S. Pat. No. 5,441,050). In another embodiment, the molecule is labeled with a fluorescent compound and is detected in the patient using a fluorescence responsive scanning instrument. In another embodiment, the molecule is labeled with a positron emitting metal and is detected in the patent using positron emission-tomography. In yet another embodiment, the molecule is labeled with a paramagnetic label and is detected in a patient using magnetic resonance imaging (MRI).

Gene Therapy

In a specific embodiment, nucleic acids comprising sequences encoding antibodies or functional derivatives thereof, are administered to treat, inhibit or prevent a disease or disorder associated with aberrant expression and/or activity of a polypeptide of the invention, by way of gene therapy. Gene therapy refers to therapy performed by the administration to a subject of an expressed or expressible nucleic acid. In this embodiment of the invention, the nucleic acids produce their encoded protein that mediates a therapeutic effect.

Any of the methods for gene therapy available in the art can be used according to the present invention. Exemplary methods are described below.

For general reviews of the methods of gene therapy, see Goldspiel et al., Clinical Pharmacy 12:488-505 (1993); Wu and Wu, Biotherapy 3:87-95 (1991); Tolstoshev, Ann. Rev. Pharmacol. Toxicol. 32:573-596 (1993); Mulligan, Science 260:926-932 (1993); and Morgan and Anderson, Ann. Rev. Biochem. 62:191-217 (1993); May, TIBTECH 11(5):155-215 (1993). Methods commonly known in the art of recombinant DNA technology which can be used are described in Ausubel et al. (eds.), Current Protocols in Molecular Biology, John Wiley & Sons, NY (1993); and Kriegler, Gene Transfer and Expression, A Laboratory Manual, Stockton Press, NY (1990).

In a preferred aspect, the compound comprises nucleic acid sequences encoding an antibody, said nucleic acid sequences being part of expression vectors that express the antibody or fragments or chimeric proteins or heavy or light chains thereof in a suitable host. In particular, such nucleic acid sequences have promoters operably linked to the antibody coding region, said promoter being inducible or constitutive, and, optionally, tissue-specific. In another particular embodiment, nucleic acid molecules are used in which the antibody coding sequences and any other desired sequences are flanked by regions that promote homologous recombination at a desired site in the genome, thus providing for intrachromosomal expression of the antibody encoding nucleic acids (Koller and Smithies, Proc. Natl. Acad. Sci. USA 86:8932-8935 (1989); Zijlstra et al., Nature 342:435-438 (1989). In specific embodiments, the expressed antibody molecule is a single chain antibody; alternatively, the nucleic acid sequences include sequences encoding both the heavy and light chains, or fragments thereof, of the antibody.

Delivery of the nucleic acids into a patient may be either direct, in which case the patient is directly exposed to the nucleic acid or nucleic acid-carrying vectors, or indirect, in which case, cells are first transformed with the nucleic acids in vitro, then transplanted into the patient. These two approaches are known, respectively, as in vivo or ex vivo gene therapy.

In a specific embodiment, the nucleic acid sequences are directly administered in vivo, where it is expressed to produce the encoded product. This can be accomplished by any of numerous methods known in the art, e.g., by constructing them as part of an appropriate nucleic acid expression vector and administering it so that they become intracellular, e.g., by infection using defective or attenuated retrovirals or other viral vectors (see U.S. Pat. No. 4,980,286), or by direct injection of naked DNA, or by use of microparticle bombardment (e.g., a gene gun; Biolistic, Dupont), or coating with lipids or cell-surface receptors or transfecting agents, encapsulation in liposomes, microparticles, or microcapsules, or by administering them in linkage to a peptide which is known to enter the nucleus, by administering it in linkage to a ligand subject to receptor-mediated endocytosis (see, e.g., Wu and Wu, J. Biol. Chem. 262:4429-4432 (1987)) (which can be used to target cell types specifically expressing the receptors), etc. In another embodiment, nucleic acid-ligand complexes can be formed in which the ligand comprises a fusogenic viral peptide to disrupt endosomes, allowing the nucleic acid to avoid lysosomal degradation. In yet another embodiment, the nucleic acid can be targeted in vivo for cell specific uptake and expression, by targeting a specific receptor (see, e.g., PCT Publications WO 92/06180; WO 92/22635; WO92/20316; WO93/14188, WO 93/20221). Alternatively, the nucleic acid can be introduced intracellularly and incorporated within host cell DNA for expression, by homologous recombination (Koller and Smithies, Proc. Natl. Acad. Sci. USA 86:8932-8935 (1989); Zijlstra et al., Nature 342:435-438 (1989)).

In a specific embodiment, viral vectors that contains nucleic acid sequences encoding an antibody of the invention are used. For example, a retroviral vector can be used (see Miller et al., Meth. Enzymol. 217:581-599 (1993)). These retroviral vectors contain the components necessary for the correct packaging of the viral genome and integration into the host cell DNA. The nucleic acid sequences encoding the antibody to be used in gene therapy are cloned into one or more vectors, which facilitates delivery of the gene into a patient. More detail about retroviral vectors can be found in Boesen et al., Biotherapy 6:291-302 (1994), which describes the use of a retroviral vector to deliver the mdr1 gene to hematopoietic stem cells in order to make the stem cells more resistant to chemotherapy. Other references illustrating the use of retroviral vectors in gene therapy are: Clowes et al., J. Clin. Invest. 93:644-651 (1994); Kiem et al., Blood 83:1467-1473 (1994); Salmons and Gunzberg, Human Gene Therapy 4:129-141 (1993); and Grossman and Wilson, Curr. Opin. in Genetics and Devel. 3:110-114 (1993).

Adenoviruses are other viral vectors that can be used in gene therapy. Adenoviruses are especially attractive vehicles for delivering genes to respiratory epithelia. Adenoviruses naturally infect respiratory epithelia where they cause a mild disease. Other targets for adenovirus-based delivery systems are liver, the central nervous system, endothelial cells, and muscle. Adenoviruses have the advantage of being capable of infecting non-dividing cells. Kozarsky and Wilson, Current Opinion in Genetics and Development 3:499-503 (1993) present a review of adenovirus-based gene therapy. Bout et al., Human Gene Therapy 5:3-10 (1994) demonstrated the use of adenovirus vectors to transfer genes to the respiratory epithelia of rhesus monkeys. Other instances of the use of adenoviruses in gene therapy can be found in Rosenfeld et al., Science 252:431-434 (1991); Rosenfeld et al., Cell 68:143-155 (1992); Mastrangeli et al., J. Clin. Invest. 91:225-234 (1993); PCT Publication W094/12649; and Wang, et al., Gene Therapy 2:775-783 (1995). In a preferred embodiment, adenovirus vectors are used.

Adeno-associated virus (AAV) has also been proposed for use in gene therapy (Walsh et al., Proc. Soc. Exp. Biol. Med. 204:289-300 (1993); U.S. Pat. No. 5,436,146).

Another approach to gene therapy involves transferring a gene to cells in tissue culture by such methods as electroporation, lipofection, calcium phosphate mediated transfection, or viral infection. Usually, the method of transfer includes the transfer of a selectable marker to the cells. The cells are then placed under selection to isolate those cells that have taken up and are expressing the transferred gene. Those cells are then delivered to a patient.

In this embodiment, the nucleic acid is introduced into a cell prior to administration in vivo of the resulting recombinant cell. Such introduction can be carried out by any method known in the art, including but not limited to transfection, electroporation, microinjection, infection with a viral or bacteriophage vector containing the nucleic acid sequences, cell fusion, chromosome-mediated gene transfer, microcell-mediated gene transfer, spheroplast fusion, etc. Numerous techniques are known in the art for the introduction of foreign genes into cells (see, e.g., Loeffler and Behr, Meth. Enzymol. 217:599-618 (1993); Cohen et al., Meth. Enzymol. 217:618-644 (1993); Cline, Pharmac. Ther. 29:69-92m (1985) and may be used in accordance with the present invention, provided that the necessary developmental and physiological functions of the recipient cells are not disrupted. The technique should provide for the stable transfer of the nucleic acid to the cell, so that the nucleic acid is expressible by the cell and preferably heritable and expressible by its cell progeny.

The resulting recombinant cells can be delivered to a patient by various methods known in the art. Recombinant blood cells (e.g., hematopoietic stem or progenitor cells) are preferably administered intravenously. The amount of cells envisioned for use depends on the desired effect, patient state, etc., and can be determined by one skilled in the art.

Cells into which a nucleic acid can be introduced for purposes of gene therapy encompass any desired, available cell type, and include but are not limited to epithelial cells, endothelial cells, keratinocytes, fibroblasts, muscle cells, hepatocytes; blood cells such as T lymphocytes, B lymphocytes, monocytes, macrophages, neutrophils, eosinophils, megakaryocytes, granulocytes; various stem or progenitor cells, in particular hematopoietic stem or progenitor cells, e.g., as obtained from bone marrow, umbilical cord blood, peripheral blood, fetal liver, etc.

In a preferred embodiment, the cell used for gene therapy is autologous to the patient.

In an embodiment in which recombinant cells are used in gene therapy, nucleic acid sequences encoding an antibody are introduced into the cells such that they are expressible by the cells or their progeny, and the recombinant cells are then administered in vivo for therapeutic effect. In a specific embodiment, stem or progenitor cells are used. Any stem and/or progenitor cells which can be isolated and maintained in vitro can potentially be used in accordance with this embodiment of the present invention (see e.g. PCT Publication WO 94/08598; Stemple and Anderson, Cell 71:973-985 (1992); Rheinwald, Meth. Cell Bio. 21A:229 (1980); and Pittelkow and Scott, Mayo Clinic Proc. 61:771 (1986)).

In a specific embodiment, the nucleic acid to be introduced for purposes of gene therapy comprises an inducible promoter operably linked to the coding region, such that expression of the nucleic acid is controllable by controlling the presence or absence of the appropriate inducer of transcription. Demonstration of Therapeutic or Prophylactic Activity The compounds or pharmaceutical compositions of the invention are preferably tested in vitro, and then in vivo for the desired therapeutic or prophylactic activity, prior to use in humans. For example, in vitro assays to demonstrate the therapeutic or prophylactic utility of a compound or pharmaceutical composition include, the effect of a compound on a cell line or a patient tissue sample. The effect of the compound or composition on the cell line and/or tissue sample can be determined utilizing techniques known to those of skill in the art including, but not limited to, rosette formation assays and cell lysis assays. In accordance with the invention, in vitro assays which can be used to determine whether administration of a specific compound is indicated, include in vitro cell culture assays in which a patient tissue sample is grown in culture, and exposed to or otherwise administered a compound, and the effect of such compound upon the tissue sample is observed.

Therapeutic/Prophylactic Administration and Composition

The invention provides methods of treatment, inhibition and prophylaxis by administration to a subject of an effective amount of a compound or pharmaceutical composition of the invention, preferably an antibody of the invention. In a preferred aspect, the compound is substantially purified (e.g., substantially free from substances that limit its effect or produce undesired side-effects). The subject is preferably an animal, including but not limited to animals such as cows, pigs, horses, chickens, cats, dogs, etc., and is preferably a mammal, and most preferably human.

Formulations and methods of administration that can be employed when the compound comprises a nucleic acid or an immunoglobulin are described above; additional appropriate formulations and routes of administration can be selected from among those described herein below.

Various delivery systems are known and can be used to administer a compound of the invention, e.g., encapsulation in liposomes, microparticles, microcapsules, recombinant cells capable of expressing the compound, receptor-mediated endocytosis (see, e.g., Wu and Wu, J. Biol. Chem. 262:4429-4432 (1987)), construction of a nucleic acid as part of a retroviral or other vector, etc. Methods of introduction include but are not limited to intradermal, intramuscular, intraperitoneal, intravenous, subcutaneous, intranasal, epidural, and oral routes. The compounds or compositions may be administered by any convenient route, for example by infusion or bolus injection, by absorption through epithelial or mucocutaneous linings (e.g., oral mucosa, rectal and intestinal mucosa, etc.) and may be administered together with other biologically active agents. Administration can be systemic or local. In addition, it may be desirable to introduce the pharmaceutical compounds or compositions of the invention into the central nervous system by any suitable route, including intraventricular and intrathecal injection; intraventricular injection may be facilitated by an intraventricular catheter, for example, attached to a reservoir, such as an Ommaya reservoir. Pulmonary administration can also be employed, e.g., by use of an inhaler or nebulizer, and formulation with an aerosolizing agent.

In a specific embodiment, it may be desirable to administer the pharmaceutical compounds or compositions of the invention locally to the area in need of treatment; this may be achieved by, for example, and not by way of limitation, local infusion during surgery, topical application, e.g., in conjunction with a wound dressing after surgery, by injection, by means of a catheter, by means of a suppository, or by means of an implant, said implant being of a porous, non-porous, or gelatinous material, including membranes, such as sialastic membranes, or fibers. Preferably, when administering a protein, including an antibody, of the invention, care must be taken to use materials to which the protein does not absorb.

In another embodiment, the compound or composition can be delivered in a vesicle, in particular a liposome (see Langer, Science 249:1527-1533 (1990); Treat et al., in Liposomes in the Therapy of Infectious Disease and Cancer, Lopez-Berestein and Fidler (eds.), Liss, New York, pp. 353-365 (1989); Lopez-Berestein, ibid., pp. 317-327; see generally ibid.)

In yet another embodiment, the compound or composition can be delivered in a controlled release system. In one embodiment, a pump may be used (see Langer, supra; Sefton, CRC Crit. Ref. Biomed. Eng. 14:201 (1987); Buchwald et al., Surgery 88:507 (1980); Saudek et al., N. Engl. J. Med. 321: 574 (1989)). In another embodiment, polymeric materials can be used (see Medical Applications of Controlled Release, Langer and Wise (eds.), CRC Pres., Boca Raton, Fla. (1974); Controlled Drug Bioavailability, Drug Product Design and Performance, Smolen and Ball (eds.), Wiley, New York (1984); Ranger and Peppas, J., Macromol. Sci. Rev. Macromol. Chem. 23:61 (1983); see also Levy et al., Science 228: 190 (1985); During et al., Ann. Neurol. 25:351 (1989); Howard et al., J.Neurosurg. 71:105 (1989)). In yet another embodiment, a controlled release system can be placed in proximity of the therapeutic target, i.e., the brain, thus requiring only a fraction of the systemic dose (see, e.g., Goodson, in Medical Applications of Controlled Release, supra, vol. 2, pp. 115-138 (1984)).

Other controlled release systems are discussed in the review by Langer (Science 249:1527-1533 (1990)).

In a specific embodiment where the compound of the invention is a nucleic acid encoding a protein, the nucleic acid can be administered in vivo to promote expression of its encoded protein, by constructing it as part of an appropriate nucleic acid expression vector and administering it so that it becomes intracellular, e.g., by use of a retroviral vector (see U.S. Pat. No. 4,980,286), or by direct injection, or by use of microparticle bombardment (e.g., a gene gun; Biolistic, Dupont), or coating with lipids or cell-surface receptors or transfecting agents, or by administering it in linkage to a homeobox-like peptide which is known to enter the nucleus (see e.g., Joliot et al., Proc. Natl. Acad. Sci. USA 88:1864-1868 (1991)), etc. Alternatively, a nucleic acid can be introduced intracellularly and incorporated within host cell DNA for expression, by homologous recombination.

The present invention also provides pharmaceutical compositions. Such compositions comprise a therapeutically effective amount of a compound, and a pharmaceutically acceptable carrier. In a specific embodiment, the term "pharmaceutically acceptable" means approved by a regulatory agency of the Federal or a state government or listed in the U.S. Pharmacopeia or other generally recognized pharmacopeia for use in animals, and more particularly in humans. The term "carrier" refers to a diluent, adjuvant, excipient, or vehicle with which the therapeutic is administered. Such pharmaceutical carriers can be sterile liquids, such as water and oils, including those of petroleum, animal, vegetable or synthetic origin, such as peanut oil, soybean oil, mineral oil, sesame oil and the like. Water is a preferred carrier when the pharmaceutical composition is administered intravenously. Saline solutions and aqueous dextrose and glycerol solutions can also be employed as liquid carriers, particularly for injectable solutions. Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The composition, if desired, can also contain minor amounts of wetting or emulsifying agents, or pH buffering agents. These compositions can take the form of solutions, suspensions, emulsion, tablets, pills, capsules, powders, sustained-release formulations and the like. The composition can be formulated as a suppository, with traditional binders and carriers such as triglycerides. Oral formulation can include standard carriers such as pharmaceutical grades of mannitol, lactose, starch, magnesium stearate, sodium saccharine, cellulose, magnesium carbonate, etc. Examples of suitable pharmaceutical carriers are described in "Remington's Pharmaceutical Sciences" by E. W. Martin. Such compositions will contain a therapeutically effective amount of the compound, preferably in purified form, together with a suitable amount of carrier so as to provide the form for proper administration to the patient. The formulation should suit the mode of administration.

In a preferred embodiment, the composition is formulated in accordance with routine procedures as a pharmaceutical composition adapted for intravenous administration to human beings. Typically, compositions for intravenous administration are solutions in sterile isotonic aqueous buffer. Where necessary, the composition may also include a solubilizing agent and a local anesthetic such as lignocaine to ease pain at the site of the injection. Generally, the ingredients are supplied either separately or mixed together in unit dosage form, for example, as a dry lyophilized powder or water free concentrate in a hermetically sealed container such as an ampoule or sachette indicating the quantity of active agent. Where the composition is to be administered by infusion, it can be dispensed with an infusion bottle containing sterile pharmaceutical grade water or saline. Where the composition is administered by injection, an ampoule of sterile water for injection or saline can be provided so that the ingredients may be mixed prior to administration.

The compounds of the invention can be formulated as neutral or salt forms. Pharmaceutically acceptable salts include those formed with anions such as those derived from hydrochloric, phosphoric, acetic, oxalic, tartaric acids, etc., and those formed with cations such as those derived from sodium, potassium, ammonium, calcium, ferric hydroxides, isopropylamine, triethylamine, 2-ethylamino ethanol, histidine, procaine, etc.

The amount of the compound of the invention which will be effective in the treatment, inhibition and prevention of a disease or disorder associated with aberrant expression and/or activity of a polypeptide of the invention can be determined by standard clinical techniques. In addition, in vitro assays may optionally be employed to help identify optimal dosage ranges. The precise dose to be employed in the formulation will also depend on the route of administration, and the seriousness of the disease or disorder, and should be decided according to the judgment of the practitioner and each patient's circumstances. Effective doses may be extrapolated from dose-response curves derived from in vitro or animal model test systems.

For antibodies, the dosage administered to a patient is typically 0.1 mg/kg to 100 mg/kg of the patient's body weight. Preferably, the dosage administered to a patient is between 0.1 mg/kg and 20 mg/kg of the patient's body weight, more preferably 1 mg/kg to 10 mg/kg of the patient's body weight. Generally, human antibodies have a longer half-life within the human body than antibodies from other species due to the immune response to the foreign polypeptides. Thus, lower dosages of human antibodies and less frequent administration is often possible. Further, the dosage and frequency of administration of antibodies of the invention may be reduced by enhancing uptake and tissue penetration (e.g., into the brain) of the antibodies by modifications such as, for example, lipidation.

The invention also provides a pharmaceutical pack or kit comprising one or more containers filled with one or more of the ingredients of the pharmaceutical compositions of the invention. Optionally associated with such container(s) can be a notice in the form prescribed by a governmental agency regulating the manufacture, use or sale of pharmaceuticals or biological products, which notice reflects approval by the agency of manufacture, use or sale for human administration.

Diagnosis and Imaging

Labeled antibodies, and derivatives and analogs thereof, which specifically bind to a polypeptide of interest can be used for diagnostic purposes to detect, diagnose, or monitor diseases and/or disorders associated with the aberrant expression and/or activity of a polypeptide of the invention. The invention provides for the detection of aberrant expression of a polypeptide of interest, comprising (a) assaying the expression of the polypeptide of interest in cells or body fluid of an individual using one or more antibodies specific to the polypeptide interest and (b) comparing the level of gene expression with a standard gene expression level, whereby an increase or decrease in the assayed polypeptide gene expression level compared to the standard expression level is indicative of aberrant expression.

The invention provides a diagnostic assay for diagnosing a disorder, comprising (a) assaying the expression of the polypeptide of interest in cells or body fluid of an individual using one or more antibodies specific to the polypeptide interest and (b) comparing the level of gene expression with a standard gene expression level, whereby an increase or decrease in the assayed polypeptide gene expression level compared to the standard expression level is indicative of a particular disorder. With respect to cancer, the presence of a relatively high amount of transcript in biopsied tissue from an individual may indicate a predisposition for the development of the disease, or may provide a means for detecting the disease prior to the appearance of actual clinical symptoms. A more definitive diagnosis of this type may allow health professionals to employ preventative measures or aggressive treatment earlier thereby preventing the development or further progression of the cancer.

Antibodies of the invention can be used to assay protein levels in a biological sample using classical immunohistological methods known to those of skill in the art (e.g., see Jalkanen, et al., J. Cell. Biol. 101:976-985 (1985); Jalkanen, et al., J. Cell . Biol. 105:3087-3096 (1987)). Other antibody-based methods useful for detecting protein gene expression include immunoassays, such as the enzyme linked immunosorbent assay (ELISA) and the radioimmunoassay (RJA). Suitable antibody assay labels are known in the art and include enzyme labels, such as, glucose oxidase; radioisotopes, such as radioisotopes, such as iodine ($^{131}$I, $^{125}$I, $^{123}$I, $^{121}$I), carbon ($^{14}$C), sulfur ($^{35}$S), tritium ($^{3}$H), indium ($^{115m}$In, $^{113m}$In, $^{112}$In, $^{111}$In), and technetium ($^{99}$Tc, $^{99m}$Tc), thallium ($^{201}$Ti), gallium ($^{68}$Ga, $^{67}$Ga), palladium ($^{103}$Pd), molybdenum ($^{99}$Mo), xenon ($^{133}$Xe), fluorine ($^{18}$F), $^{153}$Sm, $^{177}$Lu, $^{159}$Gd, $^{149}$Pm, $^{140}$La, $^{175}$Yb, $^{166}$Ho, $^{90}$Y, $^{47}$Sc, $^{186}$Re, $^{188}$Re, $^{142}$Ph, $^{105}$Rh, $^{97}$Ru; luminescent labels, such as luminol; and fluorescent labels, such as fluorescein and rhodamine, and biotin.

One aspect of the invention is the detection and diagnosis of a disease or disorder associated with aberrant expression of a polypeptide of interest in an animal, preferably a mammal and most preferably a human. In one embodiment, diagnosis comprises: a) administering (for example, parenterally, subcutaneously, or intraperitoneally) to a subject an effective amount of a labeled molecule which specifically binds to the polypeptide of interest; b) waiting for a time interval following the administering for permitting the labeled molecule to preferentially concentrate at sites in the subject where the polypeptide is expressed (and for unbound labeled molecule to be cleared to background level); c) determining background level; and d) detecting the labeled molecule in the subject, such that detection of labeled molecule above the background level indicates that the subject has a particular disease or disorder associated with aberrant expression of the polypeptide of interest. Background level can be determined by various methods including, comparing the amount of labeled molecule detected to a standard value previously determined for a particular system.

It will be understood in the art that the size of the subject and the imaging system used will determine the quantity of imaging moiety needed to produce diagnostic images. In the case of a radioisotope moiety, for a human subject, the quantity of radioactivity injected will normally range from about 5 to 20 millicuries of 99mTc. The labeled antibody or antibody fragment will then preferentially accumulate at the location of cells which contain the specific protein. In vivo tumor imaging is described in S. W. Burchiel et al., "Immunopharmacokinetics of Radiolabeled Antibodies and Their Fragments." (Chapter 13 in Tumor Imaging: The Radiochemical Detection of Cancer, S. W. Burchiel and B. A. Rhodes, eds., Masson Publishing Inc. (1982).

Depending on several variables, including the type of label used and the mode of administration, the time interval following the administration for permitting the labeled molecule to preferentially concentrate at sites in the subject and for unbound labeled molecule to be cleared to background level is 6 to 48 hours or 6 to 24 hours or 6 to 12 hours. In another embodiment the time interval following administration is 5 to 20 days or 5 to 10 days.

In an embodiment, monitoring of the disease or disorder is carried out by repeating the method for diagnosing the disease or disease, for example, one month after initial diagnosis, six months after initial diagnosis, one year after initial diagnosis, etc.

Presence of the labeled molecule can be detected in the patient using methods known in the art for in vivo scanning. These methods depend upon the type of label used. Skilled artisans will be able to determine the appropriate method for detecting a particular label. Methods and devices that may be used in the diagnostic methods of the invention include, but are not limited to, computed tomography (CT), whole body scan such as position emission tomography (PET), magnetic resonance imaging (MRI), and sonography.

In a specific embodiment, the molecule is labeled with a radioisotope and is detected in the patient using a radiation responsive surgical instrument (Thurston et al., U.S. Pat. No. 5,441,050). In another embodiment, the molecule is labeled with a fluorescent compound and is detected in the patient using a fluorescence responsive scanning instrument. In another embodiment, the molecule is labeled with a positron emitting metal and is detected in the patent using positron emission-tomography. In yet another embodiment, the molecule is labeled with a paramagnetic label and is detected in a patient using magnetic resonance imaging (MRI).

Kits

The present invention provides kits that can be used in the above methods. In one embodiment, a kit comprises an antibody of the invention, preferably a purified antibody, in one or more containers. In a specific embodiment, the kits of the present invention contain a substantially isolated polypeptide comprising an epitope which is specifically immunoreactive with an antibody included in the kit. Preferably, the kits of the present invention further comprise a control antibody which does not react with the polypeptide of interest. In another specific embodiment, the kits of the present invention contain a means for detecting the binding of an antibody to a polypeptide of interest (e.g., the antibody may be conjugated to a detectable substrate such as a fluorescent compound, an enzymatic substrate, a radioactive compound or a luminescent compound, or a second antibody which recognizes the first antibody may be conjugated to a detectable substrate).

In another specific embodiment of the present invention, the kit is a diagnostic kit for use in screening serum containing antibodies specific against proliferative and/or cancerous polynucleotides and polypeptides. Such a kit may include a control antibody that does not react with the polypeptide of interest. Such a kit may include a substantially isolated polypeptide antigen comprising an epitope which is specifically immunoreactive with at least one anti-polypeptide antigen antibody. Further, such a kit includes means for detecting the binding of said antibody to the antigen (e.g., the antibody may be conjugated to a fluorescent compound such as fluorescein or rhodamine which can be detected by flow cytometry). In specific embodiments, the kit may include a recombinantly produced or chemically synthesized polypeptide antigen. The polypeptide antigen of the kit may also be attached to a solid support.

In a more specific embodiment the detecting means of the above-described kit includes a solid support to which said polypeptide antigen is attached. Such a kit may also include a non-attached reporter-labeled anti-human antibody. In this embodiment, binding of the antibody to the polypeptide antigen can be detected by binding of the said reporter-labeled antibody.

In an additional embodiment, the invention includes a diagnostic kit for use in screening serum containing antigens of the polypeptide of the invention. The diagnostic kit includes a substantially isolated antibody specifically immunoreactive with polypeptide or polynucleotide antigens, and means for detecting the binding of the polynucleotide or polypeptide antigen to the antibody. In one embodiment, the antibody is attached to a solid support. In a specific embodiment, the antibody may be a monoclonal antibody. The detecting means of the kit may include a second, labeled monoclonal antibody. Alternatively, or in addition, the detecting means may include a labeled, competing antigen.

In one diagnostic configuration, test serum is reacted with a solid phase reagent having a surface-bound antigen obtained by the methods of the present invention. After binding with specific antigen antibody to the reagent and removing unbound serum components by washing, the reagent is reacted with reporter-labeled anti-human antibody to bind reporter to the reagent in proportion to the amount of bound anti-antigen antibody on the solid support. The reagent is again washed to remove unbound labeled antibody, and the amount of reporter associated with the reagent is determined. Typically, the reporter is an enzyme which is detected by incubating the solid phase in the presence of a suitable fluorometric, luminescent or colorimetric substrate (Sigma, St. Louis, Mo.).

The solid surface reagent in the above assay is prepared by known techniques for attaching protein material to solid support material, such as polymeric beads, dip sticks, 96-well plate or filter material. These attachment methods generally include non-specific adsorption of the protein to the support or covalent attachment of the protein, typically through a free amine group, to a chemically reactive group on the solid support, such as an activated carboxyl, hydroxyl, or aldehyde group. Alternatively, streptavidin coated plates can be used in conjunction with biotinylated antigen(s).

Thus, the invention provides an assay system or kit for carrying out this diagnostic method. The kit generally includes a support with surface-bound recombinant antigens, and a reporter-labeled anti-human antibody for detecting surface-bound anti-antigen antibody.

Formulations and Administration

The G-protein Chemokine Receptor polypeptide composition (preferably containing a polypeptide which is a soluble form of the G-protein Chemokine Receptor extracellular domains) will be formulated and dosed in a fashion consistent with good medical practice, taking into account the clinical condition of the individual patient (especially the side effects of treatment with G-protein Chemokine Receptor polypeptide alone), the site of delivery of the G-protein Chemokine Receptor polypeptide composition, the method of administration, the scheduling of administration, and other factors known to practitioners. The "effective amount" of G-protein Chemokine Receptor polypeptide for purposes herein is thus determined by such considerations.

As a general proposition, the total pharmaceutically effective amount of G-protein Chemokine Receptor polypeptide administered parenterally per dose will be in the range of about 1 microgram/kg/day to 10 mg/kg/day of patient body weight, although, as noted above, this will be subject to therapeutic discretion. More preferably, this dose is at least 0.01 mg/kg/day, and most preferably for humans between about 0.01 and 1 mg/kg/day.

In another embodiment, the G-protein Chemokine Receptor polypeptide of the invention is administered to a human at a dose betweeen 0.0001 and 0.045 mg/kg/day, preferably, at a dose between 0.0045 and 0.045 mg/kg/day, and more preferably, at a dose of about 45 microgram/kg/day in humans; and at a dose of about 3 mg/kg/day in mice.

If given continuously, the G-protein Chemokine Receptor polypeptide is typically administered at a dose rate of about 1 microgram/kg/hour to about 50 micrograms/kg/hour, either by 1-4 injections per day or by continuous subcutaneous infusions, for example, using a mini-pump. An intravenous bag solution may also be employed.

The length of treatment needed to observe changes and the interval following treatment for responses to occur appears to vary depending on the desired effect.

In a specific embodiment, the total pharmaceutically effective amount of G-protein Chemokine Receptor polypeptide administered parenterally per dose will be in the range of about 0.1 microgram/kg/day to 45 micrograms/kg/day of patient body weight, although, as noted above, this will be subject to therapeutic discretion. More preferably, this dose is at least 0.1 microgram/kg/day, and most preferably for humans between about 0.01 and 50 micrograms/kg/day for the protein. N G-protein Chemokine Receptor may be administered as a continuous infusion, multiple dicreet injections per day (e.g., three or more times daily, or twice daily), single injection per day, or as discreet injections given intermitently (e.g., twice daily, once daily, every other day, twice weekly, weekly, biweekly, monthly, bimonthly, and quarterly). If given continuously, the G-protein Chemokine Receptor polypeptide is typically administered at a dose rate of about 0.001 to 10 microgram/kg/hour to about 50 micrograms/kg/hour, either by 1-4 injections per day or by continuous subcutaneous infusions, for example, using a mini-pump.

Effective dosages of the compositions of the present invention to be administered may be determined through procedures well known to those in the art which address such parameters as biological half-life, bioavailability, and toxicity. Such determination is well within the capability of those skilled in the art, especially in light of the detailed disclosure provided herein.

Bioexposure of an organism to G-protein Chemokine Receptor polypeptide during therapy may also play an important role in determining a therapeutically and/or pharmacologically effective dosing regime. Variations of dosing such as repeated administrations of a relatively low dose of G-protein Chemokine Receptor polypeptide for a relatively long period of time may have an effect which is therapeutically and/or pharmacologically distinguishable from that achieved with repeated administrations of a relatively high dose of G-protein Chemokine Receptor for a relatively short period of time.

Using the equivalent surface area dosage conversion factors supplied by Freireich, E. J., et al. (*Cancer Chemotherapy Reports* 50(4):219-44 (1966)), one of ordinary skill in the art is able to conveniently convert data obtained from the use of G-protein Chemokine Receptor in a given experimental system into an accurate estimation of a pharmaceutically effective amount of G-protein Chemokine Receptor polypeptide to be administered per dose in another experimental system. Experimental data obtained through the administration of G-protein Chemokine Receptor in mice may converted through the conversion factors supplied by Freireich, et al., to accurate estimates of pharmaceutically effective doses of G-protein Chemokine Receptor in rat, monkey, dog, and human. The following conversion table (Table IV) is a summary of the data provided by Freireich, et al. Table IV gives approximate factors for converting doses expressed in terms of mg/kg from one species to an equivalent surface area dose expressed as mg/kg in another species tabulated.

TABLE IV

Equivalent Surface Area Dosage Conversion Factors.

| FROM | TO | | | | |
|---|---|---|---|---|---|
| | Mouse (20 g) | Rat (150 g) | Monkey (3.5 kg) | Dog (8 kg) | Human (60 kg) |
| Mouse | 1 | 1/2 | 1/4 | 1/6 | 1/12 |
| Rat | 2 | 1 | 1/2 | 1/4 | 1/7 |
| Monkey | 4 | 2 | 1 | 3/5 | 1/3 |
| Dog | 6 | 4 | 5/3 | 1 | 1/2 |
| Human | 12 | 7 | 3 | 2 | 1 |

Thus, for example, using the conversion factors provided in table TV, a dose of 50 mg/kg in the mouse converts to an appropriate dose of 12.5 mg/kg in the monkey because (50 mg/kg)×(1/4)=12.5 mg/kg. As an additional example, doses of 0.02, 0.08, 0.8, 2, and 8 mg/kg in the mouse equate to effect doses of 1.667 micrograms/kg, 6.67 micrograms/kg, 66.7 micrograms/kg, 166.7 micrograms/kg, and 0.667 mg/kg, respectively, in the human.

Pharmaceutical compositions containing G-protein Chemokine Receptor polypeptides of the invention may be administered orally, rectally, parenterally, subcutaneously, intracistemally, intravaginally, intraperitoneally, topically (as by powders, ointments, drops or transdermal patch), bucally, or as an oral or nasal spray (e.g., via inhalation of a vapor or powder). In one embodiment, "pharmaceutically acceptable carrier" means a non-toxic solid, semisolid or liquid filler, diluent, encapsulating material or formulation auxiliary of any type. In a specific embodiment, "pharmaceutically acceptable" means approved by a regulatory agency of the federal or a state government or listed in the U.S. Pharmacopeia or other generally recognized pharmacopeia for use in animals, and more particularly humans. Nonlimiting examples of suitable pharmaceutical carriers according to this embodiment are provided in "Remington's Pharmaceutical Sciences" by E. W. Martin, and include sterile liquids, such as water and oils, including those of petroleum, animal, vegetable or synthetic origin, such as peanut oil, soybean oil, mineral oil, sesame oil and the like. Water is a preferred carrier when the pharmaceutical composition is administered intravenously. Saline solutions and aqueous dextrose and glycerol solutions can be employed as liquid carriers, particularly for injectable solutions. The composition, if desired, can also contain minor amounts of wetting or emulsifying agents, or pH buffering agents. These compositions can take the form of solutions, suspensions, emulsion, tablets, pills, capsules, powders, sustained-release formulations and the like.

The term "parenteral" as used herein refers to modes of administration which include intravenous, intramuscular, intraperitoneal, intrastemal, subcutaneous and intraarticular injection and infusion.

In a preferred embodiment, G-protein Chemokine Receptor compositions of the invention (including polypeptides, polynucleotides, and antibodies, and agonists and/or antagonists thereof) are administered subcutaneously.

In another preferred embodiment, G-protein Chemokine Receptor compositions of the invention (including polypeptides, polynucleotides, and antibodies, and agonists and/or antagonists thereof) are administered intravenously.

G-protein Chemokine Receptor compositions of the invention are also suitably administered by sustained-release systems. Suitable examples of sustained-release compositions include suitable polymeric materials (such as, for example, semi-permeable polymer matrices in the form of shaped articles, e.g., films, or mirocapsules), suitable hydrophobic materials (for example as an emulsion in an acceptable oil) or ion exchange resins, and sparingly soluble derivatives (such as, for example, a sparingly soluble salt).

Sustained-release matrices include polylactides (U.S. Pat. No. 3,773,919, EP 58,481), copolymers of L-glutamic acid and gamma-ethyl-L-glutamate (Sidman, U. et al., *Biopolymers* 22:547-556 (1983)), poly (2-hydroxyethyl methacrylate) (R. Langer et al., *J. Biomed. Mater. Res.* 15:167-277 (1981), and R. Langer, *Chem. Tech.* 12:98-105 (1982)), ethylene vinyl acetate (R. Langer et al., Id.) or poly-D-(−)-3-hydroxybutyric acid (EP 133,988).

In a preferred embodiment, C-protein Chemokine Receptor compositions of the invention are formulated in a biodegradable, polymeric drug delivery system, for example as described in U.S. Pat. Nos. 4,938,763; 5,278,201; 5,278,202; 5,324,519; 5,340,849; and 5,487,897 and in International Publication Numbers WO01/35929, WO00/24374, and WO00/06117 which are hereby incorporated by reference in their entirety. In specific preferred embodiments the G-protein Chemokine Receptor compositions of the invention are formulated using the ATRIGEL® Biodegradable System of Atrix Laboratories, Inc. (Fort Collins, Colo.).

Examples of biodegradable polymers which can be used in the formulation of G-protein Chemokine Receptor compositions, include but are not limited to, polylactides, polyglycolides, polycaprolactones, polyanhydrides, polyamides, polyurethanes, polyesteramides, polyorthoesters, polydioxanones, polyacetals, polyketals, polycarbonates, polyorthocarbonates, polyphosphazenes, polyhydroxybutyrates, polyhydroxyvalerates, polyalkylene oxalates, polyalkylene succinates, poly(malic acid), poly(amino acids), poly(methyl vinyl ether), poly(maleic anhydride), polyvinylpyrrolidone, polyethylene glycol, polyhydroxycellulose, chitin, chitosan, and copolymers, terpolymers, or combinations or mixtures of the above materials. The preferred polymers are those that have a lower degree of crystallization and are more hydrophobic. These polymers and copolymers are more soluble in the biocompatible solvents than:the highly crystalline polymers such as polyglycolide and chitin which also have a high degree of hydrogen-bonding. Preferred materials with the desired solubility parameters are the polylactides, polycaprolactones, and copolymers of these with glycolide in which there are more amorphous regions to enhance solubility. In specific preferred embodiments, the biodegradable polymers which can be used in the formulation of G-protein Chemokine Receptor compositions are poly(lactide-co-glycolides). Polymer properties such as molecular weight, hydrophobicity, and lactide/glycolide ratio may be modified to obtain the desired drug G-protein Chemokine Receptor release profile (See, e.g., Ravivarapu et al., Journal of Pharmaceutical Sciences 89:732-741 (2000), which is hereby incorporated by reference in its entirety).

It is also preferred that the solvent for the biodegradable polymer be non-toxic, water miscible, and otherwise biocompatible. Examples of such solvents include, but are not limited to, N-methyl-2-pyrrolidone, 2-pyrrolidone, C2 to C6 alkanols, C1 to C15 alcohols, dils, triols, and tetraols such as ethanol, glycerine propylene glycol, butanol; C3 to C15 alkyl ketones such as acetone, diethyl ketone and methyl ethyl ketone; C3 to C15 esters such as methyl acetate, ethyl acetate, ethyl lactate; alkyl ketones such as methyl ethyl ketone, C1 to C15 amides such as dimethylformamide, dimethylacetamide and caprolactam; C3 to C20 ethers such as tetrahydrofuran, or solketal; tweens, triacetin, propylene carbonate, decylmethylsulfoxide, dimethyl sulfoxide, oleic acid, 1-dodecylazacycloheptan-2-one, Other preferred solvents are benzyl alchohol, benzyl benzoate, dipropylene glycol, tributyrin, ethyl oleate, glycerin, glycofural, isopropyl myristate, isopropyl palmitate, oleic acid, polyethylene glycol, propylene carbonate, and triethyl citrate. The most preferred solvents are N-methyl-2-pyrrolidone, 2-pyrrolidone, dimethyl sulfoxide, triacetin, and propylene carbonate because of the solvating ability and their compatibility.

Additionally, formulations comprising G-protein Chemokine Receptor compositions and a biodegradable polymer may also include release-rate modification agents and/or pore-forming agents. Examples of release-rate modification agents include, but are not limited to, fatty acids, triglycerides, other like hydrophobic compounds, organic solvents, plasticizing compounds and hydrophilic compounds. Suitable release rate modification agents include, for example, esters of mono-, di-, and tricarboxylic acids, such as 2-ethoxyethyl acetate, methyl acetate, ethyl acetate, diethyl phthalate, dimethyl phthalate, dibutyl phthalate, dimethyl adipate, dimethyl succinate, dimethyl oxalate, dimethyl citrate, triethyl citrate, acetyl tributyl citrate, acetyl triethyl citrate, glycerol triacetate, di(n-butyl) sebecate, and the like; polyhydroxy alcohols, such as propylene glycol, polyethylene glycol, glycerin, sorbitol, and the like; fatty acids; triesters of glycerol, such as triglycerides, epoxidized soybean oil, and other epoxidized vegetable oils; sterols, such as cholesterol; alcohols, such as C.sub.6-C.sub.12 alkanols, 2-ethoxyethanol. The release rate modification agent may be used singly or in combination with other such agents. Suitable combinations of release rate modification agents include, but are not limited to, glycerin/propylene glycol, sorbitol/glycerine, ethylene oxide/propylene oxide, butylene glycol/adipic acid, and the like. Preferred release rate modification agents include, but are not limited to, dimethyl citrate, triethyl citrate, ethyl heptanoate, glycerin, and hexanediol. Suitable pore-forming agents that may be used in the polymer composition include, but are not limited to, sugars such as sucrose and dextrose, salts such as sodium chloride and sodium carbonate, polymers such as hydroxylpropylcellulose, carboxymethylcellulose, polyethylene glycol, and polyvinylpyrrolidone. Solid crystals that will provide a defined pore size, such as salt or sugar, are preferred.

In specific preferred embodiments the G-protein Chemokine Receptor compositions of the invention are formulated using the BEMA™ BioErodible Mucoadhesive System, MCA™ MucoCutaneous Absorption System, SMP™ Solvent MicroParticle System, or BCP™ BioCompatible Polymer System of Atrix Laboratories, Inc. (Fort Collins, Colo.).

Sustained-release compositions also include liposomally entrapped compositions of the invention (see generally, Langer, Science 249:1527-1533 (1990); Treat et al., in *Liposomes in the Therapy of Infectious Disease and Cancer*, Lopez-Berestein and Fidler (eds.), Liss, New York, pp. 317-327 and 353-365 (1989)). Liposomes containing G-protein Chemokine Receptor polypeptide may be prepared by methods known per se: DE 3,218,121; Epstein et al., Proc. Natl. Acad. Sci. (USA) 82:3688-3692 (1985); Hwang et al., Proc. Natl. Acad. Sci. (USA) 77:4030-4034 (1980); EP 52,322; EP 36,676; EP 88,046; EP 143,949; EP 142,641; Japanese Pat. Appl. 83-118008; U.S. Pat. Nos. 4,485,045 and 4,544,545; and EP 102,324. Ordinarily, the liposomes are of the small (about 200-800 Angstroms) unilamellar type in which the lipid content is greater than about 30 mol. percent cholesterol, the selected proportion being adjusted for the optimal G-protein Chemokine Receptor polypeptide therapy.

In another embodiment systained release compositions of the invention include crystal formulations known in the art.

In yet an additional embodiment, the compositions of the invention are delivered by way of a pump (see Langer, supra; Sefton, CRC Crit. Ref. Biomed. Eng. 14:201 (1987); Buchwald et al., Surgery 88:507 (1980); Saudek et al., N. Engl. J. Med. 321:574 (1989)).

Other controlled release systems are discussed in the review by Langer (*Science* 249:1527-1533 (1990)).

For parenteral administration, in one embodiment, the G-protein Chemokine Receptor polypeptide is formulated generally by mixing it at the desired degree of purity, in a unit dosage injectable form (solution, suspension, or emulsion), with a pharmaceutically acceptable carrier, i.e., one that is non-toxic to recipients at the dosages and concentrations employed and is compatible with other ingredients of the formulation. For example, the formulation preferably does not include oxidizing agents and other compounds that are known to be deleterious to polypeptides.

Generally, the formulations are prepared by contacting the G-protein Chemokine Receptor polypeptide uniformly and intimately with liquid carriers or finely divided solid carriers or both. Then, if necessary, the product is shaped into the desired formulation. Preferably the carrier is a parenteral carrier, more preferably a solution that is isotonic with the blood of the recipient. Examples of such carrier vehicles include water, saline, Ringer's solution, and dextrose solution. Non-aqueous vehicles such as fixed oils and ethyl oleate are also useful herein, as well as liposomes.

The carrier suitably contains minor amounts of additives such as substances that enhance isotonicity and chemical stability. Such materials are non-toxic to recipients at the dosages and concentrations employed, and include buffers such as phosphate, citrate, succinate, acetic acid, and other organic acids or their salts; antioxidants such as ascorbic acid; low molecular weight (less than about ten residues) polypeptides, e.g., polyarginine or tripeptides; proteins, such as serum albumin, gelatin, or immunoglobulins; hydrophilic polymers such as polyvinylpyrrolidone; amino acids, such as glycine, glutamic acid, aspartic acid, or arginine; monosaccharides, disaccharides, and other carbohydrates including cellulose or its derivatives, glucose, manose, sucrose, or dextrins; chelating agents such as EDTA; sugar alcohols such as mannitol or sorbitol; counterions such as sodium; preservatives, such as cresol, phenol, chlorobutanol, benzyl alcohol and parabens, and/or nonionic surfactants such as polysorbates, poloxamers, or PEG.

The G-protein Chemokine Receptor polypeptide is typically formulated in such vehicles at a concentration of about 0.001 mg/ml to 100 mg/ml, or 0.1 mg/ml to 100 mg/ml, preferably 1-10 mg/ml or 1-10 mg/ml, at a pH of about 3 to 10, or 3 to 8, more preferably 5-8, most preferably 6-7. It will be understood that the use of certain of the foregoing excipients, carriers, or stabilizers will result in the formation of G-protein Chemokine Receptor polypeptide salts.

G-protein Chemokine Receptor polypeptide to be used for therapeutic administration must be sterile. Sterility is readily accomplished by filtration through sterile filtration membranes (e.g., 0.2 micron membranes). Therapeutic G-protein Chemokine Receptor polypeptide compositions generally are placed into a container having a sterile access port, for example, an intravenous solution bag or vial having a stopper pierceable by a hypodermic injection needle.

G-protein Chemokine Receptor polypeptide ordinarily will be stored in unit or multi-dose containers, for example, sealed ampoules or vials, as an aqueous solution or as a lyophilized formulation for reconstitution. As an example of a lyophilized formulation, 10-ml vials are filled with 5 ml of sterile-filtered 1% (w/v) aqueous G-protein Chemokine Receptor polypeptide-solution, and the resulting mixture is lyophilized. The infusion solution is prepared by reconstituting the lyophilized G-protein Chemokine Receptor polypeptide using bacteriostatic Water-for-Injection.

Alternatively, G-protein Chemokine Receptor polypeptide is stored in single dose containers in lyophilized form. The infusion selection is reconstituted using a sterile carrier for injection.

The invention also provides a pharmaceutical pack or kit comprising one or more containers filled with one or more of the ingredients of the pharmaceutical compositions of the invention. Optionally, associated with such container(s) is a notice in the form prescribed by a governmental agency regulating the manufacture, use or sale of pharmaceuticals or biological products, which notice reflects approval by the agency of manufacture, use or sale for human administration. In addition, the polypeptides of the present invention may be employed in conjunction with other therapeutic compounds.

The compositions of the invention may be administered alone or in combination with other adjuvants. Adjuvants that may be administered with the compositions of the invention include, but are not limited to, alum, alum plus deoxycholate (ImmunoAg), MTP-PE (Biocine Corp.), QS21 (Genentech, Inc.), BCG, and MPL. In a specific embodiment, compositions of the invention are administered in combination with alum. In another specific embodiment, compositions of the invention are administered in combination with QS-21. Further adjuvants that may be administered with the compositions of the invention include, but are not limited to, Monophosphoryl lipid immunomodulator, AdjuVax 100a, QS-21, QS-18, CRL1005, Aluminum salts, MF-59, and Virosomal adjuvant technology. Vaccines that may be administered with the compositions of the invention include, but are not limited to, vaccines directed toward protection against MMR (measles, mumps, rubella), polio, varicella, tetanus/diptheria, hepatitis A, hepatitis B, haemophilus influenzae B, whooping cough, pneumonia, influenza, Lyme's Disease, rotavirus, cholera, yellow fever, Japanese encephalitis, poliomyelitis, rabies, typhoid fever, and pertussis, and/or PNEUMOVAX-23™. Combinations may be administered either concomitantly, e.g., as an admixture, separately but simultaneously or concurrently; or sequentially. This includes presentations in which the combined agents are administered together as a therapeutic mixture, and also procedures in which the combined agents are administered separately but simultaneously, e.g., as through separate intravenous lines into the same individual. Administration "in combination" further includes the separate administration of one of the compounds or agents given first, followed by the second.

In another specific embodiment, compositions of the invention are used in combination with PNEUMOVAX-23™ to treat, prevent, and/or diagnose infection and/or any disease, disorder, and/or condition associated therewith. In one embodiment, compositions of the invention are used in combination with PNEUMOVAX-23™ to treat, prevent, and/or diagnose any Gram positive bacterial infection and/or any disease, disorder, and/or condition associated therewith. In another embodiment, compositions of the invention are used in combination with PNEUMOVAX-23™ to treat, prevent, and/or diagnose infection and/or any disease, disorder, and/or condition associated with one or more members of the genus *Enterococcus* and/or the genus *Streptococcus*. In another embodiment, compositions of the invention are used in any combination with PNEUMOVAX-23™ to treat, prevent, and/ or diagnose infection and/or any disease, disorder, and/or condition associated with one or more members of the Group B streptococci. In another embodiment, compositions of the invention are used in combination with PNEUMOVAX-23™ to treat, prevent, and/or diagnose infection and/or any disease, disorder, and/or condition associated with *Streptococcus pneumoniae*.

The compositions of the invention may be administered alone or in combination with other therapeutic agents, including but not limited to, chemotherapeutic agents, antibiotics, antivirals, steroidal and non-steroidal anti-inflammatories, conventional immunotherapeutic agents and cytokines. Combinations may be administered either concomitantly, e.g., as an admixture, separately but simultaneously or concurrently; or sequentially. This includes presentations in which the combined agents are administered together as a therapeutic mixture, and also procedures in which the combined agents are administered separately but simultaneously, e.g., as through separate intravenous lines into the same individual. Administration "in combination" further includes the separate administration of one of the compounds or agents given first, followed by the second.

In a highly preferred embodiment, the compositions of the invention are administered alone or in combination with an anti-inflammatory agent. Anti-inflammatory agents that may be administered with the compositions of the invention include, but are not limited to, glucocorticoids and the non-steroidal anti-inflammatories, aminoarylcarboxylic acid derivatives, arylacetic acid derivatives, arylbutyric acid derivatives, arylcarboxylic acids, arylpropionic acid derivatives, pyrazoles, pyrazolones, salicylic acid derivatives, thiazinecarboxamides, e-acetamidocaproic acid, S-adenosylmethionine, 3-amino-4-hydroxybutyric acid, amixetrine, bendazac, benzydamine, bucolome, difenpiramide, ditazol, emorfazone, guaiazulene, nabumetone, nimesulide, orgotein, oxaceprol, paranyline, perisoxal, pifoxime, proquazone, proxazole, and tenidap.

In a highly preferred embodiment, compositions of the invention are administered alone or in combination with conventional nonspecific immunosuppressive agents, that may be administered in combination with the compositions of the invention include, but are not limited to, steroids, cyclosporine, cyclosporine analogs, cyclophosphamide methylprednisone, prednisone, azathioprine, FK-506, 15-deoxyspergualin, and other immunosuppressive agents that act by suppressing the function of responding T cells.

Additional immunosuppressants preparations that may be administered with the compositions of the invention include, but are not limited to, ORTHOCLONE™ (OKT3), SAND-IMMUNE™/NEORAL™/SANGDYA™ (cyclosporin), PROGRAF™ (tacrolimus), CELLCEPT™ (mycophenolate), Azathioprine, glucorticosteroids, and RAPAMUNE™ (sirolimus). In a specific embodiment, immunosuppressants may be used to prevent rejection of organ or bone marrow transplantation.

In an additional embodiment, the compositions of the invention are administered in combination with cytokines. Cytokines that may be administered with the compositions of the invention include, but are not limited to, GM-CSF, G-CSF, IL-1alpha, IL-1beta, IL-2, IL-3, IL-4, IL-5, IL-6, IL-7, IL-8, IL-9, IL-10, IL-11, IL-12, IL-13, IL-14, IL-15, IL-16, IL-17, IL-18, IL-19, IL-20, IL-21, anti-CD40, CD40L, IFN-gamma and TNF-alpha. In one embodiment, the compositions of the invention are administered in combination with one or more chemokines. In specific embodiments, the compositions of the invention are administered in combination with an α(C× C) chemokine selected from the group consisting of gamma-interferon inducible protein-10 (γIP-10), interleukin-8 (IL-8), platelet factor-4 (PF4), neutrophil activating protein (NAP-2), GRO-α, GRO-β, GRO-γ, neutrophil-activating peptide (ENA-78), granulocyte chemoattractant protein-2 (GCP-2), and stromal cell-derived factor-1 (SDF-1, or pre-B cell stimulatory factor (PBSF)); and/or a β(CC) chemokine selected from the group consisting of: RANTES (regulated on activation, normal T expressed and secreted), macrophage inflammatory protein-1 alpha (MIP-1α), macrophage inflammatory protein-1 beta (MIP-1β), monocyte chemotactic protein-1 (MCP-1), monocyte chemotactic protein-2 (MCP-2), monocyte chemotactic protein-3 (MCP-3), monocyte chemotactic protein-4 (MCP-4) macrophage inflammatory protein-1 gamma (MIP-1γ), macrophage inflammatory protein-3 alpha (MIP-3α), macrophage inflammatory protein-3 beta (MIP-3β), macrophage inflammatory protein-4 (MIP-4/DC-CK-1/PARC), eotaxin, Exodus, and 1-309; and/or the γ(C) chemokine, lymphotactin.

In an additional embodiment, compositions of the invention are administered alone or in combination with one or more intravenous immune globulin preparations. Intravenous immune globulin preparations that may be administered with the compositions of the invention include, but not limited to, GAMMAR™, IVEEGAM™, SANDOGLOBULIN™, GAMMAGARD S/D™, and GAMIMUNE™. In a specific embodiment, compositions of the invention are administered in combination with intravenous immune globulin preparations in transplantation therapy (e.g., bone marrow transplant).

In additional embodiments, compositions of the invention may be administered in combination with anti-opportunistic infection agents. Anti-opportunistic agents that may be administered in combination with the compositions of the invention, include, but are not limited to, TRIMETHOPRIM-SULFAMETHOXAZOLE™, DAPSONE™, PENTAMIDINE™, ATOVAQUONE™, ISONIAZID™, RIFAMPIN™, PYRAZINAMIDE™, ETHAMBUTOL™, RIFABUTIN™, CLARITHROMYCIN™, AZITHROMYCIN™, GANCICLOVIR™, FOSCARNET™, CIDOFOVIR™, FLUCONAZOLE™, ITRACONAZOLE™, KETOCONAZOLE™, ACYCLOVIR™, FAMCICOLVIR™, PYRIMETHAMINE™, LEUCOVORIN™, NEUPOGEN™ (filgrastim/G-CSF), and LEUKINE™ (sargramostim/GM-CSF). In a specific embodiment, compositions of the invention are used in any combination with TRI-METHOPRIM-SULFAMETHOXAZOLE™, DAPSONE™, PENTAMIDINE™, and/or ATOVAQUONE™ to prophylactically treat or prevent an opportunistic *Pneumocystis carinii* pneumonia infection. In another specific embodiment, compositions of the invention are used in any combination with ISONIAZID™, RIFAMPIN™, PYRAZINAMIDE™, and/or ETHAMBUTOL™ to prophylactically treat or prevent an opportunistic *Mycobacterium avium* complex infection. In another specific embodiment, compositions of the invention are used in any combination with RIFABUTIN™, CLARITHROMYCIN™, and/or AZITHROMYCIN™ to prophylactically treat or prevent an opportunistic *Mycobacterium tuberculosis* infection. In another specific embodiment, compositions of the invention are used in any combination with GANCICLOVIR™, FOSCARNET™, and/or CIDOFOVIR™ to prophylactically treat or prevent an opportunistic cytomegalovirus infection. In another specific embodiment, compositions of the invention are used in any combination with FLUCONAZOLE™, ITRACONAZOLE™, and/or KETOCONAZOLE™ to prophylactically treat or prevent an opportunistic fungal infection. In another specific embodiment, compositions of the invention are used in any combination with ACYCLOVIR™ and/or FAMCICOLVIR™ to prophylactically treat or prevent an opportunistic herpes simplex virus type I and/or type II infection. In another specific embodiment, compositions of the invention are used in any combination with PYRIMETHAMINE™ and/or LEUCOVORIN™ to prophylactically treat or prevent an opportunistic *Toxoplasma gondii* infection. In another specific embodiment, compositions of the invention are used in any combination with LEUCOVORIN™ and/or NEUPOGEN™ to prophylactically treat or prevent an opportunistic bacterial infection.

In a further embodiment, the compositions of the invention are administered in combination with an antiviral agent. Antiviral agents that may be administered with the compositions of the invention include, but are not limited to, acyclovir, ribavirin, amantadine, and remantidine.

In a further embodiment, the compositions of the invention are administered in combination with an antibiotic agent. Antibiotic agents that may be administered with the compositions of the invention include, but are not limited to, amoxicillin, aminoglycosides, beta-lactam (glycopeptide), beta-lactamases, clindamycin, chloramphenicol, cephalosporins, ciprofloxacin, ciprofloxacin, erythromycin, fluoroquinolones, macrolides, metronidazole, penicillins, quinolones, rifampin, streptomycin, sulfonamide, tetracyclines, trimethoprim, trimethoprim-sulfamthoxazole, and vancomycin.

In another embodiment, compostions of the invention are administered in combination with a chemotherapeutic agent. Chemotherapeutic agents that may be administered with the compositions of the invention include, but are not limited to, antibiotic derivatives (e.g., doxorubicin, bleomycin, daunorubicin, and dactinomycin); antiestrogens (e.g., tamoxifen); antimetabolites (e.g., fluorouracil, 5-FU, methotrexate, floxuridine, interferon alpha-2b, glutamic acid, plicamycin, mercaptopurine, and 6-thioguanine); cytotoxic agents (e.g., carmustine, BCNU, lomustine, CCNU, cytosine arabinoside, cyclophosphamide, estramustine, hydroxyurea, procarbazine, mitomycin, busulfan, cis-platin, and vincristine sulfate); hormones (e.g., medroxyprogesterone, estramustine phosphate sodium, ethinyl estradiol, estradiol, megestrol acetate, methyltestosterone, diethylstilbestrol diphosphate, chlortrianisene, and testolactone); nitrogen mustard derivatives (e.g., mephalen, chorambucil, mechlorethamine (nitrogen mustard) and thiotepa); steroids and combinations (e.g., bethamethasone sodium phosphate); and others (e.g., dicarbazine, asparaginase, mitotane, vincristine sulfate, vinblastine sulfate, and etoposide).

In a specific embodiment, compositions of the invention are administered in combination with CHOP (cyclophosphamide, doxorubicin, vincristine, and prednisone) or any combination of the components of CHOP. In another embodiment, compositions of the invention are administered in combination with Rituximab. In a further embodiment, compositions of the invention are administered with Rituxmab and CHOP, or Rituxmab and any combination one or more of the components of CHOP.

In an additional embodiment, the compositions of the invention are administered in combination with Fibroblast Growth Factors. Fibroblast Growth Factors that may be administered with the compositions of the invention include, but are not limited to, FGF-1, FGF-2, FGF-3, FGF-4, FGF-5, FGF-6, FGF-7, FGF-8, FGF-9, FGF-10, FGF-11, FGF-12, FGF-13, FGF-14, and FGF-15.

The invention also encompasses combining the polynucleotides and/or polypeptides of the invention (and/or agonists or antagonists thereof) with other proposed or conventional hematopoietic therapies. Thus, for example, the polynucleotides and/or polypeptides of the invention (and/or agonists or antagonists thereof) can be combined with compounds that singly exhibit erythropoietic stimulatory effects, such as erythropoietin, testosterone, progenitor cell stimulators, insulin-like growth factor, prostaglandins, serotonin, cyclic AMP, prolactin, and triiodothyzonine. Also encompassed are combinations of the compositions of the invention with compounds generally used to treat aplastic anemia, such as, for example, methenolene, stanozolol, and nandrolone; to treat iron-deficiency anemia, such as, for example, iron preparations; to treat malignant anemia, such as, for example, vitamin $B_{12}$ and/or folic acid; and to treat hemolytic anemia, such as, for example, adrenocortical steroids, e.g., corticoids. See e.g., Resegotti et al., Panminerva Medica, 23:243-248 (1981); Kurtz, FEBS Letters, 14a:105-108 (1982); McGonigle et al., Kidney Int., 25:437-444 (1984); and Pavlovic-Kantera, Expt. Hematol., 8(supp. 8) 283-291 (1980), the contents of each of which are hereby incorporated by reference in their entireties.

Compounds that enhance the effects of or synergize with erythropoietin are also useful as adjuvants herein, and include but are not limited to, adrenergic agonists, thyroid hormones, androgens, hepatic erythropoietic factors, erythrotropins, and erythrogenins, See for e.g., Dunn, "Current Concepts in Erythropoiesis", John Wiley and Sons (Chichester, England, 1983); Kalmani, Kidney Int., 22:383-391 (1982); Shahidi, New Eng. J. Med., 289:72-80 (1973); Urabe et al., J. Exp. Med., 149:1314-1325 (1979); Billat et al., Expt. Hematol., 10:133-140 (1982); Naughton et al., Acta Haemat, 69:171-179 (1983); Cognote et al. in abstract 364, Proceedings 7th Intl. Cong. of Endocrinology (Quebec City, Quebec, Jul. 1-7, 1984); and Rothman et al., 1982, J. Surg. Oncol., 20:105-108 (1982). Methods for stimulating hematopoiesis comprise administering a hematopoietically effective amount (i.e., an amount which effects the formation of blood cells) of a pharmaceutical composition containing polynucleotides and/or poylpeptides of the invention (and/or agonists or antagonists thereof) to a patient. The polynucleotides and/or polypeptides of the invention and/or agonists or antagonists thereof is administered to the patient by any suitable technique, including but not limited to, parenteral, sublingual, topical, intrapulmonary and intranasal, and those techniques further discussed herein. The pharmaceutical composition optionally contains one or more members of the group consisting of erythropoietin, testosterone, progenitor cell stimulators, insulin-like growth factor, prostaglandins, serotonin, cyclic AMP, prolactin, triiodothyzonine, methenolene, stanozolol, and nandrolone, iron preparations, vitamin $B_{12}$, folic acid and/or adrenocortical steroids.

In additional prefered embodiments, the compositions of the invention are administered in combination with hematopoietic growth factors. Hematopoietic growth factors that may be administered with the compositions of the invention included, but are not limited to, LEUKINE™ (SARGRAMOSTIM™) and NEUPOGEN™ (FILGRASTIM™).

In one embodiment, the compositions of the invention are administered in combination with members of the TNF family. TNF, TNF-related or TNF-like molecules that may be administered with the compositions of the invention include, but are not limited to, soluble forms of TNF-alpha, lymphotoxin-alpha (LT-alpha, also known as TNF-beta), LT-beta (found in complex heterotrimer LT-alpha2-beta), OPGL, FasL, CD27L, CD30L, CD40L, 4-IBBL, DcR3, OX40L, TNF-gamma (International Publication No. WO 96/14328), TRAIL, AIM-II (International Publication No. WO 97/34911), APRIL (International Publication Number WO 97/33902; *J. Exp. Med.* 188(6):1185-1190 (1998)), endokine-alpha (International Publication No. WO 98/07880), Neutrokine-alpha (Internatioanl Application Publication No. WO 98/18921), OPG, OX40, and nerve growth factor (NGF), and soluble forms of Fas, CD30, CD27, CD40 and 4-IBB, TR2 (International Publication No. WO 96/34095), DR3 (International Publication No. WO 97/33904), DR4 (International Publication No. WO 98/32856), TR5 (International Publication No. WO 98/30693), TR6 (International Publication No. WO 98/30694), TR7 (International Publication No. WO 98/41629), TRANK, TR9 (International Publication No. WO 98/56892), 312C2 (International Publication No. WO 98/06842), and TR12, and soluble forms of BCMA (See e.g., Laabis et al., Nucleic acids research, 22(7) 1147-1154 (1994); Genbank Accession Number Z29574), CD154, CD70, and CD153.

In certain embodiments, compositions of the invention are administered in combination with antiretroviral agents, nucleoside reverse transcriptase inhibitors, non-nucleoside reverse transcriptase inhibitors, and/or protease inhibitors. Nucleoside reverse transcriptase inhibitors that may be administered in combination with the compositions of the invention, include, but are not limited to, RETROVIR™ (zidovudine/AZT), VIDEX™ (didanosine/ddi), HIVID™ (zalcitabine/ddC), ZERIT™ (stavudine/d4T), EPIVIR™ (lamivudine/3TC), and COMBIVIR™ (zidovudine/lamivudine). Non-nucleoside reverse transcriptase inhibitors that may be administered in combination with the compositions of the invention, include, but are not limited to, VIRAMUE™ (nevirapine), RESCRIPTOR™ (delavirdine), and SUSTIVA™ (efavirenz). Protease inhibitors that may be administered in combination with the compositions of the invention, include, but are not limited to, CRIXIVAN™ (indinavir), NORVIR™ (ritonavir), INVIRASE™ (saquinavir), and VIRACEPT™ (nelfinavir). In a specific embodiment, antiretroviral agents, nucleoside reverse transcriptase inhibitors, non-nucleoside reverse transcriptase inhibitors, and/or protease inhibitors may be used in any combination with compositions of the invention to treat AIDS and/or to prevent or treat HIV infection.

Additional NRTIs include LODENOSINE™ (F-ddA; an acid-stable adenosine NRTI; Triangle/Abbott; COVIRACIL™ (emtricitabine/FTC; structurally related to lamivudine (3TC) but with 3- to 10-fold greater activity in vitro; Triangle/Abbott); dOTC (BCH-10652, also structurally related to lamivudine but retains activity against a substantial proportion of lamivudine-resistant isolates; Biochem Pharma); Adefovir (refused approval for anti-HIV therapy by FDA; Gilead Sciences); PREVEON® (Adefovir Dipivoxil, the active prodrug of adefovir; its active form is PMEA-pp); TENOFOVIR™ (bis-POC PMPA, a PMPA prodrug; Gilead); DAPD/DXG (active metabolite of DAPD; Triangle/Abbott); D-D4FC (related to 3TC, with activity against AZT/3TC-resistant virus); GW420867X (Glaxo Wellcome); ZIAGEN™ (abacavir/159U89; Glaxo Wellcome Inc.); CS-87 (3'azido-2',3'-dideoxyuridine; WO 99/66936); and S-acyl-2-thioethyl (SATE)-bearing prodrug forms of β-L-FD4C and β-L-FddC (WO 98/17281).

Additional NNRTIs include COACTINON™ (Emivirine/MKC-442, potent NNRTI of the HEPT class; Triangle/Abbott); CAPRAVIRINE™ (AG-1549/S-1153, a next generation NNRTI with activity against viruses containing the K103N mutation; Agouron); PNU-142721 (has 20- to 50-fold greater activity than its predecessor delavirdine and is active against K103N mutants; Pharmacia & Upjohn); DPC-961 and DPC-963 (second-generation derivatives of efavirenz, designed to be active against viruses with the K103N mutation; DuPont); GW-420867X (has 25-fold greater activity than HBY097 and is active against K103N mutants; Glaxo Wellcome); CALANOLIDE A (naturally occurring agent from the latex tree; active against viruses containing either or both the Y181C and K103N mutations); and Propolis (WO 99/49830).

Additional protease inhibitors include LOPINAVIR™ (ABT378/r; Abbott Laboratories); BMS-232632 (an azapeptide; Bristol-Myres Squibb); TIPRANAVIR™ (PNU-140690, a non-peptic dihydropyrone; Pharmacia & Upjohn); PD-178390 (a nonpeptidic dihydropyrone; Parke-Davis); BMS 232632 (an azapeptide; Bristol-Myers Squibb); L-756, 423 (an indinavir analog; Merck); DMP-450 (a cyclic urea compound; Avid & DuPont); AG-1776 (a peptidomimetic with in vitro activity against protease inhibitor-resistant viruses; Agouron); VX-175/GW-433908 (phosphate prodrug of amprenavir; Vertex & Glaxo Welcome); CGP61755 (Ciba); and AGENERASE™ (amprenavir; Glaxo Wellcome Inc.).

Additional antiretroviral agents include fusion inhibitors/gp41 binders. Fusion inhibitors/gp41 binders include T-20 (a peptide from residues 643-678 of the HIV gp41 transmembrane protein ectodomain which binds to gp41 in its resting state and prevents transformation to the fusogenic state; Trimeris) and T-1249 (a second-generation fusion inhibitor; Trimeris).

Additional antiretroviral agents include fusion inhibitors/chemokine receptor antagonists. Fusion inhibitors/chemokine receptor antagonists include CXCR4 antagonists such as AMD 3100 (a bicyclam), SDF-1 and its analogs, and ALX40-4C (a cationic peptide), T22 (an 18 amino acid peptide; Trimeris) and the T22 analogs T134 and T140; CCR5 antagonists such as RANTES (9-68), AOP-RANTES , NNY-RANTES, and TAK-779; and CCR5/CXCR4 antagonists such as NSC 651016 (a distamycin analog). Also included are CCR2B, CCR3, and CCR6 antagonists. Chemokine recpetor agonists such as RANTES, SDF-1, MrP-1α, MIP-1β, etc., may also inhibit fusion.

Additional antiretroviral agents include integrase inhibitors. Integrase inhibitors include dicaffeoylquinic (DFQA) acids; L-chicoric acid (a dicaffeoyltartaric (DCTA) acid); quinalizarin (QLC) and related anthraquinones; ZINTEVIR™ (AR 177, an oligonucleotide that probably acts at cell surface rather than being a true integrase inhibitor; Arondex); and naphthols such as those disclosed in WO 98/50347.

Additional antiretroviral agents include hydroxyurea-like compunds such as BCX-34 (a purine nucleoside phosphorylase inhibitor; Biocryst); ribonucleotide reductase inhibitors such as DIDOX™ (Molecules for Health); inosine monophosphate dehydrogenase (IMPDH) inhibitors sucha as VX-497 (Vertex); and mycopholic acids such as CellCept (mycophenolate mofetil; Roche).

Additional antiretroviral agents include inhibitors of viral integrase, inhibitors of viral genome nuclear translocation such as arylene bis(methylketone) compounds; inhibitors of HIV entry such as AOP-RANTES, NNY-RANTES, RANTES-IgG fusion protein, soluble complexes of RANTES and glycosaminoglycans (GAG), and AMD-3100; nucleocapsid zinc finger inhibitors such as dithiane compounds; targets of HIV Tat and Rev; and pharmacoenhancers such as ABT-378.

Other antiretroviral therapies and adjunct therapies include cytokines and lymphokines such as MIP-1α, MIP-1β, SDF-1α, IL-2, PROLEUKIN™ (aldesleukin/L2-7001; Chiron), IL-4, IL-10, IL-12, and IL-13; interferons such as IFN-α2a; antagonists of TNFs, NFκB, GM-CSF, M-CSF, and IL-10; agents that modulate immune activation such as cyclosporin and prednisone; vaccines such as Remune™ (HIV Immunogen), APL 400-003 (Apollon), recombinant gp120 and fragments, bivalent (B/E) recombinant envelope glycoprotein, rgp120CM235, MN rgp120, SF-2 rgp120, gp120/soluble CD4 complex, Delta JR-FL protein, branched synthetic peptide derived from discontinuous gp120 C3/C4 domain, fusion-competent immunogens, and Gag, Pol, Nef, and Tat vaccines; gene-based therapies such as genetic suppressor elements (GSEs; WO 98/54366), and intrakines (genetically modified CC chemokines targetted to the ER to block surface expression of newly synthesized CCR5 (Yang et al., PNAS 94:11567-72 (1997); Chen et al., Nat. Med. 3:1110-16 (1997)); antibodies such as the anti-CXCR4 antibody 12G5, the anti-CCR5 antibodies 2D7, 5C7, PA8, PA9, PA10, PA11, PA12, and PA14, the anti-CD4 antibodies Q4120 and RPA-T4, the anti-CCR3 antibody 7B11, the anti-gp120 antibodies 17b, 48d, 447-52D, 257-D, 268-D and 50.1, anti-Tat antibodies, anti-TNF-α antibodies, and monoclonal antibody 33A; aryl hydrocarbon (AH) receptor agonists and antagonists such as TCDD, 3,3',4,4',5-pentachlorobiphenyl, 3,3'),4,4'-tetrachlorobiphenyl, and α-naphthoflavone (WO 98/30213); and antioxidants such as γ-L-glutamyl-L-cysteine ethyl ester (γ-GCE; WO 99/56764).

In additional embodiments, the compositions of the invention are administered in combination with other therapeutic or prophylactic regimens, such as, for example, radiation therapy.

Agonists and Antagonists—Assays and Molecules

The polynucleotides and polypeptides of the present invention may be employed as research reagents and materials for discovery of treatments and diagnostics to human disease.

The G-protein chemokine receptors of the present invention may be employed in a process for screening for compounds which activate (agonists) or inhibit activation (antagonists) of the receptor polypeptide of the present invention.

In general, such screening procedures involve providing appropriate cells which express the receptor polypeptide of the present invention on the surface thereof. Such cells include cells from mammals, yeast, drosophila or E. Coli. In particular, a polynucleotide encoding the receptor of the present invention is employed to transfect cells to thereby express the G-protein chemokine receptor. The expressed receptor is then contacted with a test compound to observe binding, stimulation or inhibition of a functional response.

One such screening procedure involves the use of melanophores which are transfected to express the G-protein chemokine receptor of the present invention. Such a screening technique is described in PCT WO 92/01810 published Feb. 6, 1992.

Thus, for example, such assay may be employed for screening for a compound which inhibits activation of the receptor polypeptide of the present invention by contacting the melanophore cells which encode the receptor with both the receptor ligand and a compound to be screened. Inhibition of the signal generated by the ligand indicates that a compound is a potential antagonist for the receptor, i.e., inhibits activation of the receptor.

The screen may be employed for determining a compound which activates the receptor by contacting such cells with compounds to be screened and determining whether such compound generates a signal, i.e., activates the receptor.

Other screening techniques include the use of cells which express the G-protein chemokine receptor (for example, transfected CHO cells) in a system which measures extracellular pH changes caused by receptor activation, for example, as described in Science, volume 246, pages 181-296 (October 1989). For example, compounds may be contacted with a cell which expresses the receptor polypeptide of the present invention and a second messenger response, e.g. signal transduction or pH changes, may be measured to determine whether the potential compound activates or inhibits the receptor.

Another such screening technique involves introducing RNA encoding the G-protein chemokine receptor into Xenopus oocytes to transiently express the receptor. The receptor oocytes may-then be contacted with the receptor ligand and a compound to be screened, followed by detection of inhibition or activation of a calcium signal in the case of screening for compounds which are thought to inhibit activation of the receptor.

Another screening technique involves expressing the G-protein chemokine receptor in which the receptor is linked to a phospholipase C or D. As representative examples of such cells, there may be mentioned endothelial cells, smooth muscle cells, embryonic kidney cells, etc. The screening may be accomplished as hereinabove-described by detecting activation of the receptor or inhibition of activation of the receptor from the phospholipase second signal.

Another method involves screening for compounds which inhibit activation of the receptor polypeptide of the present invention by determining the inhibition of binding of a labeled ligand to cells which have the receptor on the surface thereof. Such a method comprises transfecting a eukaryotic cell with DNA encoding the G-protein chemokine receptor of the present invention such that the cell expresses the receptor on its surface and contacting the cell with a compound in the presence of a labeled form of a known ligand. The ligand can be labeled, e.g., by radioactivity. The amount of labeled ligand bound to the receptors is measured, e.g., by measuring radioactivity of the receptors. If the compound binds to the receptor as determined by a reduction of labeled ligand which binds to the receptors, the binding of labeled ligand to the receptor is inhibited.

The invention also provides a method of screening compounds to identify those which enhance or block the action of G-protein Chemokine Receptor polypeptide on cells, such as its interaction with G-protein Chemokine Receptor binding molecules such as ligand molecules. An agonist is a compound which increases the natural biological functions of G-protein Chemokine Receptor or which functions in a manner similar to G-protein Chemokine Receptor while antagonists decrease or eliminate such functions.

In another embodiment, the invention provides a method for identifying a ligand protein or other ligand-binding protein which binds specifically to G-protein Chemokine Receptor polypeptide. For example, a cellular compartment, such as a membrane or a preparation thereof, may be prepared from a cell that expresses a molecule that binds G-protein Chemokine Receptor ligand (e.g., ITAC, MIG, or IP-10). The preparation is incubated with labeled G-protein Chemokine Receptor ligand and complexes of G-protein Chemokine Receptor ligand bound to G-protein Chemokine Receptor or other binding protein are isolated and characterized according to routine methods known in the art. Alternatively, the G-protein Chemokine Receptor ligand polypeptide may be bound to a solid support so that binding molecules solubilized from cells are bound to the column and then eluted and characterized according to routine methods.

In the assay of the invention for agonists or antagonists, a cellular compartment, such as a membrane or a preparation thereof, may be prepared from a cell that expresses a molecule that binds G-protein Chemokine Receptor such as a molecule of a signaling or regulatory pathway modulated by G-protein Chemokine Receptor. The preparation is incubated with labeled G-protein Chemokine Receptor in the absence or the presence of a candidate molecule which may be a G-protein Chemokine Receptor agonist or antagonist. The ability of the candidate molecule to bind the binding molecule is reflected in decreased binding of the labeled ligand. Molecules which bind gratuitously, i.e., without inducing the effects of G-protein Chemokine Receptor on binding the G-protein Chemokine Receptor binding molecule, are most likely to be good antagonists. Molecules that bind well and elicit effects that are the same as or closely related to G-protein Chemokine Receptor are agonists.

G-protein Chemokine Receptor-like effects of potential agonists and antagonists may by measured, for instance, by determining activity of a second messenger system following interaction of the candidate molecule with a cell or appropriate cell preparation, and comparing the effect with that of G-protein Chemokine Receptor or molecules that elicit the same effects as G-protein Chemokine Receptor. Second messenger systems that may be useful in this regard include but are not limited to AMP guanylate cyclase, ion channel or phosphoinositide hydrolysis second messenger systems.

Another example of an assay for G-protein Chemokine Receptor antagonists is a competitive assay that combines G-protein Chemokine Receptor and a potential antagonist with membrane-bound ligand molecules or recombinant G-protein Chemokine Receptor ligang molecules under appropriate conditions for a competitive inhibition assay. G-protein Chemokine Receptor can be labeled, such as by radioactivity, such that the number of G-protein Chemokine Receptor molecules bound to a ligand molecule can be determined accurately to assess the effectiveness of the potential antagonist.

Potential antagonists include small organic molecules, peptides, polypeptides, and antibodies that bind to a polypeptide of the invention and thereby inhibit or extinguish its activity. Potential antagonists also may be small organic molecules, a peptide, a polypeptide such as a closely related protein or antibody that binds the same sites on a binding molecule, such as a ligand molecule, without inducing G-protein Chemokine Receptor induced activities, thereby preventing the action of G-protein Chemokine Receptor by excluding G-protein Chemokine Receptor from binding.

Other potential antagonists include antisense molecules. An antisense construct prepared through the use of antisense technology, may be used to control gene expression through triple-helix formation or antisense DNA or RNA, both of which methods are based on binding of a polynucleotide to DNA or RNA. For example, the 5' coding portion of the polynucleotide sequence, which encodes for the mature polypeptides of the present invention, is used to design an antisense RNA oligonucleotide of from about 10 to 40 base pairs in length. A DNA oligonucleotide is designed to be complementary to a region of the gene involved in transcription (triple helix—see Lee et al., Nucl. Acids Res., 6:3073 (1979); Cooney et al, Science, 241:456 (1988); and Dervan et al., Science, 251: 1360 (1991)), thereby preventing transcription and the production of G-protein chemokine receptor. The antisense RNA oligonucleotide hybridizes to the mRNA in vivo and blocks translation of mRNA molecules into G-protein coupled receptor (antisense—Okano, J. Neurochem., 56:560 (1991); Oligodeoxynucleotides as Antisense Inhibitors of Gene Expression, CRC Press, Boca Raton, Fla. (1988)). The oligonucleotides described above can also be delivered to cells such that the antisense RNA or DNA may be expressed in vivo to inhibit production of G-protein chemokine receptor.

Antisense technology can be used to control gene expression through antisense DNA or RNA or through triple-helix formation. Antisense techniques are discussed, for example, in Okano, J. Neurochem. 56: 560 (1991); "Oligodeoxynucleotides as Antisense Inhibitors of Gene Expression, CRC Press, Boca Raton, Fla. (1988). Antisense technology can be used to control gene expression through antisense DNA or RNA, or through triple-helix formation. Antisense techniques are discussed for example, in Okano, J., Neurochem. 56:560 (1991); Ogliodeoxynucleotides as Antisense Inhibitors of Gene Expression, CRC Press, Boca Raton, Fla. (1988). Triple helix formation is discussed in, for instance Lee et al., Nucleic Acids Research 6: 3073 (1979); Cooney et al., Science 241: 456 (1988); and Dervan et al., Science 251: 1360 (1991). The methods are based on binding of a polynucleotide to a complementary DNA or RNA. For example, the 5' coding portion of a polynucleotide that encodes the extracellular domain of the polypeptide of the present invention may be used to design an antisense RNA oligonucleotide of from about 10 to 40 base pairs in length. A DNA oligonucleotide is designed to be complementary to a region of the gene involved in transcription thereby preventing transcription and the production of G-protein Chemokine Receptor. The antisense RNA oligonucleotide hybridizes to the mRNA in vivo and blocks translation of the mRNA molecule into G-protein Chemokine Receptor polypeptide. The oligonucleotides described above can also be delivered to cells such that the antisense RNA or DNA may be expressed in vivo to inhibit production of G-protein Chemokine Receptor.

In one embodiment, the G-protein Chemokine Receptor antisense nucleic acid of the invention is produced intracellularly by transcription from an exogenous sequence. For example, a vector or a portion thereof, is transcribed, producing an antisense nucleic acid (RNA) of the invention. Such a vector would contain a sequence encoding the C-protein Chemokine Receptor antisense nucleic acid. Such a vector can remain episomal or become chromosomally integrated, as long as it can be transcribed to produce the desired antisense RNA. Such vectors can be constructed by recombinant DNA technology methods standard in the art. Vectors can be plasmid, viral, or others know in the art, used for replication and expression in vertebrate cells. Expression of the sequence encoding G-protein Chemokine Receptor, or fragments thereof, can be by any promoter known in the art to act in vertebrate, preferably human cells. Such promoters can be inducible or constitutive. Such promoters include, but are not limited to, the SV40 early promoter region (Bemoist and Chambon, Nature 29:304-310 (1981), the promoter contained in the 3' long terminal repeat of Rous sarcoma virus (Yamamoto et al., Cell 22:787-797 (1980), the herpes thymidine promoter (Wagner et al., Proc. Natl. Acad. Sci. U.S.A. 78:1441-1445 (1981), the regulatory sequences of the metallothionein gene (Brinster, et al., Nature 296:39-42 (1982)), etc.

The antisense nucleic acids of the invention comprise a sequence complementary to at least a portion of an RNA transcript of a G-protein Chemokine Receptor gene. However, absolute complementarity, although preferred, is not required. A sequence "complementary to at least a portion of an RNA," referred to herein, means a sequence having sufficient complementarity to be able to hybridize with the RNA, forming a stable duplex; in the case of double stranded G-protein Chemokine Receptor antisense nucleic acids, a single strand of the duplex DNA may thus be tested, or triplex formation may be assayed. The ability to hybridize will depend on both the degree of complementarity and the length of the antisense nucleic acid Generally, the larger the hybridizing nucleic acid, the more base mismatches with a G-protein Chemokine Receptor RNA it may contain and still form a stable duplex (or triplex as the case may be). One skilled in the art can ascertain a tolerable degree of mismatch by use of standard procedures to determine the melting point of the hybridized complex.

Oligonucleotides that are complementary to the 5' end of the message, e.g., the 5' untranslated sequence up to and including the AUG initiation codon, should work most efficiently at inhibiting translation. However, sequences complementary to the 3' untranslated sequences of mRNAs have been shown to be effective at inhibiting translation of mRNAs as well. See generally, Wagner, R., 1994, Nature 372:333-335. Thus, oligonucleotides complementary to either the 5'- or 3'-non-translated, non-coding regions of G-protein Chemokine Receptor shown in FIG. 1, respectively, could be used in an antisense approach to inhibit translation of endogenous G-protein Chemokine Receptor mRNA. Oligonucleotides complementary to the 5' untranslated region of the mRNA should include the complement of the AUG start codon. Antisense oligonucleotides complementary to mRNA coding regions are less efficient inhibitors of translation but could be used in accordance with the invention. Whether designed to hybridize to the 5'-, 3'- or coding region of G-protein Chemokine Receptor mRNA, antisense nucleic acids should be at least six nucleotides in length, and are preferably oligonucleotides ranging from 6 to about 50 nucleotides in length. In specific aspects the oligonucleotide is at least 10 nucleotides, at least 17 nucleotides, at least 25 nucleotides or at least 50 nucleotides.

The polynucleotides of the invention can be DNA or RNA or chimeric mixtures or derivatives or modified versions thereof, single-stranded or double-stranded. The oligonucleotide can be modified at the base moiety, sugar moiety, or phosphate backbone, for example, to improve stability of the molecule, hybridization, etc. The oligonucleotide may include other appended groups such as peptides (e.g., for targeting host cell receptors in vivo), or agents facilitating transport across the cell membrane (see, e.g., Letsinger et al., 1989, Proc. Natl. Acad. Sci. U.S.A. 86:6553-6556; Lemaitre et al., Proc. Natl. Acad. Sci. 84:648-652 (1987); PCT Publication No. WO88/09810, published Dec. 15, 1988) or the blood-brain barrier (see, e.g., PCT Publication No. WO89/10134, published Apr. 25, 1988), hybridization-triggered cleavage agents. (See, e.g., Krol et al., BioTechniques 6:958-976 (1988)) or intercalating agents. (See, e.g., Zon, Pharm. Res. 5:539-549 (1988)). To this end, the oligonucleotide may be conjugated to another molecule, e.g., a peptide, hybridization triggered cross-linking agent, transport agent, hybridization-triggered cleavage agent, etc.

The antisense oligonucleotide may comprise at least one modified base moiety which is selected from the group including, but not limited to, 5-fluorouracil, 5-bromouracil, 5-chlorouracil, 5-iodouracil, hypoxanthine, xantine, 4-acetylcytosine, 5-(carboxyhydroxylmethyl)uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5-methoxycarboxymethyluracil, 5-methoxyuracil, 2-methylthio-N6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl) uracil, (acp3)w, and 2,6-diaminopurine.

The antisense oligonucleotide may also comprise at least one modified sugar moiety selected from the group including, but not limited to, arabinose, 2-fluoroarabinose, xylulose, and hexose.

In yet another embodiment, the antisense oligonucleotide comprises at least one modified phosphate backbone selected from the group including, but not limited to, a phosphorothioate, a phosphorodithioate, a phosphoramidothioate, a phosphoramidate, a phosphordiamidate, a methylphosphonate, an alkyl phosphotriester, and a form acetal or analog thereof.

In yet another embodiment, the antisense oligonucleotide is an alpha-anomeric oligonucleotide. An alpha-anomeric oligonucleotide forms specific double-stranded hybrids with complementary RNA in which, contrary to the usual beta-units, the strands run parallel to each other (Gautier et al., Nucl. Acids Res. 15:6625-6641 (1987)). The oligonucleotide is a 2-0-methylribonucleotide (Inoue et al., Nucl. Acids Res. 15:6131-6148 (1987)), or a chimeric RNA-DNA analogue (Inoue et al., FEBS Lett. 215:327-330 (1997)).

Polynucleotides of the invention may be synthesized by standard methods known in the art, e.g. by use of an automated DNA synthesizer (such as are commercially available from Biosearch, Applied Biosystems, etc.). As examples, phosphorothioate oligonucleotides may be synthesized by the method of Stein et al. (Nucl. Acids Res. 16:3209 (1988)), methylphosphonate oligonucleotides can be prepared by use of controlled pore glass polymer supports (Sarin et al., Proc. Natl. Acad. Sci. U.S.A. 85:7448-7451 (1988)), etc.

While antisense nucleotides complementary to the G-protein Chemokine Receptor coding region sequence could be used, those complementary to the transcribed untranslated region are most preferred.

Potential antagonists according to the invention also include catalytic RNA, or a ribozyme (See, e.g., PCT International Publication WO 90/11364, published Oct. 4, 1990; Sarver et al, Science 247:1222-1225 (1990). While ribozymes that cleave mRNA at site specific recognition sequences can be used to destroy G-protein Chemokine Receptor mRNAs, the use of hammerhead ribozymes is preferred. Hammerhead ribozymes cleave mRNAs at locations dictated by flanking regions that form complementary base pairs with the target mRNA. The sole requirement is that the target mRNA have the following sequence of two bases: 5'-UG-3'. The construction and production of hammerhead ribozymes is well known in the art and is described more fully in Haseloff and Gerlach, Nature 334:585-591 (1988). There are numerous potential hammerhead ribozyme cleavage sites within the nucleotide sequence of G-protein Chemokine Receptor (FIG. 1). Preferably, the ribozyme is engineered so that the cleavage recognition site is located near the 5' end of the G-protein Chemokine Receptor mRNA; i.e., to increase efficiency and minimize the intracellular accumulation of non-functional mRNA transcripts.

As in the antisense approach, the ribozymes of the invention can be composed of modified oligonucleotides (e.g. for improved stability, targeting, etc.) and should be delivered to cells which express G-protein Chemokine Receptor in vivo. DNA constructs encoding the ribozyme may be introduced into the cell in the same manner as described above for the introduction of antisense encoding DNA. A preferred method of delivery involves using a DNA construct "encoding" the ribozyme under the control of a strong constitutive promoter, such as, for example, pol III or pol II promoter, so that transfected cells will produce sufficient quantities of the ribozyme to destroy endogenous G-protein Chemokine Receptor messages and inhibit translation. Since ribozymes unlike antisense molecules, are catalytic, a lower intracellular concentration is required for efficiency.

Endogenous gene expression can also be reduced by inactivating or "knocking out" the G-protein Chemokine Receptor gene and/or its promoter using targeted homologous recombination. (E.g., see Smithies et al., Nature 317:230-234 (1985); Thomas & Capecchi, Cell 51:503-512 (1987); Thompson et al., Cell 5:313-321 (1989); each of which is incorporated by reference herein in its entirety). For example, a mutant, non-functional polynucleotide of the invention (or a completely unrelated DNA sequence) flanked by DNA homologous to the endogenous polynucleotide sequence (either the coding regions or regulatory regions of the gene) can be used, with or without a selectable marker and/or a negative selectable marker, to transfect cells that express polypeptides of the invention in vivo. In another embodiment, techniques known in the art are used to generate knockouts in cells that contain, but do not express the gene of interest. Insertion of the DNA construct, via targeted homologous recombination, results in inactivation of the targeted gene. Such approaches are particularly suited in research and agricultural fields where modifications to embryonic stem cells can be used to generate animal offspring with an inactive targeted gene (e.g., see Thomas & Capecchi 1987 and Thompson 1989, supra). However this approach can be routinely adapted for use in humans provided the recombinant DNA constructs are directly administered or targeted to the required site in vivo using appropriate viral vectors that will be apparent to those of skill in the art. The contents of each of the documents recited in this paragraph is herein incorporated by reference in its entirety.

A small molecule which binds to the G-protein chemokine receptor, making it inaccessible to ligands such that normal biological activity is prevented, for example small peptides or non-peptide antagonists, may also be used to inhibit activation of the receptor polypeptide of the present invention.

A soluble form of the G-protein chemokine receptor, e.g. a fragment of the receptors, may be used to inhibit activation of the receptor by binding to the ligand to a polypeptide of the present invention and preventing the ligand from interacting with membrane bound G-protein chemokine receptors.

In other embodiments, antagonists according to the present invention include soluble forms of G-protein Chemokine Receptor (e.g., fragments of G-protein Chemokine Receptor shown in FIG. 1 (SEQ ID NO:2) or more preferably FIG. 2 (SEQ ID NO:4) that include the ligand binding domain and/or extracellular domain of G-protein Chemokine Receptor). Such soluble forms of the G-protein Chemokine Receptor, which may be naturally occurring or synthetic, antagonize G-protein Chemokine Receptor mediated signaling by competing with native G-protein Chemokine Receptor for binding to G-protein Chemokine Receptor ligand (e.g., MIG, ITAC, IP-10), and/or by forming a multimer that may or may not be capable of binding the receptor, but which is incapable of inducing signal transduction. Preferably, these antagonists inhibit G-protein Chemokine Receptor mediated stimulation of lymphocyte (e.g., T-cell) proliferation, differentiation, and/or activation. Antagonists of the present invention also include antibodies specific for G-protein Chemokine Receptor-Fc fusion proteins.

An antibody may antagonize a G-protein chemokine receptor of the present invention, or in some cases an oligopeptide, which bind to the G-protein chemokine receptor but does not elicit a second messenger response such that the activity of the G-protein chemokine receptors is prevented. Antibodies include anti-idiotypic antibodies which recognize unique determinants generally associated with the antigen-binding site of an antibody. Potential antagonist compounds also include proteins which are closely related to the ligand of the G-protein chemokine receptors, i.e. a fragment of the ligand, which have lost biological function and when binding to the G-protein chemokine receptor elicit no response.

Polyclonal and monoclonal antibody agonists or antagonists according to the present invention can be raised according to the methods disclosed in Tartaglia and Goeddel, *J. Biol. Chem.* 267(7):4304-4307(1992)); Tartaglia et al., *Cell* 73:213-216 (1993)), and PCT Application WO 94/09137 and are preferably specific to (i.e., bind uniquely to polypeptides of the invention having the amino acid sequence of SEQ ID NO:2, or more preferably of SEQ ID NO:4. The term "antibody" (Ab) or "monoclonal antibody" (mAb) as used herein is meant to include intact molecules as well as fragments thereof (such as, for example, Fab and F(ab') fragments) which are capable of binding an antigen. Fab, Fab' and F(ab') fragments lack the Fe fragment intact antibody, clear more rapidly from the circulation, and may have less non-specific tissue binding of an intact antibody (Wahl et al., *J. Nucl. Med.*, 24:316-325 (1983)).

In a preferred method, antibodies according to the present invention are mAbs. Such mAbs can be prepared using hybridoma technology (Kohler and Millstein, *Nature* 256:495-497 (1975) and U.S. Pat. No. 4,376,110; Harlow et al., *Antibodies*: A Laboratory Manual, Cold Spring Harbor Laboratory Press, Cold Spring Harbor, N.Y., 1988; *Monoclonal Antibodies and Hybridomas: A New Dimension in Biological Analyses*, Plenum Press, New York, N.Y., 1980; Campbell, "Monoclonal Antibody Technology," In: *Laboratory Techniques in Biochemistry and Molecular Biology*, Volume 13 (Burdon et al., eds.), Elsevier, Amsterdam (1984)).

Proteins and other compounds which bind the G-protein Chemokine Receptor domains are also candidate agonists and antagonists according to the present invention. Such binding compounds can be "captured" using the yeast two-hybrid system (Fields and Song, *Nature* 340:245-246 (1989)). A modified version of the yeast two-hybrid system has been described by Roger Brent and his colleagues (Gyuris, *Cell* 75:791-803 (1993); Zervos et al., *Cell* 72:223-232 (1993)). Preferably, the yeast two-hybrid system is used according to the present invention to capture compounds which bind to the extracellular domain, intracellular, transmembrane, and one or both of the cysteine rich domains of the G-protein Chemokine Receptor. Such compounds are good candidate agonists and antagonists of the present invention.

For example, using the two-hybrid assay described above, the extracellular or intracellular domain of the G-protein Chemokine Receptor, or a portion thereof (e.g., one or both of the cysteine rich domains), may be used to identify cellular proteins which interact with G-protein Chemokine Receptor the receptor in vivo. Such an assay may also be used to identify ligands with potential agonistic or antagonistic activity of G-protein Chemokine Receptor receptor function. This screening assay has previously been used to identify protein which interact with the cytoplasmic domain of the murine TNF-RII and led to the identification of two receptor associated proteins. Rothe et al., *Cell* 78:681 (1994). Such proteins and amino acid sequences which bind to the cytoplasmic domain of the G-protein Chemokine Receptor are good candidate agonist and antagonist of the present invention.

Other screening techniques include the use of cells which express the polypeptide of the present invention (for example, transfected CHO cells) in a system which measures extracellular pH changes caused by receptor activation, for example, as described in *Science*, 246:181-296 (1989). In another example, potential agonists or antagonists may be contacted with a cell which expresses the polypeptide of the present invention and a second messenger response, e.g., signal transduction may be measured to determine whether the potential antagonist or agonist is effective.

Agonists according to the present invention include naturally occurring and synthetic compounds. Preferred agonists are fragments of G-protein Chemokine Receptor polypeptides of the invention which stimulate lymphocyte (e.g., T cell) proliferation, differentiation and/or activation. Further preferred agonists include polyclonal and monoclonal antibodies raised against the G-protein Chemokine Receptor polypeptides of the invention, or a fragment thereof In further embodiments of the invention, cells that are genetically engineered to express the polypeptides of the invention, or alternatively, that are genetically engineered not to express the polypeptides of the invention (e.g., knockouts) are administered to a patient in vivo. Such cells may be obtained from the patient (i.e., animal, including human) or an MHC compatible donor and can include, but are not limited to fibroblasts, bone marrow cells, blood cells (e.g., lymphocytes), adipocytes, muscle cells, endothelial cells etc. The cells are genetically engineered in vitro using recombinant DNA techniques to introduce the coding sequence of polypeptides of the invention into the cells, or alternatively, to disrupt the coding sequence and/or endogenous regulatory sequence associated with the polypeptides of the invention, e.g., by transduction (using viral vectors, and preferably vectors that integrate the transgene into the cell genome) or transfection procedures, including, but not limited to, the use of plasmids, cosmids, YACs, naked DNA, electroporation, liposomes, etc. The coding sequence of the polypeptides of the invention can be placed under the control of a strong constitutive or inducible promoter or promoter/enhancer to achieve expression, and preferably secretion, of the polypeptides of the invention. The engineered cells which express and preferably secrete the polypeptides of the invention can be introduced into the patient systemically, e.g., in the circulation, or intraperitoneally.

Alternatively, the cells can be incorporated into a matrix and implanted in the body, e.g., genetically engineered fibroblasts can be implanted as part of a skin graft; genetically engineered endothelial cells can be implanted as part of a lymphatic or vascular graft. (See, for example, Anderson et al. U.S. Pat. No. 5,399,349; and Mulligan & Wilson, U.S. Pat. No. 5,460,959 each of which is incorporated by reference herein in its entirety).

When the cells to be administered are non-autologous or non-MHC compatible cells, they can be administered using well known techniques which prevent the development of a host immune response against the introduced cells. For example, the cells may be introduced in an encapsulated form which, while allowing for an exchange of components with the immediate extracellular environment, does not allow the introduced cells to be recognized by the host immune system.

In yet another embodiment of the invention, the activity of G-protein Chemokine Receptor polypeptide can be reduced using a "dominant negative." To this end, constructs which encode defective G-protein Chemokine Receptor polypeptide, such as, for example, mutants lacking all or a portion of a transmembrane domain, can be used in gene therapy approaches to diminish the activity of G-protein Chemokine Receptor on appropriate target cells. For example, nucleotide sequences that direct host cell expression of G-protein Chemokine Receptor polypeptide in which all or a portion of a transmembrane domain is altered or missing can be introduced into monocytic cells or other cells or tissues (either by in vivo or ex vivo gene therapy methods described herein or otherwise known in the art). Alternatively, targeted homologous recombination can be utilized to introduce such deletions or mutations into the subject's endogenous G-protein Chemokine Receptor gene in monocytes. The engineered cells will express non-functional G-protein Chemokine Receptor polypeptides (i.e., a receptor (e.g., multimer) that may be capable of binding, but which is incapable of inducing signal transduction).

Diagnostic Assays and Therapeutics

The compounds which bind to and activate the G-protein chemokine receptors of the present invention may be employed to stimulate haematopoiesis, wound healing, coagulation, angiogenesis, to treat tumors, chronic infections, leukemia, T-cell mediated auto-immune diseases, parasitic infections, psoriasis, and to stimulate growth factor activity.

The compounds which bind to and inhibit the G-protein chemokine receptors of the present invention may be employed to treat allergy, atherogenesis, anaphylaxis, malignancy, chronic and acute inflammation, histamine and IgE-mediated allergic reactions, prostaglandin-independent fever, bone marrow failure, silicosis, sarcoidosis, rheumatoid arthritis, shock and hyper-eosinophilic syndrome.

In highly preferred embodiments, G-protein chemokine receptors of the present invention may be used in the diagnosis, prognosis, prevention and/or treatment of diseases and/or disorders relating to diseases and disorders of the immune system (See, for example, "Immune Activity" section below), diseases and/or disorders relating to cell proliferation (See, for example, "Hyperproliferative Disorders" section below), and/or diseases or disorders relating to infections ((See, for example, "Infectious Disease" section below).

In certain embodiments, a G-protein chemokine receptor, and fragments and variants thereof, may be used to treat a disease and/or disorder relating to a neoplastic disease (e.g., leukemia, cancer, and/or as described below under "Hyperproliferative Disorders").

In additional embodiments, a G-protein chemokine receptor, and fragments and variants thereof, may be used to treat a neoplasm located in a tissue selected from the group consisting of: colon, abdomen, bone, breast, digestive system, liver, pancreas, prostate, peritoneum, lung, blood (e.g., leukemia), endocrine glands (adrenal, parathyroid, pituitary, testicles, ovary, thymus, thyroid), uterus, eye, head and neck, nervous (central and peripheral), lymphatic system, pelvic, skin, soft tissue, spleen, thoracic, and urogenital.

In other embodiments, a G-protein chemokine receptor, and fragments and variants thereof, may be used to treat a pre-neoplastic condition, selected from the group consisting of: hyperplasia (e.g., endometrial hyperplasia and/or as described in the section entitled "Hyperproliferative Disorders"), metaplasia (e.g., connective tissue metaplasia, atypical metaplasia, and/or as described in the section entitled "Hyperproliferative Disorders"), and dysplasia (e.g., cervical dysplasia, and bronchopulmonary dysplasia).

In additional embodiments, a G-protein chemokine, and fragments and variants thereof, may be used to treat a benign dysproliferative disorder selected from the group consisting of: benign tumors, fibrocystic conditions, tissue hypertrophy, and/or as described in the section entitled "Hyperproliferative Disorders".

In additional embodiments, a G-protein chemokine receptor, and fragments and variants thereof, may be used to treat a disease and/or disorder selected from the group consisting of: anemia, pancytopenia, leukopenia, thrombocytopenia, leukemias, Hodgkin's disease, non-Hodgkin's lymphoma, acute lymphocytic anemia (ALL), plasmacytomas, multiple myeloma, Burkitt's lymphoma, arthritis, asthma, AIDS, autoimmune disease, rheumatoid arthritis, granulomatous disease, immune deficiency, inflammatory bowel disease, sepsis, neutropenia, neutrophilia, psoriasis, an immune reaction to a transplanted organ and/or tissue, systemic lupus erythematosis, hemophilia, hypercoagulation, diabetes mellitus, endocarditis, meningitis, Lyme Disease, and allergies.

More generally, G-protein chemokine receptors of the invention may be useful for the diagnosis, prognosis, prevention and/or treatment of diseases and/or disorders associated with the following systems.

Immune Activity

Polynucleotides, polypeptides, antibodies, and/or agonists or antagonists of the present invention may be useful in treating, preventing, diagnosing and/or prognosing diseases, disorders, and/or conditions of the immune system, by, for example, activating or inhibiting the proliferation, differentiation, or mobilization (chemotaxis) of immune cells. Immune cells develop through a process called hematopoiesis, producing myeloid (platelets, red blood cells, neutrophils, and macrophages) and lymphoid (B and T lymphocytes) cells from pluripotent stem cells. The etiology of these immune diseases, disorders, and/or conditions may be genetic, somatic, such as cancer and some autoimmune diseases, acquired (e.g., by chemotherapy or toxins), or infectious. Moreover, polynucleotides, polypeptides, antibodies, and/or agonists or antagonists of the present invention can be used as a marker or detector of a particular immune system disease or disorder.

In another embodiment, a polypeptide of the invention, or polynucleotides, antibodies, agonists, or antagonists corresponding to that polypeptide, may be used to treat diseases and disorders of the immune system and/or to inhibit or enhance an immune response generated by cells associated with the tissue(s) in which the polypeptide of the invention is expressed.

Polynucleotides, polypeptides, antibodies, and/or agonists or antagonists of the present invention may be useful in treating, preventing, diagnosing, and/or prognosing immunodeficiencies, including both congenital and acquired immunodeficiencies. Examples of B cell immunodeficiencies in which immunoglobulin levels B cell function and/or B cell numbers are decreased include: X-linked agammaglobulinemia (Bruton's disease), X-linked infantile agammaglobulinemia, X-linked immunodeficiency with hyper IgM, non X-linked immunodeficiency with hyper IgM, X-linked lymphoproliferative syndrome (XLP), agammaglobulinemia including congenital and acquired agammaglobulinemia, adult onset agammaglobulinemia, late-onset agammaglobulinemia, dysgammaglobulinemia, hypogammaglobulinemia, unspecified hypogammaglobulinemia, recessive agammaglobulinemia (Swiss type), Selective IgM deficiency, selective IgA deficiency, selective IgG subclass deficiencies, IgG subclass deficiency (with or without IgA deficiency), Ig deficiency with increased IgM, IgG and IgA deficiency with increased IgM, antibody deficiency with normal or elevated Igs, Ig heavy chain deletions, kappa chain deficiency, B cell lymphoproliferative disorder (BLPD), common variable immunodeficiency (CVID), common variable immunodeficiency (CVI) (acquired), and transient hypogammaglobulinemia of infancy.

In specific embodiments, ataxia-telangiectasia or conditions associated with ataxia-telangiectasia are treated, prevented, diagnosed, and/or prognosing using the polypeptides or polynucleotides of the invention, and/or agonists or antagonists thereof.

Examples of congenital immunodeficiencies in which T cell and/or B cell function and/or number is decreased include, but are not limited to: DiGeorge anomaly, severe combined immunodeficiencies (SCID) (including, but not limited to, X-linked SCID, autosomal recessive SCID, adenosine deaminase deficiency, purine nucleoside phosphorylase (PNP) deficiency, Class II MHC deficiency (Bare lymphocyte syndrome), Wiskott-Aldrich syndrome, and ataxia telangiectasia), thymic hypoplasia, third and fourth pharyngeal pouch syndrome, 22q11.2 deletion, chronic mucocutaneous candidiasis, natural killer cell deficiency (NK), idiopathic CD4+ T-lymphocytopenia, immunodeficiency with predominant T cell defect (unspecified), and unspecified immunodeficiency of cell mediated immunity.

In specific embodiments, DiGeorge anomaly or conditions associated with DiGeorge anomaly are treated, prevented, diagnosed, and/or prognosed using polypeptides or polynucleotides of the invention, or antagonists or agonists thereof.

Other immunodeficiencies that may be treated, prevented, diagnosed, and/or prognosed using polypeptides or polynucleotides of the invention, and/or agonists or antagonists thereof, include, but are not limited to, chronic granulomatous disease, Chédiak-Higashi syndrome, myeloperoxidase deficiency, leukocyte glucose-6-phosphate dehydrogenase deficiency, X-linked lymphoproliferative syndrome (XLP), leukocyte adhesion deficiency, complement component deficiencies (including C1, C2, C3, C4, C5, C6, C7, C8 and/or C9 deficiencies), reticular dysgenesis, thymic alymphoplasia-aplasia, immunodeficiency with thymoma, severe congenital leukopenia, dysplasia with immunodeficiency, neonatal neutropenia, short limbed dwarfism, and Nezelof syndrome-combined immunodeficiency with Igs.

In a preferred embodiment, the immunodeficiencies and/or conditions associated with the immunodeficiencies recited above are treated, prevented, diagnosed and/or prognosed using polynucleotides, polypeptides, antibodies, and/or agonists or antagonists of the present invention.

In a preferred embodiment polynucleotides, polypeptides, antibodies, and/or agonists or antagonists of the present invention could be used as an agent to boost immunoresponsiveness among immunodeficient individuals. In specific embodiments, polynucleotides, polypeptides, antibodies, and/or agonists or antagonists of the present invention could be used as an agent to boost immunoresponsiveness among B cell and/or T cell immunodeficient individuals.

The polynucleotides, polypeptides, antibodies, and/or agonists or antagonists of the present invention may be useful in treating, preventing, diagnosing and/or prognosing autoimmune disorders. Many autoimmune disorders result from inappropriate recognition of self as foreign material by immune cells. This inappropriate recognition results in an immune response leading to the destruction of the host tissue. Therefore, the administration of polynucleotides and polypeptides of the invention that can inhibit an immune response, particularly the proliferation, differentiation, or chemotaxis of T-cells, may be an effective therapy in preventing autoimmune disorders.

Autoimmune diseases or disorders that may be treated, prevented, diagnosed and/or prognosed by polynucleotides, polypeptides, antibodies, and/or agonists or antagonists of the present invention include, but are not limited to, one or more of the following: systemic lupus erythematosus, rheumatoid arthritis, ankylosing spondylitis, multiple sclerosis, autoimmune thyroiditis, Hashimoto's thyroiditis, autoimmune hemolytic anemia, hemolytic anemia, thrombocytopenia, autoimmune thrombocytopenia purpura, autoimmune neonatal thrombocytopenia, idiopathic thrombocytopenia purpura, purpura (e.g., Henloch-Scoenlein purpura), autoimmunocytopenia, Goodpasture's syndrome,. Pemphigus vulgaris, myasthenia gravis, Grave's disease (hyperthyroidism), and insulin-resistant diabetes mellitus.

Additional disorders that are likely to have an autoimmune component that may be treated, prevented, and/or diagnosed with the compositions of the invention include, but are not limited to, type II collagen-induced arthritis, antiphospholipid syndrome, dermatitis, allergic encephalomyelitis, myocarditis, relapsing polychondritis, rheumatic heart disease, neuritis, uveitis ophthalmia, polyendocrinopathies, Reiter's Disease, Stiff-Man Syndrome, autoimmune pulmonary inflammation, autism, Guillain-Barre Syndrome, insulin dependent diabetes mellitus, and autoimmune inflammatory eye disorders.

Additional disorders that are likely to have an autoimmune component that may be treated, prevented, diagnosed and/or prognosed with the compositions of the invention include, but are not limited to, scleroderma with anti-collagen antibodies (often characterized, e.g., by nucleolar and other nuclear antibodies), mixed connective tissue disease (often characterized, e.g., by antibodies to extractable nuclear antigens (e.g., ribonucleoprotein)), polymyositis (often characterized, e.g., by nonhistone ANA), pernicious anemia (often characterized, e.g., by antiparietal cell, microsomes, and intrinsic factor antibodies), idiopathic Addison's disease (often characterized, e.g., by humoral and cell-mediated adrenal cytotoxicity, infertility (often characterized, e.g., by antispermatozoal antibodies), glomerulonephritis (often characterized, e.g., by glomerular basement membrane antibodies or immune complexes), bullous pemphigoid (often characterized, e.g., by IgG and complement in basement membrane), Sjogren's syndrome (often characterized, e.g., by multiple tissue antibodies, and/or a specific nonhistone ANA (SS-B)), diabetes mellitus (often characterized, e.g., by cell-mediated and humoral islet cell antibodies), and adrenergic drug resistance (including adrenergic drug resistance with asthma or cystic fibrosis) (often characterized, e.g., by beta-adrenergic receptor antibodies).

Additional disorders that may have an autoimmune component that may be treated, prevented, diagnosed and/or prognosed with the compositions of the invention include, but are not limited to, chronic active hepatitis (often characterized, e.g., by smooth muscle antibodies), primary biliary cirrhosis (often characterized, e.g., by mitochondria antibodies), other endocrine gland failure (often characterized, e.g., by specific tissue antibodies in some cases), vitiligo (often characterized, e.g., by melanocyte antibodies), vasculitis (often characterized, e.g., by Ig and complement in vessel walls and/or low serum complement), post-MI (often characterized, e.g., by myocardial antibodies), cardiotomy syndrome (often characterized, e.g., by myocardial antibodies), urticaria (often characterized, e.g., by IgG and IgM antibodies to IgE), atopic dermatitis (often characterized, e.g., by IgG and IgM antibodies to IgE), asthma (often characterized, e.g., by IgG and IgM antibodies to IgE), and many other inflammatory, granulomatous, degenerative, and atrophic disorders.

In a preferred embodiment, the autoimmune diseases and disorders and/or conditions associated with the diseases and disorders recited above are treated, prevented, diagnosed and/or prognosed using for example, antagonists or agonists, polypeptides or polynucleotides, or antibodies of the present invention. In a specific preferred embodiment, rheumatoid arthritis is treated, prevented, and/or diagnosed using polynucleotides, polypeptides, antibodies, and/or agonists or antagonists of the present invention.

In another specific preferred embodiment, systemic lupus erythematosus is treated, prevented, and/or diagnosed using polynucleotides, polypeptides, antibodies, and/or agonists or antagonists of the present invention. In another specific preferred embodiment, idiopathic thrombocytopenia purpura is treated, prevented, and/or diagnosed using polynucleotides, polypeptides, antibodies, and/or agonists or antagonists of the present invention.

In another specific preferred embodiment IgA nephropathy is treated, prevented, and/or diagnosed using polynucleotides, polypeptides, antibodies, and/or agonists or antagonists of the present invention.

In a preferred embodiment, the autoimmune diseases and disorders and/or conditions associated with the diseases and disorders recited above are treated, prevented, diagnosed and/or prognosed using polynucleotides, polypeptides, antibodies, and/or agonists or antagonists of the present invention.

In preferred embodiments, polypeptides, antibodies, polynucleotides and/or agonists or antagonists of the present invention are used as a immunosuppressive agent(s).

Polynucleotides, polypeptides, antibodies, and/or agonists or antagonists of the present invention may be useful in treating, preventing, prognosing, and/or diagnosing diseases, disorders, and/or conditions of hematopoietic cells. Polynucleotides, polypeptides, antibodies, and/or agonists or antagonists of the present invention could be used to increase differentiation and proliferation of hematopoietic cells, including the pluripotent stem cells, in an effort to treat or prevent those diseases, disorders, and/or conditions associated with a decrease in certain (or many) types hematopoietic cells, including but not limited to, leukopenia, neutropenia, anemia, and thrombocytopenia. Alternatively, Polynucleotides, polypeptides, antibodies, and/or agonists or antagonists of the present invention could be used to increase differentiation and proliferation of hematopoietic cells, including the pluripotent stem cells, in an effort to treat or prevent those diseases, disorders, and/or conditions associated with an increase in certain (or many) types of hematopoietic cells, including but not limited to, histiocytosis.

Allergic reactions and conditions, such as asthma (particularly allergic asthma) or other respiratory problems, may also be treated, prevented, diagnosed and/or prognosed using polypeptides, antibodies, or polynucleotides of the invention, and/or agonists or antagonists thereof. Moreover, these molecules can be used to treat, prevent, prognose, and/or diagnose anaphylaxis, hypersensitivity to an antigenic molecule, or blood group incompatibility.

Additionally, polypeptides or polynucleotides of the invention, and/or agonists or antagonists thereof, may be used to treat, prevent, diagnose and/or prognose IgE-mediated allergic reactions. Such allergic reactions include, but are not limited to, asthma, rhinitis, and eczema. In specific embodiments, polynucleotides, polypeptides, antibodies, and/or agonists or antagonists of the present invention may be used to modulate IgE concentrations in vitro or in vivo.

Moreover, polynucleotides, polypeptides, antibodies, and/or agonists or antagonists of the present invention have uses in the diagnosis, prognosis, prevention, and/or treatment of inflammatory conditions. For example, since polypeptides, antibodies, or polynucleotides of the invention, and/or agonists or antagonists of the invention may inhibit the activation, proliferation and/or differentiation of cells involved in an inflammatory response, these molecules can be used to prevent and/or treat chronic and acute inflammatory conditions.

Such inflammatory conditions include, but are not limited to, for example, inflammation associated with infection (e.g., septic shock, sepsis, or systemic inflammatory response syndrome), ischemia-reperfusion injury, endotoxin lethality, complement-mediated hyperacute rejection, nephritis, cytokine or chemokine induced lung injury, inflammatory bowel disease, Crohn's disease, over production of cytokines (e.g., TNF or IL-1.), respiratory disorders (e.g., asthma and allergy); gastrointestinal disorders (e.g., inflammatory bowel disease); cancers (e.g., gastric, ovarian, lung, bladder, liver, and breast); CNS disorders (e.g., multiple sclerosis; ischemic brain injury and/or stroke, traumatic brain injury, neurodegenerative disorders (e.g., Parkinson's disease and Alzheimer's disease); AIDS-related dementia; and prion disease); cardiovascular disorders (e.g., atherosclerosis, myocarditis, cardiovascular disease, and cardiopulmonary bypass complications); as well as many additional diseases, conditions, and disorders that are characterized by inflammation (e.g., hepatitis, rheumatoid arthritis, gout, trauma, pancreatitis, sarcoidosis, dermatitis, renal ischemia-reperfusion injury, Grave's disease, systemic lupus erythematosus, diabetes mellitus, and allogenic transplant rejection).

Because inflammation is a fundamental defense mechanism, inflammatory disorders can effect virtually any tissue of the body. Accordingly, polynucleotides, polypeptides, and antibodies of the invention, as well as agonists or antagonists thereof, have uses in the treatment of tissue-specific inflammatory disorders, including, but not limited to, adrenalitis, alveolitis, angiocholecystitis, appendicitis, balanitis, blepharitis, bronchitis, bursitis, carditis, cellulitis, cervicitis, cholecystitis, chorditis, cochlitis, colitis, conjunctivitis, cystitis, dermatitis, diverticulitis, encephalitis, endocarditis, esophagitis, eustachitis, fibrositis, folliculitis, gastritis, gastroenteritis, gingivitis, glossitis, hepatosplenitis, keratitis, labyrinthitis, laryngitis, lymphangitis, mastitis, media otitis, meningitis, metritis, mucitis, myocarditis, myositis, myringitis, nephritis, neuritis, orchitis, osteochondritis, otitis, pericarditis, peritendonitis, peritonitis, pharyngitis, phlebitis, poliomyelitis, prostatitis, pulpitis, retinitis, rhinitis, salpingitis, scleritis, sclerochoroiditis, scrotitis, sinusitis, spondylitis, steatitis, stomatitis, synovitis, syringitis, tendonitis, tonsillitis, urethritis, and vaginitis.

In specific embodiments, polypeptides, antibodies, or polynucleotides of the invention, and/or agonists or antagonists thereof, are useful to diagnose, prognose, prevent, and/or treat organ transplant rejections and graft-versus-host disease. Organ rejection occurs by host immune cell destruction of the transplanted tissue through an immune response. Similarly, an immune response is also involved in GVHD, but, in this case, the foreign transplanted immune cells destroy the host tissues. Polypeptides, antibodies, or polynucleotides of the invention, and/or agonists or antagonists thereof, that inhibit an immune response, particularly the activation, proliferation, differentiation, or chemotaxis of T-cells, may be an effective therapy in preventing organ rejection or GVHD. In specific embodiments, polypeptides, antibodies, or polynucleotides of the invention, and/or agonists or antagonists thereof, that inhibit an immune response, particularly the activation, proliferation, differentiation, or chemotaxis of T-cells, may be an effective therapy in preventing experimental allergic and hyperacute xenograft rejection.

In other embodiments, polypeptides, antibodies, or polynucleotides of the invention, and/or agonists or antagonists thereof, are useful to diagnose, prognose, prevent, and/or treat immune complex diseases, including, but not limited to, serum sickness, post streptococcal glomerulonephritis, polyarteritis nodosa, and immune complex-induced vasculitis.

Polypeptides, antibodies, polynucleotides and/or agonists or antagonists of the invention can be used to treat, detect, and/or prevent infectious agents. For example, by increasing the immune response, particularly increasing the proliferation activation and/or differentiation of B and/or T cells, infectious diseases may be treated, detected, and/or prevented. The immune response may be increased by either enhancing an existing immune response, or by initiating a new immune response. Alternatively, polynucleotides, polypeptides, antibodies, and/or agonists or antagonists of the present invention may also directly inhibit the infectious agent (refer to section of application listing infectious agents, etc), without necessarily eliciting an immune response.

In another embodiment, polypeptides, antibodies, polynucleotides and/or agonists or antagonists of the present invention are used as a vaccine adjuvant that enhances immune responsiveness to an antigen. In a specific embodiment, polypeptides, antibodies, polynucleotides and/or agonists or antagonists of the present invention are used as an adjuvant to enhance tumor-specific immune responses.

In another specific embodiment, polypeptides, antibodies, polynucleotides and/or agonists or antagonists of the present invention are used as an adjuvant to enhance anti-viral immune responses. Anti-viral immune responses that may be enhanced using the compositions of the invention as an adjuvant, include virus and virus associated diseases or symptoms described herein or otherwise known in the art. In specific embodiments, the compositions of the invention are used as an adjuvant to enhance an immune response to a virus, disease, or symptom selected from the group consisting of: AIDS, meningitis, Dengue, EBV, and hepatitis (e.g., hepatitis B). In another specific embodiment, the compositions of the invention are used as an adjuvant to enhance an immune response to a virus, disease, or symptom selected from the group consisting of: HIV/AIDS, respiratory syncytial virus, Dengue, rotavirus, Japanese B encephalitis, influenza A and B, parainfluenza, measles, cytomegalovirus, rabies, Junin, Chikungunya, Rift Valley Fever, herpes simplex, and yellow fever.

In another specific embodiment, polypeptides, antibodies, polynucleotides and/or agonists or antagonists of the present invention are used as an adjuvant to enhance anti-bacterial or anti-fungal immune responses. Anti-bacterial or anti-fungal immune responses that may be enhanced using the compositions of the invention as an adjuvant, include bacteria or fungus and bacteria or fungus associated diseases or symptoms described herein or otherwise known in the art. In specific embodiments, the compositions of the invention are used as an adjuvant to enhance an immune response to a bacteria or fungus, disease, or symptom selected from the group consisting of: tetanus, Diphtheria, botulism, and meningitis type B.

In another specific embodiment, the compositions of the invention are used as an adjuvant to enhance an immune response to a bacteria or fungus, disease, or symptom selected from the group consisting of: *Vibrio cholerae, Mycobacterium leprae, Salmonella typhi, Salmonella paratyphi, Meisseria meningitidis, Streptococcus pneumoniae*, Group B *streptococcus, Shigella* spp., Enterotoxigenic *Escherichia coli*, Enterohemorrhagic *E. coli*, and *Borrelia burgdorferi*.

In another specific embodiment, polypeptides, antibodies, polynucleotides and/or agonists or antagonists of the present invention are used as an adjuvant to enhance anti-parasitic immune responses. Anti-parasitic immune responses that may be enhanced using the compositions of the invention as an adjuvant, include parasite and parasite associated diseases or symptoms described herein or otherwise known in the art. In specific embodiments, the compositions of the invention are used as an adjuvant to enhance an immune response to a parasite. In another specific embodiment, the compositions of the invention are used as an adjuvant to enhance an immune response to Plasmodium (malaria) or Leishmania.

In another specific embodiment, polypeptides, antibodies, polynucleotides and/or agonists or antagonists of the present invention may also be employed to treat infectious diseases including silicosis, sarcoidosis, and idiopathic pulmonary fibrosis; for example, by preventing the recruitment and activation of mononuclear phagocytes.

In another specific embodiment, polypeptides, antibodies, polynucleotides and/or agonists or antagonists of the present invention are used as an antigen for the generation of antibodies to inhibit or enhance immune mediated responses against polypeptides of the invention.

In one embodiment, polypeptides, antibodies, polynucleotides and/or agonists or antagonists of the present invention are administered to an animal (e.g., mouse, rat, rabbit, hamster, guinea pig, pigs, micro-pig, chicken, camel, goat, horse, cow, sheep, dog, cat, non-human primate, and human, most preferably human) to boost the immune system to produce increased quantities of one or more antibodies (e.g., IgG, IgA, IgM, and IgE), to induce higher affinity antibody production and immunoglobulin class switching (e.g., IgG, IgA, IgM, and IgE), and/or to increase an immune response.

In another specific embodiment, polypeptides, antibodies, polynucleotides and/or agonists or antagonists of the present invention are used as a stimulator of B cell responsiveness to pathogens.

In another specific embodiment, polypeptides, antibodies, polynucleotides and/or agonists or antagonists of the present invention are used as an activator of T cells.

In another specific embodiment, polypeptides, antibodies, polynucleotides and/or agonists or antagonists of the present invention are used as an agent that elevates the immune status of an individual prior to their receipt of immunosuppressive therapies.

In another specific embodiment, polypeptides, antibodies, polynucleotides and/or agonists or antagonists of the present invention are used as an agent to induce higher affinity antibodies.

In another specific embodiment, polypeptides, antibodies, polynucleotides and/or agonists or antagonists of the present invention are used as an agent to increase serum immunoglobulin concentrations.

In another specific embodiment, polypeptides, antibodies, polynucleotides and/or agonists or antagonists of the present invention are used as an agent to accelerate recovery of immunocompromised individuals.

In another specific embodiment, polypeptides, antibodies, polynucleotides and/or agonists or antagonists of the present invention are used as an agent to boost immunoresponsiveness among aged populations and/or neonates.

In another specific embodiment, polypeptides, antibodies, polynucleotides and/or agonists or antagonists of the present invention are used as an immune system enhancer prior to, during, or after bone marrow transplant and/or other transplants (e.g., allogeneic or xenogeneic organ transplantation). With respect to transplantation, compositions of the invention may be administered prior to, concomitant with, and/or after transplantation. In a specific embodiment, compositions of the invention are administered after transplantation, prior to the beginning of recovery of T-cell populations. In another specific embodiment, compositions of the invention are first administered after transplantation after the beginning of recovery of T cell populations, but prior to full recovery of B cell populations.

In another specific embodiment, polypeptides, antibodies, polynucleotides and/or agonists or antagonists of the present invention are used as an agent to boost immunoresponsiveness among individuals having an acquired loss of B cell function. Conditions resulting in an acquired loss of B cell function that may be ameliorated or treated by administering the polypeptides, antibodies, polynucleotides and/or agonists or antagonists thereof, include, but are not limited to, HIV Infection, AIDS, bone marrow transplant, and B cell chronic lymphocytic leukemia (CLL).

In another specific embodiment, polypeptides, antibodies, polynucleotides and/or agonists or antagonists of the present invention are used as an agent to boost immunoresponsiveness among individuals having a temporary immune deficiency. Conditions resulting in a temporary immune deficiency that may be ameliorated or treated by administering the polypeptides, antibodies, polynucleotides and/or agonists or antagonists thereof, include, but are not limited to, recovery from viral infections (e.g., influenza), conditions associated with malnutrition, recovery from infectious mononucleosis, or conditions associated with stress, recovery from measles, recovery from blood transfusion, and recovery from surgery.

In another specific embodiment, polypeptides, antibodies, polynucleotides and/or agonists or antagonists of the present invention are used as a regulator of antigen presentation by monocytes, dendritic cells, and/or B-cells. In one embodiment, polynucleotides, polypeptides, antibodies, and/or agonists or antagonists of the present invention enhance antigen presentation or antagonizes antigen presentation in vitro or in vivo. Moreover, in related embodiments, said enhancement or antagonism of antigen presentation may be useful as an anti-tumor treatment or to modulate the immune system.

In another specific embodiment, polypeptides, antibodies, polynucleotides and/or agonists or antagonists of the present invention are used as an agent to direct an individual's immune system towards development of a humoral response (i.e. TH2) as opposed to a TH1 cellular response.

In another specific embodiment, polypeptides, antibodies, polynucleotides and/or agonists or antagonists of the present invention are used as a means to induce tumor prolifertion and thus make it more susceptible to anti-neoplastic agents. For example, multiple myeloma is a slowly dividing disease and is thus refractory to virtually all anti-neoplastic neoplacstic regimens. If these cells were forced to proliferate more rapidly their susceptibility profile would likely change.

In another specific embodiment, polypeptides, antibodies, polynucleotides and/or agonists or antagonists of the present invention are used as a stimulator of B cell production in pathologies such as AIDS, chronic lymphocyte disorder and/or Common Variable Immunodificiency.

In another specific embodiment, polypeptides, antibodies, polynucleotides and/or agonists or antagonists of the present invention are used as a therapy for generation and/or regeneration of lymphoid tissues following surgery, trauma or genetic defect. In another specific embodiment, polypeptides, antibodies, polynucleotides and/or agonists or antagonists of the present invention are used in the pretreatment of bone marrow samples prior to transplant.

In another specific embodiment, polypeptides, antibodies, polynucleotides and/or agonists or antagonists of the present invention are used as a gene-based therapy for genetically inherited disorders resulting in immuno-incompetence/immunodeficiency such as observed among SCID patients.

In another specific embodiment, polypeptides, antibodies, polynucleotides and/or agonists or antagonists of the present invention are used as a means of activating monocytes/macrophages to defend against parasitic diseases that effect monocytes such as Leishmania.

In another specific embodiment, polypeptides, antibodies, polynucleotides and/or agonists or antagonists of the present invention are used as a means of regulating secreted cytokines that are elicited by polypeptides of the invention.

In another embodiment, polypeptides, antibodies, polynucleotides and/or agonists or antagonists of the present invention are used in one or more of the applications decribed herein, as they may apply to veterinary medicine.

In another specific embodiment, polypeptides, antibodies, polynucleotides and/or agonists or antagonists of the present invention are used as a means of blocking various aspects of immune responses to foreign agents or self. Examples of diseases or conditions in which blocking of certain aspects of immune responses may be desired include autoimmune disorders such as lupus, and arthritis, as well as immunoresponsiveness to skin allergies, inflammation, bowel disease, injury and diseases/disorders associated with pathogens.

In another specific embodiment, polypeptides, antibodies, polynucleotides and/or agonists or antagonists of the present invention are used as a therapy for preventing the B cell proliferation and Ig secretion associated with autoimmune diseases such as idiopathic thrombocytopenic purpura, systemic lupus erythematosus and multiple sclerosis.

In another specific embodiment, polypeptides, antibodies, polynucleotides and/or agonists or antagonists of the present invention are used as a inhibitor of B and/or T cell migration in endothelial cells. This activity disrupts tissue architecture or cognate responses and is useful, for example in disrupting immune responses, and blocking sepsis.

In another specific embodiment, polypeptides, antibodies, polynucleotides and/or agonists or antagonists of the present invention are used as a therapy for chronic hypergammaglobulinemia evident in such diseases as monoclonal gammopathy of undetermined significance (MGUS), Waldenstrom's disease, related idiopathic monoclonal gammopathies, and plasmacytomas.

In another specific embodiment, polypeptides, antibodies, polynucleotides and/or agonists or antagonists of the present invention may be employed for instance to inhibit polypeptide chemotaxis and activation of macrophages and their precursors, and of neutrophils, basophils, B lymphocytes and some T-cell subsets, e.g., activated and CD8 cytotoxic T cells and natural killer cells, in certain autoimmune and chronic inflammatory and infective diseases. Examples of autoimmune diseases are described herein and include multiple sclerosis, and insulin-dependent diabetes.

The polypeptides, antibodies, polynucleotides and/or agonists or antagonists of the present invention may also be employed to treat idiopathic hyper-eosinophilic syndrome by, for example, preventing eosinophil production and migration.

In another specific embodiment, polypeptides, antibodies, polynucleotides and/or agonists or antagonists of the present invention are used to enhance or inhibit complement mediated cell lysis.

In another specific embodiment, polypeptides, antibodies, polynucleotides and/or agonists or antagonists of the present invention are used to enhance or inhibit antibody dependent cellular cytotoxicity.

In another specific embodiment, polypeptides, antibodies, polynucleotides and/or agonists or antagonists of the present invention may also be employed for treating atherosclerosis, for example, by preventing monocyte infiltration in the artery wall.

In another specific embodiment, polypeptides, antibodies, polynucleotides and/or agonists or antagonists of the present invention may be employed to treat adult respiratory distress syndrome (ARDS).

In another specific embodiment, polypeptides, antibodies, polynucleotides and/or agonists or antagonists of the present invention may be useful for stimulating wound and tissue repair, stimulating angiogenesis, and/or stimulating the repair of vascular or lymphatic diseases or disorders. Additionally, agonists and antagonists of the invention may be used to stimulate the regeneration of mucosal surfaces.

In a specific embodiment, polynucleotides or polypeptides, and/or agonists thereof are used to diagnose, prognose, treat, and/or prevent a disorder characterized by primary or acquired immunodeficiency, deficient serum immunoglobulin production, recurrent infections, and/or immune system dysfunction. Moreover, polynucleotides or polypeptides, and/or agonists thereof may be used to treat or prevent infections of the joints, bones, skin, and/or parotid glands, bloodborne infections (e.g., sepsis, meningitis, septic arthritis, and/ or osteomyelitis), autoimmune diseases (e.g., those disclosed herein), inflammatory disorders, and malignancies, and/or any disease or disorder or condition associated with these infections, diseases, disorders and/or malignancies) including, but not limited to, CVID, other primary immune deficiencies, HIV disease, CLL, recurrent bronchitis, sinusitis, otitis media, conjunctivitis, pneumonia, hepatitis, meningitis, herpes zoster (e.g., severe herpes zoster), and/or pneumocystis carnii. Other diseases and disorders that may be prevented, diagnosed, prognosed, and/or treated with polynucleotides or polypeptides, and/or agonists of the present invention include, but are not limited to, HIV infection, HTLV-BLV infection, lymphopenia, phagocyte bactericidal dysfunction anemia, thrombocytopenia, and hemoglobinuria.

In another embodiment, polynucleotides, polypeptides, antibodies, and/or agonists or antagonists of the present invention are used to treat, and/or diagnose an individual having common variable immunodeficiency disease ("CVID"; also known as "acquired agammaglobulinemia" and "acquired hypogammaglobulinemia") or a subset of this disease.

In a specific embodiment, polynucleotides, polypeptides, antibodies, and/or agonists or antagonists of the present invention may be used to diagnose, prognose, prevent, and/or treat cancers or neoplasms including immune cell or immune tissue-related cancers or neoplasms. Examples of cancers or neoplasms that may be prevented, diagnosed, or treated by polynucleotides, polypeptides, antibodies, and/or agonists or antagonists of the present invention include, but are not limited to, acute myelogenous leukemia, chronic myelogenous leukemia, Hodgkin's disease, non-Hodgkin's lymphoma, acute lymphocytic anemia (ALL) Chronic lymphocyte leukemia, plasmacytomas, multiple myeloma, Burkitt's lymphoma, EBV-transformed diseases, and/or diseases and disorders described in the section entitled "Hyperproliferative Disorders" elsewhere herein.

In another specific embodiment, polypeptides, antibodies, polynucleotides and/or agonists or antagonists of the present invention are used as a therapy for decreasing cellular proliferation of Large B-cell Lymphomas.

In another specific embodiment, polypeptides, antibodies, polynucleotides and/or agonists or antagonists of the present invention are used as a means of decreasing the involvement of B cells and Ig associated with Chronic Myelogenous Leukemia.

In specific embodiments, the compositions of the invention are used as an agent to boost immunoresponsiveness among B cell immunodeficient individuals, such as, for example, an individual who has undergone a partial or complete splenectomy.

Antagonists of the invention include, for example, binding and/or inhibitory antibodies, antisense nucleic acids, ribozymes or soluble forms of the polypeptides of the present invention (e.g., Fe fusion protein; see, e.g., Example 9). Agonists of the invention include, for example, binding or stimulatory antibodies, and soluble forms of the polypeptides (e.g., Fe fusion proteins; see, e.g., Example 9), polypeptides, antibodies, polynucleotides and/or agonists or antagonists of the present invention may be employed in a composition with a pharmaceutically acceptable carrier, e.g., as described herein.

In another embodiment, polypeptides, antibodies, polynucleotides and/or agonists or antagonists of the present invention are administered to an animal (including, but not limited to, those listed above, and also including transgenic animals) incapable of producing functional endogenous antibody molecules or having an otherwise compromised endogenous immune system, but which is capable of producing human immunoglobulin molecules by means of a reconstituted or partially reconstituted immune system from another animal (see, e.g., published PCT Application Nos. WO98/24893, WO/9634096, WO/9633735, and WO/9110741). Administration of polypeptides, antibodies, polynucleotides and/or agonists or antagonists of the present invention to such animals is useful for the generation of monoclonal antibodies against the polypeptides, antibodies, polynucleotides and/or agonists or antagonists of the present invention.

Chemotaxis

Polynucleotides or polypeptides, as well as agonists or antagonists of the present invention may have chemotaxis activity. A chemotaxic molecule attracts or mobilizes cells (e.g., monocytes, fibroblasts, neutrophils, T-cells, mast cells, eosinophils, epithelial and/or endothelial cells) to a particular site in the body, such as inflammation, infection, or site of hyperproliferation. The mobilized cells can then fight off and/or heal the particular trauma or abnormality.

Polynucleotides or polypeptides, as well as agonists or antagonists of the present invention may increase chemotaxic activity of particular cells. These chemotactic molecules can then be used to treat inflammation, infection, hyperproliferative disorders, or any immune system disorder by increasing the number of cells targeted to a particular location in the body. For example, chemotaxic molecules can be used to treat wounds and other trauma to tissues by attracting immune cells to the injured location. Chemotactic molecules of the present invention can also attract fibroblasts, which can be used to treat wounds.

It is also contemplated that polynucleotides or polypeptides, as well as agonists or antagonists of the present invention may inhibit chemotactic activity. These molecules could also be used to treat disorders. Thus, polynucleotides or polypeptides, as well as agonists or antagonists of the present invention could be used as an inhibitor of chemotaxis.

Hyperproliferative Disorders

In certain embodiments, polynucleotides or polypeptides, or agonists or antagonists of the present invention can be used to treat or detect hyperproliferative disorders, including neoplasms. Polynucleotides or polypeptides, or agonists or antagonists of the present invention may inhibit the proliferation of the disorder through direct or indirect interactions. Alternatively, Polynucleotides or polypeptides, or agonists or antagonists of the present invention may proliferate other cells which can inhibit the hyperproliferative disorder.

For example, by increasing an immune response, particularly increasing antigenic qualities of the hyperproliferative disorder or by proliferating, differentiating, or mobilizing T-cells, hyperproliferative disorders can be treated. This immune response may be increased by either enhancing an existing immune response, or by initiating a new immune response. Alternatively, decreasing an immune response may also be a method of treating hyperproliferative disorders, such as a chemotherapeutic agent.

Examples of hyperproliferative disorders that can be treated or detected by polynucleotides or polypeptides, or agonists or antagonists of the present invention include, but are not limited to neoplasms located in the: colon, abdomen, bone, breast, digestive system, liver, pancreas, peritoneum, endocrine glands (adrenal, parathyroid, pituitary, testicles, ovary, thymus, thyroid), eye, head and neck, nervous (central and peripheral), lymphatic system, pelvis, skin, soft tissue, spleen, thorax, and urogenital tract.

Similarly, other hyperproliferative disorders can also be treated or detected by polynucleotides or polypeptides, or agonists or antagonists of the present invention. Examples of such hyperproliferative disorders include, but are not limited to: Acute Childhood Lymphoblastic Leukemia, Acute Lymphoblastic Leukemia, Acute Lymphocytic Leukemia, Acute Myeloid Leukemia, Adrenocortical Carcinoma, Adult (Primary) Hepatocellular Cancer, Adult (Primary) Liver Cancer, Adult Acute Lymphocytic Leukemia, Adult Acute Myeloid Leukemia, Adult Hodgkin's Disease, Adult Hodgkin's Lymphoma, Adult Lymphocytic Leukemia, Adult Non-Hodgkin's Lymphoma, Adult Primary Liver Cancer, Adult Soft Tissue Sarcoma, AIDS-Related Lymphoma, AIDS-Related Malignancies, Anal Cancer, Astrocytoma, Bile Duct Cancer, Bladder Cancer, Bone Cancer, Brain Stem Glioma, Brain Tumors, Breast Cancer, Cancer of the Renal Pelvis and Ureter, Central Nervous System (Primary) Lymphoma, Central Nervous System Lymphoma, Cerebellar Astrocytoma, Cerebral Astrocytoma, Cervical Cancer, Childhood (Primary) Hepatocellular Cancer, Childhood (Primary) Liver Cancer, Childhood Acute Lymphoblastic Leukemia, Childhood Acute Myeloid Leukemia, Childhood Brain Stem Glioma, Childhood Cerebellar Astrocytoma, Childhood Cerebral Astrocytoma, Childhood Extracranial Germ Cell Tumors, Childhood Hodgkin's Disease, Childhood Hodgkin's Lymphoma, Childhood Hypothalamic and Visual Pathway Glioma, Childhood Lymphoblastic Leukemia, Childhood Medulloblastoma, Childhood Non-Hodgkin's Lymphoma, Childhood Pineal and Supratentorial Primitive Neuroectodermal Tumors, Childhood Primary Liver Cancer, Childhood Rhabdomyosarcoma, Childhood Soft Tissue Sarcoma, Childhood Visual Pathway and Hypothalamic Glioma, Chronic Lymphocytic Leukemia, Chronic Myelogenous Leukemia, Colon Cancer, Cutaneous T-Cell Lymphoma, Endocrine Pancreas Islet Cell Carcinoma, Endometrial Cancer, Ependymoma, Epithelial Cancer, Esophageal Cancer, Ewing's Sarcoma and Related Tumors, Exocrine Pancreatic Cancer, Extracranial Germ Cell Tumor, Extragonadal Germ Cell Tumor, Extrahepatic Bile Duct Cancer, Eye Cancer, Female Breast Cancer, Gaucher's Disease, Gallbladder Cancer, Gastric Cancer, Gastrointestinal Carcinoid Tumor, Gastrointestinal Tumors, Germ Cell Tumors, Gestational Trophoblastic Tumor, Hairy Cell Leukemia, Head and Neck Cancer, Hepatocellular Cancer, Hodgkin's Disease, Hodgkin's Lymphoma, Hypergammaglobulinemia, Hypopharyngeal Cancer, Intestinal Cancers, Intraocular Melanoma, Islet Cell Carcinoma, Islet Cell Pancreatic Cancer, Kaposi's Sarcoma, Kidney Cancer, Laryngeal Cancer, Lip and Oral Cavity Cancer, Liver Cancer, Lung Cancer, Lymphoproliferative Disorders, Macroglobulinemia, Male Breast Cancer, Malignant Mesothelioma, Malignant Thymoma, Medulloblastoma, Melanoma, Mesothelioma, Metastatic Occult Primary Squamous Neck Cancer, Metastatic Primary Squamous Neck Cancer, Metastatic Squamous Neck Cancer, Multiple Myeloma, Multiple Myeloma/Plasma Cell Neoplasm, Myelodysplastic Syndrome, Myclogenous Leukemia, Myeloid Leukemia, Mycloproliferative Disorders, Nasal Cavity and Paranasal Sinus Cancer, Nasopharyngeal Cancer, Neuroblastoma, Non-Hodgkin's Lymphoma During Pregnancy, Nonmelanoma Skin Cancer, Non-Small Cell Lung Cancer, Occult Primary Metastatic Squamous Neck Cancer, Oropharyngeal Cancer, Osteo-/Malignant Fibrous Sarcoma, Osteosarcoma/Malignant Fibrous Histiocytoma, Osteosarcoma/Malignant Fibrous Histiocytoma of Bone, Ovarian Epithelial Cancer, Ovarian Germ Cell Tumor, Ovarian Low Malignant Potential Tumor, Pancreatic Cancer, Paraproteinemias, Purpura, Parathyroid Cancer, Penile Cancer, Pheochromocytoma, Pituitary Tumor, Plasma Cell Neoplasm/Multiple Myeloma, Primary Central Nervous System Lymphoma, Primary Liver Cancer, Prostate Cancer, Rectal Cancer, Renal Cell Cancer, Renal Pelvis and Ureter Cancer, Retinoblastoma, Rhabdomyosarcoma, Salivary Gland Cancer, Sarcoidosis Sarcomas, Sezary Syndrome, Skin Cancer, Small Cell Lung Cancer, Small Intestine Cancer, Soft Tissue Sarcoma, Squamous Neck Cancer, Stomach Cancer, Supratentorial Primitive Neuroectodermal and Pineal Tumors, T-Cell Lymphoma, Testicular Cancer, Thymoma, Thyroid Cancer, Transitional Cell Cancer of the Renal Pelvis and Ureter, Transitional Renal Pelvis and Ureter Cancer, Trophoblastic Tumors, Ureter and Renal Pelvis Cell Cancer, Urethral Cancer, Uterine Cancer, Uterine Sarcoma, Vaginal Cancer, Visual Pathway and Hypothalamic Glioma, Vulvar Cancer, Waldenstrom's Macroglobulinemia, Wilms' Tumor, and any other hyperproliferative disease, besides neoplasia, located in an organ system listed above.

In another preferred embodiment, polynucleotides or polypeptides, or agonists or antagonists of the present invention are used to diagnose, prognose, prevent, and/or treat premalignant conditions and to prevent progression to a neoplastic or malignant state, including but not limited to those disorders described above. Such uses are indicated in conditions known or suspected of preceding progression to neoplasia or cancer, in particular, where non-neoplastic cell growth consisting of hyperplasia, metaplasia, or most particularly, dysplasia has occurred (for review of such abnormal growth conditions, see Robbins and Angell, 1976, Basic Pathology, 2d Ed., W. B. Saunders Co., Philadelphia, pp. 68-79.)

Hyperplasia is a form of controlled cell proliferation, involving an increase in cell number in a tissue or organ, without significant alteration in structure or function. Hyperplastic disorders which can be diagnosed, prognosed, prevented, and/or treated with compositions of the invention (including polynucleotides, polypeptides, agonists or antagonists) include, but are not limited to, angiofollicular mediastinal lymph node hyperplasia, angiolymphoid hyperplasia with eosinophilia, atypical melanocytic hyperplasia, basal cell hyperplasia, benign giant lymph node hyperplasia, cementum hyperplasia, congenital adrenal hyperplasia, congenital sebaceous hyperplasia, cystic hyperplasia, cystic hyperplasia of the breast, denture hyperplasia, ductal hyperplasia, endometrial hyperplasia, fibromuscular hyperplasia, focal epithelial hyperplasia, gingival hyperplasia, inflammatory fibrous hyperplasia, inflammatory papillary hyperplasia, intravascular papillary endothelial hyperplasia, nodular hyperplasia of prostate, nodular regenerative hyperplasia, pseudoepitheliomatous hyperplasia, senile sebaceous hyperplasia, and verrucous hyperplasia.

Metaplasia is a form of controlled cell growth in which one type of adult or fully differentiated cell substitutes for another type of adult cell. Metaplastic disorders which can be diagnosed, prognosed, prevented, and/or treated with compositions of the invention (including polynucleotides, polypeptides, agonists or antagonists) include, but are not limited to, agnogenic myeloid metaplasia, apocrine metaplasia, atypical metaplasia, autoparenchymatous metaplasia, connective tissue metaplasia, epithelial metaplasia, intestinal metaplasia, metaplastic anemia, metaplastic ossification, metaplastic polyps, myeloid metaplasia, primary myeloid metaplasia, secondary myeloid metaplasia, squamous metaplasia, squamous metaplasia of amnion, and symptomatic myeloid metaplasia.

Dysplasia is frequently a forerunner of cancer, and is found mainly in the epithelia; it is the most disorderly form of non-neoplastic cell growth, involving a loss in individual cell uniformity and in the architectural orientation of cells. Dysplastic cells often have abnormally large, deeply stained nuclei, and exhibit pleomorphism. Dysplasia characteristically occurs where there exists chronic irritation or inflammation. Dysplastic disorders which can be diagnosed, prognosed, prevented, and/or treated with compositions of the invention (including polynucleotides, polypeptides, agonists or antagonists) include, but are not limited to, anhidrotic ectodermal dysplasia, anterofacial dysplasia, asphyxiating thoracic dysplasia, atriodigital dysplasia, bronchopulmonary dysplasia, cerebral dysplasia, cervical dysplasia, chondroectodermal dysplasia, cleidocranial dysplasia, congenital ectodermal dysplasia, craniodiaphysial dysplasia, craniocarpotarsal dysplasia, craniometaphysial dysplasia, dentin dysplasia, diaphysial dysplasia, ectodermal dysplasia, enamel dysplasia, encephalo-ophthalmic dysplasia, dysplasia epiphysialis hemimelia, dysplasia epiphysialis multiplex, dysplasia epiphysialis punctata, epithelial dysplasia, faciodigitogenital dysplasia, familial fibrous dysplasia of jaws, familial white folded dysplasia, fibromuscular dysplasia, fibrous dysplasia of bone, florid osseous dysplasia, hereditary renal-retinal dysplasia, hidrotic ectodermal dysplasia, hypohidrotic ectodermal dysplasia, lymphopenic thymic dysplasia, mammary dysplasia, mandibulofacial dysplasia, metaphysial dysplasia, Mondini dysplasia, monostotic fibrous dysplasia, mucoepithelial dysplasia, multiple epiphysial dysplasia, oculoauriculovertebral dysplasia, oculodentodigital dysplasia, oculovertebral dysplasia, odontogenic dysplasia, ophthalmomandibulomelic dysplasia, periapical cemental dysplasia, polyostotic fibrous dysplasia, pseudoachondroplastic spondyloepiphysial dysplasia, retinal dysplasia, septo-optic dysplasia, spondyloepiphysial dysplasia, and ventriculoradial dysplasia.

Additional pre-neoplastic disorders which can be diagnosed, prognosed, prevented, and/or treated with compositions of the invention (including polynucleotides, polypeptides, agonists or antagonists) include, but are not limited to, benign dysproliferative disorders (e.g., benign tumors, fibrocystic conditions, tissue hypertrophy, intestinal polyps, colon polyps, and esophageal dysplasia), leukoplakia, keratoses, Bowen's disease, Farmer's Skin, solar cheilitis, and solar keratosis.

In another embodiment, a polypeptide of the invention, or polynucleotides, antibodies, agonists, or antagonists corresponding to that polypeptide, may be used to diagnose and/or prognose disorders associated with the tissue(s) in which the polypeptide of the invention is expressed.

In another embodiment, polynucleotides, polypeptides, antibodies, and/or agonists or antagonists of the present invention conjugated to a toxin or a radioactive isotope, as described herein, may be used to treat cancers and neoplasms, including, but not limited to those described herein. In a further preferred embodiment, polynucleotides, polypeptides, antibodies, and/or agonists or antagonists of the present invention conjugated to a toxin or a radioactive isotope, as described herein, may be used to treat acute myelogenous leukemia.

Additionally, polynucleotides, polypeptides, and/or agonists or antagonists of the invention may affect apoptosis, and therefore, would be useful in treating a number of diseases associated with increased cell survival or the inhibition of apoptosis. For example, diseases associated with increased cell survival or the inhibition of apoptosis that could be diagnosed, prognosed, prevented, and/or treated by polynucleotides, polypeptides, and/or agonists or antagonists of the invention, include cancers (such as follicular lymphomas, carcinomas with p53 mutations, and hormone-dependent tumors, including, but not limited to colon cancer, cardiac tumors, pancreatic cancer, melanoma, retinoblastoma, glioblastoma, lung cancer, intestinal cancer, testicular cancer, stomach cancer, neuroblastoma, myxoma, myoma, lymphoma, endothelioma, osteoblastoma, osteoclastoma, osteosarcoma, chondrosarcoma, adenoma, breast cancer, prostate cancer, Kaposi's sarcoma and ovarian cancer); autoimmune disorders such as, multiple sclerosis, Sjogren's syndrome, Hashimoto's thyroiditis, biliary cirrhosis, Behcet's disease, Crohn's disease, polymyositis, systemic lupus erythematosus and immune-related glomerulonephritis and rheumatoid arthritis) and viral infections (such as herpes viruses, pox viruses and adenoviruses), inflammation, graft v. host disease, acute graft rejection, and chronic graft rejection.

In preferred embodiments, polynucleotides, polypeptides, and/or agonists or antagonists of the invention are used to inhibit growth, progression, and/or metastasis of cancers, in particular those listed above.

Additional diseases or conditions associated with increased cell survival that could be diagnosed, prognosed, prevented, and/or treated by polynucleotides, polypeptides, and/or agonists or antagonists of the invention, include, but are not limited to, progression, and/or metastases of malignancies and related disorders such as leukemia (including acute leukemias (e.g., acute lymphocytic leukemia, acute myelocytic leukemia (including myeloblastic, promyelocytic, myelomonocytic, monocytic, and erythroleukemia)) and chronic leukemias (e.g., chronic myelocytic (granulocytic) leukemia and chronic lymphocytic leukemia)), polycythemia vera, lymphomas (e.g., Hodgkin's disease and non-Hodgkin's disease), multiple myeloma, Waldenstrom's macroglobulinemia, heavy chain disease, and solid tumors including, but not limited to, sarcomas and carcinomas such as fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilm's tumor, cervical cancer, testicular tumor, lung carcinoma, small cell lung carcinoma, bladder carcinoma, epithelial carcinoma, glioma, astrocytoma, medulloblastoma, craniopharyngioma, ependymoma, pinealoma, emangioblastoma, acoustic neuroma, oligodendroglioma, menangioma, melanoma, neuroblastoma, and retinoblastoma.

Diseases associated with increased apoptosis that could be diagnosed, prognosed, prevented, and/or treated by polynucleotides, polypeptides, and/or agonists or antagonists of the invention, include AIDS; neurodegenerative disorders (such as Alzheimer's disease, Parkinson's disease, amyotrophic lateral sclerosis, retinitis pigmentosa, cerebellar degeneration and brain tumor or prior associated disease); autoimmune disorders (such as, multiple sclerosis, Sjogren's syndrome, Hashimoto's thyroiditis, biliary cirrhosis, Behcet's disease, Crohn's disease, polymyositis, systemic lupus erythematosus and immune-related glomerulonephritis and rheumatoid arthritis) myelodysplastic syndromes (such as aplastic anemia), graft v. host disease, ischemic injury (such as that caused by myocardial infarction, stroke and reperfusion injury), liver injury (e.g., hepatitis related liver injury, ischemia/reperfusion injury, cholestasis (bile duct injury) and liver cancer); toxin-induced liver disease (such as that caused by alcohol), septic shock, cachexia and anorexia.

Hyperproliferative diseases and/or disorders that could be diagnosed, prognosed, prevented, and/or treated by polynucleotides, polypeptides, and/or agonists or antagonists of the invention, include, but are not limited to, neoplasms located in the liver, abdomen, bone, breast, digestive system, pancreas, peritoneum, endocrine glands (adrenal, parathyroid, pituitary, testicles, ovary, thymus, thyroid), eye, head and neck, nervous system (central and peripheral), lymphatic system, pelvis, skin, soft tissue, spleen, thorax, and urogenital tract.

Similarly, other hyperproliferative disorders can also be diagnosed, prognosed, prevented, and/or treated by polynucleotides, polypeptides, and/or agonists or antagonists of the invention. Examples of such hyperproliferative disorders include, but are not limited to: hypergammaglobulinemia, lymphoproliferative disorders, paraproteinemias, purpura, sarcoidosis, Sezary Syndrome, Waldenstron's macroglobulinemia, Gaucher's Disease, histiocytosis, and any other hyperproliferative disease, besides neoplasia, located in an organ system listed above.

Another preferred embodiment utilizes polynucleotides of the present invention to inhibit aberrant cellular division, by gene therapy using the present invention, and/or protein fusions or fragments thereof.

Thus, the present invention provides a method for treating cell proliferative disorders by inserting into an abnormally proliferating cell a polynucleotide of the present invention, wherein said polynucleotide represses said expression.

Another embodiment of the present invention provides a method of treating cell-proliferative disorders in individuals comprising administration of one or more active gene copies of the present invention to an abnormally proliferating cell or cells. In a preferred embodiment, polynucleotides of the present invention is a DNA construct comprising a recombinant expression vector effective in expressing a DNA sequence encoding said polynucleotides. In another preferred embodiment of the present invention, the DNA construct encoding the poynucleotides of the present invention is inserted into cells to be treated utilizing a retrovirus, or more preferably an adenoviral vector (See G J. Nabel, et. al., PNAS 1999 96: 324-326, which is hereby incorporated by reference). In a most preferred embodiment, the viral vector is defective and will not transform non-proliferating cells, only proliferating cells. Moreover, in a preferred embodiment, the polynucleotides of the present invention inserted into proliferating cells either alone, or in combination with or fused to other polynucleotides, can then be modulated via an external stimulus (i.e. magnetic, specific small molecule, chemical, or drug administration, etc.), which acts upon the promoter upstream of said polynucleotides to induce expression of the encoded protein product. As such the beneficial therapeutic affect of the present invention may be expressly modulated (i.e. to increase, decrease, or inhibit expression of the present invention) based upon said external stimulus.

Polynucleotides of the present invention may be useful in repressing expression of oncogenic genes or antigens. By "repressing expression of the oncogenic genes " is intended the suppression of the transcription of the gene, the degradation of the gene transcript (pre-message RNA), the inhibition of splicing, the destruction of the messenger RNA, the prevention of the post-translational modifications of the protein, the destruction of the protein, or the inhibition of the normal function of the protein.

For local administration to abnormally proliferating cells, polynucleotides of the present invention may be administered by any method known to those of skill in the art including, but not limited to transfection, electroporation, microinjection of cells, or in vehicles such as liposomes, lipofectin, or as naked polynucleotides, or any other method described throughout the specification. The polynucleotide of the present invention may be delivered by known gene delivery systems such as, but not limited to, retroviral vectors (Gilboa, J. Virology 44:845 (1982); Hocke, Nature 320:275 (1986); Wilson, et al., Proc. Natl. Acad. Sci. U.S.A. 85:3014), vaccinia virus system (Chakrabarty et al., Mol. Cell Biol. 5:3403 (1985) or other efficient DNA delivery systems (Yates et al., Nature 313:812 (1985)) known to those skilled in the art. These references are exemplary only and are hereby incorporated by reference. In order to specifically deliver or transfect cells which are abnormally proliferating and spare non-dividing cells, it is preferable to utilize a retrovirus, or adenoviral (as described in the art and elsewhere herein) delivery system known to those of skill in the art. Since host DNA replication is required for retroviral DNA to integrate and the retrovirus will be unable to self replicate due to the lack of the retrovirus genes needed for its life cycle. Utilizing such a retroviral delivery system for polynucleotides of the present invention will target said gene and constructs to abnormally proliferating cells and will spare the non-dividing normal cells.

The polynucleotides of the present invention may be delivered directly to cell proliferative disorder/disease sites in internal organs, body cavities and the like by use of imaging devices used to guide an injecting needle directly to the disease site. The polynucleotides of the present invention may also be administered to disease sites at the time of surgical intervention.

By "cell proliferative disease" is meant any human or animal disease or disorder, affecting any one or any combination of organs, cavities, or body parts, which is characterized by single or multiple local abnormal proliferations of cells, groups of cells, or tissues, whether benign or malignant.

Any amount of the polynucleotides of the present invention may be administered as long as it has a biologically inhibiting effect on the proliferation of the treated cells. Moreover, it is possible to administer more than one of the polynucleotide of the present invention simultaneously to the same site. By "biologically inhibiting" is meant partial or total growth inhibition as well as decreases in the rate of proliferation or growth of the cells. The biologically inhibitory dose may be determined by assessing the effects of the polynucleotides of the present invention on target malignant or abnormally proliferating cell growth in tissue culture, tumor growth in animals and cell cultures, or any other method known to one of ordinary skill in the art.

The present invention is further directed to antibody-based therapies which involve administering of anti-polypeptides and anti-polynucleotide antibodies to a mammalian, preferably human, patient for treating one or more of the described disorders. Methods for producing anti-polypeptides and anti-polynucleotide antibodies polyclonal and monoclonal antibodies are described in detail elsewhere herein. Such antibodies may be provided in pharmaceutically acceptable compositions as known in the art or as described herein.

A summary of the ways in which the antibodies of the present invention may be used therapeutically includes binding polynucleotides or polypeptides of the present invention locally or systemically in the body or by direct cytotoxicity of the antibody, e.g. as mediated by complement (CDC) or by effector cells (ADCC). Some of these approaches are described in more detail below. Armed with the teachings provided herein, one of ordinary skill in the art will know how to use the antibodies of the present invention for diagnostic, monitoring or therapeutic purposes without undue experimentation.

In particular, the antibodies, fragments and derivatives of the present invention are useful for treating a subject having or developing cell proliferative and/or differentiation disorders as described herein. Such treatment comprises administering a single or multiple doses of the antibody, or a fragment, derivative, or a conjugate thereof.

The antibodies of this invention may be advantageously utilized in combination with other monoclonal or chimeric antibodies, or with lymphokines or hematopoietic growth factors, for example., which serve to increase the number or activity of effector cells which interact with the antibodies.

It is preferred to use high affinity and/or potent in vivo inhibiting and/or neutralizing antibodies against polypeptides or polynucleotides of the present invention, fragments or regions thereof, for both immunoassays directed to and therapy of disorders related to polynucleotides or polypeptides, including fragments thereof, of the present invention. Such antibodies, fragments, or regions, will preferably have an affinity for polynucleotides or polypeptides, including fragments thereof Preferred binding affinities include those with a dissociation constant or Kd less than $5 \times 10^{-6}$M, $10^{-6}$M, $5 \times 10^{-7}$M, $10^{-7}$M, $5 \times 10^{-8}$M, $10^{-8}$M, $5 \times 10^{-9}$M, $10^{-9}$M, $5 \times 10^{-10}$M, $10^{-10}$M, $5 \times 10^{-11}$M, $10^{-11}$M, $5 \times 10^{-12}$M, $10^{-12}$M, $5 \times 10^{-13}$M, $10^{-13}$M, $5 \times 10^{-14}$M, $10^{-14}$M, $5 \times 10^{-15}$M, and $10^{-15}$M.

Moreover, polypeptides of the present invention are useful in inhibiting the angiogenesis of proliferative cells or tissues, either alone, as a protein fusion, or in combination with other polypeptides directly or indirectly, as described elsewhere herein. In a most preferred embodiment, said anti-angiogenesis effect may be achieved indirectly, for example, through the inhibition of hematopoietic, tumor-specific cells, such as tumor-associated macrophages (See Joseph I B, et al. J Natl Cancer Inst, 90(21):1648-53 (1998), which is hereby incorporated by reference). Antibodies directed to polypeptides or polynucleotides of the present invention may also result in inhibition of angiogenesis directly, or indirectly (See Witte L, et al., Cancer Metastasis Rev. 17(2):155-61 (1998), which is hereby incorporated by reference)).

Polypeptides, including protein fusions, of the present invention, or fragments thereof may be useful in inhibiting proliferative cells or tissues through the induction of apoptosis. Said polypeptides may act either directly, or indirectly to induce apoptosis of proliferative cells and tissues, for example in the activation of a death-domain receptor, such as tumor necrosis factor (TNF) receptor-1, CD95 (Fas/APO-1), TNF-receptor-related apoptosis-mediated protein (TRAMP) and TNF-related apoptosis-inducing ligand (TRAIL) receptor-1 and -2 (See Schulze-Osthoff K, et.al., Eur J Biochem 254(3):439-59 (1998), which is hereby incorporated by reference). Moreover, in another preferred embodiment of the present invention, said polypeptides may induce apoptosis through other mechanisms, such as in the activation of other proteins which will activate apoptosis, or through stimulating the expression of said proteins, either alone or in combination with small molecule drugs or adjuviants, such as apoptonin, galectins, thioredoxins, anti-inflammatory proteins (See for example, Mutat Res 400(1-2):447-55 (1998), Med Hypotheses.50(5):423-33 (1998), Chem Biol Interact. April 24;111-112:23-34 (1998), J Mol Med.76(6):402-12 (1998), Int J Tissue React;20(1):3-15 (1998), which are all hereby incorporated by reference).

Polypeptides, including protein fusions to, or fragments thereof, of the present invention are useful in inhibiting the metastasis of proliferative cells or tissues. Inhibition may occur as a direct result of administering polypeptides, or antibodies directed to said polypeptides as described elsewhere herein, or indirectly, such as activating the expression of proteins known to inhibit metastasis, for example alpha 4 integrins, (See, e.g., Curr Top Microbiol Immunol 1998;231: 125-41, which is hereby incorporated by reference). Such thereapeutic affects of the present invention may be achieved either alone, or in combination with small molecule drugs or adjuvants.

In another embodiment, the invention provides a method of delivering compositions containing the polypeptides of the invention (e.g., compositions containing polypeptides or polypeptide antibodies associated with heterologous polypeptides, heterologous nucleic acids, toxins, or prodrugs) to targeted cells expressing the polypeptide of the present invention. Polypeptides or polypeptide antibodies of the invention may be associated with heterologous polypeptides, heterologous nucleic acids, toxins, or prodrugs via hydrophobic, hydrophilic, ionic and/or covalent interactions.

Polypeptides, protein fusions to, or fragments thereof, of the present invention are useful in enhancing the immunogenicity and/or antigenicity of proliferating cells or tissues, either directly, such as would occur if the polypeptides of the present invention 'vaccinated' the immune response to respond to proliferative antigens and immunogens, or indirectly, such as in activating the expression of proteins known to enhance the immune response (e.g. chemokines), to said antigens and immunogens.

Infectious Disease

Polynucleotides or polypeptides, as well as agonists or antagonists of the present invention can be used to treat or detect infectious agents. For example, by increasing the immune response, particularly increasing the proliferation and differentiation of B and/or T cells, infectious diseases may be treated. The immune response may be increased by either enhancing an existing immune response, or by initiating a new immune response. Alternatively, polynucleotides or polypeptides, as well as agonists or antagonists of the present invention may also directly inhibit the infectious agent, without necessarily eliciting an immune response.

Viruses are one example of an infectious agent that can cause disease or symptoms that can be treated or detected by a polynucleotide or polypeptide and/or agonist or antagonist of the present invention. Examples of viruses, include, but are not limited to Examples of viruses, include, but are not limited to the following DNA and RNA viruses and viral families: Arbovirus, Adenoviridae, Arenaviridae, Arterivirus, Bimaviridae, Bunyaviridae, Caliciviridae, Circoviridae, Coronaviridae, Dengue, EBV, HIV, Flaviviridae, Hepadnaviridae (Hepatitis), Herpesviridae (such as, Cytomegalovirus, Herpes Simplex, Herpes Zoster), Mononegavirus (e.g., Paramyxoviridae, Morbillivirus, Rhabdoviridae), Orthomyxoviridae (e.g., Influenza A, Influenza B, and parainfluenza), Papiloma virus, Papovaviridae, Parvoviridae, Picomaviridae, Poxviridae (such as Smallpox or Vaccinia), Reoviridae (e.g., Rotavirus), Retroviridae (HTLV-I, HTLV-II, Lentivirus), and Togaviridae (e.g., Rubivirus). Viruses falling within these families can cause a variety of diseases or symptoms, including, but not limited to: arthritis, bronchiollitis, respiratory syncytial virus, encephalitis, eye infections (e.g., conjunctivitis, keratitis), chronic fatigue syndrome, hepatitis (A, B, C, E, Chronic Active, Delta), Japanese B encephalitis, Junin, Chikungunya, Rift Valley fever, yellow fever, meningitis, opportunistic infections (e.g., AIDS), pneumonia, Burkitt's Lymphoma, chickenpox, hemorrhagic fever, Measles, Mumps, Parainfluenza, Rabies, the common cold, Polio, leukemia, Rubella, sexually transmitted diseases, skin diseases (e.g., Kaposi's, warts), and viremia, polynucleotides or polypeptides, or agonists or antagonists of the invention, can be used to treat or detect any of these symptoms or diseases. In specific embodiments, polynucleotides, polypeptides, or agonists or antagonists of the invention are used to treat: meningitis, Dengue, EBV, and/or hepatitis (e.g., hepatitis B). In an additional specific embodiment polynucleotides, polypeptides, or agonists or antagonists of the invention are used to treat patients nonresponsive to one or more other commercially available hepatitis vaccines. In a further specific embodiment polynucleotides, polypeptides, or agonists or antagonists of the invention are used to treat AIDS.

Similarly, bacterial and fungal agents that can cause disease or symptoms and that can be treated or detected by a polynucleotide or polypeptide and/or agonist or antagonist of the present invention include, but not limited to, the following Gram-Negative and Gram-positive bacteria, bacterial families, and fungi: *Actinomyces* (e.g., *Norcardia*), Acinetobacter, *Cryptococcus neoformans, Aspergillus*, Bacillaceae (e.g., *Bacillus anthrasis*), Bacteroides (e.g., *Bacteroides fragilis*), Blastomycosis, *Bordetella, Borrelia* (e.g., *Borrelia burgdorferi*), Brucella, Candidia, *Campylobacter, Chlamydia, Clostridium* (e.g., *Clostridium botulinum, Clostridium dificile, Clostridium perfringens, Clostridium tetani*), *Coccidioides, Corynebacterium* (e.g., *Corynebacterium diptheriae*), *Cryptococcus*, Dermatocycoses, *E. coli* (e.g., Enterotoxigenic *E. coli* and Enterohemorrhagic *E. coli*), Enterobacter (e.g. *Enterobacter aerogenes*), Enterobacteriaceac (*Klebsiella, Salmonella* (e.g., *Salmonella typhi, Salmonella enteritidis, Salmonella typhi*), Serratia, Yersinia, Shigella), Erysipelothrix, *Haemophilus* (e.g., *Haemophilus influenza* type B), *Helicobacter, Legionella* (e.g., *Legionella pneumophila*), Leptospira, Listeria (e.g., *Listeria monocytogenes*), Mycoplasma, Mycobacterium (e.g., *Mycobacterium leprae* and *Mycobacterium tuberculosis*), *Vibrio* (e.g., *Vibrio cholerae*), Neisseriaceae (e.g., *Neisseria gonorrhea, Neisseria meningitidis*), Pasteurellacea, *Proteus, Pseudomonas* (e.g., *Pseudomonas aeruginosa*), Rickettsiaceae, Spirochetes (e.g., *Treponema* spp., *Leptospira* spp., *Borrelia* spp.), *Shigella* spp., *Staphylococcus* (e.g., *Staphylococcus aureus*), *Meningiococcus, Pneumococcus* and *Streptococcus* (e.g., *Streptococcus pneumoniae* and Groups A, B, and C Streptococci), and Ureaplasmas. These bacterial, parasitic, and fungal families can cause diseases or symptoms, including, but not limited to: antibiotic-resistant infections, bacteremia, endocarditis, septicemia, eye infections (e.g., conjunctivitis), uveitis, tuberculosis, gingivitis, bacterial diarrhea, opportunistic infections (e.g., AIDS related infections), paronychia, prosthesis-related infections, dental caries, Reiter's Disease, respiratory tract infections, such as Whooping Cough or Empyema, sepsis, Lyme Disease, Cat-Scratch Disease, dysentery, paratyphoid fever, food poisoning, Legionella disease, chronic and acute inflammation, erythema, yeast infections, typhoid, pneumonia, gonorrhea, meningitis (e.g., mengitis types A and B), chlamydia, syphillis, diphtheria, leprosy, brucellosis, peptic ulcers, anthrax, spontaneous abortions, birth defects, pneumonia, lung infections, ear infections, deafness, blindness, lethargy, malaise, vomiting, chronic diarrhea, Crohn's disease, colitis, vaginosis, sterility, pelvic inflammatory diseases, candidiasis, paratuberculosis, tuberculosis, lupus, botulism, gangrene, tetanus, impetigo, Rheumatic Fever, Scarlet Fever, sexually transmitted diseases, skin diseases (e.g., cellulitis, dermatocycoses), toxemia, urinary tract infections, wound infections, noscomial infections. Polynucleotides or polypeptides, agonists or antagonists of the invention, can be used to treat or detect any of these symptoms or diseases. In specific embodiments, polynucleotides, polypeptides, agonists or antagonists of the invention are used to treat: tetanus, diptheria, botulism, and/or meningitis type B.

Moreover, parasitic agents causing disease or symptoms that can be treated, prevented, and/or diagnosed by a polynucleotide or polypeptide and/or agonist or antagonist of the present invention include, but not limited to, the following families or class: Amebiasis, Babesiosis, Coccidiosis, Cryptosporidiosis, Dientamoebiasis, Dourine, Ectoparasitic, Giardias, Helminthiasis, Leishmaniasis, Schistisoma, Theileriasis, Toxoplasmosis, Trypanosomiasis, and Trichomonas and Sporozoans (e.g., *Plasmodium virax, Plasmodium falciparium, Plasmodium malariae* and *Plasmodium ovale*). These parasites can cause a variety of diseases or symptoms, including, but not limited to: Scabies, Trombiculiasis, eye infections, intestinal disease (e.g., dysentery, giardiasis), liver disease, lung disease, opportunistic infections (e.g., AIDS related), malaria, pregnancy complications, and toxoplasmosis, polynucleotides or polypeptides, or agonists or antagonists of the invention, can be used to treat, prevent, and/or diagnose any of these symptoms or diseases. In specific embodiments, polynucleotides, polypeptides, or agonists or antagonists of the invention are used to treat, prevent, and/or diagnose malaria.

Polynucleotides or polypeptides, as well as agonists or antagonists of the present invention of the present invention could either be by administering an effective amount of a polypeptide to the patient, or by removing cells from the patient, supplying the cells with a polynucledtide of the present invention, and returning the engineered cells to the patient (ex vivo therapy). Moreover, the polypeptide or polynucleotide of the present invention can be used as an antigen in a vaccine to raise an immune response against infectious disease.

Diseases at the Cellular Level

Diseases associated with increased cell survival or the inhibition of apoptosis that could be treated, prevented, diagnosed, and/or prgnosed using polynucleotides or polypeptides, as well as antagonists or agonists of the present invention, include cancers (such as follicular lymphomas, carcinomas with p53 mutations, and hormone-dependent tumors, including, but not limited to colon cancer, cardiac tumors, pancreatic cancer, melanoma, retinoblastoma, glioblastoma, lung cancer, intestinal cancer, testicular cancer, stomach cancer, neuroblastoma, myxoma, myoma, lymphoma, endothelioma, osteoblastoma, osteoclastoma, osteosarcoma, chondrosarcoma, adenoma, breast cancer, prostate cancer, Kaposi's sarcoma and ovarian cancer); autoimmune disorders (such as, multiple sclerosis, Sjogren's syndrome, Hashimoto's thyroiditis, biliary cirrhosis, Behcet's disease, Crohn's disease, polymyositis, systemic lupus erythematosus and immune-related glomerulonephritis and rheumatoid arthritis) and viral infections (such as herpes viruses, pox viruses and adenoviruses), inflammation, graft v. host disease, acute graft rejection, and chronic graft rejection.

In preferred embodiments, polynucleotides, polypeptides, and/or antagonists of the invention are used to inhibit growth, progression, and/or metasis of cancers, in particular those listed above.

Additional diseases or conditions associated with increased cell survival that could be treated or detected by polynucleotides or polypeptides, or agonists or antagonists of the present invention include, but are not limited to, progression, and/or metastases of malignancies and related disorders such as leukemia (including acute leukemias (e.g., acute lymphocytic leukemia, acute myelocytic leukemia (including myeloblastic, promyelocytic, myelomonocytic, monocytic, and erythroleukemia)) and chronic leukemias (e.g., chronic myelocytic (granulocytic) leukemia and chronic lymphocytic leukemia)), polycythemia vera, lymphomas (e.g., Hodgkin's disease and non-Hodgkin's disease), multiple myeloma, Waldenstrom's macroglobulinemia, heavy chain disease, and solid tumors including, but not limited to, sarcomas and carcinomas such as fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilm's tumor, cervical cancer, testicular tumor, lung carcinoma, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, menangioma, melanoma, neuroblastoma, and retinoblastoma.

Diseases associated with increased apoptosis that could be treated, prevented, diagnosed, and/or prognosedusing polynucleotides or polypeptides, as well as agonists or antagonists of the present invention, include, but are not limited to, AIDS; neurodegenerative disorders (such as Alzheimer's disease, Parkinson's disease, Amyotrophic lateral sclerosis, Retinitis pigmentosa, Cerebellar degeneration and brain tumor or prior associated disease); autoimmune disorders (such as, multiple sclerosis, Sjogren's syndrome, Hashimoto's thyroiditis, biliary cirrhosis, Behcet's disease, Crohn's disease, polymyositis, systemic lupus erythematosus and immune-related glomerulonephritis and rheumatoid arthritis) myelodysplastic syndromes (such as aplastic anemia), graft v. host disease, ischemic injury (such as that caused by myocardial infarction, stroke and reperfusion injury), liver injury (e.g., hepatitis related liver injury, ischemia/reperfusion injury, cholestosis (bile duct injury) and liver cancer); toxin-induced liver disease (such as that caused by alcohol), septic shock, cachexia and anorexia.

Binding Activity

A polypeptide of the present invention may be used to screen for molecules that bind to the polypeptide or for molecules to which the polypeptide binds. The binding of the polypeptide and the molecule may activate (agonist), increase, inhibit (antagonist), or decrease activity of the polypeptide or the molecule bound. Examples of such molecules include antibodies, oligonucleotides, proteins (e.g., receptors),or small molecules.

Preferably, the molecule is closely related to the natural ligand of the polypeptide, e.g., a fragment of the ligand, or a natural substrate, a ligand, a structural or functional mimetic. (See, Coligan et al., Current Protocols in Immunology 1(2): Chapter 5 (1991). Similarly, the molecule can be closely related to the natural receptor to which the polypeptide binds, or at least, a fragment of the receptor capable of being bound by the polypeptide (e.g., active site). In either case, the molecule can be rationally designed using known techniques.

Preferably, the screening for these molecules involves producing appropriate cells which express the polypeptide. Preferred cells include cells from mammals, yeast, Drosophila, or E. coli. Cells expressing the polypeptide (or cell membrane containing the expressed polypeptide) are then preferably contacted with a test compound potentially containing the molecule to observe binding, stimulation, or inhibition of activity of either the polypeptide or the molecule.

The assay may simply test binding of a candidate compound to the polypeptide, wherein binding is detected by a label, or in an assay involving competition with a labeled competitor. Further, the assay may test whether the candidate compound results in a signal generated by binding to the polypeptide.

Alternatively, the assay can be carried out using cell-free preparations, polypeptide/molecule affixed to a solid support, chemical libraries, or natural product mixtures. The assay may also simply comprise the steps of mixing a candidate compound with a solution containing a polypeptide, measuring polypeptide/molecule activity or binding, and comparing the polypeptide/molecule activity or binding to a standard.

Preferably, an ELISA assay can measure polypeptide level or activity in a sample (e.g., biological sample) using a monoclonal or polyclonal antibody. The antibody can measure polypeptide level or activity by either binding, directly or indirectly, to the polypeptide or by competing with the polypeptide for a substrate.

Additionally, the receptor to which the polypeptide of the present invention binds can be identified by numerous methods known to those of skill in the art, for example, ligand panning and FACS sorting (Coligan, et al., Current Protocols in Immun., 1(2), Chapter 5, (1991)). For example, expression cloning is employed wherein polyadenylated RNA is prepared from a cell responsive to the polypeptides, for example, NIH3T3 cells which are known to contain multiple receptors for the FGF family proteins, and SC-3 cells, and a cDNA library created from this RNA is divided into pools and used to transfect COS cells or other cells that are not responsive to the polypeptides. Transfected cells which are grown on glass slides are exposed to the polypeptide of the present invention, after they have been labeled. The polypeptides can be labeled by a variety of means including iodination or inclusion of a recognition site for a site-specific protein kinase.

Following fixation and incubation, the slides are subjected to auto-radiographic analysis. Positive pools are identified and sub-pools are prepared and re-transfected using an iterative sub-pooling and re-screening process, eventually yielding a single clones that encodes the putative receptor.

As an alternative approach for receptor identification, the labeled polypeptides can be photoaffinity linked with cell membrane or extract preparations that express the receptor molecule. Cross-linked material is resolved by PAGE analysis and exposed to X-ray film. The labeled complex containing the receptors of the polypeptides can be excised, resolved into peptide fragments, and subjected to protein microsequencing. The amino acid sequence obtained from microsequencing would be used to design a set of degenerate oligonucleotide probes to screen a cDNA library to identify the genes encoding the putative receptors.

Moreover, the techniques of gene-shuffling, motif-shuffling, exon-shuffling, and/or codon-shuffling (collectively referred to as "DNA shuffling") may be employed to modulate the activities of the polypeptide of the present invention thereby effectively generating agonists and antagonists of the polypeptide of the present invention. See generally, U.S. Pat. Nos. 5,605,793, 5,811,238, 5,830,721, 5,834,252, and 5,837, 458, and Patten, P. A., et al., Curr. Opinion Biotechnol. 8:724-33 (1997); Harayama, S. Trends Biotechnol. 16(2):76-82 (1998); Hansson, L. O., et al., J. Mol. Biol. 287:265-76 (1999); and Lorenzo, M. M. and Blasco, R. Biotechniques 24(2):308-13 (1998); each of these patents and publications are hereby incorporated by reference). In one embodiment, alteration of polynucleotides and corresponding polypeptides may be achieved by DNA shuffling. DNA shuffling involves the assembly of two or more DNA segments into a desired molecule by homologous, or site-specific, recombination. In another embodiment, polynucleotides and corresponding polypeptides may be altered by being subjected to random mutagenesis by error-prone PCR, random nucleotide insertion or other methods prior to recombination. In another embodiment, one or more components, motifs, sections, parts, domains, fragments, etc., of the polypeptide of the present invention may be recombined with one or more components, motifs, sections, parts, domains, fragments, etc. of one or more heterologous molecules. In preferred embodiments, the heterologous molecules are family members. In further preferred embodiments, the heterologous molecule is a growth factor such as, for example, platelet-derived growth factor (PDGF), insulin-like growth factor (IGF-I), transforming growth factor (TGF)-alpha, epidermal growth factor (EGF), fibroblast growth factor (FGF), TGF-beta, bone morphogenetic protein (BMP)-2, BMP-4, BMP-5, BMP-6, BMP-7, activins A and B, decapentaplegic(dpp), 60A, OP-2, dorsalin, growth differentiation factors (GDFs), nodal, MIS, inhibin-alpha, TGF-beta1, TGF-beta2, TGF-beta3, TGF-beta5, and glial-derived neurotrophic factor (GDNF).

Other preferred fragments are biologically active fragments of the polypeptide of the present invention. Biologically active fragments are those exhibiting activity similar, but not necessarily identical, to an activity of the polypeptide of the present invention. The biological activity of the fragments may include an improved desired activity, or a decreased undesirable activity.

Additionally, this invention provides a method of screening compounds to identify those which modulate the action of the polypeptide of the present invention. An example of such an assay comprises combining a mammalian fibroblast cell, a the polypeptide of the present invention, the compound to be screened and $^3$[H] thymidine under cell culture conditions where the fibroblast cell would normally proliferate. A control assay may be performed in the absence of the compound to be screened and compared to the amount of fibroblast proliferation in the presence of the compound to determine if the compound stimulates proliferation by determining the uptake of 3[H] thymidine in each case. The amount of fibroblast cell proliferation is measured by liquid scintillation chromatography which measures the incorporation of $^3[H]$ thymidine. Both agonist and antagonist compounds may be identified by this procedure.

In another method, a mammalian cell or membrane preparation expressing a receptor for a polypeptide of the present invention is incubated with a labeled polypeptide of the present invention in the presence of the compound. The ability of the compound to enhance or block this interaction could then be measured. Alternatively, the response of a known second messenger system following interaction of a compound to be screened and the receptor is measured and the ability of the compound to bind to the receptor and elicit a second messenger response is measured to determine if the compound is a potential agonist or antagonist. Such second messenger systems include but are not limited to, cAMP guanylate cyclase, ion channels or phosphoinositide hydrolysis.

All of these above assays can be used as diagnostic or prognostic markers. The molecules discovered using these assays can be used to treat disease or to bring about a particular result in a patient (e.g., blood vessel growth) by activating or inhibiting the polypeptide/molecule. Moreover, the assays can discover agents which may inhibit or enhance the production of the polypeptides of the invention from suitably manipulated cells or tissues.

Therefore, the invention includes a method of identifying compounds which bind to a polypeptide of the invention comprising the steps of: (a) incubating a candidate binding compound with a polypeptide of the present invention; and (b) determining if binding has occurred. Moreover, the invention includes a method of identifying agonists/antagonists comprising the steps of: (a) incubating a candidate compound with a polypeptide of the present invention, (b) assaying a biological activity, and (b) determining if a biological activity of the polypeptide has been altered.

Targeted Delivery

In another embodiment, the invention provides a method of delivering compositions to targeted cells expressing a receptor for a polypeptide of the invention, or cells expressing a cell bound form of a polypeptide of the invention.

As discussed herein, polypeptides or antibodies of the invention may be associated with heterologous polypeptides, heterologous nucleic acids, toxins, or prodrugs via hydrophobic, hydrophilic, ionic and/or covalent interactions. In one embodiment, the invention provides a method for the specific delivery of compositions of the invention to cells by administering polypeptides of the invention (including antibodies) that are associated with heterologous polypeptides or nucleic acids. In one example, the invention provides a method for delivering a therapeutic protein into the targeted cell. In another example, the invention provides a method for delivering a single stranded nucleic acid (e.g., antisense or ribozymes) or double stranded nucleic acid (e.g., DNA that can integrate into the cell's genome or replicate episomally and that can be transcribed) into the targeted cell.

In another embodiment, the invention provides a method for the specific destruction of cells (e.g., the destruction of tumor cells) by administering polypeptides of the invention (e.g., polypeptides of the invention or antibodies of the invention) in association with toxins or cytotoxic prodrugs.

By "toxin" is meant compounds that bind and activate endogenous cytotoxic effector systems, radioisotopes, holotoxins, modified toxins, catalytic subunits of toxins, or any molecules or enzymes not normally present in or on the surface of a cell that under defined conditions cause the cell's death. Toxins that may be used according to the methods of the invention include, but are not limited to, radioisotopes known in the art, compounds such as, for example, antibodies (or complement fixing containing portions thereof) that bind an inherent or induced endogenous cytotoxic effector system, thymidine kinase, endonuclease, RNAse, alpha toxin, ricin, abrin, Pseudomonas exotoxin A, diphtheria toxin, saporin, momordin, gelonin, pokeweed antiviral protein, alpha-sarcin and cholera toxin. By "cytotoxic prodrug" is meant a non-toxic compound that is converted by an enzyme, normally present in the cell, into a cytotoxic compound. Cytotoxic prodrugs that may be used according to the methods of the invention include, but are not limited to, glutamyl derivatives of benzoic acid mustard alkylating agent, phosphate derivatives of etoposide or mitomycin C, cytosine arabinoside, daunorubisin, and phenoxyacetamide derivatives of doxorubicin.

Drug Screening

Further contemplated is the use of the polypeptides of the present invention, or the polynucleotides encoding these polypeptides, to screen for molecules which modify the activities of the polypeptides of the present invention. Such a method would include contacting the polypeptide of the present invention with a selected compound(s) suspected of having antagonist or agonist activity, and assaying the activity of these polypeptides following binding.

This invention is particularly useful for screening therapeutic compounds by using the polypeptides of the present invention, or binding fragments thereof, in any of a variety of drug screening techniques. The polypeptide or fragment employed in such a test may be affixed, to a solid support, expressed on a cell surface, free in solution, or located intracellularly. One method of drug screening utilizes eukaryotic or prokaryotic host cells which are stably transformed with recombinant nucleic acids expressing the polypeptide or fragment. Drugs are screened against such transformed cells in competitive binding assays. One may measure, for example, the formulation of complexes between the agent being tested and a polypeptide of the present invention.

Thus, the present invention provides methods of screening for drugs or any other agents which affect activities mediated by the polypeptides of the present invention. These methods comprise contacting such an agent with a polypeptide of the present invention or a fragment thereof and assaying for the presence of a complex between the agent and the polypeptide or a fragment thereof, by methods well known in the art. In such a competitive binding assay, the agents to screen are typically labeled. Following incubation, free agent is separated from that present in bound form, and the amount of free or uncomplexed label is a measure of the ability of a particular agent to bind to the polypeptides of the present invention.

Another technique for drug screening provides high throughput screening for compounds having suitable binding affinity to the polypeptides of the present invention, and is described in great detail in European Patent Application 84/03564, published on Sep. 13, 1984, which is incorporated herein by reference herein. Briefly stated, large numbers of different small peptide test compounds are synthesized on a solid substrate, such as plastic pins or some other surface. The peptide test compounds are reacted with polypeptides of the present invention and washed. Bound polypeptides are then detected by methods well known in the art. Purified polypeptides are coated directly onto plates for use in the aforementioned drug screening techniques. In addition, non-neutralizing antibodies may be used to capture the peptide and immobilize it on the solid support.

This invention also contemplates the use of competitive drug screening assays in which neutralizing antibodies capable of binding polypeptides of the present invention specifically compete with a test compound for binding to the polypeptides or fragments thereof. In this manner, the antibodies are used to detect the presence of any peptide which shares one or more antigenic epitopes with a polypeptide of the invention.

Antisense and Ribozyme (Antagonists)

In specific embodiments, antagonists according to the present invention are nucleic acids corresponding to the sequences contained in SEQ ID NO:1, or more preferably SEQ ID NO:3, or the complementary strands thereof, and/or to cDNA sequences contained in ATCC Deposit NO:97334. In one embodiment, antisense sequence is generated internally, by the organism, in another embodiment, the antisense sequence is separately administered (see, for example, O'Connor, J., Neurochem. 56:560 (1991). Oligodeoxynucleotides as Antisense Inhibitors of Gene Expression, CRC Press, Boca Raton, Fla. (1988). Antisense technology can be used to control gene expression through antisense DNA or RNA, or through triple-helix formation. Antisense techniques are discussed for example, in Okano, J., Neurochem. 56:560 (1991); Oligodeoxynucleotides as Antisense Inhibitors of Gene Expression, CRC Press, Boca Raton, Fla. (1988). Triple helix formation is discussed in, for instance, Lee et al., Nucleic Acids Research 6:3073 (1979); Cooney et al., Science 241:456 (1988); and Dervan et al., Science 251:1300 (1991). The methods are based on binding of a polynucleotide to a complementary DNA or RNA.

For example, the use of c-myc and c-myb antisense RNA constructs to inhibit the growth of the non-lymphocytic leukemia cell line HL-60 and other cell lines was previously described. (Wickstrom et al. (1988); Anfossi et al. (1989)). These experiments were performed in vitro by incubating cells with the oligoribonucleotide. A similar procedure for in vivo use is described in WO 91/15580. Briefly, a pair of oligonucleotides for a given antisense RNA is produced as follows: A sequence complementary to the first 15 bases of the open reading frame is flanked by an EcoR1 site on the 5 end and a HindIII site on the 3 end. Next, the pair of oligonucleotides is heated at 90° C. for one minute and then annealed in 2× ligation buffer (20 mM TRIS HCl pH 7.5, 10 mM MgCl2, 10 MM dithiothreitol (DTT) and 0.2 mM ATP) and then ligated to the EcoR1/Hind III site of the retroviral vector PMV7 (WO 91/15580).

For example, the 5' coding portion of a polynucleotide that encodes the polypeptide of the present invention may be used to design an antisense RNA oligonucleotide of from about 10 to 40 base pairs in length. A DNA oligonucleotide is designed to be complementary to a region of the gene involved in transcription thereby preventing transcription and the production of the receptor. The antisense RNA oligonucleotide hybridizes to the mRNA in vivo and blocks translation of the mRNA molecule into receptor polypeptide.

In one embodiment, the antisense nucleic acid of the invention is produced intracellularly by transcription from an exogenous sequence. For example, a vector or a. portion thereof, is transcribed, producing an antisense nucleic acid (RNA) of the invention. Such a vector would contain a sequence encoding the antisense nucleic acid. Such a vector can remain episomal or become chromosomally integrated, as long as it can be transcribed to produce the desired antisense RNA. Such vectors can be constructed by recombinant DNA technology methods standard in the art. Vectors can be plasmid, viral, or others known in the art, used for replication and expression in vertebrate cells. Expression of the sequence encoding the polypeptide of the present invention or fragments thereof, can be by any promoter known in the art to act in vertebrate, preferably human cells. Such promoters can be inducible or constitutive. Such promoters include, but are not limited to, the SV40 early promoter region (Bernoist and Chambon, Nature 29:304-310 (1981), the promoter contained in the 3' long terminal repeat of Rous sarcoma virus (Yamamoto et al., Cell 22:787-797 (1980), the herpes thymidine promoter (Wagner et al., Proc. Natl. Acad. Sci. U.S.A. 78:1441-1445 (1981), the regulatory sequences of the metallothionein gene (Brinster, et al., Nature 296:39-42 (1982)), etc.

The antisense nucleic acids of the invention comprise a sequence complementary to at least a portion of an RNA transcript of a gene of the present invention. However, absolute complementarity, although preferred, is not required. A sequence "complementary to at least a portion of an RNA," referred to herein, means a sequence having sufficient complementarity to be able to hybridize with the RNA, forming a stable duplex; in the case of double stranded antisense nucleic acids, a single strand of the duplex DNA may thus be tested, or triplex formation may be assayed. The ability to hybridize will depend on both the degree of complementarity and the length of the antisense nucleic acid. Generally, the larger the hybridizing nucleic acid, the more base mismatches with a RNA it may contain and still form a stable duplex (or triplex as the case may be). One skilled in the art can ascertain a tolerable degree of mismatch by use of standard procedures to determine the melting point of the hybridized complex.

Oligonucleotides that are complementary to the 5' end of the message, e.g., the 5' untranslated sequence up to and including the AUG initiation codon, should work most efficiently at inhibiting translation. However, sequences complementary to the 3' untranslated sequences of mRNAs have been shown to be effective at inhibiting translation of mRNAs as well. See generally, Wagner, R., 1994, Nature 372:333-335. Thus, oligonucleotides complementary to either the 5'- or 3'-non-translated, non-coding regions of polynucleotide sequences described herein could be used in an antisense approach to inhibit translation of endogenous mRNA. Oligonucleotides complementary to the 5' untranslated region of the mRNA should include the complement of the AUG start codon. Antisense oligonucleotides complementary to mRNA coding regions are less efficient inhibitors of translation but could be used in accordance with the invention. Whether designed to hybridize to the 5'-, 3'- or coding region of mRNA of the present invention, antisense nucleic acids should be at least six nucleotides in length, and are preferably oligonucleotides ranging from 6 to about 50 nucleotides in length. In specific aspects the oligonucleotide is at least 10 nucleotides, at least 17 nucleotides, at least 25 nucleotides or at least 50 nucleotides.

The polynucleotides of the invention can be DNA or RNA or chimeric mixtures or derivatives or modified versions thereof, single-stranded or double-stranded. The oligonucleotide can be modified at the base moiety, sugar moiety, or phosphate backbone, for example, to improve stability of the molecule, hybridization, etc. The oligonucleotide may include other appended groups such as peptides (e.g., for targeting host cell receptors in vivo), or agents facilitating transport across the cell membrane (see, e.g., Letsinger et al., 1989, Proc. Natl. Acad. Sci. U.S.A. 86:6553-6556; Lemaitre et al., 1987, Proc. Natl. Acad. Sci. 84:648-652; PCT Publication No. WO88/09810, published Dec. 15, 1988) or the blood-brain barrier (see, e.g., PCT Publication No. WO89/10134, published Apr. 25, 1988), hybridization-triggered cleavage agents. (See, e.g., Krol et al., 1988, BioTechniques 6:958-976) or intercalating agents. (See, e.g., Zon, 1988, Pharm. Res. 5:539-549). To this end, the oligonucleotide may be conjugated to another molecule, e.g., a peptide, hybridization triggered cross-linking agent, transport agent, hybridization-triggered cleavage agent, etc.

The antisense oligonucleotide may comprise at least one modified base moiety which is selected from the group including, but not limited to, 5-fluorouracil, 5-bromouracil, 5-chlorouracil, 5-iodouracil, hypoxanthine, xantine, 4-acetylcytosine, 5-(carboxyhydroxylmethyl) uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl) uracil, (acp3)w, and 2,6-diaminopurine.

The antisense oligonucleotide may also comprise at least one modified sugar moiety selected from the group including, but not limited to, arabinose, 2-fluoroarabinose, xylulose, and hexose.

In yet another embodiment, the antisense oligonucleotide comprises at least one modified phosphate backbone selected from the group including, but not limited to, a phosphorothioate, a phosphorodithioate, a phosphoramidothioate, a phosphoramidate, a phosphordiamidate, a methylphosphonate, an alkyl phosphotriester, and a formacetal or analog thereof.

In yet another embodiment, the antisense oligonucleotide is an a-anomeric oligonucleotide. An a-anomeric oligonucleotide forms specific double-stranded hybrids with complementary RNA in which, contrary to the usual b-units, the strands run parallel to each other (Gautier et al., 1987, Nucl. Acids Res. 15:6625-6641). The oligonucleotide is a 2'-0-methylribonucleotide (Inoue et al., 1987, Nucl. Acids Res. 15:6131-6148), or a chimeric RNA-DNA analogue (Inoue et al., 1987, FEBS Lett. 215:327-330).

Polynucleotides of the invention may be synthesized by standard methods known in the art, e.g. by use of an automated DNA synthesizer (such as are commercially available from Biosearch, Applied Biosystems, etc.). As examples, phosphorothioate oligonucleotides may be synthesized by the method of Stein et al. (1988, Nucl. Acids Res. 16:3209), methylphosphonate oligonucleotides can be prepared by use of controlled pore glass polymer supports (Sarin et al., 1988, Proc. Natl. Acad. Sci. U.S.A. 85:7448-7451), etc.

While antisense nucleotides complementary to the coding region sequence could be used, those complementary to the transcribed untranslated region are most preferred.

Potential antagonists according to the invention also include catalytic RNA, or a ribozyme (See, e.g., PCT International Publication WO 90/11364, published Oct. 4, 1990; Sarver et al, Science 247:1222-1225 (1990). While ribozymes that cleave mRNA at site specific recognition sequences can be used to destroy mRNAs, the use of hammerhead ribozymes is preferred. Hammerhead ribozymes cleave mRNAs at locations dictated by flanking regions that form complementary base pairs with the target mRNA. The sole requirement is that the target mRNA have the following sequence of two bases: 5'-UG-3'. The construction and production of hammerhead ribozymes is well known in the art and is described more fully in Haseloff and Gerlach, Nature 334:585-591 (1988). There are numerous potential hammerhead ribozyme cleavage sites within the nucleotide sequence of SEQ ID NO:1 and SEQ ID NO:3. Preferably, the ribozyme is engineered so that the cleavage recognition site is located near the 5' end of the mRNA; i.e., to increase efficiency and minimize the intracellular accumulation of non-functional mRNA transcripts.

As in the antisense approach, the ribozymes of the invention can be composed of modified oligonucleotides (e.g., for improved stability, targeting, etc.) and should be delivered to cells which express in vivo. DNA constructs encoding the ribozyme may be introduced into the cell in the same manner as described above for the introduction of antisense encoding DNA. A preferred method of delivery involves using a DNA construct "encoding" the ribozyme under the control of a strong constitutive promoter, such as, for example, pol III or pol II promoter, so that transfected cells will produce sufficient quantities of the ribozyme to destroy endogenous messages and inhibit translation. Since ribozymes unlike antisense molecules, are catalytic, a lower intracellular concentration is required for efficiency.

Antagonist/agonist compounds may be employed to inhibit the cell growth and proliferation effects of the polypeptides of the present invention on neoplastic cells and tissues, i.e. stimulation of angiogenesis of tumors, and, therefore, retard or prevent abnormal cellular growth and proliferation, for example, in tumor formation or growth.

The antagonist/agonist may also be employed to prevent hyper-vascular diseases, and prevent the proliferation of epithelial lens cells after extracapsular cataract surgery. Prevention of the mitogenic activity of the polypeptides of the present invention may also be desirous in cases such as restenosis after balloon angioplasty.

The antagonist/agonist may also be employed to prevent the growth of scar tissue during wound healing.

The antagonist/agonist may also be employed to treat the diseases described herein.

Thus, the invention provides a method of treating disorders or diseases, including but not limited to the disorders or diseases listed throughout this application, associated with overexpression of a polynucleotide of the present invention by administering to a patient (a) an antisense molecule directed to the polynucleotide of the present invention, and/or (b) a ribozyme directed to the polynucleotide of the present invention.

Binding Peptides and Other Molecules

The invention also encompasses screening methods for identifying polypeptides and nonpolypeptides that bind polypeptides of the invention, and the binding molecules identified thereby. These binding molecules are useful, for example, as agonists and antagonists of the polypeptides of the invention. Such agonists and antagonists can be used, in accordance with the invention, in the therapeutic embodiments described in detail, below.

This method comprises the steps of:

(a) contacting polypeptides of the invention with a plurality of molecules; and (b) identifying a molecule that binds the polypeptides of the invention.

The step of contacting the polypeptides of the invention with the plurality of molecules may be effected in a number of ways. For example, one may contemplate immobilizing the polypeptides on a solid support and bringing a solution of the plurality of molecules in contact with the immobilized polypeptides. Such a procedure would be akin to an affinity chromatographic process, with the affinity matrix being comprised of the immobilized polypeptides of the invention. The molecules having a selective affinity for the polypeptides can then be purified by affinity selection. The nature of the solid support, process for attachment of the polypeptides to the solid support, solvent, and conditions of the affinity isolation or selection are largely conventional and well known to those of ordinary skill in the art.

Alternatively, one may also separate a plurality of polypeptides into substantially separate fractions comprising a subset of or individual polypeptides. For instance, one can separate the plurality of polypeptides by gel electrophoresis, column chromatography, or like method known to those of ordinary skill for the separation of polypeptides. The individual polypeptides can also be produced by a transformed host cell in such a way as to be expressed on or about its outer surface (e.g., a recombinant phage). Individual isolates can then be "probed" by the polypeptides of the invention, optionally in the presence of an inducer should one be required for expression, to determine if any selective affinity interaction takes place between the polypeptides and the individual clone. Prior to contacting the polypeptides with each fraction comprising individual polypeptides, the polypeptides could first be transferred to a solid support for additional convenience. Such a solid support may simply be a piece of filter membrane, such as one made of nitrocellulose or nylon. In this manner, positive clones could be identified from a collection of transformed host cells of an expression library, which harbor a DNA construct encoding a polypeptide having a selective affinity for polypeptides of the invention. Furthermore, the amino acid sequence of the polypeptide having a selective affinity for the polypeptides of the invention can be determined directly by conventional means or the coding sequence of the DNA encoding the polypeptide can frequently be determined more conveniently. The primary sequence can then be deduced from the corresponding DNA sequence. If the amino acid sequence is to be determined from the polypeptide itself, one may use microsequencing techniques. The sequencing technique may include mass spectroscopy.

In certain situations, it may be desirable to wash away any unbound polypeptides from a mixture of the polypeptides of the invention and the plurality of polypeptides prior to attempting to determine or to detect the presence of a selective affinity interaction. Such a wash step may be particularly desirable when the polypeptides of the invention or the plurality of polypeptides are bound to a solid support.

The plurality of molecules provided according to this method may be provided by way of diversity libraries, such as random or combinatorial peptide or nonpeptide libraries which can be screened for molecules that specifically bind polypeptides of the invention. Many libraries are known in the art that can be used, e.g., chemically synthesized libraries, recombinant (e.g., phage display libraries), and in vitro translation-based libraries. Examples of chemically synthesized libraries are described in Fodor et al., 1991, Science 251:767-773; Houghten et al., 1991, Nature 354:84-86; Lam et al., 1991, Nature 354:82-84; Medynski, 1994, Bio/Technology 12:709-710;Gallop et al., 1994, J. Medicinal Chemistry 37(9):1233-1251; Ohlmeyer et al., 1993, Proc. Natl. Acad. Sci. USA 90:10922-10926; Erb et al., 1994, Proc. Natl. Acad. Sci. USA 91:11422-11426; Houghten et al., 1992, Biotechniques 13:412; Jayawickreme et al., 1994, Proc. Natl. Acad. Sci. USA 91:1614-1618; Salmon et al., 1993, Proc. Natl. Acad. Sci. USA 90:11708-11712; PCT Publication No. WO 93/20242; and Brenner and Lerner, 1992, Proc. Natl. Acad. Sci. USA 89:5381-5383.

Examples of phage display libraries are described in Scott and Smith, 1990, Science 249:386-390; Devlin et al., 1990, Science, 249:404-406; Christian, R. B., et al., 1992, J. Mol. Biol. 227:711-718); Lenstra, 1992, J. Immunol. Meth. 152: 149-157; Kay et al., 1993, Gene 128:59-65; and PCT Publication No. WO 94/18318 dated Aug. 18, 1994.

In vitro translation-based libraries include but are not limited to those described in PCT Publication No. WO 91/05058 dated Apr. 18, 1991; and Mattheakis et al., 1994, Proc. Natl. Acad. Sci. USA 91:9022-9026.

By way of examples of nonpeptide libraries, a benzodiazepine library (see e.g., Bunin et al., 1994, Proc. Natl. Acad. Sci. USA 91:4708-4712) can be adapted for use. Peptoid libraries (Simon et al., 1992, Proc. Natl. Acad. Sci. USA 89:9367-9371) can also be used. Another example of a library that can be used, in which the amide functionalities in peptides have been permethylated to generate a chemically transformed combinatorial library, is described by Ostresh et al. (1994, Proc. Natl. Acad. Sci. USA 91:11138-11142).

The variety of non-peptide libraries that are useful in the present invention is great. For example, Ecker and Crooke, 1995, Bio/Technology 13:351-360 list benzodiazepines, hydantoins, piperazinediones, biphenyls, sugar analogs, beta-mercaptoketones, arylacetic acids, acylpiperidines, benzopyrans, cubanes, xanthines, aminimides, and oxazolones as among the chemical species that form the basis of various libraries.

Non-peptide libraries can be classified broadly into two types: decorated monomers and oligomers. Decorated monomer libraries employ a relatively simple scaffold structure upon which a variety functional groups is added. Often the scaffold will be a molecule with a known useful pharmacological activity. For example, the scaffold might be the benzodiazepine structure.

Non-peptide oligomer libraries utilize a large number of monomers that are assembled together in ways that create new shapes that depend on the order of the monomers. Among the monomer units that have been used are carbamates, pyrrolinones, and morpholinos. Peptoids, peptide-like oligomers in which the side chain is attached to the alpha amino group rather than the alpha carbon, form the basis of another version of non-peptide oligomer libraries. The first non-peptide oligomer libraries utilized a single type of monomer and thus contained a repeating backbone. Recent libraries have utilized more than one monomer, giving the libraries added flexibility.

Screening the libraries can be accomplished by any of a variety of commonly known methods. See, e.g., the following references, which disclose screening of peptide libraries: Parmley and Smith, 1989, Adv. Exp. Med. Biol. 251:215-218; Scott and Smith, 1990, Science 249:386-390; Fowlkes et al., 1992; BioTechniques 13:422-427; Oldenburg et al., 1992, Proc. Natl. Acad. Sci. USA 89:5393-5397; Yu et al., 1994, Cell 76:933-945; Staudt et al., 1988, Science 241:577-580; Bock et al., 1992, Nature 355:564-566; Tuerk et al., 1992, Proc. Natl. Acad. Sci. USA 89:6988-6992; Ellington et al., 1992, Nature 355:850-852; U.S. Pat. No. 5,096,815, U.S. Pat. No. 5,223,409, and U.S. Pat. No. 5,198,346, all to Ladner et al.; Rebar and Pabo, 1993, Science 263:671-673; and CT Publication No. WO 94/18318.

In a specific embodiment, screening to identify a molecule that binds polypeptides of the invention can be carried out by contacting the library members with polypeptides of the invention immobilized on a solid phase and harvesting those library members that bind to the polypeptides of the invention. Examples of such screening methods, termed "panning" techniques are described by way of example in Parmley and Smith, 1988, Gene 73:305-318; Fowlkes et al., 1992, BioTechniques 13:422-427; PCT Publication No. WO 94/18318; and in references cited herein.

In another embodiment, the two-hybrid system for selecting interacting proteins in yeast (Fields and Song, 1989, Nature 340:245-246; Chien et al., 1991, Proc. Natl. Acad. Sci. USA 88:9578-9582) can be used to identify molecules that specifically bind to polypeptides of the invention.

Where the binding molecule is a polypeptide, the polypeptide can be conveniently selected from any peptide library, including random peptide libraries, combinatorial peptide libraries, or biased peptide libraries. The term "biased" is used herein to mean that the method of generating the library is manipulated so as to restrict one or more parameters that govern the diversity of the resulting collection of molecules, in this case peptides.

Thus, a truly random peptide library would generate a collection of peptides in which the probability of finding a particular amino acid at a given position of the peptide is the same for all 20 amino acids. A bias can be introduced into the library, however, by specifying, for example, that a lysine occur every fifth amino acid or that positions 4, 8, and 9 of a decapeptide library be fixed to include only arginine. Clearly, many types of biases can be contemplated, and the present invention is not restricted to any particular bias. Furthermore, the present invention contemplates specific types of peptide libraries, such as phage displayed peptide libraries and those that utilize a DNA construct comprising a lambda phage vector with a DNA insert.

As mentioned above, in the case of a binding molecule that is a polypeptide, the polypeptide may have about 6 to less than about 60 amino acid residues, preferably about 6 to about 10 amino acid residues, and most preferably, about 6 to about 22 amino acids. In another embodiment, a binding polypeptide has in the range of 15-100 amino acids, or 20-50 amino acids.

The selected binding polypeptide can be obtained by chemical synthesis or recombinant expression.

Anti-Angiogenesis Activity

The naturally occurring balance between endogenous stimulators and inhibitors of angiogenesis is one in which inhibitory influences predominate. Rastinejad et al., *Cell* 56:345-355 (1989). In those rare instances in which neovascularization occurs under normal physiological conditions, such as wound healing, organ regeneration, embryonic development, and female reproductive processes, angiogenesis is stringently regulated and spatially and temporally delimited. Under conditions of pathological angiogenesis such as that characterizing solid tumor growth, these regulatory controls fail. Unregulated angiogenesis becomes pathologic and sustains progression of many neoplastic and non-neoplastic diseases. A number of serious diseases are dominated by abnormal neovascularization including solid tumor growth and metastases, arthritis, some types of eye disorders, and psoriasis. See, e.g., reviews by Moses et al., *Biotech.* 9:630-634 (1991); Folkman et al., *N. Engl. J. Med.,* 333:1757-1763 (1995); Auerbach et al., *J. Microvasc. Res.* 29:401-411 (1985); Folkman, Advances in Cancer Research, eds. Klein and Weinhouse, Academic Press, New York, pp. 175-203 (1985); Patz, *Am. J. Opthalmol.* 94:715-743 (1982); and Folkman et al., Science 221:719-725 (1983). In a number of pathological conditions, the process of angiogenesis contributes to the disease state. For example, significant data have accumulated which suggest that the growth of solid tumors is dependent on angiogenesis. Folkman and Klagsbrun, *Science* 235:442-447 (1987).

The present invention provides for treatment of diseases or disorders associated with neovascularization by administration of the polynucleotides and/or polypeptides of the invention, as well as agonists or antagonists of the present invention. Malignant and metastatic conditions which can be treated with the polynucleotides and polypeptides, or agonists or antagonists of the invention include, but are not limited to, malignancies, solid tumors, and cancers described herein and otherwise known in the art (for a review of such disorders, see Fishman et al., Medicine, 2d Ed., J. B. Lippincott Co., Philadelphia (1985)).Thus, the present invention provides a method of treating an angiogenesis-related disease and/or disorder, comprising administering to an individual in need thereof a therapeutically effective amount of a polynucleotide, polypeptide, antagonist and/or agonist of the invention. For example, polynucleotides, polypeptides, antagonists and/or agonists may be utilized in a variety of additional methods in order to therapeutically treat a cancer or tumor. Cancers which may be treated with polynucleotides, polypeptides, antagonists and/or agonists include, but are not limited to solid tumors, including prostate, lung, breast, ovarian, stomach, pancreas, larynx, esophagus, testes, liver, parotid, biliary tract, colon, rectum, cervix, uterus, endometrium, kidney, bladder, thyroid cancer; primary tumors and metastases; melanomas; glioblastoma; Kaposi's sarcoma; leiomyosarcoma; non-small cell lung cancer; colorectal cancer; advanced malignancies; and blood born tumors such as leukemias. For example, polynucleotides, polypeptides, antagonists and/or agonists may be delivered topically, in order to treat cancers such as skin cancer, head and neck tumors, breast tumors, and Kaposi's sarcoma.

Within yet other aspects, polynucleotides, polypeptides, antagonists and/or agonists may be utilized to treat superficial forms of bladder cancer by, for example, intravesical administration. Polynucleotides, polypeptides, antagonists and/or agonists may be delivered directly into the tumor, or near the tumor site, via injection or a catheter. Of course, as the artisan of ordinary skill will appreciate, the appropriate mode of administration will vary according to the cancer to be treated. Other modes of delivery are discussed herein.

Polynucleotides, polypeptides, antagonists and/or agonists may be useful in treating other disorders, besides cancers, which involve angiogenesis. These disorders include, but are not limited to: benign tumors, for example hemangiomas, acoustic neuromas, neurofibromas, trachomas, and pyogenic granulomas; artheroscleric plaques; ocular angiogenic diseases, for example, diabetic retinopathy, retinopathy of prematurity, macular degeneration, corneal graft rejection, neovascular glaucoma, retrolental fibroplasia, rubeosis, retinoblastoma, uvietis and Pterygia (abnormal blood vessel growth) of the eye; rheumatoid arthritis; psoriasis; delayed wound healing; endometriosis; vasculogenesis; granulations; hypertrophic scars (keloids); nonunion fractures; scleroderma; trachoma; vascular adhesions; myocardial angiogenesis; coronary collaterals; cerebral collaterals; arteriovenous malformations; ischemic limb angiogenesis; Osler-Webber Syndrome; plaque neovascularization; telangiectasia; hemophiliac joints; angiofibroma; fibromuscular dysplasia; wound granulation; Crohn's disease; and atherosclerosis.

For example, within one aspect of the present invention methods are provided for treating hypertrophic scars and keloids, comprising the step of administering a polynucleotide, polypeptide, antagonist and/or agonist of the invention to a hypertrophic scar or keloid.

Within one embodiment of the present invention polynucleotides, polypeptides, antagonists and/or agonists of the invention are directly injected into a hypertrophic scar or keloid, in order to prevent the progression of these lesions. This therapy is of particular value in the prophylactic treatment of conditions which are known to result in the development of hypertrophic scars and keloids (e.g., burns), and is preferably initiated after the proliferative phase has had time to progress (approximately 14 days after the initial injury), but before hypertrophic scar or keloid development. As noted above, the present invention also provides methods for treating neovascular diseases of the eye, indluding for example, corneal neovascularization, neovascular glaucoma, proliferative diabetic retinopathy, retrolental fibroplasia and macular degeneration.

Moreover, Ocular disorders associated with neovascularization which can be treated with the polynucleotides and polypeptides of the present invention (including agonists and/or antagonists) include, but are not limited to: neovascular glaucoma, diabetic retinopathy, retinoblastoma, retrolental fibroplasia, uveitis, retinopathy of prematurity macular degeneration, corneal graft neovascularization, as well as other eye inflammatory diseases, ocular tumors and diseases associated with choroidal or iris neovascularization. See, e.g., reviews by Waltman et al., *Am. J. Ophthal.* 85:704-710 (1978) and Gartner et al., *Surv. Ophthal.* 22:291-312 (1978).

Thus, within one aspect of the present invention methods are provided for treating neovascular diseases of the eye such as corneal neovascularization (including corneal graft neovascularization), comprising the step of administering to a patient a therapeutically effective amount of a compound (as described above) to the cornea, such that the formation of blood vessels is inhibited. Briefly, the cornea is a tissue which normally lacks blood vessels. In certain pathological conditions however, capillaries may extend into the cornea from the pericorneal vascular plexus of the limbus. When the cornea becomes vascularized, it also becomes clouded, resulting in a decline in the patient's visual acuity. Visual loss may become complete if the cornea completely opacitates. A wide variety of disorders can result in corneal neovascularization, including for example, corneal infections (e.g., trachoma, herpes simplex keratitis, leishmaniasis and onchocerciasis), immunological processes (e.g., graft rejection and Stevens-Johnson's syndrome), alkali burns, trauma, inflammation (of any cause), toxic and nutritional deficiency states, and as a complication of wearing contact lenses.

Within particularly preferred embodiments of the invention, may be prepared for topical administration in saline (combined with any of the preservatives and antimicrobial agents commonly used in ocular preparations), and administered in eyedrop form. The solution or suspension may be prepared in its pure form and administered several times daily. Alternatively, anti-angiogenic compositions, prepared as described above, may also be administered directly to the cornea. Within preferred embodiments, the anti-angiogenic composition is prepared with a muco-adhesive polymer which binds to cornea. Within further embodiments, the anti-angiogenic factors or anti-angiogenic compositions may be utilized as an adjunct to conventional steroid therapy. Topical therapy may also be useful prophylactically in corneal lesions which are known to have a high probability of inducing an angiogenic response (such as chemical burns). In these instances the treatment, likely in combination with steroids, may be instituted immediately to help prevent subsequent complications.

Within other embodiments, the compounds described above may be injected directly into the corneal stroma by an ophthalmologist under microscopic guidance. The preferred site of injection may vary with the morphology of the individual lesion, but the goal of the administration would be to place the composition at the advancing front of the vasculature (i.e., interspersed between the blood vessels and the normal cornea). In most cases this would involve perilimbic corneal injection to "protect" the cornea from the advancing blood vessels. This method may also be utilized shortly after a corneal insult in order to prophylactically prevent corneal neovascularization. In this situation the material could be injected in the perilimbic cornea interspersed between the corneal lesion and its undesired potential limbic blood supply. Such methods may also be utilized in a similar fashion to prevent capillary invasion of transplanted corneas. In a sustained-release form injections might only be required 2-3 times per year. A steroid could also be added to the injection solution to reduce inflammation resulting from the injection itself.

Within another aspect of the present invention, methods are provided for treating neovascular glaucoma, comprising the step of administering to a patient a therapeutically effective amount of a polynucleotide, polypeptide, antagonist and/or agonist to the eye, such that the formation of blood vessels is inhibited. In one embodiment, the compound may be administered topically to the eye in order to treat early forms of neovascular glaucoma. Within other embodiments, the compound may be implanted by injection into the region of the anterior chamber angle. Within other embodiments, the compound may also be placed in any location such that the compound is continuously released into the aqueous humor. Within another aspect of the present invention, methods are provided for treating proliferative diabetic retinopathy, comprising the step of administering to a patient a therapeutically effective amount of a polynucleotide, polypeptide, antagonist and/or agonist to the eyes, such that the formation of blood vessels is inhibited.

Within particularly preferred embodiments of the invention, proliferative diabetic retinopathy may be treated by injection into the aqueous humor or the vitreous, in order to increase the local concentration of the polynucleotide, polypeptide, antagonist and/or agonist in the retina. Preferably, this treatment should be initiated prior to the acquisition of severe disease requiring photocoagulation.

Within another aspect of the present invention, methods are provided for treating retrolental fibroplasia, comprising the step of administering to a patient a therapeutically effective amount of a polynucleotide, polypeptide, antagonist and/or agonist to the eye, such that the formation of blood vessels is inhibited. The compound may be administered topically, via intravitreous injection and/or via intraocular implants.

Additionally, disorders which can be treated with the polynucleotides, polypeptides, agonists and/or agonists include, but are not limited to, hemangioma, arthritis, psoriasis, angiofibroma, atherosclerotic plaques, delayed wound healing, granulations, hemophilic joints, hypertrophic scars, nonunion fractures, Osler-Weber syndrome, pyogenic granuloma, scleroderma, trachoma, and vascular adhesions.

Moreover, disorders and/or states, which can be treated-prevented, diagnosed, and/or prognosed with the polynucleotides, polypeptides, agonists and/or agonists of the invention include, but are not limited to, solid tumors, blood born tumors such as leukemias, tumor metastasis, Kaposi's sarcoma, benign tumors, for example hemangiomas, acoustic neuromas, neurofibromas, trachomas, and pyogenic granulomas, rheumatoid arthritis, psoriasis, ocular angiogenic diseases, for example, diabetic retinopathy, retinopathy of prematurity, macular degeneration, corneal graft rejection, neovascular glaucoma, retrolental fibroplasia, rubeosis, retinoblastoma, and uveitis, delayed wound healing, endometriosis, vascluogenesis, granulations, hypertrophic scars (keloids), nonunion fractures, scleroderma, trachoma, vascular adhesions, myocardial angiogenesis, coronary collaterals, cerebral collaterals, arteriovenous malformations, ischemic limb angiogenesis, Osler-Webber Syndrome, plaque neovascularization, telangiectasia, hemophiliac joints, angiofibroma fibromuscular dysplasia, wound granulation, Crohn's disease, atherosclerosis, birth control agent by preventing vascularization required for embryo implantation controlling menstruation, diseases that have angiogenesis as a pathologic consequence such as cat scratch disease (Rochele minalia quintosa), ulcers (Helicobacter pylori), Bartonellosis and bacillary angiomatosis.

In one aspect of the birth control method, an amount of the compound sufficient to block embryo implantation is administered before or after intercourse and fertilization have occurred, thus providing an effective method of birth control, possibly a "morning after" method. Polynucleotides, polypeptides, agonists and/or agonists may also be used in controlling menstruation or administered as either a peritoneal lavage fluid or for peritoneal implantation in the treatment of endometriosis.

Polynucleotides, polypeptides, agonists and/or agonists of the present invention may be incorporated into surgical sutures in order to prevent stitch granulomas.

Polynucleotides, polypeptides, agonists and/or agonists may be utilized in a wide variety of surgical procedures. For example, within one aspect of the present invention a compositions (in the form of, for example, a spray or film) may be utilized to coat or spray an area prior to removal of a tumor, in order to isolate normal surrounding tissues from malignant tissue, and/or to prevent the spread of disease to surrounding tissues. Within other aspects of the present invention, compositions (e.g., in the form of a spray) may be delivered via endoscopic procedures in order to coat tumors, or inhibit angiogenesis in a desired locale. Within yet other aspects of the present invention, surgical meshes which have been coated with anti-angiogenic compositions of the present invention may be utilized in any procedure wherein a surgical mesh might be utilized. For example, within one embodiment of the invention a surgical mesh laden with an anti-angiogenic composition may be utilized during abdominal cancer resection surgery (e.g., subsequent to colon resection) in order to provide support to the structure, and to release an amount of the anti-angiogenic factor.

Within further aspects of the present invention, methods are provided for treating tumor excision sites, comprising administering a polynucleotide, polypeptide, agonist and/or agonist to the resection margins of a tumor subsequent to excision, such that the local recurrence of cancer and the formation of new blood vessels at the site is inhibited. Within one embodiment of the invention, the anti-angiogenic compound is administered directly to the tumor excision site (e.g., applied by swabbing, brushing or otherwise coating the resection margins of the tumor with the anti-angiogenic compound). Alternatively, the anti-angiogenic compounds may be incorporated into known surgical pastes prior to administration. Within particularly preferred embodiments of the invention, the anti-angiogenic compounds are applied after hepatic resections for malignancy, and after neurosurgical operations.

Within one aspect of the present invention, polynucleotides, polypeptides, agonists and/or agonists may be administered to the resection margin of a wide variety of tumors, including for example, breast, colon, brain and hepatic tumors. For example, within one embodiment of the invention, anti-angiogenic compounds may be administered to the site of a neurological tumor subsequent to excision, such that the formation of new blood vessels at the site are inhibited.

The polynucleotides, polypeptides, agonists and/or agonists of the present invention may also be administered along with other anti-angiogenic factors. Representative examples of other anti-angiogenic factors include: Anti-Invasive Factor, retinoic acid and derivatives thereof, paclitaxel, Suramin, Tissue Inhibitor of Metalloproteinase-1, Tissue Inhibitor of Metalloproteinase-2, Plasminogen Activator Inhibitor-1, Plasminogen Activator Inhibitor-2, and various forms of the lighter "d group" transition metals.

Lighter "d group" transition metals include, for example, vanadium, molybdenum, tungsten, titanium, niobium, and tantalum species. Such transition metal species may form transition metal complexes. Suitable complexes of the above-mentioned transition metal species include oxo transition metal complexes.

Representative examples of vanadium complexes include oxo vanadium complexes such as vanadate and vanadyl complexes. Suitable vanadate complexes include metavanadate and orthovanadate complexes such as, for example, ammonium metavanadate, sodium metavanadate, and sodium orthovanadate. Suitable vanadyl complexes include, for example, vanadyl acetylacetonate and vanadyl sulfate including vanadyl sulfate hydrates such as vanadyl sulfate mono- and trihydrates.

Representative examples of tungsten and molybdenum complexes also include oxo complexes. Suitable oxo tungsten complexes include tungstate and tungsten oxide complexes. Suitable tungstate complexes include ammonium tungstate, calcium tungstate, sodium tungstate dihydrate, and tungstic acid. Suitable tungsten oxides include tungsten (IV) oxide and tungsten (VI) oxide. Suitable oxo molybdenum complexes include molybdate, molybdenum oxide, and molybdenyl complexes. Suitable molybdate complexes include ammonium molybdate and its hydrates, sodium molybdate and its hydrates, and potassium molybdate and its hydrates. Suitable molybdenum oxides include molybdenum (VI) oxide, molybdenum (VI) oxide, and molybdic acid. Suitable molybdenyl complexes include, for example, molybdenyl acetylacetonate. Other suitable tungsten and molybdenum complexes include hydroxo derivatives derived from, for example, glycerol, tartaric acid, and sugars.

A wide variety of other anti-angiogenic factors may also be utilized within the context of the present invention. Representative examples include platelet factor 4; protamine sulphate; sulphated chitin derivatives (prepared from queen crab shells), (Murata et al., Cancer Res. 51:22-26, 1991); Sulphated Polysaccharide Peptidoglycan Complex (SP-PG) (the function of this compound may be enhanced by the presence of steroids such as estrogen, and tamoxifen citrate); Staurosporine; modulators of matrix metabolism, including for example, proline analogs, cishydroxyproline, d,L-3,4-dehydroproline, Thiaproline, alpha,alpha-dipyridyl, aminopropionitrile fumarate; 4-propyl-5-(4-pyridinyl)-2(3H)-oxazolone; Methotrexate; Mitoxantrone; Heparin; Interferons; 2 Macroglobulin-serum; ChIMP-3 (Pavloff et al., J. Bio. Chem. 267:17321-17326, 1992); Chymostatin (Tomkinson et al., Biochem J. 286:475-480, 1992); Cyclodextrin Tetradecasulfate; Eponemycin; Camptothecin; Fumagillin (Ingber et al., Nature 348:555-557, 1990); Gold Sodium Thiomalate ("GST"; Matsubara and Ziff, J. Clin. Invest. 79:1440-1446, 1987); anticollagenase-serum; alpha2-antiplasmin (Holmes et al., J. Biol. Chem. 262(4):1659-1664, 1987); Bisantrene (National Cancer Institute); Lobenzarit disodium (N-(2)-carboxyphenyl-4-chloroanthronilic acid disodium or "CCA"; Takeuchi et al., Agents Actions 36:312-316, 1992); Thalidomide; Angostatic steroid; AGM-1470; carboxynaminolmidazole; and metalloproteinase inhibitors such as BB94.

Wound Healing and Epithelial Cell Proliferation

In accordance with yet a further aspect of the present invention, there is provided a process for utilizing polynucleotides or polypeptides, as well as agonists or antagonists of the present invention, for therapeutic purposes, for example, to stimulate epithelial cell proliferation and basal keratinocytes for the purpose of wound healing, and to stimulate hair follicle production and healing of dermal wounds. Polynucleotides or polypeptides, as well as agonists or antagonists of the present invention, may be clinically useful in stimulating wound healing including surgical wounds, excisional wounds, deep wounds involving damage of the dermis and epidermis, eye tissue wounds, dental tissue wounds, oral cavity wounds, diabetic ulcers, dermal ulcers, cubitus ulcers, arterial ulcers, venous stasis ulcers, burns resulting from heat exposure or chemicals, and other abnormal wound healing conditions such as uremia, malnutrition, vitamin deficiencies and complications associated with systemic treatment with steroids, radiation therapy and antineoplastic drugs and antimetabolites. Polynucleotides or polypeptides, as well as agonists or antagonists of the present invention, could be used to promote dermal reestablishment subsequent to dermal loss.

Polynucleotides or polypeptides, as well as agonists or antagonists of the present invention, could be used to increase the adherence of skin grafts to a wound bed and to stimulate re-epithelialization from the wound bed. The following are types of grafts that polynucleotides or polypeptides, agonists or antagonists of the present invention, could be used to increase adherence to a wound bed: autografts, artificial skin, allografts, autodermic graft, autoepdermic grafts, avacular grafts, Blair-Brown grafts, bone graft, brephoplastic grafts, cutis graft, delayed graft, dermic graft, epidermic graft, fascia graft, full thickness graft, heterologous graft, xenograft, homologous graft, hyperplastic graft, lamellar graft, mesh graft, mucosal graft, Ollier-Thiersch graft, omenpal graft, patch graft, pedicle graft, penetrating graft, split skin graft, thick split graft. Polynucleotides or polypeptides, as well as agonists or antagonists of the present invention, can be used to promote skin strength and to improve the appearance of aged skin.

It is believed that polynucleotides or polypeptides, as well as agonists or antagonists of the present invention, will also produce changes in hepatocyte proliferation, and epithelial cell proliferation in the lung, breast, pancreas, stomach, small intestine, and large intestine. Polynucleotides or polypeptides, as well as agonists or antagonists of the present invention, could promote proliferation of epithelial cells such as sebocytes, hair follicles, hepatocytes, type II pneumocytes, mucin-producing goblet cells, and other epithelial cells and their progenitors contained within the skin, lung, liver, and gastrointestinal tract. Polynucleotides or polypeptides, agonists or antagonists of the present invention, may promote proliferation of endothelial cells, keratinocytes, and basal keratinocytes.

Polynucleotides or polypeptides, as well as agonists or antagonists of the present invention, could also be used to reduce the side effects of gut toxicity that result from radiation, chemotherapy treatments or viral infections. Polynucleotides or polypeptides, as well as agonists or antagonists of the present invention, may have a cytoprotective effect on the small intestine mucosa. Polynucleotides or polypeptides, as well as agonists or antagonists of the present invention, may also stimulate healing of mucositis (mouth ulcers) that result from chemotherapy and viral infections.

Polynucleotides or polypeptides, as well as agonists or antagonists of the present invention, could further be used in full regeneration of skin in full and partial thickness skin defects, including burns, (i.e., repopulation of hair follicles, sweat glands, and sebaceous glands), treatment of other skin defects such as psoriasis. Polynucleotides or polypeptides, as well as agonists or antagonists of the present invention, could be used to treat epidermolysis bullosa, a defect in adherence of the epidermis to the underlying dermis which results in frequent, open and painful blisters by accelerating reepithelialization of these lesions. Polynucleotides or polypeptides, as well as agonists or antagonists of the present invention, could also be used to treat gastric and doudenal ulcers and help heal by scar formation of the mucosal lining and regeneration of glandular mucosa and duodenal mucosal lining more rapidly. Inflammatory bowel diseases, such as Crohn's disease and ulcerative colitis, are diseases which result in destruction of the mucosal surface of the small or large intestine, respectively. Thus, polynucleotides or polypeptides, as well as agonists or antagonists of the present invention, could be used to promote the resurfacing of the mucosal surface to aid more rapid healing and to prevent progression of inflammatory bowel disease. Treatment with polynucleotides or polypeptides, agonists or antagonists of the present invention, is expected to have a significant effect on the production of mucus throughout the gastrointestinal tract and could be used to protect the intestinal mucosa from injurious substances that are ingested or following surgery. Polynucleotides or polypeptides, as well as agonists or antagonists of the present invention, could be used to treat diseases associate with the under expression.

Moreover, polynucleotides or polypeptides, as well as agonists or antagonists of the present invention, could be used to prevent and heal damage to the lungs due to various pathological states. Polynucleotides or polypeptides, as well as agonists or antagonists of the present invention, which could stimulate proliferation and differentiation and promote the repair of alveoli and brochiolar epithelium to prevent or treat acute or chronic lung damage. For example, emphysema, which results in the progressive loss of aveoli, and inhalation injuries, i.e., resulting from smoke inhalation and burns, that cause necrosis of the bronchiolar epithelium and alveoli could be effectively treated using polynucleotides or polypeptides, agonists or antagonists of the present invention. Also, polynucleotides or polypeptides, as well as agonists or antagonists of the present invention, could be used to stimulate the proliferation of and differentiation of type II pneumocytes, which may help treat or prevent disease such as hyaline membrane diseases, such as infant respiratory distress syndrome and bronchopulmonary displasia, in premature infants.

Polynucleotides or polypeptides, as well as agonists or antagonists of the present invention, could stimulate the proliferation and differentiation of hepatocytes and, thus, could be used to alleviate or treat liver diseases and pathologies such as fulminant liver failure caused by cirrhosis, liver damage caused by viral hepatitis and toxic substances (i.e., acetaminophen, carbon tetraholoride and other hepatotoxins known in the art).

In addition, polynucleotides or polypeptides, as well as agonists or antagonists of the present invention, could be used treat or prevent the onset of diabetes mellitus. In patients with newly diagnosed Types I and II diabetes, where some islet cell function remains, polynucleotides or polypeptides, as well as agonists or antagonists of the present invention, could be used to maintain the islet function so as to alleviate, delay or prevent permanent manifestation of the disease. Also, polynucleotides or polypeptides, as well as agonists or antagonists of the present invention, could be used as an auxiliary in islet cell transplantation to improve or promote islet cell function.

Regeneration

Polynucleotides or polypeptides, as well as agonists or antagonists of the present invention can be used to differentiate, proliferate, and attract cells, leading to the regeneration of tissues. (See, Science 276:59-87 (1997)). The regeneration of tissues could be used to repair, replace, or protect tissue damaged by congenital defects, trauma (wounds, burns, incisions, or ulcers), age, disease (e.g. osteoporosis, osteoarthritis, periodontal disease, liver failure), surgery, including cosmetic plastic surgery, fibrosis, reperfusion injury, or systemic cytokine damage.

Tissues that could be regenerated using the present invention include organs (e.g., pancreas, liver, intestine, kidney, skin, endothelium), muscle (smooth, skeletal or cardiac), vasculature (including vascular and lymphatics), nervous, hematopoietic, and skeletal (bone, cartilage, tendon, and ligament) tissue. Preferably, regeneration occurs without or decreased scarring. Regeneration also may include angiogenesis.

Moreover, polynucleotides or polypeptides, as well as agonists or antagonists of the present invention, may increase regeneration of tissues difficult to heal. For example, increased tendon/ligament regeneration would quicken recovery time after damage. Polynucleotides or polypeptides, as well as agonists or antagonists of the present invention could also be used prophylactically in an effort to avoid damage. Specific diseases that could be treated include of tendinitis, carpal tunnel syndrome, and other tendon or ligament defects. A further example of tissue regeneration of non-healing wounds includes pressure ulcers, ulcers associated with vascular insufficiency, surgical, and traumatic wounds.

Similarly, nerve and brain tissue could also be regenerated by using polynucleotides or polypeptides, as well as agonists or antagonists of the present invention, to proliferate and differentiate nerve cells. Diseases that could be treated using this method include central and peripheral nervous system diseases, neuropathies, or mechanical and traumatic disorders (e.g., spinal cord disorders, head trauma, cerebrovascular disease, and stoke). Specifically, diseases associated with peripheral nerve injuries, peripheral neuropathy (e.g., resulting from chemotherapy or other medical therapies), localized neuropathies, and central nervous system diseases (e.g., Alzheimer's disease, Parkinson's disease, Huntington's disease, amyotrophic lateral sclerosis, and Shy-Drager syndrome), could all be treated using the polynucleotides or polypeptides, as well as agonists or antagonists of the present invention.

Gastrointestinal Disorders

Polynucleotides or polypeptides, or agonists or antagonists of the present invention, may be used to treat, prevent, diagnose, and/or prognose gastrointestinal disorders, including inflammatory diseases and/or conditions, infections, cancers (e.g., intestinal neoplasms (carcinoid tumor of the small intestine, non-Hodgkin's lymphoma of the small intestine, small bowel lymphoma)), and ulcers, such as peptic ulcers.

Gastrointestinal disorders include dysphagia, odynophagia, inflammation of the esophagus, peptic esophagitis, gastric reflux, submucosal fibrosis and stricturing, Mallory-Weiss lesions, leiomyomas, lipomas, epidermal cancers, adeoncarcinomas, gastric retention disorders, gastroenteritis, gastric atrophy, gastric/stomach cancers, polyps of the stomach, autoimmune disorders such as pernicious anemia, pyloric stenosis, gastritis (bacterial, viral, eosinophilic, stress-induced, chronic erosive, atrophic, plasma cell, and Menetrier's), and peritoneal diseases (e.g., chyloperioneum, hemoperitoneum, mesenteric cyst, mesenteric lymphadenitis, mesenteric vascular occlusion, panniculitis, neoplasms, peritonitis, pneumoperitoneum, bubphrenic abscess,).

Gastrointestinal disorders also include disorders associated with the small intestine, such as malabsorption syndromes, distension, irritable bowel syndrome, sugar intolerance, celiac disease, duodenal ulcers, duodenitis, tropical sprue, Whipple's disease, intestinal lymphangiectasia, Crohn's disease, appendicitis, obstructions of the ileum, Meckel's diverticulum, multiple diverticula, failure of complete rotation of the small and large intestine, lymphoma, and bacterial and parasitic diseases (such as Traveler's diarrhea, typhoid and paratyphoid, cholera, infection by Roundworms (*Ascariasis lumbricoides*), Hookworms (*Ancylostoma duodenale*), Threadworms (*Enterobius vermicularis*), Tapeworms (*Taenia saginata, Echinococcus granulosus*, Diphyllobothrium spp., and *T. solium*).

Liver diseases and/or disorders include intrahepatic cholestasis (alagille syndrome, biliary liver cirrhosis), fatty liver (alcoholic fatty liver, reye syndrome), hepatic vein thrombosis, hepatolentricular degeneration, hepatomegaly, hepatopulmonary syndrome, hepatorenal syndrome, portal hypertension (esophageal and gastric varices), liver abscess (amebic liver abscess), liver cirrhosis (alcoholic, biliary and experimental), alcoholic liver diseases (fatty liver, hepatitis, cirrhosis), parasitic (hepatic echinococcosis, fascioliasis, amebic liver abscess), jaundice (hemolytic, hepatocellular, and cholestatic), cholestasis, portal hypertension, liver enlargement, ascites, hepatitis (alcoholic hepatitis, animal hepatitis, chronic hepatitis (autoimmune, hepatitis B, hepatitis C, hepatitis D, drug induced), toxic hepatitis, viral human hepatitis (hepatitis A, hepatitis B, hepatitis C, hepatitis D, hepatitis E), Wilson's disease, granulomatous hepatitis, secondary biliary cirrhosis, hepatic encephalopathy, portal hypertension, varices, hepatic encephalopathy, primary biliary cirrhosis, primary sclerosing cholangitis, hepatocellular adenoma, hemangiomas, bile stones, liver failure (hepatic encephalopathy, acute liver failure), and liver neoplasms (angiomyolipoma, calcified liver metastases, cystic liver metastases, epithelial tumors, fibrolamellar hepatocarcinoma, focal nodular hyperplasia, hepatic adenoma, hepatobiliary cystadenoma, hepatoblastoma, hepatocellular carcinoma, hepatoma, liver cancer, liver hemangioendothelioma, mesenchymal hamartoma, mesenchymal tumors of liver, nodular regenerative hyperplasia, benign liver tumors (Hepatic cysts [Simple cysts, Polycystic liver disease, Hepatobiliary cystadenoma, Choledochal cyst], Mesenchymal tumors [Mesenchymal hamartoma, Infantile hemangioendothelioma, Hemangioma, Peliosis hepatis, Lipomas, Inflammatory pseudotumor, Miscellaneous], Epithelial tumors [Bile duct epithelium (Bile duct hamartoma, Bile duct adenoma), Hepatocyte (Adenoma, Focal nodular hyperplasia, Nodular regenerative hyperplasia)], malignant liver tumors [hepatocellular, hepatoblastoma, hepatocellular carcinoma, cholangiocellular, cholangiocarcinoma, cystadenocarcinoma, tumors of blood vessels, angiosarcoma, Karposi's sarcoma, hemangioendothelioma, other tumors, embryonal sarcoma, fibrosarcoma, leiomyosarcoma, rhabdomyosarcoma, carcinosarcoma, teratoma, carcinoid, squamous carcinoma, primary lymphoma]), peliosis hepatis, erythrohepatic porphyria, hepatic porphyria (acute intermittent porphyria, porphyria cutanea tarda), Zellweger syndrome).

Pancreatic diseases and/or disorders include acute pancreatitis, chronic pancreatitis (acute necrotizing pancreatitis, alcoholic pancreatitis), neoplasms (adenocarcinoma of the pancreas, cystadenocarcinoma, insulinoma, gastrinoma, and glucagonoma, cystic neoplasms, islet-cell tumors, pancreoblastoma), and other pancreatic diseases (e.g., cystic fibrosis, cyst (pancreatic pseudocyst, pancreatic fistula, insufficiency)).

Gallbladder diseases include gallstones (cholelithiasis and choledocholithiasis), postcholecystectomy syndrome, diverticulosis of the gallbladder, acute cholecystitis, chronic cholecystitis, bile duct tumors, and mucocele.

Diseases and/or disorders of the large intestine include antibiotic-associated colitis, diverticulitis, ulcerative colitis, acquired megacolon, abscesses, fungal and bacterial infections, anorectal disorders (e.g., fissures, hemorrhoids), colonic diseases (colitis, colonic neoplasms [colon cancer, adenomatous colon polyps (e.g., villous adenoma), colon carcinoma, colorectal cancer], colonic diverticulitis, colonic diverticulosis, megacolon [Hirschsprung disease, toxic megacolon]; sigmoid diseases [proctocolitis, sigmoin neoplasms]), constipation, Crohn's disease, diarrhea (infantile diarrhea, dysentery), duodenal diseases (duodenal neoplasms, duodenal obstruction, duodenal ulcer, duodenitis), enteritis (enterocolitis), HIV enteropathy, ileal diseases (ileal neoplasms, ileitis), immunoproliferative small intestinal disease, inflammatory bowel disease (ulcerative colitis, Crohn's disease), intestinal atresia, parasitic diseases (anisakiasis, balantidiasis, blastocystis infections, cryptosporidiosis, dientamoebiasis, amebic dysentery, giardiasis), intestinal fistula (rectal fistula), intestinal neoplasms (cecal neoplasms, colonic neoplasms, duodenal neoplasms, ileal neoplasms, intestinal polyps, jejunal neoplasms, rectal neoplasms), intestinal obstruction (afferent loop syndrome, duodenal obstruction, impacted feces, intestinal pseudo-obstruction [cecal volvulus], intussusception), intestinal perforation, intestinal polyps (colonic polyps, gardner syndrome, peutz-jeghers syndrome), jejunal diseases (jejunal neoplasms), malabsorption syndromes (blind loop syndrome, celiac disease, lactose intolerance, short bowl syndrome, tropical sprue, whipple's disease), mesenteric vascular occlusion, pneumatosis cystoides intestinalis, protein-losing enteropathies (intestinal lymphagiectasis), rectal diseases (anus diseases, fecal incontinence, hemorrhoids, proctitis, rectal fistula, rectal prolapse, rectocele), peptic ulcer (duodenal ulcer, peptic esophagitis, hemorrhage, perforation, stomach ulcer, Zollinger-Ellison syndrome), postgastrectomy syndromes (dumping syndrome), stomach diseases (e.g., achlorhydria, duodenogastric reflux (bile reflux), gastric antral vascular ectasia, gastric fistula, gastric outlet obstruction, gastritis (atrophic or hypertrophic), gastroparesis, stomach dilatation, stomach diverticulum, stomach neoplasms (gastric cancer, gastric polyps, gastric adenocarcinoma, hyperplastic gastric polyp), stomach rupture, stomach ulcer, stomach volvulus), tuberculosis, visceroptosis, vomiting (e.g., hematemesis, hyperemesis gravidarum, postoperative nausea and vomiting) and hemorrhagic colitis.

Further diseases and/or disorders of the gastrointestinal system include biliary tract diseases, such as, gastroschisis, fistula (e.g., biliary fistula, esophageal fistula, gastric fistula, intestinal fistula, pancreatic fistula), neoplasms (e.g., biliary tract neoplasms, esophageal neoplasms, such as adenocarcinoma of the esophagus, esophageal squamous cell carcinoma, gastrointestinal neoplasms, pancreatic neoplasms, such as adenocarcinoma of the pancreas, mucinous cystic neoplasm of the pancreas, pancreatic cystic neoplasms, pancreatoblastoma, and peritoneal neoplasms), esophageal disease (e.g., bullous diseases, candidiasis, glycogenic acanthosis, ulceration, barrett esophagus varices, atresia, cyst, diverticulum (e.g., Zenker's diverticulum), fistula (e.g., tracheoesophageal fistula), motility disorders (e.g., CREST syndrome, deglutition disorders, achalasia, spasm, gastroesophageal reflux), neoplasms, perforation (e.g., Boerhaave syndrome, Mallory-Weiss syndrome), stenosis, esophagitis, diaphragmatic hernia (e.g., hiatal hernia); gastrointestinal diseases, such as, gastroenteritis (e.g., cholera morbus, norwalk virus infection), hemorrhage (e.g., hematemesis, melena, peptic ulcer hemorrhage), stomach neoplasms (gastric cancer, gastric polyps, gastric adenocarcinoma, stomach cancer)), hernia (e.g., congenital diaphragmatic hernia, femoral hernia, inguinal hernia, obturator hernia, umbilical hernia, ventral hernia), and intestinal diseases (e.g., cecal diseases (appendicitis, cecal neoplasms)).

Neural Activity and Neurological Diseases

The polynucleotides, polypeptides and agonists or antagonists of the invention may be used for the diagnosis and/or treatment of diseases, disorders, damage or injury of the brain and/or nervous system. Nervous system disorders that can be treated with the compositions of the invention (e.g., polypeptides, polynucleotides, and/or agonists or antagonists), include, but are not limited to, nervous system injuries, and diseases or disorders which result in either a disconnection of axons, a diminution or degeneration of neurons, or demyelination. Nervous system lesions which may be treated in a patient (including human and non-human mammalian patients) according to the methods of the invention, include but are not limited to, the following lesions of either the central (including spinal cord, brain) or peripheral nervous systems: (1) ischemic lesions, in which a lack of oxygen in a portion of the nervous system results in neuronal injury or death, including cerebral infarction or ischemia, or spinal cord infarction or ischemia; (2) traumatic lesions, including lesions caused by physical injury or associated with surgery, for example, lesions which sever a portion of the nervous system, or compression injuries; (3) malignant lesions, in which a portion of the nervous system is destroyed or injured by malignant tissue which is either a nervous system associated malignancy or a malignancy derived from non-nervous system tissue; (4) infectious lesions, in which a portion of the nervous system is destroyed or injured as a result of infection, for example, by an abscess or associated with infection by human immunodeficiency virus, herpes zoster, or herpes simplex virus or with Lyme disease, tuberculosis, or syphilis; (5) degenerative lesions, in which a portion of the nervous system is destroyed or injured as a result of a degenerative process including but not limited to, degeneration associated with Parkinson's disease, Alzheimer's disease, Huntington's chorea, or amyotrophic lateral sclerosis (ALS); (6) lesions associated with nutritional diseases or disorders, in which a portion of the nervous system is destroyed or injured by a nutritional disorder or disorder of metabolism including, but not limited to, vitamin B12 deficiency, folic acid deficiency, Wernicke disease, tobacco-alcohol amblyopia, Marchiafava-Bignami disease (primary degeneration of the corpus callosum), and alcoholic cerebellar degeneration; (7) neurological lesions associated with systemic diseases including, but not limited to, diabetes (diabetic neuropathy, Bell's palsy), systemic lupus erythematosus, carcinoma, or sarcoidosis; (8) lesions caused by toxic substances including alcohol, lead, or particular neurotoxins; and (9) demyelinated lesions in which a portion of the nervous system is destroyed or injured by a demyelinating disease including, but not limited to, multiple sclerosis, human immunodeficiency virus-associated myelopathy, transverse myelopathy or various etiologies, progressive multifocal leukoencephalopathy, and central pontine myelinolysis.

In one embodiment, the polypeptides, polynucleotides, or agonists or antagonists of the invention are used to protect neural cells from the damaging effects of hypoxia. In a further preferred embodiment, the polypeptides, polynucleotides, or agonists or antagonists of the invention are used to protect neural cells from the damaging effects of cerebral hypoxia. According to this embodiment, the compositions of the invention are used to treat or prevent neural cell injury associated with cerebral hypoxia. In one non-exclusive aspect of this embodiment, the polypeptides, polynucleotides, or agonists or antagonists of the invention, are used to treat or prevent neural cell injury associated with cerebral ischemia. In another non-exclusive aspect of this embodiment, the polypeptides, polynucleotides, or agonists or antagonists of the invention are used to treat or prevent neural cell injury associated with cerebral infarction.

In another preferred embodiment, the polypeptides, polynucleotides, or agonists or antagonists of the invention are used to treat or prevent neural cell injury associated with a stroke. In a specific embodiment, the polypeptides, polynucleotides, or agonists or antagonists of the invention are used to treat or prevent cerebral neural cell injury associated with a stroke.

In another preferred embodiment, the polypeptides, polynucleotides, or agonists or antagonists of the invention are used to treat or prevent neural cell injury associated with a heart attack. In a specific embodiment, the polypeptides, polynucleotides, or agonists or antagonists of the invention are used to treat or prevent cerebral neural cell injury associated with a heart attack.

The compositions of the invention which are useful for treating or preventing a nervous system disorder may be selected by testing for biological activity in promoting the survival or differentiation of neurons. For example, and not by way of limitation, compositions of the invention which elicit any of the following effects may be useful according to the invention: (1) increased survival time of neurons in culture either in the presence or absence of hypoxia or hypoxic conditions; (2) increased sprouting of neurons in culture or in vivo; (3) increased production of a neuron-associated molecule in culture or in vivo, e.g., choline acetyltransferase or acetylcholinesterase with respect to motor neurons; or (4) decreased symptoms of neuron dysfunction in vivo. Such effects may be measured by any method known in the art. In preferred, non-limiting embodiments, increased survival of neurons may routinely be measured using a method set forth herein or otherwise known in the art, such as, for example, in Zhang et al., *Proc Natl Acad Sci USA* 97:3637-42 (2000) or in Arakawa et al., *J. Neurosci.*, 10:3507-15 (1990); increased sprouting of neurons may be detected by methods known in the art, such as, for example, the methods set forth in Pestronk et al., *Exp. Neurol.*, 70:65-82 (1980), or Brown et al., *Ann. Rev. Neurosci.*, 4:17-42 (1981); increased production of neuron-associated molecules may be measured by bioassay, enzymatic assay, antibody binding, Northern blot assay, etc., using techniques known in the art and depending on the molecule to be measured; and motor neuron dysfunction may be measured by assessing the physical manifestation of motor neuron disorder, e.g., weakness, motor neuron conduction velocity, or functional disability.

In specific embodiments, motor neuron disorders that may be treated according to the invention include, but are not limited to, disorders such as infarction, infection, exposure to toxin, trauma, surgical damage, degenerative disease or malignancy that may affect motor neurons as well as other components of the nervous system, as well as disorders that selectively affect neurons such as amyotrophic lateral sclerosis, and including, but not limited to, progressive spinal muscular atrophy, progressive bulbar palsy, primary lateral sclerosis, infantile and juvenile muscular atrophy, progressive bulbar paralysis of childhood (Fazio-Londe syndrome), poliomyelitis and the post polio syndrome, and Hereditary Motorsensory Neuropathy (Charcot-Marie-Tooth Disease).

Further, polypeptides or polynucleotides of the invention may play a role in neuronal survival; synapse formation; conductance; neural differentiation, etc. Thus, compositions of the invention (including polynucleotides, polypeptides, and agonists or antagonists) may be used to diagnose and/or treat or prevent diseases or disorders associated with these roles, including, but not limited to, learning and/or cognition disorders. The compositions of the invention may also be useful in the treatment or prevention of neurodegenerative disease states and/or behavioural disorders. Such neurodegenerative disease states and/or behavioral disorders include, but are not limited to, Alzheimer's Disease, Parkinson's Disease, Huntington's Disease, Tourette Syndrome, schizophrenia, mania, dementia, paranoia, obsessive compulsive disorder, panic disorder, learning disabilities, ALS, psychoses, autism, and altered behaviors, including disorders in feeding, sleep patterns, balance, and perception. In addition, compositions of the invention may also play a role in the treatment, prevention and/or detection of developmental disorders associated with the developing embryo, or sexually-linked disorders.

Additionally, polypeptides, polynucleotides and/or agonists or antagonists of the invention, may be useful in protecting neural cells from diseases, damage, disorders, or injury, associated with cerebrovascular disorders including, but not limited to, carotid artery diseases (e.g., carotid artery thrombosis, carotid stenosis, or Moyamoya Disease), cerebral amyloid angiopathy, cerebral aneurysm, cerebral anoxia, cerebral arteriosclerosis, cerebral arteriovenous malformations, cerebral artery diseases, cerebral embolism and thrombosis (e.g., carotid artery thrombosis, sinus thrombosis, or Wallenberg's Syndrome), cerebral hemorrhage (e.g., epidural or subdural hematoma, or subarachnoid hemorrhage), cerebral infarction, cerebral ischemia (e.g., transient cerebral ischemia, Subclavian Steal Syndrome, or vertebrobasilar insufficiency), vascular dementia (e.g., multi-infarct), leukomalacia, periventricular, and vascular headache (e.g., cluster headache or migraines).

In accordance with yet a further aspect of the present invention, there is provided a process for utilizing polynucleotides or polypeptides, as well as agonists or antagonists of the present invention, for therapeutic purposes, for example, to stimulate neurological cell proliferation and/or differentiation. Therefore, polynucleotides, polypeptides, agonists and/or antagonists of the invention may be used to treat and/or detect neurologic diseases. Moreover, polynucleotides or polypeptides, or agonists or antagonists of the invention, can be used as a marker or detector of a particular nervous system disease or disorder.

Examples of neurologic diseases which can be treated or detected with polynucleotides, polypeptides, agonists, and/or antagonists of the present invention include brain diseases, such as metabolic brain diseases which includes phenylketonuria such as maternal phenylketonuria, pyruvate carboxylase deficiency, pyruvate dehydrogenase complex deficiency, Wernicke's Encephalopathy, brain edema, brain neoplasms such as cerebellar neoplasms which include infratentorial neoplasms, cerebral ventricle neoplasms such as choroid plexus neoplasms, hypothalamic neoplasms, supratentorial neoplasms, canavan disease, cerebellar diseases such as cerebellar ataxia which include spinocerebellar degeneration such as ataxia telangiectasia, cerebellar dyssynergia, Friederich's Ataxia, Machado-Joseph Disease, olivopontocerebellar atrophy, cerebellar neoplasms such as infratentorial neoplasms, diffuse cerebral sclerosis such as encephalitis periaxialis, globoid cell leukodystrophy, metachromatic leukodystrophy and subacute sclerosing panencephalitis.

Additional neurologic diseases which can be treated or detected with polynucleotides, polypeptides, agonists, and/or antagonists of the present invention include cerebrovascular disorders (such as carotid artery diseases which include carotid artery thrombosis, carotid stenosis and Moyamoya Disease), cerebral amyloid angiopathy, cerebral aneurysm, cerebral anoxia, cerebral arteriosclerosis, cerebral arteriovenous malformations, cerebral artery diseases, cerebral embolism and thrombosis such as carotid artery thrombosis, sinus thrombosis and Wallenberg's Syndrome, cerebral hemorrhage such as epidural hematoma, subdural hematoma and subarachnoid hemorrhage, cerebral infarction, cerebral ischemia such as transient cerebral ischemia, Subclavian Steal Syndrome and vertebrobasilar insufficiency, vascular dementia such as multi-infarct dementia, periventricular leukomalacia, vascular headache such as cluster headache and migraine.

Additional neurologic diseases which can be treated or detected with polynucleotides, polypeptides, agonists, and/or antagonists of the present invention include dementia such as AIDS Dementia Complex, presenile dementia such as Alzheimer's Disease and Creutzfeldt-Jakob Syndrome, senile dementia such as Alzheimer's Disease and progressive supranuclear palsy, vascular dementia such as multi-infarct dementia, encephalitis which include encephalitis periaxialis, viral encephalitis such as epidemic encephalitis, Japanese Encephalitis, St. Louis Encephalitis, tick-borne encephalitis and West Nile Fever, acute disseminated encephalomyelitis, meningoencephalitis such as uveomeningoencephalitic syndrome, Postencephalitic Parkinson Disease and subacute sclerosing panencephalitis, encephalomalacia such as periventricular leukomalacia, epilepsy such as generalized epilepsy which includes infantile spasms, absence epilepsy, myoclonic epilepsy which includes MERRF Syndrome, tonic-clonic epilepsy, partial epilepsy such as complex partial epilepsy, frontal lobe epilepsy and temporal lobe epilepsy, post-traumatic epilepsy, status epilepticus such as Epilepsia Partialis Continua, and Hallervorden-Spatz Syndrome.

Additional neurologic diseases which can be treated or detected with polynucleotides, polypeptides, agonists, and/or antagonists of the present invention include hydrocephalus such as Dandy-Walker Syndrome and normal pressure hydrocephalus, hypothalamic diseases such as hypothalamic neoplasms, cerebral malaria, narcolepsy which includes cataplexy, bulbar poliomyelitis, cerebri pseudotumor, Rett Syndrome, Reye's Syndrome, thalamic diseases, cerebral toxoplasmosis, intracranial tuberculoma and Zellweger Syndrome, central nervous system infections such as AIDS Dementia Complex, Brain Abscess, subdural empyema, encephalomyelitis such as Equine Encephalomyelitis, Venezuelan Equine Encephalomyelitis, Necrotizing Hemorrhagic Encephalomyelitis, Visna, and cerebral malaria.

Additional neurologic diseases which can be treated or detected with polynucleotides, polypeptides, agonists, and/or antagonists of the present invention include meningitis such as arachnoiditis, aseptic meningitis such as viral meningitis which includes lymphocytic choriomeningitis, Bacterial meningtitis which includes Haemophilus Meningtitis, Listeria Meningtitis, Meningococcal Meningtitis such as Waterhouse-Friderichsen Syndrome, Pneumococcal Meningtitis and meningeal tuberculosis, fungal meningitis such as Cryptococcal Meningtitis, subdural effusion, meningoencephalitis such as uvemeningoencephalitic syndrome, myelitis such as transverse myelitis, neurosyphilis such as tabes dorsalis, poliomyelitis which includes bulbar poliomyelitis and postpoliomyelitis syndrome, prion diseases (such as Creutzfeldt-Jakob Syndrome, Bovine Spongiform Encephalopathy, Gerstmann-Straussler Syndrome, Kuru, Scrapie), and cerebral toxoplasmosis.

Additional neurologic diseases which can be treated or detected with polynucleotides, polypeptides, agonists, and/or antagonists of the present invention include central nervous system neoplasms such as brain neoplasms that include cerebellar neoplasms such as infratentorial neoplasms, cerebral ventricle neoplasms such as choroid plexus neoplasms, hypothalamic neoplasms and supratentorial neoplasms, meningeal neoplasms, spinal cord neoplasms which include epidural neoplasms, demyclinating diseases such as Canavan Diseases, diffuse cerebral sceloris which includes adrenoleukodystrophy, encephalitis periaxialis, globoid cell leukodystrophy, diffuse cerebral sclerosis such as metachromatic leukodystrophy, allergic encephalomyelitis, necrotizing hemorrhagic encephalomyelitis, progressive multifocal leukoencephalopathy, multiple sclerosis, central pontine myelinolysis, transverse myelitis, neuromyelitis optica, Scrapie, Swayback, Chronic Fatigue Syndrome, Visna, High Pressure Nervous Syndrome, Meningism, spinal cord diseases such as amyotonia congenita, amyotrophic lateral sclerosis, spinal muscular atrophy such as Werdnig-Hoffmann Disease, spinal cord compression, spinal cord neoplasms such as epidural neoplasms, syringomyelia, Tabes Dorsalis, Stiff-Man Syndrome, mental retardation such as Angelman Syndrome, Cri-du-Chat Syndrome, De Lange's Syndrome, Down Syndrome, Gangliosidoses such as gangliosidoses G(M1), Sandhoff Disease, Tay-Sachs Disease, Hartnup Disease, homocystinuria, Laurence-Moon-Biedl Syndrome, Lesch-Nyhan Syndrome, Maple Syrup Urine Disease, mucolipidosis such as fucosidosis, neuronal ceroid-lipofuscinosis, oculocerebrorenal syndrome, phenylketonuria such as maternal phenylketonuria, Prader-Willi Syndrome, Rett Syndrome, Rubinstein-Taybi Syndrome, Tuberous Sclerosis, WAGR Syndrome, nervous system abnormalities such as holoprosencephaly, neural tube defects such as anencephaly which includes hydrangencephaly, Arnold-Chairi Deformity, encephalocele, meningocele, meningomyelocele, spinal dysraphism such as spina bifida cystica and spina bifida occulta.

Additional neurologic diseases which can be treated or detected with polynucleotides, polypeptides, agonists, and/or antagonists of the present invention include hereditary motor and sensory neuropathies which include Charcot-Marie Disease, Hereditary optic atrophy, Refsum's Disease, hereditary spastic paraplegia, Werdnig-Hoffmann Disease, Hereditary Sensory and Autonomic Neuropathies such as Congenital Analgesia and Familial Dysautonomia, Neurologic manifestations (such as agnosia that include Gerstmann's Syndrome, Amnesia such as retrograde amnesia, apraxia, neurogenic bladder, cataplexy, communicative disorders such as hearing disorders that includes deafness, partial hearing loss, loudness recruitment and tinnitus, language disorders such as aphasia which include agraphia, anomia, broca aphasia, and Wernicke Aphasia, Dyslexia such as Acquired Dyslexia, language development disorders, speech disorders such as aphasia which includes anomia, broca aphasia and Wernicke Aphasia, articulation disorders, communicative disorders such as speech disorders which include dysarthria, echolalia, mutism and stuttering, voice disorders such as aphonia and hoarseness, decerebrate state, delirium, fasciculation, hallucinations, meningism, movement disorders such as angelman syndrome, ataxia, athetosis, chorea, dystonia, hypokinesia, muscle hypotonia, myoclonus, tic, torticollis and tremor, muscle hypertonia such as muscle rigidity such as stiff-man syndrome, muscle spasticity, paralysis such as facial paralysis which includes Herpes Zoster Oticus, Gastroparesis, Hemiplegia, ophthalmoplegia such as diplopia, Duane's Syndrome, Horner's Syndrome, Chronic progressive external ophthalmoplegia such as Kearns Syndrome, Bulbar Paralysis, Tropical Spastic Paraparesis, Paraplegia such as Brown-Sequard Syndrome, quadriplegia, respiratory paralysis and vocal cord paralysis, paresis, phantom limb, taste disorders such as ageusia and dysgeusia, vision disorders such as amblyopia, blindness, color vision defects, diplopia, hemianopsia, scotoma and subnormal vision, sleep disorders such as hypersomnia which includes Kleine-Levin Syndrome, insomnia, and somnambulism, spasm such as trismus, unconsciousness such as coma, persistent vegetative state and syncope and vertigo, neuromuscular diseases such as amyotonia congenita, amyotrophic lateral sclerosis, Lambert-Eaton Myasthenic Syndrome, motor neuron disease, muscular atrophy such as spinal muscular atrophy, Charcot-Marie Disease and Werdnig-Hoffmann Disease, Postpoliomyelitis Syndrome, Muscular Dystrophy, Myasthenia Gravis, Myotonia Atrophica, Myotonia Confenita, Nemaline Myopathy, Familial Periodic Paralysis, Multiplex Paramyloclonus, Tropical Spastic Paraparesis and Stiff-Man Syndrome, peripheral nervous system diseases such as acrodynia, amyloid neuropathies, autonomic nervous system diseases such as Adie's Syndrome, Barre-Lieou Syndrome, Familial Dysautonomia, Homer's Syndrome, Reflex Sympathetic Dystrophy and Shy-Drager Syndrome, Cranial Nerve Diseases such as Acoustic Nerve Diseases such as Acoustic Neuroma which includes Neurofibromatosis 2, Facial Nerve Diseases such as Facial Neuralgia, Melkersson-Rosenthal Syndrome, ocular motility disorders which includes amblyopia, nystagmus, oculomotor nerve paralysis, ophthalmoplegia such as Duane's Syndrome, Homer's Syndrome, Chronic Progressive External Ophthalmoplegia which includes Kearns Syndrome, Strabismus such as Esotropia and Exotropia, Oculomotor Nerve Paralysis, Optic Nerve Diseases such as Optic Atrophy which includes Hereditary Optic Atrophy, Optic Disk Drusen, Optic Neuritis such as Neuromyelitis Optica, Papilledema, Trigeminal Neuralgia, Vocal Cord Paralysis, Demyelinating Diseases such as Neuromyelitis Optica and Swayback, and Diabetic neuropathies such as diabetic foot.

Additional neurologic diseases which can be treated or detected with polynucleotides, polypeptides, agonists, and/or antagonists of the present invention include nerve compression syndromes such as carpal tunnel syndrome, tarsal tunnel syndrome, thoracic outlet syndrome such as cervical rib syndrome, ulnar nerve compression syndrome, neuralgia such as causalgia, cervico-brachial neuralgia, facial neuralgia and trigeminal neuralgia, neuritis such as experimental allergic neuritis, optic neuritis, polyneuritis, polyradiculoneuritis and radiculities such as polyradiculitis, hereditary motor and sensory neuropathies such as Charcot-Marie Disease, Hereditary Optic Atrophy, Refsum's Disease, Hereditary Spastic Paraplegia and Werdnig-Hoffmann Disease, Hereditary Sensory and Autonomic Neuropathies which include Congenital Analgesia and Familial Dysautonomia, POEMS Syndrome, Sciatica, Gustatory Sweating and Tetany).

Endocrine Disorders

Polynucleotides or polypeptides, or agonists or antagonists of the present invention, may be used to treat, prevent, diagnose, and/or prognose disorders and/or diseases related to hormone imbalance, and/or disorders or diseases of the endocrine system.

Hormones secreted by the glands of the endocrine system control physical growth, sexual function, metabolism, and other functions. Disorders may be classified in two ways: disturbances in the production of hormones, and the inability of tissues to respond to hormones. The etiology of these hormone imbalance or endocrine system diseases, disorders or conditions may be genetic, somatic, such as cancer and some autoimmune diseases, acquired (e.g., by chemotherapy, injury or toxins), or infectious. Moreover, polynucleotides, polypeptides, antibodies, and/or agonists or antagonists of the present invention can be used as a marker or detector of a particular disease or disorder related to the endocrine system and/or hormone imbalance.

Endocrine system and/or hormone imbalance and/or diseases encompass disorders of uterine motility including, but not limited to: complications with pregnancy and labor (e.g., pre-term labor, post-term pregnancy, spontaneous abortion, and slow or stopped labor); and disorders and/or diseases of the menstrual cycle (e.g., dysmenorrhea and endometriosis).

Endocrine system and/or hormone imbalance disorders and/or diseases include disorders and/or diseases of the pancreas, such as, for example, diabetes mellitus, diabetes insipidus, congenital pancreatic agenesis, pheochromocytoma—islet cell tumor syndrome; disorders and/or diseases of the adrenal glands such as, for example, Addison's Disease, corticosteroid deficiency, virilizing disease, hirsutism, Cushing's Syndrome, hyperaldosteronism, pheochromocytoma; disorders and/or diseases of the pituitary gland, such as, for example, hyperpituitarism, hypopituitarism, pituitary dwarfism, pituitary adenoma, panhypopituitarism, acromegaly, gigantism; disorders and/or diseases of the thyroid, including but not limited to, hyperthyroidism, hypothyroidism, Plummer's disease, Graves' disease (toxic diffuse goiter), toxic nodular goiter, thyroiditis (Hashimoto's thyroiditis, subacute granulomatous thyroiditis, and silent lymphocytic thyroiditis), Pendred's syndrome, myxedema, cretinism, thyrotoxicosis, thyroid hormone coupling defect, thymic aplasia, Hurthle cell tumours of the thyroid, thyroid cancer, thyroid carcinoma, Medullary thyroid carcinoma; disorders and/or diseases of the parathyroid, such as, for example, hyperparathyroidism, hypoparathyroidism; disorders and/or diseases of the hypothalamus.

In specific embodiments, the polynucleotides and/or polypeptides corresponding to this gene and/or agonists or antagonists of those polypeptides (including antibodies) as well as fragments and variants of those polynucleotides, polypeptides, agonists and antagonists, may be used to diagnose, prognose, treat, prevent, or ameliorate diseases and disorders associated with aberrant glucose metabolism or glucose uptake into cells.

In a specific embodiment, the polynucleotides and/or polypeptides corresponding to this gene and/or agonists and/or antagonists thereof may be used to diagnose, prognose, treat, prevent, and/or ameliorate type I diabetes mellitus (insulin dependent diabetes mellitus, IDDM).

In another embodiment, the polynucleotides and/or polypeptides corresponding to this gene and/or agonists and/or antagonists thereof may be used to diagnose, prognose, treat, prevent, and/or ameliorate type II diabetes mellitus (insulin resistant diabetes mellitus).

Additionally, in other embodiments, the polynucleotides and/or polypeptides corresponding to this gene and/or antagonists thereof (especially neutralizing or antagonistic antibodies) may be used to diagnose, prognose, treat, prevent, or ameliorate conditions associated with (type I or type II) diabetes mellitus, including, but not limited to, diabetic ketoacidosis, diabetic coma, nonketotic hyperglycemic-hyperosmolar coma, seizures, mental confusion, drowsiness, cardiovascular disease (e.g., heart disease, atherosclerosis, microvascular disease, hypertension, stroke, and other diseases and disorders as described in the "Cardiovascular Disorders" section), dyslipidemia, kidney disease (e.g., renal failure, nephropathy other diseases and disorders as described in the "Renal Disorders" section), nerve damage, neuropathy, vision impairment (e.g., diabetic retinopathy and blindness), ulcers and impaired wound healing, infections (e.g., infectious diseases and disorders as described in the "Infectious Diseases" section, especially of the urinary tract and skin), carpal tunnel syndrome and Dupuytren's contracture.

In other embodiments, the polynucleotides and/or polypeptides corresponding to this gene and/or agonists or antagonists thereof are administered to an animal, preferably a mammal, and most preferably a human, in order to regulate the animal's weight. In specific embodiments the polynucleotides and/or polypeptides corresponding to this gene and/or agonists or antagonists thereof are administered to an animal, preferably a mammal, and most preferably a human, in order to control the animal's weight by modulating a biochemical pathway involving insulin. In still other embodiments the polynucleotides and/or polypeptides corresponding to this gene and/or agonists or antagonists thereof are administered to an animal, preferably a mammal, and most preferably a human, in order to control the animal's weight by modulating a biochemical pathway involving insulin-like growth factor.

In addition, endocrine system and/or hormone imbalance disorders and/or diseases may also include disorders and/or diseases of the testes or ovaries, including cancer. Other disorders and/or diseases of the testes or ovaries further include, for example, ovarian cancer, polycystic ovary syndrome, Klinefelter's syndrome, vanishing testes syndrome (bilateral anorchia), congenital absence of Leydig's cells, cryptorchidism, Noonan's syndrome, myotonic dystrophy, capillary haemangioma of the testis (benign), neoplasias of the testis and neo-testis.

Moreover, endocrine system and/or hormone imbalance disorders and/or diseases may also include disorders and/or diseases such as, for example, polyglandular deficiency syndromes, pheochromocytoma, neuroblastoma, multiple Endocrine neoplasia, and disorders and/or cancers of endocrine tissues.

In another embodiment, a polypeptide of the invention, or polynucleotides, antibodies, agonists, or antagonists corresponding to that polypeptide, may be used to diagnose, prognose, prevent, and/or treat endocrine diseases and/or disorders associated with the tissue(s) in which the polypeptide of the invention is expressed.

Reproductive System Disorders

The polynucleotides or polypeptides, or agonists or antagonists of the invention may be used for the diagnosis, treatment, or prevention of diseases and/or disorders of the reproductive system. Reproductive system disorders that can be treated by the compositions of the invention, include, but are not limited to, reproductive system injuries, infections, neoplastic disorders, congenital defects, and diseases or disorders which result in infertility, complications with pregnancy, labor, or parturition, and postpartum difficulties.

Reproductive system disorders and/or diseases include diseases and/or disorders of the testes, including testicular atrophy, testicular feminization, cryptorchism (unilateral and bilateral), anorchia, ectopic testis, epididymitis and orchitis (typically resulting from infections such as, for example, gonorrhea, mumps, tuberculosis, and syphilis), testicular torsion, vasitis nodosa, germ cell tumors (e.g., seminomas, embryonal cell carcinomas, teratocarcinomas, choriocarcinomas, yolk sac tumors, and teratomas), stromal tumors (e.g., Leydig cell tumors), hydrocele, hematocele, varicocele, spermatocele, inguinal hernia, and disorders of sperm production (e.g., immotile cilia syndrome, aspermia, asthenozoospermia, azoospermia, oligospermia, and teratozoospermia).

Reproductive system disorders also include disorders of the prostate gland, such as acute non-bacterial prostatitis, chronic non-bacterial prostatitis, acute bacterial prostatitis, chronic bacterial prostatitis, prostatodystonia, prostatosis, granulomatous prostatitis, malacoplakia, benign prostatic hypertrophy or hyperplasia, and prostate neoplastic disorders, including adenocarcinomas, transitional cell carcinomas, ductal carcinomas, and squamous cell carcinomas.

Additionally, the compositions of the invention may be useful in the diagnosis, treatment, and/or prevention of disorders or diseases of the penis and urethra, including inflammatory disorders, such as balanoposthitis, balanitis xerotica obliterans, phimosis, paraphimosis, syphilis, herpes simplex virus, gonorrhea, non-gonococcal urethritis, chlamydia, mycoplasma, trichomonas, HIV, AIDS, Reiter's syndrome, condyloma acuminatum, condyloma latum, and pearly penile papules; urethral abnormalities, such as hypospadias, epispadias, and phimosis; premalignant lesions, including Erythroplasia of Queyrat, Bowen's disease, Bowenoid paplosis, giant condyloma of Buscke-Lowenstein, and varrucous carcinoma; penile cancers, including squamous cell carcinomas, carcinoma in situ, verrucous carcinoma, and disseminated penile carcinoma; urethral neoplastic disorders, including penile urethral carcinoma, bulbomembranous urethral carcinoma, and prostatic urethral carcinoma; and erectile disorders, such as priapism, Peyronie's disease, erectile dysfunction, and impotence.

Moreover, diseases and/or disorders of the vas deferens include vasculititis and CBAVD (congenital bilateral absence of the vas deferens); additionally, the polynucleotides, polypeptides, and agonists or antagonists of the present invention may be used in the diagnosis, treatment, and/or prevention of diseases and/or disorders of the seminal vesicles, including hydatid disease, congenital chloride diarrhea, and polycystic kidney disease.

Other disorders and/or diseases of the male reproductive system include, for example, Klinefelter's syndrome, Young's syndrome, premature ejaculation, diabetes mellitus, cystic fibrosis, Kartagener's syndrome, high fever, multiple sclerosis, and gynecomastia.

Further, the polynucleotides, polypeptides, and agonists or antagonists of the present invention may be used in the diagnosis, treatment, and/or prevention of diseases and/or disorders of the vagina and vulva, including bacterial vaginosis, candida vaginitis, herpes simplex virus, chancroid, granuloma inguinale, lymphogranuloma venereum, scabies, human papillomavirus, vaginal trauma, vulvar trauma, adenosis, chlamydia vaginitis, gonorrhea, trichomonas vaginitis, condyloma acuminatum, syphilis, molluscum contagiosum, atrophic vaginitis, Paget's disease, lichen sclerosus, lichen planus, vulvodynia, toxic shock syndrome, vaginismus, vulvovaginitis, vulvar vestibulitis, and neoplastic disorders, such as squamous cell hyperplasia, clear cell carcinoma, basal cell carcinoma, melanomas, cancer of Bartholin's gland, and vulvar intraepithelial neoplasia.

Disorders and/or diseases of the uterus include dysmenorrhea, retroverted uterus, endometriosis, fibroids, adenomyosis, anovulatory bleeding, amenorrhea, Cushing's syndrome, hydatidiform moles, Asherman's syndrome, premature menopause, precocious puberty, uterine polyps, dysfunctional uterine bleeding (e.g., due to aberrant hormonal signals), and neoplastic disorders, such as adenocarcinomas, keiomyosarcomas, and sarcomas. Additionally, the polypeptides, polynucleotides, or agonists or antagonists of the invention may be useful as a marker or detector of, as well as in the diagnosis, treatment, and/or prevention of congenital uterine abnormalities, such as bicomuate uterus, septate uterus, simple unicornuate uterus, unicornuate uterus with a noncavitary rudimentary horn, unicornuate uterus with a non-communicating cavitary rudimentary horn, unicornuate uterus with a communicating cavitary horn, arcuate uterus, uterine didelfus, and T-shaped uterus.

Ovarian diseases and/or disorders include anovulation, polycystic ovary syndrome (Stein-Leventhal syndrome), ovarian cysts, ovarian hypofunction, ovarian insensitivity to gonadotropins, ovarian overproduction of androgens, right ovarian vein syndrome, amenorrhea, hirutism, and ovarian cancer (including, but not limited to, primary and secondary cancerous growth, Sertoli-Leydig tumors, endometriod carcinoma of the ovary, ovarian papillary serous adenocarcinoma, ovarian mucinous adenocarcinoma, and Ovarian Krukenberg tumors).

Cervical diseases and/or disorders include cervicitis, chronic cervicitis, mucopurulent cervicitis, cervical dysplasia, cervical polyps, Nabothian cysts, cervical erosion, cervical incompetence, and cervical neoplasms (including, for example, cervical carcinoma, squamous metaplasia, squamous cell carcinoma, adenosquamous cell neoplasia, and columnar cell neoplasia).

Additionally, diseases and/or disorders of the reproductive system include disorders and/or diseases of pregnancy, including miscarriage and stillbirth, such as early abortion, late abortion, spontaneous abortion, induced abortion, therapeutic abortion, threatened abortion, missed abortion, incomplete abortion, complete abortion, habitual abortion, missed abortion, and septic abortion; ectopic pregnancy, anemia, Rh incompatibility, vaginal bleeding during pregnancy, gestational diabetes, intrauterine growth retardation, polyhydramnios, HELLP syndrome, abruptio placentae, placenta previa, hyperemesis, preeclampsia, eclampsia, herpes gestationis, and urticaria of pregnancy. Additionally, the polynucleotides, polypeptides, and agonists or antagonists of the present invention may be used in the diagnosis, treatment, and/or prevention of diseases that can complicate pregnancy, including heart disease, heart failure, rheumatic heart disease, congenital heart disease, mitral valve prolapse, high blood pressure, anemia, kidney disease, infectious disease (e.g., rubella, cytomegalovirus, toxoplasmosis, infectious hepatitis, chlamydia, HIV, AIDS, and genital herpes), diabetes mellitus, Graves' disease, thyroiditis, hypothyroidism, Hashimoto's thyroiditis, chronic active hepatitis, cirrhosis of the liver, primary biliary cirrhosis, asthma, systemic lupus eryematosis, rheumatoid arthritis, myasthenia gravis, idiopathic thrombocytopenic purpura, appendicitis, ovarian cysts, gallbladder disorders, and obstruction of the intestine.

Complications associated with labor and parturition include premature rupture of the membranes, pre-term labor, post-term pregnancy, postmaturity, labor that progresses too slowly, fetal distress (e.g., abnormal heart rate (fetal or maternal), breathing problems, and abnormal fetal position), shoulder dystocia, prolapsed umbilical cord, amniotic fluid embolism, and aberrant uterine bleeding.

Further, diseases and/or disorders of the postdelivery period, including endometritis, myometritis, parametritis, peritonitis, pelvic thrombophlebitis, pulmonary embolism, endotoxemia, pyelonephritis, saphenous thrombophlebitis, mastitis, cystitis, postpartum hemorrhage, and inverted uterus.

Other disorders and/or diseases of the female reproductive system that may be diagnosed, treated, and/or prevented by the polynucleotides, polypeptides, and agonists or antagonists of the present invention include, for example, Turner's syndrome, pseudohermaphroditism, premenstrual syndrome, pelvic inflammatory disease, pelvic congestion (vascular engorgement), frigidity, anorgasmia, dyspareunia, ruptured fallopian tube, and Mittelschmerz.

Renal Disorders

Polynucleotides, polypeptides, antibodies, and/or agonists or antagonists of the present invention, may be used to treat, prevent, diagnose, and/or prognose disorders of the renal system. Renal disorders which can be diagnosed, prognosed, prevented, and/or treated with compositions of the invention include, but are not limited to, kidney failure, nephritis, blood vessel disorders of kidney, metabolic and congenital kidney disorders, urinary disorders of the kidney, autoimmune disorders, sclerosis and necrosis, electrolyte imbalance, and kidney cancers.

Kidney diseases which can be diagnosed, prognosed, prevented, and/or treated with compositions of the invention include, but are not limited to, acute kidney failure, chronic kidney failure, atheroembolic renal failure, end-stage renal disease, inflammatory diseases of the kidney (e.g., acute glomerulonephritis, postinfectious glomerulonephritis, rapidly progressive glomerulonephritis, nephrotic syndrome, membranous glomerulonephritis, familial nephrotic syndrome, membranoproliferative glomerulonephritis I and II, mesangial proliferative glomerulonephritis, chronic glomerulonephritis, acute tubulointerstitial nephritis, chronic tubulointerstitial nephritis, acute post-streptococcal glomerulonephritis (PSGN), pyelonephritis, lupus nephritis, chronic nephritis, interstitial nephritis, and post-streptococcal glomerulonephritis), blood vessel disorders of the kidneys (e.g., kidney infarction, atheroembolic kidney disease, cortical necrosis, malignant nephrosclerosis, renal vein thrombosis, renal underperfusion, renal retinopathy, renal ischemia-reperfusion, renal artery embolism, and renal artery stenosis), and kidney disorders resulting form urinary tract disease (e.g., pyelonephritis, hydronephrosis, urolithiasis (renal lithiasis, nephrolithiasis), reflux nephropathy, urinary tract infections, urinary retention, and acute or chronic unilateral obstructive uropathy.)

In addition, compositions of the invention can be used to diagnose, prognose, prevent, and/or treat metabolic and congenital disorders of the kidney (e.g., uremia, renal amyloidosis, renal osteodystrophy, renal tubular acidosis, renal glycosuria, nephrogenic diabetes insipidus, cystinuria, Fanconi's syndrome, renal fibrocystic osteosis (renal rickets), Hartnup disease, Bartter's syndrome, Liddle's syndrome, polycystic kidney disease, medullary cystic disease, medullary sponge kidney, Alport's syndrome, nail-patella syndrome, congenital nephrotic syndrome, CRUSH syndrome, horseshoe kidney, diabetic nephropathy, nephrogenic diabetes insipidus, analgesic nephropathy, kidney stones, and membranous nephropathy), and autoimmune disorders of the kidney (e.g., systemic lupus erythematosus (SLE), Goodpasture syndrome, IgA nephropathy, and IgM mesangial proliferative glomerulonephritis).

Compositions of the invention can also be used to diagnose, prognose, prevent, and/or treat sclerotic or necrotic disorders of the kidney (e.g., glomerulosclerosis, diabetic nephropathy, focal segmental glomerulosclerosis (FSGS), necrotizing glomerulonephritis, and renal papillary necrosis), cancers of the kidney (e.g., nephroma, hypernephroma, nephroblastoma, renal cell cancer, transitional cell cancer, renal adenocarcinoma, squamous cell cancer, and Wilm's tumor), and electrolyte imbalances (e.g., nephrocalcinosis, pyuria, edema, hydronephritis, proteinuria, hyponatremia, hypematremia, hypokalemia, hyperkalemia, hypocalcemia, hypercalcemia, hypophosphatemia, and hyperphosphatemia).

Polypeptides may be administered using any method known in the art, including, but not limited to, direct needle injection at the delivery site, intravenous injection, topical administration, catheter infusion, biolistic injectors, particle accelerators, gelfoam sponge depots, other commercially available depot materials, osmotic pumps, oral or suppositorial solid pharmaceutical formulations, decanting or topical applications during surgery, aerosol delivery. Such methods are known in the art. Polypeptides may be administered as part of a Therapeutic, described in more detail below. Methods of delivering polynucleotides are described in more detail herein.

Cardiovascular Disorders

Polynucleotides or polypeptides, or agonists or antagonists of the present invention, may be used to treat, prevent, diagnose, and/or prognose cardiovascular disorders, including, but not limited to, peripheral artery disease, such as limb ischemia.

Cardiovascular disorders include, but are not limited to, cardiovascular abnormalities, such as arterio-arterial fistula, arteriovenous fistula, cerebral arteriovenous malformations, congenital heart defects, pulmonary atresia, and Scimitar Syndrome. Congenital heart defects include, but are not limited to, aortic coarctation, cor triatriatum, coronary vessel anomalies, crisscross heart, dextrocardia, patent ductus arteriosus, Ebstein's anomaly, Eisenmenger complex, hypoplastic left heart syndrome, levocardia, tetralogy of fallot, transposition of great vessels, double outlet right ventricle, tricuspid atresia, persistent truncus arteriosus, and heart septal defects, such as aortopulmonary septal defect, endocardial cushion defects, Lutembacher's Syndrome, trilogy of Fallot, ventricular heart septal defects.

Cardiovascular disorders also include, but are not limited to, heart disease, such as arrhythmias, carcinoid heart disease, high cardiac output, low cardiac output, cardiac tamponade, endocarditis (including bacterial), heart aneurysm, cardiac arrest, congestive heart failure, congestive cardiomyopathy, paroxysmal dyspnea, cardiac edema, heart hypertrophy, congestive cardiomyopathy, left ventricular hypertrophy, right ventricular hypertrophy, post-infarction heart rupture, ventricular septal rupture, heart valve diseases, myocardial diseases, myocardial ischemia, pericardial effusion, pericarditis (including constrictive and tuberculous), pneumopericardium, postpericardiotomy syndrome, pulmonary heart disease, rheumatic heart disease, ventricular dysfunction, hyperemia, cardiovascular pregnancy complications, Scimitar Syndrome, cardiovascular syphilis, and cardiovascular tuberculosis.

Arrhythmias include, but are not limited to, sinus arrhythmia, atrial fibrillation, atrial flutter, bradycardia, extrasystole, Adams-Stokes Syndrome, bundle-branch block, sinoatrial block, long QT syndrome, parasystole, Lown-Ganong-Levine Syndrome, Mahaim-type pre-excitation syndrome, Wolff-Parkinson-White syndrome, sick sinus syndrome, tachycardias, and ventricular fibrillation. Tachycardias include paroxysmal tachycardia, supraventricular tachycardia, accelerated idioventricular rhythm, atrioventricular nodal reentry tachycardia, ectopic atrial tachycardia, ectopic junctional tachycardia, sinoatrial nodal reentry tachycardia, sinus tachycardia, Torsades de Pointes, and ventricular tachycardia.

Heart valve diseases include, but are not limited to, aortic valve insufficiency, aortic valve stenosis, hear murmurs, aortic valve prolapse, mitral valve prolapse, tricuspid valve prolapse, mitral valve insufficiency, mitral valve stenosis, pulmonary atresia, pulmonary valve insufficiency, pulmonary valve stenosis, tricuspid atresia, tricuspid valve insufficiency, and tricuspid valve stenosis.

Myocardial diseases include, but are not limited to, alcoholic cardiomyopathy, congestive cardiomyopathy, hypertrophic cardiomyopathy, aortic subvalvular stenosis, pulmonary subvalvular stenosis, restrictive cardiomyopathy, Chagas cardiomyopathy, endocardial fibroelastosis, endomyocardial fibrosis, Kearns Syndrome, myocardial reperfusion injury, and myocarditis.

Myocardial ischemias include, but are not limited to, coronary disease, such as angina pectoris, coronary aneurysm, coronary arteriosclerosis, coronary thrombosis, coronary vasospasm, myocardial infarction and myocardial stunning.

Cardiovascular diseases also include vascular diseases such as aneurysms, angiodysplasia, angiomatosis, bacillary angiomatosis, Hippel-Lindau Disease, Klippel-Trenaunay-Weber Syndrome, Sturge-Weber Syndrome, angioneurotic edema, aortic diseases, Takayasu's Arteritis, aortitis, Leriche's Syndrome, arterial occlusive diseases, arteritis, enarteritis, polyarteritis nodosa, cerebrovascular disorders, diabetic angiopathies, diabetic rentinopathy, embolisms, thrombosis, erythromelalgia, hemorrhoids, hepatic veno-occlusive disease, hypertension, hypotension, ischemia, peripheral vascular diseases, phlebitis, pulmonary veno-occlusive disease, Raynaud's disease, CREST syndrome, retinal vein occlusion, Scimitar syndrome, superior vena cava syndrome, telangiectasia, atacia telangiectasia, hereditary hemorrhagic telangiectasia, varicocele, varicose veins, varicose ulcer, vasculitis, and venous insufficiency.

Aneurysms include, but are not limited to, dissecting aneurysms, false aneurysms, infected aneurysms, ruptured aneurysms, aortic aneurysms, cerebral aneurysms, coronary aneurysms, heart aneurysms, and iliac aneurysms.

Arterial occlusive diseases include, but are not limited to, arteriosclerosis, intermittent claudication, carotid stenosis, fibromuscular dysplasias, mesenteric vascular occlusion, Moyamoya disease, renal artery obstruction, retinal artery occlusion, and thromoangitis obliterans.

Cerebrovascular disorders include, but are not limited to, carotid artery diseases, cerebral amyloid angiopathy, cerebral aneurysm, cerebral anoxia, cerebral arteriosclerosis, cerebral arteriovenous malformation, cerebral artery diseases, cerebral embolism and thrombosis, carotid artery thrombosis, sinus thrombosis, Wallenberg's syndrome, cerebral hemorrhage, epidural hematoma, subdural hematoma, subaraxhnoid hemorrhage, cerebral infarction, cerebral ischemia (including transient), subclavian steal syndrome, periventricular leukomalacia, vascular headache, cluster headache, migraine, and vertebrobasilar insufficiency.

Embolisms include, but are not limited to, air embolisms, amniotic fluid embolisms, cholesterol embolisms, blue toe syndrome, fat embolisms, pulmonary embolisms, and thromoboembolisms. Thrombosis include, but are not limited to, coronary thrombosis, hepatic vein thrombosis, retinal vein occlusion, carotid artery thrombosis, sinus thrombosis, Wallenberg's syndrome, and thrombophlebitis.

Ischemic disorders include, but are not limited to, cerebral ischemia, ischemic colitis, compartment syndromes, anterior compartment syndrome, myocardial ischemia, reperfusion injuries, and peripheral limb ischemia. Vasculitis includes, but is not limited to, aortitis, arteritis, Behcet's Syndrome, Churg-Strauss Syndrome, mucocutaneous lymph node syndrome, thromboangitis obliterans, hypersensitivity vasculitis, Schoenlein-Henoch purpura, allergic cutaneous vasculitis, and Wegener's granulomatosis.

Polypeptides may be administered using any method known in the art, including, but not limited to, direct needle injection at the delivery site, intravenous injection, topical administration, catheter infusion, biolistic injectors, particle accelerators, gelfoam sponge depots, other commercially available depot materials, osmotic pumps, oral or suppositorial solid pharmaceutical formulations, decanting or topical applications during surgery, aerosol delivery. Such methods are known in the art. Polypeptides may be administered as part of a Therapeutic, described in more detail below. Methods of delivering polynucleotides are described in more detail herein.

Respiratory Disorders

Polynucleotides or polypeptides, or agonists or antagonists of the present invention may be used to treat, prevent, diagnose, and/or prognose diseases and/or disorders of the respiratory system.

Diseases and disorders of the respiratory system include, but are not limited to, nasal vestibulitis, nonallergic rhinitis (e.g., acute rhinitis, chronic rhinitis, atrophic rhinitis, vasomotor rhinitis), nasal polyps, and sinusitis, juvenile angiofibromas, cancer of the nose and juvenile papillomas, vocal cord polyps, nodules (singer's nodules), contact ulcers, vocal cord paralysis, laryngoceles, pharyngitis (e.g., viral and bacterial), tonsillitis, tonsillar cellulitis, parapharyngeal abscess, laryngitis, laryngoceles, and throat cancers (e.g., cancer of the nasopharynx, tonsil cancer, larynx cancer), lung cancer (e.g., squamous cell carcinoma, small cell (oat cell) carcinoma, large cell carcinoma, and adenocarcinoma), allergic disorders (eosinophilic pneumonia, hypersensitivity pneumonitis (e.g., extrinsic allergic alveolitis, allergic interstitial pneumonitis, organic dust pneumoconiosis, allergic bronchopulmonary aspergillosis, asthma, Wegener's granulomatosis (granulomatous vasculitis), Goodpasture's syndrome)), pneumonia (e.g., bacterial pneumonia (e.g., *Streptococcus pneumoniae* (pneumoncoccal pneumonia), *Staphylococcus aureus* (staphylococcal pneumonia), Gram-negative bacterial pneumonia (caused by, e.g., *Klebsiella* and *Pseudomas* spp.), *Mycoplasma pneumoniae* pneumonia, *Hemophilus influenzae* pneumonia, *Legionella pneumophila* (Legionnaires' disease), and *Chlamydia psittaci* (Psittacosis)), and viral pneumonia (e.g., influenza, chickenpox (varicella).

Additional diseases and disorders of the respiratory system include, but are not limited to bronchiolitis, polio (poliomyelitis), croup, respiratory syncytial viral infection, mumps, erythema infectiosum (fifth disease), roseola infantum, progressive rubella panencephalitis, german measles, and subacute sclerosing panencephalitis), fungal pneumonia (e.g., Histoplasmosis, Coccidioidomycosis, Blastomycosis, fungal infections in people with severely suppressed immune systems (e.g., cryptococcosis, caused by *Cryptococcus neoformans*; aspergillosis, caused by *Aspergillus* spp.; candidiasis, caused by *Candida*; and mucormycosis)), *Pneumocystis carinii* (pneumocystis pneumonia), atypical pneumonias (e.g., *Mycoplasma* and *Chlamydia* spp.), opportunistic infection pneumonia, nosocomial pneumonia, chemical pneumonitis, and aspiration pneumonia, pleural disorders (e.g., pleurisy, pleural effusion, and pneumothorax (e.g., simple spontaneous pneumothorax, complicated spontaneous pneumothorax, tension pneumothorax)), obstructive airway diseases (e.g., asthma, chronic obstructive pulmonary disease (COPD), emphysema, chronic or acute bronchitis), occupational lung diseases (e.g., silicosis, black lung (coal workers' pneumoconiosis), asbestosis, berylliosis, occupational asthsma, byssinosis, and benign pneumoconioses), Infiltrative Lung Disease (e.g., pulmonary fibrosis (e.g., fibrosing alveolitis, usual interstitial pneumonia), idiopathic pulmonary fibrosis, desquamative interstitial pneumonia, lymphoid interstitial pneumonia, histiocytosis X (e.g., Letterer-Siwe disease, Hand-Schüller-Christian disease, eosinophilic granuloma), idiopathic pulmonary hemosiderosis, sarcoidosis and pulmonary alveolar proteinosis), Acute respiratory distress syndrome (also called, e.g., adult respiratory distress syndrome), edema, pulmonary embolism, bronchitis (e.g., viral, bacterial), bronchiectasis, atelectasis, lung abscess (caused by, e.g., *Staphylococcus aureus* or *Legionella pneumophila*), and cystic fibrosis.

Blood-Related Disorders

The polynucleotides, polypeptides, antibodies, and/or agonists or antagonists of the present invention may be used to modulate hemostatic (the stopping of bleeding) or thrombolytic (clot dissolving) activity. For example, by increasing hemostatic or thrombolytic activity, polynucleotides or polypeptides, and/or agonists or antagonists of the present invention could be used to treat or prevent blood coagulation diseases, disorders, and/or conditions (e.g., afibrinogenemia, factor deficiencies, hemophilia), blood platelet diseases, disorders, and/or conditions (e.g., thrombocytopenia), or wounds resulting from trauma, surgery, or other causes. Alternatively, polynucleotides, polypeptides, antibodies, and/or agonists or antagonists of the present invention that can decrease hemostatic or thrombolytic activity could be used to inhibit or dissolve clotting. These molecules could be important in the treatment or prevention of heart attacks (infarction), strokes, or scarring.

In specific embodiments, the polynucleotides, polypeptides, antibodies, and/or agonists or antagonists of the present invention may be used to prevent, diagnose, prognose, and/or treat thrombosis, arterial thrombosis, venous thrombosis, thromboembolism, pulmonary embolism, atherosclerosis, myocardial infarction, transient ischemic attack, unstable angina. In specific embodiments, the polynucleotides, polypeptides, antibodies, and/or agonists or antagonists of the present invention may be used for the prevention of occlusion of saphenous grafts, for reducing the risk of periprocedural thrombosis as might accompany angioplasty procedures, for reducing the risk of stroke in patients with atrial fibrillation including nonrheumatic atrial fibrillation, for reducing the risk of embolism associated with mechanical heart valves and or mitral valves disease. Other uses for the polynucleotides, polypeptides, antibodies, and/or agonists or antagonists of the present invention, include, but are not limited to, the prevention of occlusions in extrcorporeal devices (e.g., intravascular canulas, vascular access shunts in hemodialysis patients, hemodialysis machines, and cardiopulmonary bypass machines).

In another embodiment, a polypeptide of the invention, or polynucleotides, polypeptides, agonists, or antagonists corresponding to that polypeptide, may be used to prevent, diagnose, prognose, and/or treat diseases and disorders of the blood and/or blood forming organs associated with the tissue (s) in which the polypeptide of the invention is expressed.

The polynucleotides, polypeptides, antibodies, and/or agonists or antagonists of the present invention may be used to modulate hematopoietic activity (the formation of blood cells). For example, the polynucleotides, polypeptides, antibodies, and/or agonists or antagonists of the present invention may be used to increase the quantity of all or subsets of blood cells, such as, for example, erythrocytes, lymphocytes (B or T cells), myeloid cells (e.g., basophils, eosinophils, neutrophils, mast cells, macrophages) and platelets. The ability to decrease the quantity of blood cells or subsets of blood cells may be useful in the prevention, detection, diagnosis and/or treatment of anemias and leukopenias described below. Alternatively, the polynucleotides, polypeptides, antibodies, and/ or agonists or antagonists of the present invention may be used to decrease the quantity of all or subsets of blood cells, such as, for example, erythrocytes, lymphocytes (B or T cells), myeloid cells (e.g., basophils, eosinophils, neutrophils, mast cells, macrophages) and platelets. The ability to decrease the quantity of blood cells or subsets of blood cells may be useful in the prevention, detection, diagnosis and/or treatment of leukocytoses, such as, for example eosinophilia.

The polynucleotides, polypeptides, antibodies, and/or agonists or antagonists of the present invention may be used to prevent, treat, or diagnose blood dyscrasia.

Anemias are conditions in which the number of red blood cells or amount of hemoglobin (the protein that carries oxygen) in them is below normal. Anemia may be caused by excessive bleeding, decreased red blood cell production, or increased red blood cell destruction (hemolysis). The polynucleotides, polypeptides, antibodies, and/or agonists or antagonists of the present invention may be useful in treating, preventing, and/or diagnosing anemias. Anemias that may be treated prevented or diagnosed by the polynucleotides, polypeptides, antibodies, and/or agonists or antagonists of the present invention include iron deficiency anemia, hypochromic anemia, microcytic anemia, chlorosis, hereditary siderob; astic anemia, idiopathic acquired sideroblastic anemia, red cell aplasia, megaloblastic anemia (e.g., pernicious anemia, (vitamin B12 deficiency) and folic acid deficiency anemia), aplastic anemia, hemolytic anemias (e.g., autoimmune helolytic anemia, microangiopathic hemolytic anemia, and paroxysmal nocturnal hemoglobinuria). The polynucleotides, polypeptides, antibodies, and/or agonists or antagonists of the present invention may be useful in treating, preventing, and/or diagnosing anemias associated with diseases including but not limited to, anemias associated with systemic lupus erythematosus, cancers, lymphomas, chronic renal disease, and enlarged spleens. The polynucleotides, polypeptides, antibodies, and/or agonists or antagonists of the present invention may be useful in treating, preventing, and/ or diagnosing anemias arising from drug treatments such as anemias associated with methyldopa, dapsone, and/or sulfadrugs. Additionally, rhe polynucleotides, polypeptides, antibodies, and/or agonists or antagonists of the present invention may be useful in treating, preventing, and/or diagnosing anemias associated with abnormal red blood cell architecture including but not limited to, hereditary spherocytosis, hereditary elliptocytosis, glucose-6-phosphate dehydrogenase deficiency, and sickle cell anemia.

The polynucleotides, polypeptides, antibodies, and/or agonists or antagonists of the present invention may be useful in treating, preventing, and/or diagnosing hemoglobin abnormalities, (e.g., those associated with sickle cell anemia, hemoglobin C disease, hemoglobin S-C disease, and hemoglobin E disease). Additionally, the polynucleotides, polypeptides, antibodies, and/or agonists or antagonists of the present invention may be useful in diagnosing, prognosing, preventing, and/or treating thalassemias, including, but not limited to major and minor forms of alpha-thalassemia and beta-thalassemia.

In another embodiment, the polynucleotides, polypeptides, antibodies, and/or agonists or antagonists of the present invention may be useful in diagnosing, prognosing, preventing, and/or treating bleeding disorders including, but not limited to, thrombocytopenia (e.g., idiopathic thrombocytopenic purpura, and thrombotic thrombocytopenic purpura), Von Willebrand's disease, hereditary platelet disorders (e.g., storage pool disease such as Chediak-Higashi and Hermansky-Pudlak syndromes, thromboxane A2 dysfunction, thromboasthenia, and Bernard-Soulier syndrome), hemolytic-uremic syndrome, hemophelias such as hemophelia A or Factor VII deficiency and Christmas disease or Factor IX deficiency, Hereditary Hemorhhagic Telangiectsia, also known as Rendu-Osler-Weber syndrome, allergic purpura (Henoch Schonlein purpura) and disseminated intravascular coagulation.

The effect of the polynucleotides, polypeptides, antibodies, and/or agonists or antagonists of the present invention on the clotting time of blood may be monitored using any of the clotting tests known in the art including, but not limited to, whole blood partial thromboplastin time (PTT), the activated partial thromboplastin time (aPTT), the activated clotting time (ACT), the recalcified activated clotting time, or the Lee-White Clotting time.

Several diseases and a variety of drugs can cause platelet dysfunction. Thus, in a specific embodiment, the polynucleotides, polypeptides, antibodies, and/or agonists or antagonists of the present invention may be useful in diagnosing, prognosing, preventing, and/or treating acquired platelet dysfunction such as platelet dysfunction accompanying kidney failure, leukemia, multiple myeloma, cirrhosis of the liver, and systemic lupus erythematosus as well as platelet dysfunction associated with drug treatments, including treatment with aspirin, ticlopidine, nonsteroidal anti-inflammatory drugs (used for arthritis, pain, and sprains), and penicillin in high doses.

In another embodiment, the polynucleotides, polypeptides, antibodies, and/or agonists or antagonists of the present invention may be useful in diagnosing, prognosing, preventing, and/or treating diseases and disorders characterized by or associated with increased or decreased numbers of white blood cells. Leukopenia occurs when the number of white blood cells decreases below normal. Leukopenias include, but are not limited to, neutropenia and lymphocytopenia. An increase in the number of white blood cells compared to normal is known as leukocytosis. The body generates increased numbers of white blood cells during infection. Thus, leukocytosis may simply be a normal physiological parameter that reflects infection. Alternatively, leukocytosis may be an indicator of injury or other disease such as cancer. Leokocytoses, include but are not limited to, eosinophilia, and accumulations of macrophages. In specific embodiments, the polynucleotides, polypeptides, antibodies, and/or agonists or antagonists of the present invention may be useful in diagnosing, prognosing, preventing, and/or treating leukopenia. In other specific embodiments, the polynucleotides, polypeptides, antibodies, and/or agonists or antagonists of the present invention may be useful in diagnosing, prognosing, preventing, and/or treating leukocytosis.

Leukopenia may be a generalized decreased in all types of white blood cells, or may be a specific depletion of particular types of white blood cells. Thus, in specific embodiments, the polynucleotides, polypeptides, antibodies, and/or agonists or antagonists of the present invention may be useful in diagnosing, prognosing, preventing, and/or treating decreases in neutrophil numbers, known as neutropenia. Neutropenias that may be diagnosed, prognosed, prevented, and/or treated by the polynucleotides, polypeptides, antibodies, and/or agonists or antagonists of the present invention include, but are not limited to, infantile genetic agranulocytosis, familial neutropenia, cyclic neutropenia, neutropenias resulting from or associated with dietary deficiencies (e.g., vitamin B12 deficiency or folic acid deficiency), neutropenias resulting from or associated with drug treatments (e.g., antibiotic regimens such as penicillin treatment, sulfonamide treatment, anticoagulant treatment, anticonvulsant drugs, anti-thyroid drugs, and cancer chemotherapy), and neutropenias resulting from increased neutrophil destruction that may occur in association with some bacterial or viral infections, allergic disorders, autoimmune diseases, conditions in which an individual has an enlarged spleen (e.g., Felty syndrome, malaria and sarcoidosis), and some drug treatment regimens.

The polynucleotides, polypeptides, antibodies, and/or agonists or antagonists of the present invention may be useful in diagnosing, prognosing, preventing, and/or treating lymphocytopenias (decreased numbers of B and/or T lymphocytes), including, but not limited lymphocytopenias resulting from or associated with stress, drug treatments (e.g., drug treatment with corticosteroids, cancer chemotherapies, and/or radiation therapies), AIDS infection and/or other diseases such as, for example, cancer, rheumatoid arthritis, systemic lupus erythematosus, chronic infections, some viral infections and/or hereditary disorders (e.g., DiGeorge syndrome, Wiskott-Aldrich Syndome, severe combined immunodeficiency, ataxia telangiectasia).

The polynucleotides, polypeptides, antibodies, and/or agonists or antagonists of the present invention may be useful in diagnosing, prognosing, preventing, and/or treating diseases and disorders associated with macrophage numbers and/or macrophage function including, but not limited to, Gaucher's disease, Niemann-Pick disease, Letterer-Siwe disease and Hand-Schuller-Christian disease.

In another embodiment, the polynucleotides, polypeptides, antibodies, and/or agonists or antagonists of the present invention may be useful in diagnosing, prognosing, preventing, and/or treating diseases and disorders associated with eosinophil numbers and/or eosinophil function including, but not limited to, idiopathic hypereosinophilic syndrome, eosinophilia-myalgia syndrome, and Hand-Schuller-Christian disease.

In yet another embodiment, the polynucleotides, polypeptides, antibodies, and/or agonists or antagonists of the present invention may be useful in diagnosing, prognosing, preventing, and/or treating leukemias and lymphomas including, but not limited to, acute lymphocytic (lymphpblastic), leukemia (ALL), acute myeloid (myelocytic, myelogenous, myeloblastic, or myelomonocytic) leukemia, chronic lymphocytic leukemia (e.g., B cell leukemias, T cell leukemias, Sezary syndrome, and Hairy cell leukenia), chronic myelocytic (myeloid, myclogenous, or granulocytic) leukemia, Hodgkin's lymphoma, non-hodgkin's lymphoma, Burkitt's lymphoma, and mycosis fungoides.

In other embodiments, the polynucleotides, polypeptides, antibodies, and/or agonists or antagonists of the present invention may be useful in diagnosing, prognosing, preventing, and/or treating diseases and disorders of plasma cells including, but not limited to, plasma cell dyscrasias, monoclonal gammaopathies, monoclonal gammopathies of undetermined significance, multiple myeloma, macroglobulinemia, Waldenstrom's macroglobulinemia, cryoglobulinemia, and Raynaud's phenomenon.

In other embodiments, the polynucleotides, polypeptides, antibodies, and/or agonists or antagonists of the present invention may be useful in treating, preventing, and/or diagnosing myeloproliferative disorders, including but not limited to, polycythemia vera, relative polycythemia, secondary polycythemia, myelofibrosis, acute myelofibrosis, agnogenic myelod metaplasia, thrombocythemia, (including both primary and seconday thrombocythemia) and chronic myelocytic leukemia.

In other embodiments, the polynucleotides, polypeptides, antibodies, and/or agonists or antagonists of the present invention may be useful as a treatment prior to surgery, to increase blood cell production.

In other embodiments, the polynucleotides, polypeptides, antibodies, and/or agonists or antagonists of the present invention may be useful as an agent to enhance the migration, phagocytosis, superoxide production, antibody dependent cellular cytotoxicity of neutrophils, eosionophils and macrophages.

In other embodiments, the polynucleotides, polypeptides, antibodies, and/or agonists or antagonists of the present invention may be useful as an agent to increase the number of stem cells in circulation prior to stem cells pheresis. In another specific embodiment, the polynucleotides, polypeptides, antibodies, and/or agonists or antagonists of the present invention may be useful as an agent to increase the number of stem cells in circulation prior to platelet pheresis.

In other embodiments, the polynucleotides, polypeptides, antibodies, and/or agonists or antagonists of the present invention may be useful as an agent to increase cytokine production.

In other embodiments, the polynucleotides, polypeptides, antibodies, and/or agonists or antagonists of the present invention may be useful in preventing, diagnosing, and/or treating primary hematopoietic disorders.

Other Activities

A polypeptide, polynucleotide, agonist, or antagonist of the present invention, as a result of the ability to stimulate vascular endothelial cell growth, may be employed in treatment for stimulating re-vascularization of ischemic tissues due to various disease conditions such as thrombosis, arteriosclerosis, and other cardiovascular conditions. The polypeptide, polynucleotide, agonist, or antagonist of the present invention may also be employed to stimulate angiogenesis and limb regeneration, as discussed above.

A polypeptide, polynucleotide, agonist, or antagonist of the present invention may also be employed for treating wounds due to injuries, burns, post-operative tissue repair, and ulcers since they are mitogenic to various cells of different origins, such as fibroblast cells and skeletal muscle cells, and therefore, facilitate the repair or replacement of damaged or diseased tissue.

A polypeptide, polynucleotide, agonist, or antagonist of the present invention may also be employed stimulate neuronal growth and to treat and prevent neuronal damage which occurs in certain neuronal disorders or neuro-degenerative conditions such as Alzheimer's disease, Parkinson's disease, and AIDS-related complex. A polypeptide, polynucleotide, agonist, or antagonist of the present invention may have the ability to stimulate chondrocyte growth, therefore, they may be employed to enhance bone and periodontal regeneration and aid in tissue transplants or bone grafts.

A polypeptide, polynucleotide, agonist, or antagonist of the present invention may be also be employed to prevent skin aging due to sunburn by stimulating keratinocyte growth.

A polypeptide, polynucleotide, agonist, or antagonist of the present invention may also be employed for preventing hair loss, since FGF family members activate hair-forming cells and promotes melanocyte growth. Along the same lines, a polypeptide, polynucleotide, agonist, or antagonist of the present invention may be employed to stimulate growth and differentiation of hematopoietic cells and bone marrow cells when used in combination with other cytokines.

A polypeptide, polynucleotide, agonist, or antagonist of the present invention may also be employed to maintain organs before transplantation or for supporting cell culture of primary tissues. A polypeptide, polynucleotide, agonist, or antagonist of the present invention may also be employed for inducing tissue of mesodermal origin to differentiate in early embryos.

A polypeptide, polynucleotide, agonist, or antagonist of the present invention may also increase or decrease the differentiation or proliferation of embryonic stem cells, besides, as discussed above, hematopoietic lineage.

A polypeptide, polynucleotide, agonist, or antagonist of the present invention may also be used to modulate mammalian characteristics, such as body height, weight, hair color, eye color, skin, percentage of adipose tissue, pigmentation, size, and shape (e.g., cosmetic surgery). Similarly, a polypeptide, polynucleotide, agonist, or antagonist of the present invention may be used to modulate mammalian metabolism affecting catabolism, anabolism, processing, utilization, and storage of energy.

A polypeptide, polynucleotide, agonist, or antagonist of the present invention may be used to treat weight disorders, including but not limited to, obesity, cachexia, wasting disease, anorexia, and bulimia.

A polypeptide, polynucleotide, agonist, or antagonist of the present invention may be used to change a mammal's mental state or physical state by influencing biorhythms, caricadic rhythms, depression (including depressive disorders), tendency for violence, tolerance for pain, reproductive capabilities (preferably by Activin or Inhibin-like activity), hormonal or endocrine levels, appetite, libido, memory, stress, or other cognitive qualities.

A polypeptide, polynucleotide, agonist, or antagonist of the present invention may also be used as a food additive or preservative, such as to increase or decrease storage capabilities, fat content, lipid, protein, carbohydrate, vitamins, minerals, cofactors or other nutritional components.

The above-recited applications have uses in a wide variety of hosts. Such hosts include, but are not limited to, human, murine, rabbit, goat, guinea pig, camel, horse, mouse, rat, hamster, pig, micro-pig, chicken, goat, cow, sheep, dog, cat, non-human primate, and human. In specific embodiments, the host is a mouse, rabbit, goat, guinea pig, chicken, rat, hamster, pig, sheep, dog or cat. In preferred embodiments, the host is a mammal. In most preferred embodiments, the host is a human.

The compounds may be employed in combination with a suitable pharmaceutical carrier. Such compositions comprise a therapeutically effective amount of the compound and a pharmaceutically acceptable carrier or excipient. Such a carrier includes but is not limited to saline, buffered saline, dextrose, water, glycerol, ethanol, and combinations thereof. The formulation should suit the mode of administration.

The invention also provides a pharmaceutical pack or kit comprising one or more containers filled with one or more of the ingredients of the pharmaceutical compositions of the invention. Associated with such container(s) can be a notice in the form prescribed by a governmental agency regulating the manufacture, use or sale of pharmaceuticals or biological products, which notice reflects approval by the agency of manufacture, use or sale for human administration. In addition, the compounds of the present invention may be employed in conjunction with other therapeutic compounds.

The pharmaceutical compositions may be administered in a convenient manner such as by the topical, intravenous, intraperitoneal, intramuscular, subcutaneous, intranasal or intradermal routes. The pharmaceutical compositions are administered in an amount which is effective for treating and/or prophylaxis of the specific indication. In general, the pharmaceutical compositions will be administered in an amount of at least about 10 µg/kg body weight and in most cases they will be administered in an amount not in excess of about 8 mg/Kg body weight per day. In most cases, the dosage is from about 10 µg/kg to about 1 mg/kg body weight daily, taking into account the routes of administration, symptoms, etc.

Gene Therapy

The soluble G-protein chemokine receptor polypeptides and antagonists or agonists which are polypeptides, may also be employed in accordance with the present invention by expression of such polypeptides in vivo, which is often referred to as "gene therapy."

Thus, for example, cells from a patient may be engineered with a polynucleotide (DNA or RNA) encoding a polypeptide ex vivo, with the engineered cells then being provided to a patient to be treated with the polypeptide. Such methods are well-known in the art. For example, cells may be engineered by procedures known in the art by use of a retroviral particle containing RNA encoding a polypeptide of the present invention.

Similarly, cells may be engineered in vivo for expression of a polypeptide in vivo by, for example, procedures known in the art. As known in the art, a producer cell for producing a retroviral particle containing RNA encoding the polypeptide of the present invention may be administered to a patient for engineering cells in vivo and expression of the polypeptide in vivo. These and other methods for administering a polypeptide of the present invention by such method should be apparent to those skilled in the art from the teachings of the present invention. For example, the expression vehicle for engineering cells may be other than a retrovirus, for example, an adenovirus which may be used to engineer cells in vivo after combination with a suitable delivery vehicle.

Retroviruses from which the retroviral plasmid vectors hereinabove mentioned may be derived include, but are not limited to, Moloney Murine Leukemia Virus, spleen necrosis virus, retroviruses such as Rous Sarcoma Virus, Harvey Sarcoma Virus, avian leukosis virus, gibbon ape leukemia virus, human immunodeficiency virus, adenovirus, Myeloproliferative Sarcoma Virus, and mammary tumor virus. In one embodiment, the retroviral plasmid vector is derived from Moloney Murine Leukemia Virus.

The vector includes one or more promoters. Suitable promoters which may be employed include, but are not limited to, the retroviral LTR; the SV40 promoter; and the human cytomegalovirus (CMV) promoter described in Miller, et al., *Biotechniques*, Vol. 7, No. 9, 980-990 (1989), or any other promoter (e.g., cellular promoters such as eukaryotic cellular promoters including, but not limited to, the histone, pol III, and β-actin promoters). Other viral promoters which may be employed include, but are not limited to, adenovirus promoters, thymidine kinase (TK) promoters, and B19 parvovirus promoters. The selection of a suitable promoter will be apparent to those skilled in the art from the teachings contained herein.

The nucleic acid sequence encoding the polypeptide of the present invention is under the control of a suitable promoter. Suitable promoters which may be employed include, but are not limited to, adenoviral promoters, such as the adenoviral major late promoter; or hetorologous promoters, such as the cytomegalovirus (CMV) promoter; the respiratory syncytial virus (RSV) promoter; inducible promoters, such as the MMT promoter, the metallothionein promoter; heat shock promoters; the albumin promoter; the ApoAI promoter; human globin promoters; viral thymidine kinase promoters, such as the Herpes Simplex thymidine kinase promoter; retroviral LTRs (including the modified retroviral LTRs hereinabove described); the β-actin promoter; and human growth hormone promoters. The promoter also may be the native promoter which controls the genes encoding the polypeptides.

The retroviral plasmid vector is employed to transduce packaging cell lines to form producer cell lines. Examples of packaging cells which may be transfected include, but are not limited to, the PE501, PA317, ψ-2, ψ-AM, PA12, T19-14X, VT-19-17-H2, ψCRE, ψCRIP, GP+E-86, GP+envAm12, and DAN cell lines as described in Miller, *Human Gene Therapy*, Vol. 1, pgs. 5-14 (1990), which is incorporated herein by reference in its entirety. The vector may transduce the packaging cells through any means known in the art. Such means include, but are not limited to, electroporation, the use of liposomes, and $CaPO_4$ precipitation. In one alternative, the retroviral plasmid vector may be encapsulated into a liposome, or coupled to a lipid, and then administered to a host.

The producer cell line generates infectious retroviral vector particles which include the nucleic acid sequence(s) encoding the polypeptides. Such retroviral vector particles then may be employed, to transduce eukaryotic cells, either in vitro or in vivo. The transduced eukaryotic cells will express the nucleic acid sequence(s) encoding the polypeptide. Eukaryotic cells which may be transduced include, but are not limited to, embryonic stem cells, embryonic carcinoma cells, as well as hematopoietic stem cells, hepatocytes, fibroblasts, myoblasts, keratinocytes, endothelial cells, and bronchial epithelial cells.

The present invention also provides a method for determining whether a ligand not known to be capable of binding to a G-protein chemokine receptor can bind to such receptor which comprises contacting a mammalian cell which expresses a G-protein chemokine receptor with the ligand under conditions permitting binding of ligands to the G-protein chemokine receptor, detecting the presence of a ligand which binds to the receptor and thereby determining whether the ligand binds to the G-protein chemokine receptor. The systems hereinabove described for determining agonists and/or antagonists may also be employed for determining ligands which bind to the receptor.

This invention also provides a method of detecting expression of a G-protein chemokine receptor polypeptide of the present invention on the surface of a cell by detecting the presence of mRNA coding for the receptor which comprises obtaining total mRNA from the cell and contacting the mRNA so obtained with a nucleic acid probe comprising a nucleic acid molecule of at least 10 nucleotides capable of specifically hybridizing with a sequence included within the sequence of a nucleic acid molecule encoding the receptor under hybridizing conditions, detecting the presence of mRNA hybridized to the probe, and thereby detecting the expression of the receptor by the cell.

The present invention also provides a method for identifying receptors related to the receptor polypeptides of the present invention. These related receptors may be identified by homology to a G-protein chemokine receptor polypeptide of the present invention, by low stringency cross hybridization, or by identifying receptors that interact with related natural or synthetic ligands and or elicit similar behaviors after genetic or pharmacological blockade of the chemokine receptor polypeptides of the present invention.

The present invention also contemplates the use of the gene of the present invention as a diagnostic, for example, some diseases result from inherited defective genes. These genes can be detected by comparing the sequences of the defective gene with that of a normal one. Subsequently, one can verify that a "mutant" gene is associated with abnormal receptor activity. In addition, one can insert mutant receptor genes into a suitable vector for expression in a functional assay system (e.g., calorimetric assay, expression on MacConkey plates, complementation experiments, in a receptor deficient strain of HEK293 cells) as yet another means to verify or identify mutations. Once "mutant" genes have been identified, one can then screen population for carriers of the "mutant" receptor gene.

Individuals carrying mutations in the gene of the present invention may be detected at the DNA level by a variety of techniques. Nucleic acids used for diagnosis may be obtained from a patient's cells, including but not limited to such as from blood, urine, saliva, tissue biopsy and autopsy material. The genomic DNA may be used directly for detection or may be amplified enzymatically by using PCR (Saiki, et al., *Nature*, 324:163-166 1986) prior to analysis. RNA or cDNA may also be used for the same purpose. As an example, PCR primers complimentary to the nucleic acid of the instant invention can be used to identify and analyze mutations in the gene of the present invention. For example, deletions and insertions can be detected by a change in size of the amplified product in comparison to the normal genotype. Point mutations can be identified by hybridizing amplified DNA to radio labeled RNA of the invention or alternatively, radio labeled antisense DNA sequences of the invention. Perfectly matched sequences can be distinguished from mismatched duplexes by RNase A digestion or by differences in melting temperatures. Such a diagnostic would be particularly useful for prenatal or even neonatal testing.

Sequence differences between the reference gene and "mutants" may be revealed by the direct DNA sequencing method. In addition, cloned DNA segments may be used as probes to detect specific DNA segments. The sensitivity of this method is greatly enhanced when combined with PCR. For example, a sequence primer is used with double stranded PCR product or a single stranded template molecule generated by a modified PCR. The sequence determination is performed by conventional procedures with radio labeled nucleotide or by an automatic sequencing procedure with fluorescent-tags.

Genetic testing based on DNA sequence differences may be achieved by detection of alterations in the electrophoretic mobility of DNA fragments in gels with or without denaturing agents. Sequences changes at specific locations may also be revealed by nucleus protection assays, such RNase and S1 protection or the chemical cleavage method (e.g. Cotton, et al., *PNAS, USA*, 85:4397-4401 1985).

In addition, some diseases are a result of, or are characterized by changes in gene expression which can be detected by changes in the mRNA. Alternatively, the genes of the present invention can be used as a reference to identify individuals expressing a decrease of functions associated with receptors of this type.

The present invention also relates to a diagnostic assay for detecting altered levels of soluble form of the G-protein chemokine receptor polypeptides of the present invention in various tissues. Assays used to detect levels of the soluble receptor polypeptides in a sample derived from a host are well known to those of skill in the art and include radioimmunoassays, competitive-binding assays, Western blot analysis and preferably as ELISA assay.

An ELISA assay initially comprises preparing an antibody specific to antigens of the G-protein chemokine receptor polypeptides, preferably a monoclonal antibody. In addition a reporter antibody is prepared against the monoclonal antibody. To the reporter antibody is attached a detectable reagent such as radioactivity, fluorescence or in this example a horseradish peroxidase enzyme. A sample is now removed from a host and incubated on a solid support, e.g. a polystyrene dish, that binds the proteins in the sample. Any free protein binding sites on the dish are then covered by incubating with a nonspecific protein such as bovine serum albumin. Next, the monoclonal antibody is incubated in the dish during which time the monoclonal antibodies attach to any G-protein chemokine receptor proteins attached to the polystyrene dish. All unbound monoclonal antibody is washed out with buffer. The reporter antibody linked to horseradish peroxidase is now placed in the dish resulting in binding of the reporter antibody to any monoclonal antibody bound to G-protein chemokine receptor proteins. Unattached reporter antibody is then washed out. Peroxidase substrates are then added to the dish and the amount of color developed in a given time period is a measurement of the amount of G-protein chemokine receptor proteins present in a given volume of patient sample when compared against a standard curve.

Chromosome Assays

The nucleic acid molecules of the present invention are also valuable for chromosome identification.

The sequences of the present invention are also valuable for chromosome identification. The sequence is specifically targeted to and can hybridize with a particular location on an individual human chromosome. Moreover, there is a current need for identifying particular sites on the chromosome. Few chromosome marking reagents based on actual sequence data (repeat polymorphisms) are presently available for marking chromosomal location. The mapping of DNAs to chromosomes according to the present invention is an important first step in correlating those sequences with genes associated with disease.

Briefly, sequences can be mapped to chromosomes by preparing PCR primers (preferably 15-25 bp) from the cDNA. Computer analysis of the cDNA is used to rapidly select primers that do not span more than one exon in the genomic DNA, thus complicating the amplification process. These primers are then used for PCR screening of somatic cell hybrids containing individual human chromosomes. Only those hybrids containing the human gene corresponding to the primer will yield an amplified fragment.

PCR mapping of somatic cell hybrids is a rapid procedure for assigning a particular DNA to a particular chromosome. Using the present invention with the same oligonucleotide primers, sublocalization can be achieved with panels of fragments from specific chromosomes or pools of large genomic clones in an analogous manner. Other mapping strategies that can similarly be used to map to its chromosome include in situ hybridization, prescreening with labeled flow-sorted chromosomes and preselection by hybridization to construct chromosome specific-cDNA libraries.

Fluorescence in situ hybridization (FISH) of a cDNA clone to a metaphase chromosomal spread can be used to provide a precise chromosomal location in one step. This technique can be used with cDNA as short as 50 or 60 bases. For a review of this technique, see Verma et al., Human Chromosomes: a Manual of Basic Techniques, Pergamon Press, New York (1988).

Once a sequence has been mapped to a precise chromosomal location, the physical position of the sequence on the chromosome can be correlated with genetic map data. Such data are found, for example, in V. McKusick, Mendelian Inheritance in Man (available on line through Johns Hopkins University Welch Medical Library). The relationship between genes and diseases that have been mapped to the same chromosomal region are then identified through linkage analysis (coinheritance of physically adjacent genes).

Next, it is necessary to determine the differences in the cDNA or genomic sequence between affected and unaffected individuals. If a mutation is observed in some or all of the affected individuals but not in any normal individuals, then the mutation is likely to be the causative agent of the disease.

With current resolution of physical mapping and genetic mapping techniques, a cDNA precisely localized to a chromosomal region associated with the disease could be one of between 50 and 500 potential causative genes. (This assumes 1 megabase mapping resolution and one gene per 20 kb).

In certain preferred embodiments in this regard, the cDNA herein disclosed is used to clone genomic DNA of a G-protein Chemokine Receptor receptor gene. This can be accomplished using a variety of well known techniques and libraries, which generally are available commercially. The genomic DNA is then used for in situ chromosome mapping using well known techniques for this purpose.

In addition, in some cases, sequences can be mapped to chromosomes by preparing PCR primers (preferably 15-25 bp) from the cDNA. Computer analysis of the 3' untranslated region of the gene is used to rapidly select primers that do not span more than one exon in the genomic DNA, thus complicating the amplification process. These primers are then used for PCR screening of somatic cell hybrids containing individual human chromosomes.

Fluorescence in situ hybridization ("FISH") of a cDNA clone to a metaphase chromosomal spread can be used to provide a precise chromosomal location in one step. This technique can be used with cDNA as short as 50 or 60 bp. For a review of this technique, see Verma et al., *Human Chromosomes: a Manual of Basic Techniques,* Pergamon Press, New York (1988).

Once a sequence has been mapped to a precise chromosomal location, the physical position of the sequence on the chromosome can be correlated with genetic map data. Such data are found, for example, in V. McKusick, *Mendelian Inheritance in Man,* available on line through Johns Hopkins University, Welch Medical Library. The relationship between genes and diseases that have been mapped to the same chromosomal region are then identified through linkage analysis (coinheritance of physically adjacent genes).

Next, it is necessary to determine the differences in the cDNA or genomic sequence between affected and unaffected individuals. If a mutation is observed in some or all of the affected individuals but not in any normal individuals, then the mutation is likely to be the causative agent of the disease.

Having generally described the invention, the same will be more readily understood by reference to the following examples, which are provided by way of illustration and are not intended as limiting. The present invention will be further described with reference to the following examples; however, it is to be understood that the present invention is not limited to such examples. All parts or amounts, unless otherwise specified, are by weight.

In order to facilitate understanding of the following examples certain frequently occurring methods and/or terms will be described.

"Plasmids" are designated by a lower case p preceded and/or followed by capital letters and/or numbers. The starting plasmids herein are either commercially available, publicly available on an unrestricted basis, or can be constructed from available plasmids in accord with published procedures. In addition, equivalent plasmids to those described are known in the art and will be apparent to the ordinarily skilled artisan.

"Digestion" of DNA refers to catalytic cleavage of the DNA with a restriction enzyme that acts only at certain sequences in the DNA. The various restriction enzymes used herein are commercially available and their reaction conditions, cofactors and other requirements were used as would be known to the ordinarily skilled artisan. For analytical purposes, typically 1 μg of plasmid or DNA fragment is used with about 2 units of enzyme in about 20 μl of buffer solution. For the purpose of isolating DNA fragments for plasmid construction, typically 5 to 50 μg of DNA are digested with 20 to 250 units of enzyme in a larger volume. Appropriate buffers and substrate amounts for particular restriction enzymes are specified by the manufacturer. Incubation times of about I hour at 37° C. are ordinarily used, but may vary in accordance with the supplier's instructions. After digestion the reaction is electrophoresed directly on a polyacrylamide gel to isolate the desired fragment.

Size separation of the cleaved fragments is performed using 8 percent polyacrylamide gel described by Goeddel, D. et al., Nucleic Acids Res., 8:4057 (1980).

"Oligonucleotides" refers to either a single stranded polydeoxynucleotide or two complementary polydeoxynucleotide strandswhich may be chemically synthesized. Such synthetic oligonucleotides have no 5' phosphate and thus will not ligate to another oligonucleotide without adding a phosphate with an ATP in the presence of a kinase. A synthetic oligonucleotide will ligate to a fragment that has not been dephosphorylated.

"Ligation" refers to the process of forming phosphodiester bonds between two double stranded nucleic acid fragments (Maniatis, T., et al., Id., p. 146). Unless otherwise provided, ligation may be accomplished using known buffers and conditions with 10 units to T4 DNA ligase ("ligase") per 0.5 μg of approximately equimolar amounts of the DNA fragments to be ligated.

Unless otherwise stated, transformation was performed as described in the method of Graham, F. and Van der Eb, A., Virology, 52:456-457 (1973).

EXAMPLES

Example 1

Bacterial Expression and Purification of HSATU68

The DNA sequence encoding for HSATU68, ATCC #97334 is initially amplified using PCR oligonucleotide primers corresponding to the 5' and sequences of the processed HSATU68 protein (minus the signal peptide sequence) and the vector sequences 3' to the HSATU68 gene. Additional nucleotides corresponding to HSATU68 were added to the 5' and 3' sequences respectively. The 5' oligonucleotide primer has the sequence 5' CGGGATCCTC-CATGGAGTTGAGGAAGTAC 3' (SEQ ID NO: 5) contains a BamHI restriction enzyme site followed by 18 nucleotides of HSATU68 coding sequence starting from the presumed terminal amino acid of the protein. The 3' sequence 5' GGCG-GATCCCGCTCACAAGCCCGAGTAGGA 3' (SEQ ID NO: 6) contains complementary sequences to a BamHI site and is followed by 18 nucleotides of HSATU68 coding sequence. The restriction enzyme sites correspond to the restriction enzyme sites on the bacterial expression vector pQE-9 (Qiagen, Inc., Chatsworth, Calif., 91311). pQE-9 encodes antibiotic resistance (Amp$^r$), a bacterial origin of replication (ori), an IPTG-regulatable promoter operator (P/O), a ribosome binding site (RBS), a 6-His tag and restriction enzyme sites. pQE-9 was then digested with BamHI. The amplified sequences were ligated into pQE-9 and were inserted in frame with the sequence encoding for the histidine tag and the RBS. The ligation mixture was then used to transform E. coli strain M15/rep 4 (Qiagen, Inc.) by the procedure described in Sambrook, J. et al., Molecular Cloning: A Laboratory Manual, Cold Spring Laboratory Press, (1989). M15/rep4 contains multiple copies of the plasmid pREP4, which expresses the lacI repressor and also confers kanamycin resistance (Kan$^r$). Transformants are identified by their ability to grow on LB plates and ampicillin/kanamycin resistant colonies were selected. Plasmid DNA was isolated and confirmed by restriction analysis. Clones containing the desired constructs were grown overnight (O/N) in liquid culture in LB media supplemented with both Amp (100 ug/ml) and Kan (25 ug/ml). The O/N culture is used to inoculate a large culture at a ratio of 1:100 to 1:250. The cells were grown to an optical density 600 (O.D.$^{600}$) of between 0.4 and 0.6. IPTG ("Isopropyl-B-D-thiogalacto pyranoside") was then added to a final concentration of 1 mM. IPTG induces by inactivating the lacI repressor, clearing the P/O leading to increased gene expression. Cells were grown an extra 3 to 4 hours. Cells were then harvested by centrifugation. The cell pellet was solubilized in the chaotropic agent 6 Molar Guanidine HCl. After clarification, solubilized HSATU68 was purified from this solution by chromatography on a Nickel-Chelate column under conditions that allow for tight binding by proteins containing the 6-His tag (Hochuli, E. et al., J. Chromatography 411:177-184 (1984)). HSATU68 was eluted from the column in 6 molar guanidine HCl pH 5.0 and for the purpose of renaturation adjusted to 3 molar guanidine HCl, 100 mM sodium phosphate, 10 nunolar glutathione (reduced) and 2 mmolar glutathione (oxidized). After incubation in this solution for 12 hours the protein was dialyzed to 10 mmolar sodium phosphate.

Example 2

Expression of Recombinant HSATU68 in COS Cells

The expression of plasmid, HSATU68 HA is derived from a vector pcDNAI/Amp (Invitrogen) containing: 1) SV40 origin of replication, 2) ampicillin resistance gene, 3) E. coli replication origin, 4) CMV promoter followed by a polylinker region, a SV40 intron and polyadenylation site. A DNA fragment encoding the entire HSATU68 precursor and a HA tag fused in frame to its 3' end was cloned into the polylinker region of the vector, therefore, the recombinant protein expression is directed under the CMV promoter. The HA tag correspond to an epitope derived from the influenza hemagglutinin protein as previously described (I. Wilson, H. Niman, R. Heighten, A Cherenson, M. Connolly, and R. Lerner, 1984, Cell 37, 767). The infusion of HA tag to the target protein allows easy detection of the recombinant protein with an antibody that recognizes the HA epitope.

The plasmid construction strategy is described as follows:

The DNA sequence encoding for HSATU68, ATCC #97334, was constructed by PCR using two primers: the 5' primer 5' GTCCAAGCTTGCCACC ATGGAGTTGAGGAAGTAC 3' (SEQ ID NO: 7) and contains a HindIII site followed by 18 nucleotides of HSATU68 coding sequence starting from the initiation codon (underlined); the 3' sequence 5' CTGCTCGAGTCAAGCGTAGTCTGGGACGTCGTATGGGTAG CACAAGCCCGAGTAGGA 3' (SEQ ID NO: 8) contains complementary sequences to an XhoI site, translation stop codon, HA tag and the last 15 nucleotides of the HSATU68 coding sequence (not including the stop codon). Therefore, the PCR product contains a HindIII site HSATU68 coding sequence followed by HA tag fused in frame, a translation termination stop codon next to the HA tag, and an XhoI site. The PCR amplified DNA fragment and the vector, pcDNAI/Amp, were digested with HindIII and XhoI restriction enzyme and ligated. The ligation mixture was transformed into *E. coli* strain SURE (Stratagene Cloning Systems, La Jolla, Calif. 92037) the transformed culture was plated on ampicillin media plates and resistant colonies were selected. Plasmid DNA was isolated from transform ants and examined by restriction analysis for the presence of the correct fragment. For expression of the recombinant HSATU68, COS cells were transfected with the expression vector by DEAE-DEXTRAN method (J. Sambrook, E. Fritsch, T. Maniatis, Molecular Cloning: A Laboratory Manual, Cold Spring Laboratory Press, (1989)). The expression of the HSATU68 HA protein was detected by radiolabelling and immunoprecipitation method (E. Harlow, D. Lane, Antibodies: A Laboratory Manual, Cold Spring Harbor Laboratory Press, (1988)). Cells were labelled for 8 hours with $^{35}$S-cysteine two days post transfection. Culture media were then collected and cells were lysed with detergent (RIPA buffer (150 mM NaCl, 1% NP-40, 0.1% SDS, 1% NP-40, 0.5% DOC, 50 mM Tris, pH 7.5) (Wilson, I. et al., Id. 37:767 (1984)). Both cell lysate and culture media were precipitated with a HA specific monoclonal antibody. Proteins precipitated were analyzed on 15% SDS-PAGE gels.

Example 3

Cloning and Expression of HSATU68 Using the Baculovirus Expression System

The DNA sequence encoding the full length HSATU68 protein, ATCC #97334, was amplified using PCR oligonucleotide primers corresponding to the 5' and 3' sequences of the gene:

The 5' primer has the sequence: 5' CG GGATCCCTCCCATGGAGTTGAGGAAGTAC 3' (SEQ ID NO: 9) and contains a BamHI restriction enzyme site followed by 5 nucleotides resembling an efficient signal for the initiation of translation in eukaryotic cells (J. Mol. Biol. 1987, 196, 947-950, Kozak, M.), and just behind the first 6 nucleotides of the HSATU68 gene (the initiation codon for translation is "ATG"). The 3' primer has the sequence 5' CGGGATCCCGCTCACAAGCCCGAGTAGGA 3' (SEQ ID NO: 10) and contains the cleavage site for the restriction endonuclease BamHI and 18 nucleotides complementary to the 3' non-translated sequence of the HSATU68 gene. The amplified sequences were isolated from a 1% agarose gel using a commercially available kit ("Geneclean," BIO 101 Inc., La Jolla, Calif.). The fragment was then digested with the endonuclease BamHI and purified as described above. This fragment is designated F2.

The vector pRG1 (modification of pVL941 vector, discussed below) is used for the expression of the HSATU68 protein using the baculovirus expression system (for review see: Summers, M. D. and Smith, G. E. 1987, A manual of methods for baculovirus vectors and insect cell culture procedures, Texas Agricultural Experimental Station Bulletin No. 1555). This expression vector contains the strong polyhedrin promoter of the Autographa californica nuclear polyhedrosis virus (AcMNPV) followed by the recognition sites for the restriction endonuclease BamHI. The polyadenylation site of the simian virus SV40 is used for efficient polyadenylation. For an easy selection of recombinant viruses the beta-galactosidase gene from *E. coli* is inserted in the same orientation as the polyhedrin promoter followed by the polyadenylation signal of the polyhedrin gene. The polyhedrin sequences are flanked at both sides by viral sequences for the cell-mediated homologous recombination of co-transfected wild-type viral DNA. Many other baculovirus vectors could be used in place of pRG1 such as pAc373, pVL941 and pAcIM1 (Luckow, V. A. and Summers, M. D., Virology, 170: 31-39).

The plasmid was digested with the restriction enzyme BamHI and then dephosphorylated using calf intestinal phosphatase by procedures known in the art. The DNA was then isolated from a 1% agarose gel as described above. This vector DNA is designated V2.

Fragment F2 and the dephosphorylated plasmid V2 were ligated with T4 DNA ligase. *E. coli* HB101 cells were then transformed and bacteria identified that contained the plasmid (pBacHSATU68) with the HSATU68 gene using the enzyme BamHI. The sequence of the cloned fragment was confirmed by DNA sequencing.

5 µg of the plasmid pBacHSATU68 were co-transfected with 1.0 µg of a commercially available linearized baculovirus ("BaculoGold™ baculovirus DNA", Pharmingen, San Diego, Calif.) using the lipofection method (Felgner et al. Proc. Natl. Acad. Sci. USA, 84:7413-7417 (1987)).

1 µg of BaculoGold™ virus DNA and 5 µg of the plasmid pBacHSATU68 were mixed in a sterile well of a microtiter plate containing 50 µl of serum free Grace's medium (Life Technologies Inc., Gaithersburg, Md.). Afterwards 10 µl Lipofectin plus 90 µl Grace's medium were added, mixed and incubated for 15 minutes at room temperature. Then the transfection mixture was added drop wise to the Sf9 insect cells (ATCC CRL 1711) seeded in a 35 mm tissue culture plate with 1 ml Grace' medium without serum. The plate was rocked back and forth to mix the newly added solution. The plate was then incubated for 5 hours at 27° C. After 5 hours the transfection solution was removed from the plate and 1 ml of Grace's insect medium supplemented with 10% fetal calf serum was added. The plate was put back into an incubator and cultivation continued at 27° C. for four days.

After four days the supernatant was collected and a plaque assay performed similar as described by Summers and Smith (supra). As a modification an agarose gel with "Blue Gal" (Life Technologies Inc., Gaithersburg) was used which allows an easy isolation of blue stained plaques. (A detailed description of a "plaque assay" can also be found in the user's guide for insect cell culture and baculovirology distributed by Life Technologies Inc., Gaithersburg, page 9-10).

Four days after the serial dilution, the viruses were added to the cells and blue stained plaques were picked with the tip of an Eppendorf pipette. The agar containing the recombinant viruses was then resuspended in an Eppendorf tube containing 200 μl of Grace's medium. The agar was removed by a brief centrifugation and the supernatant containing the recombinant baculoviruses was used to infect Sf9 cells seeded in 35 mm dishes. Four days later the supernatants of these culture dishes were harvested and then stored at 4° C.

Sf9 cells were grown in Grace's medium supplemented with 10% heat-inactivated FBS. The cells were infected with the recombinant baculovirus V-HSATU68 at a multiplicity of infection (MOI) of 2. Six hours later the medium was removed and replaced with SF900 II medium minus methionine and cysteine (Life Technologies Inc., Gaithersburg). 42 hours later 5 μCi of $^{35}$S-methionine and 5 μCi $^{35}$S cysteine (Amersham) were added. The cells were further incubated for 16 hours before they were harvested by centrifugation and the labelled proteins visualized by SDS-PAGE and autoradiography.

Example 4

Method of Treatment Using Gene Therapy—Ex Vivo

Fibroblasts are obtained from a subject by skin biopsy. The resulting tissue is placed in tissue-culture medium and separated into small pieces. Small chunks of the tissue are placed on a wet surface of a tissue culture flask, approximately ten pieces are placed in each flask. The flask is turned upside down, closed tight and left at room temperature over night. After 24 hours at room temperature, the flask is inverted and the chunks of tissue remain fixed to the bottom of the flask and fresh media (e.g., Ham's F12 media, with 10% FBS, penicillin and streptomycin, is added. This is then incubated at 37° C. for approximately one week. At this time, fresh media is added and subsequently changed every several days. After an additional two weeks in culture, a monolayer of fibroblasts emerge. The monolayer is trypsinized and scaled into larger flasks.

pMV-7 (Kirschmeier, P. T. et al, DNA, 7:219-25 (1988)) flanked by the long terminal repeats of the Moloney munirne sarcoma virus, is digested with EcoRI and HindIII and subsequently treated with calf intestinal phosphatase. The linear vector is fractionated on agarose gel and purified, using glass beads.

The cDNA encoding a polypeptide of the present invention is amplified using PCR primers which correspond to the 5' and 3' end sequences respectively. The 5' primer contains an EcoRI site and the 3' primer contains a HindIII site. Equal quantities of the Moloney murine sarcoma virus linear backbone and the EcoRI and HindIII fragment are added together, in the presence of T4 DNA ligase. The resulting mixture is maintained under conditions appropriate for ligation of the two fragments. The ligation mixture is used to transform bacteria HB101, which are then plated onto agar-containing kanamycin for the purpose of confirming that the vector had the gene of interest properly inserted.

The amphotropic pA317 or GP+am12 packaging cells are grown in tissue culture to confluent density in Dulbecco's Modified Eagles Medium (DMEM) with 10% calf serum (CS), penicillin and streptomycin. The MSV vector containing the gene is then added to the media and the packaging cells are transduced with the vector. The packaging cells now produce infectious viral particles containing the gene (the packaging cells are now referred to as producer cells).

Fresh media is added to the transduced producer cells, and subsequently, the media is harvested from a 10 cm plate of confluent producer cells. The spent media, containing the infectious viral particles, is filtered through a millipore filter to remove detached producer cells and this media is then used to infect fibroblast cells. Media is removed from a sub-confluent plate of fibroblasts and quickly replaced with the media from the producer cells. This media is removed and replaced with fresh media. If the titer of virus is high, then virtually all fibroblasts will be infected and no selection is required. If the titer is very low, then it is necessary to use a retroviral vector that has a selectable marker, such as neo or his.

The engineered fibroblasts are then injected into the host. The fibroblasts now produce the protein product.

Example 5

Protein Fusions of a G-protein Chemokine Receptor

G-protein Chemokine Receptor polypeptides of the invention are optionally fused to other proteins. These fusion proteins can be used for a variety of applications. For example, fusion of G-protein Chemokine Receptor polypeptides to His-tag, HA-tag, protein A, IgG domains, and maltose binding protein facilitates purification. (See EP A 394,827; Traunecker, et al., Nature 331:84-86 (1988)). Similarly, fusion to IgG-1, IgG-3, and albumin increases the halflife time in vivo. Nuclear localization signals fused to G-protein Chemokine Receptor polypeptides can target the protein to a specific subcellular localization, while covalent heterodimer or homodimers can increase or decrease the activity of a fusion protein. Fusion proteins can also create chimeric molecules, having more than one function. Finally, fusion proteins can increase solubility and/or stability of the fused protein compared to the non-fused protein. All of the types of fusion proteins described above can be made using techniques known in the art or by using or routinely modifying the following protocol, which outlines the fusion of a polypeptide to an IgG molecule.

Briefly, the human Fe portion of the IgG molecule can be PCR amplified, using primers that span the 5' and 3' ends of the sequence described below (SEQ ID NO: 12). These primers also preferably contain convenient restriction enzyme sites that will facilitate cloning into an expression vector, preferably a mammalian expression vector.

For example, if the pC4 (Accession No. 209646) expression vector is used, the human Fe portion can be ligated into the BamHI cloning site. Note that the 3' BamHI site should be destroyed. Next, the vector containing the human Fe portion is re-restricted with BamHI, linearizing the vector, and G-protein Chemokine Receptor polynucleotide is ligated into this BamHI site. Note that the polynucleotide is cloned without a stop codon, otherwise a fusion protein will not be produced.

If the naturally occurring signal sequence is used to produce the secreted protein, pC4 does not need a second signal peptide. Alternatively, if the naturally occurring signal sequence is not used, the vector can be modified to include a heterologous signal sequence. (See, e.g., WO 96/34891.)

Human IgG Fe Region:

```
GGGATCCGGAGCCCAAATCTTCTGACAAAACTCACACATGCCCACCGTGCCCAGCACCTGAAT    (SEQ ID NO: 12)
TCGAGGGTGCACCGTCAGTCTTCCTCTTCCCCCCAAAACCCAAGGACACCCTCATGATCTCCCG
GACTCCTGAGGTCACATGCGTGGTGGTGGACGTAAGCCACGAAGACCCTGAGGTCAAGTTCAA
CTGGTACGTGGACGGCGTGGAGGTGCATAATGCCAAGACAAAGCCGCGGGAGGAGCAGTACA
ACAGCACGTACCGTGTGGTCAGCGTCCTCACCGTCCTGCACCAGGACTGGCTGAATGGCAAGG
AGTACAAGTGCAAGGTCTCCAACAAAGCCCTCCCAACCCCCATCGAGAAAACCATCTCCAAAG
CCAAAGGGCAGCCCCGAGAACCACAGGTGTACACCCTGCCCCCATCCCGGGATGAGCTGACCA
AGAACCAGGTCAGCCTGACCTGCCTGGTCAAAGGCTTCTATCCAAGCGACATCGCCGTGGAGT
GGGAGAGCAATGGGCAGCCGGAGAACAACTACAAGACCACGCCTCCCGTGCTGGACTCCGAC
GGCTCCTTCTTCCTCTACAGCAAGCTCACCGTGGACAAGAGCAGGTGGCAGCAGGGGAACGTC
TTCTCATGCTCCGTGATGCATGAGGCTCTGCACAACCACTACACGCAGAAGAGCCTCTCCCTGT
CTCCGGGTAAATGAGTGCGACGGCCGCGACTCTAGAGGAT
```

Example 6

Production of an Anti-G-protein Chemokine Receptor Antibody

Hybridoma Technology

The antibodies of the present invention can be prepared by a variety of methods. (See, Current Protocols, Chapter 2.) As one example of such methods, cells expressing G-protein Chemokine Receptor polypeptides are administered to an animal to induce the production of sera containing polyclonal antibodies. Such polypeptide-expressing cells are cultured in any suitable tissue culture medium, preferably in Earle's modified Eagle's medium supplemented with 10% fetal bovine serum (inactivated at about 56° C.), and supplemented with about 10 g/l of nonessential amino acids, about 1,000 U/mi of penicillin, and about 100 µg/ml of streptomycin.

In a preferred method, a preparation of G-protein Chemokine Receptor polypeptides is prepared and purified to render it substantially free of natural contaminants. Such a preparation is then introduced into an animal in order to produce polyclonal antisera of greater specific activity.

Monoclonal antibodies specific for G-protein Chemokine Receptor polypeptides of the present invention are prepared using hybridoma technology. (Kohler et al., Nature 256:495 (1975); Kohler et al., Eur. J. Immunol. 6:511 (1976); Kohler et al., Eur. J. Immunol. 6:292 (1976); Hammerling et al., in: Monoclonal Antibodies and T-Cell Hybridomas, Elsevier, N.Y., pp. 563-681 (1981)). In general, an animal (preferably a mouse) is immunized with G-protein Chemokine Receptor polypeptides of the present invention or, more preferably, with a soluble form of G-protein Chemokine Receptor.

The splenocytes of such mice are extracted and fused with a suitable myeloma cell line. Any suitable myeloma cell line may be employed in accordance with the present invention; however, it is preferable to employ the parent myeloma cell line (SP20), available from the ATCC. After fusion, the resulting hybridoma cells are selectively maintained in HAT medium, and then cloned by limiting dilution as described by Wands et al. (Gastroenterology 80:225-232 (1981)). The hybridoma cells obtained through such a selection are then assayed to identify clones that secrete antibodies capable of binding a G-protein Chemokine Receptor polypeptide of the present invention.

Alternatively, additional antibodies capable of binding to a G-protein Chemokine Receptor polypeptide of the present invention can be produced in a two-step procedure using anti-idiotypic antibodies. Such a method makes use of the fact that antibodies are themselves antigens, and therefore, it is possible to obtain an antibody that binds to a second antibody. In accordance with this method, protein specific antibodies are used to immunize an animal, preferably a mouse. The splenocytes of such an animal are then used to produce hybridoma cells, and the hybridoma cells are screened to identify clones that produce an antibody whose ability to bind to the G-protein Chemokine Receptor-specific antibody can be blocked by a G-protein Chemokine Receptor polypeptide of the present invention. Such antibodies comprise anti-idiotypic antibodies to the G-protein Chemokine Receptor-specific antibody and are used to immunize an animal to induce formation of further G-protein Chemokine Receptor-specific antibodies.

For in vivo use of antibodies in humans, an antibody is "humanized". Such antibodies can be produced using genetic constructs derived from hybridoma cells producing the monoclonal antibodies described above. Methods for producing chimeric and humanized antibodies are known in the art and are discussed herein. (See, for review, Morrison, Science 229:1202 (1985); Oi et al., BioTechniques 4:214 (1986); Cabilly et al., U.S. Pat. No. 4,816,567; Taniguchi et al., EP 171496; Morrison et al., EP 173494; Neuberger et al., WO 8601533; Robinson et al., WO 8702671; Boulianne et al., Nature 312:643 (1984); Neuberger et al., Nature 314:268 (1985).)

Isolation of antibody fragments directed against polypeptides of the present invention from a library of scFvs.

Naturally occuring V-genes isolated from human PBLs are constructed into a large library of antibody fragments which contain reactivities against polypeptides of the present invention to which the donor may or may not have been exposed (see e.g., U.S. Pat. No. 5,885,793 incorporated herein in its entirety by reference).

Rescue of the Library

A library of scFvs is constructed from the RNA of human PBLs as described in WO92/01047. To rescue phage displaying antibody fragments, approximately $10^9$ E. coli harbouring the phagemid are used to inoculate 50 ml of 2×TY containing 1% glucose and 100 ug/ml of ampicillin (2×TY-AMP-GLU) and grown to an O.D. of 0.8 with shaking. Five ml of this culture is used to innoculate 50 ml of 2×TY-AMP-GLU, 2×10$^8$ TU of Δ gene 3 helper phage (M13 Δ gene III, see WO92/01047) are added and the culture incubated at 37° C. for 45 minutes without shaking and then at 37° C. for 45 minutes with shaking. The culture is centrifuged at 4000 r.p.m. for 10 minutes and the pellet resuspended in 2 liters of 2×TY containing 100 ug/ml ampicillin and 50 ug/ml kanamycin and grown overnight. Phage are prepared as described in WO92/01047.

M13 Δ gene III is prepared as follows: M13 Δ gene III helper phage does not encode gene III protein, hence the phage(mid) displaying antibody fragments have a greater avidity of binding to antigen. Infectious M13 Δ gene III particles are made by growing the helper phage in cells harboring a pUC19 derivative supplying the wild type gene III protein during phage morphogenesis. The culture is incubated for 1 hour at 37° C. without shaking and then for a further hour at 37° C. with shaking. Cells are pelleted (IEC-Centra 8, 4000 revs/min for 10 min), resuspended in 300 ml 2×TY broth containing 100 ug ampicillin/ml and 25 ug kanamycin/ml (2×TY-AMP-KAN) and grown overnight, shaking at 37° C. Phage particles are purified and concentrated from the culture medium by two PEG-precipitations (Sambrook et al., 1990), resuspended in 2 ml PBS and passed through a 0.45 um filter (Minisart NML; Sartorius) to give a final concentration of approximately $10^{13}$ transducing units/ml (ampicillin-resistant clones).

Panning of the Library

Immunotubes (Nunc) are coated overnight in PBS with 4 ml of either 100 mg/ml or 10 mg/ml of a polypeptide of the present invention. Tubes are blocked with 2% Marvel-PBS for 2 hours at 37° C. and then washed 3 times in PBS. Approximately $10^{13}$ TU of phage are applied to the tube and incubated for 30 minutes at room temperature tumbling on an over and under turntable and then left to stand for another 1.5 hours. Tubes are washed 10 times with PBS 0.1% Tween-20 and 10 times with PBS. Phage are eluted by adding 1 ml of 100 mM triethylamine and rotating 15 minutes on an under and over turntable after which the solution is immediately neutralized with 0.5 ml of 1.0M Tris-HCl, pH 7.4. Phage are then used to infect 10 ml of mid-log E. coli TG1 by incubating eluted phage with bacteria for 30 minutes at 37° C. The E. coli are then plated on TYE plates containing 1% glucose and 100 ug/ml ampicillin. The resulting bacterial library is then rescued with Δ gene III helper phage as described above to prepare phage for a subsequent round of selection. This process is then repeated for a total of 4 rounds of affinity purification with tube-washing increased to 20 times with PBS, 0.1% Tween-20 and 20 times with PBS for rounds 3 and 4.

Characterization of Binders

Eluted phage from the 3rd and 4th rounds of selection are used to infect E. coli HB 2151 and soluble scFv is produced (Marks, et al., 1991) from single colonies for assay. ELISAs are performed with microtitre plates coated with either 10 pg/ml of the polypeptide of the present invention in 50 mM bicarbonate pH 9.6. Clones positive in ELISA are further characterized by PCR fingerprinting (see e.g., WO92/01047) and then by sequencing.

Example 7

Method of Determining Alterations in the G-protein Chemokine Receptor Gene

RNA is isolated from entire families or individual patients presenting with a phenotype of interest (such as a disease). cDNA is then generated from these RNA samples using protocols known in the art. (See, Sambrook.) The cDNA is then used as a template for PCR, employing primers surrounding regions of interest in SEQ ID NOS: 1 and 2, or more preferably SEQ ID NOS 3 and 4. Suggested PCR conditions consist of 35 cycles at 95° C. for 30 seconds; 60-120 seconds at 52-58° C.; and 60-120 seconds at 70° C. using buffer solutions described in Sidransky, D., et al., Science 252:706 (1991).

PCR products are then sequenced using primers labeled at their 5' end with T4 polynucleotide kinase, employing SequiTherm Polymerase. (Epicentre Technologies). The intron-exon borders of selected exons of G-protein Chemokine Receptor are also determined and genomic PCR products analyzed to confirm the results. PCR products harboring suspected mutations in G-protein Chemokine Receptor is then cloned and sequenced to validate the results of the direct sequencing.

PCR products of G-protein Chemokine Receptor are cloned into T-tailed vectors as described in Holton, T. A. and Graham, M. W., Nucleic Acids Research, 19:1156 (1991) and sequenced with T7 polymerase (United States Biochemical). Affected individuals are identified by mutations in G-protein Chemokine Receptor not present in unaffected individuals.

Genomic rearrangements are also observed as a method of determining alterations in the G-protein Chemokine Receptor gene. Genomic clones isolated using techniques known in the art are nick-translated with digoxigenindeoxy-uridine 5'-triphosphate (Boehringer Manheim), and FISH performed as described in Johnson, Cg. et al., Methods Cell Biol. 35:73-99 (1991). Hybridization with the labeled probe is carried out using a vast excess of human cot-1 DNA for specific hybridization to the G-protein Chemokine Receptor genomic locus.

Chromosomes are counterstained with 4,6-diamino-2-phenylidole and propidium iodide, producing a combination of C- and R-bands. Aligned images for precise mapping are obtained using a triple-band filter set (Chroma Technology, Brattleboro, Vt.) in combination with a cooled charge-coupled device camera (Photometrics, Tucson, Ariz.) and variable excitation wavelength filters. (Johnson, Cv. et al., Genet. Anal. Tech. Appl., 8:75 (1991).) Image collection, analysis and chromosomal fractional length measurements are performed using the ISee Graphical Program System. (Inovision Corporation, Durham, N.C.) Chromosome alterations of the genomic region of G-protein Chemokine Receptor (hybridized by the probe) are identified as insertions, deletions, and translocations. These G-protein Chemokine Receptor alterations are used as a diagnostic marker for an associated disease.

Example 8

Method of Detecting Abnormal Levels of G-protein Chemokine Receptor in a Biological Sample G-protein Chemokine Receptor polypeptides can be detected in a biological sample, and if an increased or decreased level of G-protein Chemokine Receptor is detected, this polypeptide is a marker for a particular phenotype. Methods of detection are numerous, and thus, it is understood that one skilled in the art can modify the following assay to fit their particular needs.

For example, antibody-sandwich ELISAs are used to detect G-protein Chemokine Receptor in a sample, preferably a biological sample. Wells of a microtiter 4 plate are coated with specific antibodies to G-protein Chemokine Receptor, at a final concentration of 0.2 to 10 ug/ml. The antibodies are either monoclonal or polyclonal and are produced using technique known in the art. The wells are blocked so that nonspecific binding of G-protein Chemokine Receptor to the well is reduced.

The coated wells are then incubated for >2 hours at RT with a sample containing G-protein Chemokine Receptor. Preferably, serial dilutions of the sample should be used to validate results. The plates are then washed three times with deionized or distilled water to remove unbounded G-protein Chemokine Receptor.

Next, 50 ul of specific antibody-alkaline phosphatase conjugate, at a concentration of 25-400 ng, is added and incubated for 2 hours at room temperature. The plates are again washed three times with deionized or distilled water to remove unbounded conjugate.

75 ul of 4-methylumbelliferyl phosphate (MUP) or p-nitrophenyl phosphate (NPP) substrate solution is then added to each well and incubated 1 hour at room temperature to allow cleavage of the substrate and flourescence. The flourescence is measured by a microtiter plate reader. A standard curve is prepared using the experimental results from serial dilutions of a control sample with the sample concentration plotted on the X-axis (log scale) and fluorescence or absorbance on the Y-axis (linear scale). The G-protein Chemokine Receptor polypeptide concentration in a sample is then interpolated using the standard curve based on the measured flourescence of that sample.

Example 9

Method of Treating Decreased Levels of G-protein Chemokine Receptor

The present invention relates to a method for treating an individual in need of a decreased level of G-protein Chemokine Receptor biological activity in the body comprising, administering to such an individual a composition comprising a therapeutically effective amount of G-protein Chemokine Receptor antagonist. Preferred antagonists for use in the present invention are G-protein Chemokine Receptor-specific antibodies.

Moreover, it will be appreciated that conditions caused by a decrease in the standard or normal expression level of G-protein Chemokine Receptor in an individual can be treated by administering G-protein Chemokine Receptor, preferably in a soluble and/or secreted form. Thus, the invention also provides a method of treatment of an individual in need of an increased level of G-protein Chemokine Receptor polypeptide comprising administering to such an individual a pharmaceutical composition comprising an amount of G-protein Chemokine Receptor to increase the biological activity level of G-protein Chemokine Receptor in such an individual.

For example, a patient with decreased levels of G-protein Chemokine Receptor polypeptide receives a daily dose 0.1-100 ug/kg of the polypeptide for six consecutive days. Preferably, the polypeptide is in a soluble and/or secreted form.

Example 10

Method of Treating Increased Levels of G-protein Chemokine Receptor

The present invention also relates to a method for treating an individual in need of an increased level of G-protein Chemokine Receptor biological activity in the body comprising administering to such an individual a composition comprising a therapeutically effective amount of G-protein Chemokine Receptor or an agonist thereof.

Antisense technology is used to inhibit production of G-protein Chemokine Receptor. This technology is one example of a method of decreasing levels of G-protein Chemokine Receptor polypeptide, preferably a soluble and/or secreted form, due to a variety of etiologies, such as cancer.

For example, a patient diagnosed with abnormally increased levels of G-protein Chemokine Receptor is administered intravenously antisense polynucleotides at 0.5, 1.0, 1.5, 2.0 and 3.0 mg/kg day for 21 days. This treatment is repeated after a 7-day rest period if it is determined to be well tolerated.

Example 11

Method of Treatment Using Gene Therapy—In Vivo

Another aspect of the present invention is using in vivo gene therapy methods to treat disorders, diseases and conditions. The gene therapy method relates to the introduction of naked nucleic acid (DNA, RNA, and antisense DNA or RNA) G-protein Chemokine Receptor sequences into an animal to increase or decrease the expression of the G-protein Chemokine Receptor polypeptide. The G-protein Chemokine Receptor polynucleotide may be operatively linked to a promoter or any other genetic elements necessary for the expression of the G-protein Chemokine Receptor polypeptide by the target tissue. Such gene therapy and delivery techniques and methods are known in the art, see, for example, WO90/11092, WO98/11779; U.S. Pat. Nos. 5,693,622, 5,705,151, 5,580, 859; Tabata H. et al., Cardiovasc. Res. 35:470-479 (1997); Chao J. et al., Pharmacol. Res. 35:517-522 (1997); Wolff J. A. Neuromuscul. Disord. 7:314-318 (1997); Schwartz B. et al., Gene Ther. 3:405-411 (1996); Tsurumi Y. et al., Circulation 94:3281-3290 (1996) (incorporated herein by reference).

The G-protein Chemokine Receptor polynucleotide constructs may be delivered by any method that delivers injectable materials to the cells of an animal, such as, injection into the interstitial space of tissues (heart, muscle, skin, lung, liver, intestine and the like). The G-protein Chemokine Receptor polynucleotide constructs can be delivered in a pharmaceutically acceptable liquid or aqueous carrier.

The term "naked" polynucleotide, DNA or RNA, refers to sequences that are free from any delivery vehicle that acts to assist, promote, or facilitate entry into the cell, including viral sequences, viral particles, liposome formulations, lipofectin or precipitating agents and the like. However, the G-protein Chemokine Receptor polynucleotides may also be delivered in liposome formulations (such as those taught in Felgner P. L., et al. Ann. NY Acad. Sci. 772:126-139 (1995), and Abdallah B., et al. Biol. Cell 85(1):1-7 (1995)) which can be prepared by methods well known to those skilled in the art.

The G-protein Chemokine Receptor polynucleotide vector constructs used in the gene therapy method are preferably constructs that will not integrate into the host genome nor will they contain sequences that allow for replication. Any strong promoter known to those skilled in the art can be used for driving the expression of DNA. Unlike other gene therapies techniques, one major advantage of introducing naked nucleic acid sequences into target cells is the transitory nature of the polynucleotide synthesis in the cells. Studies have shown that non-replicating DNA sequences can be introduced into cells to provide production of the desired polypeptide for periods of up to six months.

The G-protein Chemokine Receptor polynucleotide construct can be delivered to the interstitial space of tissues within the an animal, including of muscle, skin, brain, lung, liver, spleen, bone marrow, thymus, heart, lymph, blood, bone, cartilage, pancreas, kidney, gall bladder, stomach, intestine, testis, ovary, uterus, rectum, nervous system, eye, gland, and connective tissue. Interstitial space of the tissues comprises the intercellular fluid, mucopolysaccharide matrix among the reticular fibers of organ tissues, elastic fibers in the walls of vessels or chambers, collagen fibers of fibrous tissues, or that same matrix within connective tissue ensheathing muscle cells or in the lacunae of bone. It is similarly the space occupied by the plasma of the circulation and the lymph fluid of the lymphatic channels. Delivery to the interstitial space of muscle tissue is preferred for the reasons discussed below. They may be conveniently delivered by injection into the tissues comprising these cells. They are preferably delivered to and expressed in persistent, non-dividing cells that are differentiated, although delivery and expression may be achieved in non-differentiated or less completely differentiated cells, such as, for example, stem cells of blood or skin fibroblasts. In vivo muscle cells are particularly competent in their ability to take up and express polynucleotides.

For the naked G-protein Chemokine Receptor polynucleotide injection, an effective dosage amount of DNA or RNA will be in the range of from about 0.05 g/kg body weight to about 50 mg/kg body weight. Preferably the dosage will be from about 0.005 mg/kg to about 20 mg/kg and more preferably from about 0.05 mg/kg to about 5 mg/kg. Of course, as the artisan of ordinary skill will appreciate, this dosage will vary according to the tissue site of injection. The appropriate and effective dosage of nucleic acid sequence can readily be determined by those of ordinary skill in the art and may depend on the condition being treated and the route of administration. The preferred route of administration is by the parenteral route of injection into the interstitial space of tissues. However, other parenteral routes may also be used, such as, inhalation of an aerosol formulation particularly for delivery to lungs or bronchial tissues, throat or mucous membranes of the nose. In addition, naked G-protein Chemokine Receptor polynucleotide constructs can be delivered to arteries during angioplasty by the catheter used in the procedure.

The dose response effects of injected G-protein Chemokine Receptor polynucleotide in muscle in vivo are determined as follows. Suitable G-protein Chemokine Receptor template DNA for production of mRNA coding for G-protein Chemokine Receptor polypeptide is prepared in accordance with a standard recombinant DNA methodology. The template DNA, which may be either circular or linear, is either used as naked DNA or complexed with liposomes. The quadriceps muscles of mice are then injected with various amounts of the template DNA.

Five to six week old female and male Balb/C mice are anesthetized by intraperitoneal injection with 0.3 ml of 2.5% Avertin. A 1.5 cm incision is made on the anterior thigh, and the quadriceps muscle is directly visualized. The G-protein Chemokine Receptor template DNA is injected in 0.1 ml of carrier in a 1 cc syringe through a 27 gauge needle over one minute, approximately 0.5 cm from the distal insertion site of the muscle into the knee and about 0.2 cm deep. A suture is placed over the injection site for future localization, and the skin is closed with stainless steel clips.

After an appropriate incubation time (e.g., 7 days) muscle extracts are prepared by excising the entire quadriceps. Every fifth 15 um cross-section of the individual quadriceps muscles is histochemically stained for G-protein Chemokine Receptor protein expression. A time course for G-protein Chemokine Receptor protein expression may be done in a similar fashion except that quadriceps from different mice are harvested at different times. Persistence of G-protein Chemokine Receptor DNA in muscle following injection may be determined by Southern blot analysis after preparing total cellular DNA and HIRT supernatants from injected and control mice. The results of the above experimentation in mice can be use to extrapolate proper dosages and other treatment parameters in humans and other animals using G-protein Chemokine Receptor naked DNA.

Example 12

Gene Therapy Using Endogenous G-protein Chemokine Receptor Gene

Another method of gene therapy according to the present invention involves operably associating the endogenous G-protein Chemokine Receptor sequence with a promoter via homologous recombination as described, for example, in U.S. Pat. No. 5,641,670, issued Jun. 24, 1997; International Publication Number WO 96/29411; International Publication Number WO 94/12650; Koller et al., Proc. Natl. Acad. Sci. USA 86:8932-8935 (1989); and Zijlstra et al., Nature 342: 435-438 (1989). This method involves the activation of a gene which is present in the target cells, but which is not expressed in the cells, or is expressed at a lower level than desired. Polynucleotide constructs are made which contain a promoter and targeting sequences, which are homologous to the 5' non-coding sequence of endogenous G-protein Chemokine Receptor, flanking the promoter. The targeting sequence will be sufficiently near the 5' end of G-protein Chemokine Receptor so the promoter will be operably linked to the endogenous sequence upon homologous recombination. The promoter and the targeting sequences can be amplified using PCR. Preferably, the amplified promoter contains distinct restriction enzyme sites on the 5' and 3' ends. Preferably, the 3' end of the first targeting sequence contains the same restriction enzyme site as the 5' end of the amplified promoter and the 5' end of the second targeting sequence contains the same restriction site as the 3' end of the amplified promoter.

The amplified promoter and the amplified targeting sequences are digested with the appropriate restriction enzymes and subsequently treated with calf intestinal phosphatase. The digested promoter and digested targeting sequences are added together in the presence of T4 DNA ligase. The resulting mixture is maintained under conditions appropriate for ligation of the two fragments. The construct is size fractionated on an agarose gel then purified by phenol extraction and ethanol precipitation.

In this Example, the polynucleotide constructs are administered as naked polynucleotides via electroporation. However, the polynucleotide constructs may also be administered with transfection-facilitating agents, such as liposomes, viral sequences, viral particles, precipitating agents, etc. Such methods of delivery are known in the art.

Once the cells are transfected, homologous recombination will take place. This results in the promoter being operably linked to the endogenous G-protein Chemokine Receptor sequence. This results in the expression of G-protein Chemokine Receptor in the cell. Expression may be detected by immunological staining or any other method known in the art.

Fibroblasts are obtained from a subject by skin biopsy. The resulting tissue is placed in DMEM+10% fetal calf serum. Exponentially growing or early stationary phase fibroblasts are trypsinized and rinsed from the plastic surface with nutrient medium. An aliquot of the cell suspension is removed for counting, and the remaining cells are subjected to centrifugation. The supernatant is aspirated and the pellet is resuspended in 5 ml of electroporation buffer (20 mM HEPES pH 7.3, 137 mM NaCl, 5 mM KCl, 0.7 mM Na2 HPO4, 6 mM dextrose). The cells are recentrifuged, the supernatant aspirated, and the cells resuspended in electroporation buffer containing 1 mg/ml acetylated bovine serum albumin. The final cell suspension contains approximately $3 \times 10^6$ cells/ml. Electroporation should be performed immediately following resuspension.

Plasmid DNA is prepared according to standard techniques. For example, to construct a plasmid for targeting to the G-protein Chemokine Receptor locus, plasmid pUC18 (MBI Fermentas, Amherst, N.Y.) is digested with HindIII. The CMV promoter is amplified by PCR with an XbaI site on the 5' end and a BamHI site on the 3'end. Two G-protein Chemokine Receptor non-coding sequences are amplified via PCR: one G-protein Chemokine Receptor non-coding sequence (G-protein Chemokine Receptor fragment 1) is amplified with a HindIII site at the 5' end and an Xba site at the 3'end; the other G-protein Chemokine Receptor non-coding sequence (G-protein Chemokine Receptor fragment 2) is amplified with a BamHI site at the 5'end and a HindIII site at the 3'end. The CMV promoter and G-protein Chemokine Receptor fragments are digested with the appropriate enzymes (CMV promoter-XbaI and BamHI; G-protein Chemokine Receptor fragment 1-XbaI; G-protein Chemokine Receptor fragment 2-BamHI) and ligated together. The resulting ligation product is digested with HindIII, and ligated with the HindIII-digested pUC18 plasmid.

Plasmid DNA is added to a sterile cuvette with a 0.4 cm electrode gap (Bio-Rad). The final DNA concentration is generally at least 120 µg/ml. 0.5 ml of the cell suspension (containing approximately $1.5 \times 10^6$ cells) is then added to the cuvette, and the cell suspension and DNA solutions are gently mixed. Electroporation is performed with a Gene-Pulser apparatus (Bio-Rad). Capacitance and voltage are set at 960 µF and 250-300 V, respectively. As voltage increases, cell survival decreases, but the percentage of surviving cells that stably incorporate the introduced DNA into their genome increases dramatically. Given these parameters, a pulse time of approximately 14-20 mSec should be observed.

Electroporated cells are maintained at room temperature for approximately 5 min, and the contents of the cuvette are then gently removed with a sterile transfer pipette. The cells are added directly to 10 ml of prewarmed nutrient media (DMEM with 15% calf serum) in a 10 cm dish and incubated at 37° C. The following day, the media is aspirated and replaced with 10 ml of fresh media and incubated for a further 16-24 hours.

The engineered fibroblasts are then injected into the host, either alone or after having been grown to confluence on cytodex 3 microcarrier beads. The fibroblasts now produce the protein product. The fibroblasts can then be introduced into a patient as described above.

Example 13

Identification and Cloning of VH and VL Domains

One method to identfy and clone VH and VL domains from cell lines expressing a particular antibody is to perform PCR with VH and VL specific primers on cDNA made from the antibody expressing cell lines. Briefly, RNA is isolated from the cell lines and used as a template for RT-PCR designed to amplify the VH and VL domains of the antibodies expressed by the EBV cell lines. Cells may be lysed in the TRIzol® reagent (Life Technologies, Rockville. Md.) and extracted with one-fifth volume of chloroform. After addition of chloroform, the solution is allowed to incubate at room temperature for 10 minutes, and the centrifuged at 14,000 rpm for 15 minutes at 4° C. in a tabletop centrifuge. The supernatant is collected and RNA is precipitated using an equal volume of isopropanol. Precipitated RNA is pelleted by centrifuging at 14,000 rpm for 15 minutes at 4° C. in a tabletop centrifuge. Following centrifugation, the supernatant is discarded and washed with 75% ethanol. Follwing washing, the RNA is centrifuged again at 800 rpm for 5 minutes at 4° C. The supernatant is discarded and the pellet allowed to air dry. RNA is the dissolved in DEPC water and heated to 60° C. for 10 minutes. Quantities of RNA can be determined using optical density measurements.

cDNA may be synthesized, according to methods well-known in the art, from 1.5-2.5 micrograms of RNA using reverse transcriptase and random hexamer primers. cDNA is then used as a template for PCR amplification of VH and VL domains. Primers used to amplify VH and VL genes are shown in the Table below. Typically a PCR reaction makes use of a single 5' primer and a single 3' primer. Sometimes, when the amount of available RNA template is limiting, or for greater efficiency, groups of 5' and/or 3' primers may be used. For example, sometimes all five VH-5' primers and all JH3' primers are used in a single PCR reaction. The PCR reaction is carried out in a 50 microliter-volume containing 1× PCR buffer, 2 mM of each dNTP, 0.7 units of High Fidelity Taq polymerse, 5' primer mix, 3' primer mix and 7.5 microliters of cDNA. The 5' and 3' primer mix of both VH and VL can be made by pooling together 22 pmole and 28 pmole, respectively, of each of the individual primers. PCR conditions are: 96° C. for 5 minutes; followed by 25 cycles of 94° C. for 1 minute, 50° C. for 1 minute, and 72° C. for 1 minute; followed by an extension cycle of 72° C. for 10 minutes. After the reaction is completed, sample tubes are stored 4° C.

Table V: Primer Sequences Used to Amplify VH and VL Domains.

TABLE V

Primer Sequences Used to Amplify VH and VL domains.

| Primer name | SEQ ID NO | Primer Sequence (5'-3') |
|---|---|---|
| VH Primers | | |
| Hu VH1-5' | 13 | CAGGTGCAGCTGGTGCAGTCTGG |
| Hu VH2-5' | 14 | CAGGTCAACTTAAGGGAGTCTGG |
| Hu VH3-5' | 15 | GAGGTGCAGCTGGTGGAGTCTGG |

TABLE V-continued

Primer Sequences Used to Amplify VH and VL domains.

| Primer name | SEQ ID NO | Primer Sequence (5'-3') |
|---|---|---|
| Hu VH4-5' | 16 | CAGGTGCAGCTGCAGGAGTCGGG |
| Hu VH5-5' | 17 | GAGGTGCAGCTGTTGCAGTCTGC |
| Hu VH6-5' | 18 | CAGGTACAGCTGCAGCAGTCAGG |
| Hu JH1,2-5' | 19 | TGAGGAGACGGTGACCAGGGTGCC |
| Hu JH3-5' | 20 | TGAAGAGACGGTGACCATTGTCCC |
| Hu JH4,5-5' | 21 | TGAGGAGACGGTGACCAGGGTTCC |
| Hu JH6-5' | 22 | TGAGGAGACGGTGACCGTGGTCCC |
| VL Primers | | |
| Hu Vkappa1-5' | 23 | GACATCCAGATGACCCAGTCTCC |
| Hu Vkappa2a-5' | 24 | GATGTTGTGATGACTCAGTCTCC |
| Hu Vkappa2b-5' | 25 | GATATTGTGATGACTCAGTCTCC |
| Hu Vkappa3-5' | 26 | GAAATTGTGTTGACGCAGTCTCC |
| Hu Vkappa4-5' | 27 | GACATCGTGATGACCCAGTCTCC |
| Hu Vkappa5-5' | 28 | GAAACGACACTCACGCAGTCTCC |
| Hu Vkappa6-5' | 29 | GAAATTGTGCTGACTCAGTCTCC |
| Hu Vlambda1-5' | 30 | CAGTCTGTGTTGACGCAGCCGCC |
| Hu Vlambda2-5' | 31 | CAGTCTGCCCTGACTCAGCCTGC |
| Hu Vlambda3-5' | 32 | TCCTATGTGCTGACTCAGCCACC |
| Hu Vlambda3b-5' | 33 | TCTTCTGAGCTGACTCAGGACCC |
| Hu Vlambda4-5' | 34 | CACGTTATACTGACTCAACCGCC |
| Hu Vlambda5-5' | 35 | CAGGCTGTGCTCACTCAGCCGTC |
| Hu Vlambda6-5' | 36 | AATTTTATGCTGACTCAGCCCCA |
| Hu Jkappa1-3' | 37 | ACGTTTGATTTCCACCTTGGTCCC |
| Hu Jkappa2-3' | 38 | ACGTTTGATCTCCAGCTTGGTCCC |
| Hu Jkappa3-3' | 39 | ACGTTTGATATCCACTTTGGTCCC |
| Hu Jkappa4-3' | 40 | ACGTTTGATCTCCACCTTGGTCCC |
| Hu Jkappa5-3' | 41 | ACGTTTAATCTCCAGTCGTGTCCC |
| Hu Jambda1-3' | 42 | CAGTCTGTGTTGACGCAGCCGCC |
| Hu Jlambda2-3' | 43 | CAGTCTGCCCTGACTCAGCCTGC |
| Hu Jlambda3--3' | 44 | TCCTATGTGCTGACTCAGCCACC |
| Hu Jlambda3b-3' | 45 | TCTTCTGAGCTGACTCAGGACCC |
| Hu Jlambda4-3' | 46 | CACGTTATACTGACTCAACCGCC |
| Hu Jlambda5-3' | 47 | CAGGCTGTGCTCACTCAGCCGTC |
| Hu Jlambda6-3' | 48 | AATTTTATGCTGACTCAGCCCCA |

PCR samples are then electrophoresed on a 1.3% agarose gel. DNA bands of the expected sizes (~506 base pairs for VH domains, and 344 base pairs for VL domains) can be cut out of the gel and purified using methods well known in the art. Purified PCR products can be ligated into a PCR cloning vector (TA vector from Invitrogen Inc., Carlsbad, Calif.). Individual cloned PCR products can be isolated after transfection of E. coli and blue/white color selection. Cloned PCR products may then be sequenced using methods commonly known in the art.

The PCR bands containing the VH domain and the VL domains can also be used to create full-length Ig expression vectors. VH and VL domains can be cloned into vectors containing the nucleotide sequences of a heavy (e.g., human IgG1 or human IgG4) or light chain (human kappa or human lambda) constant regions such that a complete heavy or light chain molecule could be expressed from these vectors when transfected into an appropriate host cell. Further, when cloned heavy and light chains are both expressed in one cell line (from either one or two vectors), they can assemble into a complete functional antibody molecule that is secreted into the cell culture medium. Methods using polynucleotides encoding VH and VL antibody domain to generate expression vectors that encode complete antibody molecules are well known within the art.

Example 14

Methods of Inhibiting G-protein Coupled Receptor Activity Using Transmembrane Fragments WO 94/05695 and U.S. Pat. No. 5,508,384 set forth sequences of transmembrane regions for 74 GPCRs. The WO 94/05695 patent publication describes and claims polypeptides corresponding to fragments or homologous sequences of GPCRs which can bind a GPCR ligand or which can modulate ligand binding. Both references disclose that a membrane spanning fragment of the third TM domain of the dopamine D2 receptor specifically bound a ligand of the intact receptor in a simple, small unilamellar vesicle model. The fragment used was terminated with a lysine (which is positively charged at physiological pH) at one end and with an aspartic acid (which is negatively charged at physiological pH) at the other. This peptide would not be expected to insert readily into a biological membrane.

In contrast, this example relates to modulating, especially inhibiting, biological activities of G-protein Chemokine Receptor by exposing it to molecules which interfere with correct receptor assembly. In particular, synthetic, isolated and/or recombinant peptides, fragments and/or consensus peptides of the transmembrane domain of G-protein Chemokine Receptor inhibit G-protein Chemokine Receptor mediated signal transduction. Charged residues may be added at one terminus to promote correct orientation of the peptide in the membrane. In particular, addition of two negatively charged residues, such as Asp, at the extracellular terminus of the fragment enhances antagonist activity.

Fragments of the transmembrane domain can be synthesized by flow-through solid phase peptide synthesis on 432A Applied Biosystems Peptide Synthesizer utilizing Fmoc amino acid derivatives. To overcome aggregation that may occur during synthsis of the peptides and that may lead to blockage of the growing peptide chain, FmocHmb derivatives of Ala, Val, and Leu are introduced. Charged residues are added to the peptide termini to assure a proper orientation of the peptides during penetration into the cellular membrane, and to improve solubility of hydrophobic peptides. Purity of the peptides is assessed by reverse phase HPLC and the structures are confirmed by matrix-assisted laser-desorption time-of-flight (MALDI-TOF) mass spectrometry (Tarasova et al., Ad. Exp. Med. Biol., Plenum Press, NY, pp. 201-206 (1998).)

The antagonistic effect of the fragments is-tested on human kidney carcinoma (HEK) cells stably expressing the G-protein Chemokine Receptor. RANTES is used as the agonist. Cells grown on Nunc cover glass chamber slides are incubated with 1 µM Fura-2/AM for 20 min. in a $CO_2$ incubator, rinsed with PBS, and mounted on the stage of a Zeiss Axiovert inverted microscope. $[Ca^{2+}]i$ measurements are performed using an Attofluor digital imaging system (Atto Instruments). Fluorescence is monitored by an intensified CCD camera using a 505 cut-off filter. Calibrations of $[Ca^{2+}]i$ is performed using $Ca^{2+}$ standards containing 1 µM Fura. The antagonist activity of the fragments is further optimized as described in Examples 1-4 of WO 99/43711.

The antagonist activity of the fragments is also tested by the ability to inhibit G-protein Chemokine Receptor-HIV cell fusion, and the ability to inhibit binding of a labeled ligand of G-protein Chemokine Receptor, by methods well-known in the art and as described for CXCR4 in WO 99/4371 1.

Example 15

G-protein Chemokine Receptor Transgenic Animals

The G-protein Chemokine Receptor polypeptides can also be expressed in transgenic animals. Animals of any species, including, but not limited to, mice, rats, rabbits, hamsters, guinea pigs, pigs, micro-pigs, goats, sheep, cows and non-human primates, e.g., baboons, monkeys, and chimpanzees may be used to generate transgenic animals. In a specific embodiment, techniques described herein or otherwise known in the art, are used to express polypeptides of the invention in humans, as part of a gene therapy protocol.

Any technique known in the art may be used to introduce the transgene (i.e., polynucleotides of the invention) into animals to produce the founder lines of transgenic animals. Such techniques include, but are not limited to, pronuclear microinjection (Paterson et al., Appl. Microbiol. Biotechnol. 40:691-698 (1994); Carver et al., Biotechnology (NY) 11:1263-1270 (1993); Wright et al., Biotechnology (NY) 9:830-834 (1991); and Hoppe et al., U.S. Pat. No. 4,873,191 (1989)); retrovirus mediated gene transfer into germ lines (Van der Putten et al., Proc. Natl. Acad. Sci., USA 82:6148-6152 (1985)), blastocysts or embryos; gene targeting in embryonic stem cells (Thompson et al., Cell 56:313-321 (1989)); electroporation of cells or embryos (Lo, 1983, Mol Cell. Biol. 3:1803-1814 (1983)); introduction of the polynucleotides of the invention using a gene gun (see, e.g., Ulmer et al., Science 259:1745 (1993); introducing nucleic acid constructs into embryonic pleuripotent stem cells and transferring the stem cells back into the blastocyst; and sperm-mediated gene transfer (Lavitrano et al., Cell 57:717-723 (1989); etc. For a review of such techniques, see Gordon, "Transgenic Animals," Intl. Rev. Cytol. 115:171-229 (1989), which is incorporated by reference herein in its entirety.

Any technique known in the art may be used to produce transgenic clones containing polynucleotides of the invention, for example, nuclear transfer into enucleated oocytes of nuclei from cultured embryonic, fetal, or adult cells induced to quiescence (Campell et al., Nature 380:64-66 (1996); Wilmut et al., Nature 385:810-813 (1997)).

The present invention provides for transgenic animals that carry the transgene in all their cells, as well as animals which carry the transgene in some, but not all their cells, i.e., mosaic animals or chimeric. The transgene may be integrated as a single transgene or as multiple copies such as in concatamers, e.g., head-to-head tandems or head-to-tail tandems. The transgene may also be selectively introduced into and activated in a particular cell type by following, for example, the teaching of Lasko et al. (Lasko et al., Proc. Natl. Acad. Sci. USA 89:6232-6236 (1992)). The regulatory sequences required for such a cell-type specific activation will depend upon the particular cell type of interest, and will be apparent to those of skill in the art. When it is desired that the polynucleotide transgene be integrated into the chromosomal site of the endogenous gene, gene targeting is preferred.

Briefly, when such a technique is to be utilized, vectors containing some nucleotide sequences homologous to the endogenous gene are designed for the purpose of integrating, via homologous recombination with chromosomal sequences, into and disrupting the function of the nucleotide sequence of the endogenous gene. The transgene may also be selectively introduced into a particular cell type, thus inactivating the endogenous gene in only that cell type, by following, for example, the teaching of Gu et al. (Gu et al., Science 265:103-106 (1994)). The regulatory sequences required for such a cell-type specific inactivation will depend upon the particular cell type of interest, and will be apparent to those of skill in the art. The contents of each of the documents recited in this paragraph is herein incorporated by reference in its entirety.

In addition to expressing the polypeptide of the present invention in a ubiquitous or tissue specific manner in transgenic animals, it would also be routine for one skilled in the art to generate constructs which regulate expression of the polypeptide by a variety of other means (for example, developmentally or chemically regulated expression).

Once transgenic animals have been generated, the expression of the recombinant gene may be assayed utilizing standard techniques. Initial screening may be accomplished by Southern blot analysis or PCR techniques to analyze animal tissues to verify that integration of the transgene has taken place. The level of mRNA expression of the transgene in the tissues of the transgenic animals may also be assessed using techniques which include, but are not limited to, Northern blot analysis of tissue samples obtained from the animal, in situ hybridization analysis, and reverse transcriptase-PCR (rt-PCR). Samples of transgenic gene-expressing tissue may also be evaluated immunocytochemically or immunohistochemically using antibodies specific for the transgene product.

Once the founder animals are produced, they may be bred, inbred, outbred, or crossbred to produce colonies of the particular animal. Examples of such breeding strategies include, but are not limited to: outbreeding of founder animals with more than one integration site in order to establish separate lines; inbreeding of separate lines in order to produce compound transgenics that express the transgene at higher levels because of the effects of additive expression of each transgene; crossing of heterozygous transgenic animals to produce animals homozygous for a given integration site in order to both augment expression and eliminate the need for screening of animals by DNA analysis; crossing of separate homozygous lines to produce compound heterozygous or homozygous lines; and breeding to place the transgene on a distinct background that is appropriate for an experimental model of interest.

Transgenic animals of the invention have uses which include, but are not limited to, animal model systems useful in elaborating the biological function of G-protein Chemokine Receptor polypeptides, studying diseases, disorders, and/or conditions associated with aberrant G-protein Chemokine Receptor expression, and in screening for compounds effective in ameliorating such diseases, disorders, and/or conditions.

Example 16

G-protein Chemokine Receptor Knock-Out Animals

Endogenous G-protein Chemokine Receptor gene expression can also be reduced by inactivating or "knocking out" the G-protein Chemokine Receptor gene and/or its promoter using targeted homologous recombination. (E.g., see Smithies et al., Nature 317:230-234 (1985); Thomas & Capecchi, Cell 51:503-512 (1987); Thompson et al., Cell 5:313-321 (1989); each of which is incorporated by reference herein in its entirety). For example, a mutant, non-functional polynucleotide of the invention (or a completely unrelated DNA sequence) flanked by DNA homologous to the endogenous polynucleotide sequence (either the coding regions or regulatory regions of the gene) can be used, with or without a selectable marker and/or a negative selectable marker, to transfect cells that express polypeptides of the invention in vivo. In another embodiment, techniques known in the art are used to generate knockouts in cells that contain, but do not express the gene of interest. Insertion of the DNA construct, via targeted homologous recombination, results in inactivation of the targeted gene. Such approaches are particularly suited in research and agricultural fields where modifications to embryonic stem cells can be used to generate animal offspring with an inactive targeted gene (e.g., see Thomas & Capecchi 1987 and Thompson 1989, supra). However this approach can be routinely adapted for use in humans provided the recombinant DNA constructs are directly administered or targeted to the required site in vivo using appropriate viral vectors that will be apparent to those of skill in the art.

In further embodiments of the invention, cells that are genetically engineered to express the polypeptides of the invention, or alternatively, that are genetically engineered not to express the polypeptides of the invention (e.g., knockouts) are administered to a patient in vivo. Such cells may be obtained from the patient (i.e., animal, including human) or an MHC compatible donor and can include, but are not limited to fibroblasts, bone marrow cells, blood cells (e.g., lymphocytes), adipocytes, muscle cells, endothelial cells etc. The cells are genetically engineered in vitro using recombinant DNA techniques to introduce the coding sequence of polypeptides of the invention into the cells, or alternatively, to disrupt the coding sequence and/or endogenous regulatory sequence associated with the polypeptides of the invention, e.g., by transduction (using viral vectors, and preferably vectors that integrate the transgene into the cell genome) or transfection procedures, including, but not limited to, the use of plasmids, cosmids, YACs, naked DNA, electroporation, liposomes, etc. The coding sequence of the polypeptides of the invention can be placed under the control of a strong constitutive or inducible promoter or promoter/enhancer to achieve expression, and preferably secretion, of the G-protein Chemokine Receptor polypeptides. The engineered cells which express and, in one embodiment, preferably secrete the polypeptides of the invention can be introduced into the patient systemically, e.g., in the circulation, or intraperitoneally.

Alternatively, the cells can be incorporated into a matrix and implanted in the body, e.g., genetically engineered fibroblasts can be implanted as part of a skin graft; genetically engineered endothelial cells can be implanted as part of a lymphatic or vascular graft. (See, for example, Anderson et al. U.S. Pat. No. 5,399,349; and Mulligan & Wilson, U.S. Pat. No. 5,460,959 each of which is incorporated by reference herein in its entirety).

When the cells to be administered are non-autologous or non-MHC compatible cells, they can be administered using well known techniques which prevent the development of a host immune response against the introduced cells. For example, the cells may be introduced in an encapsulated form which, while allowing for an exchange of components with the immediate extracellular environment, does not allow the introduced cells to be recognized by the host immune system.

Knock-out animals of the invention have uses which include, but are not limited to, animal model systems useful in elaborating the biological function of G-protein Chemokine Receptor polypeptides, studying diseases, disorders, and/or conditions associated with aberrant G-protein Chemokine Receptor expression, and in screening for compounds effective in ameliorating such diseases, disorders, and/or conditions.

Example 17

Assays Detecting Stimulation or Inhibition of B Cell Proliferation and Differentiation Generation of functional humoral immune responses requires both soluble and cognate signaling between B-lineage cells and their microenvironment. Signals may impart a positive stimulus that allows a B-lineage cell to continue its programmed development, or a negative stimulus that instructs the cell to arrest its current developmental pathway. To date, numerous stimulatory and inhibitory signals have been found to influence B cell responsiveness including IL-2, IL-4, IL-5, IL-6, IL-7, IL10, IL-13, IL-14 and IL-15. Interestingly, these signals are by themselves weak effectors but can, in combination with various co-stimulatory proteins, induce activation, proliferation, differentiation, homing, tolerance and death among B cell populations.

One of the best studied classes of B-cell co-stimulatory proteins is the TNF-superfamily. Within this family CD40, CD27, and CD30 along with their respective ligands CD154, CD70, and CD153 have been found to regulate a variety of immune responses. Assays which allow for the detection and/or observation of the proliferation and differentiation of these B-cell populations and their precursors are valuable tools in determining the effects various proteins may have on these B-cell populations in terms of proliferation and differentiation. Listed below are two assays designed to allow for the detection of the differentiation, proliferation, or inhibition of B-cell populations and their precursors.

In Vitro Assay: Purified G-protein Chemokine Receptor protein, or truncated forms thereof, or purified G-protein Chemokine Receptor ligand is assessed for its ability to induce activation, proliferation, differentiation or inhibition and/or death in B-cell populations and their precursors. The activity of G-protein Chemokine Receptor protein on purified human tonsillar B cells, measured qualitatively over the dose range from 0.1 to 10,000 ng/mL, is assessed in a standard B-lymphocyte co-stimulation assay in which purified tonsillar B cells are cultured in the presence of either formalin-fixed Staphylococcus aureus Cowan I (SAC) or immobilized anti-human IgM antibody as the priming agent. Second signals such as IL-2 and IL-15 synergize with SAC and IgM crosslinking to elicit B cell proliferation as measured by tritiated-thymidine incorporation. Novel synergizing agents can be readily identified using this assay. The assay involves isolating human tonsillar B cells by magnetic bead (MACS) depletion of CD3-positive cells. The resulting cell population is greater than 95% B cells as assessed by expression of CD45R(B220).

Various dilutions of each sample are placed into individual wells of a 96-well plate to which are added $10^5$ B-cells suspended in culture medium (RPMI 1640 containing 10% FBS, $5\times10^{-5}$M 2ME, 100 ug/ml penicillin, 10 ug/mi streptomycin, and $10^{-5}$ dilution of SAC) in a total volume of 150 ul. Proliferation or inhibition is quantitated by a 20 h pulse (1 uCi/well) with 3H-thymidine (6.7 Ci/mM) beginning 72 h post factor addition. The positive and negative controls are IL2 and medium respectively.

In Vivo Assay: BALB/c mice are injected (i.p.) twice per day with buffer only, or 2 mg/Kg of G-protein Chemokine Receptor protein, or truncated forms thereof or G-protein Chemokine Receptor ligand. Mice receive this treatment for 4 consecutive days, at which time they are sacrificed and various tissues and serum collected for analyses. Comparison of H&E sections from normal and G-protein Chemokine Receptor protein-treated spleens identify the results of the activity of G-protein Chemokine Receptor protein on spleen cells, such as the diffusion of peri-arterial lymphatic sheaths, and/or significant increases in the nucleated cellularity of the red pulp regions, which may indicate the activation of the differentiation and proliferation of B-cell populations. Immunohistochemical studies using a B cell marker, anti-CD45R(B220), are used to determine whether any physiological changes to splenic cells, such as splenic disorganization, are due to increased B-cell representation within loosely defined B-cell zones that infiltrate established T-cell regions.

Flow cytometric analyses of the spleens from G-protein Chemokine Receptor protein-treated mice is used to indicate whether G-protein Chemokine Receptor protein specifically increases the proportion of ThB+, CD45R(B220) dull B cells over that which is observed in control mice.

Likewise, a predicted consequence of increased mature B-cell representation in vivo is a relative increase in serum Ig titers. Accordingly, serum IgM and IgA levels are compared between buffer and G-protein Chemokine Receptor protein-treated mice.

The studies described in this example test activity in G-protein Chemokine Receptor protein. However, one skilled in the art could easily modify the exemplified studies to test the activity of G-protein Chemokine Receptor polynucleotides (e.g., gene therapy), agonists (including ligands), and/or antagonists of G-protein Chemokine Receptor.

Example 18

T Cell Proliferation Assay

A CD3-induced proliferation assay is performed on PBMCs and is measured by the uptake of $^3$H-thymidine. The assay is performed as follows. Ninety-six well plates are coated with 100 µl/well of mAb to CD3 (HIT3a, Pharmingen) or isotype-matched control mAb (B33.1) overnight at 4° C. (1 µg/ml in 0.05M bicarbonate buffer, pH 9.5), then washed three times with PBS. PBMC are isolated by F/H gradient centrifugation from human peripheral blood and added to quadruplicate wells ($5\times10^4$/well) of mAb coated plates in RPMI containing 10% FCS and P/S in the presence of varying concentrations of G-protein Chemokine Receptor protein (total volume 200 µl). Relevant protein buffer and medium alone are controls. After 48 hr. culture at 37° C., plates are spun for 2 min. at 1000 rpm and 100 µl of supernatant is removed and stored −20° C. for measurement of IL-2 (or other cytokines) if effect on proliferation is observed. Wells are supplemented with 100 µl of medium containing 0.5 µCi of $^3$H-thymidine and cultured at 37° C. for 18-24 hr. Wells are harvested and incorporation of $^3$H-thymidine used as a measure of proliferation. Anti-CD3 alone is the positive control for proliferation. IL-2 (100 U/ml) is also used as a control which enhances proliferation. Control antibody which does not induce proliferation of T cells is used as the negative controls for the effects of G-protein Chemokine Receptor proteins.

The studies described in this example test activity in G-protein Chemokine Receptor protein. However, one skilled in the art could easily modify the exemplified studies to test the activity of G-protein Chemokine Receptor polynucleotides (e.g., gene therapy), agonists (including ligands), and/or antagonists of G-protein Chemokine Receptor.

Example 19

Herpes Virus Immortalized T cells Which Express the G-protein Chemokine Receptor The construction of a Herpes Virus immortalized T cell line which expresses the G-protein Chemokine Receptor is described in Vella, et al., *J. Virol. Methods* 79:51-63 (1999). This or a similar cell line is useful to assay agonists and antagonists in the methods disclosed herein.

Example 20

Isolation of G-protein Chemokine Receptor Ligands and Antibodies

A general method for solubilizing CCR5 in its native state that may be used in ligand and antibody screening assays is disclosed in Mirzabekov et al., *J. Biol. Chem.* 274:28745-50 (1999). A method of selecting CCR5 antibody from a phage disply library of human antibodies is disclosed in Osbourn et al., *Nat. Biotechnol.* 16:778-81 (1998). Lee et al. disclose that the epitope recognized by the CCR5-specific antibody 2D7 is a preferred target for antibodies to inhibit HIV entry. Lee et al. *J. Biol. Chem.* 274:9617-26 (1999). Other methods of screening for ligands and antibodies are well known in the art and are described herein.

Numerous modifications and variations of the present invention are possible in light of the above teachings and, therefore, within the scope of the appended claims, the invention may be practiced otherwise than as particularly described.

The entire disclosure of each document cited (including patents, patent applications, journal articles, abstracts, laboratory manuals, books, or other disclosures) in the Background of the Invention, Detailed Description, and Examples is hereby incorporated herein by reference.

Further, the Sequence Listing submitted herewith is hereby incorporated by reference in its entirety.

What is claimed is:

1. An isolated protein comprising a polypeptide having an amino acid sequence selected from the group consisting of:
   (a) amino acid residues 1 to 415 of SEQ ID NO:2; and
   (b) the amino acid sequence of the full-length polypeptide encoded by the cDNA clone contained in ATCC Deposit No. 97334.

2. The isolated protein of claim 1, wherein the amino acid sequence is (a).

3. The isolated protein of claim 1, wherein the amino acid sequence is (b).

4. The isolated protein of claim 1 wherein the protein comprises a heterologous polypeptide.

5. The isolated protein of claim 4, wherein the heterologous polypeptide is recombinant human albumin.

6. The isolated protein of claim 4, wherein the heterologous polypeptide is a human IgG Fc region.

7. The isolated protein of claim 1, wherein said isolated protein is fused to polyethylene glycol.

8. The isolated protein of claim 1, wherein said isolated protein is glycosylated.

9. A composition comprising the isolated protein of claim 1.

10. A protein produced by a method comprising:
    (a) culturing a cell under conditions suitable to produce the protein of claim 1; and
    (b) recovering the protein.

* * * * *

UNITED STATES PATENT AND TRADEMARK OFFICE
CERTIFICATE OF CORRECTION

| | | |
|---|---|---|
| PATENT NO. | : 7,888,466 B2 | Page 1 of 1 |
| APPLICATION NO. | : 10/411284 | |
| DATED | : February 15, 2011 | |
| INVENTOR(S) | : Li | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 2245 days.

Signed and Sealed this
Ninth Day of August, 2011

David J. Kappos
*Director of the United States Patent and Trademark Office*

SEQUENCE LISTING

<160> NUMBER OF SEQ ID NOS: 50

<210> SEQ ID NO 1
<211> LENGTH: 1876
<212> TYPE: DNA
<213> ORGANISM: Homo sapiens
<220> FEATURE:
<221> NAME/KEY: CDS
<222> LOCATION: (173)..(1417)
<223> OTHER INFORMATION:

<400> SEQUENCE: 1

```
cctgaaggga gagcagggag agagaggaca gtggccagag agggctctgg gcactggagg      60
gacgctcttc ttcctgccca ggggtccctg ggccgatggg atcacgcaga agaatgcgag     120
agaagcagcc tttgagaagg gaagtcacta tcccagagcc agactgagc gg atg gag     178
                                                        Met Glu
                                                          1 ttg agg aag tac ggc cct gga aga ctg gcg ggg aca gtt ata gga gga      226
Leu Arg Lys Tyr Gly Pro Gly Arg Leu Ala Gly Thr Val Ile Gly Gly
         5                  10                  15 gct gct cag agt aaa tca cag act aaa tca gac tca atc aca aaa gag      274
Ala Ala Gln Ser Lys Ser Gln Thr Lys Ser Asp Ser Ile Thr Lys Glu
     20                  25                  30 ttc ctg cca ggc ctt tac aca gcc cct tcc tcc ccg ttc ccg ccc tca      322
Phe Leu Pro Gly Leu Tyr Thr Ala Pro Ser Ser Pro Phe Pro Pro Ser
 35                  40                  45                  50 cag gtg agt gac cac caa gtg cta aat gac gcc gag gtt gcc gcc ctc      370
Gln Val Ser Asp His Gln Val Leu Asn Asp Ala Glu Val Ala Ala Leu
                 55                  60                  65 ctg gag aac ttc agc tct tcc tat gac tat gga gaa aac gag agt gac      418
Leu Glu Asn Phe Ser Ser Ser Tyr Asp Tyr Gly Glu Asn Glu Ser Asp
             70                  75                  80 tcg tgc tgt acc tcc ccg ccc tgc cca cag gac ttc agc ctg aac ttc      466
Ser Cys Cys Thr Ser Pro Pro Cys Pro Gln Asp Phe Ser Leu Asn Phe
         85                  90                  95 gac cgg gcc ttc ctg cca gcc ctc tac agc ctc ctc ttt ctg ctg ggg      514
Asp Arg Ala Phe Leu Pro Ala Leu Tyr Ser Leu Leu Phe Leu Leu Gly
    100                 105                 110 ctg ctg ggc aac ggc gcg gtg gca gcc gtg ctg ctg agc cgg cgg aca      562
Leu Leu Gly Asn Gly Ala Val Ala Ala Val Leu Leu Ser Arg Arg Thr
115                 120                 125                 130 gcc ctg agc agc acc gac acc ttc ctg ctc cac cta gct gta gca gac      610
Ala Leu Ser Ser Thr Asp Thr Phe Leu Leu His Leu Ala Val Ala Asp
                135                 140                 145 acg ctg ctg gtg ctg aca ctg ccg ctc tgg gca gtg gac gct gcc gtc      658
Thr Leu Leu Val Leu Thr Leu Pro Leu Trp Ala Val Asp Ala Ala Val
            150                 155                 160 cag tgg gtc ttt ggc tct ggc ctc tgc aaa gtg gca ggt gcc ctc ttc      706
Gln Trp Val Phe Gly Ser Gly Leu Cys Lys Val Ala Gly Ala Leu Phe
        165                 170                 175 aac atc aac ttc tac gca gga gcc ctg ctg gcc tgc atc agc ttt      754
Asn Ile Asn Phe Tyr Ala Gly Ala Leu Leu Ala Cys Ile Ser Phe
    180                 185                 190 gac cgc tac ctg aac ata gtt cat gcc acc cag ctc tac cgc cgg ggg      802
Asp Arg Tyr Leu Asn Ile Val His Ala Thr Gln Leu Tyr Arg Arg Gly
195                 200                 205                 210 ccc ccg gcc cgc gtg acc ctc acc tgc ctg gct gtc tgg ggg ctc tgc      850
Pro Pro Ala Arg Val Thr Leu Thr Cys Leu Ala Val Trp Gly Leu Cys
                215                 220                 225
```

```
ctg ctt ttc gcc ctc cca gac ttc atc ttc ctg tcg gcc cac cac gac        898
Leu Leu Phe Ala Leu Pro Asp Phe Ile Phe Leu Ser Ala His His Asp
            230                 235                 240 gag cgc ctc aac gcc acc cac tgc caa tac aac ttc cca cag gtg ggc        946
Glu Arg Leu Asn Ala Thr His Cys Gln Tyr Asn Phe Pro Gln Val Gly
        245                 250                 255 cgc acg gct ctg cgg gtg ctg cag ctg gtg gct ggc ttt ctg ctg ccc        994
Arg Thr Ala Leu Arg Val Leu Gln Leu Val Ala Gly Phe Leu Leu Pro
    260                 265                 270 ctg ctg gtc atg gcc tac tgc tat gcc cac atc ctg gcc gtg ctg ctg       1042
Leu Leu Val Met Ala Tyr Cys Tyr Ala His Ile Leu Ala Val Leu Leu
275                 280                 285                 290 gtt tcc agg ggc cag cgg cgc ctg cgg gcc atg cgg ctg gtg gtg gtg       1090
Val Ser Arg Gly Gln Arg Arg Leu Arg Ala Met Arg Leu Val Val Val
                295                 300                 305 gtc gtg gtg gcc ttt gcc ctc tgc tgg acc ccc tat cac ctg gtg gtg       1138
Val Val Val Ala Phe Ala Leu Cys Trp Thr Pro Tyr His Leu Val Val
            310                 315                 320 ctg gtg gac atc ctc atg gac ctg ggc gct ttg gcc cgc aac tgt ggc       1186
Leu Val Asp Ile Leu Met Asp Leu Gly Ala Leu Ala Arg Asn Cys Gly
        325                 330                 335 cga gaa agc agg gta gac gtg gcc aag tcg gtc acc tca ggc ctg ggc       1234
Arg Glu Ser Arg Val Asp Val Ala Lys Ser Val Thr Ser Gly Leu Gly
    340                 345                 350 tac atg cac tgc tgc ctc aac ccg ctg ctc tat gcc ttt gta ggg gtc       1282
Tyr Met His Cys Cys Leu Asn Pro Leu Leu Tyr Ala Phe Val Gly Val
355                 360                 365                 370 aag ttc cgg gag cgg atg tgg atg ctg ctc ttg cgc ctg ggc tgc ccc       1330
Lys Phe Arg Glu Arg Met Trp Met Leu Leu Leu Arg Leu Gly Cys Pro
                375                 380                 385 aac cag aga ggg ctc cag agg cag cca tcg tct tcc cgc cgg gat tca       1378
Asn Gln Arg Gly Leu Gln Arg Gln Pro Ser Ser Ser Arg Arg Asp Ser
            390                 395                 400 tcc tgg tct gag acc tca gag gcc tcc tac tcg ggc ttg tgaggccgga       1427
Ser Trp Ser Glu Thr Ser Glu Ala Ser Tyr Ser Gly Leu
        405                 410                 415 atccgggctc ccctttcgcc cacagtctga cttccccgca ttccaggctc ctccctccct   1487
ctgccggctc tggctctccc caatatcctc gctcccggga ctcactggca gcccagcac    1547 caccaggtct cccgggaagc caccctccca gctctgagga ctgcaccatt gctgctcctt   1607
agctgccaag cccatcctg ccgcccgagg tggctgcctg gagccccact gcccttctca   1667
tttggaaact aaaacttcat cttccccaag tgcggggagt acaaggcatg gcgtagaggg   1727
tgctgcccca tgaagccaca gcccaggcct ccagctcagc agtgactgtg gccatggtcc   1787
ccaagacctc tatatttggt cttttatttt tatgtctaaa atcctgctta aaacttttca   1847
ataaacaaga tcgtcaggaa aaaaaaaa                                      1876

<210> SEQ ID NO 2
<211> LENGTH: 415
<212> TYPE: PRT
<213> ORGANISM: Homo sapiens

<400> SEQUENCE: 2

Met Glu Leu Arg Lys Tyr Gly Pro Gly Arg Leu Ala Gly Thr Val Ile
1               5                   10                  15

Gly Gly Ala Ala Gln Ser Lys Ser Gln Thr Lys Ser Asp Ser Ile Thr
            20                  25                  30
```

```
Lys Glu Phe Leu Pro Gly Leu Tyr Thr Ala Pro Ser Ser Pro Phe Pro
         35                  40                  45

Pro Ser Gln Val Ser Asp His Gln Val Leu Asn Asp Ala Glu Val Ala
 50                  55                  60

Ala Leu Leu Glu Asn Phe Ser Ser Tyr Asp Tyr Gly Glu Asn Glu
 65                  70                  75                  80

Ser Asp Ser Cys Cys Thr Ser Pro Cys Pro Gln Asp Phe Ser Leu
                 85                  90                  95

Asn Phe Asp Arg Ala Phe Leu Pro Ala Leu Tyr Ser Leu Leu Phe Leu
                100                 105                 110

Leu Gly Leu Leu Gly Asn Gly Ala Val Ala Ala Val Leu Leu Ser Arg
             115                 120                 125

Arg Thr Ala Leu Ser Ser Thr Asp Thr Phe Leu Leu His Leu Ala Val
 130                 135                 140

Ala Asp Thr Leu Leu Val Leu Thr Leu Pro Leu Trp Ala Val Asp Ala
145                 150                 155                 160

Ala Val Gln Trp Val Phe Gly Ser Gly Leu Cys Lys Val Ala Gly Ala
                 165                 170                 175

Leu Phe Asn Ile Asn Phe Tyr Ala Gly Ala Leu Leu Leu Ala Cys Ile
             180                 185                 190

Ser Phe Asp Arg Tyr Leu Asn Ile Val His Ala Thr Gln Leu Tyr Arg
195                 200                 205

Arg Gly Pro Pro Ala Arg Val Thr Leu Thr Cys Leu Ala Val Trp Gly
210                 215                 220

Leu Cys Leu Leu Phe Ala Leu Pro Asp Phe Ile Phe Leu Ser Ala His
225                 230                 235                 240

His Asp Glu Arg Leu Asn Ala Thr His Cys Gln Tyr Asn Phe Pro Gln
                245                 250                 255

Val Gly Arg Thr Ala Leu Arg Val Leu Gln Leu Val Ala Gly Phe Leu
             260                 265                 270

Leu Pro Leu Leu Val Met Ala Tyr Cys Tyr Ala His Ile Leu Ala Val
         275                 280                 285

Leu Leu Val Ser Arg Gly Gln Arg Arg Leu Arg Ala Met Arg Leu Val
         290                 295                 300

Val Val Val Val Val Ala Phe Ala Leu Cys Trp Thr Pro Tyr His Leu
305                 310                 315                 320

Val Val Leu Val Asp Ile Leu Met Asp Leu Gly Ala Leu Ala Arg Asn
                325                 330                 335

Cys Gly Arg Glu Ser Arg Val Asp Val Ala Lys Ser Val Thr Ser Gly
                340                 345                 350

Leu Gly Tyr Met His Cys Cys Leu Asn Pro Leu Leu Tyr Ala Phe Val
             355                 360                 365

Gly Val Lys Phe Arg Glu Arg Met Trp Met Leu Leu Leu Arg Leu Gly
370                 375                 380

Cys Pro Asn Gln Arg Gly Leu Gln Arg Gln Pro Ser Ser Ser Arg Arg
385                 390                 395                 400

Asp Ser Ser Trp Ser Glu Thr Ser Glu Ala Ser Tyr Ser Gly Leu
                405                 410                 415

<210> SEQ ID NO 3
<211> LENGTH: 1670
<212> TYPE: DNA
<213> ORGANISM: Homo sapiens
<220> FEATURE:
<221> NAME/KEY: CDS
```

<222> LOCATION: (69)..(1175)
<223> OTHER INFORMATION:

<400> SEQUENCE: 3

```
ccaaccacaa gcaccaaagc agaggggcag gcagcacacc acccagcagc cagagcacca      60 gcccagcc atg gtc ctt gag gtg agt gac cac caa gtg cta aat gac gcc     110
         Met Val Leu Glu Val Ser Asp His Gln Val Leu Asn Asp Ala
         1               5                   10 gag gtt gcc gcc ctc ctg gag aac ttc agc tct tcc tat gac tat gga     158
Glu Val Ala Ala Leu Leu Glu Asn Phe Ser Ser Ser Tyr Asp Tyr Gly
15              20                  25                  30 gaa aac gag agt gac tcg tgc tgt acc tcc ccg ccc tgc cca cag gac     206
Glu Asn Glu Ser Asp Ser Cys Cys Thr Ser Pro Pro Cys Pro Gln Asp
                35                  40                  45 ttc agc ctg aac ttc gac cgg gcc ttc ctg cca gcc ctc tac agc ctc     254
Phe Ser Leu Asn Phe Asp Arg Ala Phe Leu Pro Ala Leu Tyr Ser Leu
            50                  55                  60 ctc ttt ctg ctg ggg ctg ggc aac ggc gcg gtg gca gcc gtg ctg         302
Leu Phe Leu Leu Gly Leu Gly Asn Gly Ala Val Ala Ala Val Leu
        65                  70                  75 ctg agc cgg cgg aca gcc ctg agc agc acc gac acc ttc ctg ctc cac     350
Leu Ser Arg Arg Thr Ala Leu Ser Ser Thr Asp Thr Phe Leu Leu His
80                  85                  90 cta gct gta gca gac acg ctg ctg gtg ctg aca ctg ccg ctc tgg gca     398
Leu Ala Val Ala Asp Thr Leu Leu Val Leu Thr Leu Pro Leu Trp Ala
95                  100                 105                 110 gtg gac gct gcc gtc cag tgg gtc ttt ggc tct ggc ctc tgc aaa gtg     446
Val Asp Ala Ala Val Gln Trp Val Phe Gly Ser Gly Leu Cys Lys Val
                115                 120                 125 gca ggt gcc ctc ttc aac atc aac ttc tac gca gga gcc ctc ctg ctg     494
Ala Gly Ala Leu Phe Asn Ile Asn Phe Tyr Ala Gly Ala Leu Leu Leu
            130                 135                 140 gcc tgc atc agc ttt gac cgc tac ctg aac ata gtt cat gcc acc cag     542
Ala Cys Ile Ser Phe Asp Arg Tyr Leu Asn Ile Val His Ala Thr Gln
        145                 150                 155 ctc tac cgc cgg ggg ccc ccg gcc cgc gtg acc ctc acc tgc ctg gct     590
Leu Tyr Arg Arg Gly Pro Pro Ala Arg Val Thr Leu Thr Cys Leu Ala
    160                 165                 170 gtc tgg ggg ctc tgc ctg ctt ttc gcc ctc cca gac ttc atc ttc ctg     638
Val Trp Gly Leu Cys Leu Leu Phe Ala Leu Pro Asp Phe Ile Phe Leu
175                 180                 185                 190 tcg gcc cac cac gac gag cgc ctc aac gcc acc cac tgc caa tac aac     686
Ser Ala His His Asp Glu Arg Leu Asn Ala Thr His Cys Gln Tyr Asn
                195                 200                 205 ttc cca cag gtg ggc cgc acg gct ctg cgg gtg ctg cag ctg gtg gct     734
Phe Pro Gln Val Gly Arg Thr Ala Leu Arg Val Leu Gln Leu Val Ala
            210                 215                 220 ggc ttt ctg ctg ccc ctg ctg gtc atg gcc tac tgc tat gcc cac atc     782
Gly Phe Leu Leu Pro Leu Leu Val Met Ala Tyr Cys Tyr Ala His Ile
        225                 230                 235 ctg gcc gtg ctg ctg gtt tcc agg ggc cag cgg cgc ctg cgg gcc atg     830
Leu Ala Val Leu Leu Val Ser Arg Gly Gln Arg Arg Leu Arg Ala Met
    240                 245                 250 cgg ctg gtg gtg gtg gtc gtg gtg gcc ttt gcc ctc tgc tgg acc ccc     878
Arg Leu Val Val Val Val Val Val Ala Phe Ala Leu Cys Trp Thr Pro
255                 260                 265                 270 tat cac ctg gtg gtg ctg gtg gac atc ctc atg gac ctg ggc gct ttg     926
Tyr His Leu Val Val Leu Val Asp Ile Leu Met Asp Leu Gly Ala Leu
                275                 280                 285
```

-continued

```
gcc cgc aac tgt ggc cga gaa agc agg gta gac gtg gcc aag tcg gtc      974
Ala Arg Asn Cys Gly Arg Glu Ser Arg Val Asp Val Ala Lys Ser Val
            290                 295                 300 acc tca ggc ctg ggc tac atg cac tgc tgc ctc aac ccg ctg ctc tat     1022
Thr Ser Gly Leu Gly Tyr Met His Cys Cys Leu Asn Pro Leu Leu Tyr
        305                 310                 315 gcc ttt gta ggg gtc aag ttc cgg gag cgg atg tgg atg ctg ctc ttg     1070
Ala Phe Val Gly Val Lys Phe Arg Glu Arg Met Trp Met Leu Leu Leu
    320                 325                 330 cgc ctg ggc tgc ccc aac cag aga ggg ctc cag agg cag cca tcg tct     1118
Arg Leu Gly Cys Pro Asn Gln Arg Gly Leu Gln Arg Gln Pro Ser Ser
335                 340                 345                 350 tcc cgc cgg gat tca tcc tgg tct gag acc tca gag gcc tcc tac tcg     1166
Ser Arg Arg Asp Ser Ser Trp Ser Glu Thr Ser Glu Ala Ser Tyr Ser
                355                 360                 365 ggc ttg tga ggccggaatc cgggctcccc tttcgcccac agtctgactt             1215
Gly Leu ccccgcattc caggctcctc cctccctctg ccggctctgg ctctcccaa tatcctcgct    1275 cccgggactc actggcagcc ccagcaccac caggtctccc gggaagccac cctcccagct   1335
ctgaggactg caccattgct gctccttagc tgccaagccc catcctgccg cccgaggtgg   1395
ctgcctggag ccccactgcc cttctcattt ggaaactaaa acttcatctt ccccaagtgc   1455
ggggagtaca aggcatggcg tagagggtgc tgccccatga agccacagcc caggcctcca   1515
gctcagcagt gactgtggcc atggtcccca agacctctat atttgctctt ttatttttat   1575
gtctaaaatc ctgcttaaaa cttttcaata acaagatcg tcaggaccaa aaaaaaaaa     1635 aaaaaaaaa aaaaaaaaa aaaaaaaaa aaaaa                                 1670
```

<210> SEQ ID NO 4
<211> LENGTH: 368
<212> TYPE: PRT
<213> ORGANISM: Homo sapiens

<400> SEQUENCE: 4

```
Met Val Leu Glu Val Ser Asp His Gln Val Leu Asn Asp Ala Glu Val
1               5                   10                  15

Ala Ala Leu Leu Glu Asn Phe Ser Ser Ser Tyr Asp Tyr Gly Glu Asn
            20                  25                  30

Glu Ser Asp Ser Cys Cys Thr Ser Pro Pro Cys Pro Gln Asp Phe Ser
        35                  40                  45

Leu Asn Phe Asp Arg Ala Phe Leu Pro Ala Leu Tyr Ser Leu Leu Phe
    50                  55                  60

Leu Leu Gly Leu Leu Gly Asn Gly Ala Val Ala Ala Val Leu Leu Ser
65                  70                  75                  80

Arg Arg Thr Ala Leu Ser Ser Thr Asp Thr Phe Leu Leu His Leu Ala
                85                  90                  95

Val Ala Asp Thr Leu Leu Val Leu Thr Leu Pro Leu Trp Ala Val Asp
            100                 105                 110

Ala Ala Val Gln Trp Val Phe Gly Ser Gly Leu Cys Lys Val Ala Gly
        115                 120                 125

Ala Leu Phe Asn Ile Asn Phe Tyr Ala Gly Ala Leu Leu Leu Ala Cys
    130                 135                 140

Ile Ser Phe Asp Arg Tyr Leu Asn Ile Val His Ala Thr Gln Leu Tyr
145                 150                 155                 160

Arg Arg Gly Pro Pro Ala Arg Val Thr Leu Thr Cys Leu Ala Val Trp
                165                 170                 175
```

```
Gly Leu Cys Leu Leu Phe Ala Leu Pro Asp Phe Ile Phe Leu Ser Ala
            180                 185                 190
His His Asp Glu Arg Leu Asn Ala Thr His Cys Gln Tyr Asn Phe Pro
            195                 200                 205
Gln Val Gly Arg Thr Ala Leu Arg Val Leu Gln Leu Val Ala Gly Phe
            210                 215                 220
Leu Leu Pro Leu Leu Val Met Ala Tyr Cys Tyr Ala His Ile Leu Ala
225                 230                 235                 240
Val Leu Leu Val Ser Arg Gly Gln Arg Leu Arg Ala Met Arg Leu
                    245                 250                 255
Val Val Val Val Val Ala Phe Ala Leu Cys Trp Thr Pro Tyr His
                    260                 265                 270
Leu Val Val Leu Val Asp Ile Leu Met Asp Leu Gly Ala Leu Ala Arg
            275                 280                 285
Asn Cys Gly Arg Glu Ser Arg Val Asp Val Ala Lys Ser Val Thr Ser
            290                 295                 300
Gly Leu Gly Tyr Met His Cys Cys Leu Asn Pro Leu Leu Tyr Ala Phe
305                 310                 315                 320
Val Gly Val Lys Phe Arg Glu Arg Met Trp Met Leu Leu Leu Arg Leu
                    325                 330                 335
Gly Cys Pro Asn Gln Arg Gly Leu Gln Arg Pro Ser Ser Ser Arg
                    340                 345                 350
Arg Asp Ser Ser Trp Ser Glu Thr Ser Glu Ala Ser Tyr Ser Gly Leu
            355                 360                 365

<210> SEQ ID NO 5
<211> LENGTH: 29
<212> TYPE: DNA
<213> ORGANISM: Artificial sequence
<220> FEATURE:
<223> OTHER INFORMATION: Contains a BamHI restriction enzyme site.

<400> SEQUENCE: 5
cgggatcctc catggagttg aggaagtac                              29

<210> SEQ ID NO 6
<211> LENGTH: 30
<212> TYPE: DNA
<213> ORGANISM: Artificial sequence
<220> FEATURE:
<223> OTHER INFORMATION: Contains a BamHI restriction enzyme site.

<400> SEQUENCE: 6
ggcggatccc gctcacaagc ccgagtagga                             30

<210> SEQ ID NO 7
<211> LENGTH: 34
<212> TYPE: DNA
<213> ORGANISM: Artificial sequence
<220> FEATURE:
<223> OTHER INFORMATION: Contains a HindIII restriction enzyme site.

<400> SEQUENCE: 7
gtccaagctt gccaccatgg agttgaggaa gtac                        34

<210> SEQ ID NO 8
<211> LENGTH: 57
<212> TYPE: DNA
<213> ORGANISM: Artificial sequence
<220> FEATURE:
```

```
<223> OTHER INFORMATION: Contains sequence complementary to a XhoI
      restriction enzyme site, translation stop codon, and an HA tag.

<400> SEQUENCE: 8
ctgctcgagt caagcgtagt ctgggacgtc gtatgggtag cacaagcccg agtagga      57

<210> SEQ ID NO 9
<211> LENGTH: 31
<212> TYPE: DNA
<213> ORGANISM: Artificial sequence
<220> FEATURE:
<223> OTHER INFORMATION: Contains sequence complementary to a BamHI
      restriction enzyme site followed by 5 nucleotides resembling an
      efficient signal for the initiation of translation in eukaryotic
      cells.

<400> SEQUENCE: 9
cgggatccct cccatggagt tgaggaagta c                                  31

<210> SEQ ID NO 10
<211> LENGTH: 29
<212> TYPE: DNA
<213> ORGANISM: Artificial sequence
<220> FEATURE:
<223> OTHER INFORMATION: Contains sequence complementary to the cleavage
      site for the restriction endonuclease BamHI.

<400> SEQUENCE: 10
cgggatcccg ctcacaagcc cgagtagga                                     29

<210> SEQ ID NO 11
<211> LENGTH: 354
<212> TYPE: PRT
<213> ORGANISM: Homo sapiens

<400> SEQUENCE: 11

Met Glu Ser Asp Ser Phe Glu Asp Phe Trp Lys Gly Glu Asp Leu Ser
 1               5                  10                  15

Asn Tyr Ser Tyr Ser Ser Thr Leu Pro Pro Phe Leu Leu Asp Ala Ala
             20                  25                  30

Pro Cys Glu Pro Glu Ser Leu Glu Ile Asn Lys Tyr Phe Val Val Ile
         35                  40                  45

Ile Tyr Ala Leu Val Phe Leu Leu Ser Leu Leu Gly Asn Ser Leu Val
     50                  55                  60

Met Leu Val Ile Leu Tyr Ser Arg Val Gly Arg Ser Val Thr Asp Val
 65                  70                  75                  80

Tyr Leu Leu Asn Leu Ala Leu Ala Asp Leu Leu Phe Ala Leu Thr Leu
                 85                  90                  95

Pro Ile Trp Ala Ala Ser Lys Val Asn Gly Trp Ile Phe Gly Thr Phe
            100                 105                 110

Leu Cys Lys Val Val Ser Leu Leu Lys Glu Val Asn Phe Tyr Ser Gly
        115                 120                 125

Ile Leu Leu Leu Ala Cys Ile Ser Val Asp Arg Tyr Leu Ala Ile Val
    130                 135                 140

His Ala Thr Arg Thr Leu Thr Gln Lys Arg Tyr Leu Val Lys Phe Ile
145                 150                 155                 160

Cys Leu Ser Ile Trp Gly Leu Ser Leu Leu Ala Leu Pro Val Leu
                165                 170                 175

Leu Phe Arg Arg Thr Val Tyr Ser Ser Asn Val Ser Pro Ala Cys Tyr
            180                 185                 190
```

```
Glu Asp Met Gly Asn Asn Thr Ala Asn Trp Arg Met Leu Leu Arg Ile
            195                 200                 205
Leu Pro Gln Ser Phe Gly Phe Ile Val Pro Leu Leu Ile Met Leu Phe
        210                 215                 220
Cys Tyr Gly Phe Thr Leu Arg Thr Leu Phe Lys Ala His Met Gly Gln
225                 230                 235                 240
Lys His Arg Ala Met Arg Val Ile Phe Ala Val Val Leu Ile Phe Leu
                245                 250                 255
Leu Cys Trp Leu Pro Tyr Asn Leu Val Leu Leu Ala Asp Thr Leu Met
            260                 265                 270
Arg Thr Gln Val Ile Gln Glu Thr Cys Glu Arg Arg Asn His Ile Asp
        275                 280                 285
Arg Ala Leu Asp Ala Thr Glu Ile Leu Gly Ile Leu His Ser Cys Leu
290                 295                 300
Asn Pro Leu Ile Tyr Ala Phe Ile Gly Gln Lys Phe Arg His Gly Leu
305                 310                 315                 320
Leu Lys Ile Leu Ala Ile His Gly Leu Ile Ser Lys Asp Ser Leu Pro
                325                 330                 335
Lys Asp Ser Arg Pro Ser Phe Val Gly Ser Ser Gly His Thr Ser
            340                 345                 350
Thr Thr
```

<210> SEQ ID NO 12
<211> LENGTH: 733
<212> TYPE: DNA
<213> ORGANISM: Homo sapiens

<400> SEQUENCE: 12

```
gggatccgga gcccaaatct tctgacaaaa ctcacacatg cccaccgtgc ccagcacctg    60
aattcgaggg tgcaccgtca gtcttcctct tccccccaaa acccaaggac accctcatga   120
tctcccggac tcctgaggtc acatgcgtgg tggtggacgt aagccacgaa gaccctgagg   180
tcaagttcaa ctggtacgtg gacggcgtgg aggtgcataa tgccaagaca aagccgcggg   240
aggagcagta caacagcacg taccgtgtgg tcagcgtcct caccgtcctg caccaggact   300
ggctgaatgg caaggagtac aagtgcaagg tctccaacaa agccctccca accccatcg   360
agaaaaccat ctccaaagcc aaagggcagc ccgagaacc acaggtgtac accctgcccc   420
catcccggga tgagctgacc aagaaccagg tcagcctgac ctgcctggtc aaaggcttct   480
atccaagcga catcgccgtg gagtgggaga gcaatgggca gccggagaac aactacaaga   540
ccacgcctcc cgtgctggac tccgacggct ccttcttcct ctacagcaag ctcaccgtgg   600
acaagagcag gtggcagcag gggaacgtct tctcatgctc cgtgatgcat gaggctctgc   660
acaaccacta cacgcagaag agcctctccc tgtctccggg taaatgagtg cgacggccgc   720
gactctagag gat                                                      733
```

<210> SEQ ID NO 13
<211> LENGTH: 23
<212> TYPE: DNA
<213> ORGANISM: Artificial sequence
<220> FEATURE:
<223> OTHER INFORMATION: Degenerate VH forward primer

<400> SEQUENCE: 13

```
caggtgcagc tggtgcagtc tgg                                            23
```

```
<210> SEQ ID NO 14
<211> LENGTH: 23
<212> TYPE: DNA
<213> ORGANISM: Artificial sequence
<220> FEATURE:
<223> OTHER INFORMATION: Degenerate VH forward primer

<400> SEQUENCE: 14
caggtcaact taagggagtc tgg                                              23

<210> SEQ ID NO 15
<211> LENGTH: 23
<212> TYPE: DNA
<213> ORGANISM: Artificial sequence
<220> FEATURE:
<223> OTHER INFORMATION: Degenerate VH forward primer

<400> SEQUENCE: 15
gaggtgcagc tggtggagtc tgg                                              23

<210> SEQ ID NO 16
<211> LENGTH: 23
<212> TYPE: DNA
<213> ORGANISM: Artificial sequence
<220> FEATURE:
<223> OTHER INFORMATION: Degenerate VH forward primer

<400> SEQUENCE: 16
caggtgcagc tgcaggagtc ggg                                              23

<210> SEQ ID NO 17
<211> LENGTH: 23
<212> TYPE: DNA
<213> ORGANISM: Artificial sequence
<220> FEATURE:
<223> OTHER INFORMATION: Degenerate VH forward primer

<400> SEQUENCE: 17
gaggtgcagc tgttgcagtc tgc                                              23

<210> SEQ ID NO 18
<211> LENGTH: 23
<212> TYPE: DNA
<213> ORGANISM: Artificial sequence
<220> FEATURE:
<223> OTHER INFORMATION: Degenerate VH forward primer

<400> SEQUENCE: 18
caggtacagc tgcagcagtc agg                                              23

<210> SEQ ID NO 19
<211> LENGTH: 24
<212> TYPE: DNA
<213> ORGANISM: Artificial sequence
<220> FEATURE:
<223> OTHER INFORMATION: Degenerate JH reverse primer

<400> SEQUENCE: 19
tgaggagacg gtgaccaggg tgcc                                             24

<210> SEQ ID NO 20
<211> LENGTH: 24
<212> TYPE: DNA
<213> ORGANISM: Artificial sequence
<220> FEATURE:
<223> OTHER INFORMATION: Degenerate JH reverse primer
```

```
<400> SEQUENCE: 20
tgaagagacg gtgaccattg tccc                                          24

<210> SEQ ID NO 21
<211> LENGTH: 24
<212> TYPE: DNA
<213> ORGANISM: Artificial sequence
<220> FEATURE:
<223> OTHER INFORMATION: Degenerate JH reverse primer

<400> SEQUENCE: 21
tgaggagacg gtgaccaggg ttcc                                          24

<210> SEQ ID NO 22
<211> LENGTH: 24
<212> TYPE: DNA
<213> ORGANISM: Artificial sequence
<220> FEATURE:
<223> OTHER INFORMATION: Degenerate JH reverse primer

<400> SEQUENCE: 22
tgaggagacg gtgaccgtgg tccc                                          24

<210> SEQ ID NO 23
<211> LENGTH: 23
<212> TYPE: DNA
<213> ORGANISM: Artificial sequence
<220> FEATURE:
<223> OTHER INFORMATION: Degenerate Vkappa forward primer

<400> SEQUENCE: 23
gacatccaga tgacccagtc tcc                                           23

<210> SEQ ID NO 24
<211> LENGTH: 23
<212> TYPE: DNA
<213> ORGANISM: Artificial sequence
<220> FEATURE:
<223> OTHER INFORMATION: Degenerate Vkappa forward primer

<400> SEQUENCE: 24
gatgttgtga tgactcagtc tcc                                           23

<210> SEQ ID NO 25
<211> LENGTH: 23
<212> TYPE: DNA
<213> ORGANISM: Artificial sequence
<220> FEATURE:
<223> OTHER INFORMATION: Degenerate Vkappa forward primer

<400> SEQUENCE: 25
gatattgtga tgactcagtc tcc                                           23

<210> SEQ ID NO 26
<211> LENGTH: 23
<212> TYPE: DNA
<213> ORGANISM: Artificial sequence
<220> FEATURE:
<223> OTHER INFORMATION: Degenerate Vkappa forward primer

<400> SEQUENCE: 26
gaaattgtgt tgacgcagtc tcc                                           23

<210> SEQ ID NO 27
<211> LENGTH: 23
```

```
<212> TYPE: DNA
<213> ORGANISM: Artificial sequence
<220> FEATURE:
<223> OTHER INFORMATION: Degenerate Vkappa forward primer

<400> SEQUENCE: 27
gacatcgtga tgacccagtc tcc                                               23

<210> SEQ ID NO 28
<211> LENGTH: 23
<212> TYPE: DNA
<213> ORGANISM: Artificial sequence
<220> FEATURE:
<223> OTHER INFORMATION: Degenerate Vkappa forward primer

<400> SEQUENCE: 28
gaaacgacac tcacgcagtc tcc                                               23

<210> SEQ ID NO 29
<211> LENGTH: 23
<212> TYPE: DNA
<213> ORGANISM: Artificial sequence
<220> FEATURE:
<223> OTHER INFORMATION: Degenerate Vkappa forward primer

<400> SEQUENCE: 29
gaaattgtgc tgactcagtc tcc                                               23

<210> SEQ ID NO 30
<211> LENGTH: 23
<212> TYPE: DNA
<213> ORGANISM: Artificial sequence
<220> FEATURE:
<223> OTHER INFORMATION: Degenerate Vlambda forward primer

<400> SEQUENCE: 30
cagtctgtgt tgacgcagcc gcc                                               23

<210> SEQ ID NO 31
<211> LENGTH: 23
<212> TYPE: DNA
<213> ORGANISM: Artificial sequence
<220> FEATURE:
<223> OTHER INFORMATION: Degenerate Vlambda forward primer

<400> SEQUENCE: 31
cagtctgccc tgactcagcc tgc                                               23

<210> SEQ ID NO 32
<211> LENGTH: 23
<212> TYPE: DNA
<213> ORGANISM: Artificial sequence
<220> FEATURE:
<223> OTHER INFORMATION: Degenerate Vlambda forward primer

<400> SEQUENCE: 32
tcctatgtgc tgactcagcc acc                                               23

<210> SEQ ID NO 33
<211> LENGTH: 23
<212> TYPE: DNA
<213> ORGANISM: Artificial sequence
<220> FEATURE:
<223> OTHER INFORMATION: Degenerate Vlambda forward primer

<400> SEQUENCE: 33
```
tcttctgagc tgactcagga ccc                                    23

<210> SEQ ID NO 34
<211> LENGTH: 23
<212> TYPE: DNA
<213> ORGANISM: Artificial sequence
<220> FEATURE:
<223> OTHER INFORMATION: Degenerate Vlambda forward primer

<400> SEQUENCE: 34
cacgttatac tgactcaacc gcc                                    23

<210> SEQ ID NO 35
<211> LENGTH: 23
<212> TYPE: DNA
<213> ORGANISM: Artificial sequence
<220> FEATURE:
<223> OTHER INFORMATION: Degenerate Vlambda forward primer

<400> SEQUENCE: 35
caggctgtgc tcactcagcc gtc                                    23

<210> SEQ ID NO 36
<211> LENGTH: 23
<212> TYPE: DNA
<213> ORGANISM: Artificial sequence
<220> FEATURE:
<223> OTHER INFORMATION: Degenerate Vlambda forward primer

<400> SEQUENCE: 36
aattttatgc tgactcagcc cca                                    23

<210> SEQ ID NO 37
<211> LENGTH: 24
<212> TYPE: DNA
<213> ORGANISM: Artificial sequence
<220> FEATURE:
<223> OTHER INFORMATION: Degenerate Jkappa reverse primer

<400> SEQUENCE: 37
acgtttgatt tccaccttgg tccc                                   24

<210> SEQ ID NO 38
<211> LENGTH: 24
<212> TYPE: DNA
<213> ORGANISM: Artificial sequence
<220> FEATURE:
<223> OTHER INFORMATION: Degenerate Jkappa reverse primer

<400> SEQUENCE: 38
acgtttgatc tccagcttgg tccc                                   24

<210> SEQ ID NO 39
<211> LENGTH: 24
<212> TYPE: DNA
<213> ORGANISM: Artificial sequence
<220> FEATURE:
<223> OTHER INFORMATION: Degenerate Jkappa reverse primer

<400> SEQUENCE: 39
acgtttgata tccactttgg tccc                                   24

<210> SEQ ID NO 40
<211> LENGTH: 24
<212> TYPE: DNA
<213> ORGANISM: Artificial sequence

```
<220> FEATURE:
<223> OTHER INFORMATION: Degenerate Jkappa reverse primer

<400> SEQUENCE: 40
acgtttgatc tccaccttgg tccc                                          24

<210> SEQ ID NO 41
<211> LENGTH: 24
<212> TYPE: DNA
<213> ORGANISM: Artificial sequence
<220> FEATURE:
<223> OTHER INFORMATION: Degenerate Jkappa reverse primer

<400> SEQUENCE: 41
acgtttaatc tccagtcgtg tccc                                          24

<210> SEQ ID NO 42
<211> LENGTH: 23
<212> TYPE: DNA
<213> ORGANISM: Artificial sequence
<220> FEATURE:
<223> OTHER INFORMATION: Degenerate Jlambda reverse primer

<400> SEQUENCE: 42
cagtctgtgt tgacgcagcc gcc                                           23

<210> SEQ ID NO 43
<211> LENGTH: 23
<212> TYPE: DNA
<213> ORGANISM: Artificial sequence
<220> FEATURE:
<223> OTHER INFORMATION: Degenerate Jlambda reverse primer

<400> SEQUENCE: 43
cagtctgccc tgactcagcc tgc                                           23

<210> SEQ ID NO 44
<211> LENGTH: 23
<212> TYPE: DNA
<213> ORGANISM: Artificial sequence
<220> FEATURE:
<223> OTHER INFORMATION: Degenerate Jlambda reverse primer

<400> SEQUENCE: 44
tcctatgtgc tgactcagcc acc                                           23

<210> SEQ ID NO 45
<211> LENGTH: 23
<212> TYPE: DNA
<213> ORGANISM: Artificial sequence
<220> FEATURE:
<223> OTHER INFORMATION: Degenerate Jlambda reverse primer

<400> SEQUENCE: 45
tcttctgagc tgactcagga ccc                                           23

<210> SEQ ID NO 46
<211> LENGTH: 23
<212> TYPE: DNA
<213> ORGANISM: Artificial sequence
<220> FEATURE:
<223> OTHER INFORMATION: Degenerate Jlambda reverse primer

<400> SEQUENCE: 46
cacgttatac tgactcaacc gcc                                           23
```

```
<210> SEQ ID NO 47
<211> LENGTH: 23
<212> TYPE: DNA
<213> ORGANISM: Artificial sequence
<220> FEATURE:
<223> OTHER INFORMATION: Degenerate Jlambda reverse primer

<400> SEQUENCE: 47
caggctgtgc tcactcagcc gtc                                              23

<210> SEQ ID NO 48
<211> LENGTH: 23
<212> TYPE: DNA
<213> ORGANISM: Artificial sequence
<220> FEATURE:
<223> OTHER INFORMATION: Degenerate Jlambda reverse primer

<400> SEQUENCE: 48
aattttatgc tgactcagcc cca                                              23

<210> SEQ ID NO 49
<211> LENGTH: 17
<212> TYPE: PRT
<213> ORGANISM: Homo sapiens

<400> SEQUENCE: 49

Met Leu Gln Asn Ser Ala Val Leu Leu Leu Val Ile Ser Ala Ser
  1               5                  10                  15

Ala

<210> SEQ ID NO 50
<211> LENGTH: 22
<212> TYPE: PRT
<213> ORGANISM: Artificial sequence
<220> FEATURE:
<223> OTHER INFORMATION: Consensus signal sequence

<400> SEQUENCE: 50

Met Pro Thr Trp Ala Trp Trp Leu Phe Leu Val Leu Leu Ala Leu
  1               5                  10                  15

Trp Ala Pro Ala Arg Gly
             20
```